(12) United States Patent
Gour et al.

(10) Patent No.: US 7,268,115 B2
(45) Date of Patent: Sep. 11, 2007

(54) PEPTIDOMIMETIC MODULATORS OF CELL ADHESION

(75) Inventors: Barbara J. Gour, Kemptville (CA); Orest W. Blaschuk, Westmount (CA); Anmar Ali, Ottawa (CA); Feng Ni, Pierrefonds (CA); Zhigang Chen, Acton, MA (US); Stephanie Denise Michaud, Ottawa (CA); Shaomeng Wang, Saline, MI (US); Zenjian Hu, Rockville, MD (US)

(73) Assignee: Adherex Technologies, Inc., Ottawa (CA)

( * ) Notice: Subject to any disclaimer, the term of this patent is extended or adjusted under 35 U.S.C. 154(b) by 426 days.

(21) Appl. No.: 10/412,701

(22) Filed: Apr. 10, 2003

(65) Prior Publication Data

US 2004/0058864 A1 Mar. 25, 2004

Related U.S. Application Data

(63) Continuation of application No. 09/769,145, filed on Jan. 24, 2001, now abandoned, which is a continuation-in-part of application No. 09/491,078, filed on Jan. 24, 2000, now abandoned.

(51) Int. Cl.
*A61K 38/00* (2006.01)
(52) U.S. Cl. ........................................... 514/12
(58) Field of Classification Search ...................... None
See application file for complete search history.

(56) References Cited

U.S. PATENT DOCUMENTS

| | | | | |
|---|---|---|---|---|
| 5,784,294 | A | 7/1998 | Platt et al. | 364/496 |
| 5,939,528 | A | 8/1999 | Clardy et al. | 530/350 |
| 6,031,072 | A | 2/2000 | Blaschuk et al. | 530/317 |
| 6,326,352 | B1 | 12/2001 | Blaschuk et al. | 514/9 |
| 6,610,821 | B1 * | 8/2003 | Blaschuk et al. | 530/317 |
| 2002/0028453 | A1 | 3/2002 | Keck et al. | 435/6 |
| 2004/0006011 | A1 | 1/2004 | Gour et al. | 514/9 |

FOREIGN PATENT DOCUMENTS

| | | |
|---|---|---|
| EP | 1323440 A1 | 7/2003 |
| WO | WO 91/04745 | 4/1991 |
| WO | WO 98/02452 | 1/1998 |
| WO | WO 98/45319 | 10/1998 |
| WO | WO 99/33875 | 7/1999 |
| WO | WO 03/051842 | 6/2003 |

OTHER PUBLICATIONS

Milne et al. Pharmacophores in Drug Design and Discovery. SAR QSAR Environ. Res. 1998. vol. 9, No. 1-2, pp. 23-38.*
Chemical Abstracts Online (STN), Accession No. 1997:480306, 1997.
Chemical Abstracts Online (STN), Accession No. 1998:298188, 1998.
Cowper, A.J. et al., "Preparation of some 1,2,3,4-Tetrazoles," *Journal of the Indian Chemical Society* 58 (11): 1087-1088, Nov. 1981.
Gillespie, P. et al., "Conformational Analysis of Dipeptide Mimetics," *Peptide Science* 43(3): 191-217, 1997.
Ikeda, G.J. et al., "Synthesis, *in Vivo* Effects, Metabolsim, and Excretion of 5-(*p*-Hydroxyanilino)-1,2,3,4-thiatriazole in the Beagle Dog," *Journal of Medicinal Chemistry* 17(10): 1079-1082, Oct. 1974.
Ikeda, G.J., "Metabolism of 5-(*p*-Hydroxyanilino)-1,2,3,4-thiatriazole in Rats," *Journal of Medicinal Chemistry* 16(10): 1157-1161, Oct. 1973.
Jones, G. et al., "Development and Validation of a Genetic Algorithm for Flexible Docking," *J. Mol. Biol.* 267: 727-748, 1997.
Leahy, D.J., "Implications of Atomic-Resolution Structures for Cell Adhesion," *Annu. Rev. Cell Dev. Biol.* 13: 363-393, 1997.
Overduin, M. ey al., "Solution Structure of the Epithelial Cadherin Domain Responsible for Selective Cell Adhesion," *Science* 267: 386-389, Jan. 20, 1995.
Sandak, B. et al., "A Method for Biomolecular Structural Recognition and Docking Allowing Conformational Flexibility," *Journal of Computational Biology* 5(4): 631-654, 1998.
Shapiro, L. et al., "Structural basis of cell-cell adhesion by cadherins," *Nature* 374: 327-337.
Theriault, R.J. et al., "Microbial Hydroxylation of 5-anilino-1,2,3,4-Thiatriazole," *Applied Microbiology* 25(4): 606-611, Apr. 1973.
Wahab, A. et al., "Substituted Thiatriazoles as Possible Antitubercular Compounds," *Bollettino Chimico Farmaceutico* 117: 107-112, 1978.

* cited by examiner

*Primary Examiner*—Jon Weber
*Assistant Examiner*—Suzanne M. Noakes
(74) *Attorney, Agent, or Firm*—Seed IP Law Group PLLC

(57) ABSTRACT

Peptidomimetics of cyclic peptides, and compositions comprising such peptidomimetics are provided. The peptidomimetics have a three-dimensional structure that is substantially similar to a three-dimensional structure of a cyclic peptide that comprises a cadherin cell adhesion recognition sequence HAV. Methods for using such peptidomimetics for modulating cadherin-mediated cell adhesion in a variety of contexts are also provided.

3 Claims, 202 Drawing Sheets

| | |
|---|---|
| human n-cad | DWVIPPINLPENSRGPFPQELVRIRSDRDKNLSLRYSVTGPGAD |
| mouse n-cad | DWVIPPINLPENSRGPFPQELVRIRSDRDKNLSLRYSVTGPGAD |
| cow n-cad | DWVIPPINLPENSRGPFPQELVRIRSDRDKNLSLRYSVTGPGAD |
| human p-cad | DWVVAPISVPENGKGPFPQRLNQLKSNKDRDTKIFYSITGPGAD |
| mouse p-cad | EWVMPPIFVPENGKGPFPQRLNQLKSNKDRGTKIFYSITGPGAD |
| human e-cad | DWVIPPISCPENEKGPFPKNLVQIKSNKDKEGKVFYSITGQGAD |
| mouse e-cad | DWVIPPISCPENEKGEFPKNLVQIKSNRDKETKVFYSITGQGAD |
| | |
| human n-cad | QPPTGIFILNPISGQLSVTKPLDREQIARFHLRAHAVDINGNQV |
| mouse n-cad | QPPTGIFIINPISGQLSVTKPLDRELIARFHLRAHAVDINGNQV |
| cow n-cad | QPPTGIFIINPISGQLSVTKPLDRELIARFHLRAHAVDINGNQV |
| human p-cad | SPPEGVFAVEKETGWLLLNKPLDREEIAKYELFGHAVSENGASV |
| mouse p-cad | SPPEGVFTIEKESGWLLLHMPLDREKIVKYELYGHAVSENGASV |
| human e-cad | TPPVGVFIIERETGWLKVTEPLDRERIATYTLFSHAVSSNGNAV |
| mouse e-cad | KPPVGVFIIERETGWLKVTQPLDREAIAKYILYSHAVSSNGEAV |
| | |
| human n-cad | ENPIDIVINVIDMNDNRPEF |
| mouse n-cad | ENPIDIVINVIDMNDNRPEF |
| cow n-cad | ENPIDIVINVIDMNDNRPEF |
| human p-cad | EDPMNISIIVTDQNDHKPKF |
| mouse p-cad | EEPMNISIIVTDQNDNKPKF |
| human e-cad | EDPMEILITVTDQNDNKPEF |
| mouse e-cad | EDPMEIVITVTDQNDNRPEF |

*Fig. 2*

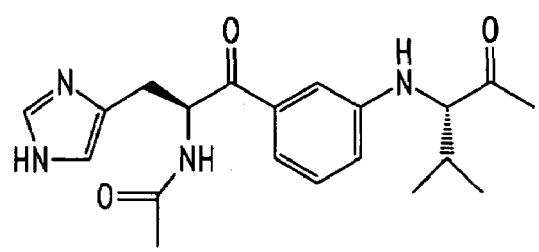
Compound 4
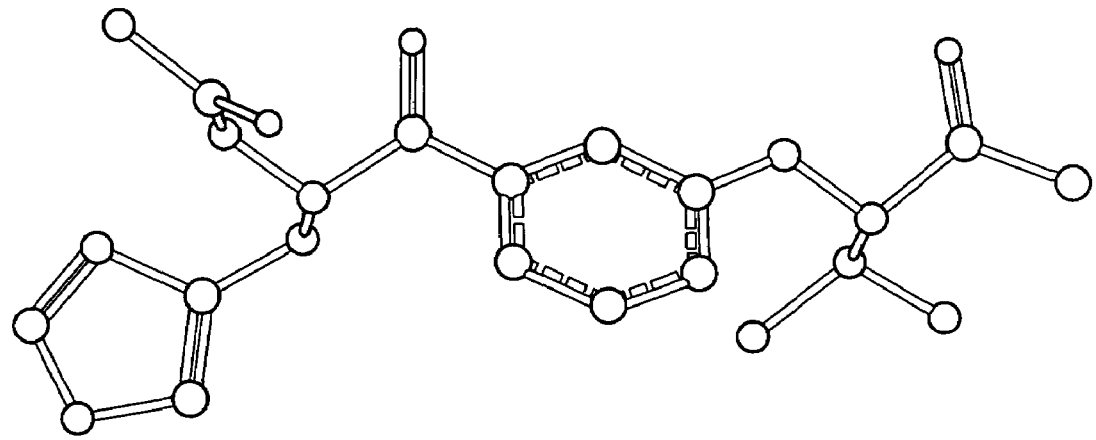
Low energy conformation of Compound 4
*Fig. 12B*

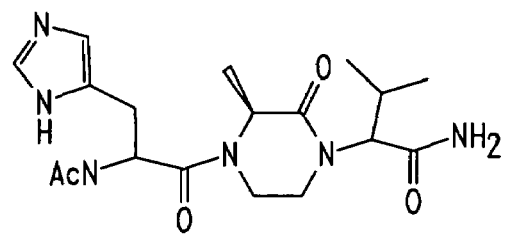
compound 10
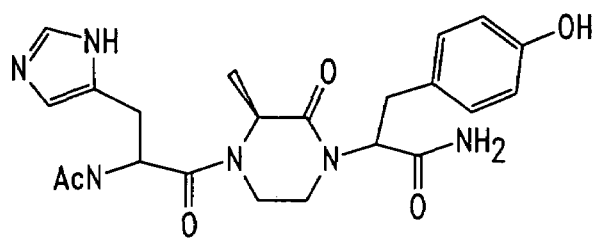
compound 11
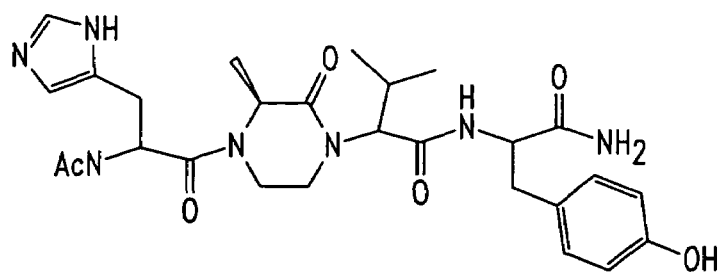
compound 12
*Fig. 13B*

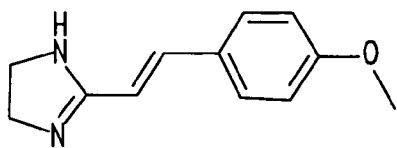
compound 20
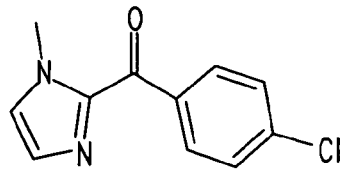
compound 21
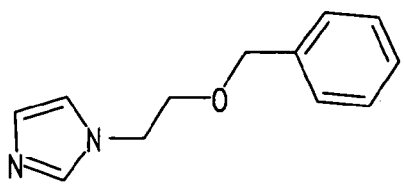
compound 22
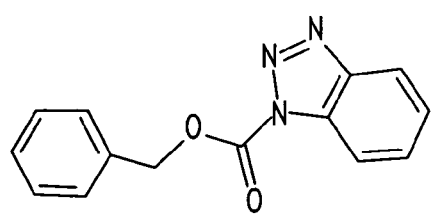
compound 23
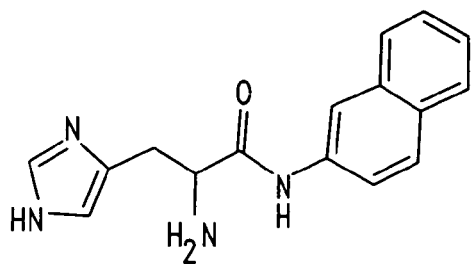
compound 24
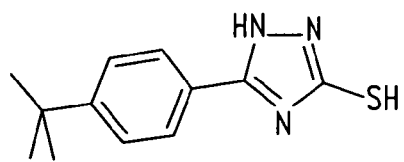
compound 25
*Fig. 15B* compound 60 compound 61 compound 62 compound 63 compound 64 compound 65

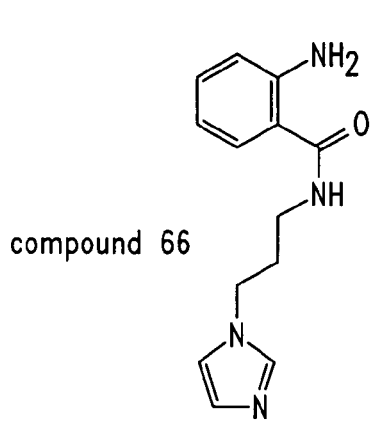
compound 66
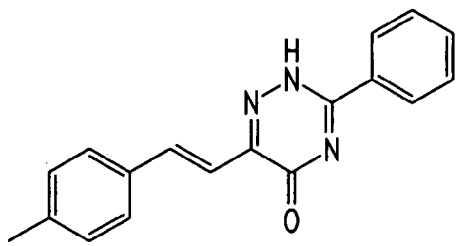
compound 67
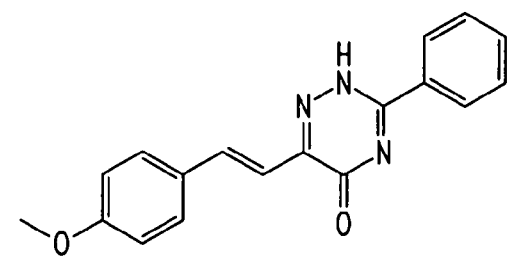
compound 68
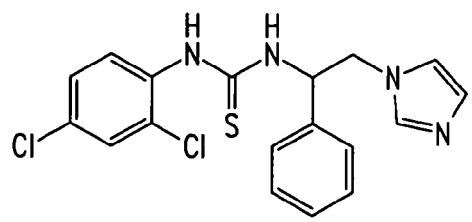
compound 69
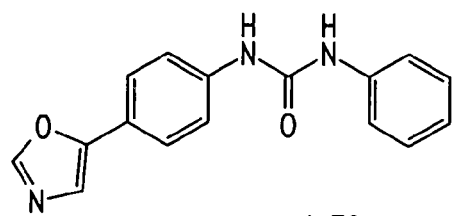
compound 70
*Fig. 15J*

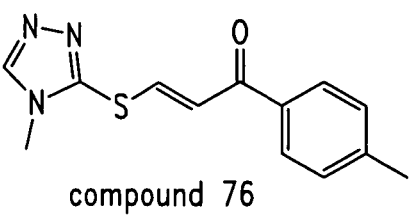
compound 76
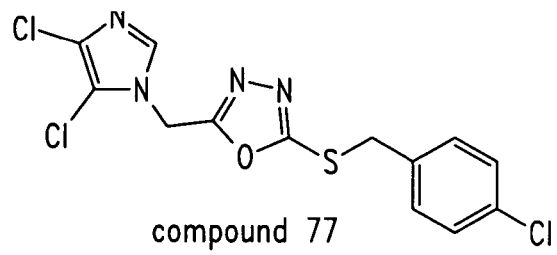
compound 77
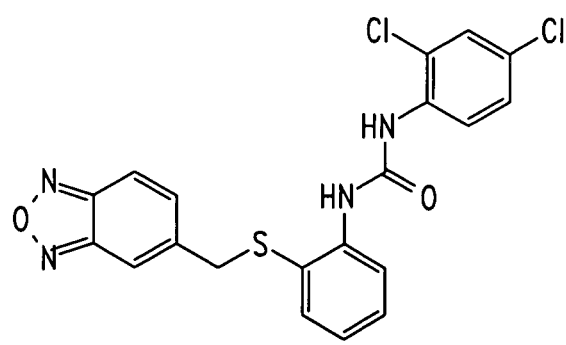
compound 78
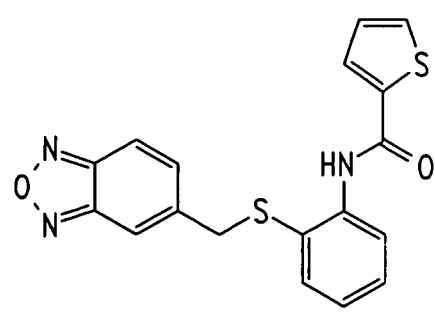
compound 79
*Fig. 15L*

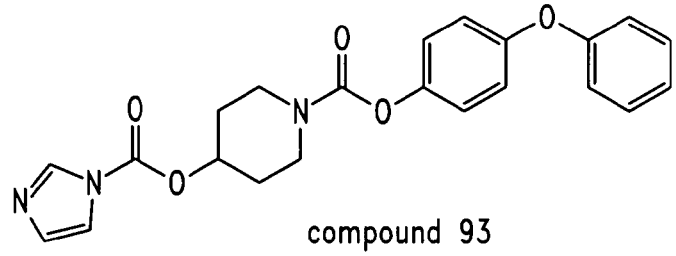
compound 93
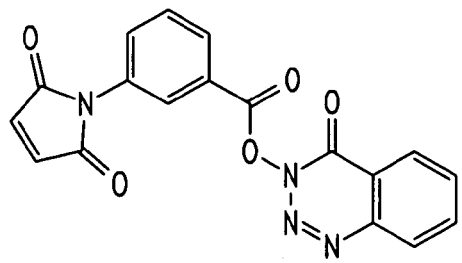
compound 94
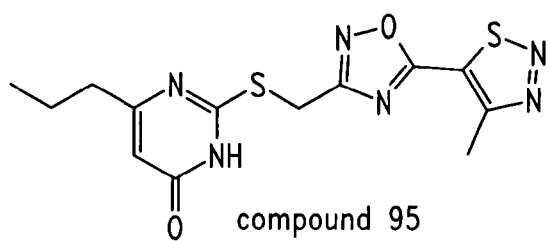
compound 95
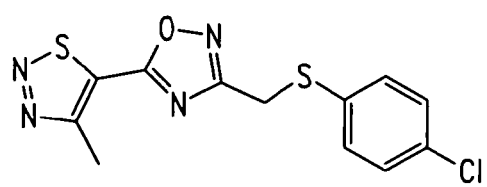
compound 96
*Fig. 150*

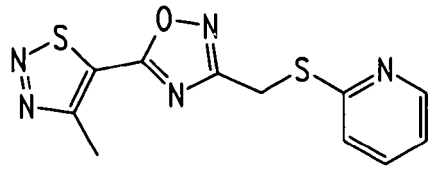
compound 97
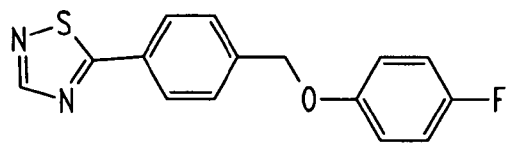
compound 98
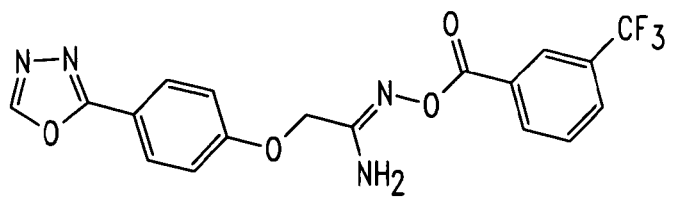
compound 99
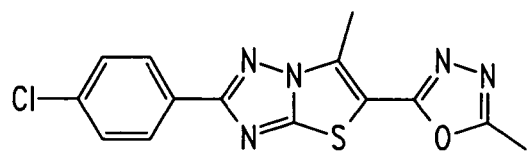
compound 100
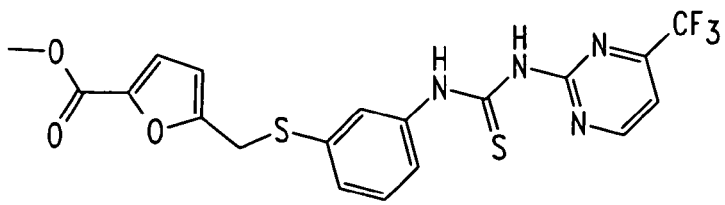
compound 101
Fig. 15P

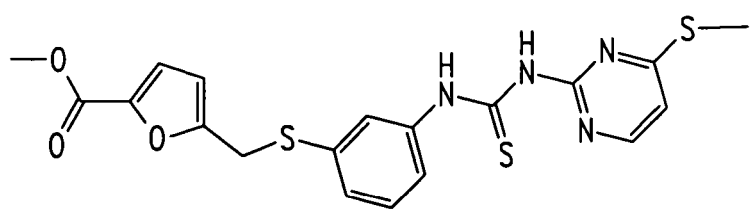
compound 102
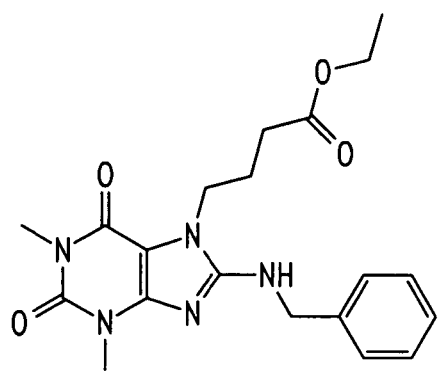
compound 103
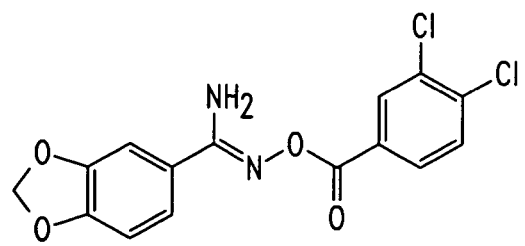
compound 104
*Fig. 15Q*

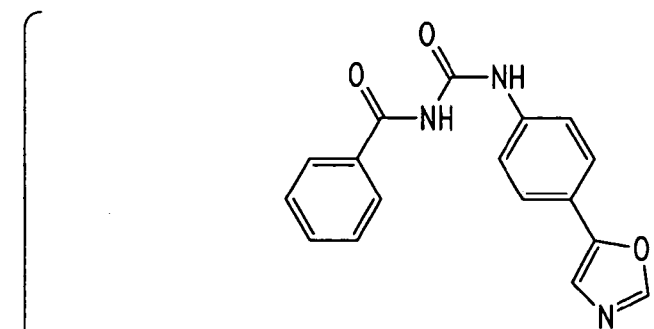
compound 105
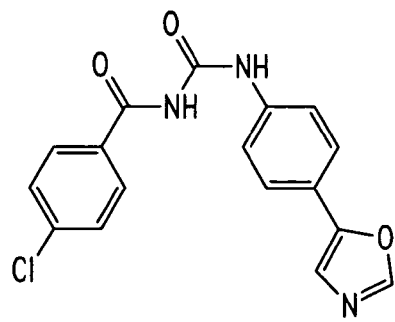
compound 106
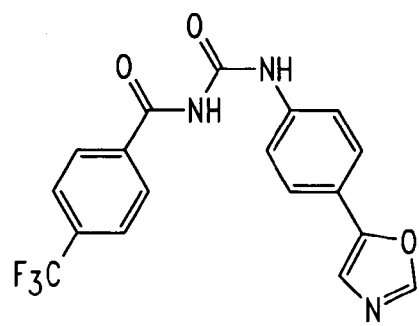
compound 107
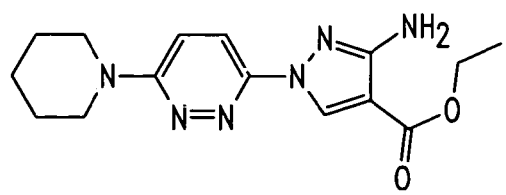
compound 108
*Fig. 15R*

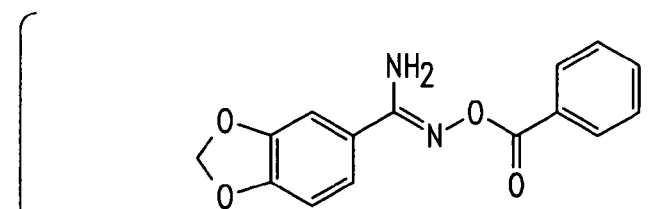
compound 109
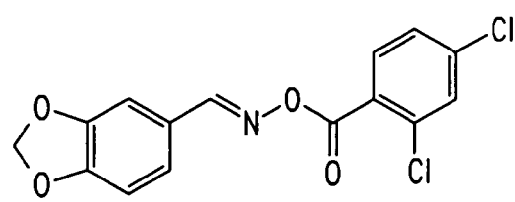
compound 110
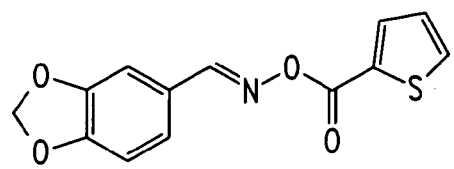
compound 111
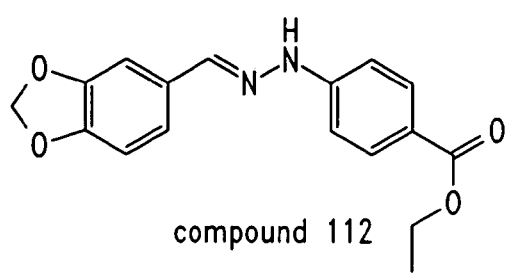
compound 112
*Fig. 15S* compound 117 compound 118 compound 119 compound 120 compound 126 compound 127 compound 128 compound 129

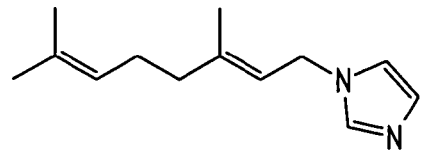
compound 136
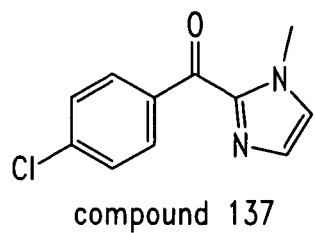
compound 137
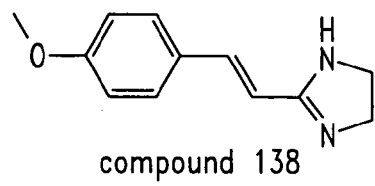
compound 138
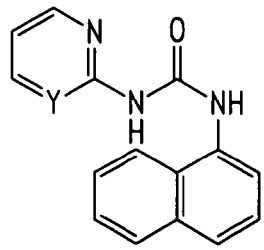
compound 139
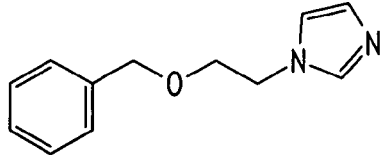
compound 140
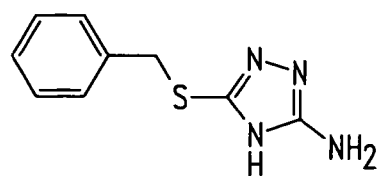
compound 141
*Fig. 15Y* compound 136 compound 137 compound 138 compound 139 compound 140 compound 141

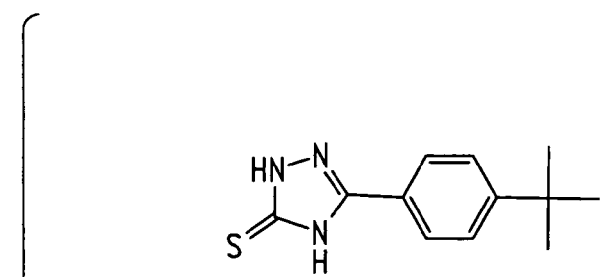
compound 147
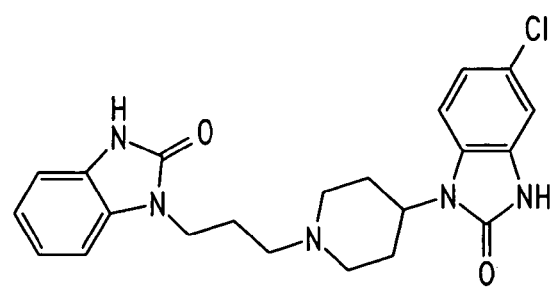
compound 148
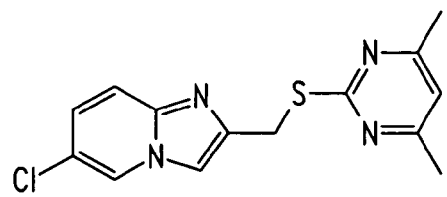
compound 149
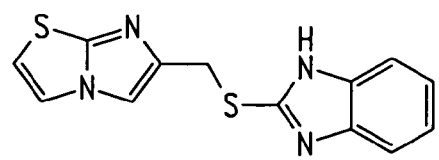
compound 150
*Fig. 15AA* compound 151 compound 152 compound 153 compound 154

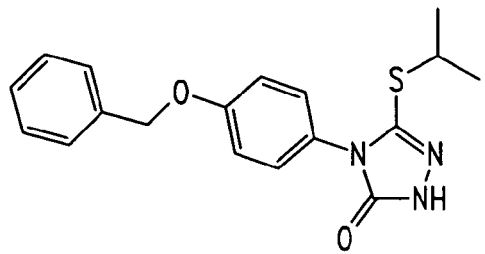
compound 155
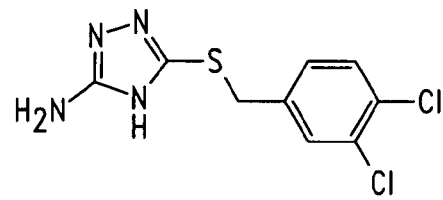
compound 156
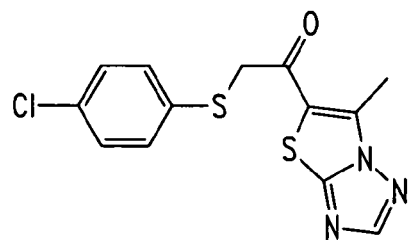
compound 157
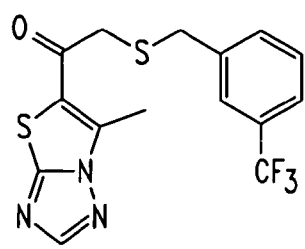
compound 158
*Fig. 15AC*

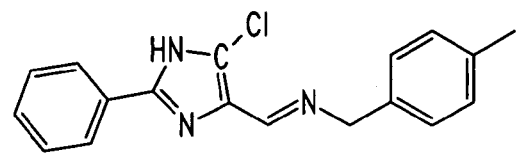
compound 159
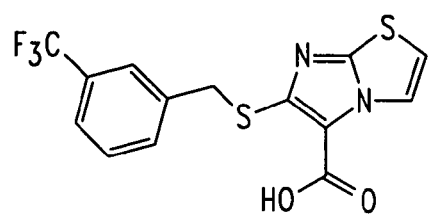
compound 160
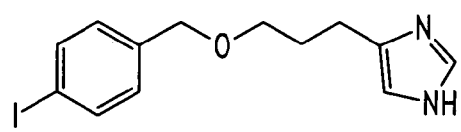
compound 161
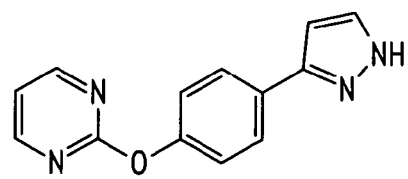
compound 162
*Fig. 15AD*

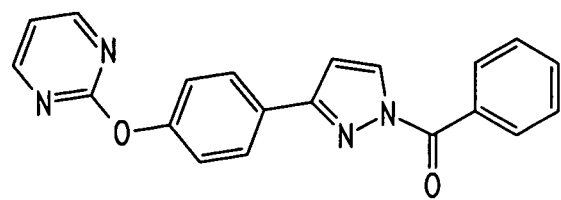
compound 163
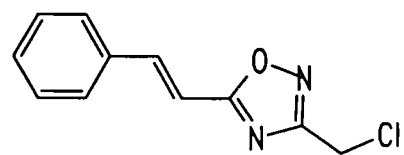
compound 164
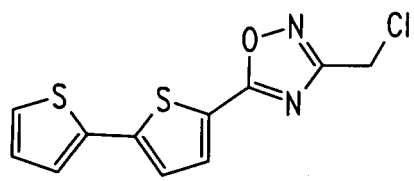
compound 165
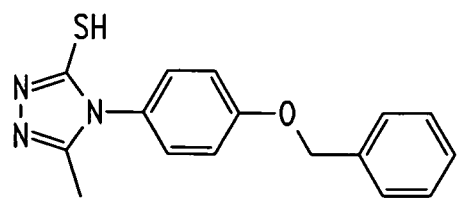
compound 166
*Fig. 15AE*

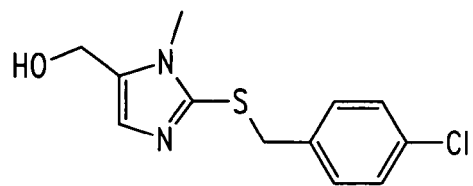
compound 167
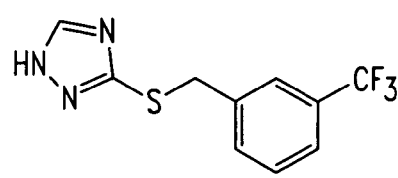
compound 168
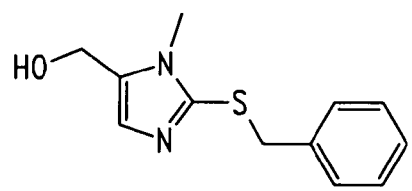
compound 169
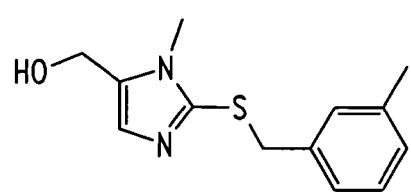
compound 170
*Fig. 15AF* compound 171 compound 172 compound 173 compound 174

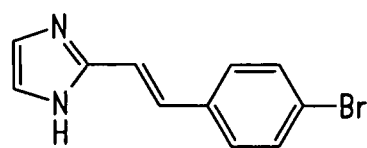
compound 175
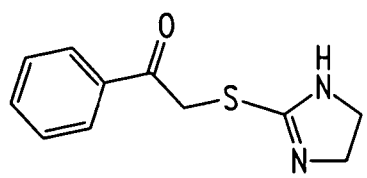
compound 176
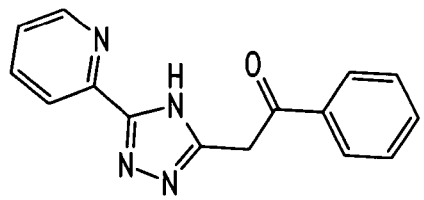
compound 177
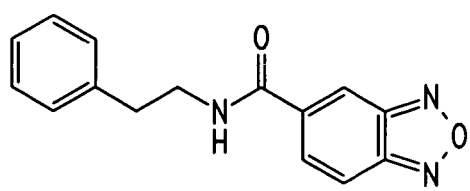
compound 178
*Fig. 15AH*

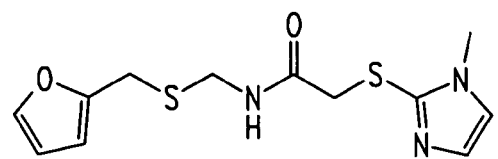
compound 179
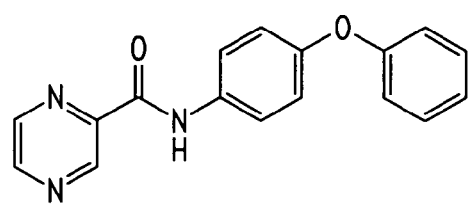
compound 180
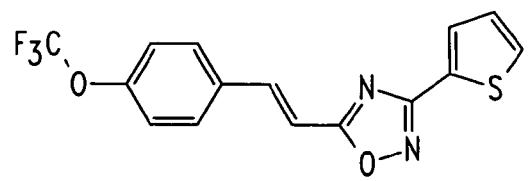
compound 181
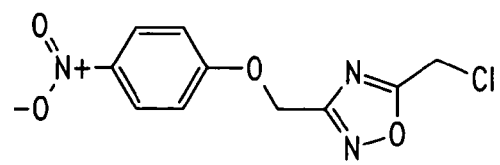
compound 182
*Fig. 15AI*

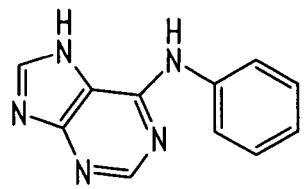
compound 183
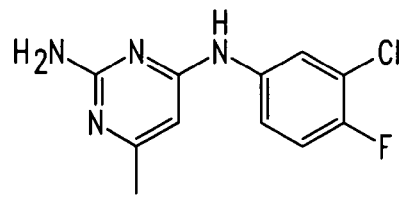
compound 184
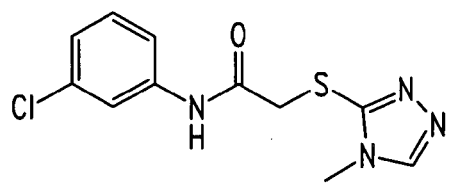
compound 185
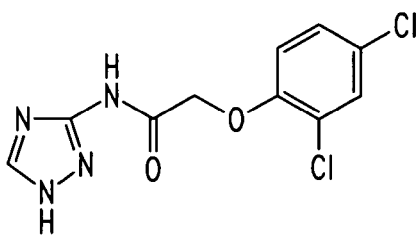
compound 186
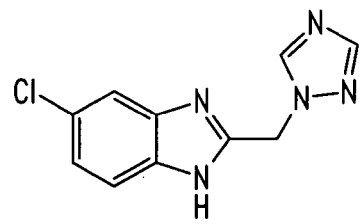
compound 187
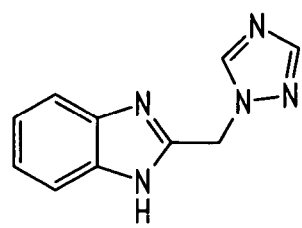
compound 188
*Fig. 15AJ*

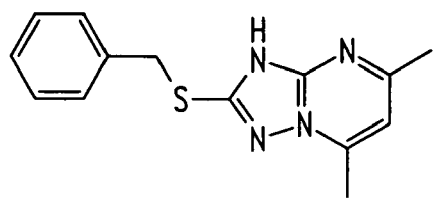
compound 189
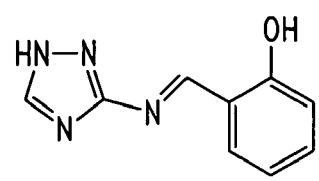
compound 190
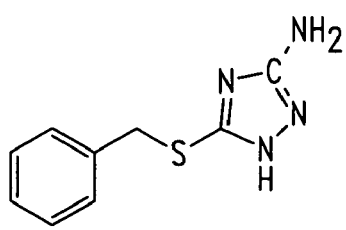
compound 191
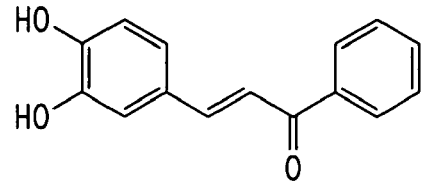
compound 192
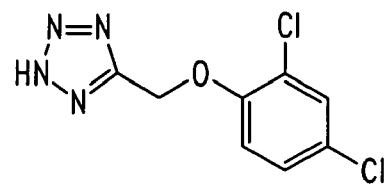
compound 193
*Fig. 15AK*

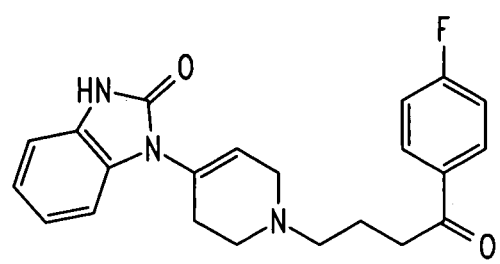
compound 194
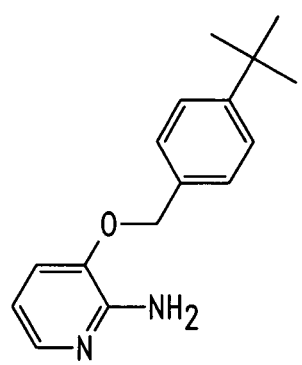
compound 195
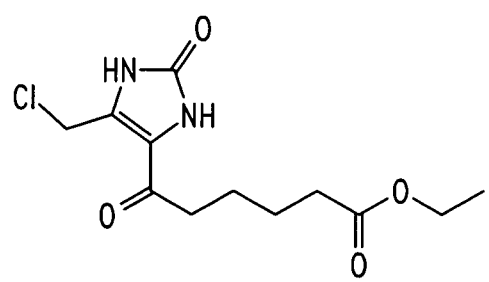
compound 196
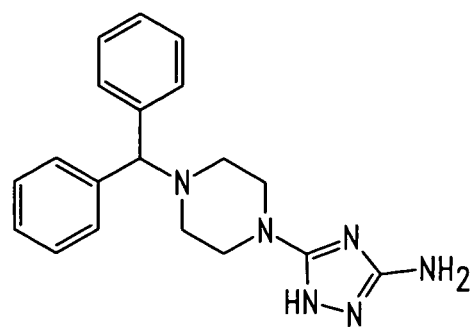
compound 197
*Fig. 15AL* compound 198 compound 199 compound 200 compound 201

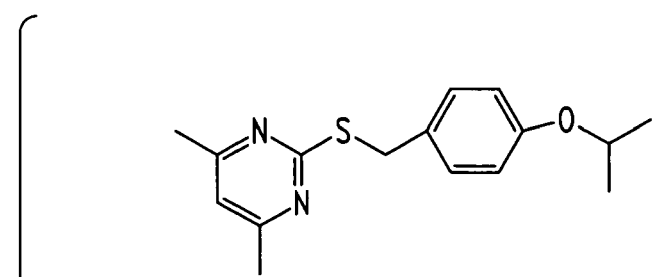
compound 202
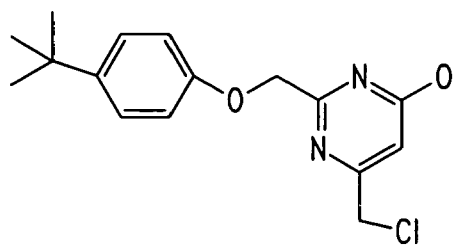
compound 203
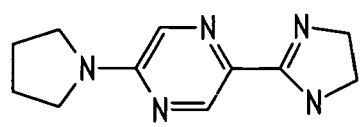
compound 204
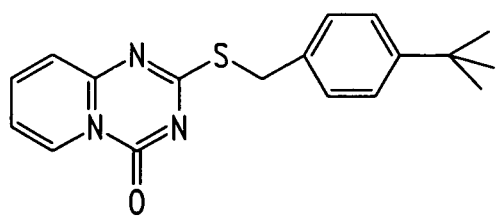
compound 205
*Fig. 15AN*

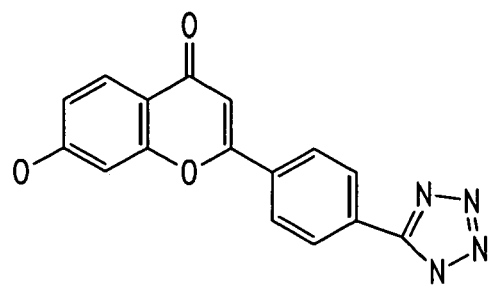
compound 206
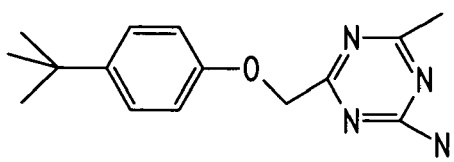
compound 207
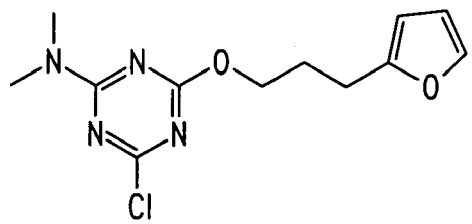
compound 208
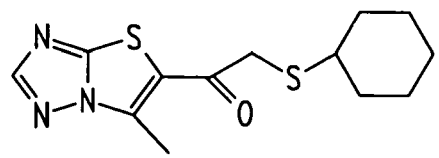
compound 209
*Fig. 15AO*

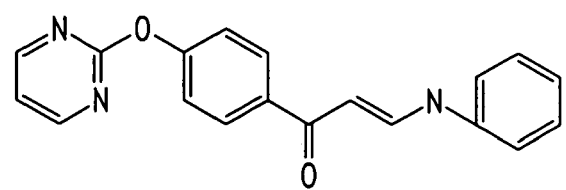
compound 210
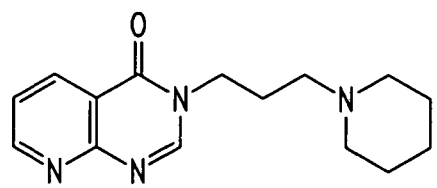
compound 211
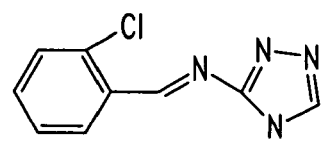
compound 212
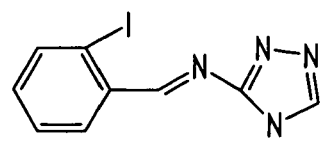
compound 213
*Fig. 15AP*

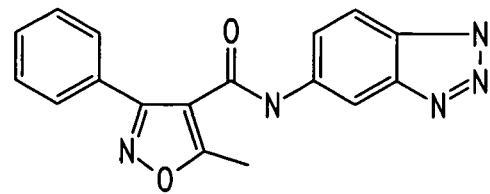
compound 214
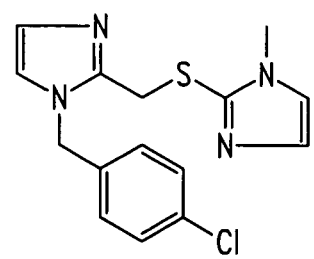
compound 215
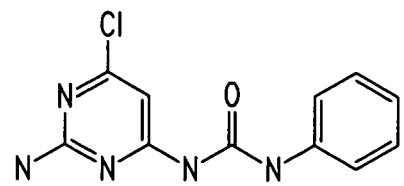
compound 216
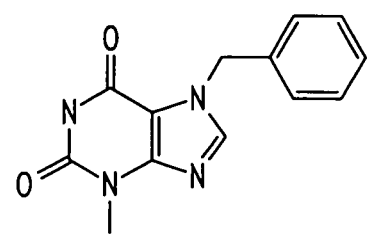
compound 217
Fig. 15AQ compound 218 compound 219 compound 220 compound 221

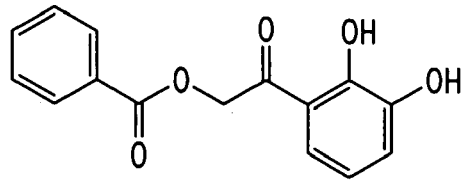
compound 222
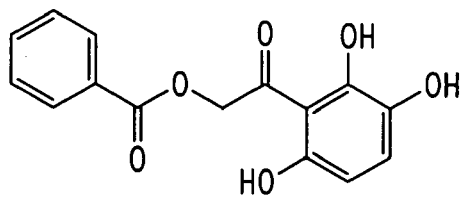
compound 223
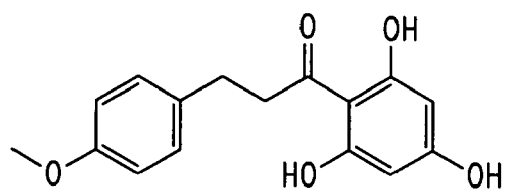
compound 224
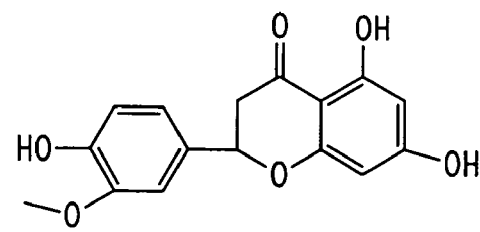
compound 225
*Fig. 15AS*

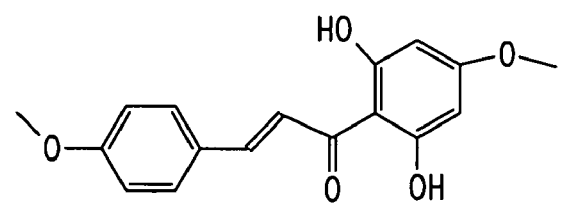
compound 226
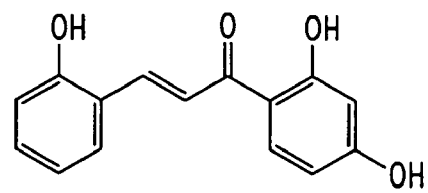
compound 227
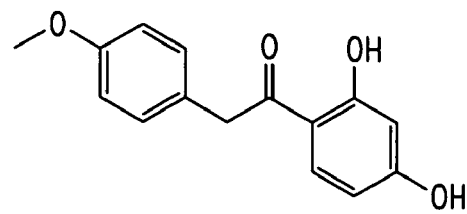
compound 228
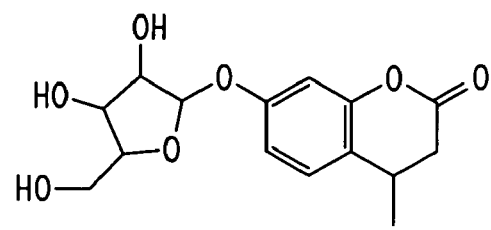
compound 229
*Fig. 15AT*

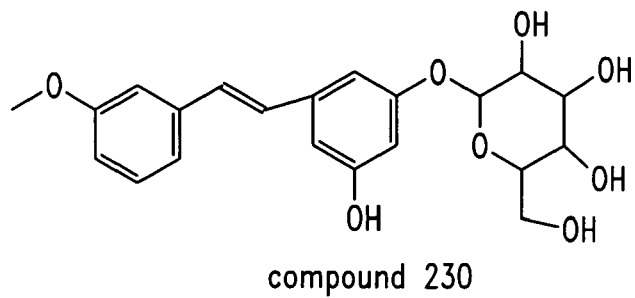
compound 230
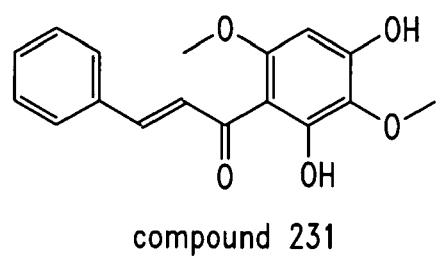
compound 231
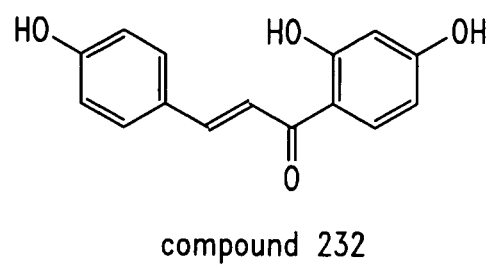
compound 232
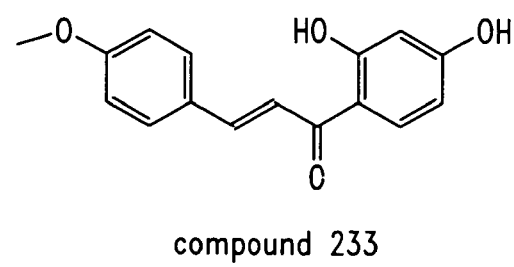
compound 233
Fig. 15AU

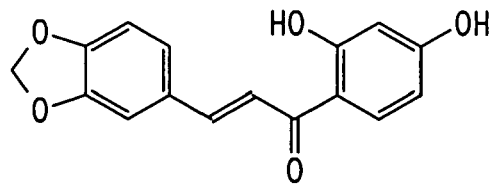
compound 234
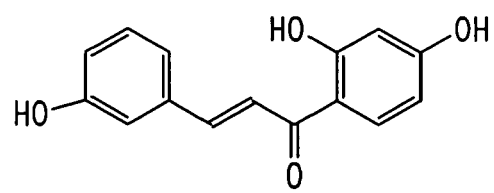
compound 235
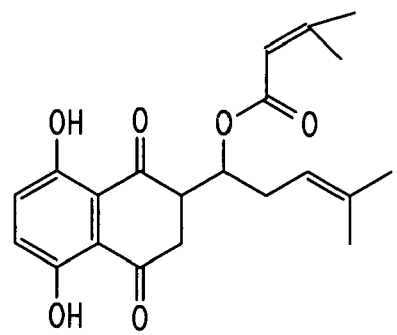
compound 236
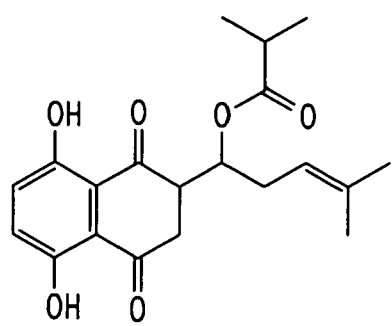
compound 237
*Fig. 15AV*

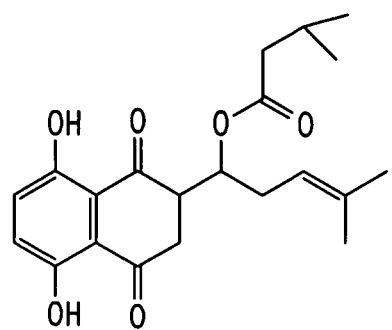
compound 238
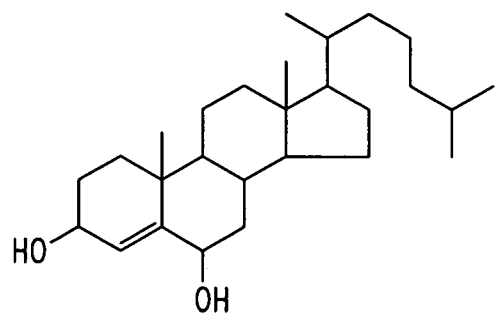
compound 239
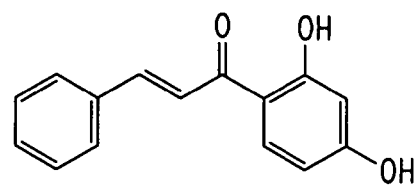
compound 240
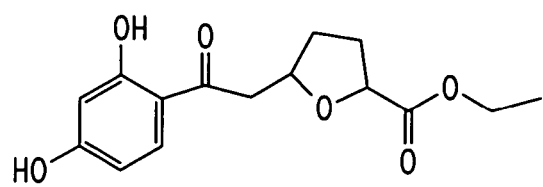
compound 241
*Fig. 15AW*

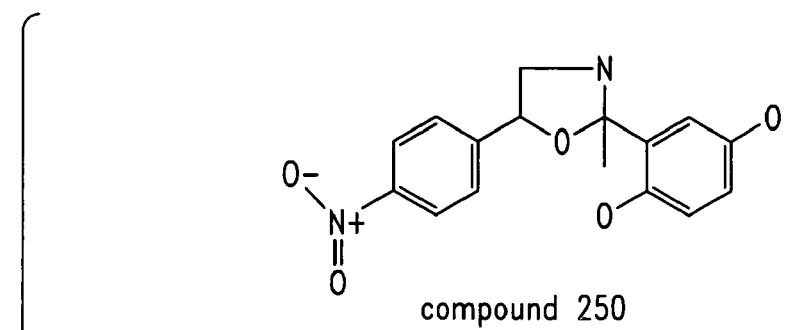
compound 250
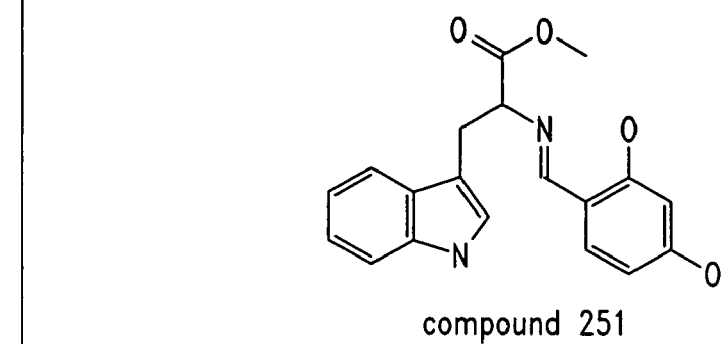
compound 251
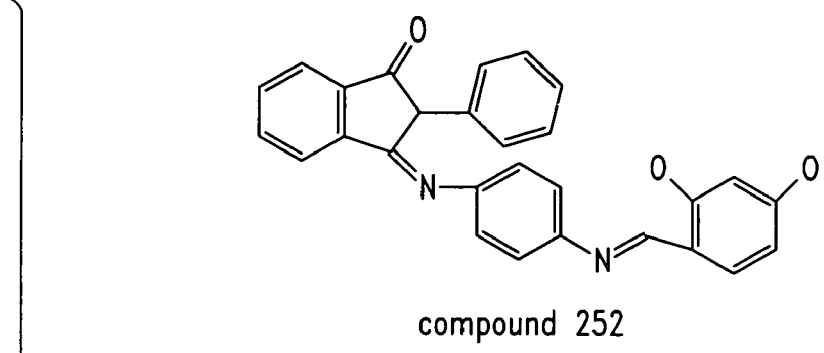
compound 252
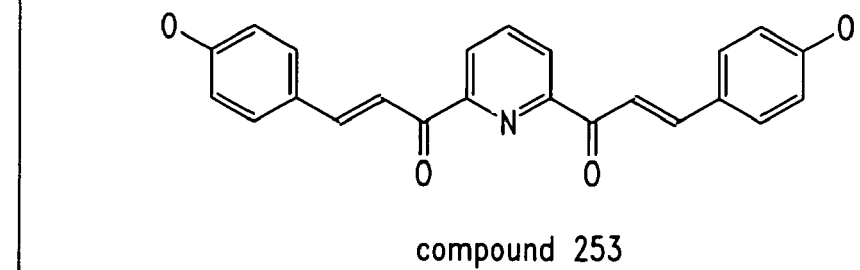
compound 253
*Fig. 15AZ*

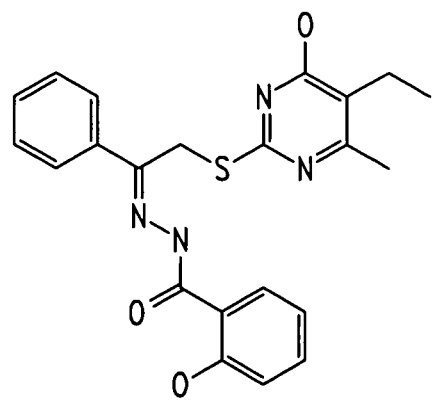
compound 254
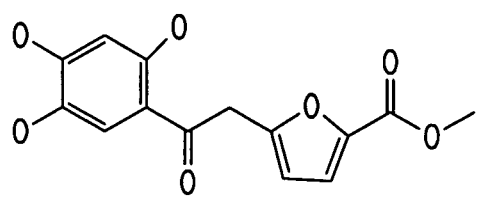
compound 255
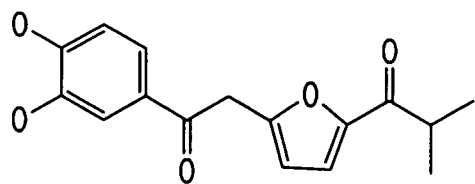
compound 256
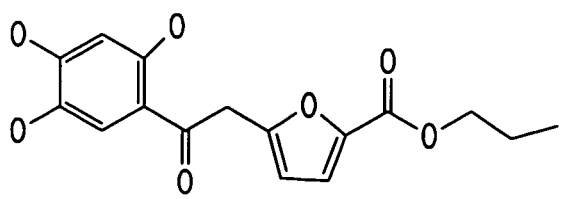
compound 257
*Fig. 15BA*

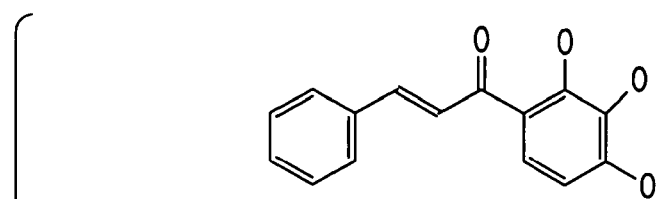
compound 258
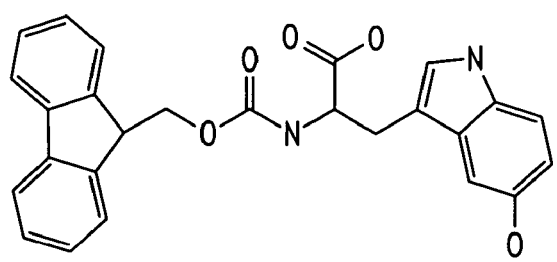
compound 259
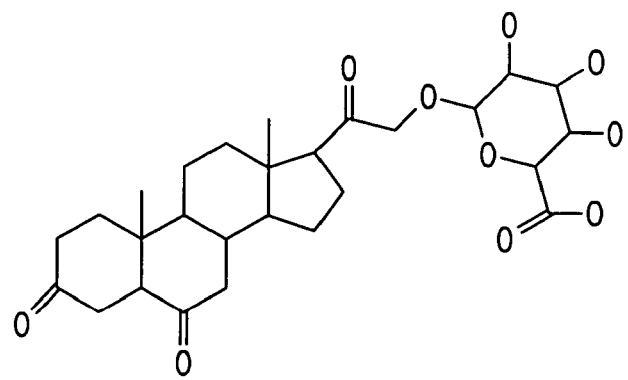
compound 260
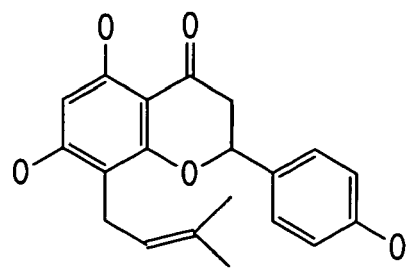
compound 261
*Fig. 15BB* compound 262 compound 263 compound 264 compound 265

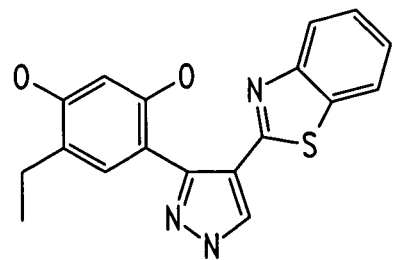
compound 266
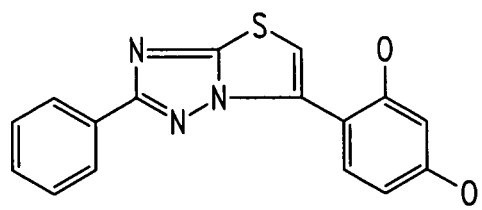
compound 267
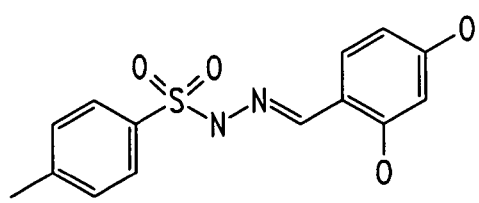
compound 268
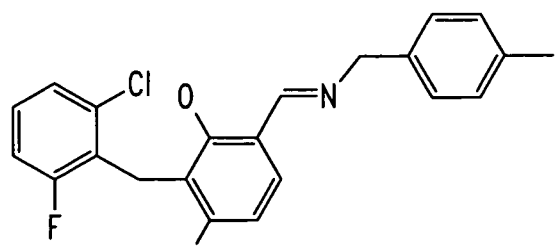
compound 269
*Fig. 15BD*

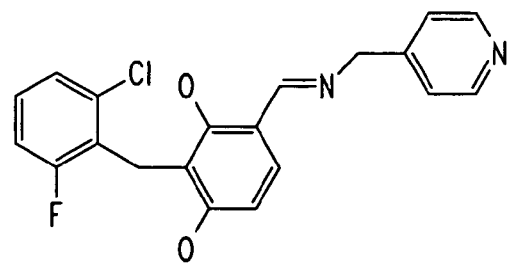
compound 270
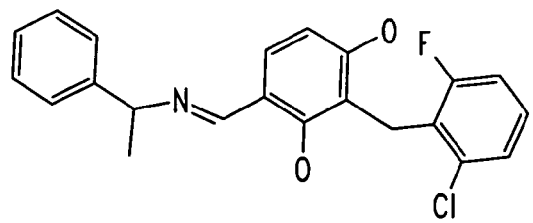
compound 271
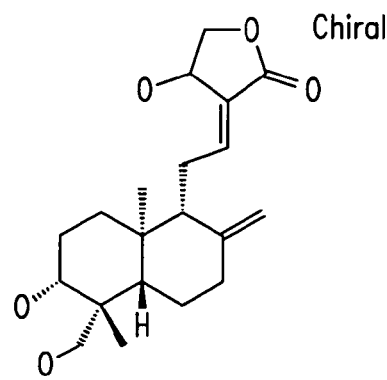
compound 272
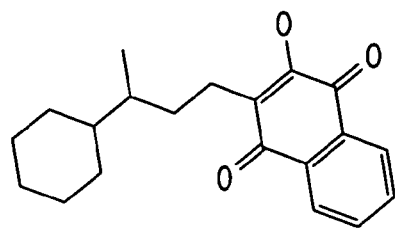
compound 273
*Fig. 15BE* compound 279 compound 280 compound 281 compound 282

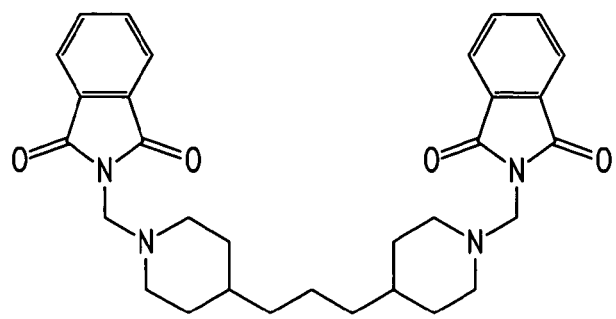
Compound 283
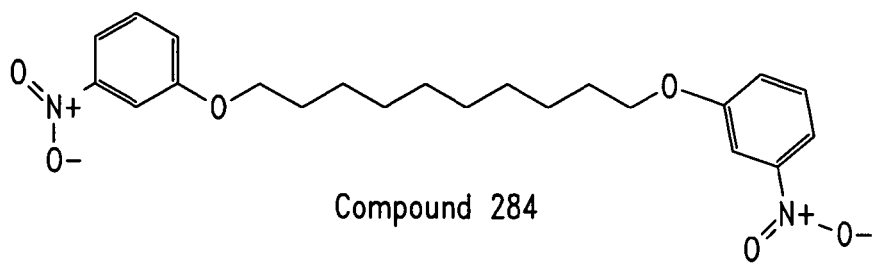
Compound 284
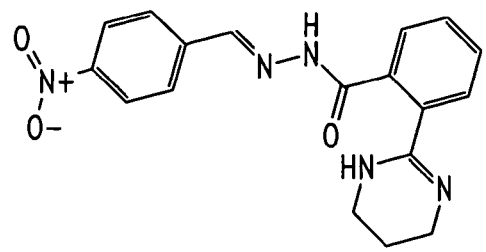
Compound 285
Fig. 17A Compound 286

Compound 287

Compound 288

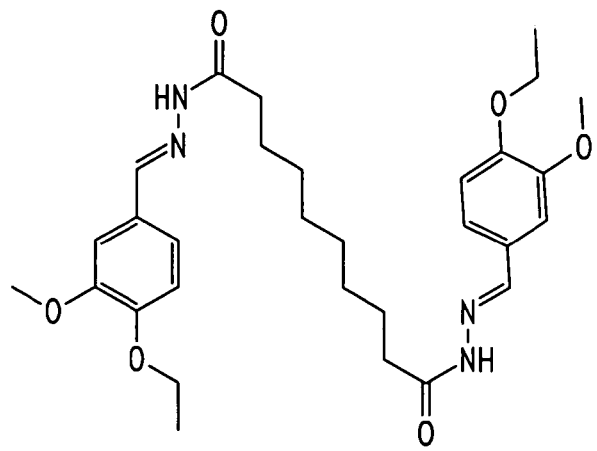
Compound 289
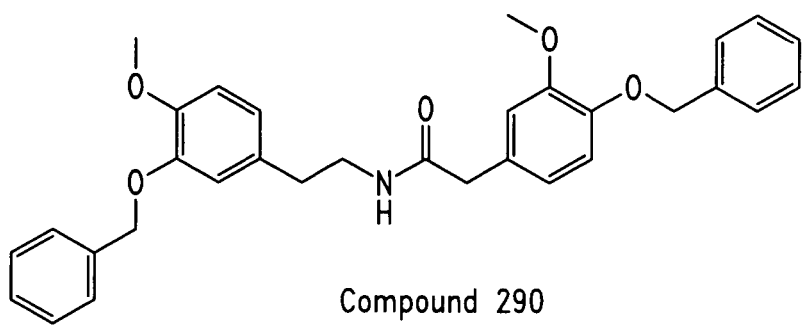
Compound 290
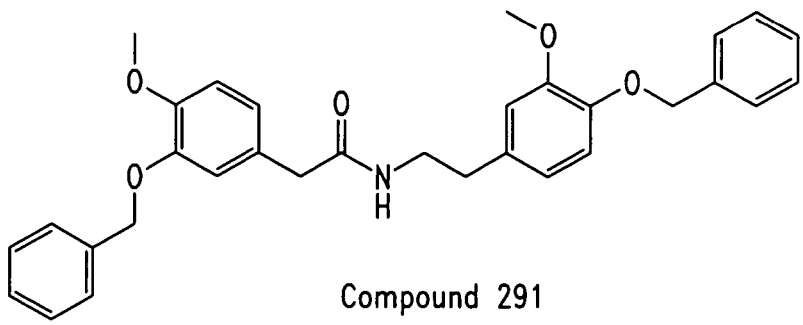
Compound 291
*Fig. 17C*

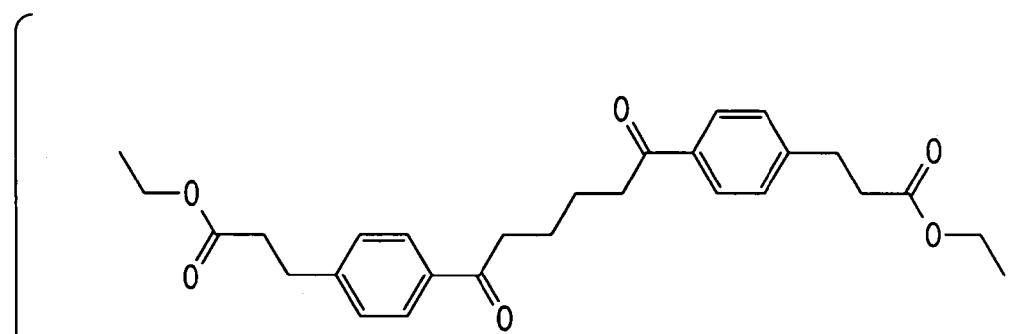
Compound 292
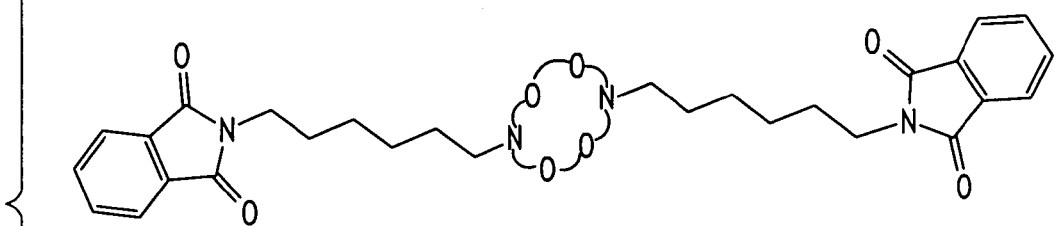
Compound 293
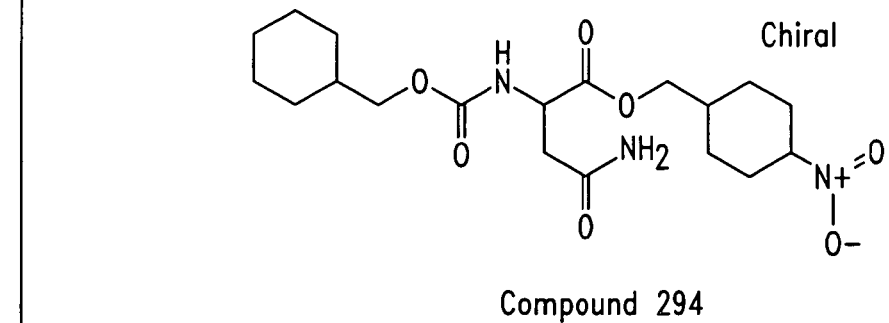
Compound 294
*Fig. 17D*

Compound 295

Compound 296

Compound 297

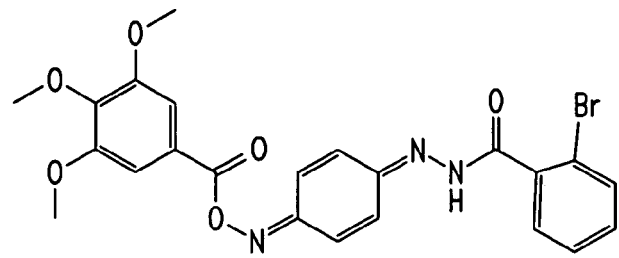
Compound 298
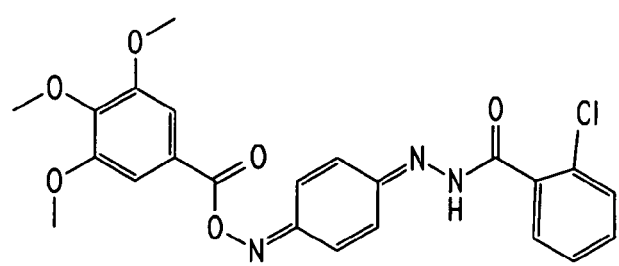
Compound 299
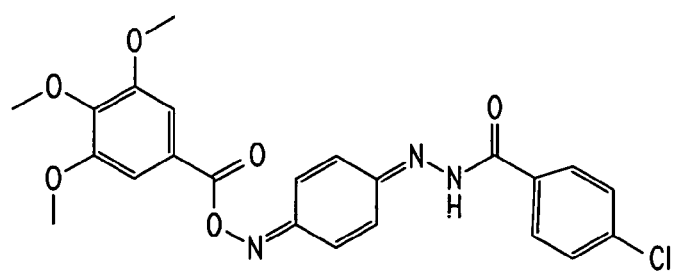
Compound 300
*Fig. 17F*

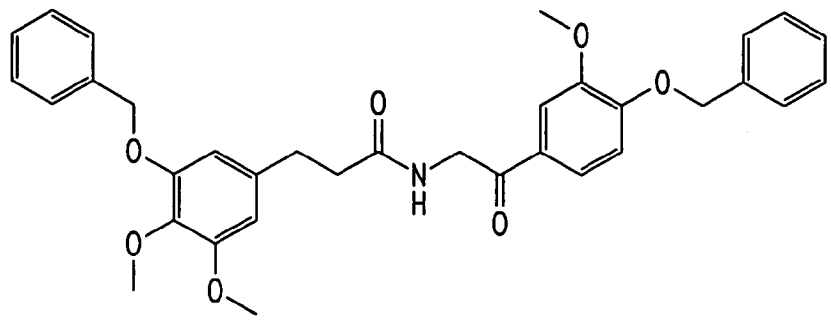
Compound 301
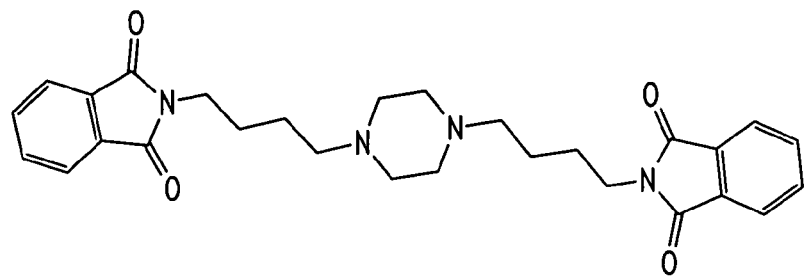
Compound 302
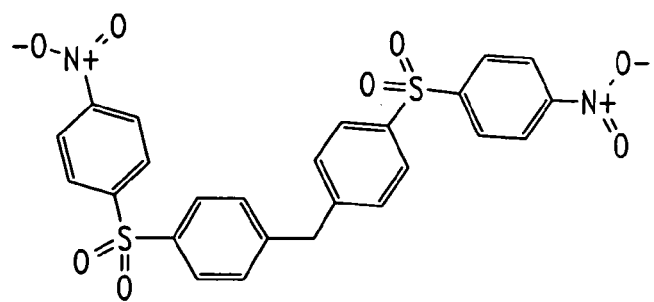
Compound 303
*Fig. 17G*

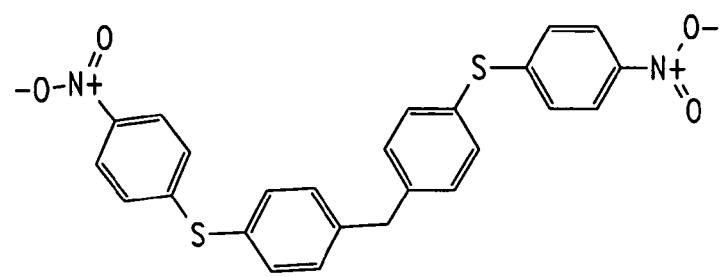
Compound 304
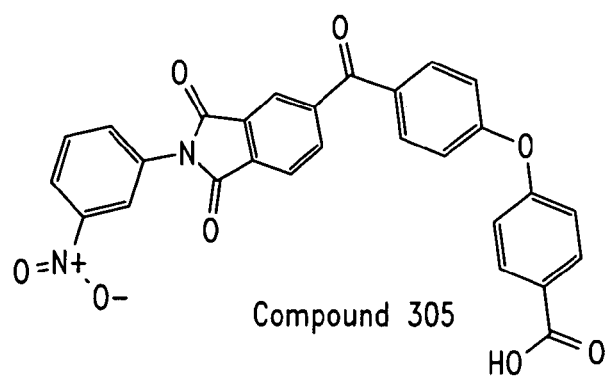
Compound 305
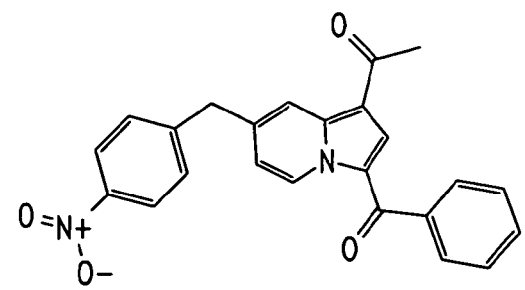
Compound 306
Fig. 17H Compound 307

Compound 308

Compound 309

Compound 310

Compound 311

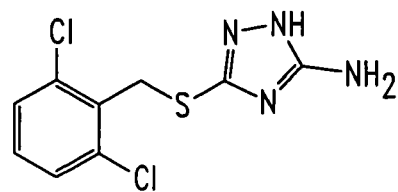
Compound 312
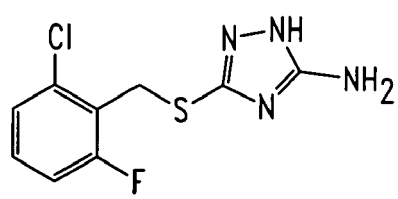
Compound 313
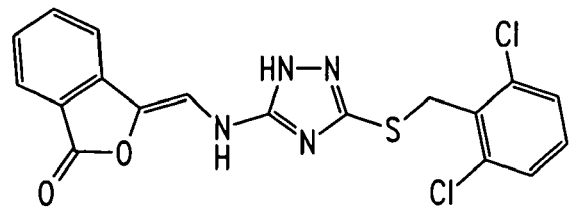
Compound 314
Fig. 18A

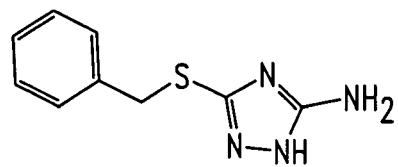
Compound 315
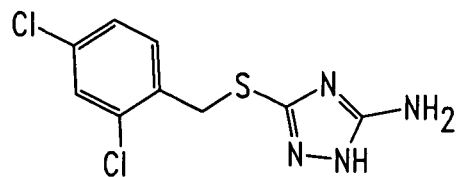
Compound 316
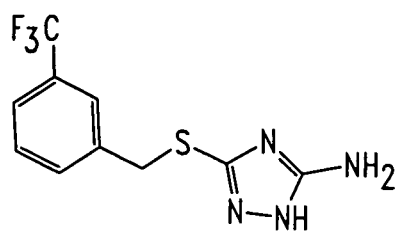
Compound 317
*Fig. 18B*

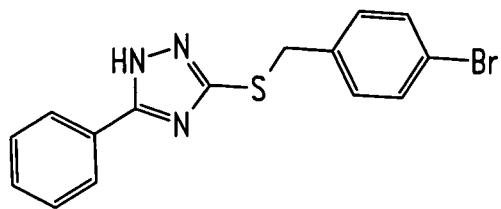
Compound 318
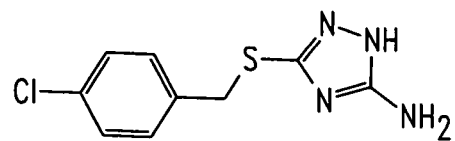
Compound 319
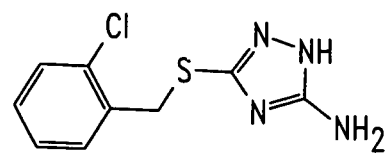
Compound 320
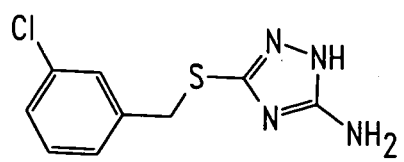
Compound 321
*Fig. 18C*

Compound 322

Compound 323

Compound 324

Compound 325

Compound 326

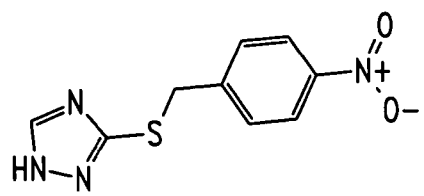
Compound 327
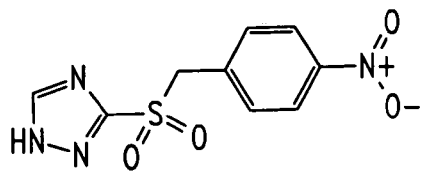
Compound 328
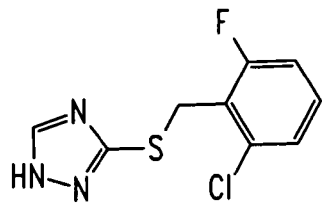
Compound 329
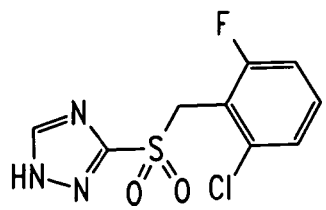
Compound 330
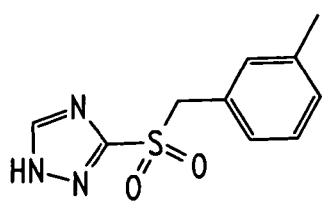
Compound 331
*Fig. 18E*

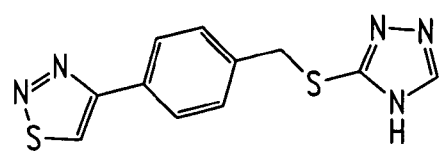
Compound 332
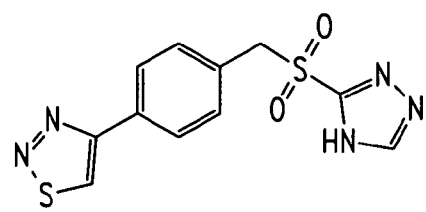
Compound 333
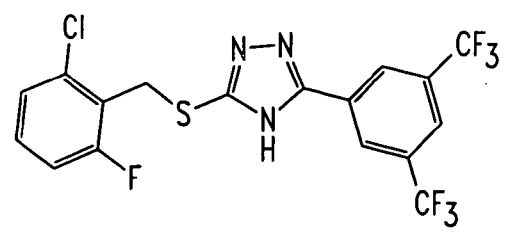
Compound 334
*Fig. 19A*

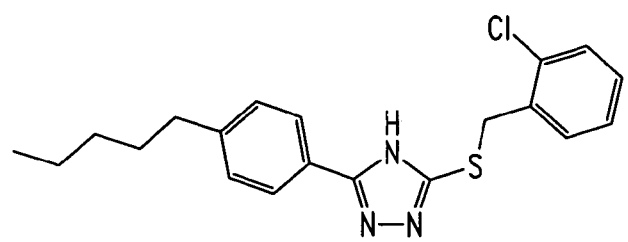
Compound 335
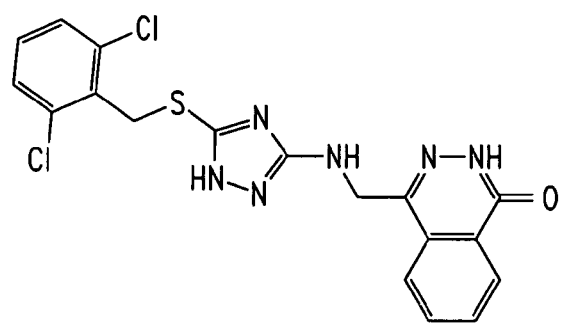
Compound 336
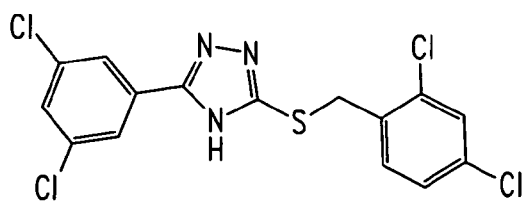
Compound 337
Fig. 19B

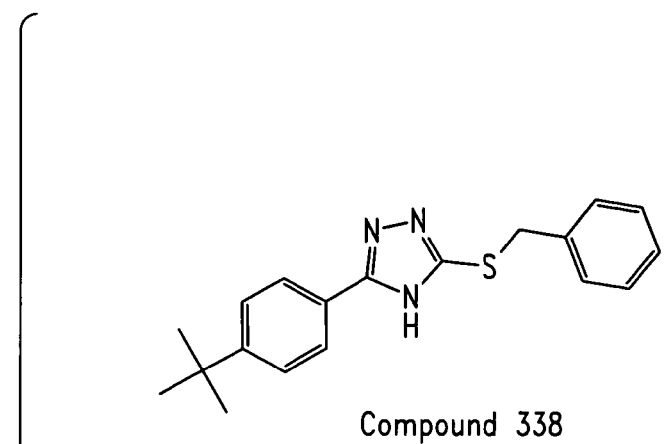
Compound 338
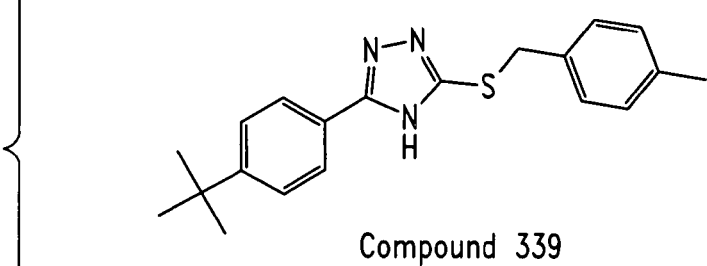
Compound 339
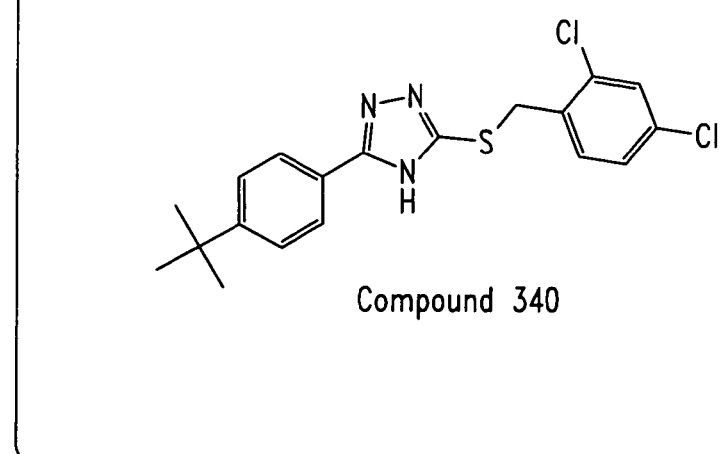
Compound 340
*Fig. 19C*

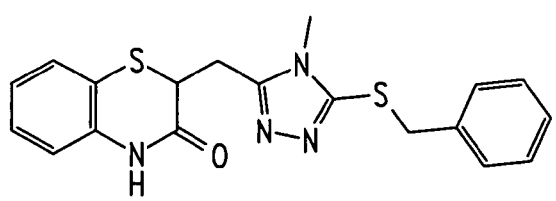
Compound 341
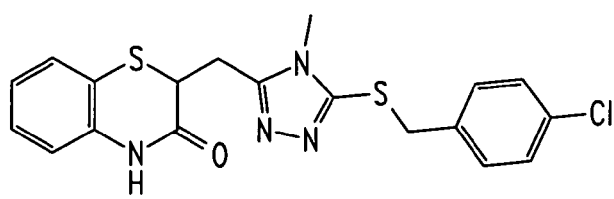
Compound 342
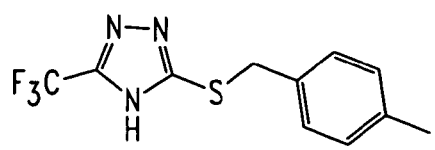
Compound 343
*Fig. 19D*

Compound 344

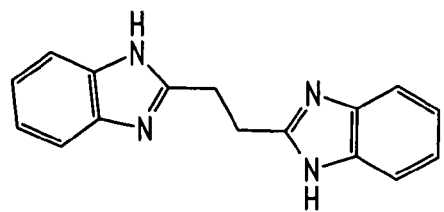
Compound 345
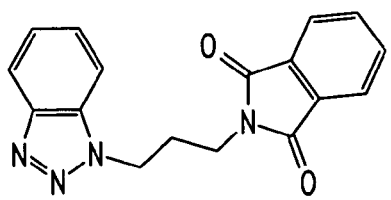
Compound 346
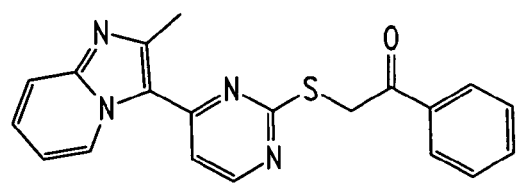
Compound 347
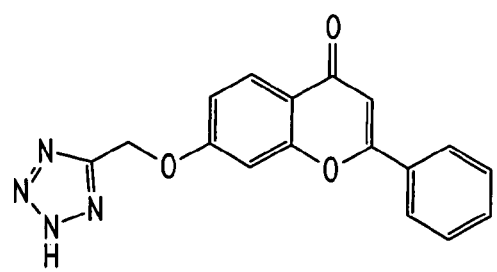
Compound 348
*Fig. 21A*

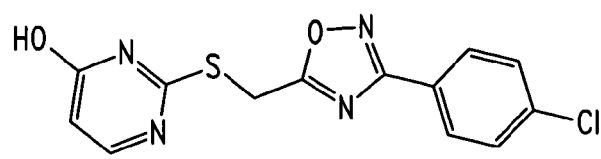
Compound 349
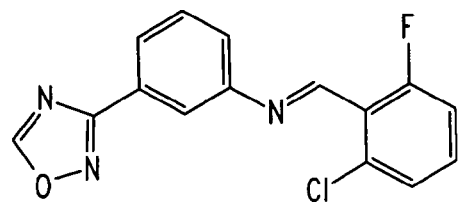
Compound 350
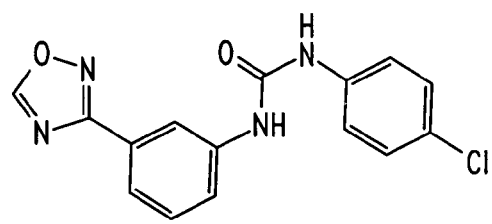
Compound 351
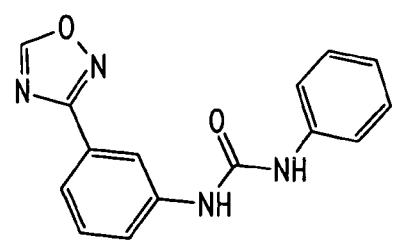
Compound 352
*Fig. 21B*

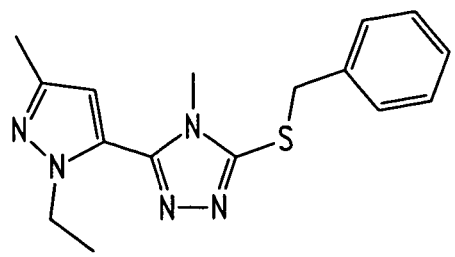
Compound 353
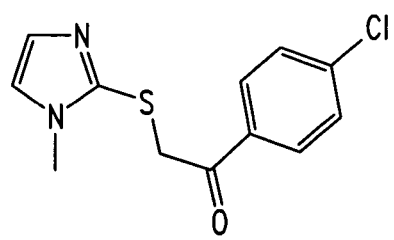
Compound 354
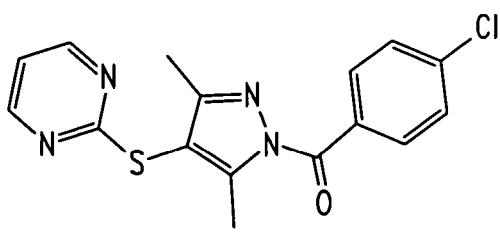
Compound 355
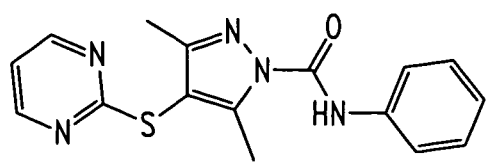
Compound 356
*Fig. 21C*

Compound 357

Compound 358

Compound 359

Compound 360

Compound 361

Compound 362

Compound 363

Compound 364

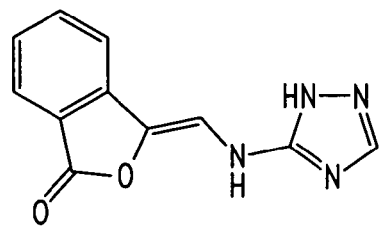
Compound 365
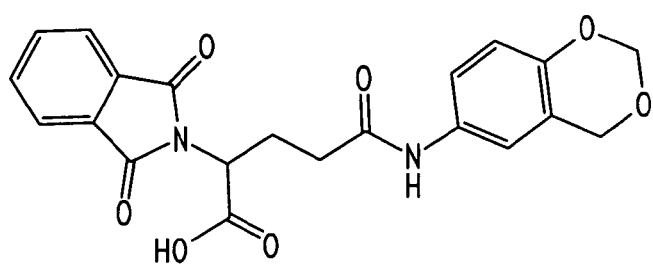
Compound 366
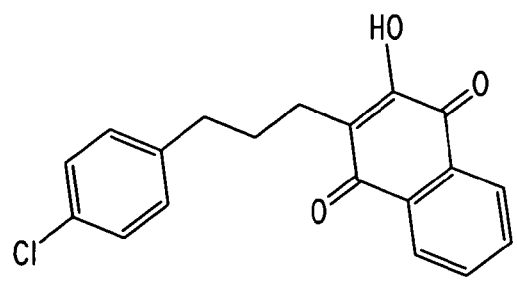
Compound 367
*Fig. 21F*

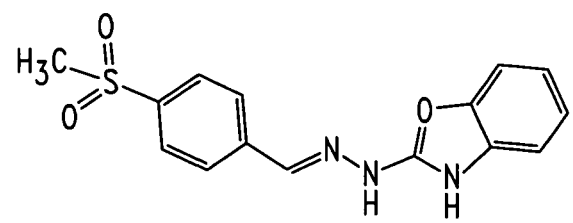
Compound 368
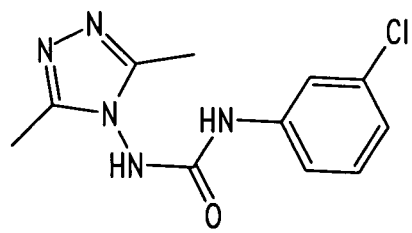
Compound 369
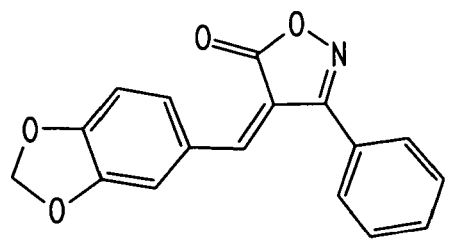
Compound 370
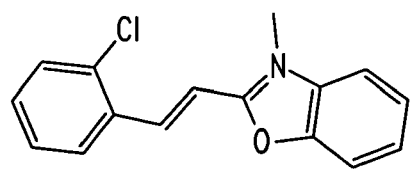
Compound 371
*Fig. 21G*

Compound 372

Compound 373

Compound 374

Compound 375

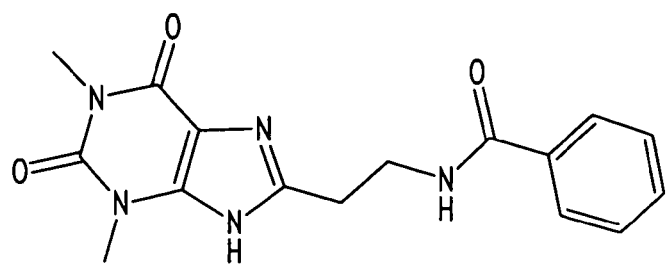
Compound 376
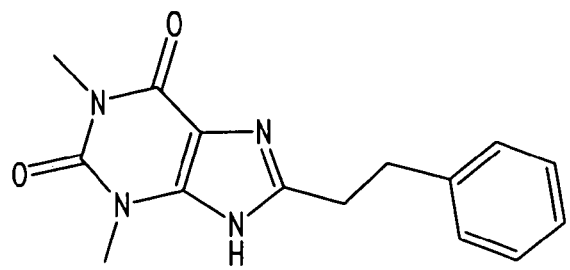
Compound 377
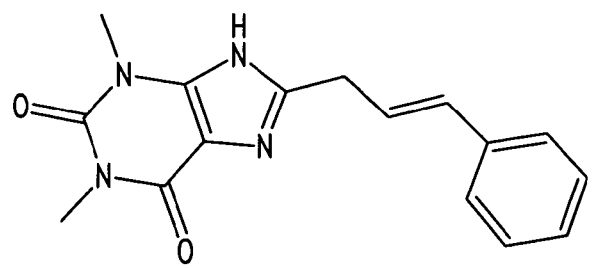
Compound 378
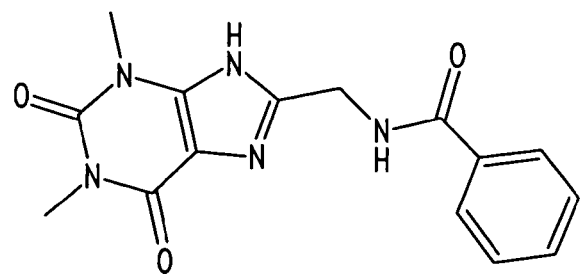
Compound 379
*Fig. 211*

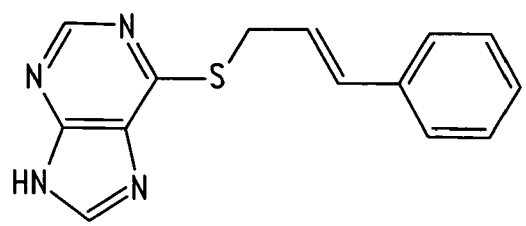
Compound 380
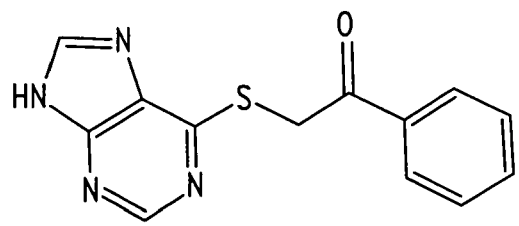
Compound 381
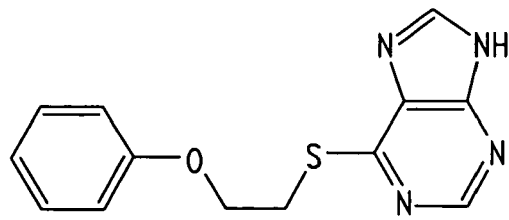
Compound 382
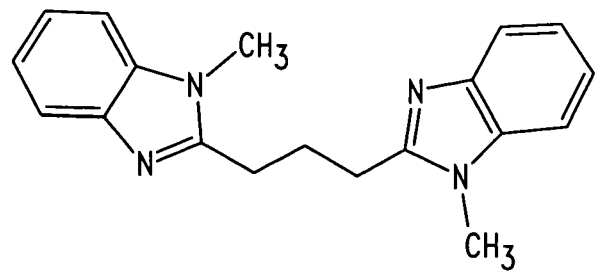
Compound 383
*Fig. 21J*

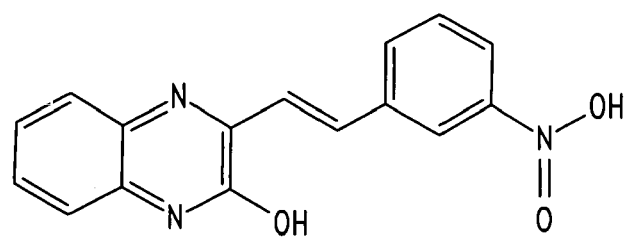
Compound 384
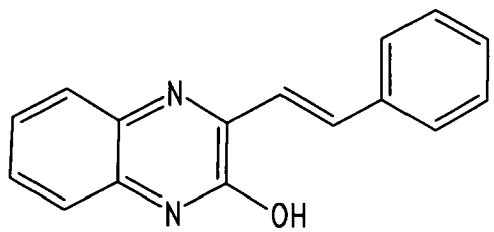
Compound 385
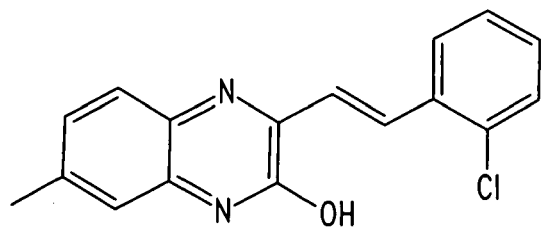
Compound 386
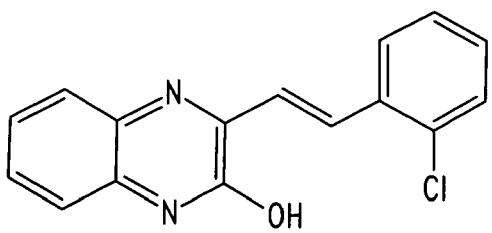
Compound 387
*Fig. 21K*

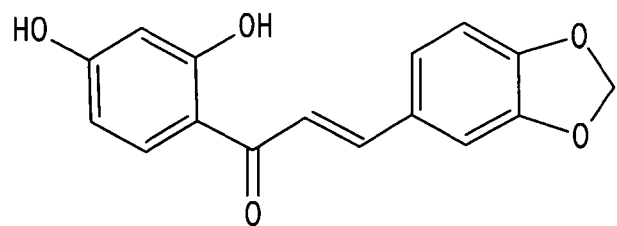
Compound 388
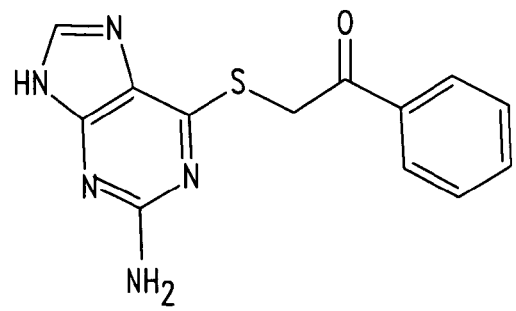
Compound 389
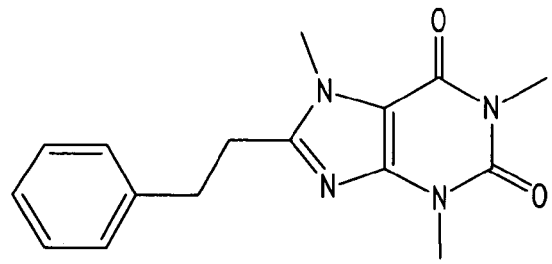
Compound 390
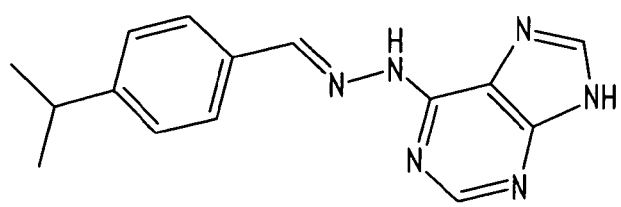
Compound 391
*Fig. 21L*

Compound 392

Compound 393

Compound 394

Compound 395

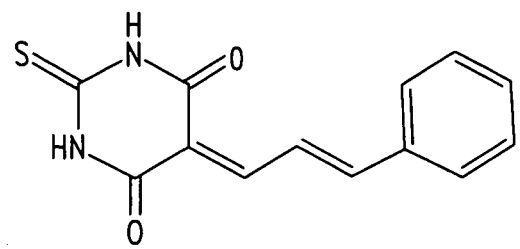
Compound 396
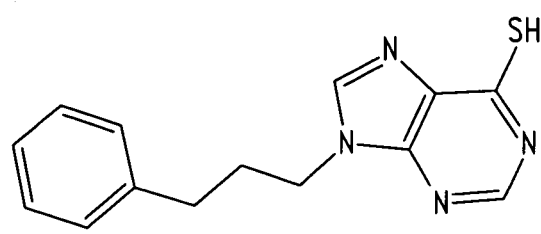
Compound 397
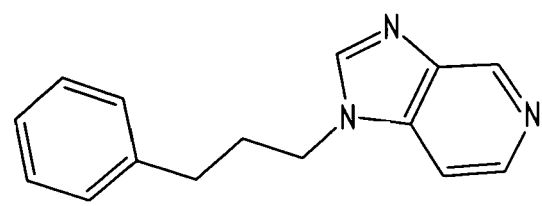
Compound 398
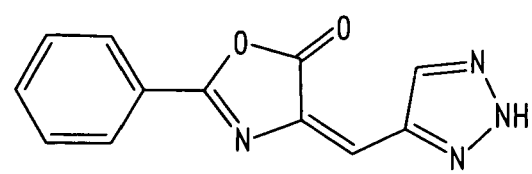
Compound 399
*Fig. 21N*

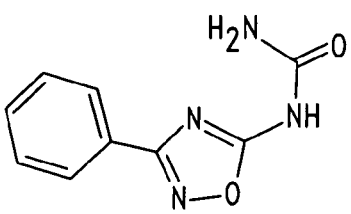
Compound 434
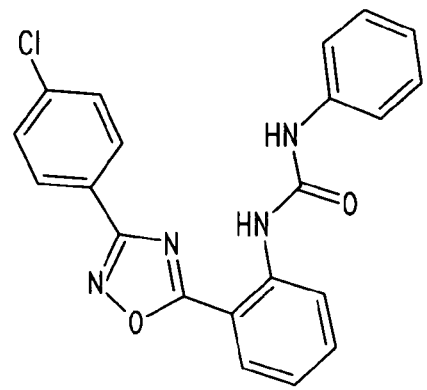
Compound 435
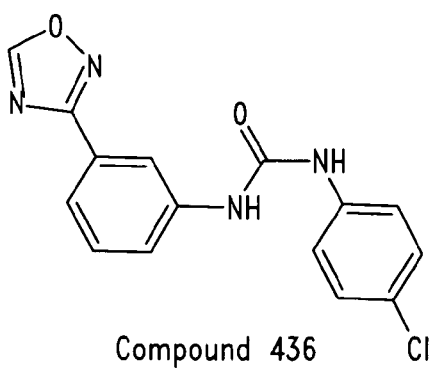
Compound 436
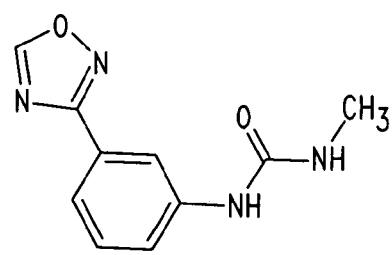
Compound 437
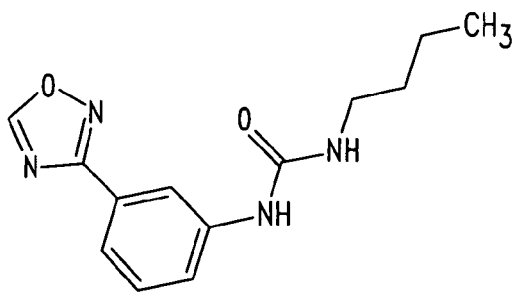
Compound 438
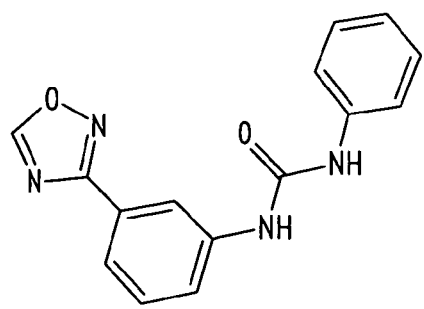
Compound 439
*Fig. 22A*

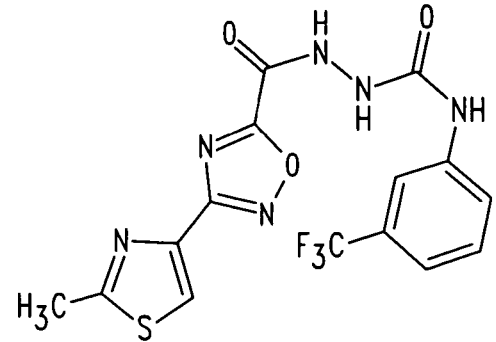
Compound 439
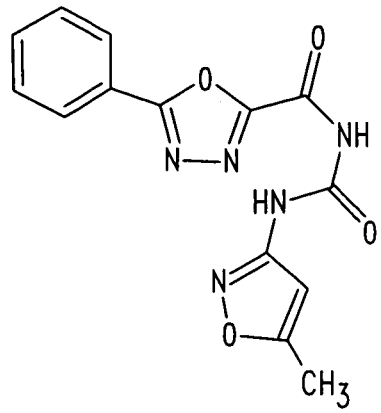
Compound 440
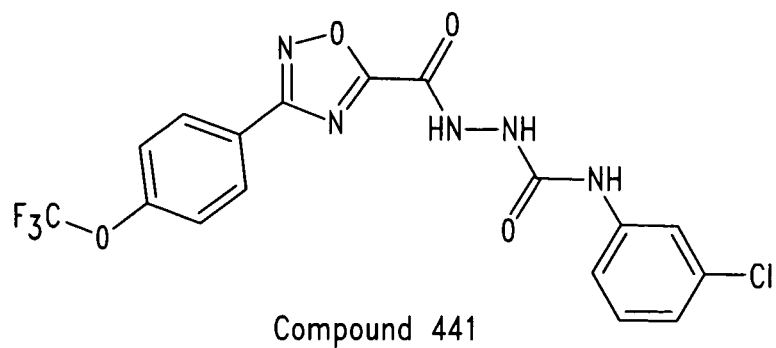
Compound 441
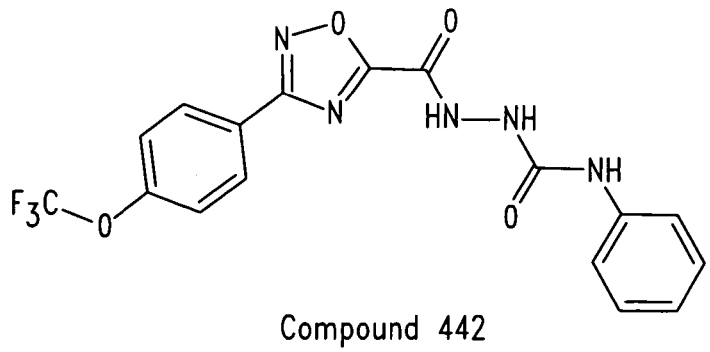
Compound 442
*Fig. 22B*

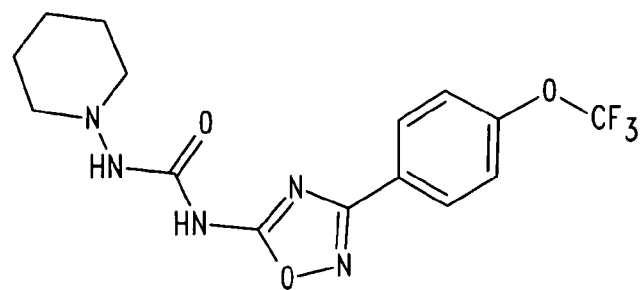
Compound 443
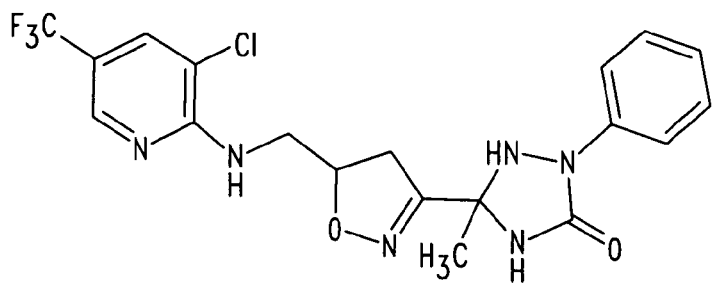
Compound 444
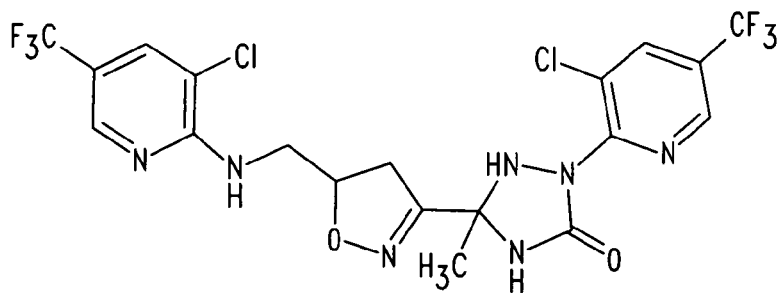
Compound 445
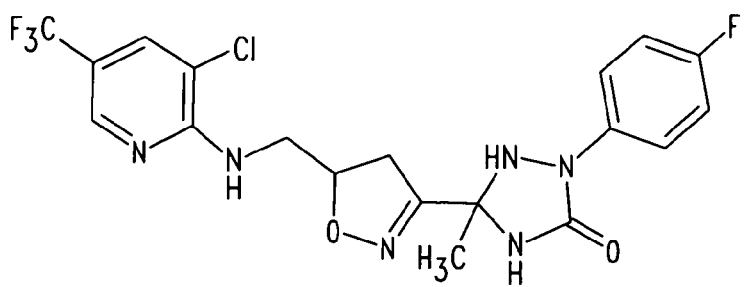
Compound 446
*Fig. 22C*

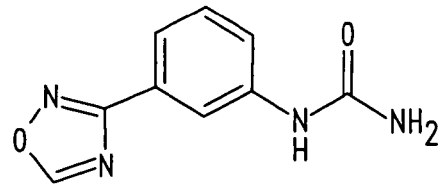
Compound 447
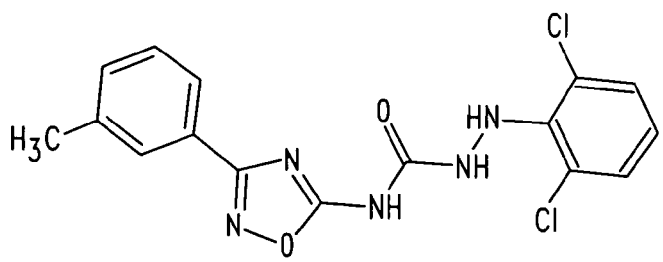
Compound 448
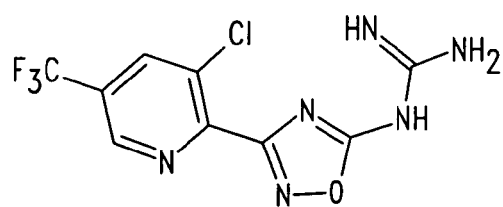
Compound 449
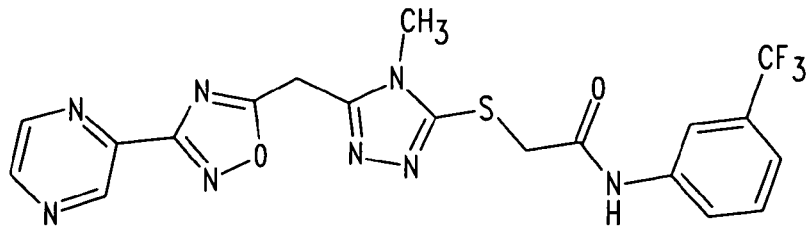
Compound 450
*Fig. 22D*

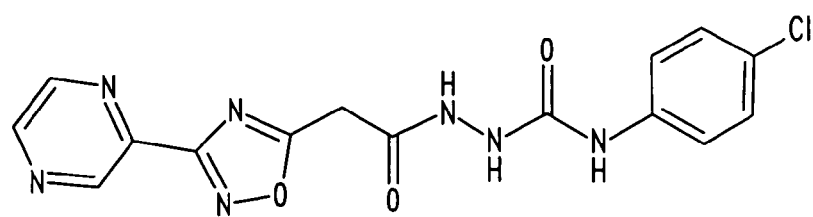
Compound 451
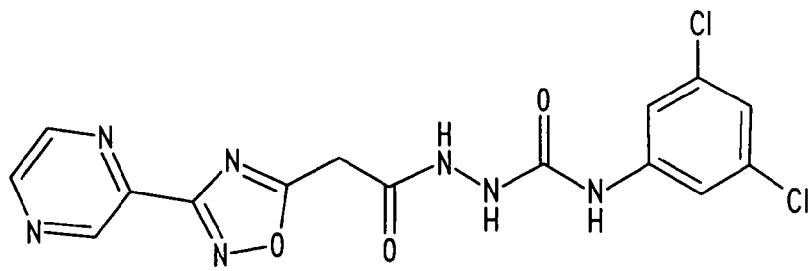
Compound 452
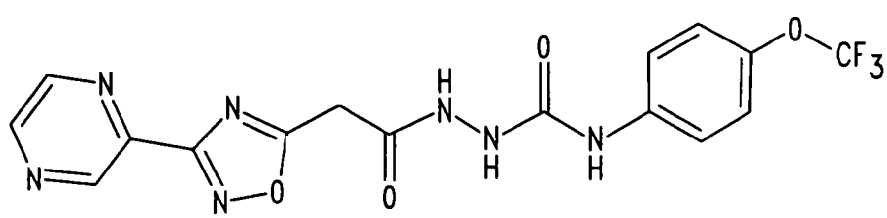
Compound 453
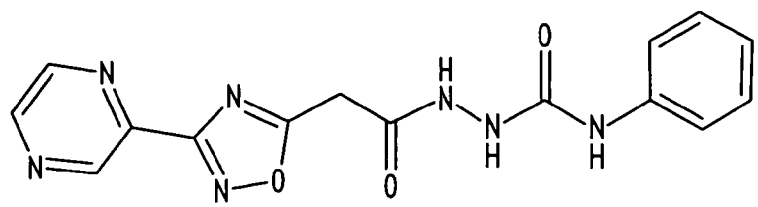
Compound 454
*Fig. 22E*

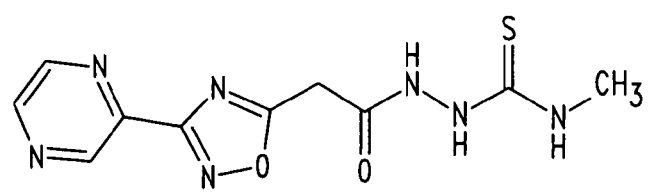
Compound 455
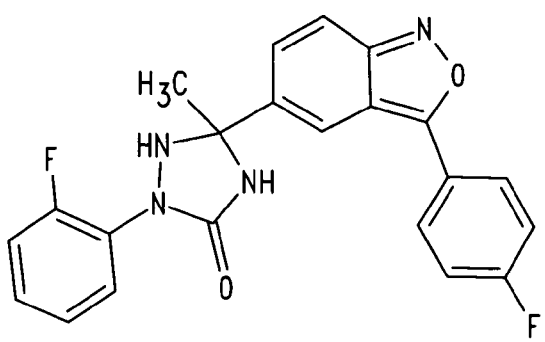
Compound 456
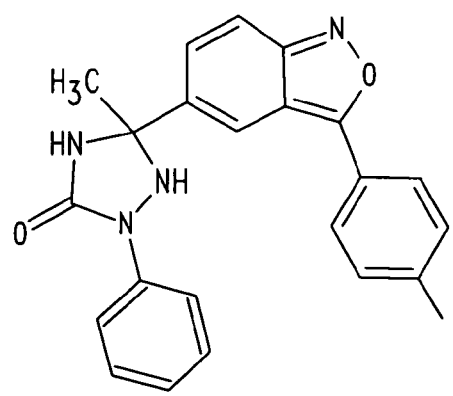
Compound 457
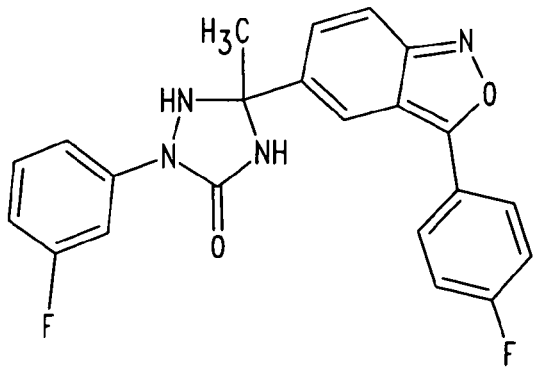
Compound 458
Fig. 22F

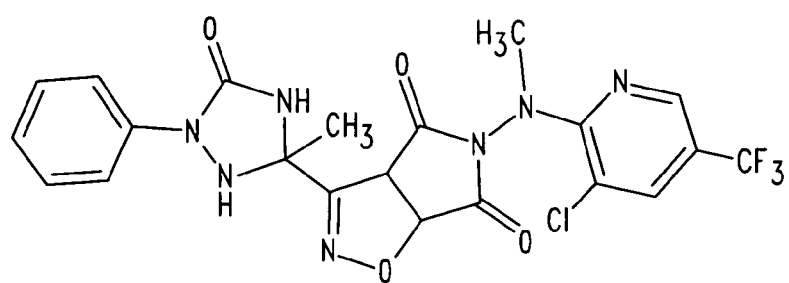
Compound 459
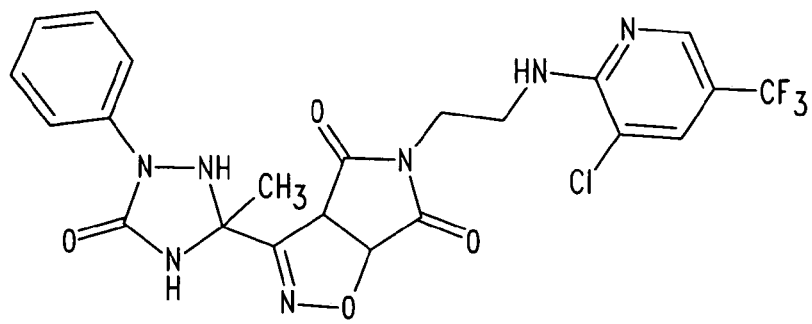
Compound 460
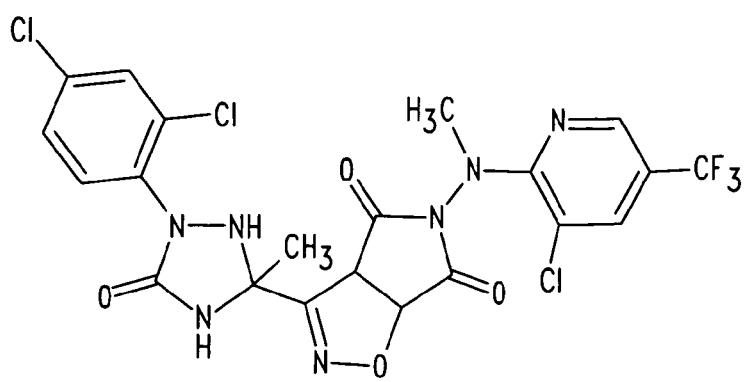
Compound 461
*Fig. 22G*

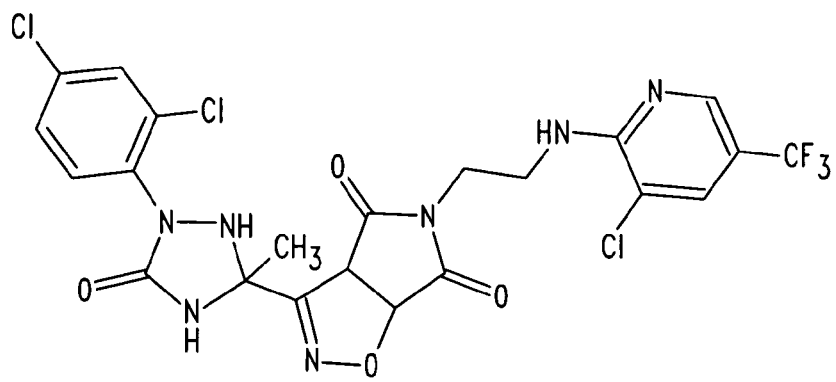
Compound 462
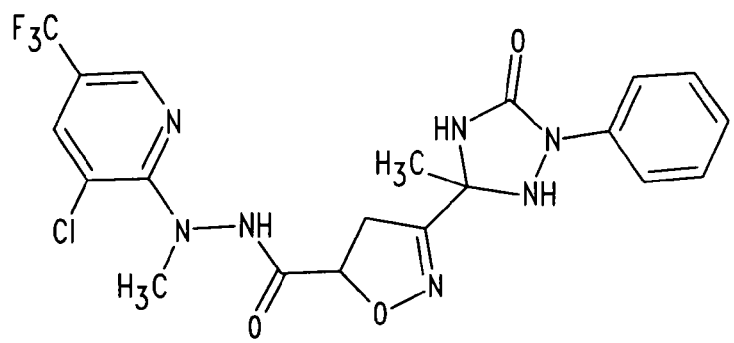
Compound 463
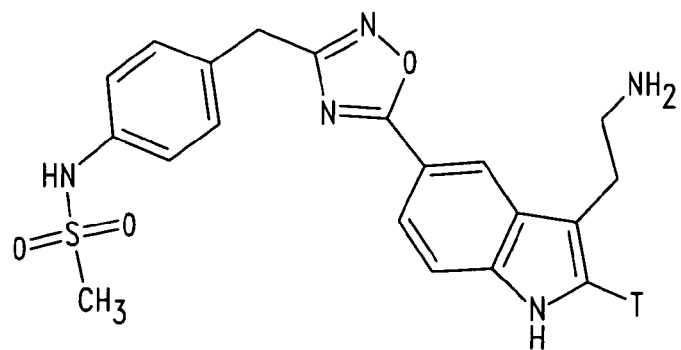
Compound 464
Fig. 22H Compound 400

Compound 401

Compound 402

Compound 403

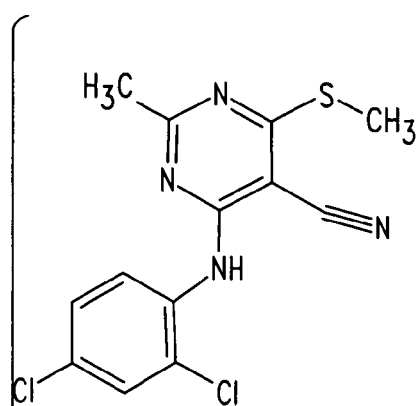
Compound 404
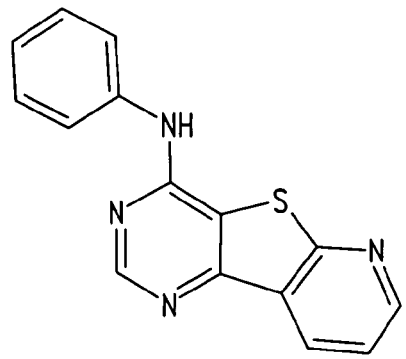
Compound 405
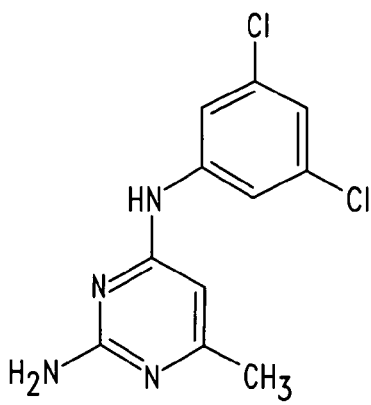
Compound 406
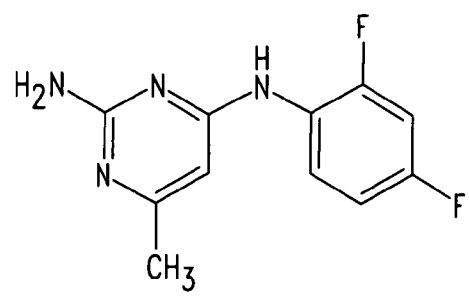
Compound 407
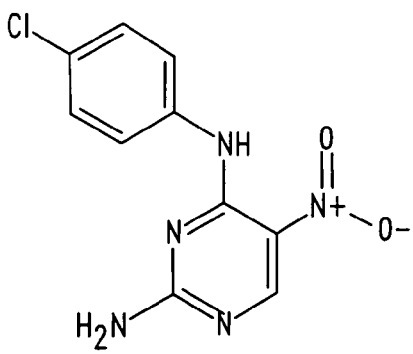
Compound 408
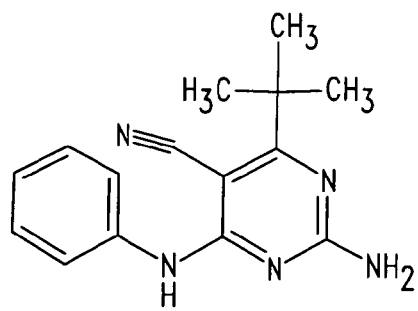
Compound 409
*Fig. 23B*

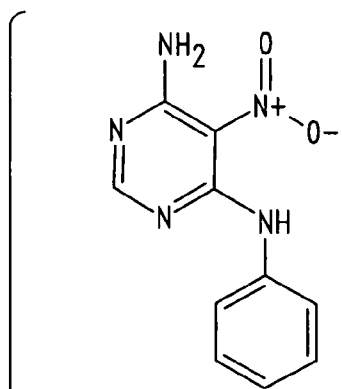
Compound 410
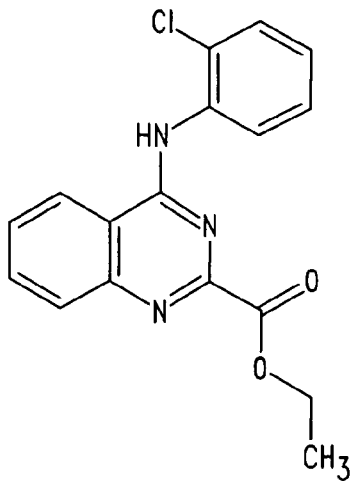
Compound 411
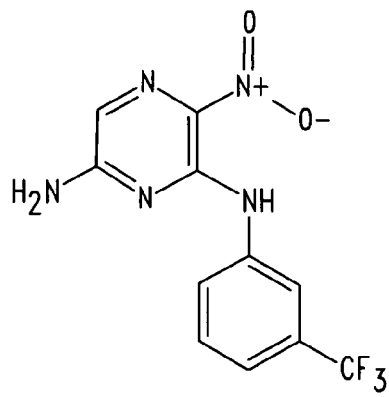
Compound 412
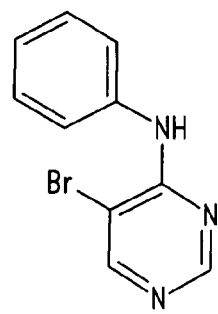
Compound 413
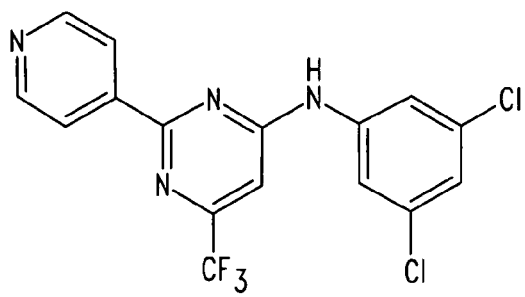
Compound 414
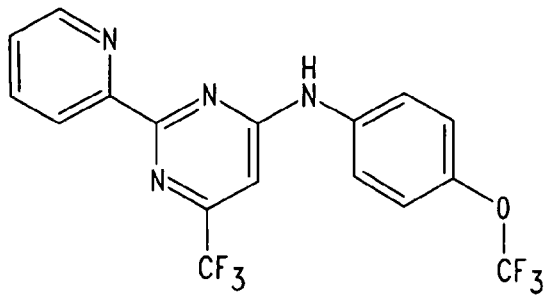
Compound 415
*Fig. 23C*

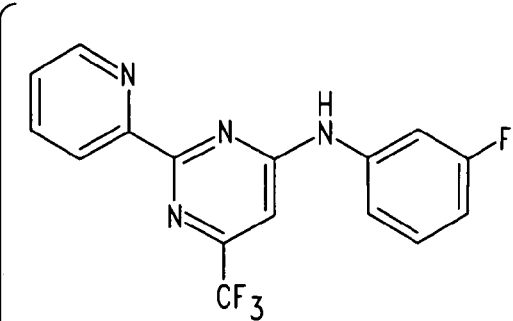
Compound 416
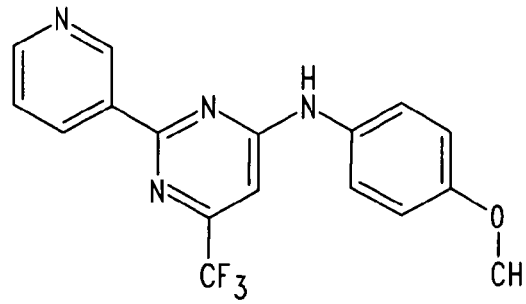
Compound 417
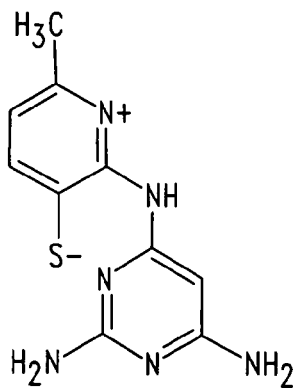
Compound 418
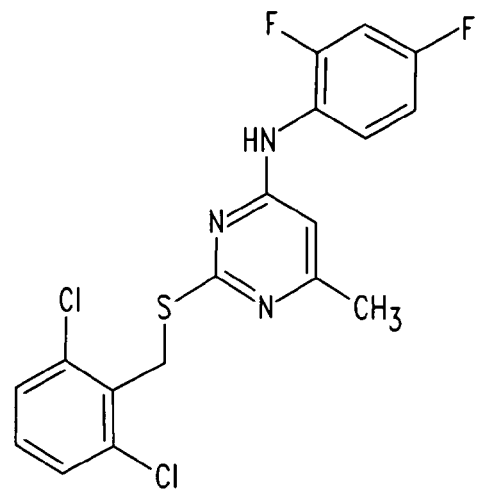
Compound 419
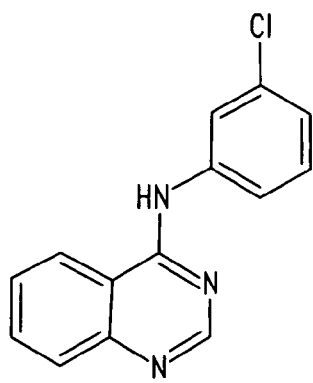
Compound 420
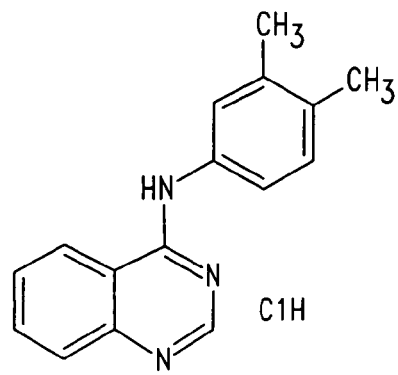
Compound 421
*Fig. 23D*

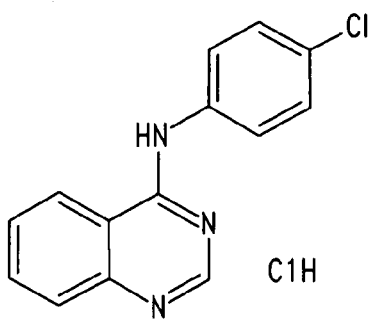
Compound 422
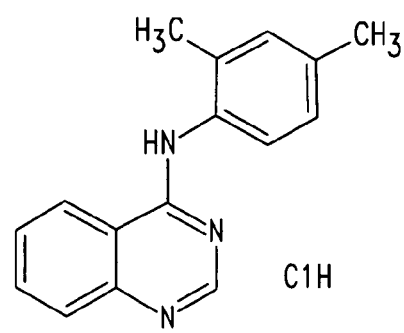
Compound 423
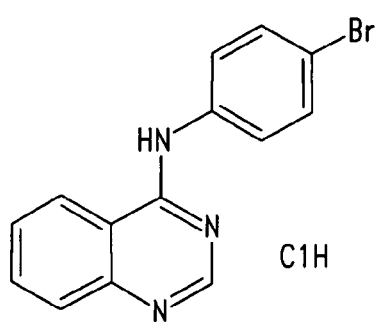
Compound 424
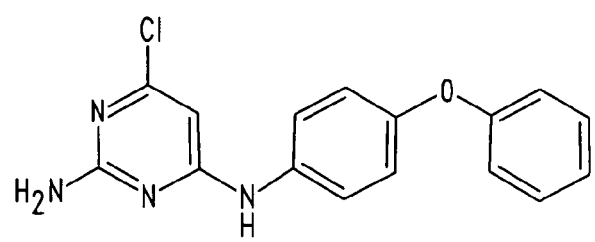
Compound 425
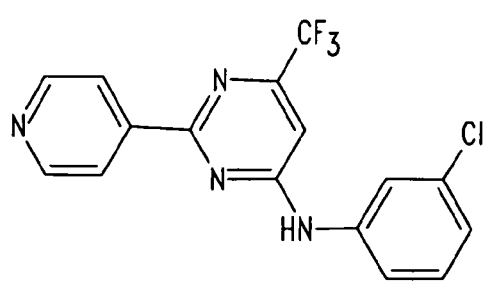
Compound 426
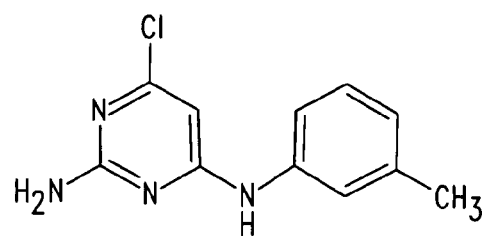
Compound 427
*Fig. 23E*

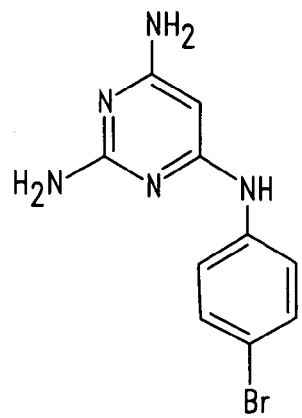
Compound 428
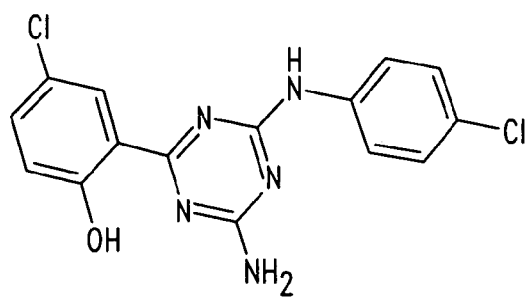
Compound 429
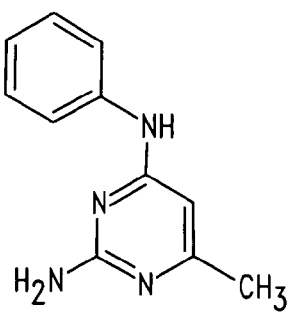
Compound 430
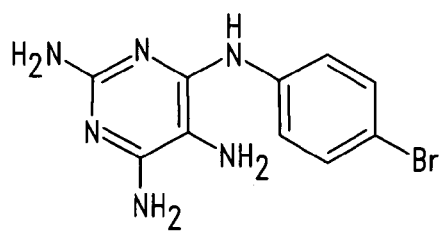
Compound 431
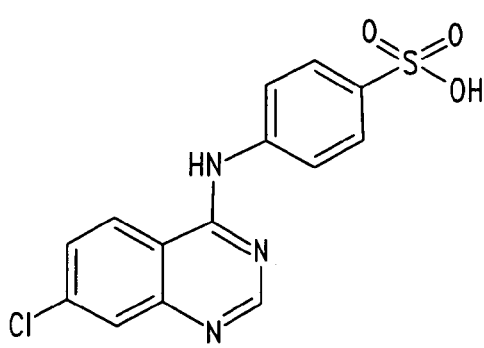
Compound 432
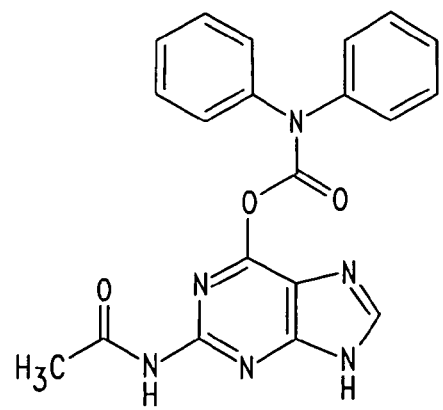
Compound 433
*Fig. 23F*

CH2COHAVC-NH2

CH2COGHAVC-NH2

CH2CONHAVC-NH2

Pharmacophore Query used in the 3D search.

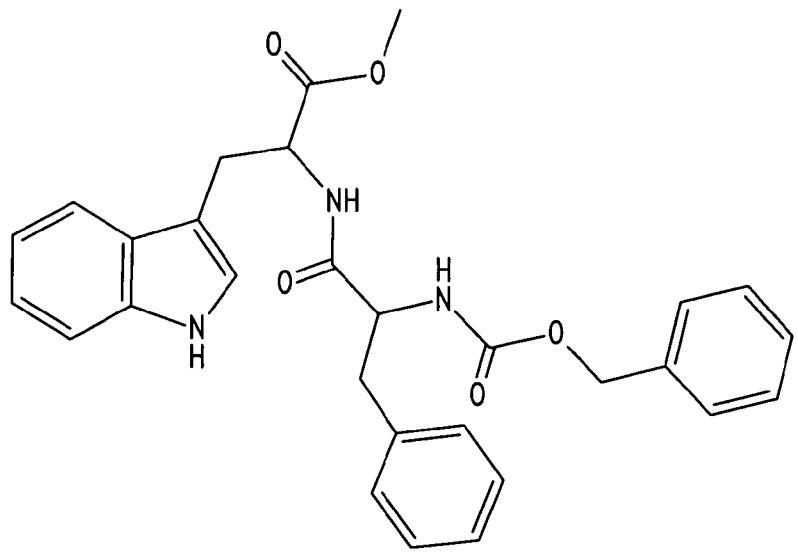
Compound 467
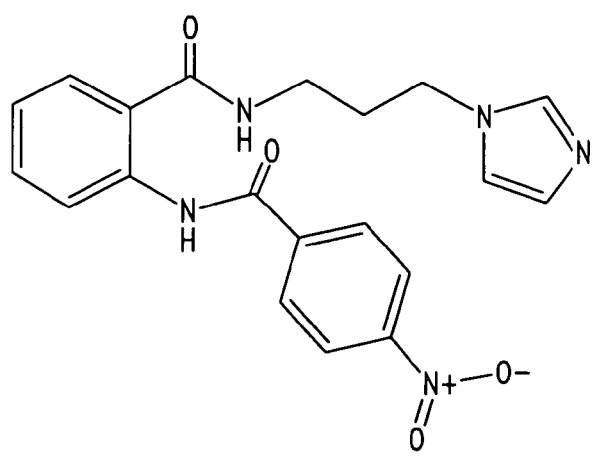
Compound 468
*Fig. 29B*

Compound 469

Compound 470

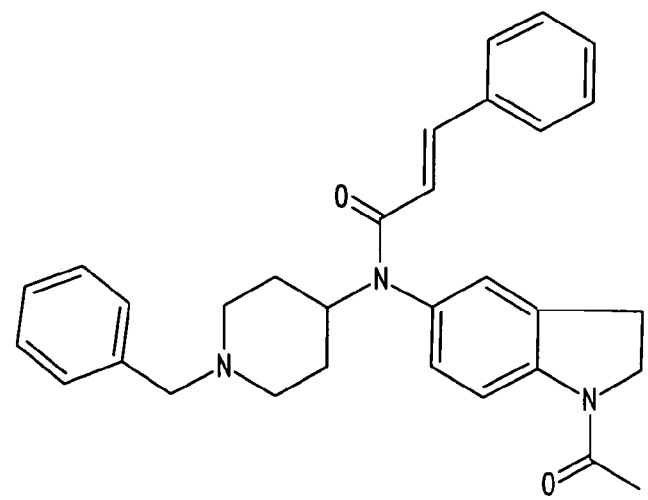
Compound 471
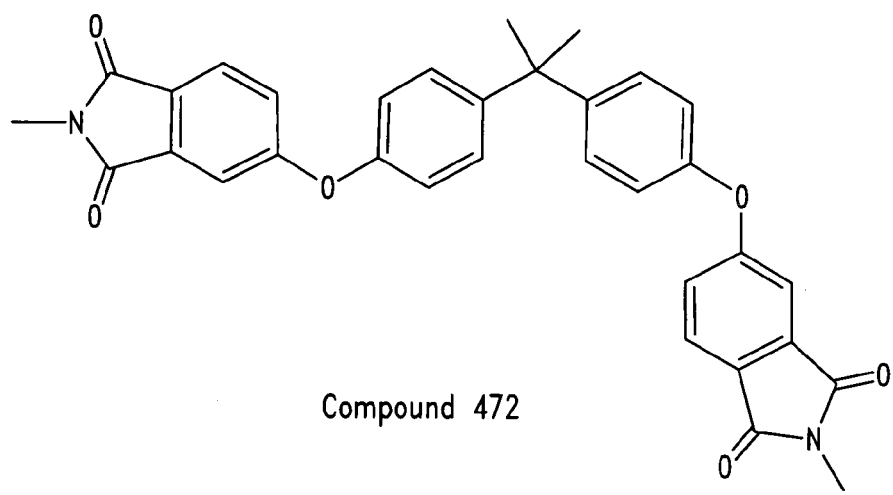
Compound 472
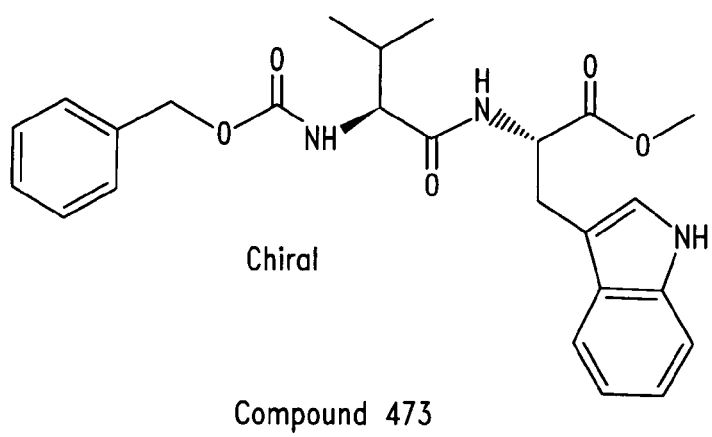
Chiral
Compound 473
*Fig. 29D*

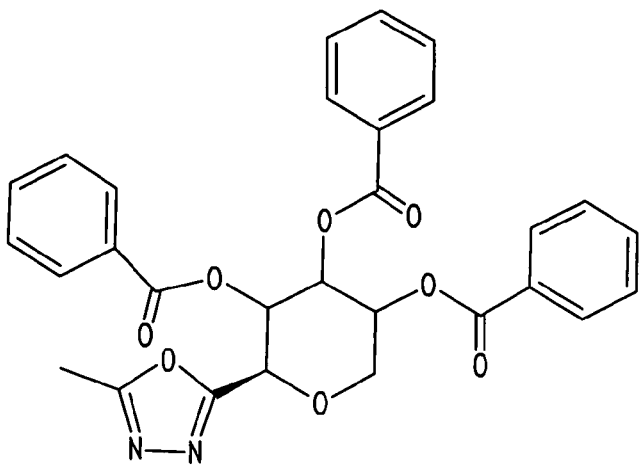
Compound 474
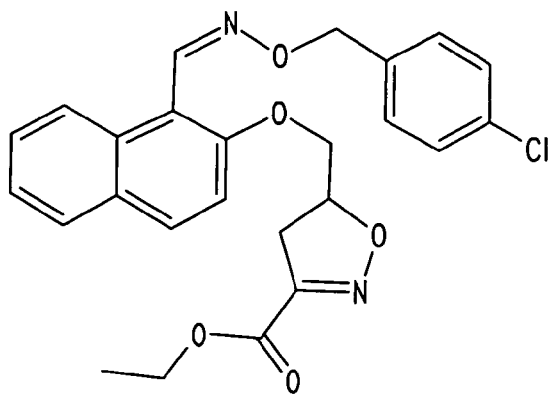
Compound 475
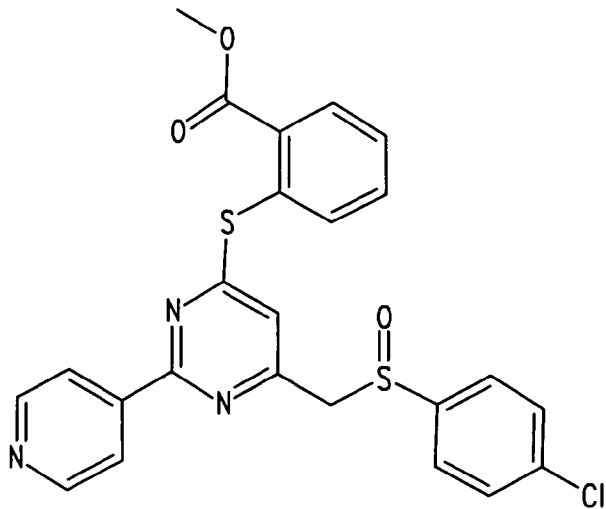
Compound 476
*Fig. 29E*

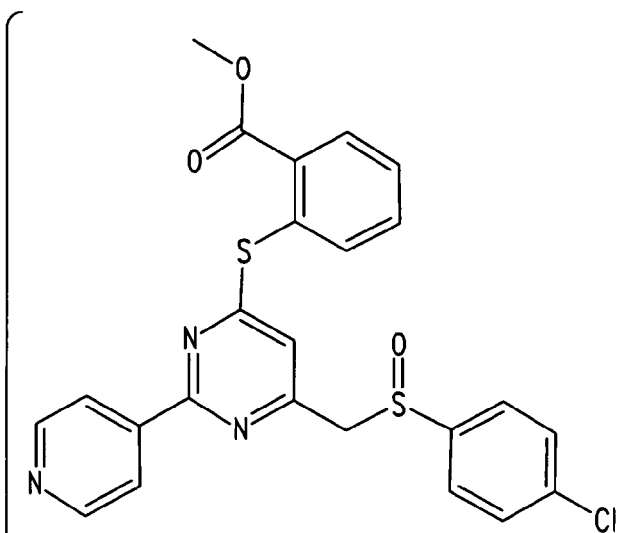
Compound 477
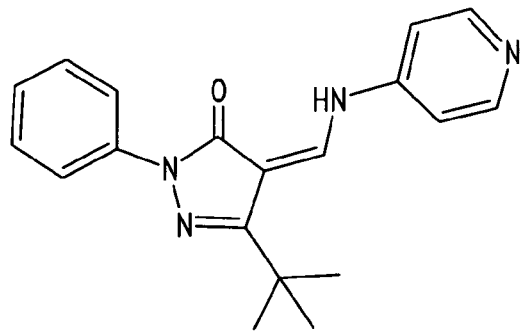
Compound 478
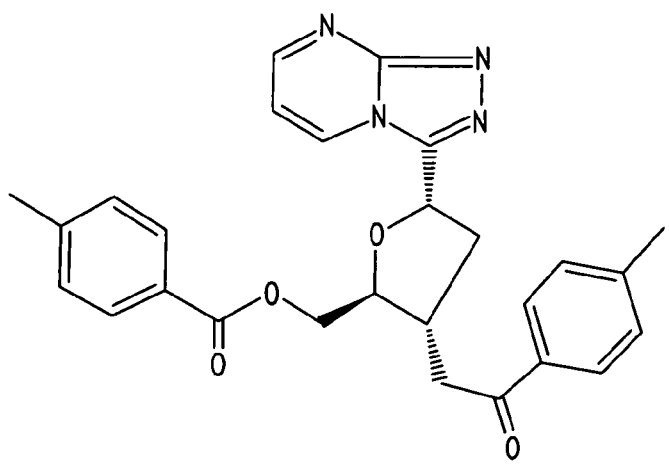
Compound 479
*Fig. 29F*

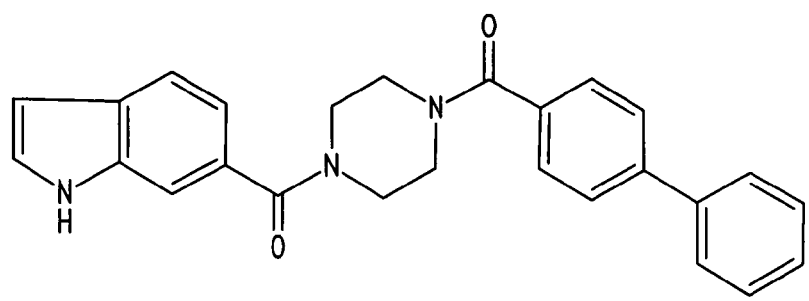
Compound 480
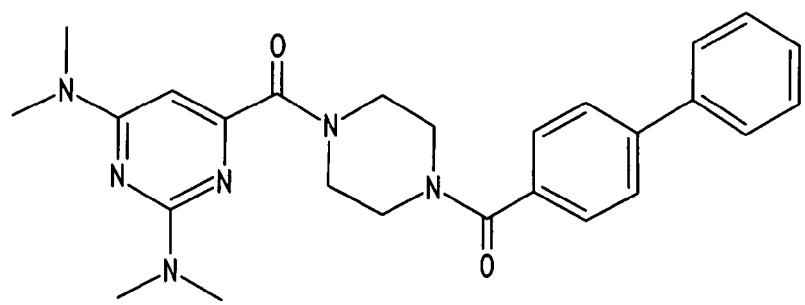
Compound 481
*Fig. 29G*

Compound 482

Compound 483

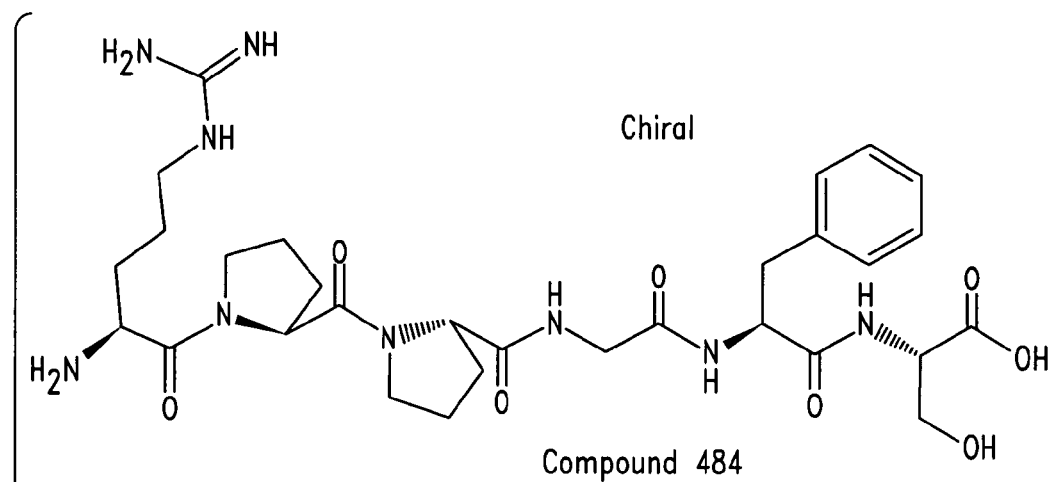
Compound 484
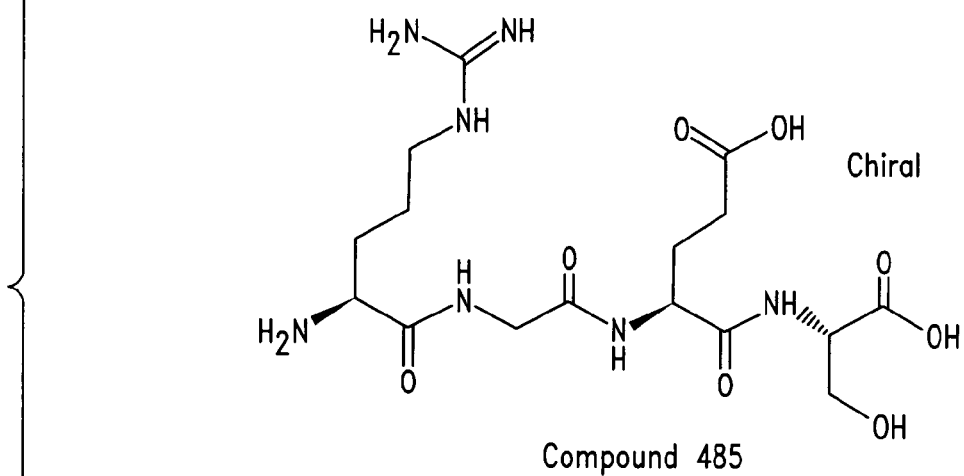
Compound 485
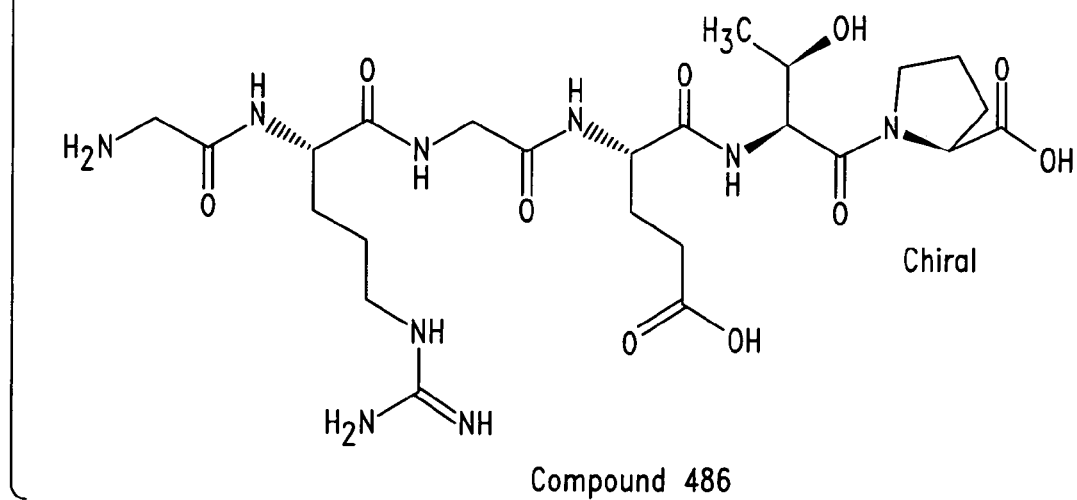
Compound 486
Fig. 31B Compound 487

Compound 488

Compound 489

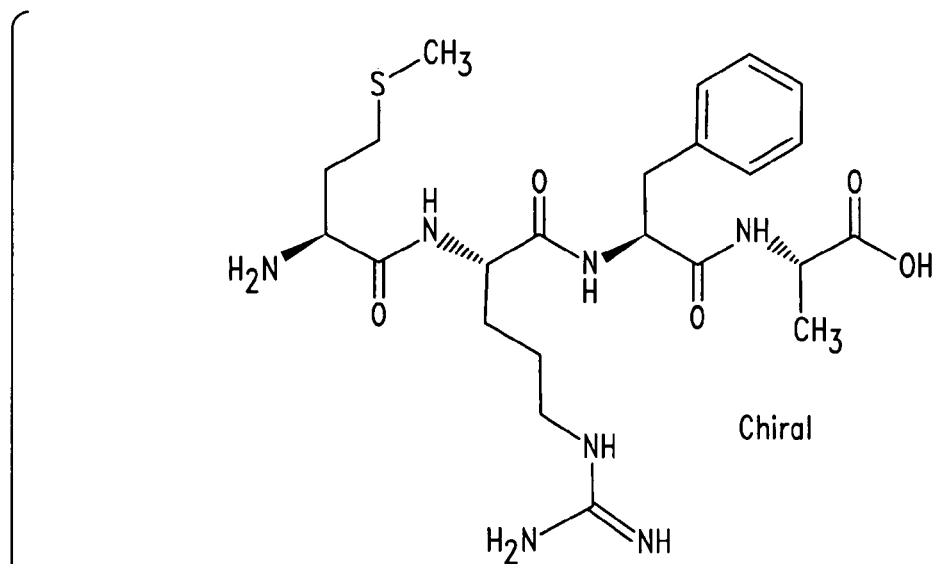
Compound 493
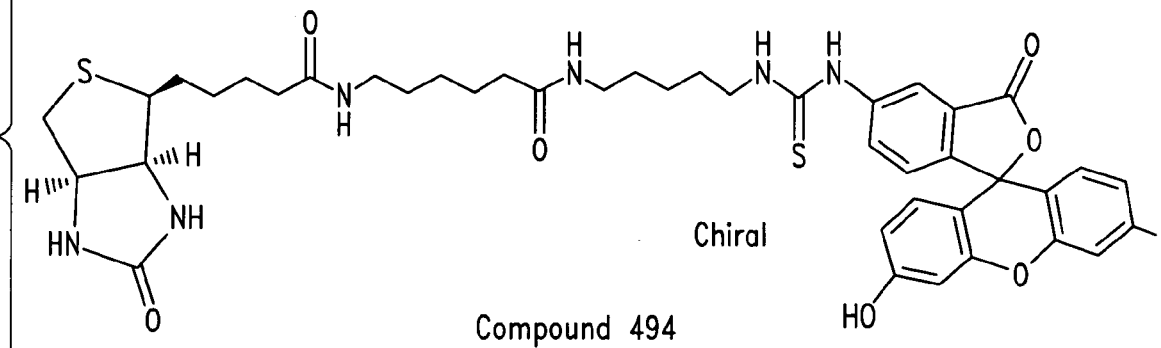
Compound 494
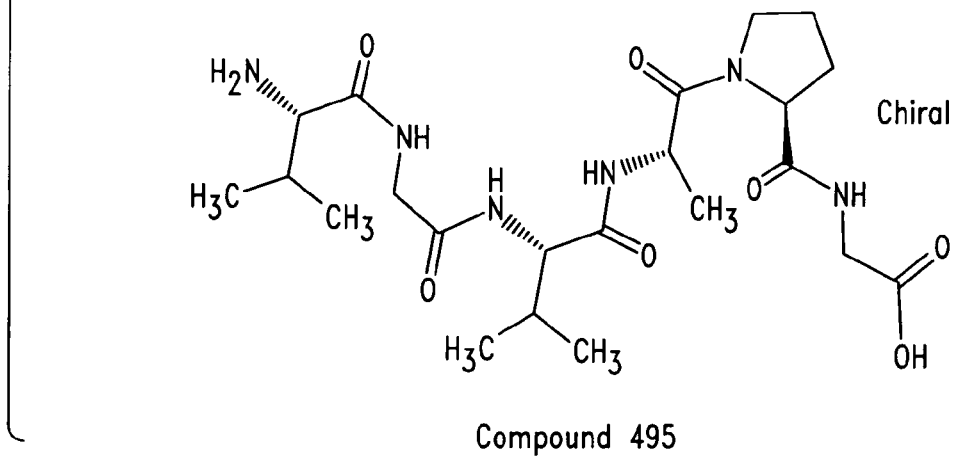
Compound 495
*Fig. 31E*

Compound 496

Compound 497

Compound 497

Compound 499

Compound 500

Compound 501

Compound 502

Compound 503

Compound 504

Compound 505

Compound 506

Compound 507

Compound 508

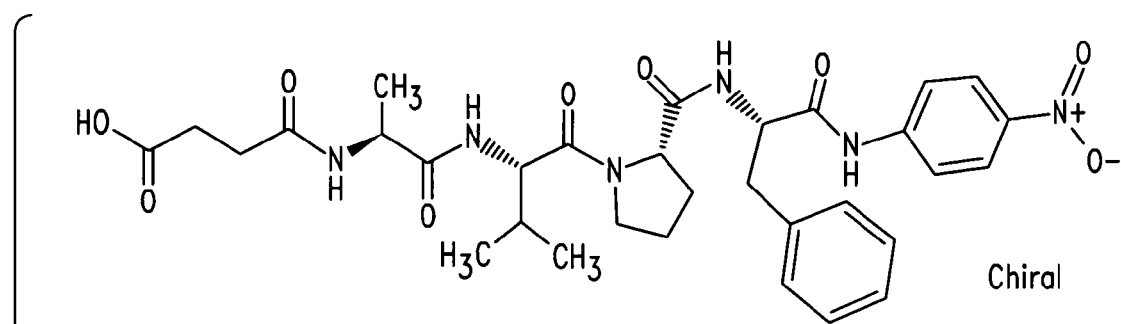
Compound 509
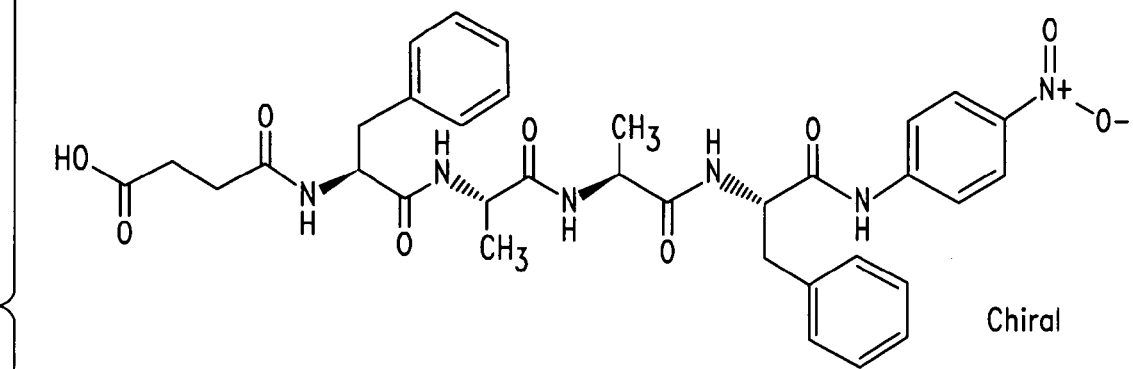
Compound 510
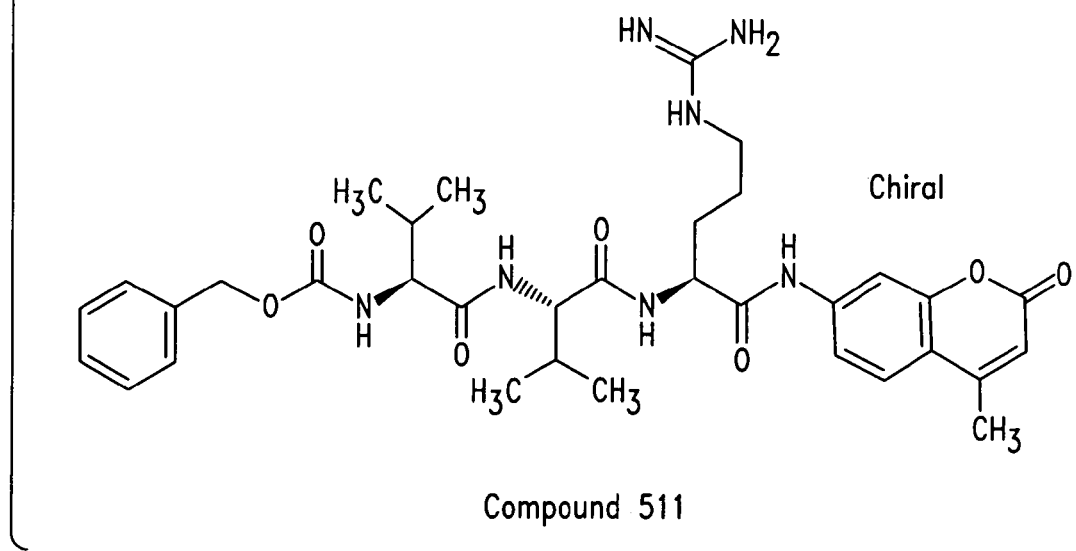
Compound 511
*Fig. 31J*

Compound 515

Compound 516

Compound 517

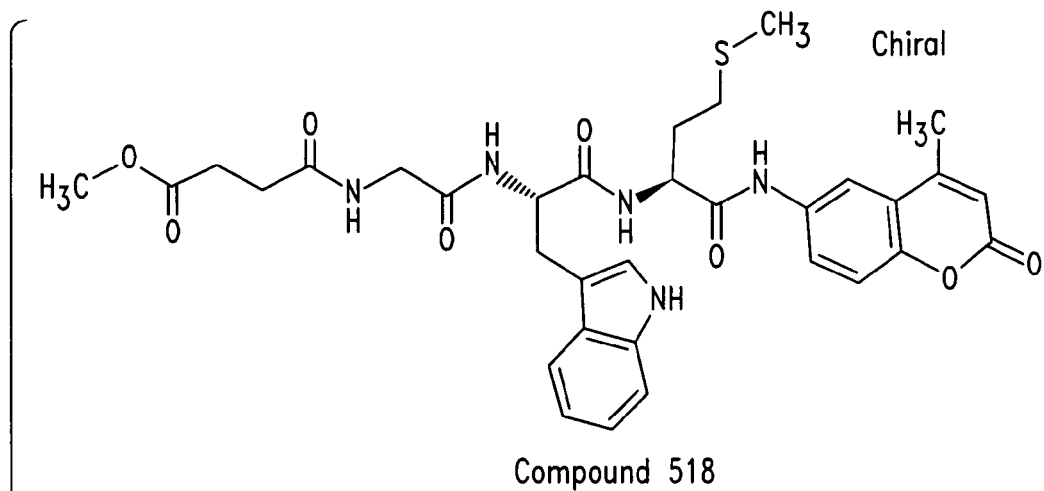
Compound 518
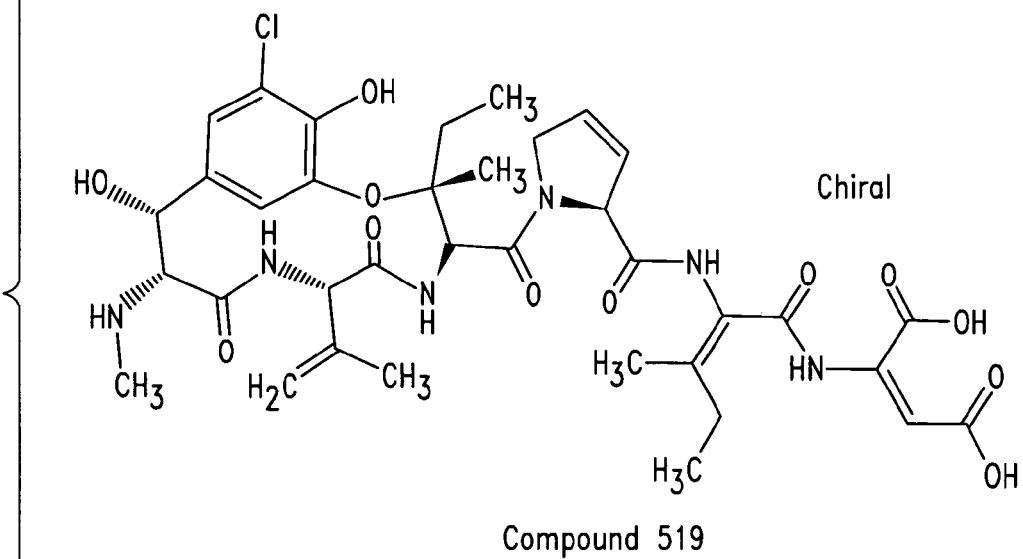
Compound 519
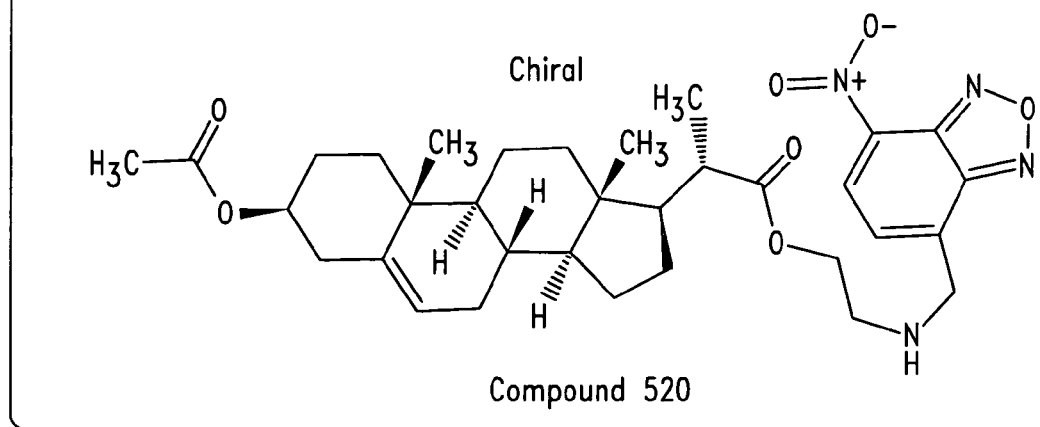
Compound 520
Fig. 31M Compound 521

Compound 522

Compound 523

Compound 530

Compound 531

Compound 532

Compound 533

Compound 534

Compound 535

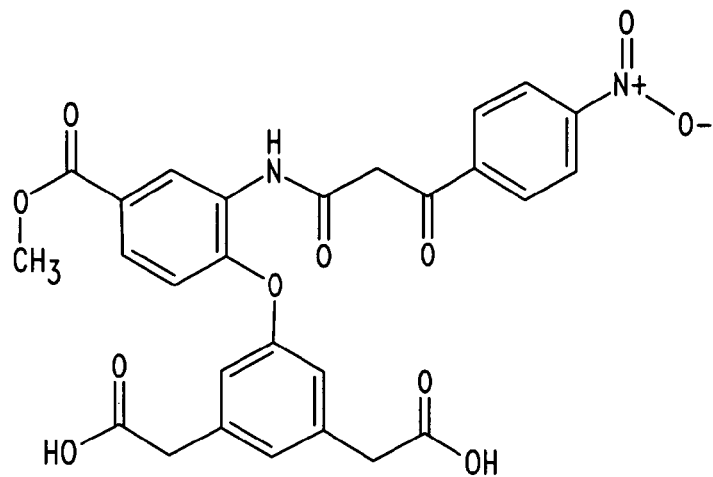
Compound 536
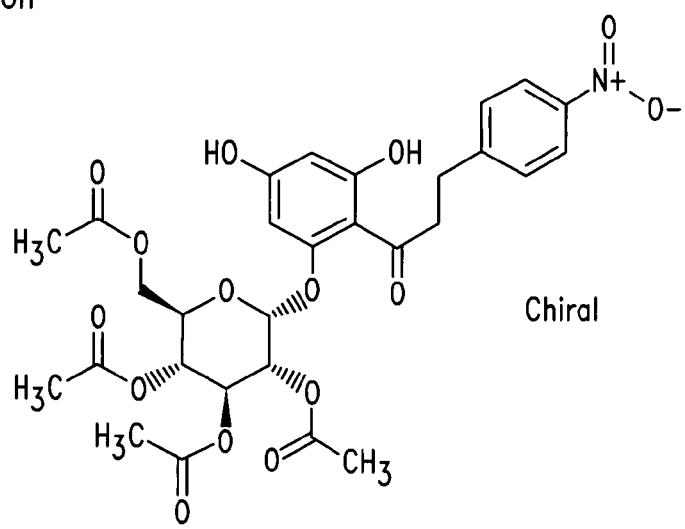
Compound 537
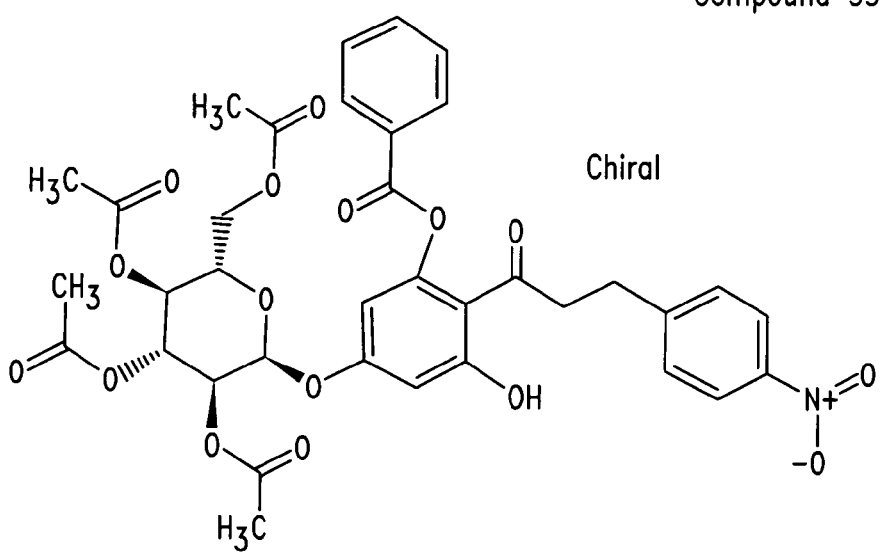
Compound 538
*Fig. 31S*

Compound 539

Compound 540

Compound 541

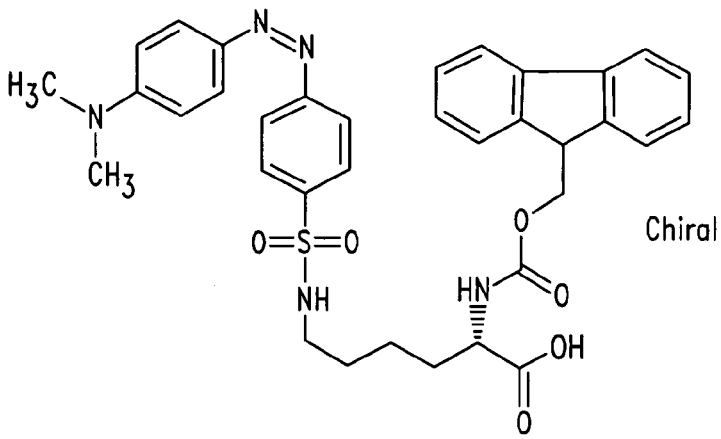
Compound 542
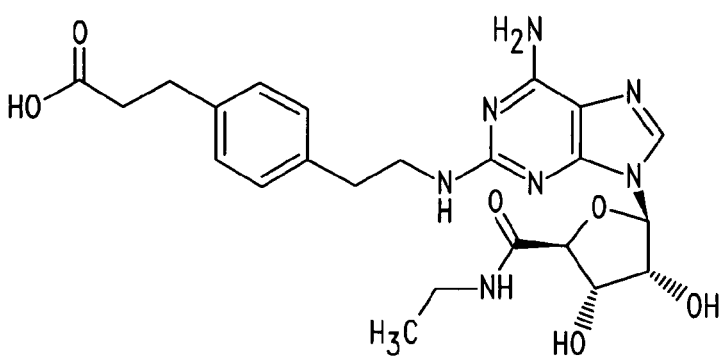
Compound 543
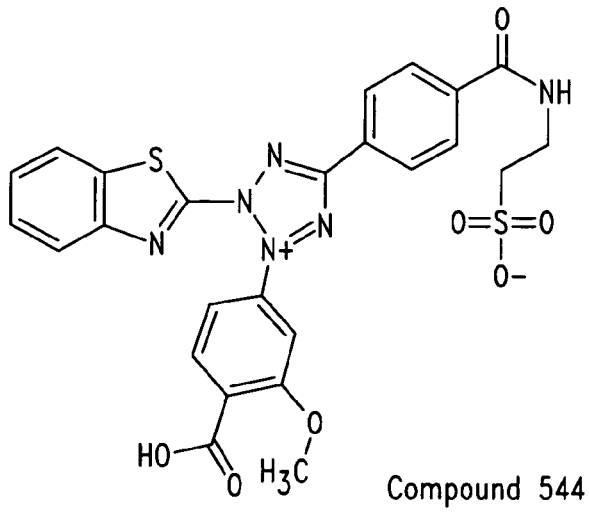
Compound 544
Fig. 31U

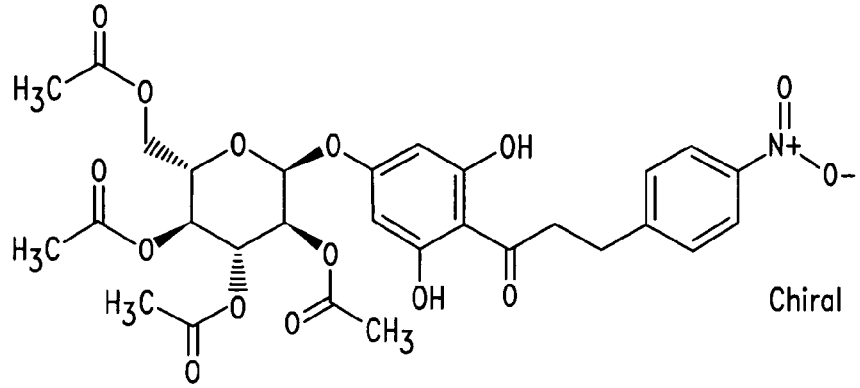
Compound 549
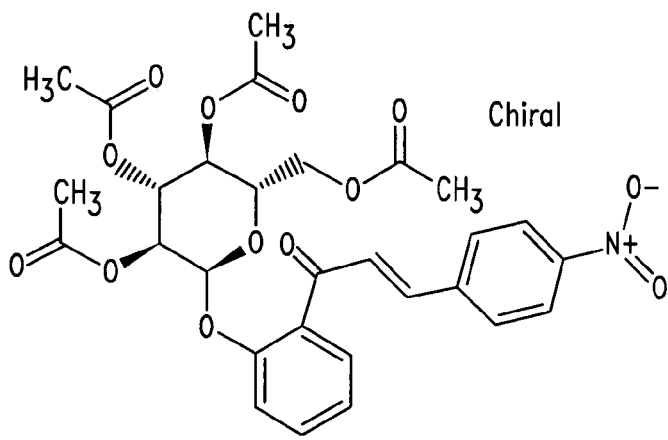
Compound 550
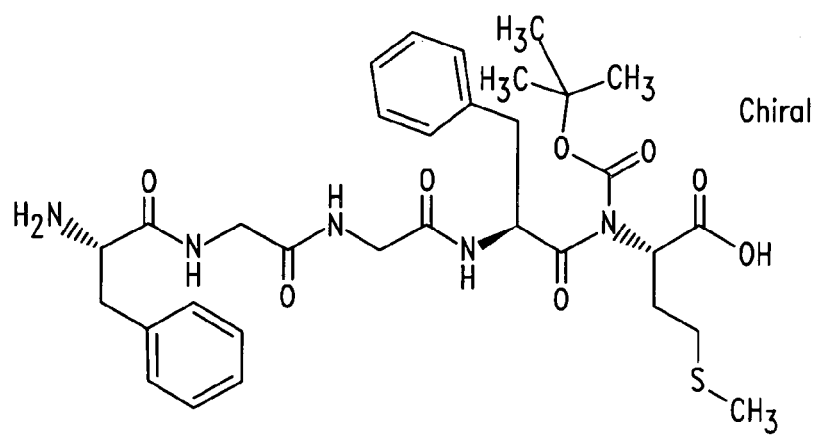
Compound 551
*Fig. 31W*

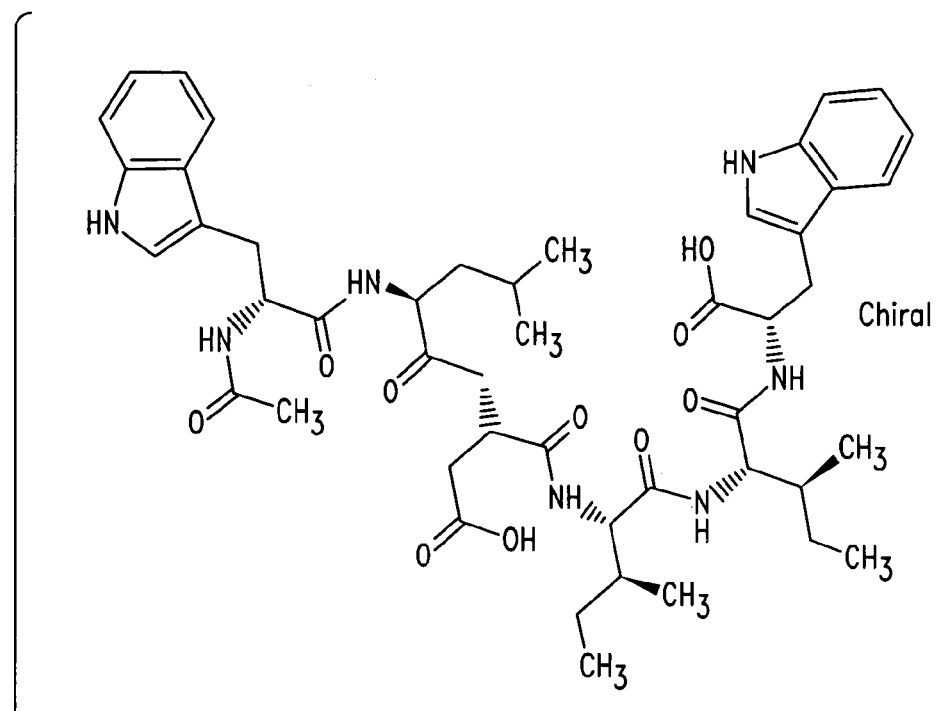
Compound 552
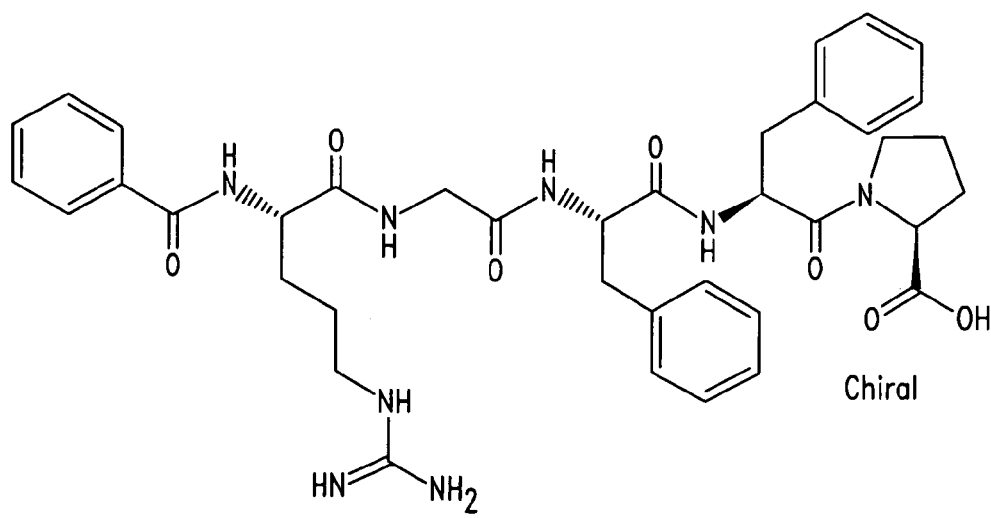
Compound 553
Fig. 31X

Compound 554

Compound 555

Compound 556

Compound 557

Compound 558

Compound 559

Compound 560

Compound 561

Compound 562

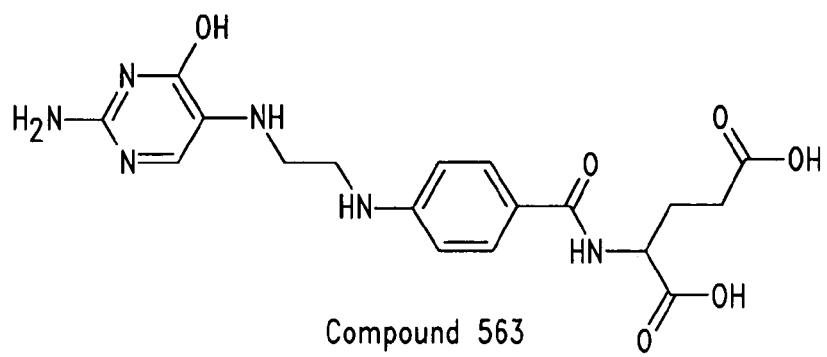
Compound 563
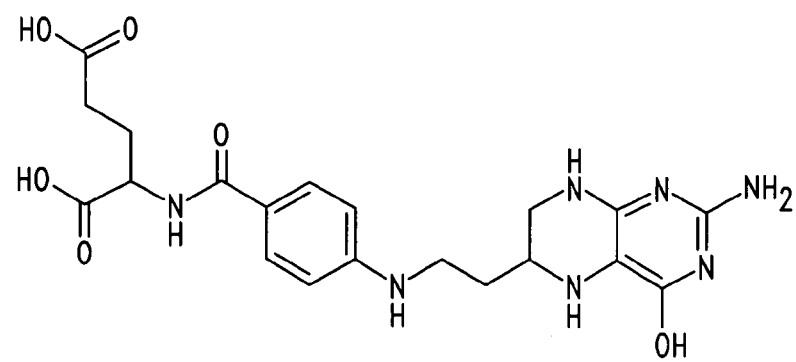
Compound 564
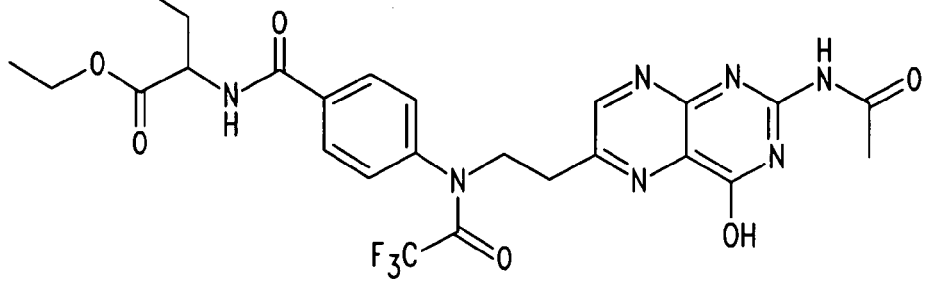
Compound 565
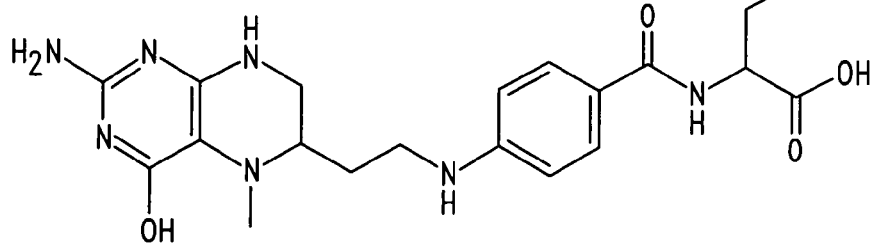
Compound 566
Fig. 31AB Compound 567

Compound 568

Compound 569

Compound 570

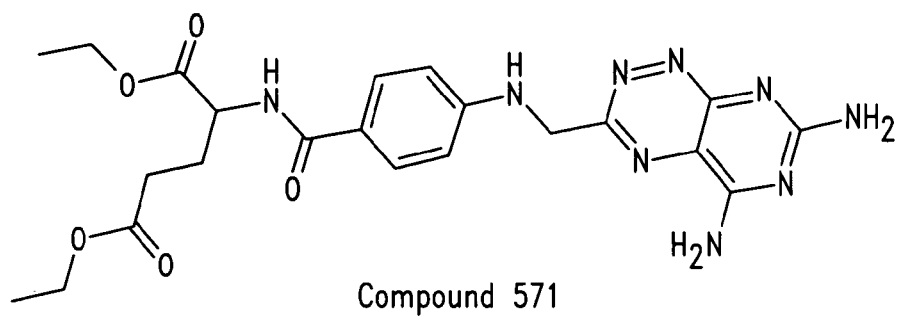
Compound 571
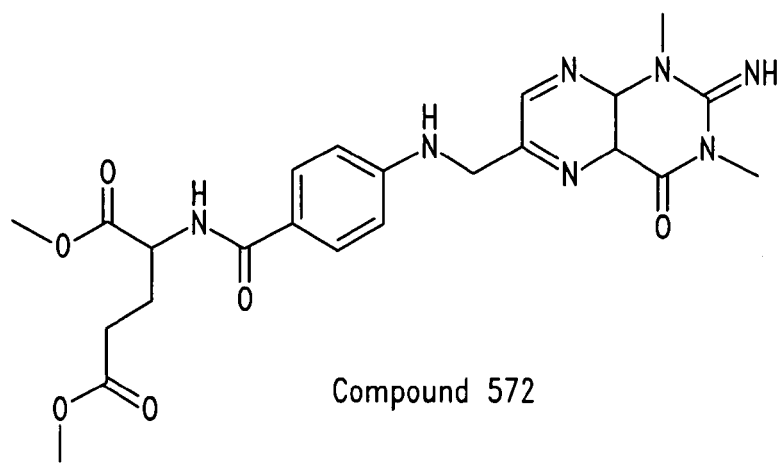
Compound 572
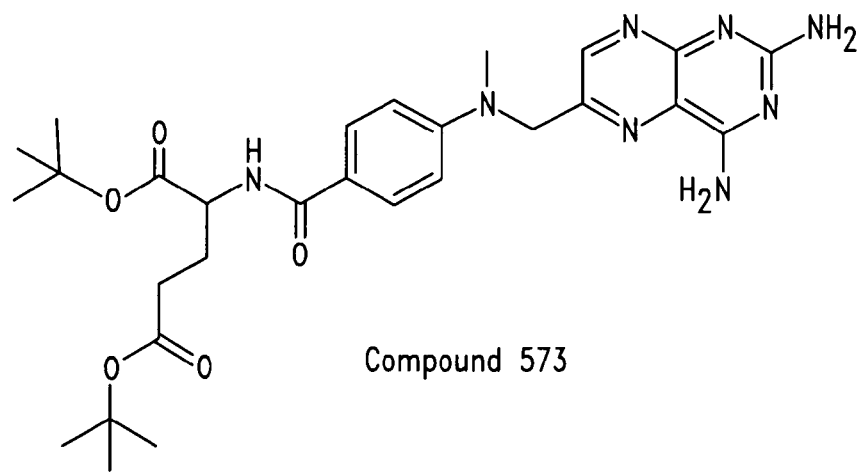
Compound 573
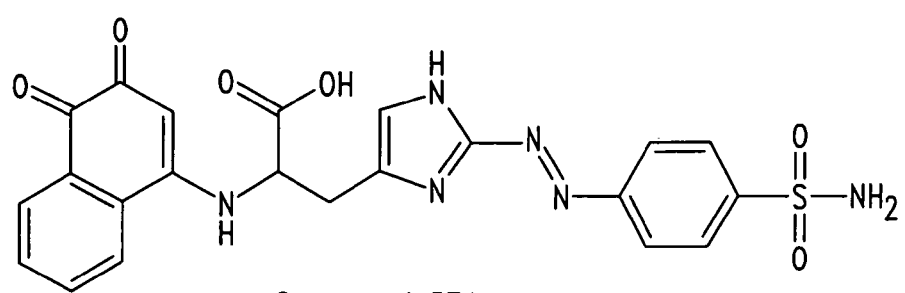
Compound 574
*Fig. 31AD*

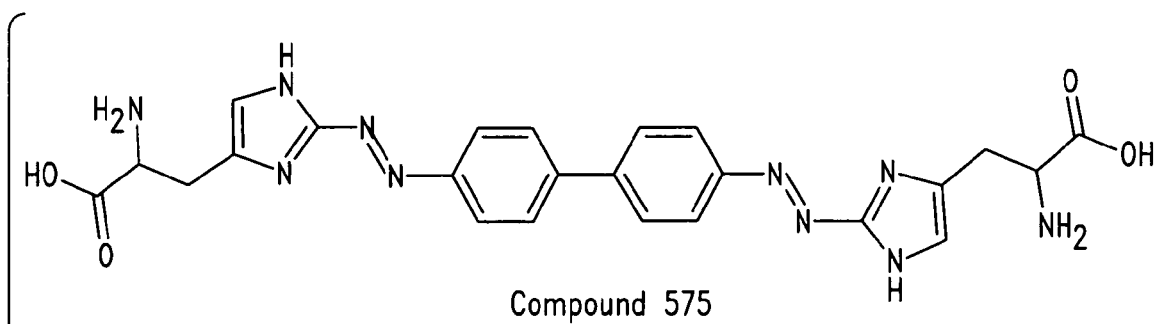
Compound 575
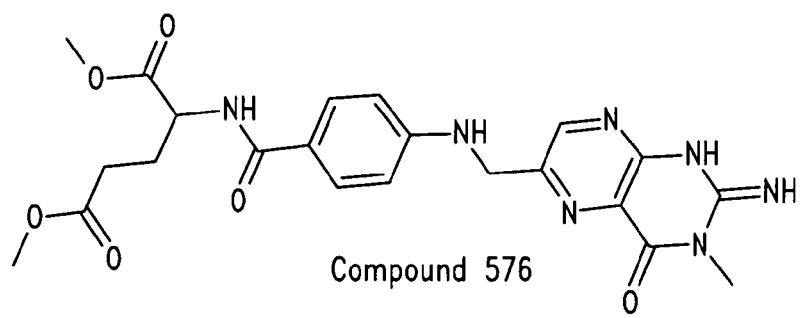
Compound 576
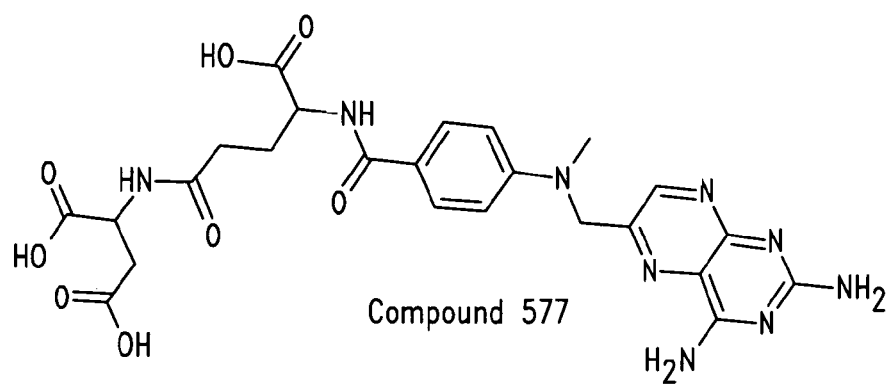
Compound 577
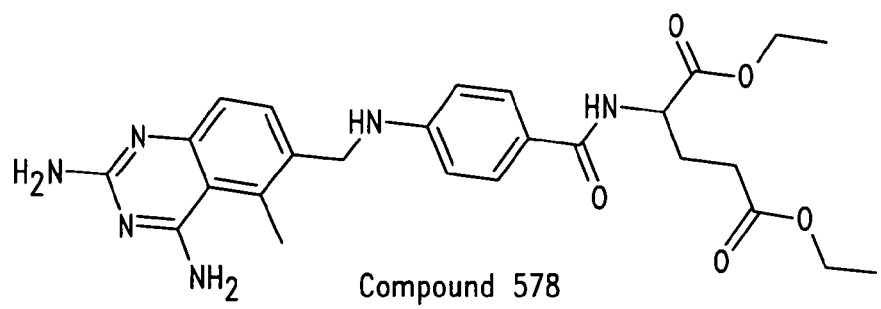
Compound 578
*Fig. 31AE*

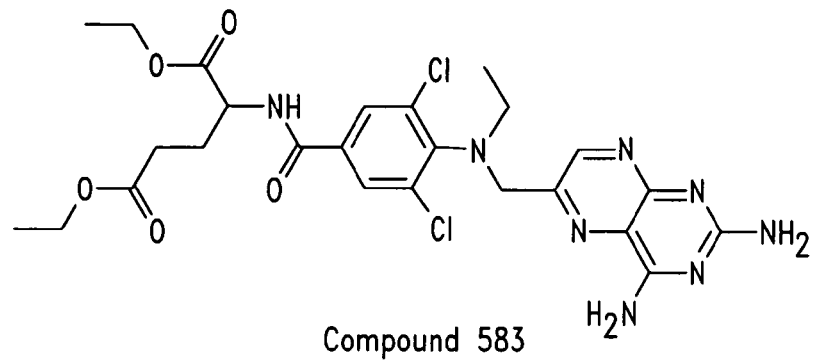
Compound 583
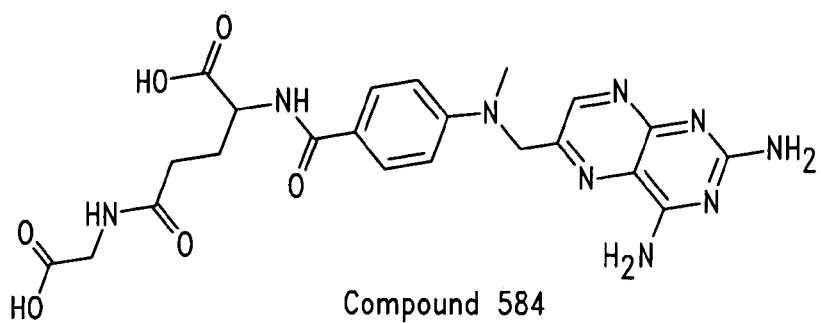
Compound 584
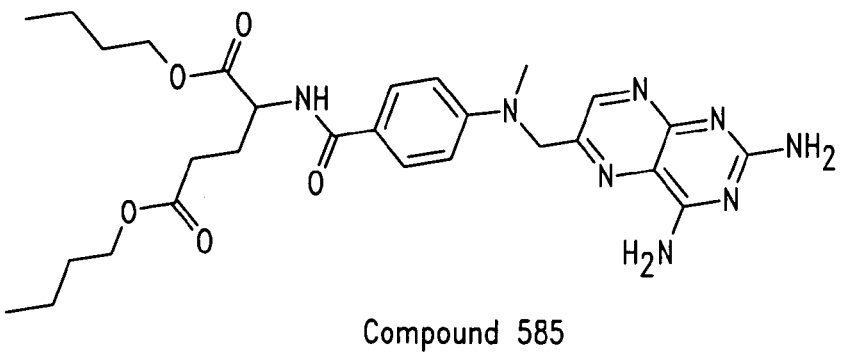
Compound 585
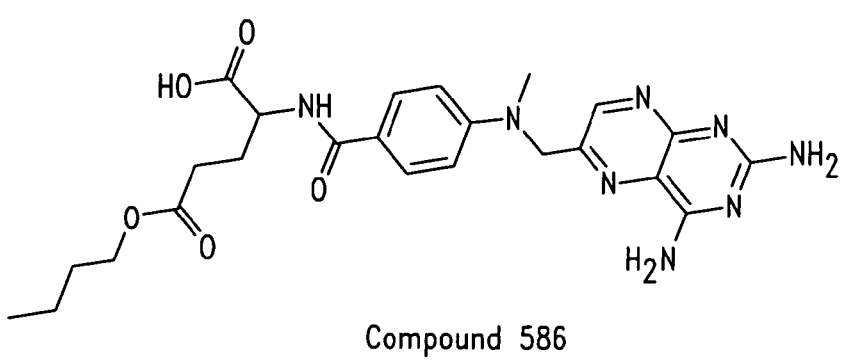
Compound 586
*Fig. 31AG*

Compound 587

Compound 588

Compound 589

Compound 590

Compound 591

Compound 592

Compound 593

SEQUENCE LISTING

<160> NUMBER OF SEQ ID NOS: 96

<210> SEQ ID NO 1
<211> LENGTH: 108
<212> TYPE: PRT
<213> ORGANISM: Homo sapiens

<400> SEQUENCE: 1

Asp Trp Val Ile Pro Pro Ile Asn Leu Pro Glu Asn Ser Arg Gly Pro
 1               5                  10                  15

Phe Pro Gln Glu Leu Val Arg Ile Arg Ser Asp Arg Asp Lys Asn Leu
            20                  25                  30

Ser Leu Arg Tyr Ser Val Thr Gly Pro Gly Ala Asp Gln Pro Pro Thr
        35                  40                  45

Gly Ile Phe Ile Leu Asn Pro Ile Ser Gly Gln Leu Ser Val Thr Lys
    50                  55                  60

Pro Leu Asp Arg Glu Gln Ile Ala Arg Phe His Leu Arg Ala His Ala
65                  70                  75                  80

Val Asp Ile Asn Gly Asn Gln Val Glu Asn Pro Ile Asp Ile Val Ile
                85                  90                  95

Asn Val Ile Asp Met Asn Asp Asn Arg Pro Glu Phe
            100                 105

<210> SEQ ID NO 2
<211> LENGTH: 108
<212> TYPE: PRT
<213> ORGANISM: Mus musculus

<400> SEQUENCE: 2

Asp Trp Val Ile Pro Pro Ile Asn Leu Pro Glu Asn Ser Arg Gly Pro
 1               5                  10                  15

Phe Pro Gln Glu Leu Val Arg Ile Arg Ser Asp Arg Asp Lys Asn Leu
            20                  25                  30

Ser Leu Arg Tyr Ser Val Thr Gly Pro Gly Ala Asp Gln Pro Pro Thr
        35                  40                  45

Gly Ile Phe Ile Ile Asn Pro Ile Ser Gly Gln Leu Ser Val Thr Lys
    50                  55                  60

Pro Leu Asp Arg Glu Leu Ile Ala Arg Phe His Leu Arg Ala His Ala
65                  70                  75                  80

Val Asp Ile Asn Gly Asn Gln Val Glu Asn Pro Ile Asp Ile Val Ile
                85                  90                  95

Asn Val Ile Asp Met Asn Asp Asn Arg Pro Glu Phe
            100                 105

<210> SEQ ID NO 3

```
<211> LENGTH: 108
<212> TYPE: PRT
<213> ORGANISM: Bos taurus

<400> SEQUENCE: 3

Asp Trp Val Ile Pro Pro Ile Asn Leu Pro Glu Asn Ser Arg Gly Pro
1               5                   10                  15

Phe Pro Gln Glu Leu Val Arg Ile Arg Ser Asp Arg Asp Lys Asn Leu
                20                  25                  30

Ser Leu Arg Tyr Ser Val Thr Gly Pro Gly Ala Asp Gln Pro Pro Thr
            35                  40                  45

Gly Ile Phe Ile Ile Asn Pro Ile Ser Gly Gln Leu Ser Val Thr Lys
        50                  55                  60

Pro Leu Asp Arg Glu Leu Ile Ala Arg Phe His Leu Arg Ala His Ala
65                  70                  75                  80

Val Asp Ile Asn Gly Asn Gln Val Glu Asn Pro Ile Asp Ile Val Ile
                85                  90                  95

Asn Val Ile Asp Met Asn Asp Asn Arg Pro Glu Phe
            100                 105

<210> SEQ ID NO 4
<211> LENGTH: 108
<212> TYPE: PRT
<213> ORGANISM: Homo sapiens

<400> SEQUENCE: 4

Asp Trp Val Val Ala Pro Ile Ser Val Pro Glu Asn Gly Lys Gly Pro
1               5                   10                  15

Phe Pro Gln Arg Leu Asn Gln Leu Lys Ser Asn Lys Asp Arg Asp Thr
                20                  25                  30

Lys Ile Phe Tyr Ser Ile Thr Gly Pro Gly Ala Asp Ser Pro Pro Glu
            35                  40                  45

Gly Val Phe Ala Val Glu Lys Glu Thr Gly Trp Leu Leu Leu Asn Lys
        50                  55                  60

Pro Leu Asp Arg Glu Glu Ile Ala Lys Tyr Glu Leu Phe Gly His Ala
65                  70                  75                  80

Val Ser Glu Asn Gly Ala Ser Val Glu Asp Pro Met Asn Ile Ser Ile
                85                  90                  95

Ile Val Thr Asp Gln Asn Asp His Lys Pro Lys Phe
            100                 105

<210> SEQ ID NO 5
<211> LENGTH: 108
<212> TYPE: PRT
<213> ORGANISM: Mus musculus

<400> SEQUENCE: 5

Glu Trp Val Met Pro Pro Ile Phe Val Pro Glu Asn Gly Lys Gly Pro
1               5                   10                  15

Phe Pro Gln Arg Leu Asn Gln Leu Lys Ser Asn Lys Asp Arg Gly Thr
                20                  25                  30

Lys Ile Phe Tyr Ser Ile Thr Gly Pro Gly Ala Asp Ser Pro Pro Glu
            35                  40                  45

Gly Val Phe Thr Ile Glu Lys Glu Ser Gly Trp Leu Leu Leu His Met
        50                  55                  60

Pro Leu Asp Arg Glu Lys Ile Val Lys Tyr Glu Leu Tyr Gly His Ala
65                  70                  75                  80
```

```
Val Ser Glu Asn Gly Ala Ser Val Glu Glu Pro Met Asn Ile Ser Ile
            85                   90                  95

Ile Val Thr Asp Gln Asn Asp Asn Lys Pro Lys Phe
            100                 105
```

<210> SEQ ID NO 6
<211> LENGTH: 108
<212> TYPE: PRT
<213> ORGANISM: Homo sapiens

<400> SEQUENCE: 6

```
Asp Trp Val Ile Pro Pro Ile Ser Cys Pro Glu Asn Glu Lys Gly Pro
 1               5                  10                  15

Phe Pro Lys Asn Leu Val Gln Ile Lys Ser Asn Lys Asp Lys Glu Gly
            20                  25                  30

Lys Val Phe Tyr Ser Ile Thr Gly Gln Gly Ala Asp Thr Pro Pro Val
            35                  40                  45

Gly Val Phe Ile Ile Glu Arg Glu Thr Gly Trp Leu Lys Val Thr Glu
        50                  55                  60

Pro Leu Asp Arg Glu Arg Ile Ala Thr Tyr Thr Leu Phe Ser His Ala
65                  70                  75                  80

Val Ser Ser Asn Gly Asn Ala Val Glu Asp Pro Met Glu Ile Leu Ile
            85                  90                  95

Thr Val Thr Asp Gln Asn Asp Asn Lys Pro Glu Phe
            100                 105
```

<210> SEQ ID NO 7
<211> LENGTH: 108
<212> TYPE: PRT
<213> ORGANISM: Mus musculus

<400> SEQUENCE: 7

```
Asp Trp Val Ile Pro Pro Ile Ser Cys Pro Glu Asn Glu Lys Gly Glu
 1               5                  10                  15

Phe Pro Lys Asn Leu Val Gln Ile Lys Ser Asn Arg Asp Lys Glu Thr
            20                  25                  30

Lys Val Phe Tyr Ser Ile Thr Gly Gln Gly Ala Asp Lys Pro Pro Val
            35                  40                  45

Gly Val Phe Ile Ile Glu Arg Glu Thr Gly Trp Leu Lys Val Thr Gln
        50                  55                  60

Pro Leu Asp Arg Glu Ala Ile Ala Lys Tyr Ile Leu Tyr Ser His Ala
65                  70                  75                  80

Val Ser Ser Asn Gly Glu Ala Val Glu Asp Pro Met Glu Ile Val Ile
            85                  90                  95

Thr Val Thr Asp Gln Asn Asp Asn Arg Pro Glu Phe
            100                 105
```

<210> SEQ ID NO 8
<211> LENGTH: 5
<212> TYPE: PRT
<213> ORGANISM: Unknown
<220> FEATURE:
<221> NAME/KEY: MOD_RES
<222> LOCATION: (2)
<223> OTHER INFORMATION: Where Xaa is any amino acid
<220> FEATURE:
<223> OTHER INFORMATION: Description of Unknown Organism: Cadherin
      Calcium Binding Motif

<400> SEQUENCE: 8

```
Asp Xaa Asn Asp Asn
1               5
```

<210> SEQ ID NO 9
<211> LENGTH: 4
<212> TYPE: PRT
<213> ORGANISM: Unknown
<220> FEATURE:
<223> OTHER INFORMATION: Description of Unknown Organism: Cadherin
      Calcium Binding Motif

<400> SEQUENCE: 9

```
Leu Asp Arg Glu
1
```

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 10

```
Cys His Ala Val Cys
1               5
```

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 11

```
Cys His Gly Val Cys
1               5
```

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Cyclic
      peptide with cadherin cell adhesion recognition
      sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 12

```
Lys His Ala Val Asp
1               5
```

<210> SEQ ID NO 13
<211> LENGTH: 5
<212> TYPE: PRT

```
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 13

Lys His Gly Val Asp
  1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence:  Cyclic
      peptide with cadherin cell adhesion recognition
      sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 14

Asp His Ala Val Lys
  1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 15

Asp His Gly Val Lys
  1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 16

Lys His Ala Val Glu
  1               5

<210> SEQ ID NO 17
<211> LENGTH: 5
<212> TYPE: PRT
<213> ORGANISM: Artificial Sequence
```

```
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 17

Lys His Gly Val Glu
 1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 18

Cys Val Ala His Cys
 1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 19

Cys Val Gly His Cys
 1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 20

Cys His Ala Val Asp Cys
 1               5

<210> SEQ ID NO 21
<211> LENGTH: 6
<212> TYPE: PRT
<213> ORGANISM: Artificial Sequence
<220> FEATURE:
```

-continued

```
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 21

Cys His Gly Val Asp Cys
 1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 22

Cys Ala His Ala Val Cys
 1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 23

Cys Ala His Gly Val Cys
 1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 24

Cys Ala His Ala Val Asp Ile Cys
 1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence:  Cyclic
```

```
              control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 25

Cys Ala His Gly Val Asp Ile Cys
 1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 26

Cys Ala His Ala Val Asp Cys
 1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 27

Cys Ala His Gly Val Asp Cys
 1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 28

Cys Arg Ala His Ala Val Asp Cys
 1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence:  Cyclic
      control peptide
```

```
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 29

Cys Arg Ala His Gly Val Asp Cys
 1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 30

Cys Leu Arg Ala His Ala Val Cys
 1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 31

Cys Leu Arg Ala His Gly Val Cys
 1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 32

Cys Leu Arg Ala His Ala Val Asp Cys
 1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
```

```
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 33

Cys Leu Arg Ala His Gly Val Asp Cys
  1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 34

Ala His Ala Val Asp Ile
  1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 35

Ala His Gly Val Asp Ile
  1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 36

Cys Ser His Ala Val Cys
  1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
```

```
      modification such as acetyl or alkoxybenzyl group
      and/or C-terminal modifications such as amide or
      ester group

<400> SEQUENCE: 37

Cys Ser His Gly Val Cys
 1               5

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 38

Cys His Ala Val Ser Cys
 1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 39

Cys His Gly Val Ser Cys
 1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 40

Cys Ser His Ala Val Ser Cys
 1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
```

```
        and/or C-terminal modifications such as amide or
        ester group

<400> SEQUENCE: 41

Cys Ser His Gly Val Ser Cys
  1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence:  Cyclic
        peptide with classical cadherin cell adhesion
        recognition sequence
<220> FEATURE:
<223> OTHER INFORMATION: Cyclic Peptide may comprise N-terminal
        modification such as acetyl or alkoxybenzyl group
        and/or C-terminal modifications such as amide or
        ester group

<400> SEQUENCE: 42

Cys Ser His Ala Val Ser Ser Cys
  1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence:  Cyclic
        control peptide
<220> FEATURE:
<223> OTHER INFORMATION: Cyclic Peptide may comprise N-terminal
        modification such as acetyl or alkoxybenzyl group
        and/or C-terminal modifications such as amide or
        ester group

<400> SEQUENCE: 43

Cys Ser His Gly Val Ser Ser Cys
  1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence:  Cyclic
        peptide with classical cadherin cell adhesion
        recognition sequence
<220> FEATURE:
<223> OTHER INFORMATION: Cyclic Peptide may comprise N-terminal
        modification such as acetyl or alkoxybenzyl group
        and/or C-terminal modifications such as amide or
        ester group

<400> SEQUENCE: 44

Cys His Ala Val Ser Ser Cys
  1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence:  Cyclic
        control peptide
<220> FEATURE:
<223> OTHER INFORMATION: Cyclic Peptide may comprise N-terminal
        modification such as acetyl or alkoxybenzyl group
        and/or C-terminal modifications such as amide or
```

```
      ester group

<400> SEQUENCE: 45

Cys His Gly Val Ser Ser Cys
  1               5

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 46

Ser His Ala Val Ser Ser
  1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 47

Ser His Gly Val Ser Ser
  1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 48

Lys Ser His Ala Val Ser Ser Asp
  1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group
```

<400> SEQUENCE: 49

Lys Ser His Gly Val Ser Ser Asp
 1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 50

Cys His Ala Val Asp Ile Cys
 1               5

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 51

Cys His Ala Val Asp Ile Asn Cys
 1               5

<210> SEQ ID NO 52
<211> LENGTH: 5
<212> TYPE: PRT
<213> ORGANISM: Unknown
<220> FEATURE:
<223> OTHER INFORMATION: Description of Unknown Organism:  Cadherin cell
      adhesion recognition sequencebound by
      alpha-6-beta-1 integrin

<400> SEQUENCE: 52

Tyr Ile Gly Ser Arg
 1               5

<210> SEQ ID NO 53
<211> LENGTH: 10
<212> TYPE: PRT
<213> ORGANISM: Unknown
<220> FEATURE:
<223> OTHER INFORMATION: Description of Unknown Organism:  Cadherin cell
      adhesion recognition sequence bound by N-CAM

<400> SEQUENCE: 53

Lys Tyr Ser Phe Asn Tyr Asp Gly Ser Glu
 1               5                  10

<210> SEQ ID NO 54
<211> LENGTH: 17
<212> TYPE: PRT

```
<213> ORGANISM: Unknown
<220> FEATURE:
<223> OTHER INFORMATION: Description of Unknown Organism:  N-CAM heparin
      sulfate binding site

<400> SEQUENCE: 54

Ile Trp Lys His Lys Gly Arg Asp Val Ile Leu Lys Lys Asp Val Arg
 1               5                  10                  15

Phe

<210> SEQ ID NO 55
<211> LENGTH: 4
<212> TYPE: PRT
<213> ORGANISM: Unknown
<220> FEATURE:
<223> OTHER INFORMATION: Description of Unknown Organism: Occluding cell
      adhesion recognition sequence

<400> SEQUENCE: 55

Leu Tyr His Tyr
 1

<210> SEQ ID NO 56
<211> LENGTH: 8
<212> TYPE: PRT
<213> ORGANISM: Unknown
<220> FEATURE:
<223> OTHER INFORMATION: Description of Unknown Organism:  Claudin cell
      adhesion recognition sequence
<220> FEATURE:
<221> NAME/KEY: MOD_RES
<222> LOCATION: (2)
<223> OTHER INFORMATION: Where Xaa is either Lysine or arginine
<220> FEATURE:
<221> NAME/KEY: MOD_RES
<222> LOCATION: (3)..(4)
<223> OTHER INFORMATION: Where Xaa is an independently selected amino
      acid residue
<220> FEATURE:
<221> NAME/KEY: MOD_RES
<222> LOCATION: (5)
<223> OTHER INFORMATION: Where Xaa is either Serine or Alanine
<220> FEATURE:
<221> NAME/KEY: MOD_RES
<222> LOCATION: (6)
<223> OTHER INFORMATION: Where Xaa is either Tyrosine or Phenylalanine
<220> FEATURE:
<221> NAME/KEY: MOD_RES
<222> LOCATION: (7)
<223> OTHER INFORMATION: Where Xaa is an independently selected amino
      acid residue

<400> SEQUENCE: 56

Trp Xaa Xaa Xaa Xaa Xaa Xaa Gly
 1               5

<210> SEQ ID NO 57
<211> LENGTH: 9
<212> TYPE: PRT
<213> ORGANISM: Unknown
<220> FEATURE:
<223> OTHER INFORMATION: Description of Unknown Organism:  Nonclassical
      cadherin cell adhesion recognition sequence
<220> FEATURE:
<221> NAME/KEY: MOD_RES
<222> LOCATION: (1)
<223> OTHER INFORMATION: Where Xaa is an independently selected amino
      acid residue
<220> FEATURE:
<221> NAME/KEY: MOD_RES
<222> LOCATION: (3)
<223> OTHER INFORMATION: Where Xaa is an independently selected amino
```

```
        acid residue
<220> FEATURE:
<221> NAME/KEY: MOD_RES
<222> LOCATION: (4)
<223> OTHER INFORMATION: Where Xaa is Isoleucine, Leucine or Valine
<220> FEATURE:
<221> NAME/KEY: MOD_RES
<222> LOCATION: (5)
<223> OTHER INFORMATION: Where Xaa is Aspartic Acid, Asparagine or
      Glutamic Acid
<220> FEATURE:
<221> NAME/KEY: MOD_RES
<222> LOCATION: (6)..(7)
<223> OTHER INFORMATION: Where Xaa is an independently selected amino
      acid residue
<220> FEATURE:
<221> NAME/KEY: MOD_RES
<222> LOCATION: (8)
<223> OTHER INFORMATION: Where Xaa is Serine, Threonine or Asparagine

<400> SEQUENCE: 57

Xaa Phe Xaa Xaa Xaa Xaa Xaa Xaa Gly
  1               5

<210> SEQ ID NO 58
<211> LENGTH: 4
<212> TYPE: PRT
<213> ORGANISM: Unknown
<220> FEATURE:
<223> OTHER INFORMATION: Description of Unknown Organism: Representative
      claudin cell adhesion recognition sequence

<400> SEQUENCE: 58

Ile Tyr Ser Tyr
  1

<210> SEQ ID NO 59
<211> LENGTH: 4
<212> TYPE: PRT
<213> ORGANISM: Unknown
<220> FEATURE:
<223> OTHER INFORMATION: Description of Unknown Organism: Representative
      claudin cell adhesion recognition sequence

<400> SEQUENCE: 59

Thr Ser Ser Tyr
  1

<210> SEQ ID NO 60
<211> LENGTH: 4
<212> TYPE: PRT
<213> ORGANISM: Unknown
<220> FEATURE:
<223> OTHER INFORMATION: Description of Unknown Organism: Representative
      claudin cell adhesion recognition sequence

<400> SEQUENCE: 60

Val Thr Ala Phe
  1

<210> SEQ ID NO 61
<211> LENGTH: 4
<212> TYPE: PRT
<213> ORGANISM: Unknown
<220> FEATURE:
<223> OTHER INFORMATION: Description of Unknown Organism: Representative
      claudin cell adhesion recognition sequence

<400> SEQUENCE: 61

Val Ser Ala Phe
```

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthesized Peptide
<220> FEATURE:
<221> NAME/KEY: MOD_RES
<222> LOCATION: (1)
<223> OTHER INFORMATION: BLOCKED by 9-fluorenymethyloxycarbonyl
<220> FEATURE:
<221> NAME/KEY: MOD_RES
<222> LOCATION: (2)
<223> OTHER INFORMATION: tert-butyl protecting group
<220> FEATURE:
<221> NAME/KEY: MOD_RES
<222> LOCATION: (4)
<223> OTHER INFORMATION: tert-butyl protecting group
<220> FEATURE:
<221> NAME/KEY: MOD_RES
<222> LOCATION: (6)
<223> OTHER INFORMATION: t-Butoxycarbonyl protecting group
<220> FEATURE:
<221> NAME/KEY: MOD_RES
<222> LOCATION: (7)
<223> OTHER INFORMATION: tert-butyl protecting group
<220> FEATURE:
<221> NAME/KEY: MOD_RES
<222> LOCATION: (9)
<223> OTHER INFORMATION: tert-butyl protecting group
<220> FEATURE:
<221> NAME/KEY: MOD_RES
<222> LOCATION: (10)
<223> OTHER INFORMATION: Methoxy terminal group

<400> SEQUENCE: 62

Cys Asp Gly Tyr Pro Lys Asp Cys Lys Gly
 1               5                  10

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthesized Cyclic Peptide
<220> FEATURE:
<221> NAME/KEY: MOD_RES
<222> LOCATION: (1)
<223> OTHER INFORMATION: 9-fluorenylmethoxycarbonyl protecting group
<220> FEATURE:
<221> NAME/KEY: MOD_RES
<222> LOCATION: (2)
<223> OTHER INFORMATION: tert-butyl protecting group
<220> FEATURE:
<221> NAME/KEY: MOD_RES
<222> LOCATION: (4)
<223> OTHER INFORMATION: tert-butyl protecting group
<220> FEATURE:
<221> NAME/KEY: MOD_RES
<222> LOCATION: (6)
<223> OTHER INFORMATION: t-butoxycarbonyl protecting group
<220> FEATURE:
<221> NAME/KEY: MOD_RES
<222> LOCATION: (7)
<223> OTHER INFORMATION: tert-butyl protecting group
<220> FEATURE:
<221> NAME/KEY: MOD_RES
<222> LOCATION: (9)
<223> OTHER INFORMATION: tert-butyl protecting group
<220> FEATURE:
<221> NAME/KEY: MOD_RES
<222> LOCATION: (10)

```
<223> OTHER INFORMATION: Methoxy terminal group

<400> SEQUENCE: 63

Cys Asp Gly Tyr Pro Lys Asp Cys Lys Gly
 1               5                  10

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthesized
      peptide
<220> FEATURE:
<221> NAME/KEY: MOD_RES
<222> LOCATION: (1)
<223> OTHER INFORMATION: Residue has t-butoxycarbonyl, and Trityl or
      Acetamidomethyl protecting groups
<220> FEATURE:
<221> NAME/KEY: MOD_RES
<222> LOCATION: (5)..(6)
<223> OTHER INFORMATION: tert-butyl protecting group
<220> FEATURE:
<221> NAME/KEY: MOD_RES
<222> LOCATION: (7)
<223> OTHER INFORMATION: Trityl or acetaminomethly protecting group

<400> SEQUENCE: 64

Cys Gly Asn Leu Ser Thr Cys Met Leu Gly
 1               5                  10

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthesized
      cyclic peptide
<220> FEATURE:
<221> NAME/KEY: MOD_RES
<222> LOCATION: (1)
<223> OTHER INFORMATION: t-butoxycarbonyl protecting group
<220> FEATURE:
<221> NAME/KEY: MOD_RES
<222> LOCATION: (5)..(6)
<223> OTHER INFORMATION: tert-butyl protecting group

<400> SEQUENCE: 65

Cys Gly Asn Leu Ser Thr Cys Met Leu Gly
 1               5                  10

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthesized
      peptide
<220> FEATURE:
<221> NAME/KEY: MOD_RES
<222> LOCATION: (2)
<223> OTHER INFORMATION: Residue has Acetamidomethyl or
      tert-Acetaminomethyl or tert-butyl protecting
      group
<220> FEATURE:
<221> NAME/KEY: MOD_RES
<222> LOCATION: (6)
<223> OTHER INFORMATION: Residue has Acetamidomethyl,
      tert-Acetamidomethyl or tert-butyl protecting group
<220> FEATURE:
<221> NAME/KEY: MOD_RES
<222> LOCATION: (9)
<223> OTHER INFORMATION: AMIDATION
```

```
<400> SEQUENCE: 66

Cys Tyr Ile Gln Asn Cys Pro Leu Gly
 1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthesized
      cyclic peptide
<220> FEATURE:
<221> NAME/KEY: MOD_RES
<222> LOCATION: (9)
<223> OTHER INFORMATION: AMIDATION

<400> SEQUENCE: 67

Cys Tyr Ile Gln Asn Cys Pro Leu Gly
 1               5

<210> SEQ ID NO 68
<211> LENGTH: 5
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group
<220> FEATURE:
<221> NAME/KEY: MOD_RES
<222> LOCATION: (5)
<223> OTHER INFORMATION: Where Xaa is beta,beta-dimethyl cysteine

<400> SEQUENCE: 68

Cys His Ala Val Xaa
 1               5

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence:  Cyclic
      Peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group
<220> FEATURE:
<221> NAME/KEY: MOD_RES
<222> LOCATION: (2)
<223> OTHER INFORMATION: Where Xaa is beta,beta-tetramethylene cysteine

<400> SEQUENCE: 69

Ile Xaa Tyr Ser His Ala Val Ser Cys Glu
 1               5                   10

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence:  Cyclic
```

```
        Peptide with classical cadherin cell adhesion
        recognition sequence
<220> FEATURE:
<223> OTHER INFORMATION: Cyclic Peptide may comprise N-terminal
        modification such as acetyl or alkoxybenzyl group
        and/or C-terminal modifications such as amide or
        ester group
<220> FEATURE:
<221> NAME/KEY: MOD_RES
<222> LOCATION: (2)
<223> OTHER INFORMATION: Where Xaa is beta,beta-pentamethylene cysteine

<400> SEQUENCE: 70

Ile Xaa Tyr Ser His Ala Val Ser Ser Cys
 1               5                  10

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence:  Cyclic
        peptide with classical cadherin cell adhesion
        recognition sequence
<220> FEATURE:
<223> OTHER INFORMATION: Cyclic Peptide may comprise N-terminal
        modification such as acetyl or alkoxybenzyl group
        and/or C-terminal modifications such as amide or
        ester group
<220> FEATURE:
<221> NAME/KEY: MOD_RES
<222> LOCATION: (1)
<223> OTHER INFORMATION: Where Xaa is beta-mercaptopropionic acid

<400> SEQUENCE: 71

Xaa Tyr Ser His Ala Val Ser Ser Cys
 1               5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence:  Cyclic
        peptide with classical cadherin cell adhesion
        recognition sequence
<220> FEATURE:
<223> OTHER INFORMATION: Cyclic Peptide may comprise N-terminal
        modification such as acetyl or alkoxybenzyl group
        and/or C-terminal modifications such as amide or
        ester group
<220> FEATURE:
<221> NAME/KEY: MOD_RES
<222> LOCATION: (1)
<223> OTHER INFORMATION: Where Xaa is
        beta,beta-pentamethylene-beta-mercaptopropionic
        acid

<400> SEQUENCE: 72

Xaa Tyr Ser His Ala Val Ser Ser Cys
 1               5

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence:  Cyclic
        peptide with classical cadherin cell adhesion
        recognition sequence
<220> FEATURE:
<221> NAME/KEY: MOD_RES
<222> LOCATION: (4)
```

<223> OTHER INFORMATION: Where Serine is D-Serine

<400> SEQUENCE: 73

His Ala Val Ser Ser
 1               5

<210> SEQ ID NO 74
<211> LENGTH: 4
<212> TYPE: PRT
<213> ORGANISM: Artificial Sequence
<220> FEATURE:
<223> OTHER INFORMATION: Description of Artificial Sequence: Synthesized
      cyclic peptide

<400> SEQUENCE: 74

Trp Gly Gly Trp
 1

<210> SEQ ID NO 75
<211> LENGTH: 15
<212> TYPE: PRT
<213> ORGANISM: Homo sapiens
<220> FEATURE:
<223> OTHER INFORMATION: Description of Artificial Sequence:
      Representative immunogen containing the HAV
      classical cadherin cell adhesion recognition
      sequence
<220> FEATURE:
<223> OTHER INFORMATION: N-cadherin with HAV cell adhesion recognition
      sequence and flanking amino acids

<400> SEQUENCE: 75

Phe His Leu Arg Ala His Ala Val Asp Ile Asn Gly Asn Gln Val
 1               5                  10                  15

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 76

Cys His Ala Val Asp Ile Asn Gly Cys
 1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 77

Ser His Ala Val Asp Ser Ser
 1               5

```
<210> SEQ ID NO 78
<211> LENGTH: 48
<212> TYPE: PRT
<213> ORGANISM: Unknown
<220> FEATURE:
<223> OTHER INFORMATION: Description of Unknown Organism: Occludin cell
      adhesion recognition sequnce and flanking amino
      acids

<400> SEQUENCE: 78

Gly Val Asn Pro Thr Ala Gln Ser Ser Gly Ser Leu Tyr Gly Ser Gln
  1               5                  10                  15

Ile Tyr Ala Leu Cys Asn Gln Phe Tyr Thr Pro Ala Ala Thr Gly Leu
             20                  25                  30

Tyr Val Asp Gln Tyr Leu Tyr His Tyr Cys Val Val Asp Pro Gln Glu
         35                  40                  45

<210> SEQ ID NO 79
<211> LENGTH: 4
<212> TYPE: PRT
<213> ORGANISM: Unknown
<220> FEATURE:
<223> OTHER INFORMATION: Description of Unknown Organism: Cadherin
      Calcium Binding Motif
<220> FEATURE:
<221> NAME/KEY: MOD_RES
<222> LOCATION: (1)
<223> OTHER INFORMATION: Where Xaa is any amino acid
<220> FEATURE:
<221> NAME/KEY: MOD_RES
<222> LOCATION: (3)
<223> OTHER INFORMATION: Where Xaa is any amino acid

<400> SEQUENCE: 79

Xaa Asp Xaa Glu
  1

<210> SEQ ID NO 80
<211> LENGTH: 4
<212> TYPE: PRT
<213> ORGANISM: Unknown
<220> FEATURE:
<223> OTHER INFORMATION: Description of Unknown Organism: Cadherin
      Calcium Binding Motif

<400> SEQUENCE: 80

Asp Val Asn Glu
  1

<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 81

Cys His Ala Val Cys Tyr
  1               5

<210> SEQ ID NO 82
```

```
<211> LENGTH: 7
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 82

Cys Phe Ser His Ala Val Cys
 1               5

<210> SEQ ID NO 83
<211> LENGTH: 8
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 83

Cys Leu Phe Ser His Ala Val Cys
 1               5

<210> SEQ ID NO 84
<211> LENGTH: 6
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 84

Cys His Ala Val Cys Ser
 1               5

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 85

Ser Cys His Ala Val Cys
 1               5

<210> SEQ ID NO 86
<211> LENGTH: 7
<212> TYPE: PRT
<213> ORGANISM: Artificial Sequence
```

```
<220> FEATURE:
<223> OTHER INFORMATION: Description of Artificial Sequence: Cyclic
      Peptide with Classical Cell Adhesion Recognition Sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 86

Cys His Ala Val Cys Ser Ser
 1               5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 87

Ser Cys His Ala Val Cys Ser
 1               5

<210> SEQ ID NO 88
<211> LENGTH: 6
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 88

Cys His Ala Val Cys Thr
 1               5

<210> SEQ ID NO 89
<211> LENGTH: 6
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 89

Cys His Ala Val Cys Glu
 1               5

<210> SEQ ID NO 90
<211> LENGTH: 6
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
```

```
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 90

Cys His Ala Val Cys Asp
 1               5

<210> SEQ ID NO 91
<211> LENGTH: 6
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 91

Cys His Ala Val Tyr Cys
 1               5

<210> SEQ ID NO 92
<211> LENGTH: 5
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group
<220> FEATURE:
<221> NAME/KEY: MOD_RES
<222> LOCATION: (5)
<223> OTHER INFORMATION: Where Xaa is beta,beta-dimethyl cysteine

<400> SEQUENCE: 92

Xaa His Ala Val Cys
 1               5

<210> SEQ ID NO 93
<211> LENGTH: 6
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 93

Cys His Ala Val Pro Cys
 1               5

<210> SEQ ID NO 94
<211> LENGTH: 4
<212> TYPE: PRT
<213> ORGANISM: Artificial Sequence
<220> FEATURE:
<223> OTHER INFORMATION: Description of Artificial Sequence: Cyclic
```

-continued

```
      Peptide with Classical Cell Adhesion Recognition Sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 94

His Ala Val Cys
  1

<210> SEQ ID NO 95
<211> LENGTH: 5
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 95

Gly His Ala Val Cys
  1               5

<210> SEQ ID NO 96
<211> LENGTH: 5
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 96

Asn His Ala Val Cys
  1               5
```

PEPTIDOMIMETIC MODULATORS OF CELL ADHESION

CROSS-REFERENCE TO RELATED APPLICATION

This application is a continuation-in-part of U.S. patent application Ser. No. 09/491,078 filed Jan. 24, 2000, now abandoned, which application is incorporated herein by reference in its entirety.

TECHNICAL FIELD

The present invention relates generally to methods for modulating cell adhesion, and more particularly to peptidomimetics of cyclic peptides comprising a cadherin cell adhesion recognition sequence, and to the use of such peptidomimetics for inhibiting or enhancing cadherin-mediated cell adhesion.

BACKGROUND OF THE INVENTION

Cell adhesion is a complex process that is important for maintaining tissue integrity and generating physical and permeability barriers within the body. All tissues are divided into discrete compartments, each of which is composed of a specific cell type that adheres to similar cell types. Such adhesion triggers the formation of intercellular junctions (i.e., readily definable contact sites on the surfaces of adjacent cells that are adhering to one another), also known as tight junctions, gap junctions and belt desmosomes. The formation of such junctions gives rise to physical and permeability barriers that restrict the free passage of cells and other biological substances from one tissue compartment to another. For example, the blood vessels of all tissues are composed of endothelial cells. In order for components in the blood to enter a given tissue compartment, they must first pass from the lumen of a blood vessel through the barrier formed by the endothelial cells of that vessel. Similarly, in order for substances to enter the body via the gut, the substances must first pass through a barrier formed by the epithelial cells of that tissue. To enter the blood via the skin, both epithelial and endothelial cell layers must be crossed.

Cell adhesion is mediated by specific cell surface adhesion molecules (CAMs). There are many different families of CAMs, including the immunoglobulin, integrin, selectin and cadherin superfamilies, and each cell type expresses a unique combination of these molecules. Cadherins are a rapidly expanding family of calcium-dependent CAMs (Munro et al., *In: Cell Adhesion and Invasion in Cancer Metastasis*, P. Brodt, ed., pp. 17–34, RG Landes Co.(Austin Tex., 1996). The classical cadherins (abbreviated CADs) are integral membrane glycoproteins that generally promote cell adhesion through homophilic interactions (a CAD on the surface of one cell binds to an identical CAD on the surface of another cell), although CADs also appear to be capable of forming heterotypic complexes with one another under certain circumstances and with lower affinity. Cadherins have been shown to regulate epithelial, endothelial, neural and cancer cell adhesion, with different CADs expressed on different cell types. N (neural)-cadherin is predominantly expressed by neural cells, endothelial cells and a variety of cancer cell types. E (epithelial)-cadherin is predominantly expressed by epithelial cells. Other CADs are P (placental)-cadherin, which is found in human skin and R (retinal)-cadherin. A detailed discussion of the classical cadherins is provided in Munro SB et al., 1996, *In: Cell Adhesion and Invasion in Cancer Metastasis*, P. Brodt, ed., pp.17–34 (RG Landes Company, Austin Tex.).

The structures of the CADs are generally similar. As illustrated in FIG. 1, CADs are composed of five extracellular domains (EC1–EC5), a single hydrophobic domain (TM) that transverses the plasma membrane (PM), and two cytoplasmic domains (CP1 and CP2). The calcium binding motifs DXNDN (SEQ ID NO:8), DXD and LDRE (SEQ ID NO:9) are interspersed throughout the extracellular domains. The first extracellular domain (EC1) contains the classical cadherin cell adhesion recognition (CAR) sequence, HAV (His-Ala-Val), along with flanking sequences on either side of the CAR sequence that may play a role in conferring specificity. Synthetic peptides containing the CAR sequence and antibodies directed against the CAR sequence have been shown to inhibit CAD-dependent processes (Munro et al., supra; Blaschuk et al., *J. Mol. Biol.* 211:679–82, 1990; Blaschuk et al., *Develop. Biol.* 139: 227–29, 1990; Alexander et al., *J. Cell. Physiol.* 156: 610–18, 1993). The three-dimensional solution and crystal structures of the EC1 domain have been determined (Overduin et al., *Science* 267:386–389, 1995; Shapiro et al., *Nature* 374:327–337, 1995).

Although cell adhesion is required for certain normal physiological functions, there are situations in which cell adhesion is undesirable. For example, many pathologies (such as autoimmune and inflammatory diseases) involve abnormal cellular adhesion. Cell adhesion may also play a role in graft rejection. In such circumstances, modulation of cell adhesion may be desirable.

In addition, permeability barriers arising from cell adhesion create difficulties for the delivery of drugs to specific tissues and tumors within the body. For example, skin patches are a convenient tool for administering drugs through the skin. However, the use of skin patches has been limited to small, hydrophobic molecules because of the epithelial and endothelial cell barriers. Similarly, endothelial cells render the blood capillaries largely impermeable to drugs, and the blood/brain barrier has hampered the targeting of drugs to the central nervous system. In addition, many solid tumors develop internal barriers that limit the delivery of anti-tumor drugs and antibodies to inner cells.

Attempts to facilitate the passage of drugs across such barriers generally rely on specific receptors or carrier proteins that transport molecules across barriers in vivo. However, such methods are often inefficient, due to low endogenous transport rates or to the poor functioning of a carrier protein with drugs. While improved efficiency has been achieved using a variety of chemical agents that disrupt cell adhesion, such agents are typically associated with undesirable side-effects, may require invasive procedures for administration and may result in irreversible effects. It has been suggested that linear synthetic peptides containing a cadherin CAR sequence may be employed for drug transport (WO 91/04745), but such peptides are often metabolically unstable and are generally considered to be poor therapeutic agents. Peptide agents are generally unsuitable for oral administration.

Accordingly, there is a need in the art for compounds that modulate cell adhesion and improve drug delivery across permeability barriers without such disadvantages. The present invention fulfills this need and further provides other related advantages.

SUMMARY OF THE INVENTION

The present invention provides peptidomimetics of cyclic peptides comprising classical cadherin cell adhesion recognition (CAR) sequences, as well as methods for modulating cadherin-mediated cell adhesion. Within certain aspects, the present invention provides cell adhesion modulating agents that comprise a structure shown in any one of FIGS. 11, 13, 15A–15BG, 17A–17J, 18A–18E, 19A–19E, 21A–21N, 22A–22H, 23A–23F, 24A–24C, 29A–29G, or 31A–31AI. In specific embodiments, a cell adhesion modulating agent comprises a structure provided as any one of compounds 1–12.

Within further aspects, methods are provided for screening a candidate compound for the ability to modulate classical cadherin-mediated cell adhesion, comprising comparing a three-dimensional structure of a candidate compound to a three-dimensional structure of a cyclic peptide that comprises the sequence His-Ala-Val within a cyclic peptide ring, wherein similarity between the structure of the candidate compound and the structure of the cyclic peptide is indicative of the ability of the candidate compound to modulate classical cadherin-mediated cell adhesion. Within certain embodiments, the cyclic peptide has the formula:

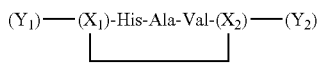

wherein $X_1$, and $X_2$ are independently selected from the group consisting of amino acid residues, with a covalent bond formed between residues $X_1$ and $X_2$; and wherein $Y_1$ and $Y_2$ are optional and, if present, are independently selected from the group consisting of amino acid residues and combinations thereof in which the residues are linked by peptide bonds. Such cyclic peptides include N—Ac—CHAVC—NH$_2$ (SEQ ID NO:10), N—Ac—CHAVDC—NH$_2$ (SEQ ID NO:20), N—Ac—CHAVC—Y—NH$_2$ (SEQ ID NO:81) and N—Ac—CHAVDC—NH$_2$ (SEQ ID NO:36). The step of comparing may be performed, for example, visually or computationally. The candidate compound may, for example, be selected from a database of three-dimensional structures, and the three-dimensional structures of a candidate compound may be determined experimentally or may be computer-generated.

Within further aspects, methods are provided for screening a candidate compound for the ability to modulate classical cadherin-mediated cell adhesion, comprising comparing a two-dimensional structure of a candidate agent to a two-dimensional structure of a compound identified using a method as described above, wherein similarity between the structure of the candidate agent and the structure of the compound is indicative of the ability of the candidate agent to modulate classical cadherin-mediated cell adhesion.

Methods are further provided, within other aspects, for identifying a compound that modulates classical cadherin-mediated cell adhesion, comprising: (a) determining a level of similarity between a three-dimensional structure of a candidate compound and a three-dimensional structure of a cyclic peptide that comprises the sequence His-Ala-Val within a cyclic peptide ring; and (b) identifying an alteration in the structure of the candidate compound that results in a three-dimensional structure with an increased similarity to the three-dimensional structure of the cyclic peptide. Certain such methods further comprise a step of identifying a second alteration in the structure of the candidate compound that results in a three-dimensional structure with a further increased similarity to the three-dimensional structure of the cyclic peptide. The alteration may result, for example, in a change in one or more parameters selected from the group consisting of hydrophobicity, steric bulk, electrostatic properties, size and bond angle.

The present invention further provides a machine-readable data storage medium, comprising a data storage material encoded with a set of NMR derived coordinates that define a three-dimensional structure of a cyclic peptide having the formula:

wherein $X_1$, and $X_2$ are independently selected from the group consisting of amino acid residues, with a covalent bond formed between residues $X_1$ and $X_2$; and wherein $Y_1$ and $Y_2$ are optional and, if present, are independently selected from the group consisting of amino acid residues and combinations thereof in which the residues are linked by peptide bonds. Within certain embodiments, the cyclic peptide is N—Ac—CHAVC—NH$_2$ (SEQ ID NO:10), N—Ac—CHAVDC—NH$_2$ (SEQ ID NO:20), N—Ac—CHAVC—Y—NH$_2$ (SEQ ID NO:81) or N—Ac—CSHAVC—NH$_2$ (SEQ ID NO:36).

The present invention further provides, within other aspects, methods for modulating classical cadherin-mediated intercellular adhesion, comprising contacting a classical cadherin-expressing cell with a cell adhesion modulating agent that comprises a peptidomimetic having a three-dimensional structure that is substantially similar to a three-dimensional structure of a cyclic peptide that comprises the sequence His-Ala-Val within a cyclic peptide ring. Certain specific cyclic peptides are as described above. Within certain embodiments, the peptidomimetic is a compound having a structure provided in any one of FIGS. 11, 13, 15A–15BG, 17A–17J, 18A–18E or 19A–19E, 21A–21N, 22A–22H, 23A–23F, 24A–24C, 29A–29G, 31A–31AI. The cell adhesion modulating agent may be present within a pharmaceutical composition comprising a physiologically acceptable carrier.

Methods are further provided for reducing unwanted cellular adhesion in a mammal, comprising administering to a mammal a cell adhesion modulating agent that inhibits cadherin-mediated cell adhesion, wherein the modulating agent comprises a peptidomimetic having a three-dimensional structure that is substantially similar to a three-dimensional structure of a cyclic peptide that comprises the sequence His-Ala-Val within a cyclic peptide ring. Certain specific cyclic peptides are as described above. Within certain embodiments, the peptidomimetic is a compound having a structure provided in any one of FIGS. 11, 13, 15A–15BG, 17A–17J, 18A–18E or 19A–19E, 21A–21N, 22A–22H, 23A–23F, 24A–24C, 29A–29G, 31A–31AI. The cell adhesion modulating agent may be present within a pharmaceutical composition comprising a physiologically acceptable carrier. The cell adhesion modulating agent may, but need not, be linked to a targeting agent.

Within further aspects, methods are provided for enhancing the delivery of a drug to a tumor in a mammal, comprising administering to a mammal: (a) a cell adhesion modulating agent that inhibits cadherin-mediated cell adhesion, wherein the modulating agent comprises a peptidomimetic having a three-dimensional structure that is substantially similar to a three-dimensional structure of a cyclic peptide that comprises the sequence His-Ala-Val within a cyclic peptide ring; and (b) a drug. Certain specific cyclic peptides are as described above. Within certain embodiments, the peptidomimetic is a compound having a structure provided in any one of FIGS. 11, 13, 15A–15BG, 17A–17J, 18A–18E, 19A–19E, 21A–21N, 22A–22H, 23A–23F, 24A–24C, 29A–29G, 31A–31AI. The cell adhesion modulating agent may be present within a pharmaceutical composition comprising a physiologically acceptable carrier. The cell adhesion modulating agent may, but need not, be linked to a targeting agent and/or to the drug. Tumors include, for example, bladder tumors, ovarian tumors and melanomas. Modulating agent may be administered to the tumor or systemically.

Methods are also provided, within further aspects, for inhibiting the development of a cancer in a mammal, comprising administering to a mammal a cell adhesion modulating agent that inhibits cadherin-mediated cell adhesion, wherein the modulating agent comprises a peptidomimetic having a three-dimensional structure that is substantially similar to a three-dimensional structure of a cyclic peptide that comprises the sequence His-Ala-Val within a cyclic peptide ring. Certain specific cyclic peptides are as described above. Within certain embodiments, the peptidomimetic is a compound having a structure provided in any one of FIGS. 11, 13, 15A–15BG, 17A–17J, 18A–18E or 19A–19E, 21A–21N, 22A–22H, 23A–23F, 24A–24C, 29A–29G, 31A–31AI. The cell adhesion modulating agent may be present within a pharmaceutical composition comprising a physiologically acceptable carrier. The cell adhesion modulating agent may, but need not, be linked to a targeting agent and/or to the drug. Cancers include, for example, carcinomas, leukemias and melanomas.

The present invention further provides methods for inhibiting angiogenesis in a mammal, comprising administering to a mammal a modulating agent that inhibits cadherin-mediated cell adhesion, wherein the modulating agent comprises a peptidomimetic having a three-dimensional structure that is substantially similar to a three-dimensional structure of a cyclic peptide that comprises the sequence His-Ala-Val within a cyclic peptide ring. Certain specific cyclic peptides are as described above. Within certain embodiments, the peptidomimetic is a compound having a structure provided in any one of FIGS. 11, 13, 15A–15BG, 17A–17J, 18A–18E or 19A–19E, 21A–21N, 22A–22H, 23A–23F, 24A–24C, 29A–29G, 31A–31AI. The cell adhesion modulating agent may be present within a pharmaceutical composition comprising a physiologically acceptable carrier. The cell adhesion modulating agent may, but need not, be linked to a targeting agent. Cancers include, for example, carcinomas, leukemias and melanomas.

Methods are further provided for enhancing drug delivery to the central nervous system of a mammal, comprising administering to a mammal a modulating agent that inhibits cadherin-mediated cell adhesion, wherein the modulating agent comprises a peptidomimetic having a three-dimensional structure that is substantially similar to a three-dimensional structure of a cyclic peptide that comprises the sequence His-Ala-Val within a cyclic peptide ring. Certain specific cyclic peptides are as described above. Within certain embodiments, the peptidomimetic is a compound having a structure provided in any one of FIGS. 11, 13, 15A–15BG, 17A–17J, 18A–18E, 19A–19E, 21A–21N, 22A–22H, 23A–23F, 24A–24C, 29A–29G, 31A–31AI. The cell adhesion modulating agent may be present within a pharmaceutical composition comprising a physiologically acceptable carrier. The cell adhesion modulating agent may, but need not, be linked to a targeting agent and/or a drug.

The present invention further provides methods for enhancing wound healing in a mammal, comprising contacting a wound in a mammal with a modulating agent that enhances cadherin-mediated cell adhesion, wherein the modulating agent comprises a peptidomimetic having a three-dimensional structure that is substantially similar to a three-dimensional structure of a cyclic peptide that comprises the sequence His-Ala-Val within a cyclic peptide ring. Certain specific cyclic peptides are as described above. Within certain embodiments, the peptidomimetic is a compound having a structure provided in any one of FIGS. 11, 13, 15A–15BG, 17A–17J, 18A–18E, 19A–19E, 21A–21N, 22A–22H, 23A–23F, 24A–24C, 29A–29G, 31A–31AI. The cell adhesion modulating agent may be present within a pharmaceutical composition comprising a physiologically acceptable carrier. The cell adhesion modulating agent may, but need not, be linked to a targeting agent and/or a support material.

Methods are further provided for enhancing adhesion of foreign tissue implanted within a mammal, comprising contacting a site of implantation of foreign tissue in a mammal with a modulating agent that enhances cadherin-mediated cell adhesion, wherein the modulating agent comprises a peptidomimetic having a three-dimensional structure that is substantially similar to a three-dimensional structure of a cyclic peptide that comprises the sequence His-Ala-Val within a cyclic peptide ring. Certain specific cyclic peptides are as described above. Within certain embodiments, the peptidomimetic is a compound having a structure provided in any one of FIGS. 11, 13, 15A–15BG, 17A–17J, 18A–18E, 19A–19E, 21A–21N, 22A–22H, 23A–23F, 24A–24C, 29A–29G, 31A–31AI. The cell adhesion modulating agent may be present within a pharmaceutical composition comprising a physiologically acceptable carrier. The cell adhesion modulating agent may, but need not, be linked to a targeting agent and/or a support material.

The present invention further provides methods for modulating the immune system of a mammal, comprising administering to a mammal a cell adhesion modulating agent that inhibits cadherin-mediated cell adhesion, wherein the modulating agent comprises a peptidomimetic having a three-dimensional structure that is substantially similar to a three-dimensional structure of a cyclic peptide that comprises the sequence His-Ala-Val within a cyclic peptide ring. Certain specific cyclic peptides are as described above. Within certain embodiments, the peptidomimetic is a compound having a structure provided in any one of FIGS. 11, 13, 15A–15BG, 17A–17J, 18A–18E, 19A–19E, 221A–21N, 22A–22H, 23A–23F, 24A–24C, 29A–29G, 31A–31AI. The cell adhesion modulating agent may be present within a pharmaceutical composition comprising a physiologically acceptable carrier. The cell adhesion modulating agent may, but need not, be linked to a targeting agent.

Methods are further provided, within other aspects, for increasing vasopermeability in a mammal, comprising administering to a mammal a cell adhesion modulating agent that inhibits cadherin-mediated cell adhesion, wherein the modulating agent comprises a peptidomimetic having a three-dimensional structure that is substantially similar to a three-dimensional structure of a cyclic peptide that comprises the sequence His-Ala-Val within a cyclic peptide ring. Certain specific cyclic peptides are as described above. Within certain embodiments, the peptidomimetic is a compound having a structure provided in any one of FIGS. 11, 13, 15A–15BG, 17A–17J, 18A–18E, 19A–19E, 21A–21N, 22A–22H, 23A–23F, 24A–24C, 29A–29G, 31A–31AI. The cell adhesion modulating agent may be present within a pharmaceutical composition comprising a physiologically acceptable carrier.

Within other aspects, the present invention provides methods for treating a demyelinating neurological disease, such as multiple sclerosis, in a mammal, comprising administering to a mammal: (a) a cell adhesion modulating agent that inhibits cadherin-mediated cell adhesion, wherein the modulating agent comprises a peptidomimetic having a three-dimensional structure that is substantially similar to a three-dimensional structure of a cyclic peptide that comprises the sequence His-Ala-Val within a cyclic peptide ring; and (b) one or more cells capable of replenishing an oligodendrocyte population. Certain specific cyclic peptides are as described above. Within certain embodiments, the peptidomimetic is a compound having a structure provided in any one of FIGS. 11, 13, 15A–15BG, 17A–17J, 18A–18E, 19A–19E, 21A–21N, 22A–22H, 23A–23F, 24A–24C, 29A–29G, 31A–31AI. The cell adhesion modulating agent may be present within a pharmaceutical composition comprising a physiologically acceptable carrier. The modulating agent may, but need not, be linked to a targeting agent and/or a drug. Suitable cells include, for example, Schwann cells, oligodendrocyte progenitor cells and oligodendrocytes.

Methods are further provided, within other aspects, for facilitating migration of an N-cadherin expressing cell on astrocytes, comprising contacting an N-cadherin expressing cell with: (a) a cell adhesion modulating agent that inhibits cadherin-mediated cell adhesion, wherein the modulating agent comprises a peptidomimetic having a three-dimensional structure that is substantially similar to a three-dimensional structure of a cyclic peptide that comprises the sequence His-Ala-Val within a cyclic peptide ring; and (b) one or more astrocytes. Certain specific cyclic peptides are as described above. Within certain embodiments, the peptidomimetic is a compound having a structure provided in any one of FIGS. 11, 13, 15A–15BG, 17A–17J, 18A–18E, 19A–19E, 21A–21N, 22A–22H, 23A–23F, 24A–24C, 29A–29G, 31A–31AI. The cell adhesion modulating agent may be present within a pharmaceutical composition comprising a physiologically acceptable carrier. The agent may, but need not, be linked to a targeting agent. The N-cadherin expressing cells may be, for example, a Schwann cell, oligodendrocyte progenitor cell or oligodendrocyte.

The present invention further provides methods for inhibiting synaptic stability in a mammal, comprising administering to a mammal a cell adhesion modulating agent that inhibits cadherin-mediated cell adhesion, wherein the modulating agent comprises a peptidomimetic having a three-dimensional structure that is substantially similar to a three-dimensional structure of a cyclic peptide that comprises the sequence His-Ala-Val within a cyclic peptide ring. Certain specific cyclic peptides are as described above. Within certain embodiments, the peptidomimetic is a compound having a structure provided in any one of FIGS. 11, 13, 15A–15BG, 17A–17J, 18A–18E, 19A–19E, 21A–21N, 22A–22H, 23A–23F, 24A–24C, 29A–29G, 31A–31AI. The cell adhesion modulating agent may be present within a pharmaceutical composition comprising a physiologically acceptable carrier.

Within further aspects, methods are provided for modulating neurite outgrowth, comprising contacting a neuron with a modulating agent that comprises a peptidomimetic having a three-dimensional structure that is substantially similar to a three-dimensional structure of a cyclic peptide that comprises the sequence His-Ala-Val within a cyclic peptide ring. Certain specific cyclic peptides are as described above. Within certain embodiments, the peptidomimetic is a compound having a structure provided in any one of FIGS. 11, 13, 15A–15BG, 17A–17J, 18A–18E, 19A–19E, 21A–21N, 22A–22H, 23A–23F, 24A–24C, 29A–29G, 31A–31AI. The cell adhesion modulating agent may be present within a pharmaceutical composition comprising a physiologically acceptable carrier. The agent may, but need not, be linked to a targeting agent and/or a drug. Neurite outgrowth may, within different embodiments, be inhibited or enhanced, and/or may be directed.

The present invention further provides, within other aspects, methods for treating spinal cord injuries in a mammal, comprising administering to a mammal a cell adhesion modulating agent that enhances neurite outgrowth, wherein the modulating agent comprises a peptidomimetic having a three-dimensional structure that is substantially similar to a three-dimensional structure of a cyclic peptide that comprises the sequence His-Ala-Val within a cyclic peptide ring. Certain specific cyclic peptides are as described above. Within certain embodiments, the peptidomimetic is a compound having a structure provided in any one of FIGS. 11, 13, 15A–15BG, 17A–17J, 18A–18E, 19A–19E, 21A–21N, 22A–22H, 23A–23F, 24A–24C, 29A–29G, 31A–31AI. The cell adhesion modulating agent may be present within a pharmaceutical composition comprising a physiologically acceptable carrier. The agent may, but need not, be linked to a targeting agent and/or a drug. Neurite outgrowth may, within different embodiments, be inhibited or enhanced, and/or directed.

Within other aspects, methods are provided for treating macular degeneration in a mammal, comprising administering to a mammal a cell adhesion modulating agent that enhances classical cadherin-mediated cell adhesion, wherein the modulating agent comprises a peptidomimetic having a three-dimensional structure that is substantially similar to a three-dimensional structure of a cyclic peptide that comprises the sequence His-Ala-Val within a cyclic peptide ring. Certain specific cyclic peptides are as described above. Within certain embodiments, the peptidomimetic is a compound having a structure provided in any one of FIGS. 11, 13, 15A–15BG, 17A–17J, 18A–18E, 19A–19E, 21A–21N, 22A–22H, 23A–23F, 24A–24C, 29A–29G, 31A–31AI. The cell adhesion modulating agent may be present within a pharmaceutical composition comprising a physiologically acceptable carrier. The agent may, but need not, be linked to a targeting agent and/or a drug.

Within further aspects, kits are provided for administering a drug via the skin of a mammal, comprising: (a) a skin patch; and (b) a cell adhesion modulating agent comprising a peptidomimetic having a three-dimensional structure that is substantially similar to a three-dimensional structure of a cyclic peptide that comprises the sequence His-Ala-Val within a cyclic peptide ring. Certain specific cyclic peptides are as described above. Within certain embodiments, the peptidomimetic is a compound having a structure provided in any one of FIGS. 11, 13, 15A–15BG, 17A–17J, 18A–18E, 19A–19E, 21A–21N, 22A–22H, 23A–23F, 24A–24C, 29A–29G, 31A–31AI.

Methods are further provided for evaluating a peptidomimetic for the ability to modulate classical cadherin-mediated cell adhesion. Certain such methods comprise: (a) culturing neurons on a monolayer of cells that express N-cadherin in the presence and absence of a peptidomimetic, under conditions and for a time sufficient to allow neurite outgrowth, wherein the peptidomimetic has a three-dimensional structure that is substantially similar to a three-dimensional structure of a cyclic peptide that comprises the sequence His-Ala-Val within a cyclic peptide ring; (b) determining a mean neurite length for said neurons; and (c) comparing the mean neurite length for neurons cultured in the presence of peptidomimetic to the neurite length for neurons cultured in the absence of the peptidomimetic, and therefrom determining whether the peptidomimetic modulates classical cadherin-mediated cell adhesion.

Within further aspects, other such methods comprise: (a) culturing cells that express a classical cadherin in the presence and absence of a peptidomimetic, under conditions and for a time sufficient to allow cell adhesion, wherein the peptidomimetic has a three-dimensional structure that is substantially similar to a three-dimensional structure of a cyclic peptide that comprises the sequence His-Ala-Val within a cyclic peptide ring; and (b) visually evaluating the extent of cell adhesion among said cells, and therefrom identifying a peptidomimetic capable of modulating cell adhesion. The cells may be, for example, endothelial, epithelial or cancer cells.

Still further such methods comprise: (a) culturing NRK cells in the presence and absence of a peptidomimetic, under conditions and for a time sufficient to allow cell adhesion, wherein the peptidomimetic has a three-dimensional structure that is substantially similar to a three-dimensional structure of a cyclic peptide that comprises the sequence His-Ala-Val within a cyclic peptide ring; and (b) comparing the level of cell surface E-cadherin for cells cultured in the presence of the peptidomimetic to the level for cells cultured in the absence of the peptidomimetic, and therefrom determining whether the peptidomimetic modulates cell adhesion.

Still further such methods comprise: (a) contacting an epithelial surface of skin with a test marker in the presence and absence of a peptidomimetic, wherein the peptidomimetic has a three-dimensional structure that is substantially similar to a three-dimensional structure of a cyclic peptide that comprises the sequence His-Ala-Val within a cyclic peptide ring; and (b) comparing the amount of test marker that passes through said skin in the presence of the peptidomimetic to the amount that passes through skin in the absence of the peptidomimetic, and therefrom determining whether the peptidomimetic modulates cell adhesion.

Within further such aspects, the methods comprise: (a) contacting a blood vessel with a peptidomimetic, wherein the peptidomimetic has a three-dimensional structure that is substantially similar to a three-dimensional structure of a cyclic peptide that comprises the sequence His-Ala-Val within a cyclic peptide ring; and (b) comparing the extent of angiogenesis of the blood vessel to a predetermined extent of angiogenesis observed for a blood vessel in the absence of the peptidomimetic, and therefrom determining whether the peptidomimetic modulates cell adhesion.

These and other aspects of the invention will become evident upon reference to the following detailed description and attached drawings. All references disclosed herein are hereby incorporated by reference in their entirety as if each were individually noted for incorporation.

BRIEF DESCRIPTION OF THE DRAWINGS

FIG. 2 provides the amino acid sequences of mammalian classical cadherin EC1 domains: human N-cadherin (SEQ ID NO:1), mouse N-cadherin (SEQ ID NO:2), cow N-cadherin (SEQ ID NO:3), human P-cadherin (SEQ ID NO:4), mouse P-cadherin (SEQ ID NO:5), human E-cadherin (SEQ ID NO:6) and mouse E-cadherin (SEQ ID NO:7).

FIG. 12B presents the structure of compound 4 and a low energy conformation of compound 4 derived from cyclization of a key element of N—Ac—CHAVC—NH$_2$ (SEQ ID NO:10).

FIGS. 13A–13B depict representative peptidomimetics derived from library synthesis using hydantoin or oxopiperazine backbones (compounds 5–12).

CHAVC—NH$_2$ (SEQ ID NO:10), and used in chemical database searches. FIG. 14A depicts the three dimensional structure of the HAV region of N—Ac—CHAVC—NH$_2$ (SEQ ID NO:10), with distances used in the pharmacophore queries indicated. FIGS. 14B and 14C depict the five pharmacophore queries derived from the pharmacophore in N—Ac—CHAVC—NH$_2$ (SEQ ID NO:10) and used in chemical database searches.

FIGS. 17A–17J depict structures of representative non-peptidyl analogues of N—Ac—CHAVC—Y—NH$_2$ (SEQ ID NO:81) derived from 3D-pharmacophore database searching using the pharmacophore query depicted in FIG. 16 (compounds 283–311).

FIGS. 18A–18E depict structures of representative non-peptidyl analogues of the active compound 35, as identified by a two-dimensional similarity search (compounds 312–331).

FIGS. 19A–19E depict structures of representative non-peptidyl analogues of the active compound 47, as identified by a two-dimensional similarity search (compounds 332–344).

FIGS. 22A–22H depict structures of representative non-peptidyl analogues of the active compound 65, as identified by a two-dimensional similarity search.

FIGS. 23A–23F depict structures of representative non-peptidyl analogues of the active compound 184, as identified by a two-dimensional similarity search (compounds 400–433).

FIGS. 29A–29G depicts structures of representative non-peptidyl analogues of N—Ac—CHAVC—Y—NH$_2$ (SEQ ID NO:81) derived from 3D-pharmacophore database searching using the pharmacophore query depicted in FIG. 25 (compounds 465–481).

DETAILED DESCRIPTION OF THE INVENTION

Figure 1:
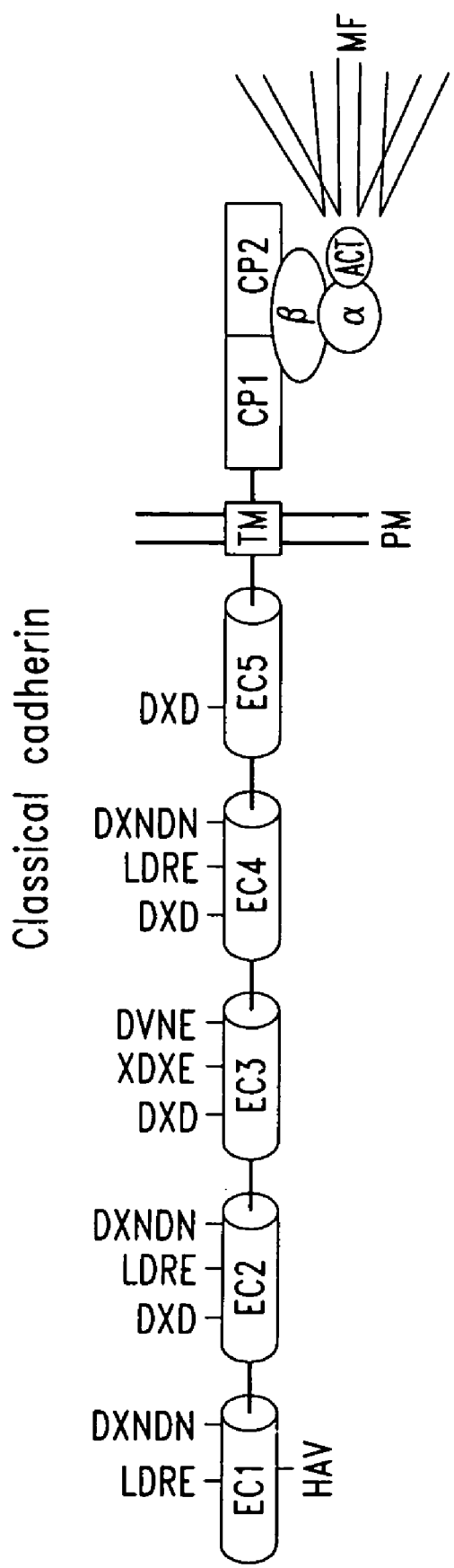
FIG. 1 is a diagram depicting the structure of classical CADs. The five extracellular domains are designated EC1–EC5, the hydrophobic domain that transverses the plasma membrane (PM) is represented by TM, and the two cytoplasmic domains are represented by CP1 and CP2. The calcium binding motifs are shown by DXNDN (SEQ ID NO:8), DXD, LDRE (SEQ ID NO:9), XDXE (SEQ ID NO:79) and DVNE (SEQ ID NO:80). The CAR sequence, HAV, is shown within EC1. Cytoplasmic proteins β-catenin (β), α-catenin (α) and α-actinin (ACT), which mediate the interaction between CADs and microfilaments (MF) are also shown.
Figure 3A:
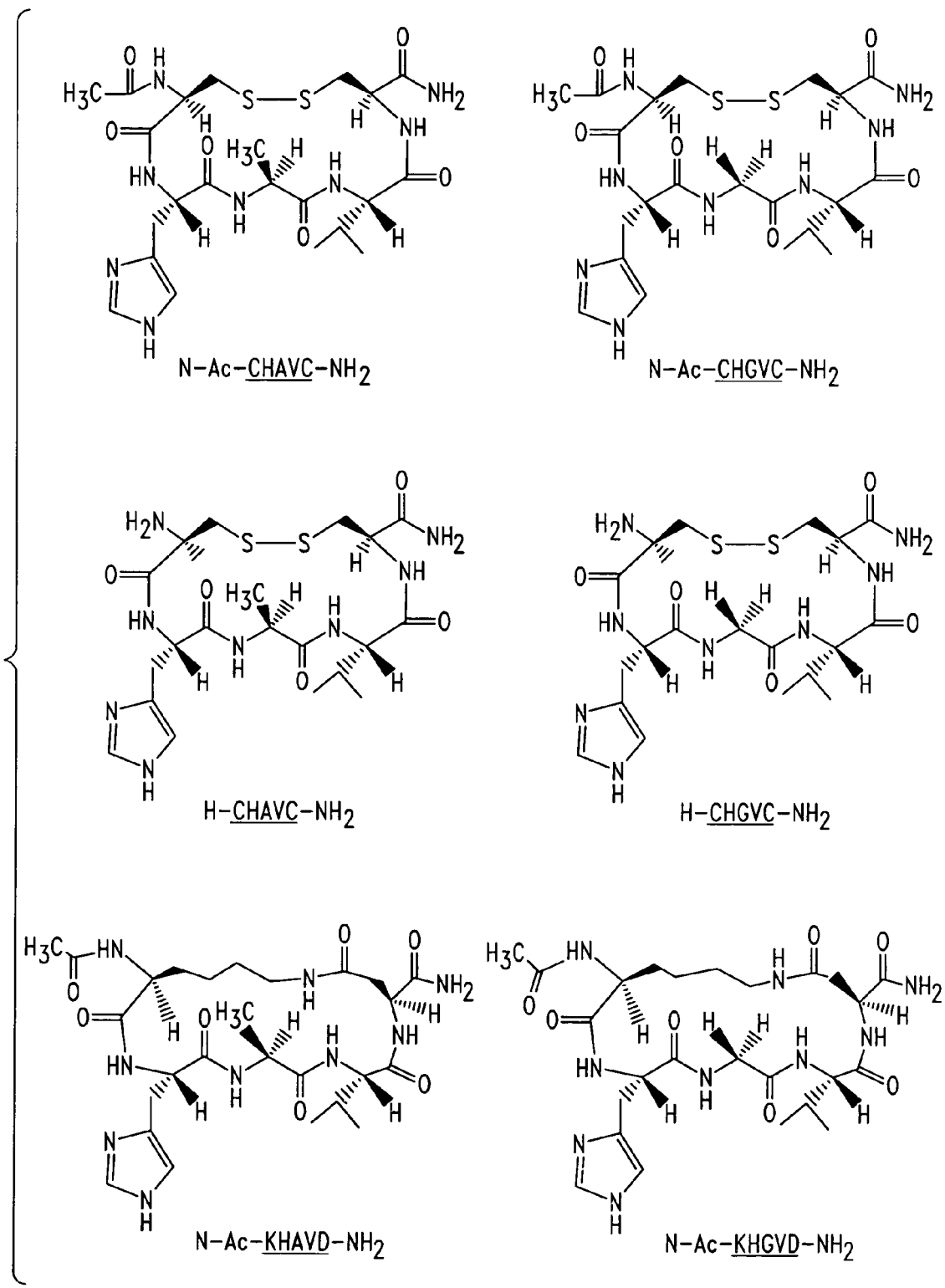
FIGS. 3A–3I provides the structures of representative cyclic peptides comprising a classical cadherin CAR sequence (structures on the left hand side; SEQ ID Nos. 10, 12, 14, 16, 18, 20, 22, 24, 26, 28, 30, 32, 34, 36, 38, 40, 42, 44, 46 and 48), along with similar, but inactive, structures (on the right; SEQ ID Nos. 11, 13, 15, 17, 19, 21, 23, 25, 27, 29, 31, 33, 35, 37, 39, 41, 43, 45, 47 and 49).
Figure 3B:
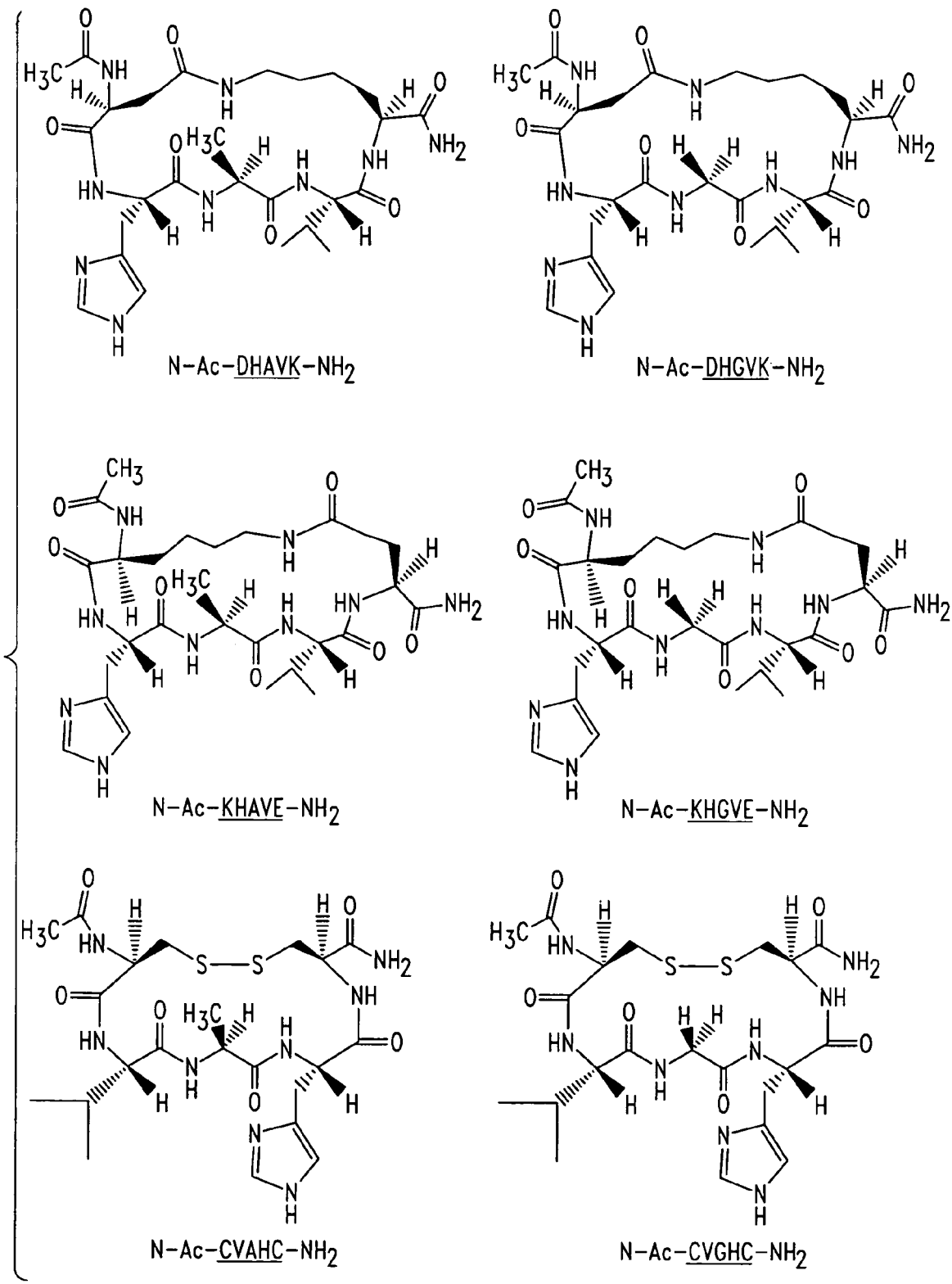
Figure 3C:
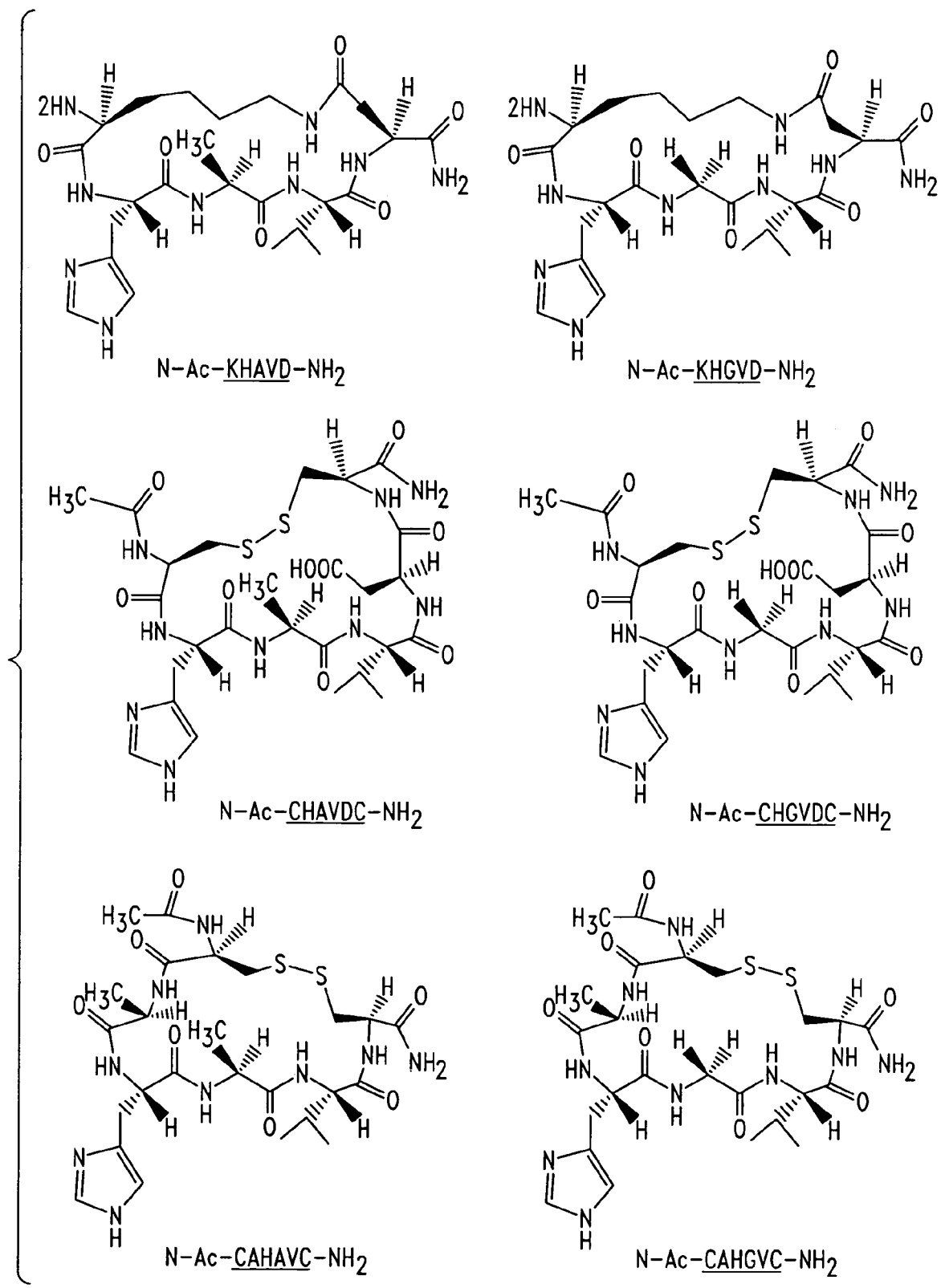
Figure 3D:
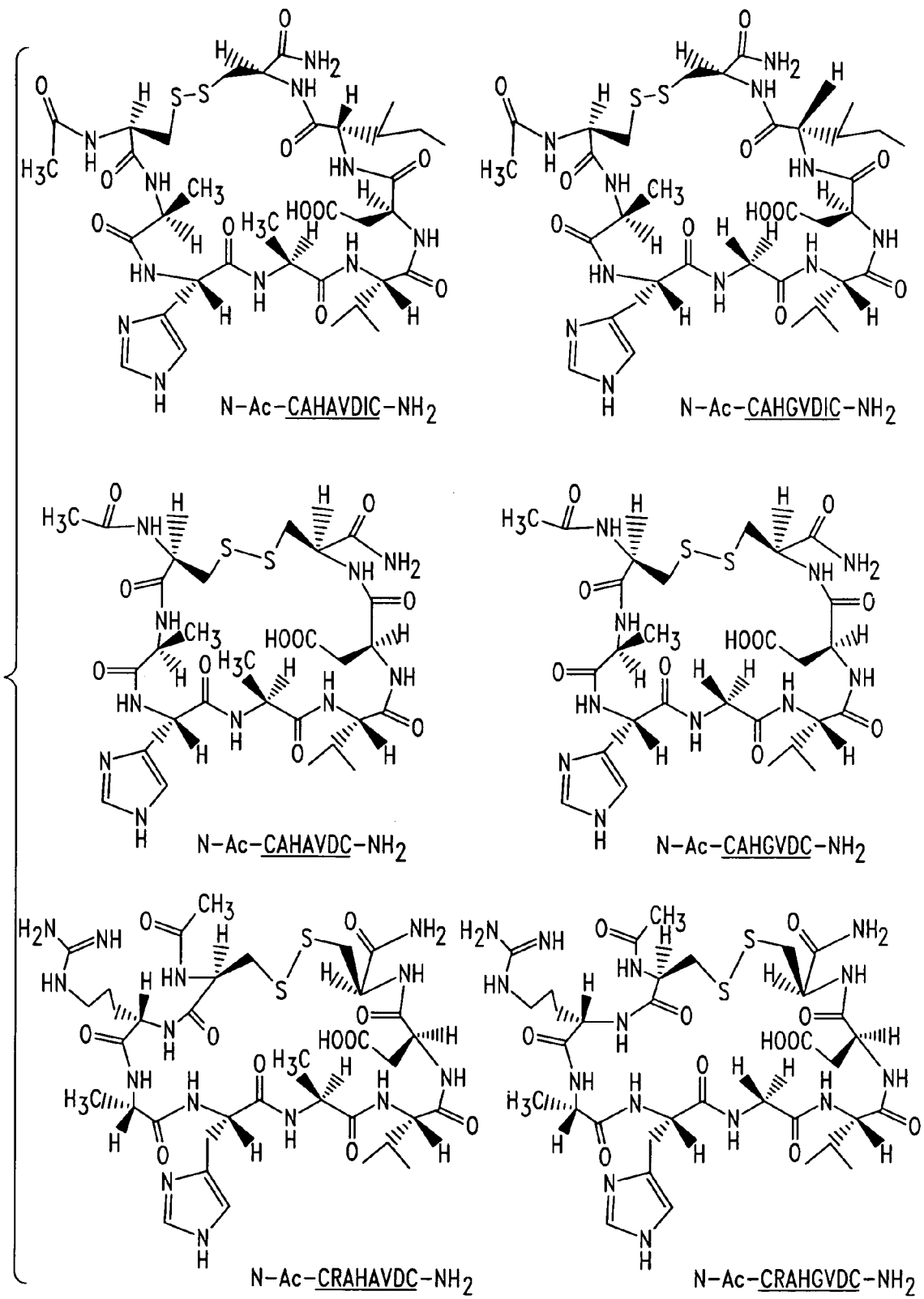
Figure 3E:
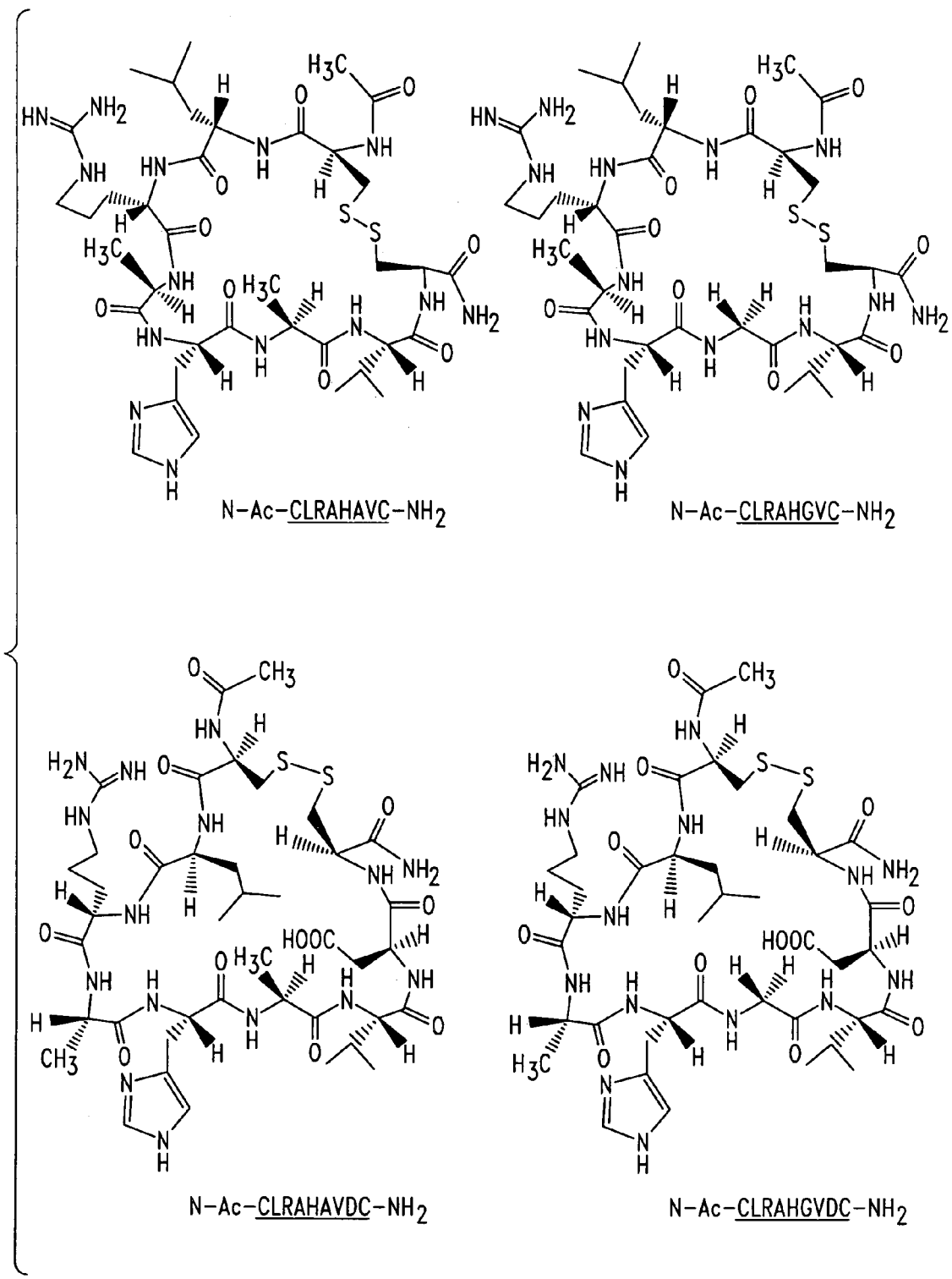
Figure 3F:
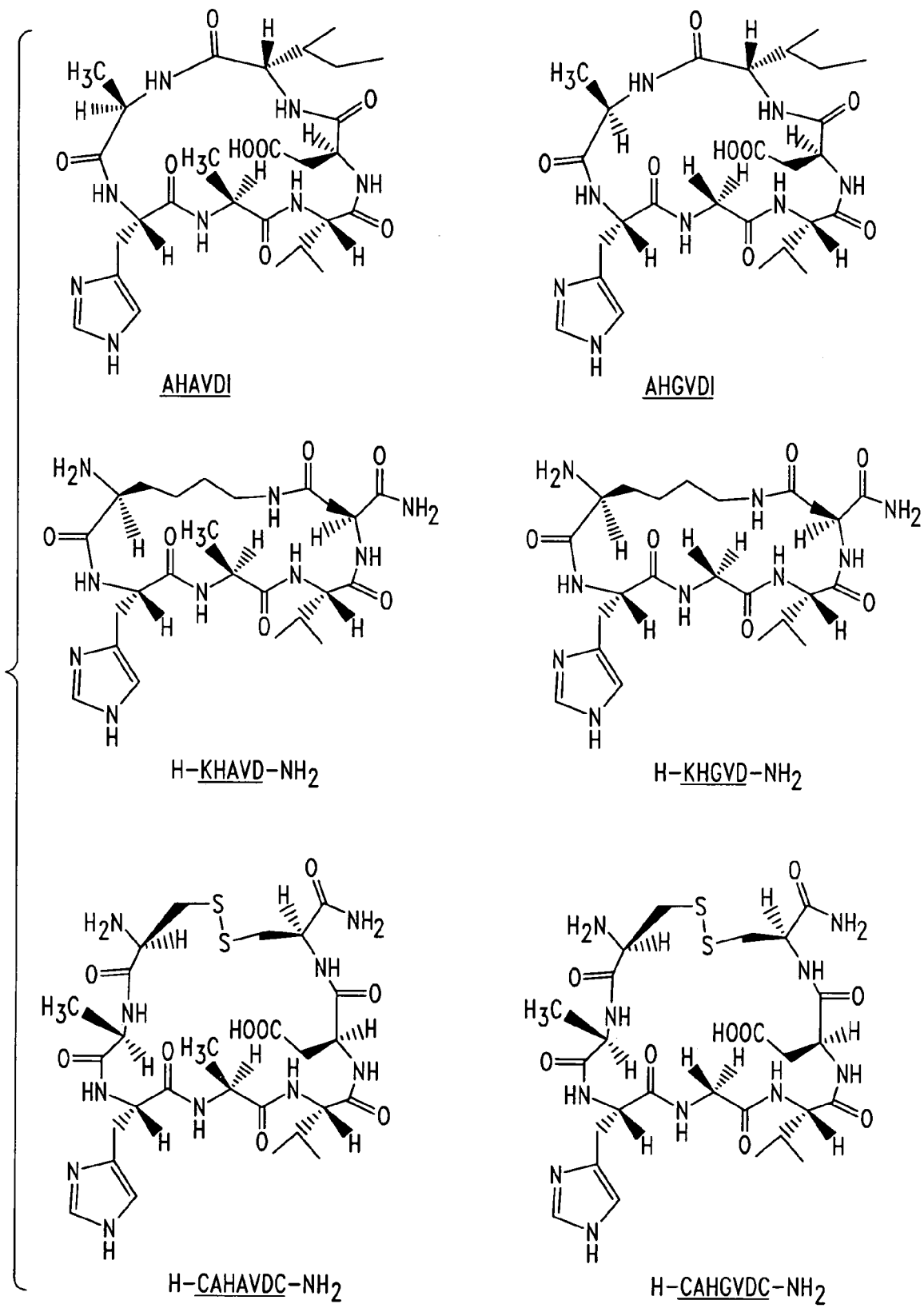
Figure 3G:
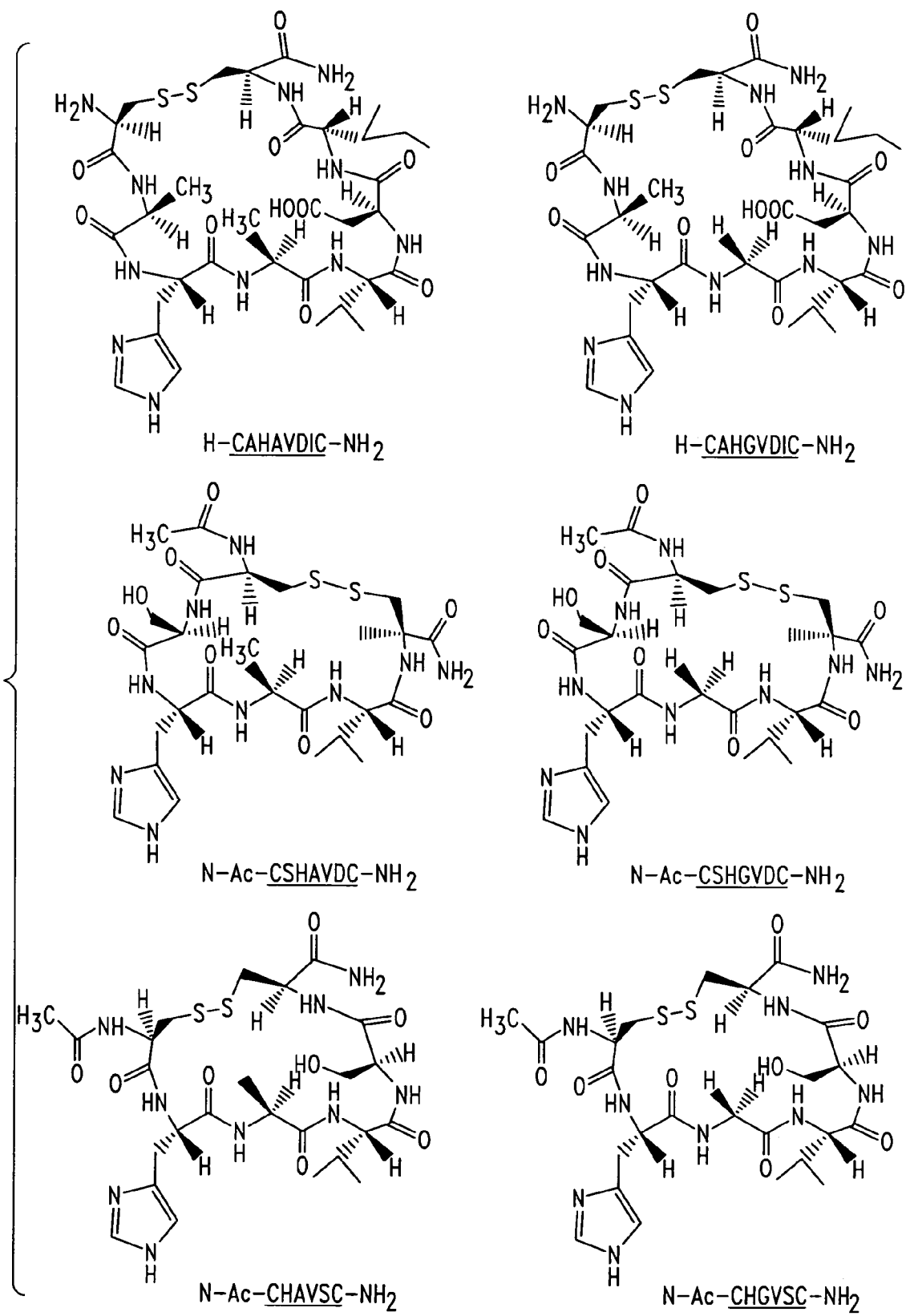
Figure 3H:
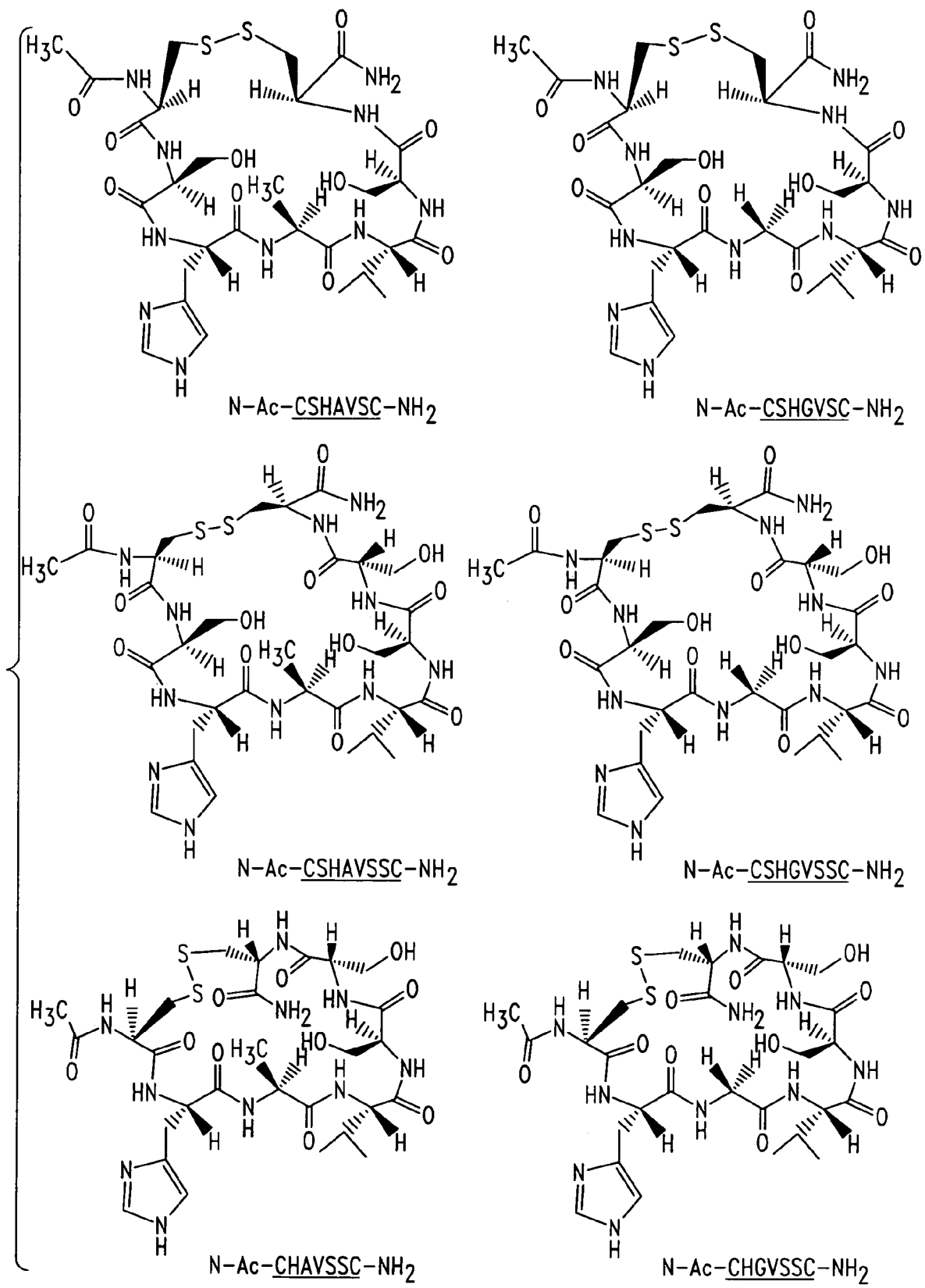
Figure 3I:
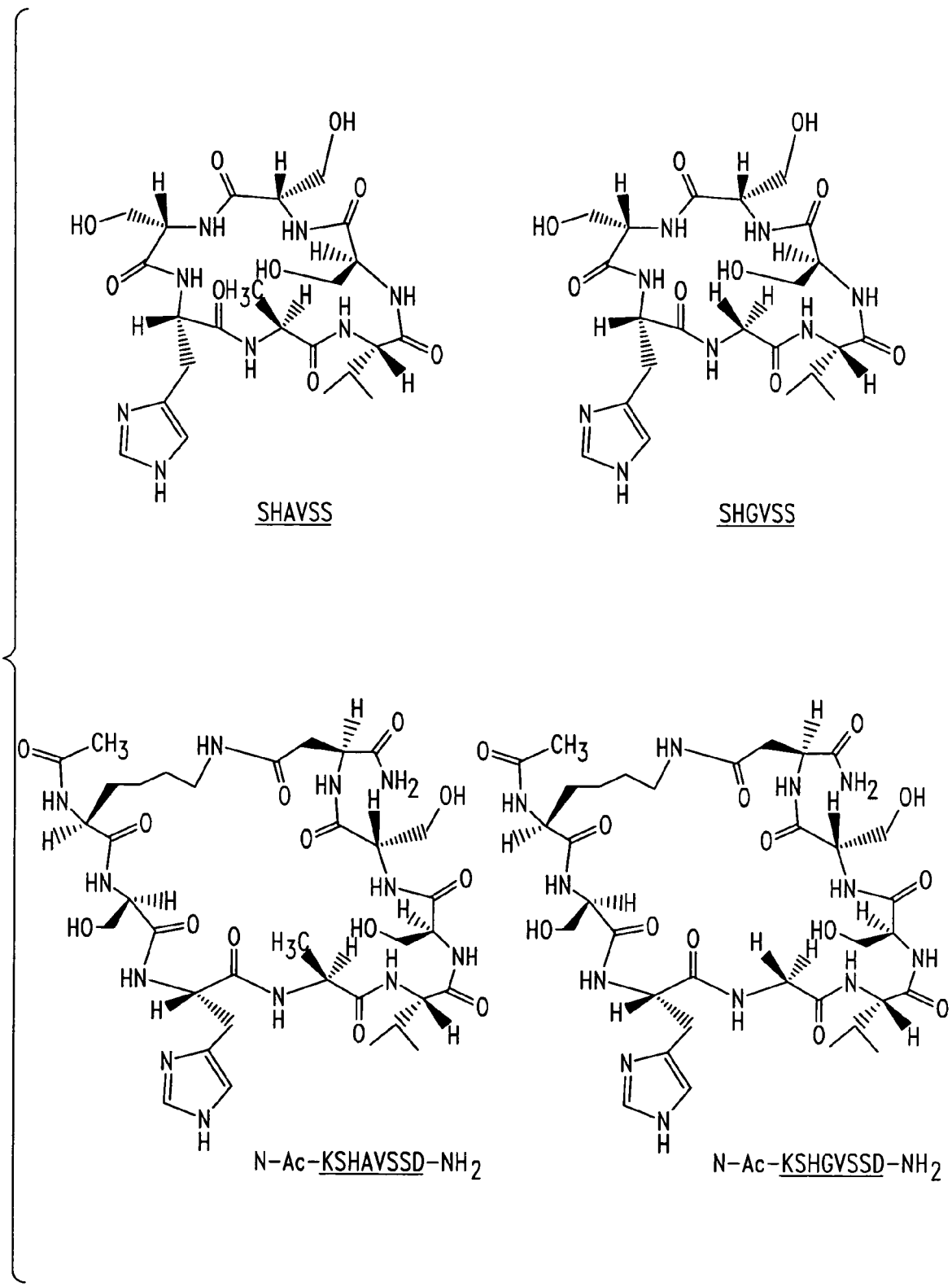

As noted above, the present invention provides cell adhesion modulating agents comprising peptidomimetics that are capable of modulating classical cadherin-mediated processes, such as cell adhesion. The peptidomimetics provided herein may be peptide or non-peptidyl analogues of cyclic peptides that contain the classical cadherin cell adhesion recognition (CAR) sequence HAV (i.e., His-Ala-Val) within the peptide ring. Peptidomimetics do not contain the sequence HAV (although a peptidomimetic may contain a portion of this sequence), but substantially retain the three-dimensional conformation of such a cyclic peptide, as well as the ability to modulate a classical cadherin-mediated process.

Certain modulating agents described herein inhibit cell adhesion. Such modulating agents may generally be used, for example, to treat diseases or other conditions characterized by undesirable cell adhesion or to facilitate drug delivery to a specific tissue or tumor. Alternatively, certain modulating agents may be used to enhance cell adhesion (e.g., to supplement or replace stitches or to facilitate wound healing) or to enhance or direct neurite outgrowth.

Cyclic Peptides

Peptidomimetics provided herein are derived from cyclic peptides. Such cyclic peptides are generally as described in PCr publication WO 98/02452. The term "cyclic peptide," as used herein, refers to a peptide or salt thereof that comprises (1) an intramolecular covalent bond between two non-adjacent residues and (2) at least one classical cadherin cell adhesion recognition (CAR) sequence HAV (His-Ala-Val). The intramolecular bond may be a backbone to backbone, side-chain to backbone or sidechain to side-chain bond (i.e., terminal functional groups of a linear peptide and/or side chain functional groups of a terminal or interior residue may be linked to achieve cyclization). Preferred intramolecular bonds include, but are not limited to, disulfide, amide and thioether bonds. Preferred cyclic peptides for use in designing a peptidomimetic satisfy the formula:

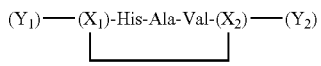

wherein $X_1$, and $X_2$ are independently selected from the group consisting of amino acid residues, with a covalent bond formed between residues $X_1$ and $X_2$; and wherein $Y_1$ and $Y_2$ are optional and, if present, are independently selected from the group consisting of amino acid residues and combinations thereof in which the residues are linked by peptide bonds.

Within certain embodiments, a cyclic peptide preferably comprises an Nacetyl group (i.e., the amino group present on the amino terminal residue of the peptide prior to cyclization is acetylated) or an N-formyl group (i.e., the amino group present on the amino terminal residue of the peptide prior to cyclization is formylated), or the amino group present on the amino terminal residue of the peptide prior to cyclization is mesylated. It has been found, within the context of the present invention, that the presence of such terminal groups may enhance cyclic peptide activity for certain applications. One particularly preferred cyclic peptide is N—Ac—CHAVC—NH$_2$ (SEQ ID NO:10). Another preferred cyclic peptide is N—Ac—CHAVC—Y—NH$_2$ (SEQ ID NO:81), and N—Ac—CHAVDC—NH$_2$ (SEQ ID NO:20) and N—Ac—CSHAVC—NH$_2$ (SEQ ID NO:36) are also preferred. Other cyclic peptides include, but are not limited to: N—Ac—CHAVDIC—NH$_2$ (SEQ ID NO:50), N—Ac—CHAVDINC—NH$_2$ (SEQ ID NO:51), N—Ac—CHAVDINGC—NH$_2$ (SEQ ID NO:76), N—Ac—CAHAVC—NH$_2$ (SEQ ID NO:22), N—Ac—CAHAVDC—NH$_2$ (SEQ ID NO:26), N—Ac—CAHAVDIC—NH$_2$ (SEQ ID NO:24), N—Ac—CRAHAVDC—NH$_2$ (SEQ ID NO:28), N—Ac—CLRAHAVC—NH$_2$ (SEQ ID NO:30), N—Ac—CLRAHAVDC—NH$_2$ (SEQ ID NO:32), N—Ac—CFSHAVC—NH$_2$ (SEQ ID NO:82), N—Ac—CLFSHAVC—NH$_2$ (SEQ ID NO:83), N—Ac—CHAVSC—NH$_2$ (SEQ ID NO:38), N—Ac—CSHAVSC—NH$_2$ (SEQ ID NO:40), N—Ac—CSHAVSSC—NH$_2$ (SEQ ID NO:42), N—Ac—CHAVSSC—NH$_2$ (SEQ ID NO:44), N—Ac—KHAVD—NH$_2$ (SEQ ID NO:12), N—Ac—DHAVK—NH$_2$ (SEQ ID NO:14), N—Ac—KHAVE-NH$_2$ (SEQ ID NO:16), N—Ac—AHAVDI—NH$_2$ (SEQ ID NO:34), N—Ac—SHAVDSS—NH$_2$ (SEQ ID NO:77), N—Ac—KSHAVSSD—NH$_2$ (SEQ ID NO:48), N—Ac—CHAVC—S—NH$_2$ (SEQ ID NO:84), N—Ac—S—CHAVC—NH$_2$ (SEQ ID NO:85), N—Ac—CHAVC—SS—NH$_2$ (SEQ ID NO:86), N—Ac—S—CHAVC—S—NH$_2$ (SEQ ID NO:87), N—Ac—CHAVC-T-NH$_2$ (SEQ ID NO:88), N—Ac—CHAVC-E-NH$_2$ (SEQ ID NO:89), N—Ac—CHAVC-D-NH$_2$ (SEQ ID NO:90), N—Ac—CHAVYC—NH$_2$ (SEQ ID NO:91), CH$_3$—SO$_2$—HN—CHAVC—Y—NH$_2$ (SEQ ID NO:81; formed by mesylation of N—Ac—CHAVC—Y—NH$_2$ (SEQ ID NO:81)), CH$_3$—SO$_2$—HN—CHAVC—NH$_2$ (SEQ ID NO:10; formed by mesylation of N—Ac—CHAVC—NH$_2$ (SEQ ID NO:10)), HC(O)—NH—CHAVC—NH$_2$ (SEQ ID NO:10; formed by formylation of N—Ac—CHAVC—NH$_2$ (SEQ ID NO:10)), N—Ac—CHAVPen-NH$_2$ (SEQ ID NO:68), N—Ac-PenHAVC—NH$_2$ (SEQ ID NO:92) and N—Ac—CHAVPC—NH$_2$ (SEQ ID NO:93). In the foregoing cyclic peptides, the underlined portion is cyclized, "Pen" is penicillamine, "N—Ac" indicates an acetylated N-terminal amino group, and "NH" indicates the terminal amino group in which N is covalently linked to hydrogen.

In addition to the CAR sequence(s), cyclic peptides generally comprise at least one additional residue, such that the size of the cyclic peptide ring ranges from 4 to about 15 residues, preferably from 5 to 10 residues. Such additional residue(s) may be present on the N-terminal and/or C-terminal side of a CAR sequence, and may be derived from sequences that flank the HAV sequence within one or more naturally occurring cadherins (e.g., N-cadherin, E-cadherin, P-cadherin, R-cadherin or other cadherins containing the HAV sequence) with or without amino acid substitutions and/or other modifications. Flanking sequences for endogenous N—, E-, P— and R-cadherin are shown in FIG. 2, and in SEQ ID NOs:1–7. Database accession numbers for representative naturally occurring cadherins are as follows: human N-cadherin M34064, mouse N-cadherin M31131 and M22556, cow N-cadherin X53615, human P-cadherin X63629, mouse P-cadherin X06340, human E-cadherin Z13009, mouse E-cadherin X06115. Alternatively, additional residues present on one or both sides of the CAR sequence(s) may be unrelated to an endogenous sequence (e.g., residues that facilitate cyclization).

Within certain preferred embodiments, as discussed below, relatively small cyclic peptides that do not contain significant sequences flanking the HAV sequence are preferred for use in designing peptidomimetics. Such peptides may contain an N-acetyl group and a C-amide group (e.g., the 5-residue rings N—Ac—CHAVC—NH$_2$ (SEQ ID NO:10), N—Ac—KHAVD—NH$_2$ (SEQ ID NO:12), H—C(O)—CHAVC—NH$_2$ (SEQ ID NO:10), CH$_3$—SO$_2$—NH—CHAVC—NH$_2$ (SEQ ID NO:10), N—Ac—CHAVC—Y—NH$_2$ (SEQ ID NO:81), H—C(O)—CHAVC—Y—NH$_2$ (SEQ ID NO:81) or CH$_3$—SO$_2$—NH—CHAVC—Y—NH$_2$ (SEQ ID NO:81)).

Within other preferred embodiments, a cyclic peptide may contain sequences that flank the HAV sequence on one or both sides that are designed to confer specificity for cell adhesion mediated by one or more specific cadherins, resulting in a conformation that provides tissue and/or cell-type specificity. Suitable flanking sequences for conferring specificity include, but are not limited to, endogenous sequences present in one or more naturally occurring cadherins, and cyclic peptides having specificity may be identified using the representative screens provided herein. For example, it has been found, within the context of the present invention, that cyclic peptides that contain additional residues derived from the native E-cadherin sequence on the N-terminal side of the CAR sequence are specific for epithelial cells (i.e., such peptides disrupt E-cadherin mediated cell adhesion to a greater extent than they disrupt N-cadherin expression). The addition of appropriate endogenous sequences may similarly result in peptides that disrupt N-cadherin mediated cell adhesion. For example, it has been found within the context of the present invention that the addition of one or more amino acid residues on the C-terminal side of the HAV sequence in an endogenous N-cadherin results in cyclic peptides that are potent inhibitors of neurite outgrowth. Peptidomimetics that are designed based on such cyclic peptides may display the specificity of the base cyclic peptide.

Cyclic peptides as described herein may comprise residues of L-amino acids, D-amino acids, or any combination thereof. Amino acids may be from natural or non-natural sources, provided that at least one amino group and at least one carboxyl group are present in the molecule; α- and β-amino acids are generally preferred. The 20 L-amino acids commonly found in proteins are identified herein by the conventional three-letter or one-letter abbreviations indicated in Table 1, and the corresponding D-amino acids are designated by a lower case one letter symbol. Cyclic peptides may also contain one or more rare amino acids (such as 4-hydroxyproline or hydroxylysine), organic acids or amides and/or derivatives of common amino acids, such as amino acids having the C-terminal carboxylate esterified (e.g. benzyl, methyl or ethyl ester) or amidated and/or having modifications of the N-terminal amino group (e.g., acetylation or alkoxycarbonylation), with or without any of a wide variety of side-chain modifications and/or substitutions (e.g., methylation, benzylation, t-butylation, tosylation, alkoxycarbonylation, and the like). Preferred derivatives include amino acids having an N-acetyl group (such that the amino group that represents the N-terminus of the linear peptide prior to cyclization is acetylated) and/or a C-terminal amide group (i.e., the carboxy terminus of the linear peptide prior to cyclization is amidated). Residues other than common amino acids that may be present with a cyclic peptide include, but are not limited to, penicillamine, β,β-tetramethylene cysteine, β,β-pentamethylene cysteine, β-mercaptopropionic acid, β,β-pentamethylene-β-mercaptopropionic acid, 2-mercaptobenzene, 2-mercaptoaniline, 2-mercaptoproline, ornithine, diaminobutyric acid, α-aminoadipic acid, m-aminomethylbenzoic acid and α,β-diaminopropionic acid.

TABLE 1

| Amino acid one-letter and three-letter abbreviations | | |
|---|---|---|
| A | Ala | Alanine |
| R | Arg | Arginine |
| D | Asp | Aspartic acid |
| N | Asn | Asparagine |
| C | Cys | Cysteine |
| Q | Gln | Glutamine |
| E | Glu | Glutamic acid |
| G | Gly | Glycine |
| H | His | Histidine |
| I | Ile | Isoleucine |
| L | Leu | Leucine |
| K | Lys | Lysine |
| M | Met | Methionine |
| F | Phe | Phenylalanine |
| P | Pro | Proline |
| S | Ser | Serine |
| T | Thr | Threonine |
| W | Trp | Tryptophan |
| Y | Tyr | Tyrosine |
| V | Val | Valine |

Cyclic peptides as described herein may be synthesized by methods well known in the art, including recombinant DNA methods and chemical synthesis. Chemical synthesis may generally be performed using standard solution phase or solid phase peptide synthesis techniques, in which a peptide linkage occurs through the direct condensation of the α-amino group of one amino acid with the α-carboxy group of the other amino acid with the elimination of a water molecule. Peptide bond synthesis by direct condensation, as formulated above, requires suppression of the reactive character of the amino group of the first and of the carboxyl group of the second amino acid. The masking substituents must permit their ready removal, without inducing breakdown of the labile peptide molecule.

In solution phase synthesis, a wide variety of coupling methods and protecting groups may be used (see Gross and Meienhofer, eds., "The Peptides: Analysis, Synthesis, Biology," Vol. 1–4 (Academic Press, 1979); Bodansky and Bodansky, "The Practice of Peptide Synthesis," 2d ed. (Springer Verlag, 1994)). In addition, intermediate purification and linear scale up are possible. Those of ordinary skill in the art will appreciate that solution synthesis requires consideration of main chain and side chain protecting groups and activation method. In addition, careful segment selection is necessary to minimize racemization during segment condensation. In particular, a high percentage of racemization may be observed when residues such as Phe-Gly are coupled. Such situations are, however, uncommon. Solubility considerations are also a factor.

Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., *J. Am. Chem. Soc.* 85:2149, 1963, which involves assembling a linear peptide chain on a resin support using protected amino acids. Solid phase peptide synthesis typically utilizes either the Boc or Fmoc strategy. The Boc strategy uses a 1% cross-linked polystyrene resin. The standard protecting group for amino functions is the tert-butyloxycarbonyl (Boc) group. This group can be removed with dilute solutions of strong acids such as 25% trifluoroacetic acid (TFA). The next Boc-amino acid is typically coupled to the amino acyl resin using dicyclohexylcarbodiimide (DCC). Following completion of the assembly, the peptide-resin is treated with anhydrous HF to cleave the benzyl ester link and liberate the free peptide. Side-chain functional groups are usually blocked during synthesis by benzyl-derived blocking groups, which are also cleaved by HF. The free peptide is then extracted from the resin with a suitable solvent, purified and characterized. Newly synthesized peptides can be purified, for example, by gel filtration, HPLC, partition chromatography and/or ion-exchange chromatography, and may be characterized by, for example, mass spectrometry or amino acid sequence analysis. In the Boc strategy, C-terminal amidated peptides can be obtained using benzhydrylamine or methylbenzhydrylamine resins, which yield peptide amides directly upon cleavage with HF.

In the procedures discussed above, the selectivity of the side-chain blocking groups and of the peptide-resin link depends upon the differences in the rate of acidolytic cleavage. Orthoganol systems have been introduced in which the side-chain blocking groups and the peptide-resin link are completely stable to the reagent used to remove the α-protecting group at each step of the synthesis. The most common of these methods involves the 9-fluorenylmethyloxycarbonyl (Fmoc) approach. Within this method, the side-chain protecting groups and the peptide-resin link are completely stable to the secondary amines used for cleaving the N-α-Fmoc group. The side-chain protection and the peptide-resin link are cleaved by mild acidolysis. The repeated contact with base makes the Merrifield resin unsuitable for Fmoc chemistry, and palkoxybenzyl esters linked to the resin are generally used. Deprotection and cleavage are generally accomplished using TFA.

Those of ordinary skill in the art will recognize that, in solid phase synthesis, deprotection and coupling reactions must go to completion and the side-chain blocking groups must be stable throughout the entire synthesis. In addition, solid phase synthesis is generally most suitable when peptides are to be made on a small scale.

Acetylation of the N-terminal can be accomplished by reacting the final peptide with acetic anhydride before cleavage from the resin. C-amidation is accomplished using an appropriate resin such as methylbenzhydrylamine resin using the Boc technology.

Following synthesis of a linear peptide, with or without N-acetylation and/or C-amidation, cyclization may be achieved by any of a variety of techniques well known in the art. Within one embodiment, a bond may be generated between reactive amino acid side chains. For example, a disulfide bridge may be formed from a linear peptide comprising two thiol-containing residues by oxidizing the peptide using any of a variety of methods. Within one such method, air oxidation of thiols can generate disulfide linkages over a period of several days using either basic or neutral aqueous media. The peptide is used in high dilution to minimize aggregation and intermolecular side reactions. This method suffers from the disadvantage of being slow but has the advantage of only producing $H_2O$ as a side product. Alternatively, strong oxidizing agents such as $I_2$ and $K_3Fe(CN)_6$ can be used to form disulfide linkages. Those of ordinary skill in the art will recognize that care must be taken not to oxidize the sensitive side chains of Met, Tyr, Trp or His. Cyclic peptides produced by this method require purification using standard techniques, but this oxidation is applicable at acid pHs. By way of example, strong oxidizing agents can be used to perform the cyclization shown below (SEQ ID NOs:62 and 63), in which the underlined portion is cyclized:

premature, nonspecific oxidation of free cysteine, as shown below (SEQ ID NOs: 64 and 65), where X and Y=S-Trt or S-Acm:

```
BocCys(X)GlyAsnLeuSer(t-Bu)Thr(t-
         Bu)Cys(Y)MetLeuGlyOH→

BocCysGlyAsnLeuSer(t-
         Bu)Thr(t-Bu)CysMetLeuGlyOH
```

DMSO, unlike $I_2$ and $K_3Fe(CN)_6$, is a mild oxidizing agent which does not cause oxidative side reactions of the nucleophilic amino acids mentioned above. DMSO is miscible with $H_2O$ at all concentrations, and oxidations can be performed at acidic to neutral pHs with harmless byproducts. Methyltrichlorosilane-diphenylsulfoxide may alternatively be used as an oxidizing agent, for concurrent deprotection/oxidation of S-Acm, S-Tacm or S-t-Bu of cysteine without affecting other nucleophilic amino acids. There are no polymeric products resulting from intermolecular disulfide bond formation. In the example below (SEQ ID NOs:66 and 67), X is Acm, Tacm or t-Bu:

```
H-Cys(X)TyrIleGlnAsnCys(X)ProLeuGly-NH2→

H-CysTyrIleGlnAsnCysProLeuGly-NH2
```

Suitable thiol-containing residues for use in such oxidation methods include, but are not limited to, cysteine, β,β-dimethyl cysteine (penicillamine or Pen), β,β-tetramethylene cysteine (Tmc), β,β-pentamethylene cysteine (Pmc), β-mercaptopropionic acid (Mpr), β,β-pentamethylene-β-mercaptopropionic acid (Pmp), 2-mercaptobenzene, 2-mercaptoaniline and 2-mercaptoproline. Peptides containing such residues are illustrated by the following representative formulas, in which the underlined portion is cyclized,

```
FmocCysAsp(t-Bu)GlyTyr(t-Bu)ProLys(Boc)Asp(t-Bu)CysLys(t-Bu)Gly-OMe→

FmocCysAsp(t-Bu)GlyTyr(t-Bu)ProLys(Boc)Asp(t-Bu)CysLys(t-Bu)Gly-OMe
```

Oxidizing agents also allow concurrent deprotection/oxidation of suitable S-protected linear precursors to avoid N-acetyl groups are indicated by N—Ac and C-terminal amide groups are represented by —$NH_2$:

| | | |
|---|---|---|
| i) | N-Ac-Cys-His-Ala-Val-Cys-$NH_2$ | (SEQ ID NO: 10) |
| ii) | N-Ac-Cys-Ala-His-Ala-Val-Asp-Lle-Cys-$NH_2$ | (SEQ ID NO: 24) |
| iii) | N-Ac-Cys-Ser-His-Ala-Val-Cys-$NH_2$ | (SEQ ID NO: 36) |
| iv) | N-Ac-Cys-His-Ala-Val-Ser-Cys-$NH_2$ | (SEQ ID NO: 38) |
| v) | N-Ac-Cys-Ala-His-Ala-Val-Asp-Cys-$NH_2$ | (SEQ ID NO: 26) |
| vi) | N-Ac-Cys-Ser-His-Ala-Val-Ser-Ser-Cys-$NH_2$ | (SEQ ID NO: 42) |
| vii) | N-Ac-Cys-His-Ala-Val-Ser-Cys-OH | (SEQ ID NO: 38) |
| viii) | H-Cys-Ala-His-Ala-Val-Asp-Cys-$NH_2$ | (SEQ ID NO: 26) |
| ix) | N-Ac-Cys-His-Ala-Val-Pen-$NH_2$ | (SEQ ID NO: 68) |
| x) | N-Ac-Ile-Tmc-Tyr-Ser-His-Ala-Val-Ser-Cys-Glu-$NH_2$ | (SEQ ID NO: 69) |
| xi) | N-Ac-Ile-Pmc-Tyr-Ser-His-Ala-Val-Ser-Ser-Cys-$NH_2$ | (SEQ ID NO: 70) |
| xii) | Mpr-Tyr-Ser-His-Ala-Val-Ser-Ser-Cys-$NH_2$ | (SEQ ID NO: 71) |
| xiii) | Pmp-Tyr-Ser-His-Ala-Val-Ser-Ser-Cys-$NH_2$ | (SEQ ID NO: 72) |

-continued xii) 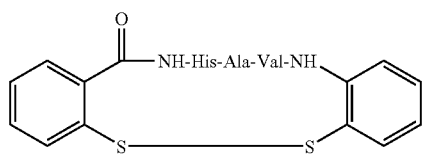

xiii) 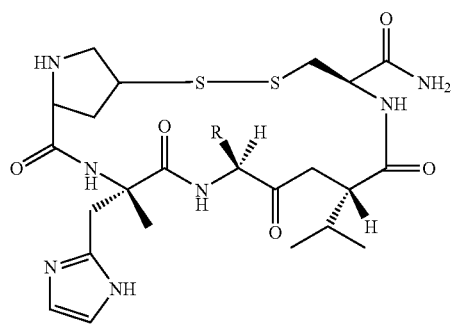

It will be readily apparent to those of ordinary skill in the art that, within each of these representative formulas, any of the above thiol-containing residues may be employed in place of one or both of the thiol-containing residues recited.

Within further embodiments, cyclization may be achieved by amide bond formation. For example, a peptide bond may be formed between terminal functional groups (i.e., the amino and carboxy termini of a linear peptide prior to cyclization). Two such cyclic peptides are AHAVDI (SEQ ID NO:34) and SHAVSS (SEQ ID NO:46), with or without an N-terminal acetyl group and/or a C-terminal amide. Within another such embodiment, the linear peptide comprises a D-amino acid (e.g., HAVsS; SEQ ID NO:73). Alternatively, cyclization may be accomplished by linking one terminus and a residue side chain or using two side chains, as in KHAVD (SEQ ID NO:12) or KSHAVSSD (SEQ ID NO:48), with or without an N-terminal acetyl group and/or a C-terminal amide. Residues capable of forming a lactam bond include lysine, ornithine (Orn), α-amino adipic acid, m-aminomethylbenzoic acid, α,β-di-aminopropionic acid, glutamate or aspartate.

Methods for forming amide bonds are well known in the art and are based on well established principles of chemical reactivity. Within one such method, carbodiimide-mediated lactam formation can be accomplished by reaction of the carboxylic acid with DCC, DIC, EDAC or DCCI, resulting in the formation of an O-acylurea that can be reacted immediately with the free amino group to complete the cyclization. The formation of the inactive N-acylurea, resulting from O→N migration, can be circumvented by converting the O-acylurea to an active ester by reaction with an N-hydroxy compound such as 1-hydroxybenzotriazole, 1-hydroxysuccinimide, 1-hydroxynorbornene carboxamide or ethyl 2-hydroximino-2-cyanoacetate. In addition to minimizing O→N migration, these additives also serve as catalysts during cyclization and assist in lowering racemization. Alternatively, cyclization can be performed using the azide method, in which a reactive azide intermediate is generated from an alkyl ester via a hydrazide. Hydrazinolysis of the terminal ester necessitates the use of a t-butyl group for the protection of side chain carboxyl functions in the acylating component. This limitation can be overcome by using diphenylphosphoryl acid (DPPA), which furnishes an azide directly upon reaction with a carboxyl group. The slow reactivity of azides and the formation of isocyanates by their disproportionation restrict the usefulness of this method. The mixed anhydride method of lactam formation is widely used because of the facile removal of reaction by-products. The anhydride is formed upon reaction of the carboxylate anion with an alkyl chloroformate or pivaloyl chloride. The attack of the amino component is then guided to the carbonyl carbon of the acylating component by the electron donating effect of the alkoxy group or by the steric bulk of the pivaloyl chloride t-butyl group, which obstructs attack on the wrong carbonyl group. Mixed anhydrides with phosphoric acid derivatives have also been successfully used. Alternatively, cyclization can be accomplished using activated esters. The presence of electron withdrawing substituents on the alkoxy carbon of esters increases their susceptibility to aminolysis. The high reactivity of esters of p-nitrophenol, N-hydroxy compounds and polyhalogenated phenols has made these "active esters" useful in the synthesis of amide bonds. The last few years have witnessed the development of benzotriazolyloxytris-(dimethylamino)phosphonium hexafluorophosphonate (BOP) and its congeners as advantageous coupling reagents. Their performance is generally superior to that of the well established carbodiimide amide bond formation reactions.

Within a further embodiment, a thioether linkage may be formed between the side chain of a thiol-containing residue and an appropriately derivatized α-amino acid. By way of example, a lysine side chain can be coupled to bromoacetic acid through the carbodiimide coupling method (DCC, EDAC) and then reacted with the side chain of any of the thiol containing residues mentioned above to form a thioether linkage. In order to form dithioethers, any two thiol containing side-chains can be reacted with dibromoethane and diisopropylamine in DMF. Examples of thiol-containing linkages are shown below:

i.
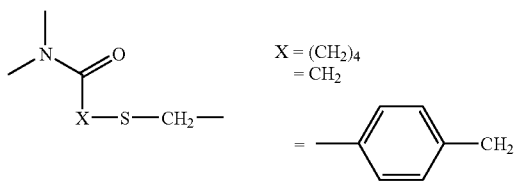
ii.
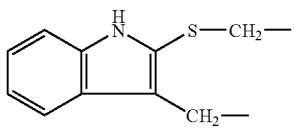

Cyclization may also be achieved using $\delta_1,\delta_1$-Ditryptophan (i.e., Ac-Trp-Gly-Gly-Trp-OMe)(SEQ ID NO:74), as shown below:

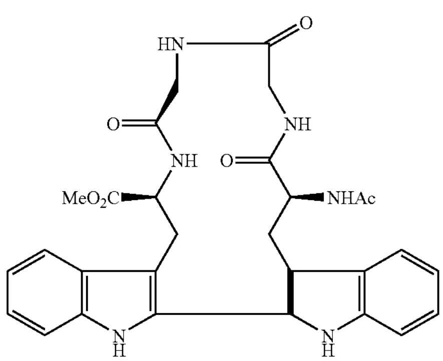

Representative structures of cyclic peptides are provided in FIG. 3. Within FIG. 3, certain cyclic peptides having the ability to modulate cell adhesion (shown on the left) are paired with similar inactive structures (on the right). The structures and formulas recited herein are provided solely for the purpose of illustration, and are not intended to limit the scope of the cyclic peptides described herein.

Three-Dimensional Structures of the HAV Pharmacophore

For designing peptidomimetics, it is beneficial to obtain a three dimensional structure for the pharmacophore of one or more cyclic peptides described above. The term "pharmacophore" refers to the collection of functional groups on a compound that are arranged in three-dimensional space in a manner complementary to the target protein, and that are responsible for biological activity as a result of compound binding to the target protein. Useful three-dimensional pharmacophore models are best derived from either crystallographic or nuclear magnetic resonance structures of the target, but can also be derived from homology models based on the structures of related targets or three-dimensional quantitative structure-activity relationships derived from a previously discovered series of active compounds.

The present invention provides pharmacophores of certain representative cyclic peptides (i.e., three-dimensional conformations of the classical cadherin CAR sequence HAV within such peptides). Such three-dimensional structures provide the information required to most efficiently direct the design and optimization of peptidomimetics.

The three-dimensional structures of cyclic peptides may generally be determined using nuclear magnetic resonance (NMR) techniques that are well known in the art. NMR data acquisition is preferably carried out in aqueous systems that closely mimic physiological conditions to ensure that a relevant structure is obtained. Briefly, NMR techniques use the magnetic properties of certain atomic nuclei (such as $^{1}H$, $^{13}C$, $^{15}N$ and $^{31}P$), which have a magnetic moment or spin, to probe the chemical environment of such nuclei. The NMR data can be used to determine distances between atoms in the molecule, which can be used to derive a three-dimensional model or the molecule.

For determining three-dimensional structures of cyclic peptides (and candidate peptidomimetics, as discussed below) proton NMR is preferably used. More specifically, when a molecule is placed in a strong magnetic field, the two spin states of the hydrogen atoms are no longer degenerate. The spin aligned parallel to the field will have a lower energy and the spin aligned antiparallel to the field will have a higher energy. At equilibrium, the spin of the hydrogen atoms will be populated according to the Boltzmann distribution equation. This equilibrium of spin populations can be perturbed to an excited state by applying radio frequency (RF) pulses. When the nuclei revert to the equilibrium state, they emit RF radiation that can be measured. The exact frequency of the emitted radiation from each nucleus depends on the molecular environment of the nucleus and is different for each atom (except for those atoms that have the same molecular environment). These different frequencies are obtained relative to a reference signal and are called chemical shifts. The nature, duration and combination of applied RF pulses can be varied greatly and different molecular properties can be probed by those of ordinary skill in the art, by selecting an appropriate combination of pulses.

For three-dimensional structure determinations, one-dimensional NMR spectra are generally insufficient, as limited information pertaining to conformation may be obtained. One-dimensional NMR is generally used to verify connectivity within a molecule and yields incomplete data concerning the orientation of side chains within a peptide. Two-dimensional NMR spectra are much more useful in this respect and allow for unambiguous determination of side-chain-to-side-chain interactions and the conformation of the peptide backbone.

Two-dimensional NMR spectra are generally presented as a contour plot in which the diagonal corresponds to a one-dimensional NMR spectrum and the cross peaks off the diagonal result from interactions between hydrogen atoms that are directly scalar coupled. Two-dimensional experiments generally contain a preparation period, an evolution period where spins are "labeled" as they process in the XY plane according to their chemical shift, a mixing period, during which correlations are made with other spins and a detection period in which a free induction decay is recorded.

Two-dimensional NMR methods are distinguished by the nature of the correlation that is probed during the mixing period. A DQF-COSY (double quantum filtered correlation spectroscopy) analysis gives peaks between hydrogen atoms that are covalently connected through one or two other atoms. Nuclear Overhauser effect spectroscopy (NOESY) gives peaks between pairs of hydrogen atoms that are close together in space, even if connected by way of a large number of intervening atoms. In total correlation spectroscopy (TOCSY), correlations are observed between all protons that share coupling partners, whether or not they are directly coupled to each other. Rotating-frame Overhauser Spectroscopy (ROESY) experiments may be thought of as the rotating frame analogue of NOESY, and yields peaks between pairs of hydrogen atoms that are close together in space. One or more such methods may be used, in conjunction with the necessary water-suppression techniques such as WATERGATE and water flip-back, to determine the three-dimensional structure of a cyclic peptide or candidate peptidomimetic under aqueous conditions. Such techniques are well known and are necessary to suppress the resonance of the solvent (HDO) during acquisition of NMR data.

By way of example, both TOCSY and NOESY may be applied to representative cyclic peptides for the purpose of determining the conformation and the assignment. The water solvent resonance may be suppressed by application of the WATERGATE procedure. A water flipback pulse may also be applied at the end of the mixing period for both TOCSY and NOESY experiments to maintain the water signal at equilibrium and to minimize the loss of amide proton resonances due to their rapid exchange at the near neutral pH conditions (i.e., pH 6.8) used in the experiment. NMR data may be processed using spectrometer software using a squared cosine window function along both directions. Baseline corrections may be applied to the NOESY, ROESY and TOCSY spectra using the standard Bruker polynomial method.

NOESY data may be acquired at several mixing times ranging from 80 ms to 250 ms. The shorter mixing time NOESY may be acquired to ensure that no diffusion effects were present in the NOESY spectrum acquired at the longer mixing times. The interproton distances may generally be determined from the 250 ms NOESY. The sequence-specific assignment of the proton resonances may be determined by standard methods (see Wuthrich, *NMR of Proteins and Nucleic Acids*, Wiley & Sons, New York, 1986), making use of both the results of the TOCSY and NOESY data. The spin systems of Ala3 and Val4 may be assigned based on the presence of strong NOEs between the amide protons and the respective side chains in conjunction with the relevant TOCSY data.

For conformational calculations, the NOE cross peaks may be initially converted to a uniform distance upper and lower bounds of 1.8–5.0 angstroms regardless of the NOE intensities. The NOE distances may be refined iteratively through a comparison of computed and experimental NOEs at the various mixing times. This refinement may be much in the spirit of the PEPFLEX-II procedure (Wang et al., Techniques in Protein Chemistry IV, 1993, Evaluation of NMR Based Structure Determination for Flexible Peptides: Application to Desmopressin p. 569), although preferably initial NOE-based distances with very loose upper bounds (e.g., 5 angstroms) are used to permit the generation of a more complete set of conformations in agreement with experimental data. Dihedral-angle constraints may be derived from the values of the $^3J$CαH coupling constants. A tolerance value of 40 degrees may be added to each of the dihedral angle constraints to account for the conformational flexibility of the peptide. Distance geometry calculations may be carried out utilizing fixed bond lengths and bond angles provided in the ECEPP/2 database (Ni et al., *Biochemistry* 31:11551–11557, 2989). The ω-angles are generally fixed at 180 degrees, but all other dihedral angles may be varied during structure optimization.

Structures with the lowest constraint violations may be subjected to energy minimization using a distance-restrained Monte Carlo method (Ripoll and Ni, *Biopolymers* 32:359–365, 1992; Ni, *J. Magn. Reson.* B106:147–155, 1995), and modified to include the ECEPP/3 force field (Ni et al., *J. Mol. Biol.* 252:656–671, 1995). All ionizable groups may be treated as charged during constrained Monte Carlo minimization of the ECEPP/3 energy. Electrostatic interactions among all charges may be screened by use of a distance-dependent dielectric to account for the absence of solvent effects in conformational energy calculations. In addition; hydrogen-bonding interactions can be reduced to 25% of the full scale, while van der Waals and electrostatic terms are kept to full strengths. These special treatments help to ensure that the conformational search is guided primarily by the experimental NMR constraints and that the computed conformations are less biased by the empirical conformational energy parameters (Warder et al., *FEBS Lett.* 411:19–26, 1997).

Low-energy conformations of the peptide from Monte Carlo calculations may be used in NOE simulations to identify proximate protons with no observable NOEs and sets of distance upper bounds that warrant recalibration. The refined set of NOE distances including distance lower bounds derived from absent NOEs are used in the next cycles of Monte Carlo calculations, until the resulting conformations produced simulate NOE spectra close to those observed experimentally (Ning et al., *Biopolymers* 34:1125–1137, 1994; Ni et al., *J. Mol. Biol.* 252:656–671, 1995). Theoretical NOE spectra may be calculated using a tumbling correlation time of 1.5 ns based on the molecular weight of the peptide and the experimental temperature (Cantor, C. R. and Schimmel, P. R. (1980) *Biophysical Chemistry*, W. H. Freeman & Co., San Francisco). All candidate peptide conformations are included with equal weights in an ensemble-averaged relaxation matrix analysis of interconverting conformations (Ni and Zhu *J. Magn. Reson.* B102:180–184, 1994). NOE simulations may also incorporate parameters to account for the local motions of the methyl groups and the effects of incomplete relaxation decay of the proton demagnitizations (Ning et al., Biopolymers 34:1125–1137, 1994). The computed NOE intensities are converted to the two-dimensional FID's (Ni, *J. Magn. Reson.* B106:147–155, 1995) using the chemical shift of assignments, estimated linewidths and coupling constants for all resolved proton resonances. Calculated FIDs may be converted to simulated NOESY spectra using identical processing procedures as used for the experimental NOE data sets.

Figure 7A:
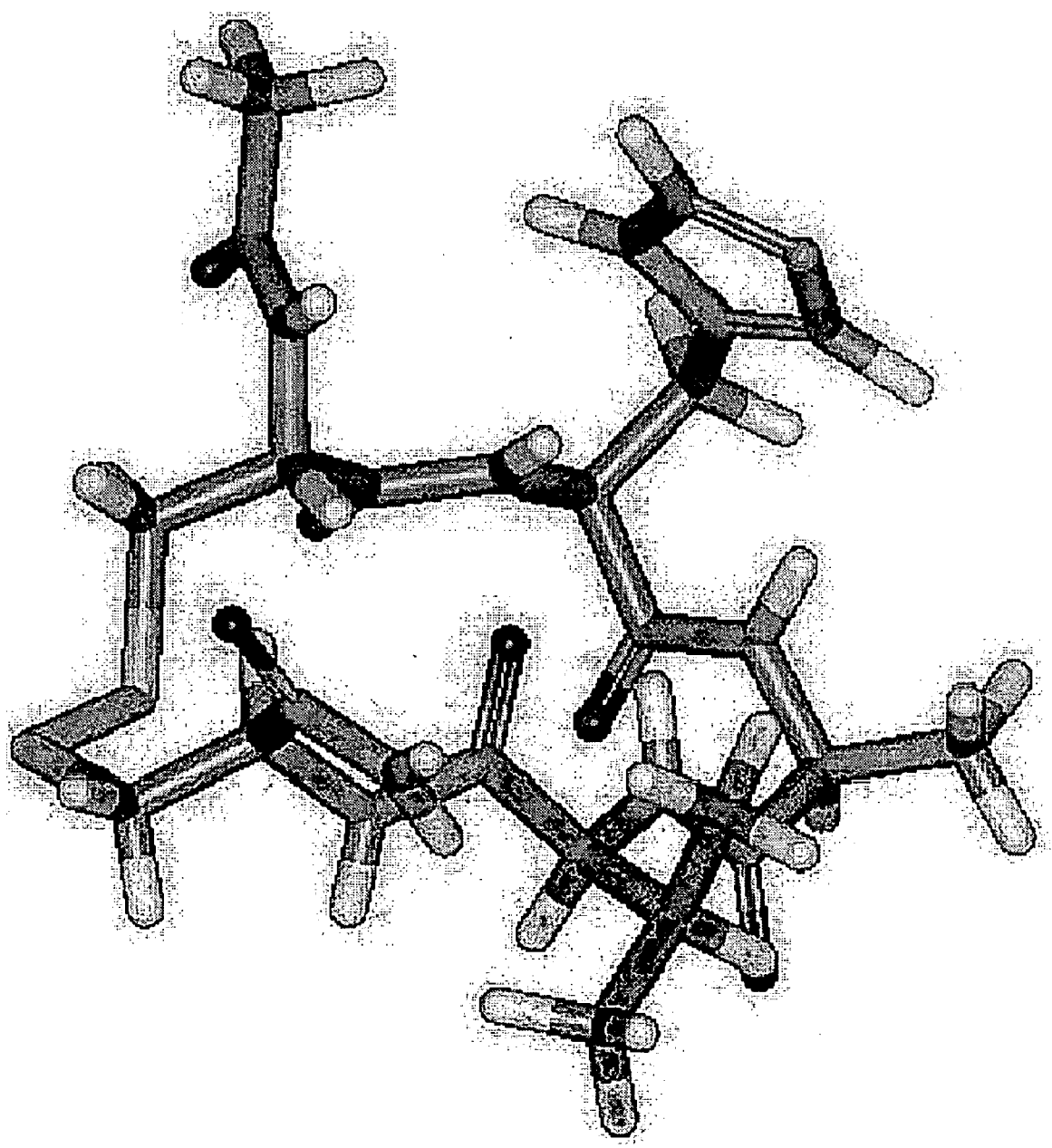
FIGS. 7A–7C depict the high resolution molecular map of the pharmacophore of N—Ac—CHAVC—NH$_2$ (SEQ ID NO:10). The three low energy conformations whose three dimensional structures most closely mimic the experimentally determined NOESY data are indicated as Structure 1 (FIG. 7A), Structure 2 (FIG. 7B) and Structure 3 (FIG. 7C).
Figure 7B:
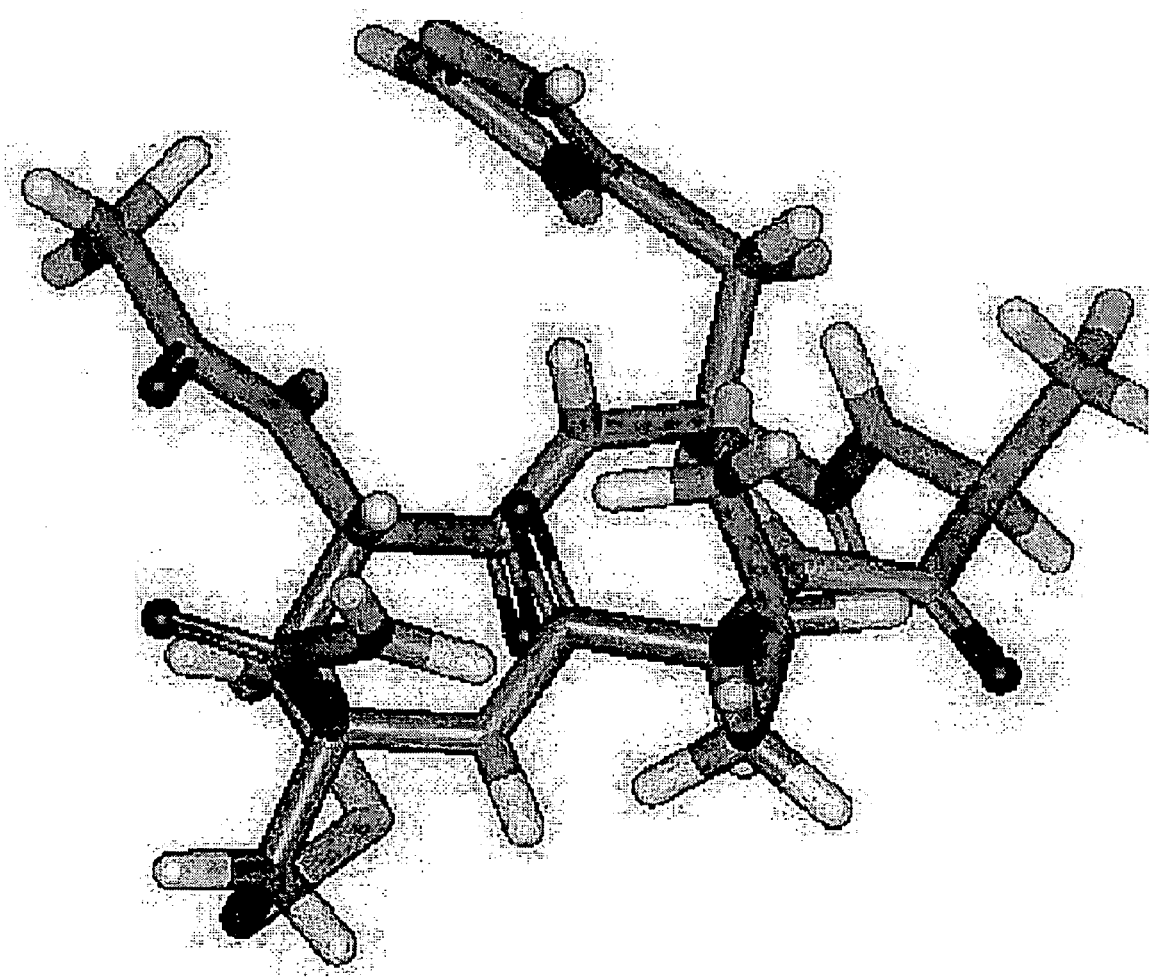
Figure 7C:
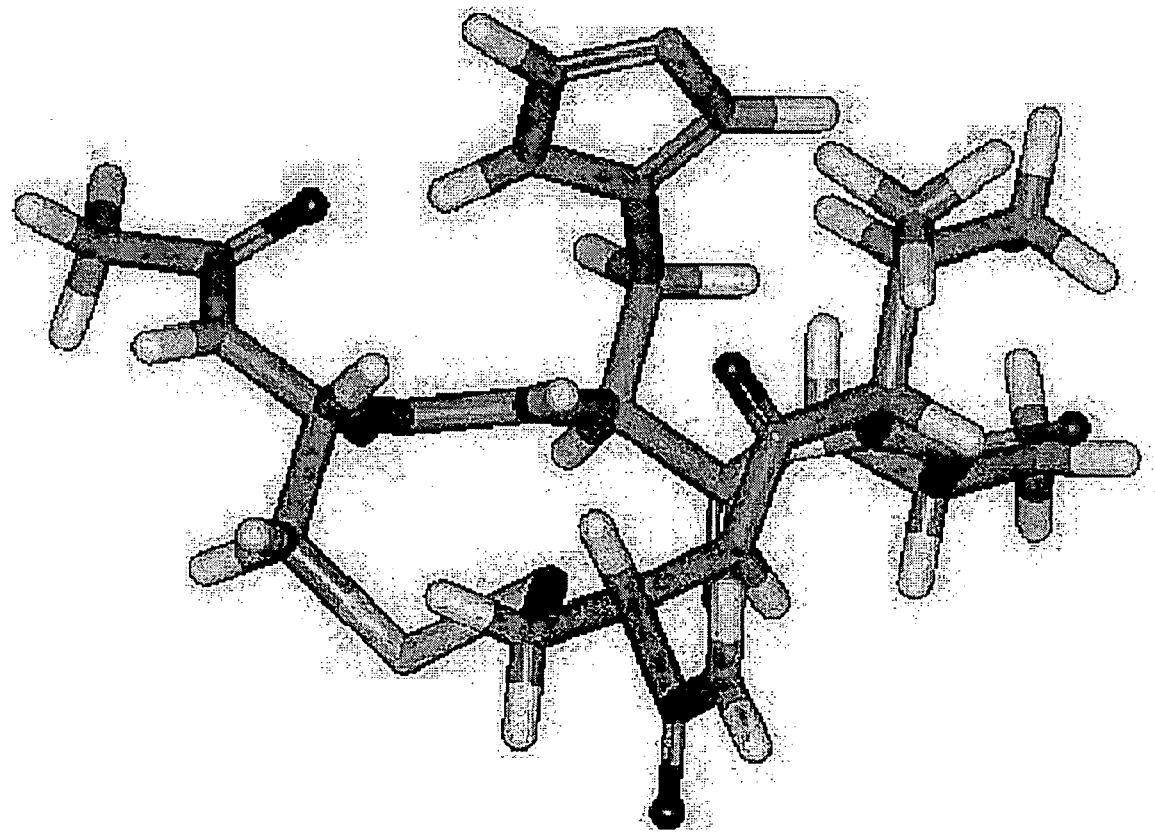
Figure 8A:
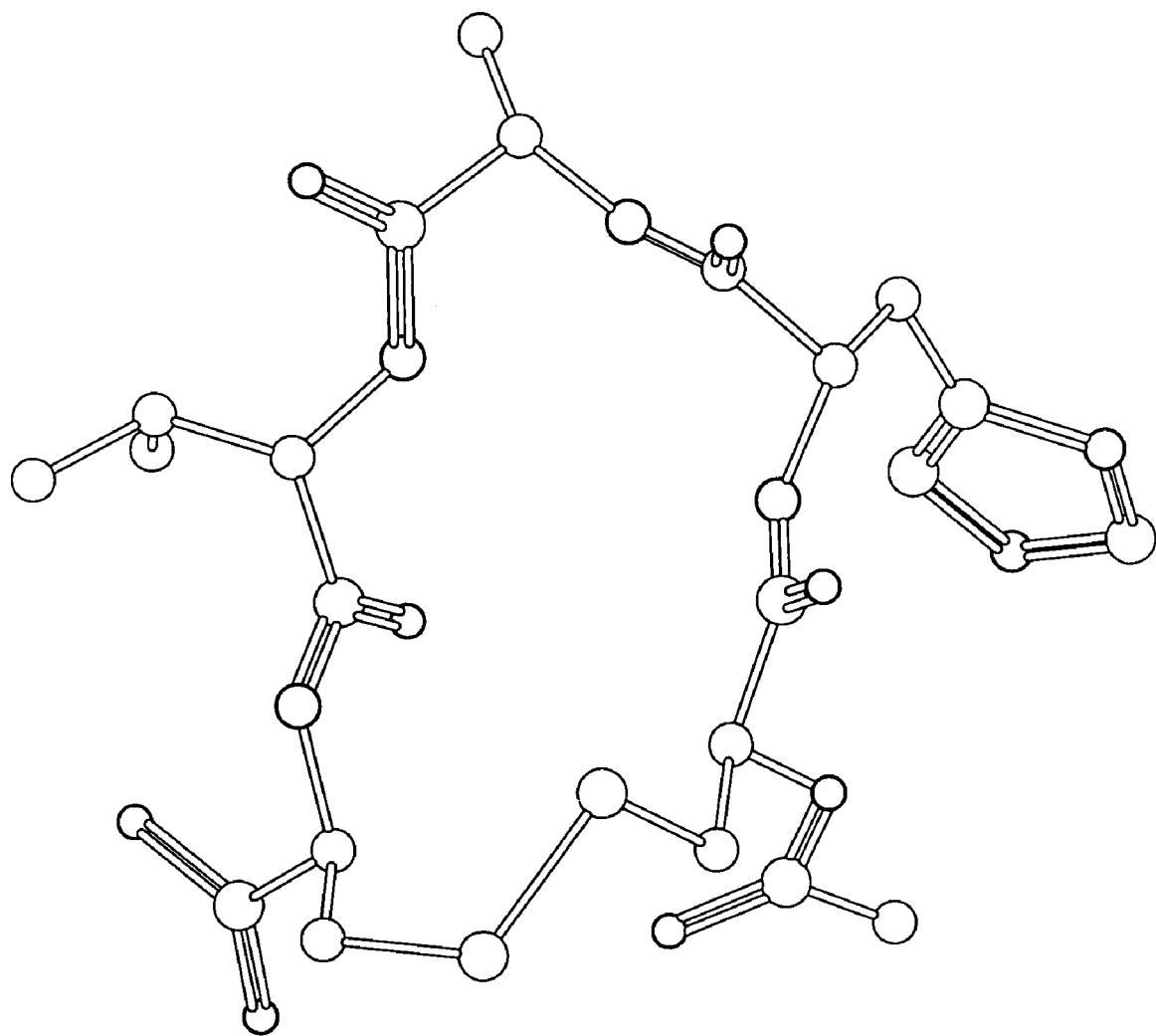
FIGS. 8A and 8B depict the 3-D conformation of the pharmacophore HAV of N—Ac—CHAVC—NH$_2$ (FIG. 8A; SEQ ID NO:10) compared to the HAV depicted in the x-ray structures of N-cadherin (FIG. 8B).
Figure 8B:
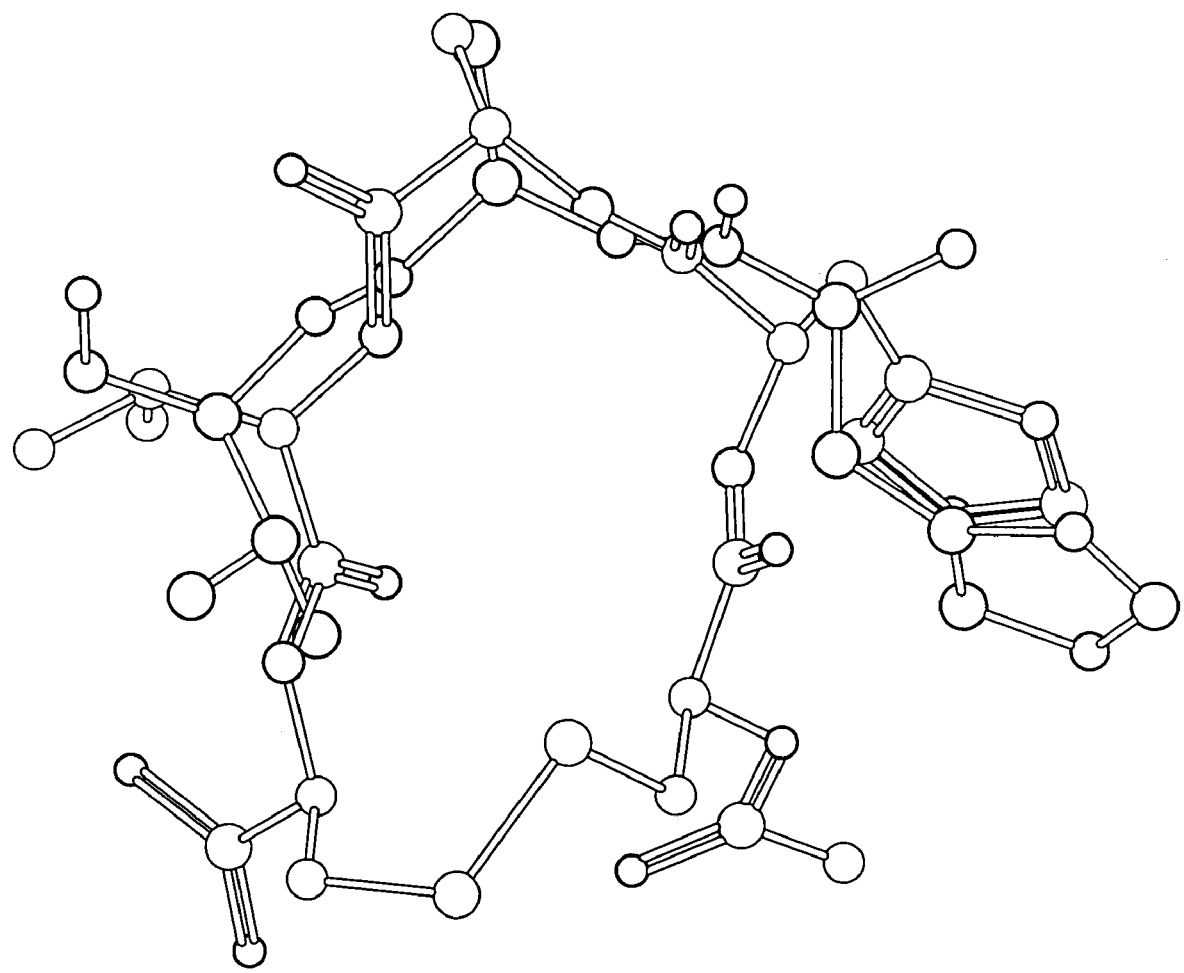
Figure 9A:
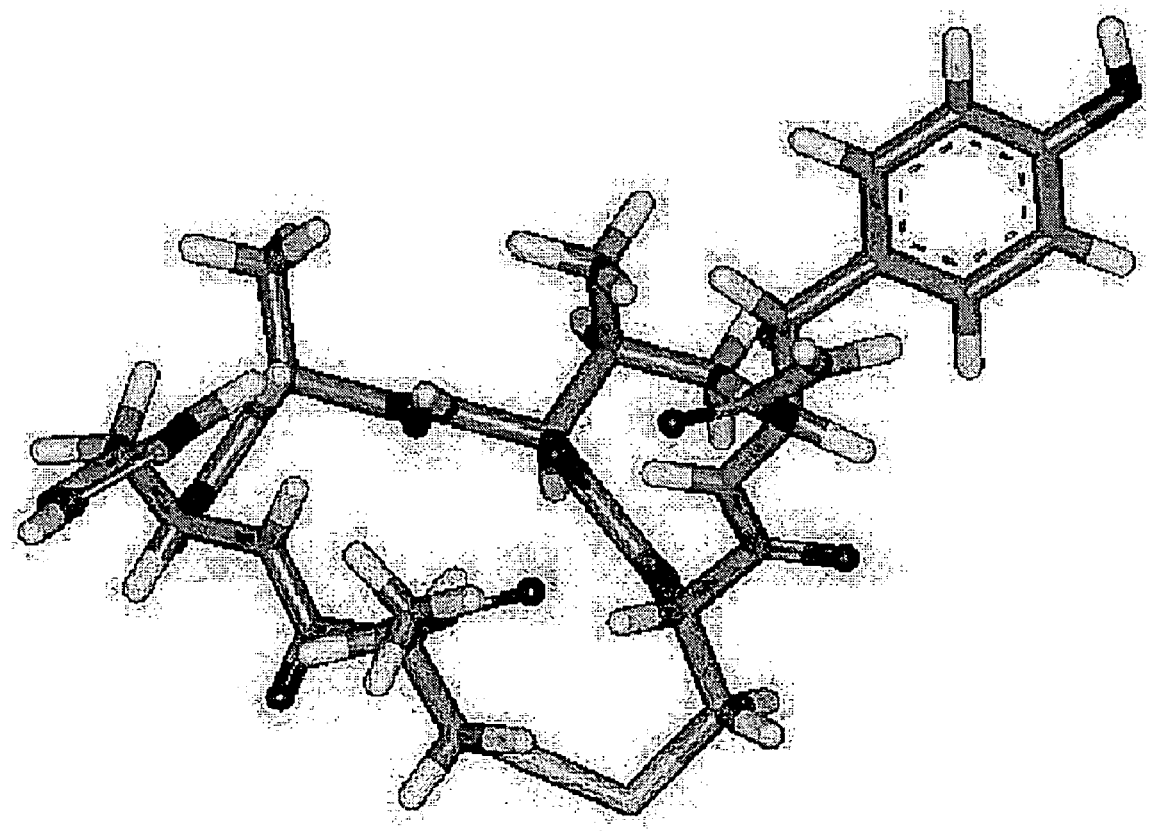
FIGS. 9A–9D depict the four low energy conformations of the high resolution molecular map of the pharmacophore of N—Ac—CHAVC—Y—NH$_2$ (SEQ ID NO:81).
Figure 9B:
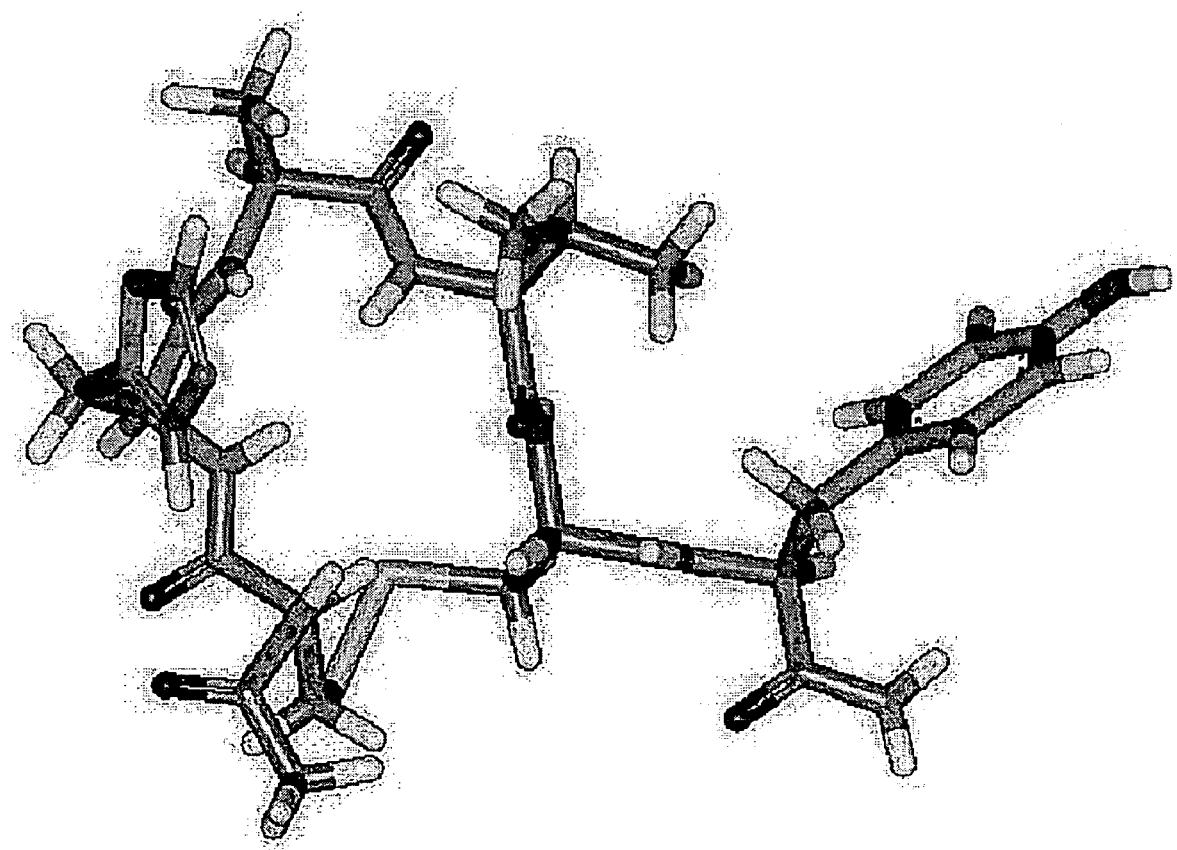
Figure 9C:
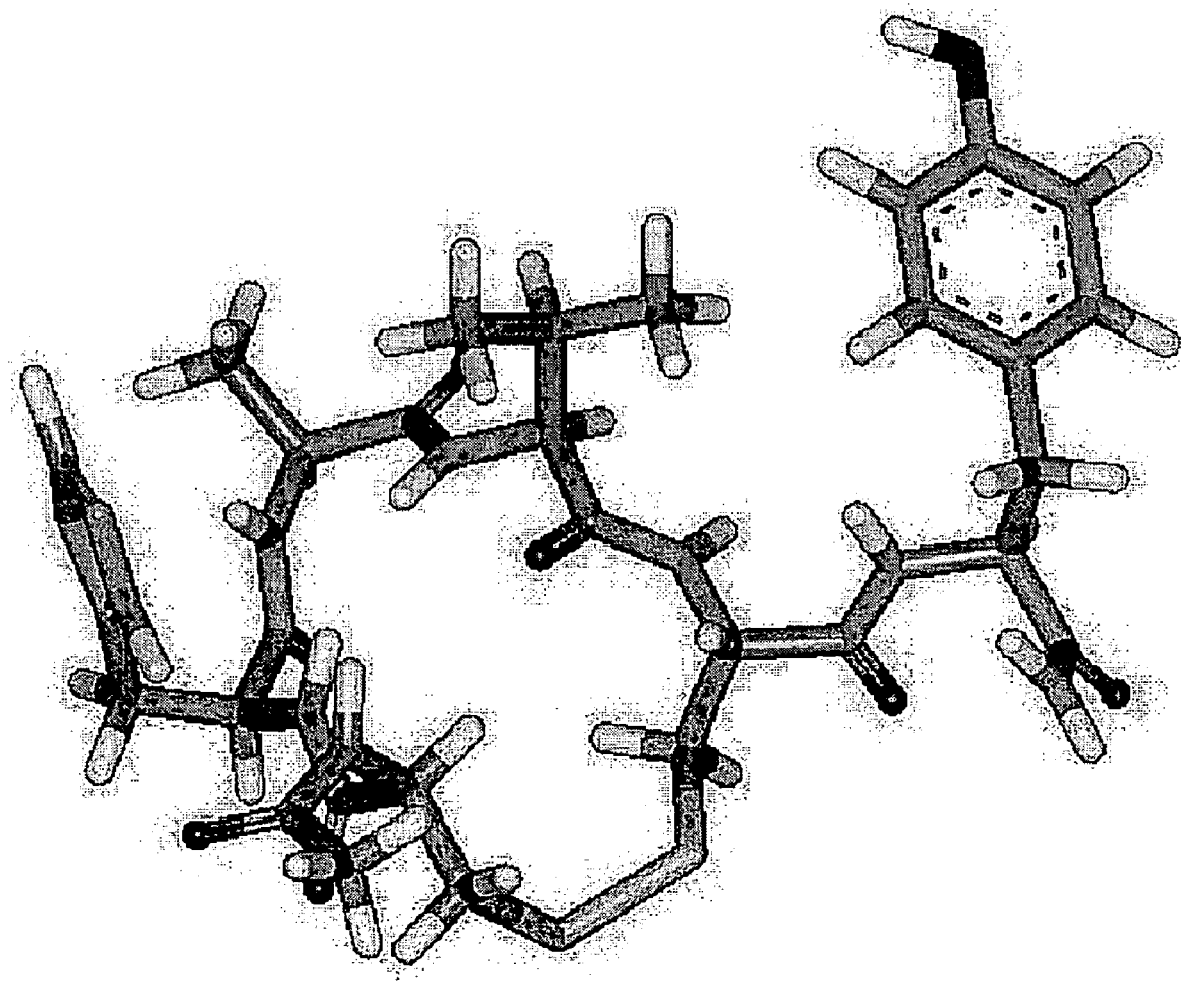
Figure 9D:
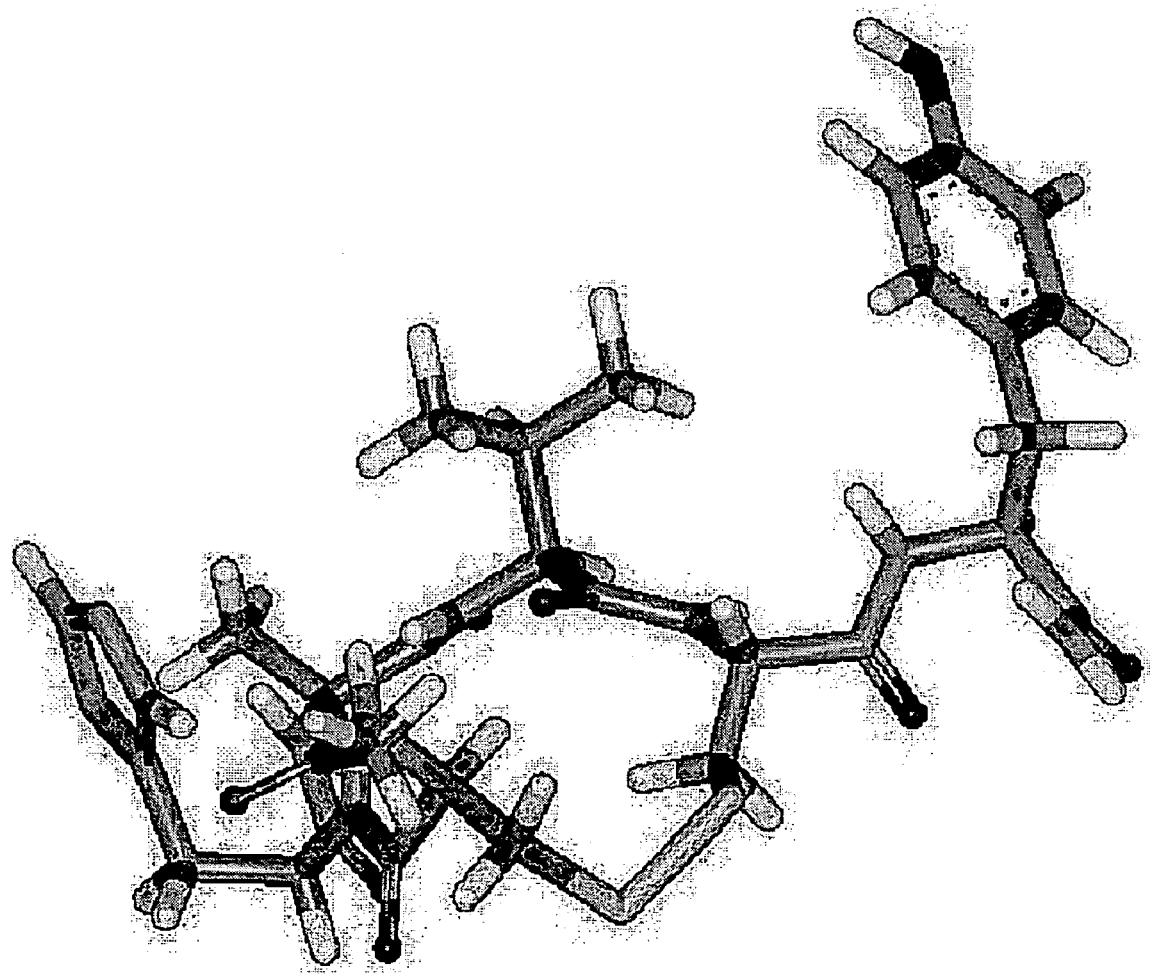
Figure 10:
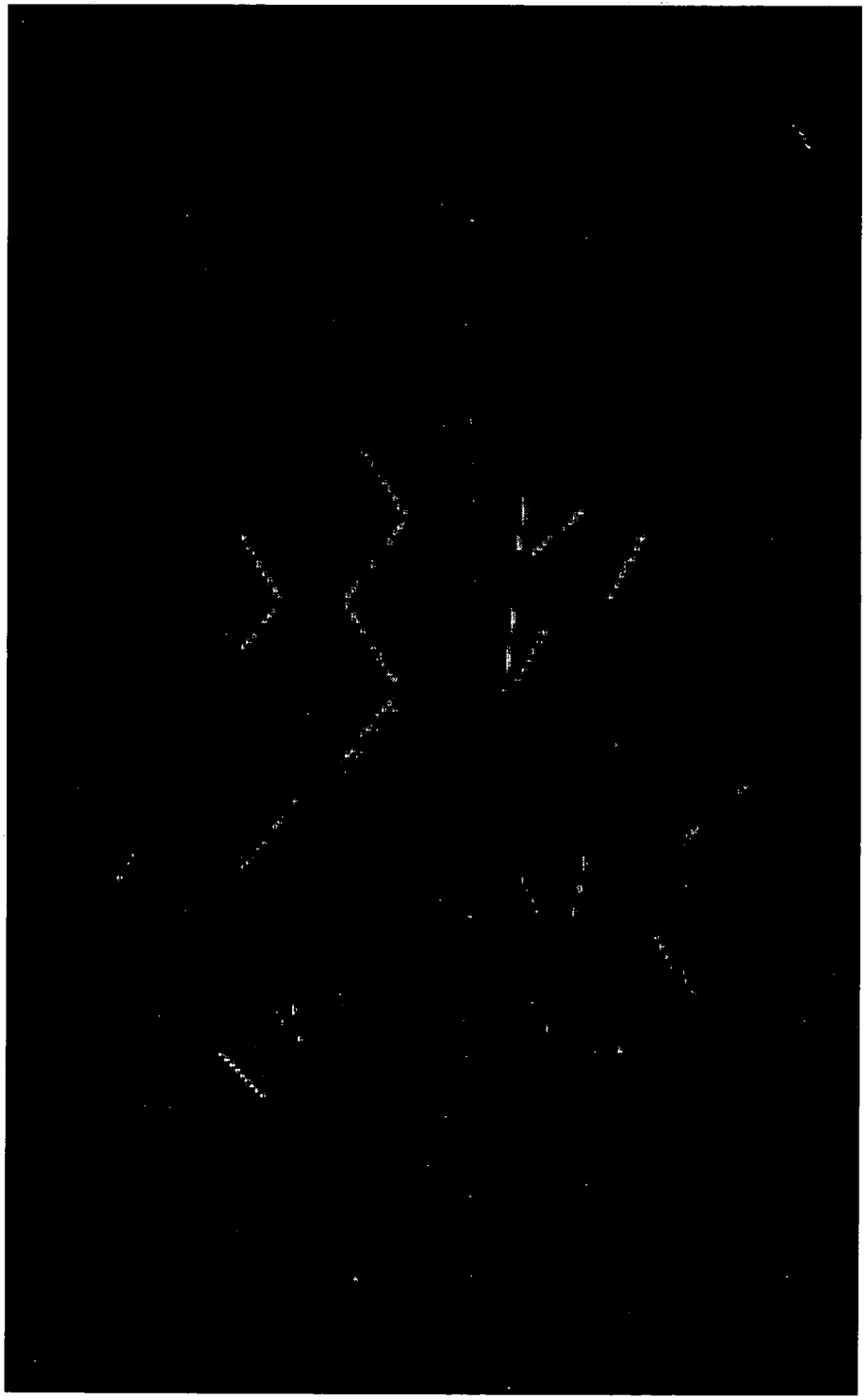
FIG. 10 depicts the overlap of the 3-D conformation of the pharmacophore HAV of N—Ac—CHAVC—NH$_2$ (SEQ ID NO:10) with the pharmacophore HAV of N—Ac—CHAVC—Y—NH$_2$ (SEQ ID NO:81).
Figure 32A:
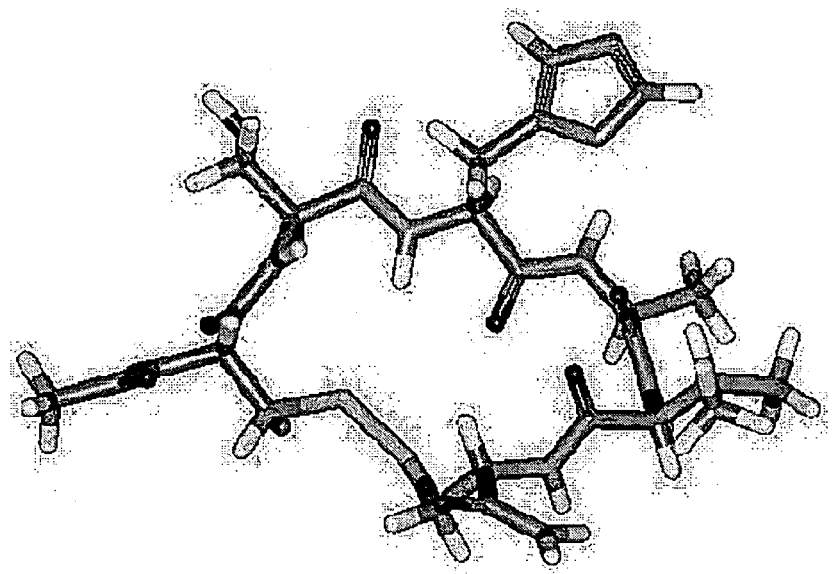
FIGS. 32A–32B depict the two low energy conformations of the high resolution map of the pharmacophore of N—Ac—CSHAVC—NH$_2$ (SEQ ID NO:36).
Figure 32B:
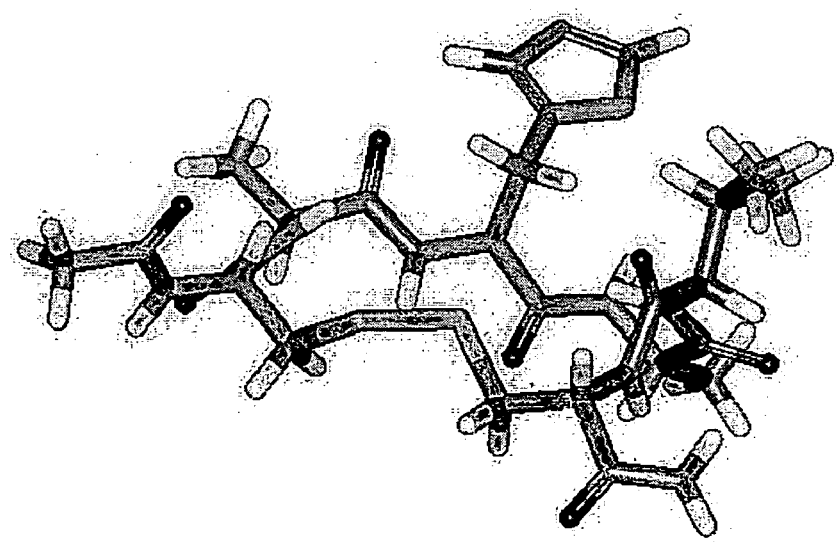

The high resolution molecular map of the pharmacophore of N—Ac—CHAVC—NH$_2$ (SEQ ID NO:10) is shown in FIGS. 7A–7C, each of which depicts one of three low energy conformations (Structure 1, Structure 2 and Structure 3). The co-ordinates for these three low energy conformations are given in Appendix 1. The conformation of HAV in N—Ac—CHAVC—NH$_{12}$ (SEQ ID NO:10) greatly resembles the conformation of the HAV in x-ray crystal structure of N-cadherin (see FIGS. 8A and 8B). The high resolution molecular map of the pharmacophore of N—Ac—CHAVC—Y—NH$_2$ (SEQ ID NO:81) is shown in FIGS. 9A–9D, each of which depicts one of the four low energy conformations. The co-ordinates for these four low energy conformations are given in Appendix 2. The high resolution molecular map of the pharmacophore of N—Ac—CHAVDC—NH$_2$ (SEQ ID NO:20) is shown in FIGS. 20A–20D, each of which depicts one of the four low energy conformations. The co-ordinates for these low energy conformations are given in Appendix 3. The high resolution molecular map of the pharmacophore of N—Ac—CSHAVC—NH$_2$ (SEQ ID NO:36) is shown in FIGS. 32A and 32B, each of which depicts one of the two low energy conformations. The co-ordinates for these low energy conformations are given in Appendix 4.

Peptidominetics

As noted above, peptidomimetics are compounds in which at least a portion of the HAV sequence within a cyclic peptide is modified, such that the three dimensional structure of the peptidomimetic remains substantially the same as that of the HAV sequence. Peptidomimetics may be peptide analogues that are, themselves, cyclic peptides containing one or more substitutions or other modifications within the HAV sequence. Alternatively, at least a portion of the HAV sequence may be replaced with a nonpeptide structure, such that the three-dimensional structure of the cyclic peptide is substantially retained. In other words, one, two or three amino acid residues within the HAV sequence may be replaced by a non-peptide structure. In addition, other peptide portions of the cyclic peptide may, but need not, be replaced with a non-peptide structure. Peptidomimetics (both peptide and non-peptidyl analogues) may have improved properties (e.g., decreased proteolysis, increased retention or increased bioavailability). Peptidomimetics generally have improved oral availability, which makes them especially suited to treatment of conditions such as cancer. It should be noted that peptidomimetics may or may not have similar two-dimensional chemical structures, but share common three-dimensional structural features and geometry. Each peptidomimetic may further have one or more unique additional binding elements. The present invention provides methods for identifying peptidomimetics, as well as a series of specific peptidomimetics of certain cyclic peptides provided herein.

All peptidomimetics provided herein have a three-dimensional structure that is substantially similar to a three-dimensional structure of a cyclic peptide as described above. In general, two three-dimensional structures are said to be substantially structurally similar to each other if their pharmacophore atomic coordinates have a root-mean square deviation (RMSD) less than or equal to 1 angstrom, as calculated using the Molecular Similarity module within the QUANTA program (QUANTA, available from Molecular Simulations Inc., San Diego, Calif.). All peptidomimetics provided herein have at least one low-energy three-dimensional structure that is substantially similar to at least one low-energy three-dimensional structure of a cyclic peptide as described above.

Low energy conformations may be identified by conformational energy calculations using, for example, the CHARMM program (Brooks et al., *J. Comput. Chem.* 4:187–217, 1983). The energy terms include bonded and non-bonded terms, including bond length energy, angle energy, dihedral angle energy, Van der Waals energy and electrostatic energy. It will be apparent that the conformational energy can be also calculated using any of a variety of other commercially available quantum mechanic or molecular mechanic programs. A low energy structure has a conformational energy that is within 50 kcal/mol of the global minimum.

The low energy conformation(s) of candidate peptidomimetics are compared to the low energy solution conformations of the cyclic peptide (as determined by NMR) to determine how closely the conformation of the candidate mimics that of the cyclic peptide. In such comparisons, particular attention should be given to the locations and orientations of the elements corresponding to the crucial side chains. If at least one of the candidate low energy conformations is substantially similar to a solution conformation of a cyclic peptide (i.e., differs with a root-mean square deviation (RMSD) of 1 angstrom or less), the candidate compound is considered a peptidomimetic. Within such analyses, low energy conformations of candidate peptidomimetics in solution may be studied using, for example, the CHARMM molecular mechanics and molecular dynamics program (Brooks et al., *J. Comput. Chem.* 4:187–217, 1983), with the TIP3P water model (Jorgensen et al., *J. Chem Phys.* 79:926–935, 1983) used to represent water molecules. The CHARM22 force field may be used to represent the designed peptidomimetics.

By way of example, low energy conformations may be identified using a combination of two procedures. The first procedure involves a simulated annealing molecular dynamics simulation approach. In this procedure, the system (which includes the designed peptidomimetics and water molecules) is heated up to above room temperature, preferably around 600K, and simulated for a period of 100 picoseconds (ps) or longer; then gradually reduced to 500K and simulated for a period of 100 ps or longer; then gradually reduced to 400K and simulated for a period of 100 ps or longer; gradually reduced to 300K and simulated for a period of 500 ps or longer. The trajectories are recorded for analysis. This simulated annealing procedure is known for its ability for efficient conformational search.

The second procedure involves the use of the self-guided molecular dynamics (SGMD) method (Wu and Wang, *J. Physical Chemistry* 102:7238–7250, 1998). The SGMD method has been demonstrated to have an extremely enhanced conformational searching capability. Using the SGMD method, simulation may be performed at 300 K for 1000 ps or longer and the trajectories recorded for analysis.

Conformational analysis may be carried out using the QUANTA molecular modeling package. First, cluster analysis may be performed using the trajectories generated from molecular dynamic simulations. From each cluster, the lowest energy conformation may be selected as the representative conformation for this cluster and may be compared to other conformational clusters. Upon cluster analysis, major conformational clusters may be identified and compared to the solution conformations of the cyclic peptide(s). The conformational comparison may be carried out using the Molecular Similarity module within the QUANTA program.

Similarity in structure may also be evaluated by visual comparison of the three-dimensional structures displayed in a graphical format, or by any of a variety of computational comparisons. For example, an atom equivalency may be defined in the peptidomimetic and cyclic peptide three-dimensional structures, and a fitting operation used to establish the level of similarity. As used herein, an "atom equivalency" is a set of conserved atoms in the two structures. A "fitting operation" may be any process by which a candidate compound structure is translated and rotated to obtain an optimum fit with the cyclic peptide structure. A fitting operation may be a rigid fitting operation (e.g., the cyclic peptide three-dimensional structure can be kept rigid and the three-dimensional structure of the peptidomimetic can be translated and rotated to obtain an optimum fit with the cyclic peptide). Alternatively, the fitting operation may use a least squares fitting algorithm that computes the optimum translation and rotation to be applied to the moving compound structure, such that the root mean square difference of the fit over the specified pairs of equivalent atoms is a minimum. Preferably, atom equivalencies may be established by the user and the fitting operation is performed using any of a variety of available software applications (e.g., QUANTA, available from Molecular Simulations Inc., San Diego, Calif.). Three-dimensional structures of candidate compounds for use in establishing substantial similarity may be determined experimentally (e.g., using NMR techniques as described herein or x-ray crystallography), or may be computer-generated using, for example, methods provided herein.

Figure 4A:
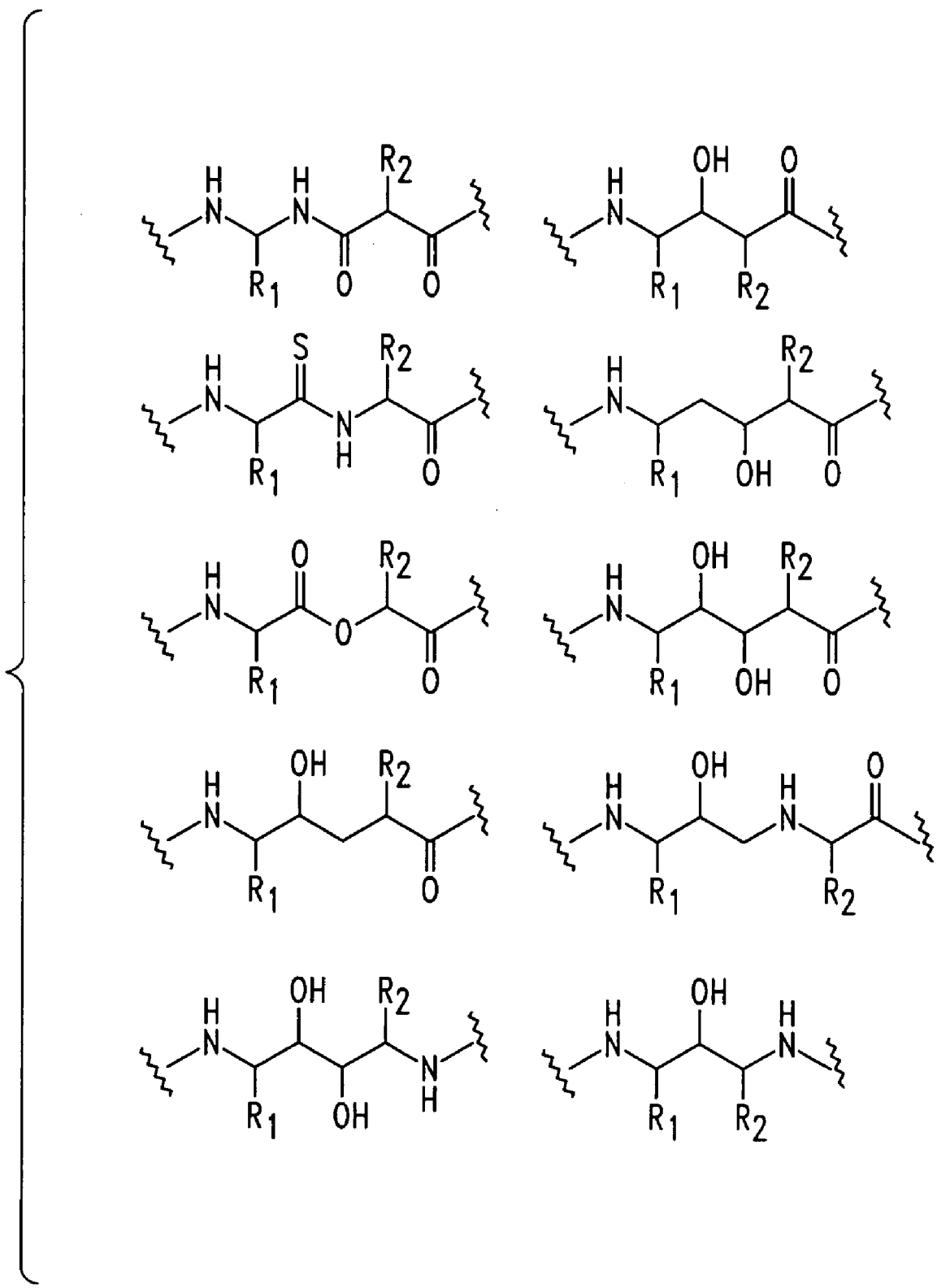
FIGS. 4A and 4B illustrate representative backbone modifications that may be present within a peptidomimetic.
Figure 4B:
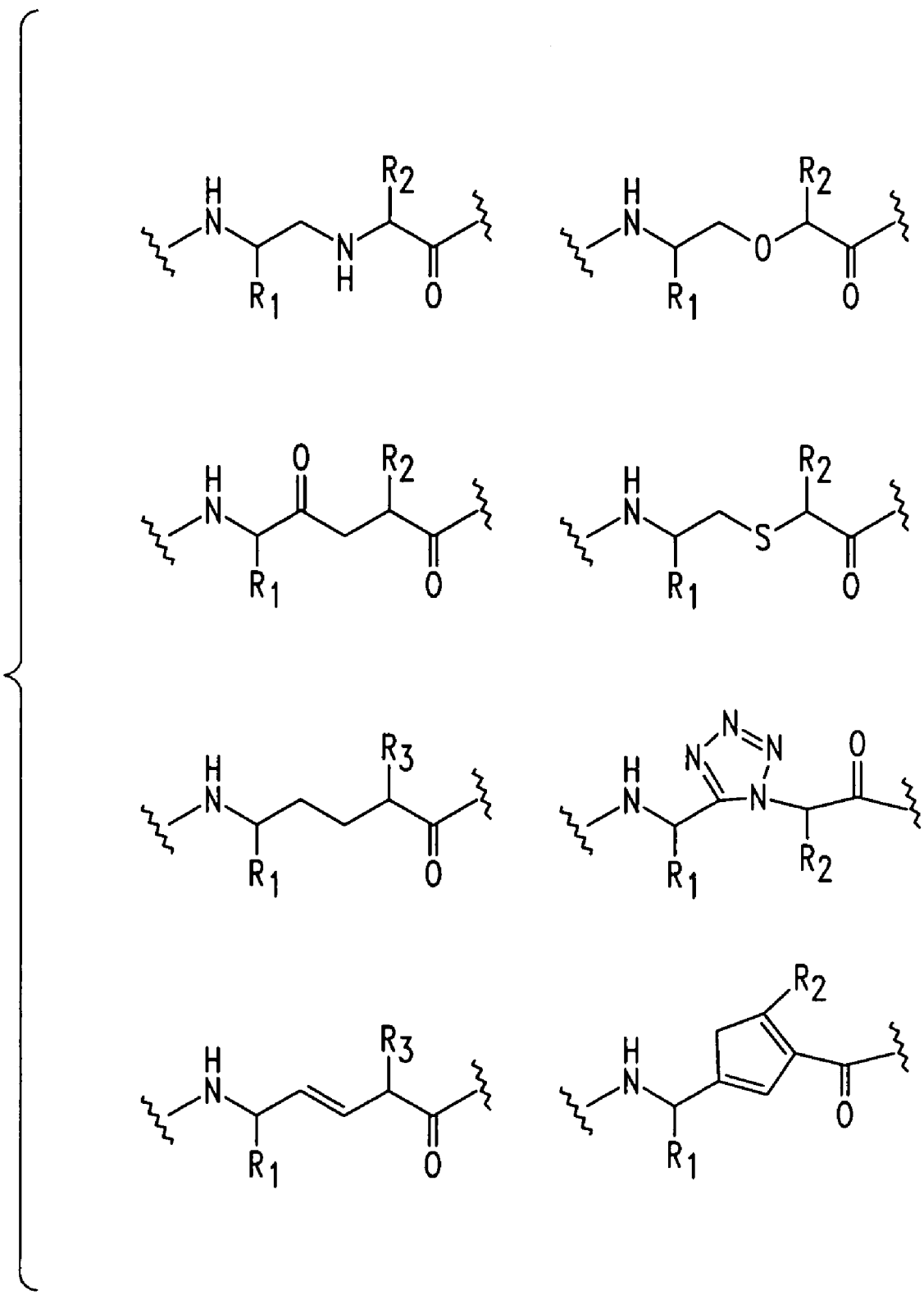
Figure 5:
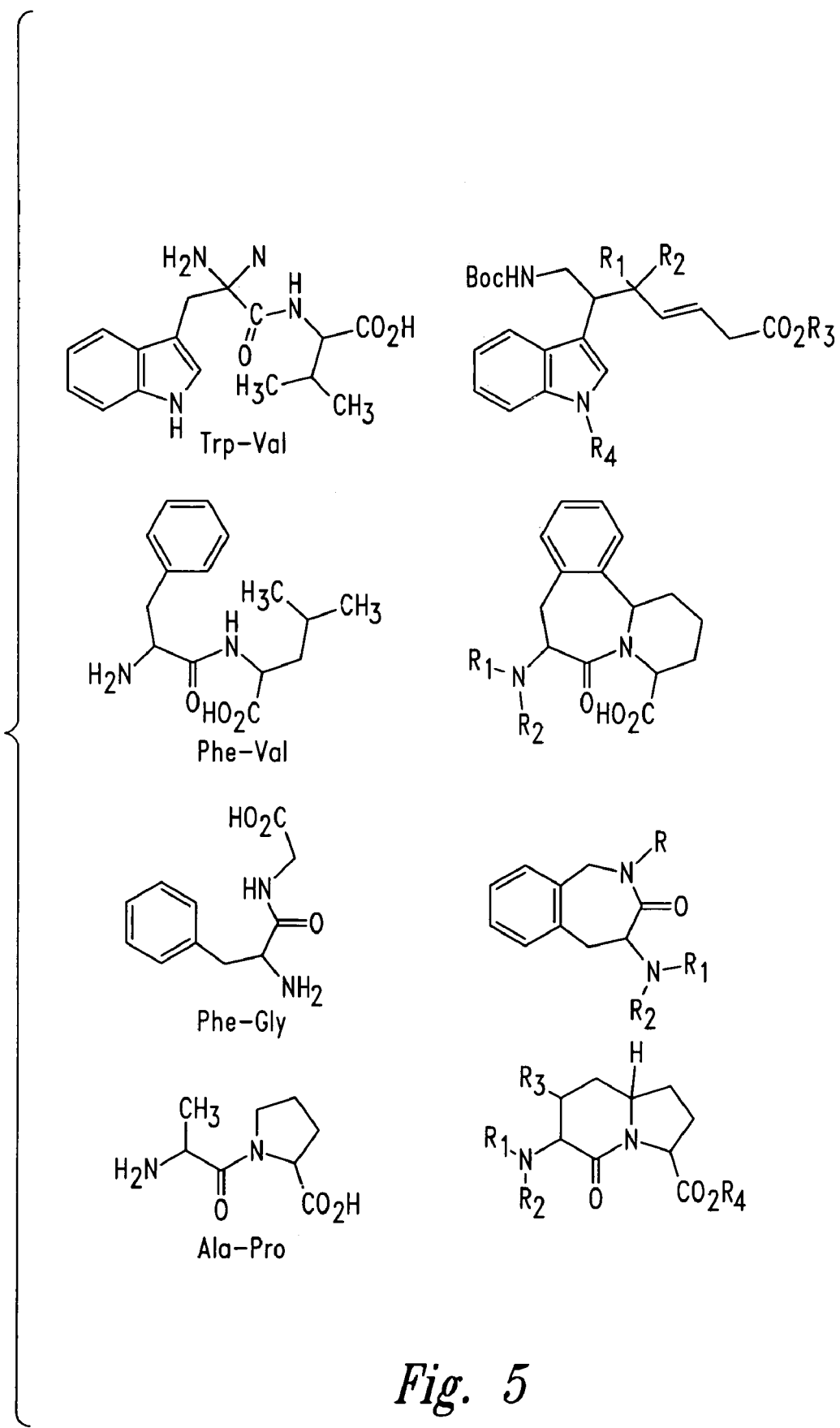
FIG. 5 illustrates representative unusual amino acids and dipeptide surrogates that may be incorporated into a peptidomimetic.
Figure 6:
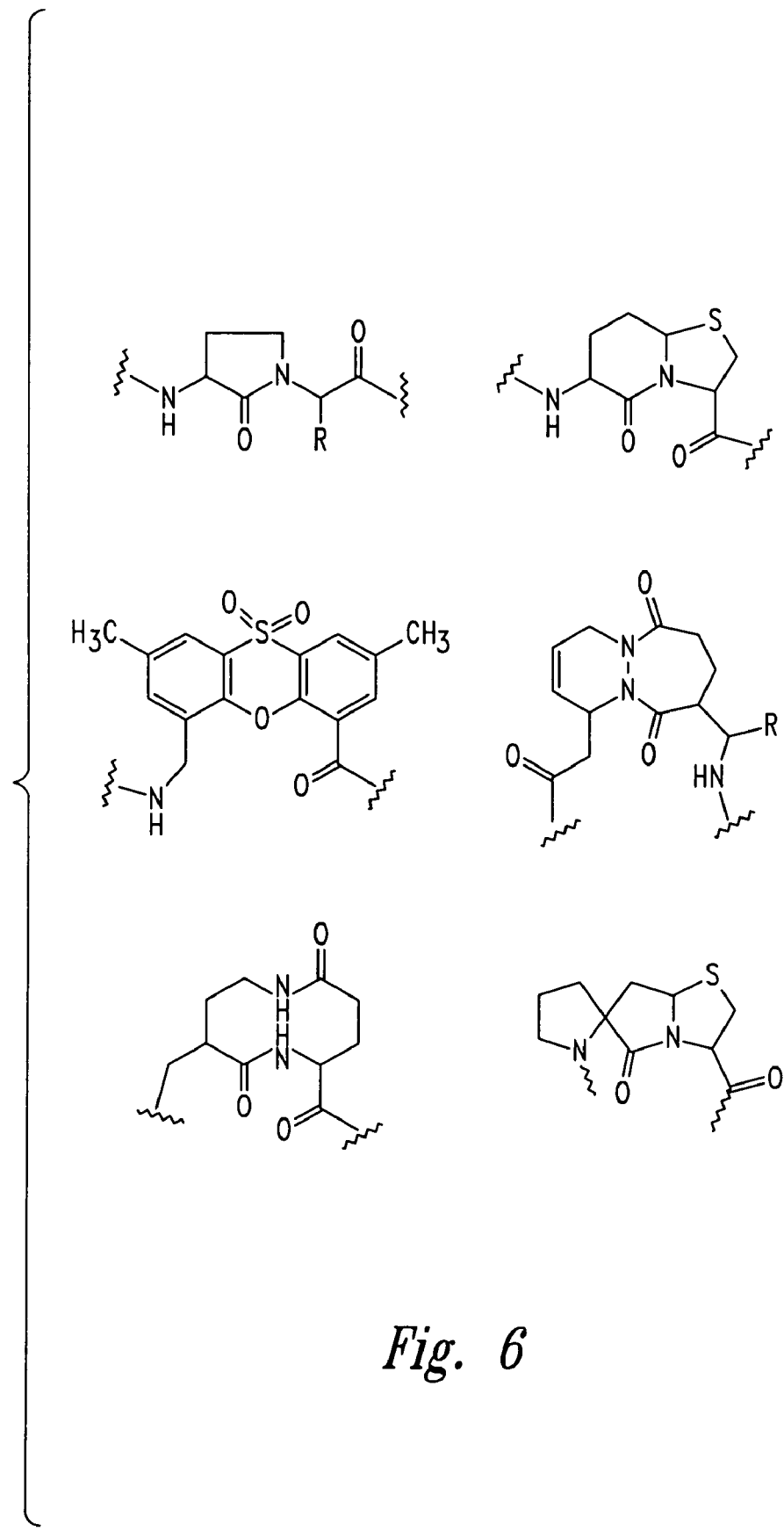
FIG. 6 illustrates representative secondary structure mimics that may be incorporated into a peptidomimetic.

Certain peptidomimetics may be designed, based on the cyclic peptide structure. For example, such peptidomimetics may mimic the local topography about the cleavable amide bonds (amide bond isosteres). Examples of backbone modifications are given in FIG. 4. These mimetics often match the peptide backbone atom-for-atom, while retaining functionality that makes important contacts with the binding sites. Amide bond mimetics may also include the incorporation of unusual amino acids or dipeptide surrogates (see FIG. 5, and other examples in Gillespie et al., *Biopolymers* 43:191–217, 1997). The conformationally rigid substructural elements found in these types of mimetics are believed to result in binding with highly favorable entropic driving forces, as compared to the more conformationally flexible peptide linkages. Backbone modifications can also impart metabolic stability towards peptidase cleavage relative to the parent peptide. Other peptidomimetics may be secondary structure mimics. Such peptidomimetics generally employ non-peptide structures to replace specific secondary structures, such as β-turns, β-sheets and α-turns (see FIG. 6).

To design a peptidomimetic, heuristic rules that have been developed through experience may be used to systematically modify a cyclic peptide. Within such modification, empirical data of various kinds are generally collected throughout an iterative refinement process. As noted above, optimal efficiency in peptidomimetic design requires a three-dimensional structure of the pharmacophore.

Figure 11:
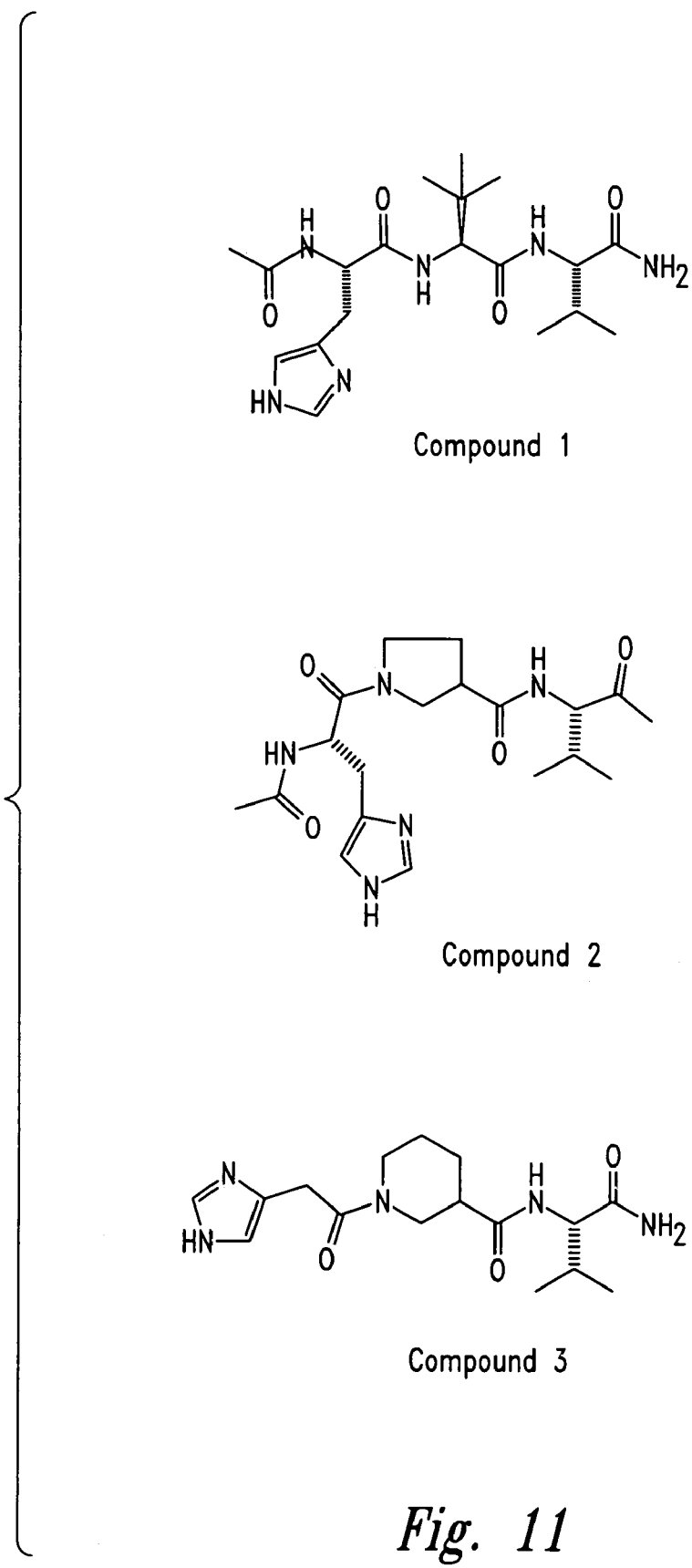
FIG. 11 depicts structures of representative peptidomimetics (compounds 1–3).

Pharmacophores as provided herein permit structure-based peptidomimetic design through, for example, peptide scaffold modification as described above. Certain peptidomimetics may be identified through visual inspection of one or more pharmacophores, as compared to the N-cadherin HAV conformation. For example, it is apparent from FIGS. 8A and 8B that the hydrophobic valine could be replaced with unnatural amino acids carrying bulky groups, such as that found in compound 1 (FIG. 11). This will restrict rotation of the amide bonds and possibly eliminate the need for cyclization. Alternatively the hydrophobic valine residue could be incorporated into a cyclic rigid structure, such as that found in compounds 2 and 3 (FIG. 11).

Peptidomimetics can also be designed based on a visual comparison of a cyclic peptide pharmacophore with a three-dimensional structure of a candidate compound, using knowledge of the structure-activity relationships of the cyclic peptide. Structure-activity studies have established important binding elements in the cyclic peptides, and have permitted the development of pharmacophore models. Peptidomimetics designed in this manner should retain these binding elements. In the case of N—Ac—CHAVC—NH$_2$ (SEQ ID NO:10), peptidomimetics should have chemical groups that mimic the three-dimensional geometry of the side chains of the histidine and valine residues. In the case of N—Ac—CHAVC—Y—NH$_2$ (SEQ ID NO:81), peptidomimetics should have chemical groups that mimic the three-dimensional geometry of the side chains of the histidine, valine and tyrosine residues.

Figure 12A:
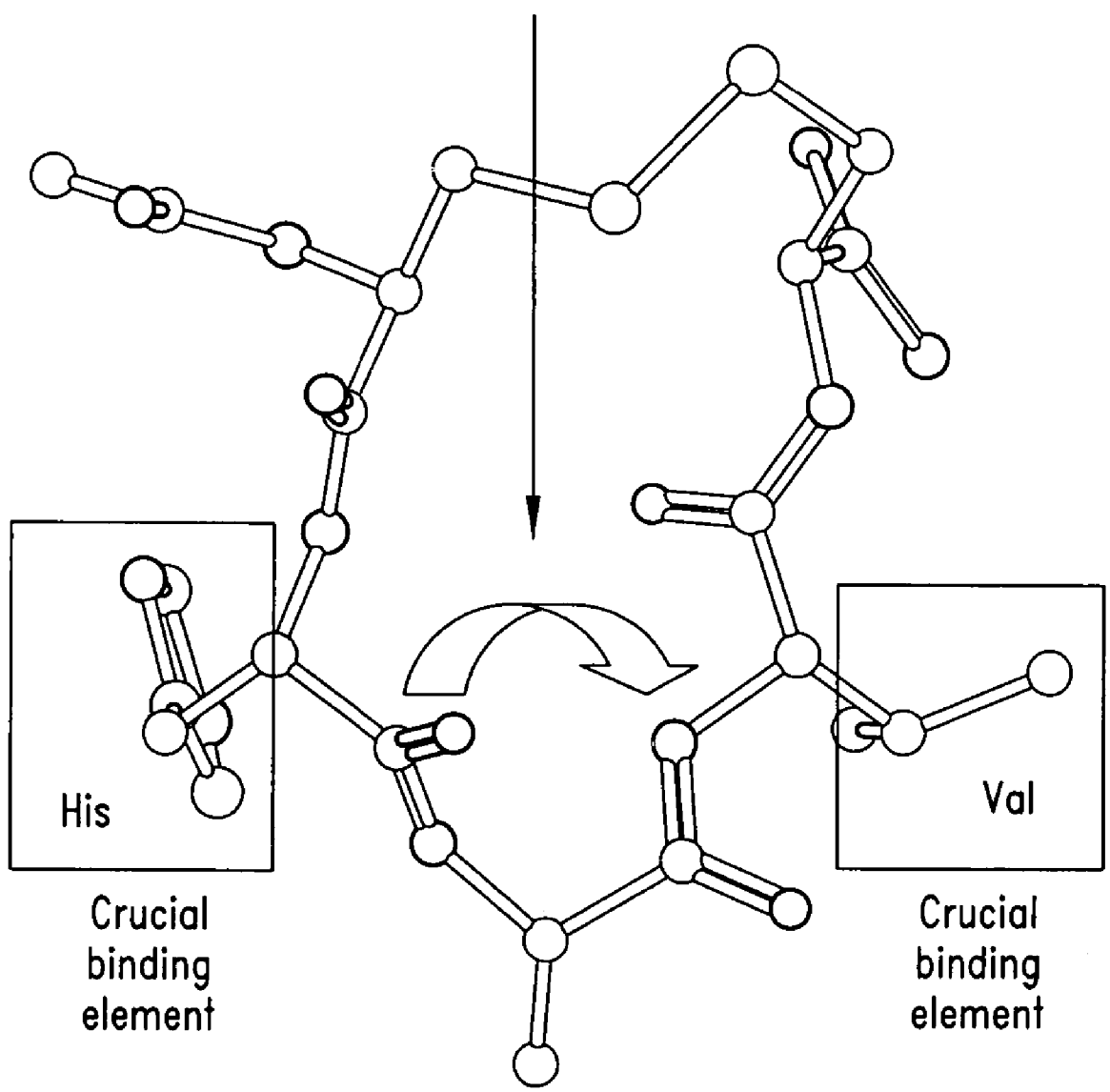
FIG. 12A depicts a cyclization scheme based upon the three-dimensional solution conformation of N—Ac—CHAVC—NH$_2$ (SEQ ID NO:10) and its solution-activity relationships.

By way of example, analysis of the solution conformations of the N—Ac—CHAVC—NH$_2$ (SEQ ID NO:10) indicates that a suitable peptidomimetic may be designed based on the cyclization indicated in FIG. 12A. This type of cyclization scheme allows the design of peptidomimetic compounds of about half the original molecular weight of N—Ac—CHAVC—NH$_2$ (SEQ ID NO:10) but with all the essential binding elements of that cyclic peptide.

Figure 12C:
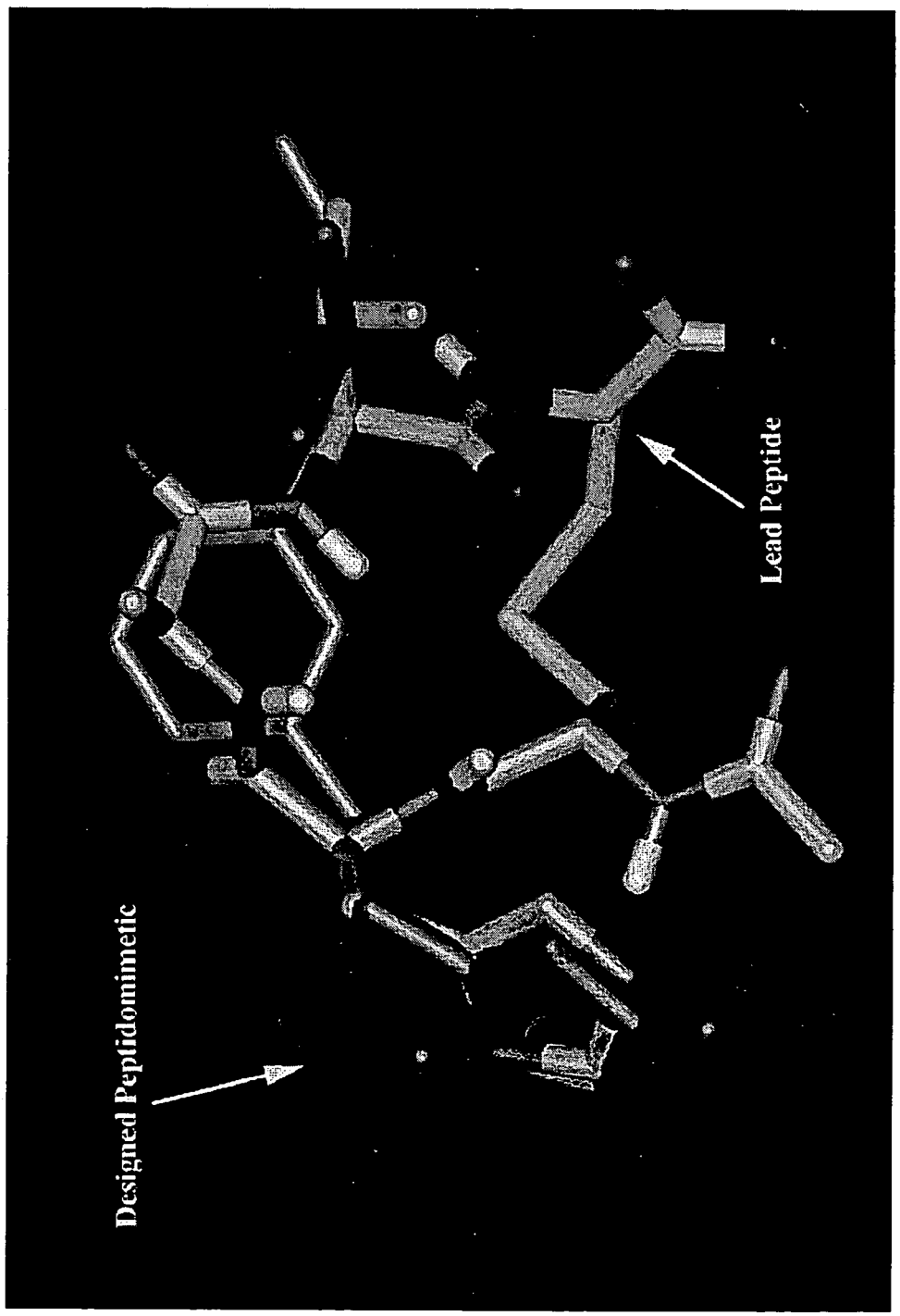
FIG. 12C presents a comparison of the three dimensional structure of the representative peptidomimetic compound 4 with the three dimensional structure of the HAV region of N—Ac—CHAVC—NH$_2$ (SEQ ID NO:10).

Based upon this information, the peptidomimetic compound 4 (FIG. 12B) was designed. FIG. 12B also shows one of its low energy conformations. Superposition of the low energy conformation of this designed peptidomimetic on one of the low energy conformations of N—Ac—CHAVC—NH$_2$ (SEQ ID NO:10) is given in FIG. 12C. The overlap in terms of the crucial binding elements indicates that compound 4 is a peptidomimetic.

Figure 12D:
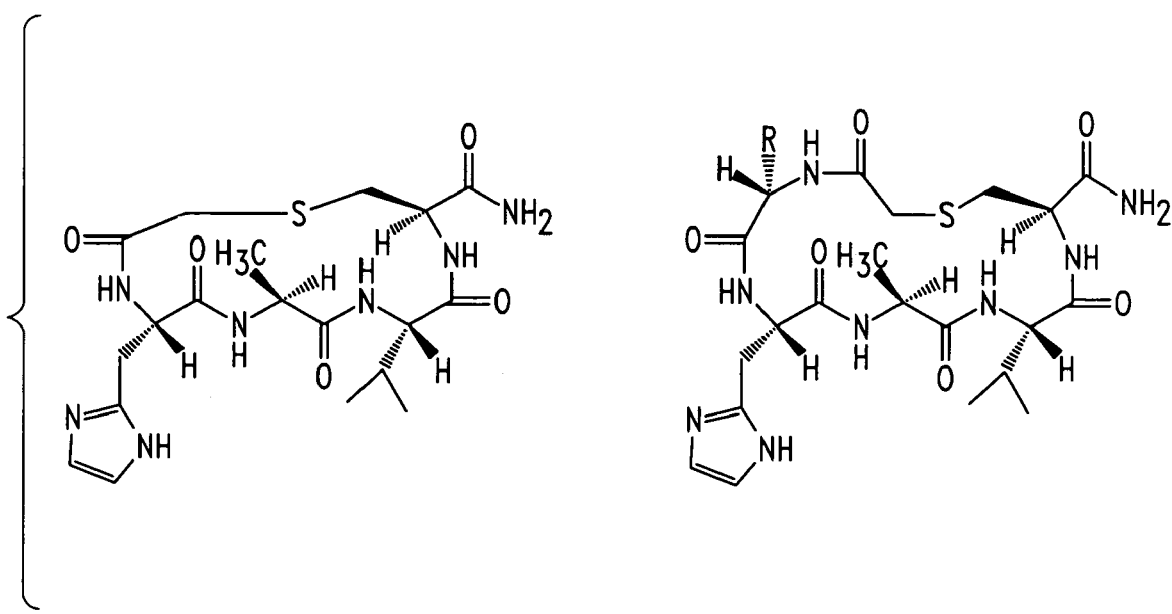
FIG. 12D depicts structures of representative peptidomimetics designed by replacing the disulfide bond of N—Ac—CHAVC—NH$_2$ (SEQ ID NO:10) with a thioether bond.

A second set of peptidomimetics may be designed around replacing the disulfide bond (—S—S—) with a thioether (—S—CH$_2$—C(O)—). The disulfide bond in general is not very stable as it can readily be reduced under acidic conditions. Replacing the disulfide bond with a thioether moiety (—S—CH$_2$—C(O)—) can significantly improve the stability of the peptide and therefore the oral availability. Two peptides that were designed in this manner, based upon the structure of N—Ac—CHAVC—NH$_2$, are shown in FIG. 12D.

Molecular modeling studies carried out on N—Ac—CHAVC—NH$_2$ (SEQ ID NO:10) indicated that the solution NMR structures could indeed be predicted using the QUANTA molecular modeling package and its associated molecular mechanics program CHARMM (Brooks, B. R.; Bruccoleri, R. E.; Olafson, B. D.; States, D. J.; Swaminathan, S.; Karplus, M. CHARMM: A program for macromolecular energy minimization and dynamics calculations. J. Comput. Chem. 1983, 4, 187–217), running on an SGI workstation with IRIX6.5. A dielectric constant of 80 can be used to simulate an aqueous environment. These modeling techniques can be used predict the conformations (FIGS. 25A–27C) of the thioethers whose structures are given in FIGS. 24A–24C. It was found that the lowest energy conformation of CH$_2$COHAVC—NH$_2$ (SEQ ID NO:96) also has the lowest RMS deviation from the co-ordinates of NMR structure 2 of N—Ac—CHAVC—NH$_2$. (SEQ ID NO:10) NMR Structure 2 is the conformation of N—Ac—CHAVC—NH$_2$ (SEQ ID NO:10) which best mimics the HAV sequence in the x-ray structure of the first extracellular domain of N-cadherin.

As an alternative to design by visual inspection, libraries (e.g., containing hydantoin and/or oxopiperazine compounds) may be made using combinatorial chemical techniques. Combinatorial chemical technology enables the parallel synthesis of organic compounds through the systematic addition of defined chemical components using highly reliable chemical reactions and robotic instrumentation. Large libraries of compounds result from the combination of all possible reactions that can be done at one site with all the possible reactions that can be done at a second, third or greater number of sites. Combinatorial chemical methods can potentially generate tens to hundreds of millions of new chemical compounds as mixtures, attached to a solid support, or as individual compounds.

Figure 13A:
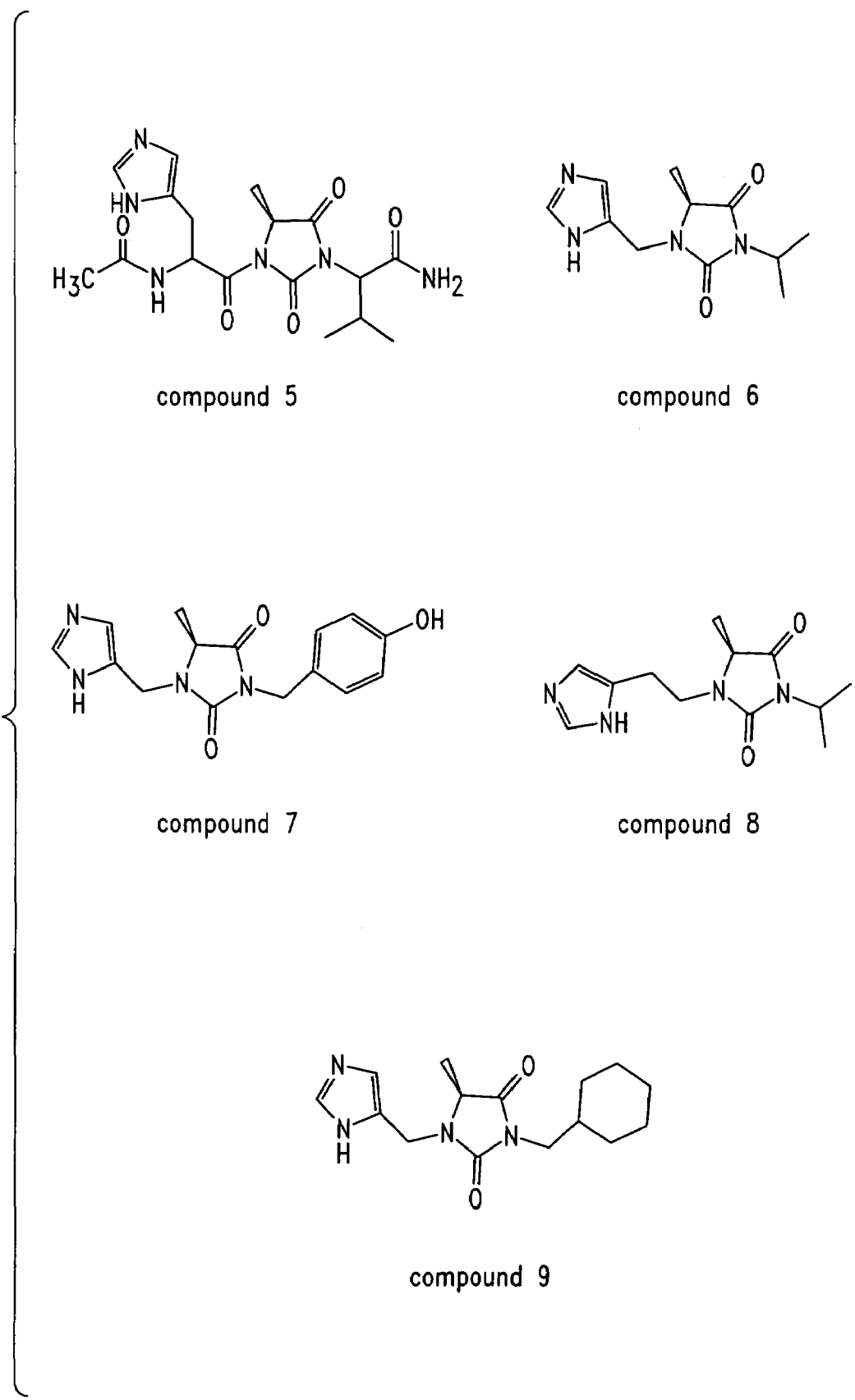

Pharmacophores can be used to facilitate the screening of such chemical libraries. For example, instead of producing all possible members of every library (resulting in an unwieldy number of compounds), library synthesis can focus on the library members with the greatest probability of interacting with the target. The integrated application of structure-based design and combinatorial chemical technologies can produce synergistic improvements in the efficiency of drug discovery. By way of example, hydantoin and oxopiperazine libraries may be limited to those compounds that involve only the addition of histidine and valine surrogates to the hydantoin or oxopiperazine backbone. Some examples of such compounds are compounds 5–12 (FIGS. 13A–13B).

Further peptidomimetics are compounds that appear to be unrelated to the original peptide, but contain functional groups positioned on a nonpeptide scaffold that serve as topographical mimics. This type of peptidomimetic is referred to herein as a "non-peptidyl analogue." Such peptidomimetics may be identified using library screens of large chemical databases. Such screens use the three-dimensional conformation of a pharmacophore to search such databases in three-dimensional space. A single three-dimensional structure may be used as a pharmacophore model in such a search. Alternatively, a pharmacophore model may be generated by considering the crucial chemical structural features present within multiple three-dimensional structures. Crucial chemical structural features of the classical cadherin HAV sequence include the His and Val residues, which are believed to participate in the interactions between one cadherin molecule and another. Without wishing to be bound by any particular theory, the side chain of the His residue is believed to form a number of hydrogen bonds and the Val residue is believed to interact hydrophobically with the adhesive surface. In the development of a pharmacophore model, these two crucial residues should be represented by appropriate chemical groups. For example the imidazole ring of histidine could be represented by any of its bioisosteres, which might include triazole, pyrazole, thiatriazole, triazolone, benzoxadiazole, pyrazine, pyrimidine, oxadiazole, tetraazole, aminopyridine, triazine, benzodioxole, benzodiazole or benzoxadiazole. Similarly valine could be replaced by any hydrophobic residue such as tert-butyl, cyclopentane, cyclohexane, any substituted phenyl, any substituted naphthalene or any substituted aromatic.

Any of a variety of databases of three-dimensional structures may be used for such searches. A database of three-dimensional structures may be prepared by generating three-dimensional structures of a database of compounds, and storing the three-dimensional structures in the form of data storage material encoded with machine-readable data. The three-dimensional structures can be displayed on a machine capable of displaying a graphical three-dimensional representation and programmed with instructions for using the data. Within preferred embodiments, three-dimensional structures are supplied as a set of coordinates that define the three-dimensional structure.

Preferably, the 3D-database contains at least 100,000 compounds, with small, non-peptidyl molecules having relatively simple chemical structures particularly preferred. It is also important that the 3D co-ordinates of the compounds in the database be accurately and correctly represented. The National Cancer Institute (NCI) 3D-database (Milne et al., *J. Chem. Inf. Comput. Sci.* 34:1219–1224, 1994) and the Available Chemicals Directory (ACD; available from MDL Information Systems, San Leandro, Calif.) are two excellent databases that can be used to generate a database of three-dimensional structures, using molecular modeling, as discussed above. For flexible molecules, which can have several low-energy conformations, it is desirable to store and search multiple conformations. The Chem-X program (Oxford Molecular Group PLC; Oxford UK) is capable of searching thousands or even millions of conformations for a flexible compound. This capability of Chem-X provides a real advantage in dealing with compounds that can adopt multiple conformations. Using this approach, although the NCI-3D database presently contains a total of 465,000 compounds, hundreds of millions of conformations can be searched in a 3D-pharmacophore searching process.

The Available Chemical Database presently contains 255,153 unique chemicals from 543 supplier catalogues. The ACD database contains about 50,000 compounds that are known drugs. To facilitate pharmacophore searching, the entire ACD database was converted into 3-D conformations, as described above, which can be searched using the Chem-X program.

Figure 14A:
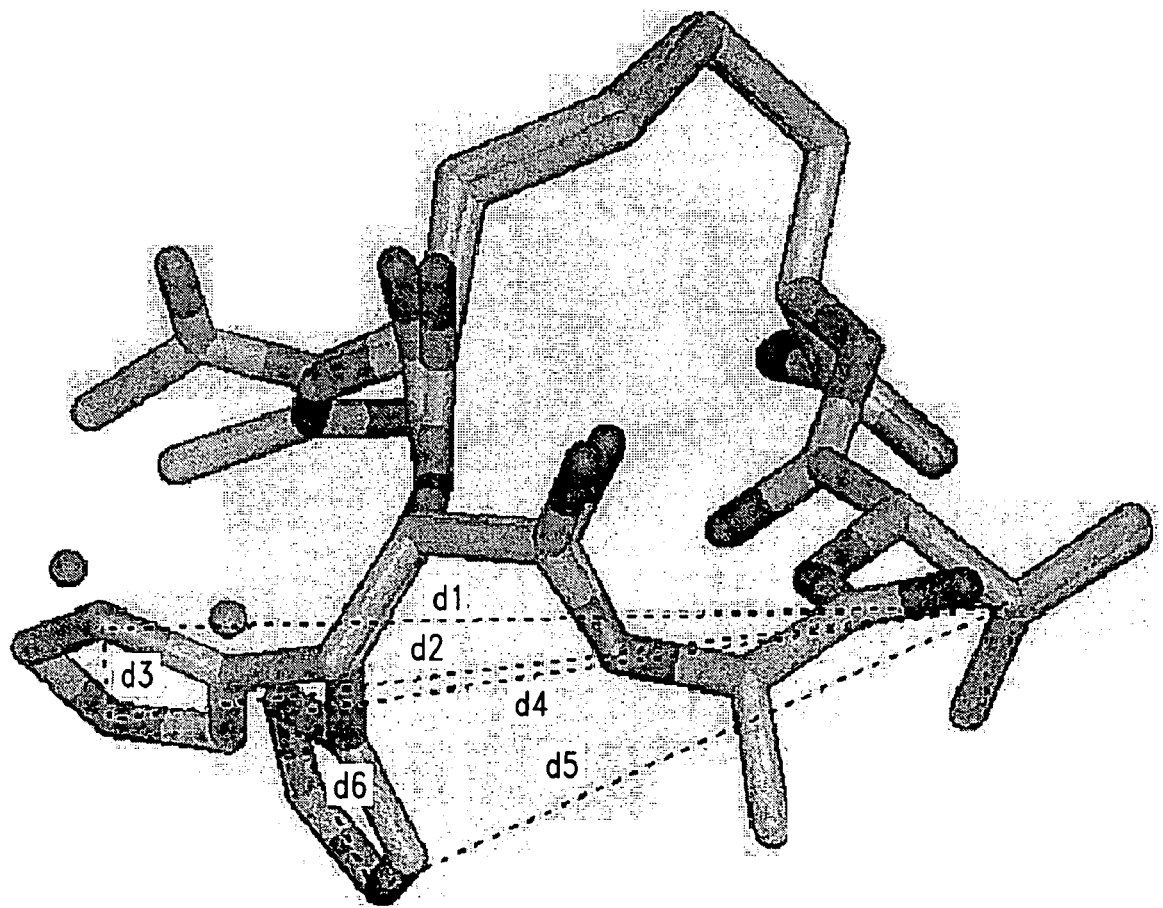
FIGS. 14A–14C illustrate the pharmacophore queries derived from the pharmacophore in N—Ac—
Figure 16:
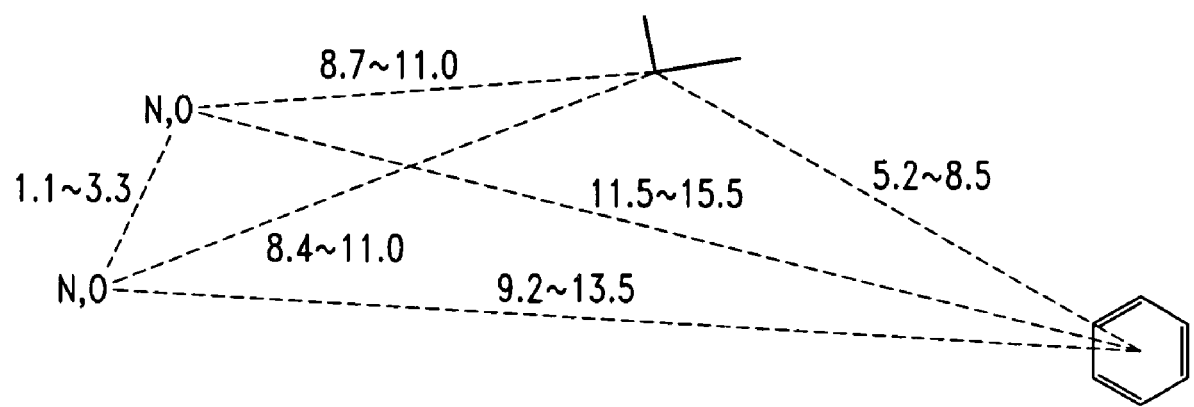
FIG. 16 depicts a pharmacophore query derived from the pharmacophore in N—Ac—CHAVC—Y—NH$_2$ (SEQ ID NO:81) and used in chemical database searches.
Figure 17B:
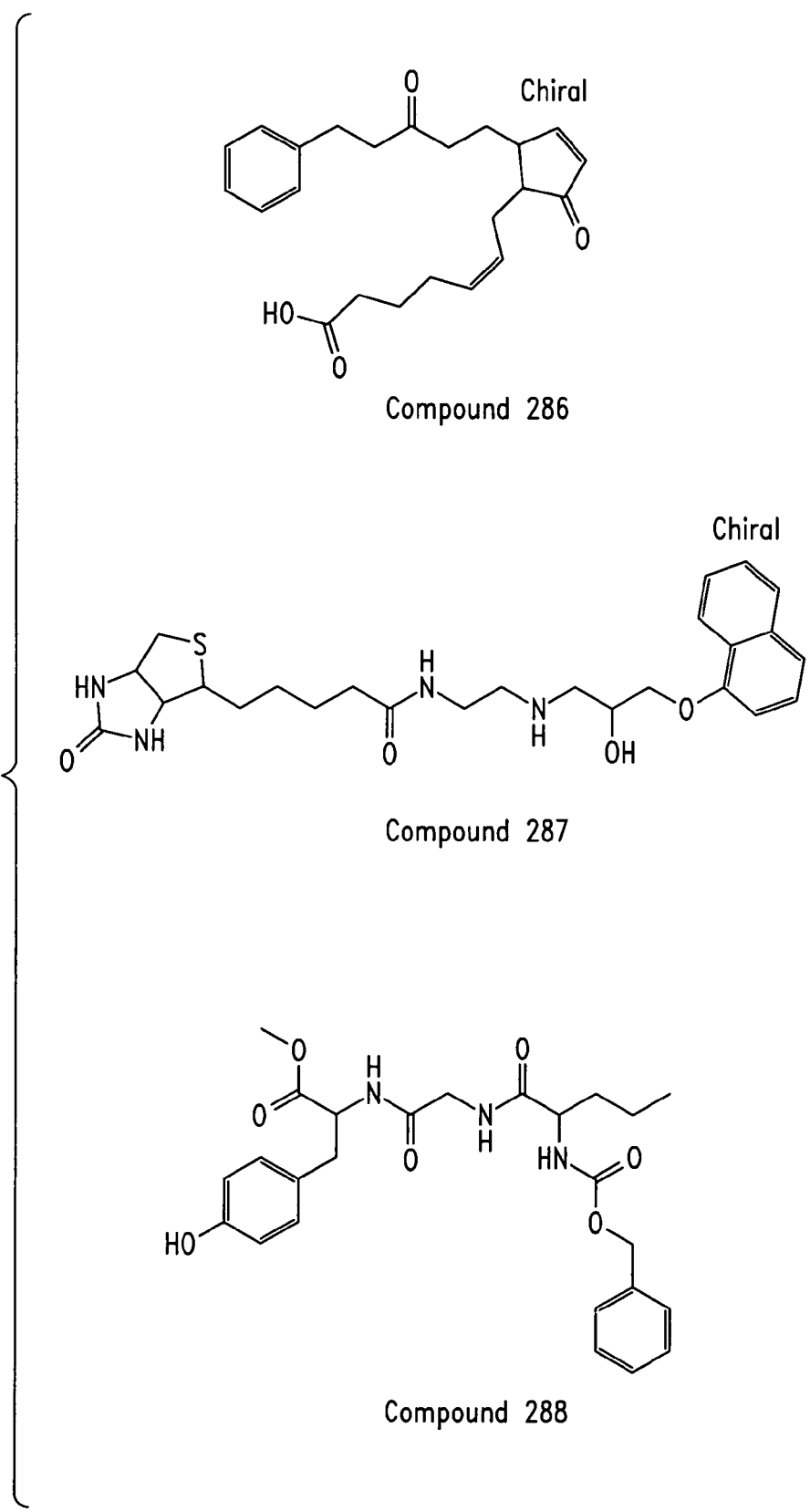
Figure 17E:
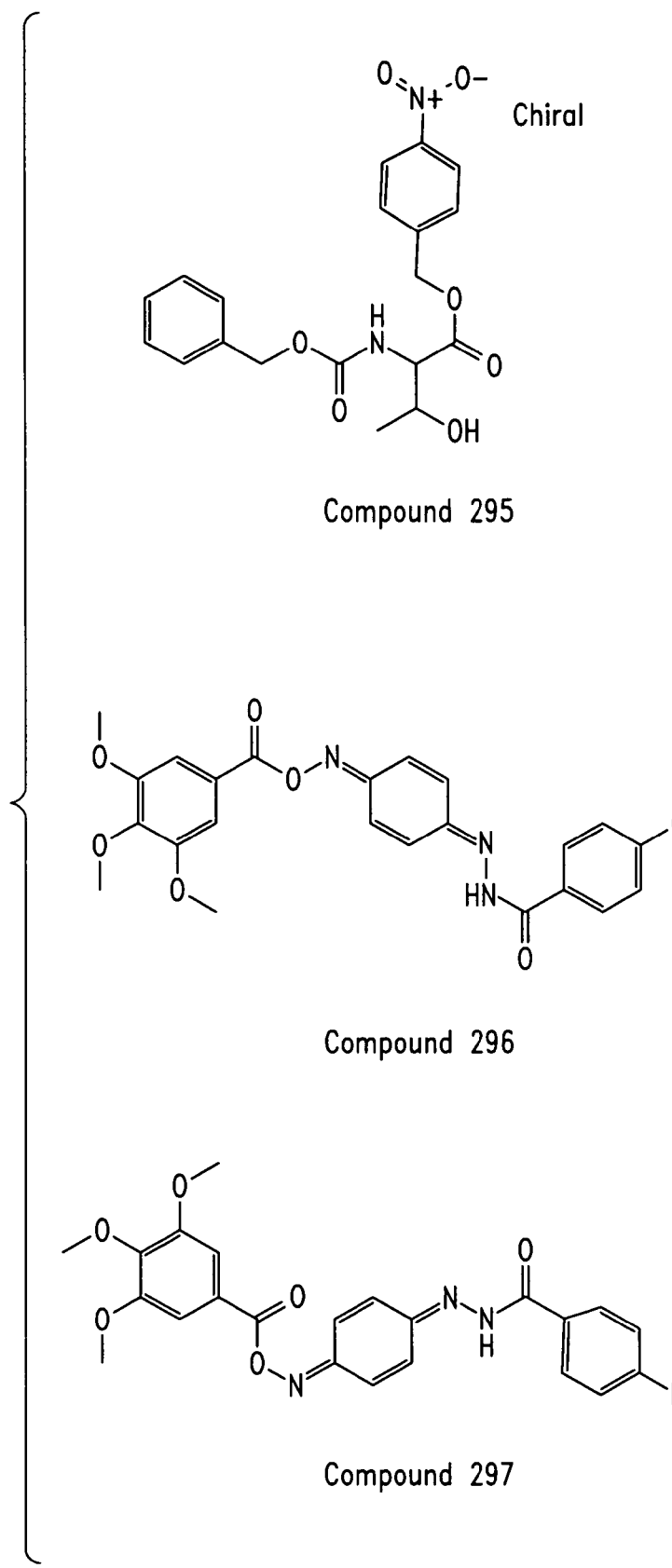
Figure 171:
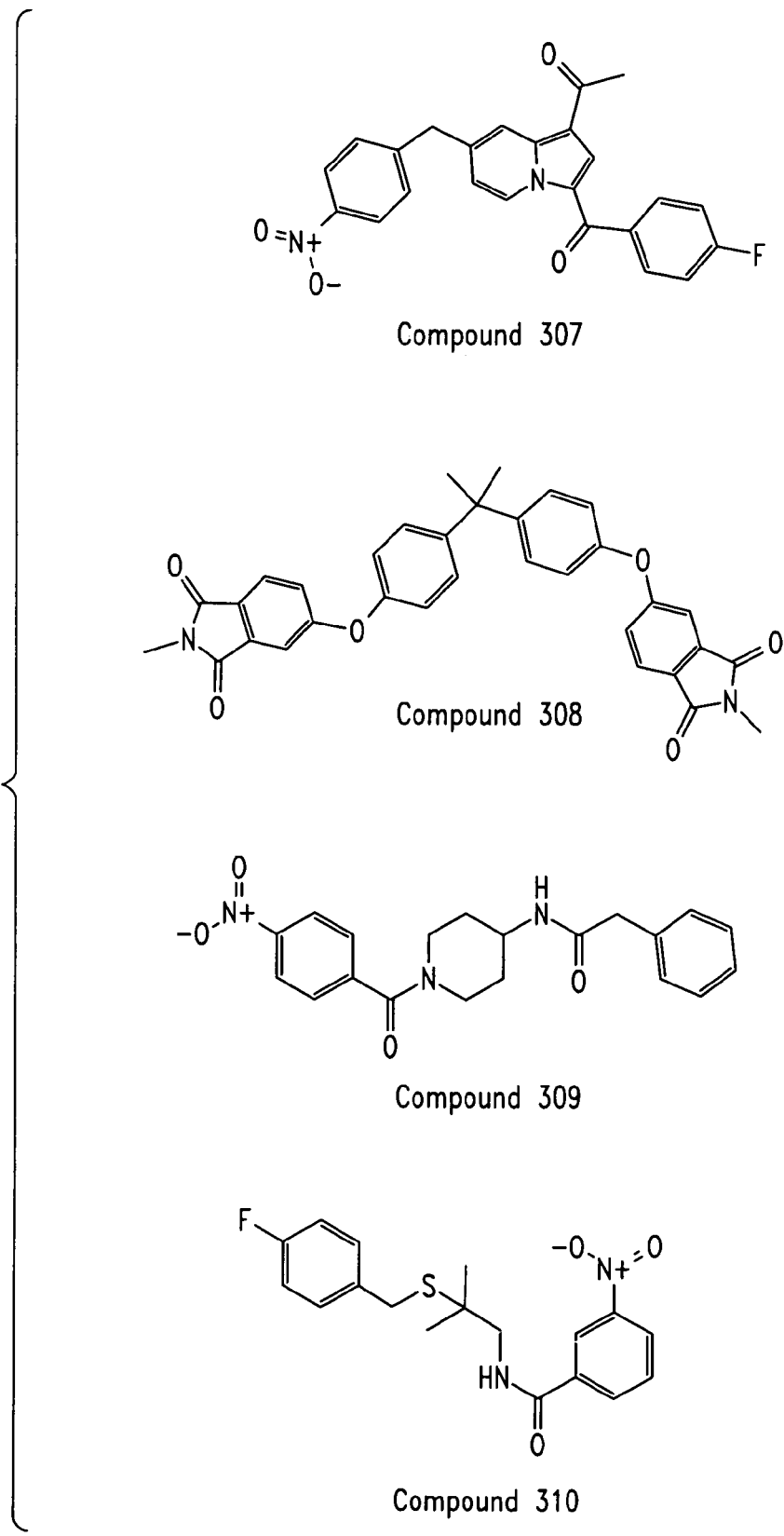
Figure 17J:
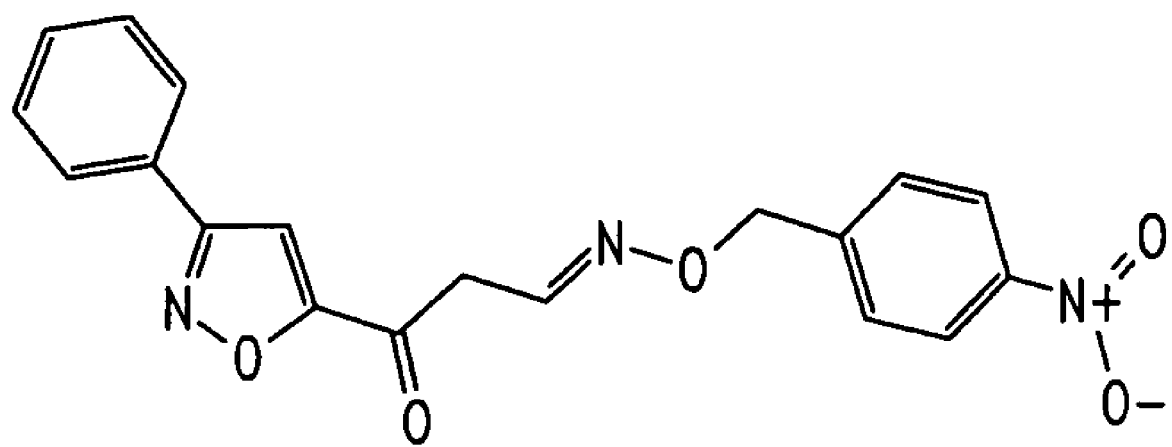
Figure 18D:
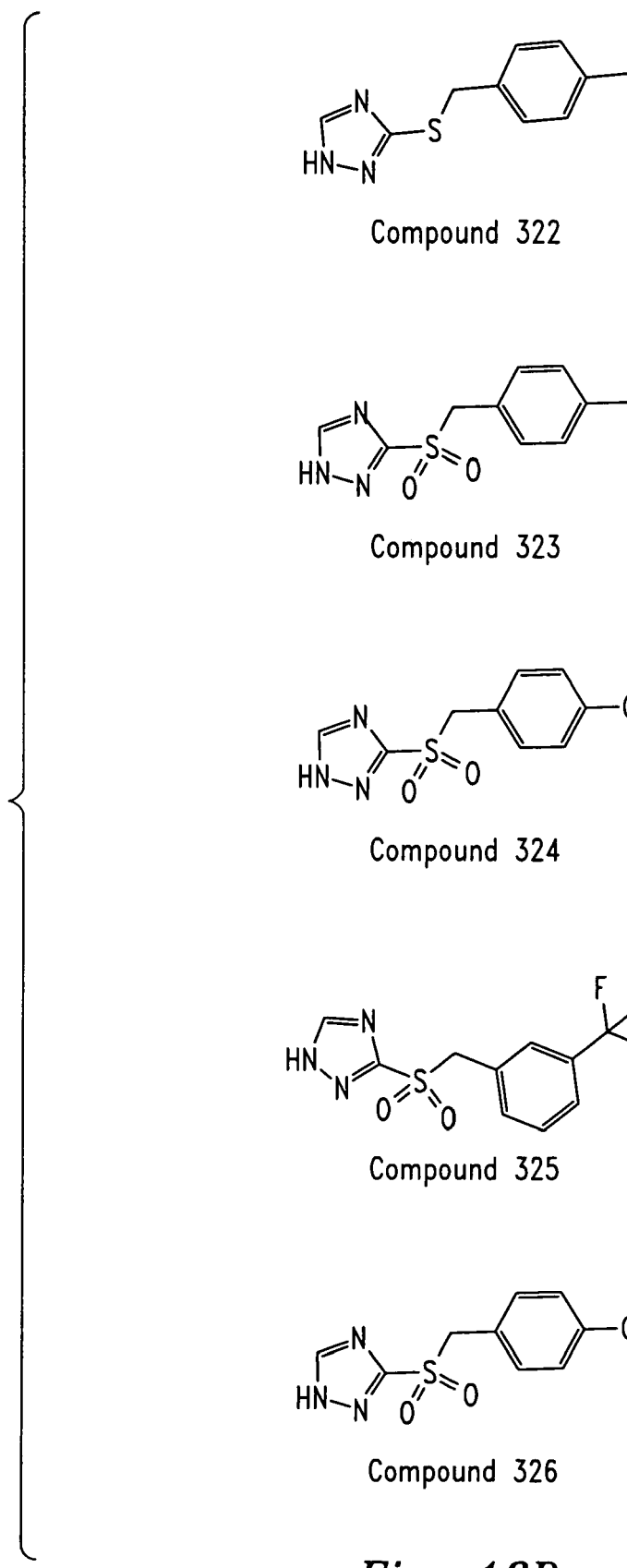
Figure 19E:
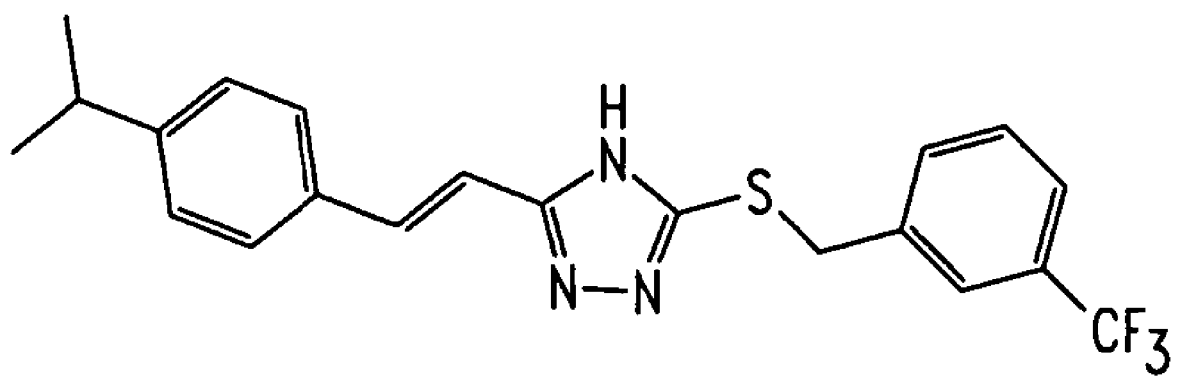
Figure 20A:
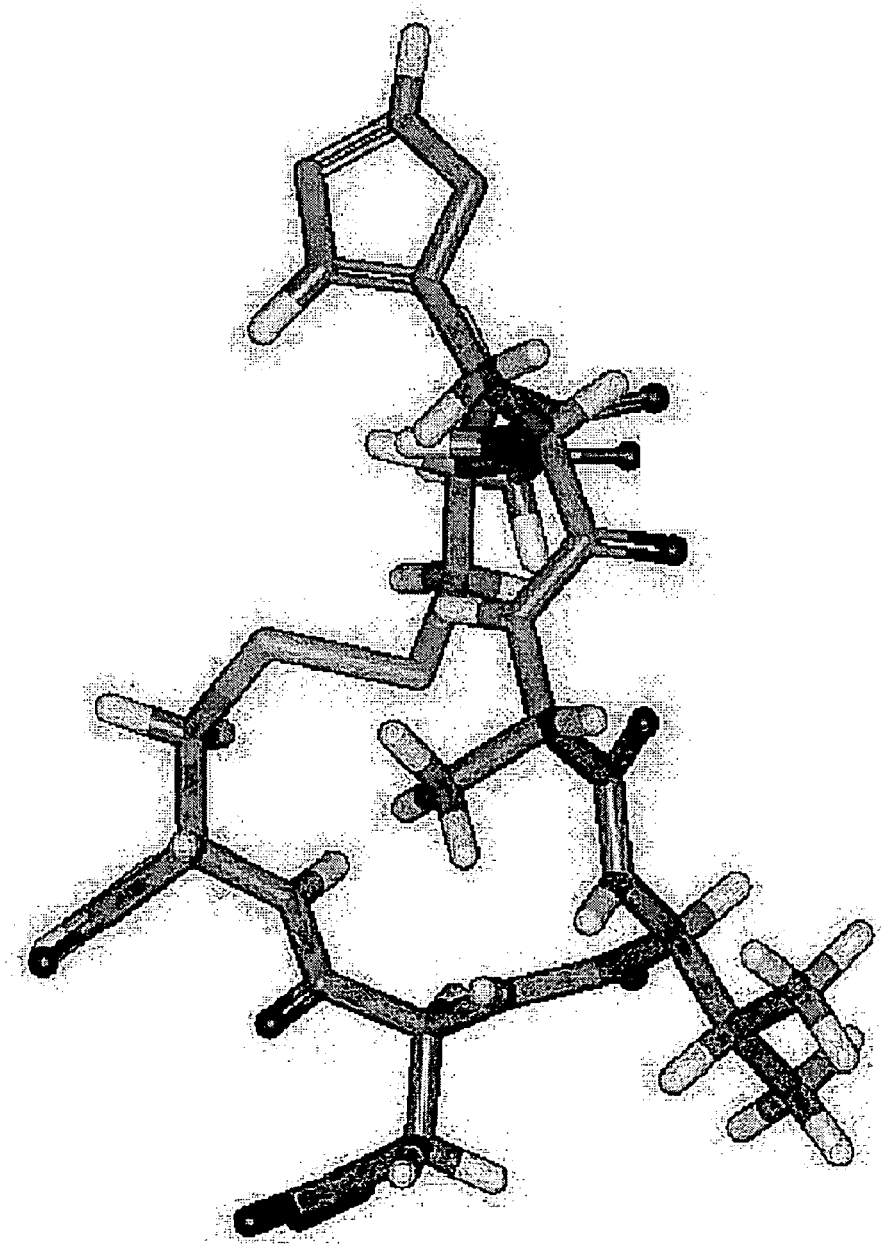
FIGS. 20A–20D depict the four low energy conformations of the high resolution molecular map of the pharmacophore of N—Ac—CHAVDC—NH$_2$ (SEQ ID NO:20).
Figure 20B:
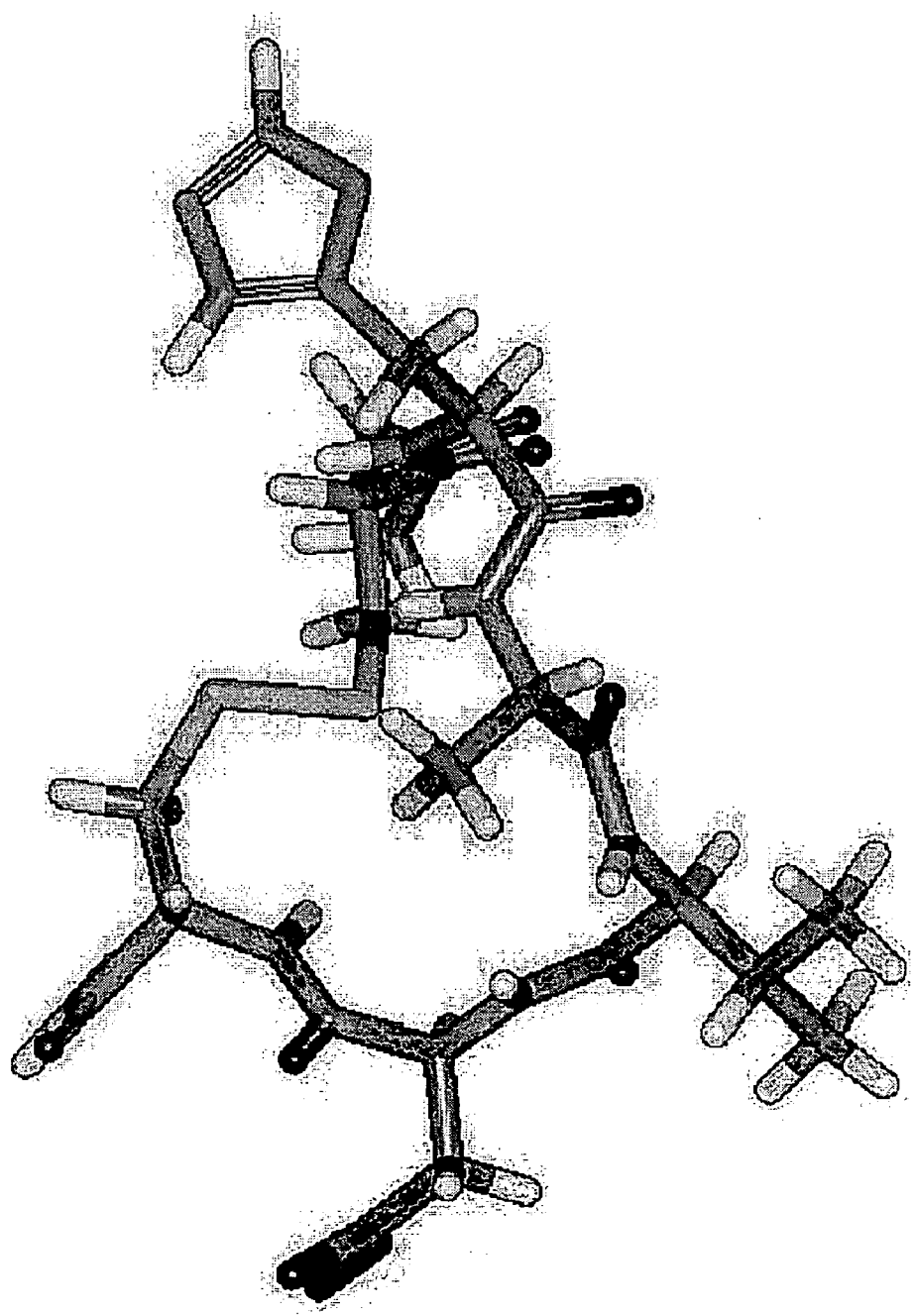
Figure 20C:
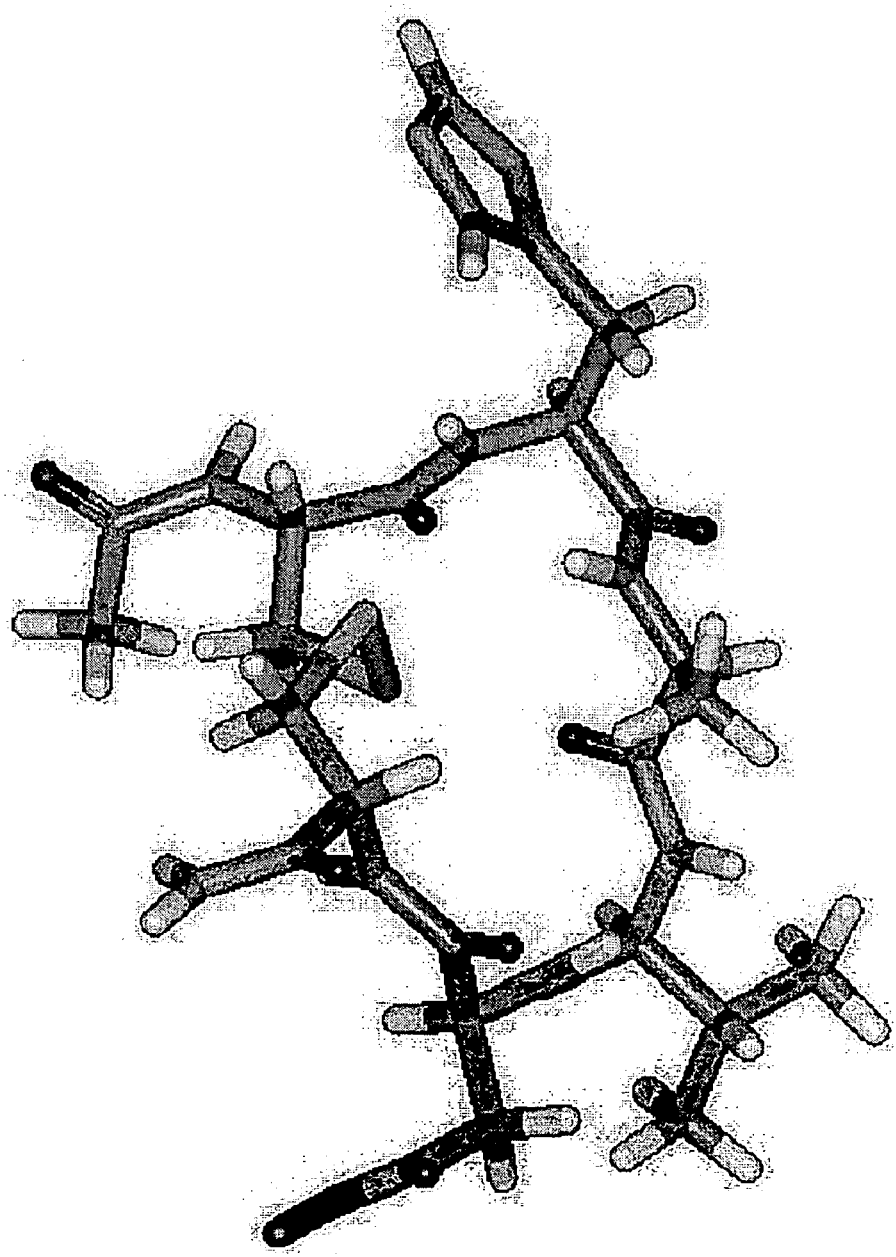
Figure 20D:
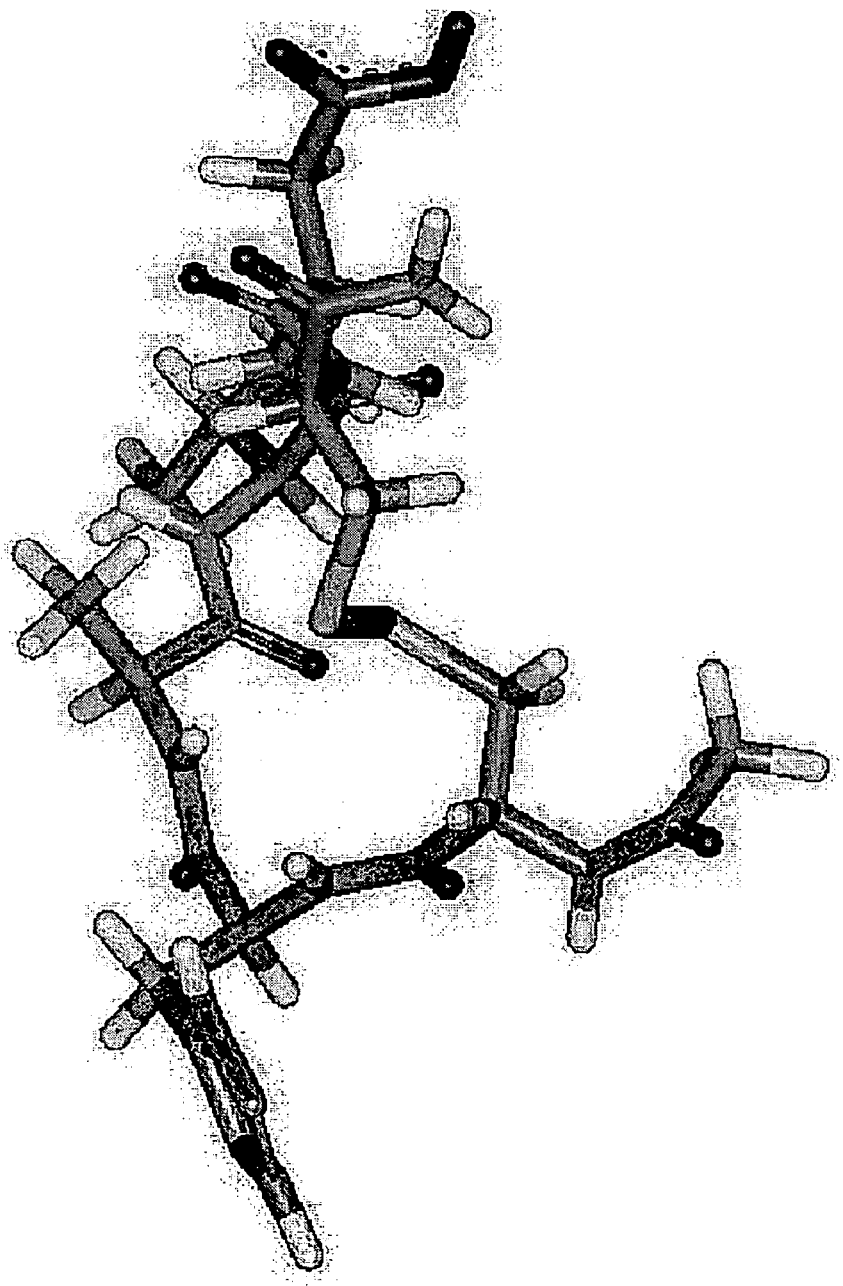
Figure 21D:
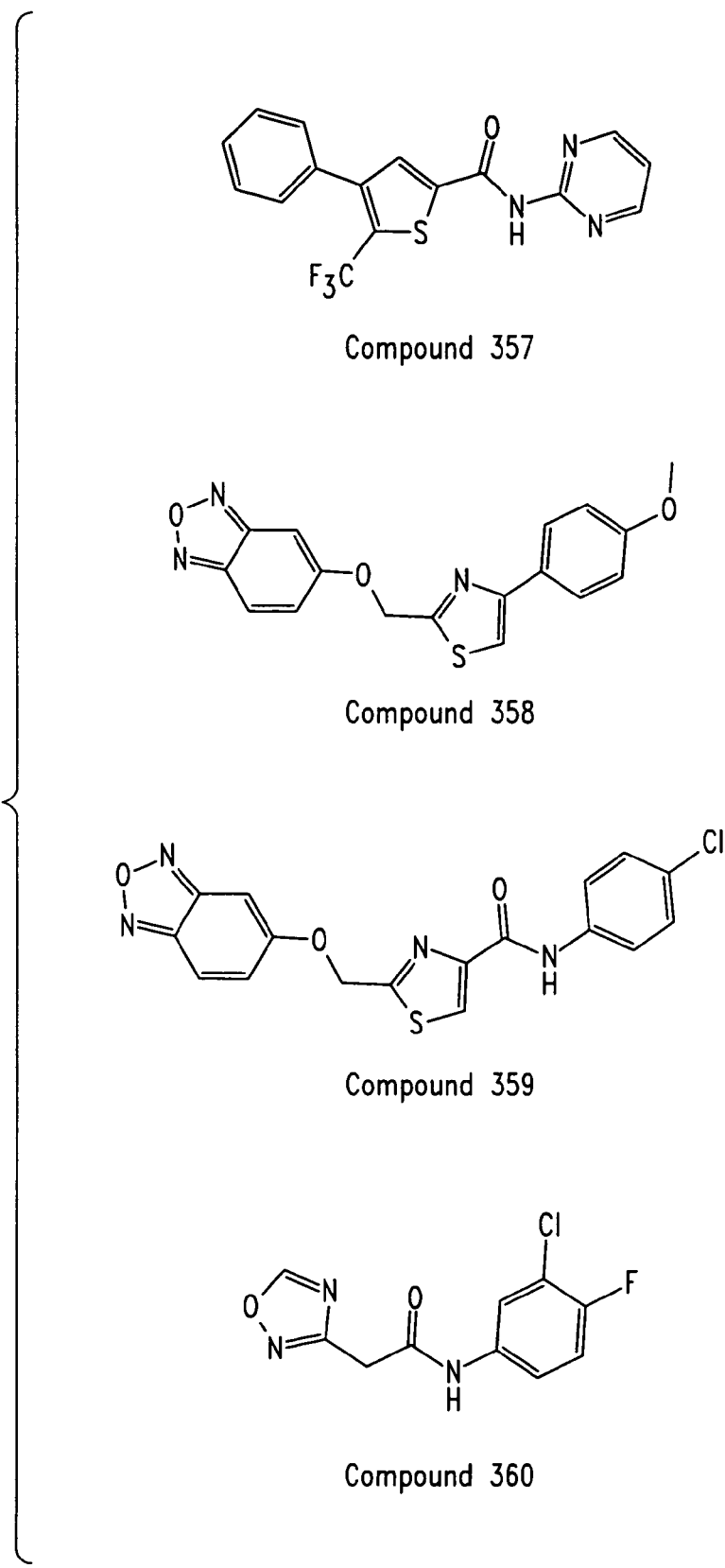
FIGS. 21A–21N depict further structures of representative non-peptidyl analogues of N—Ac—CHAVC—NH$_2$ (SEQ ID NO:10) derived from 3D-phamacophore database searching using the pharmacophore queries depicted in FIGS. 14A–14C (compounds 345–399).
Figure 21E:
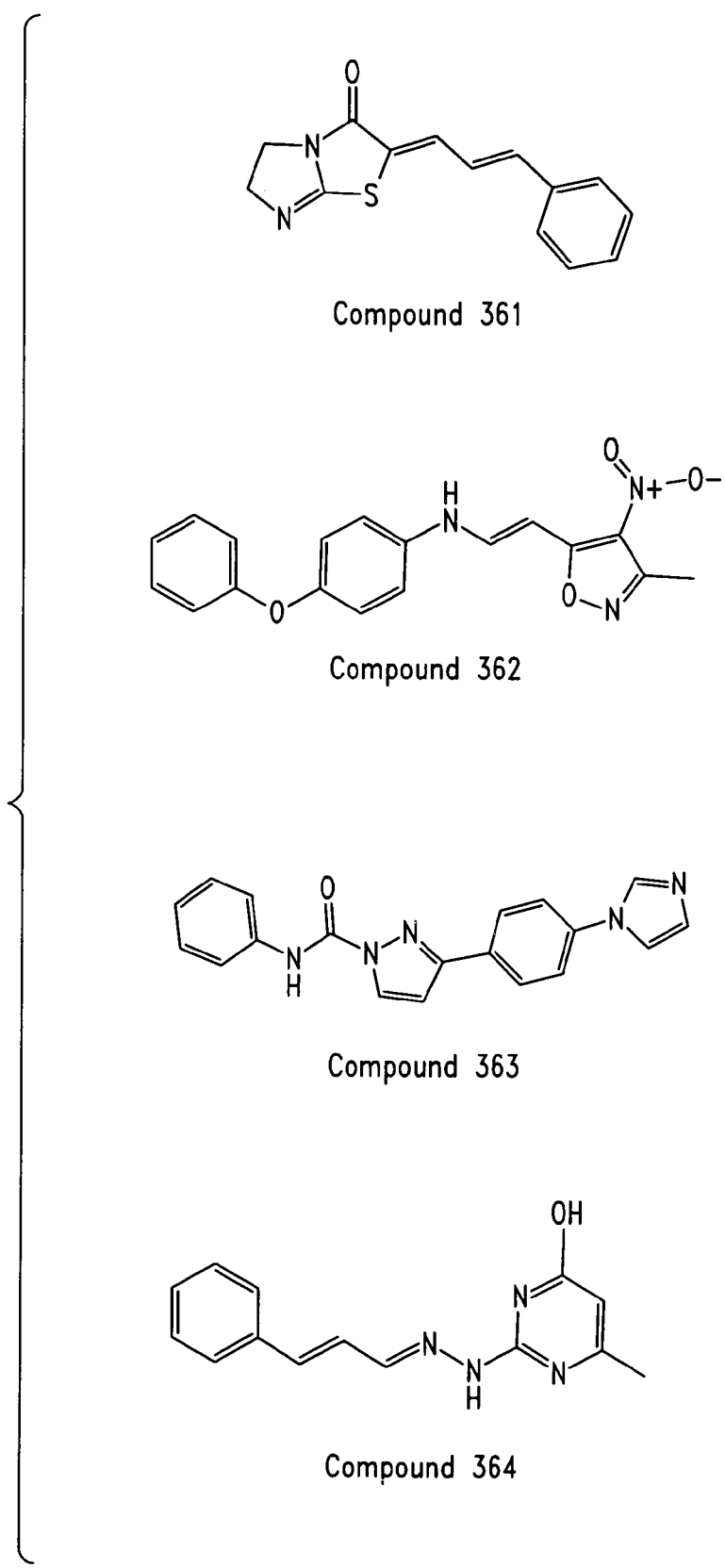
Figure 21H:
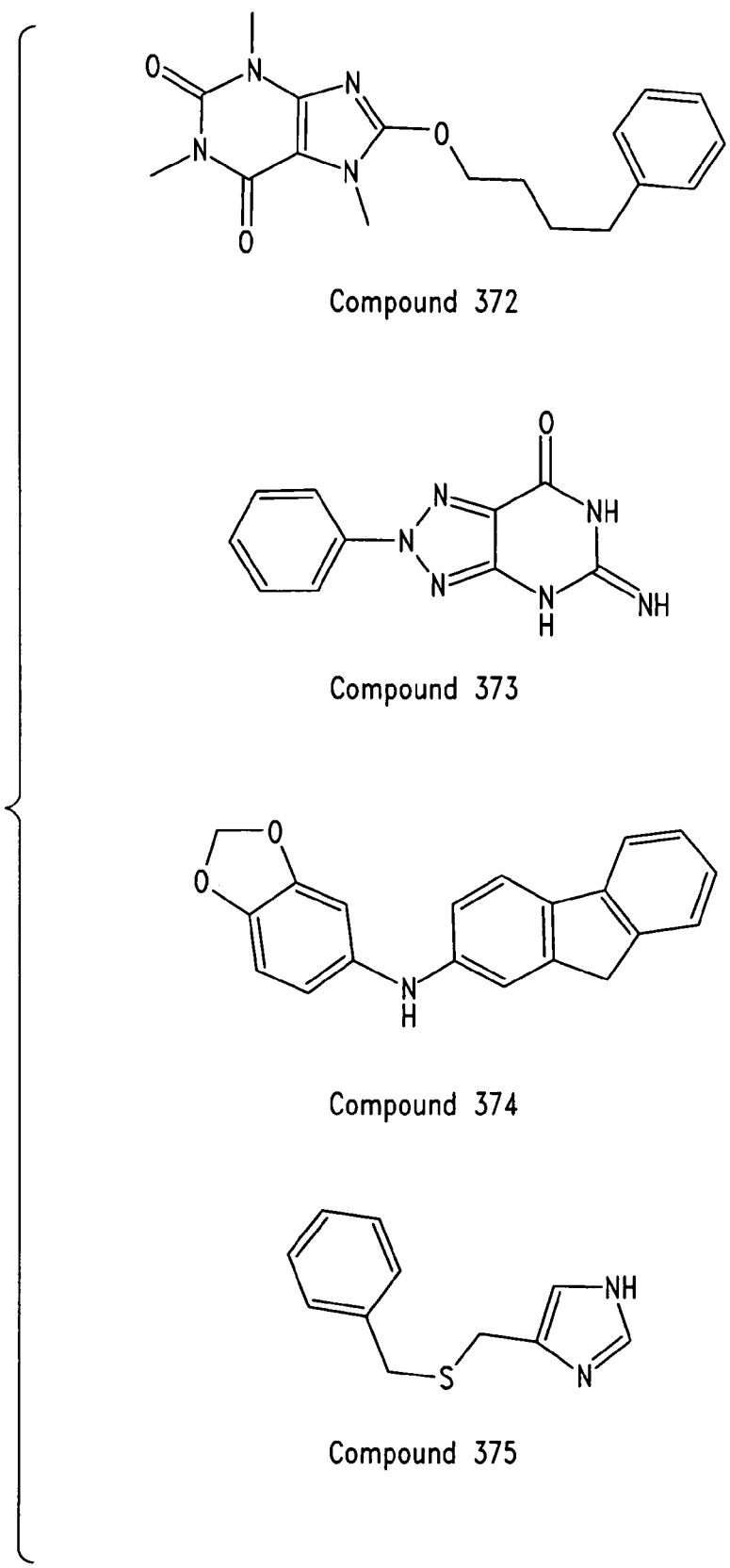
Figure 21M:
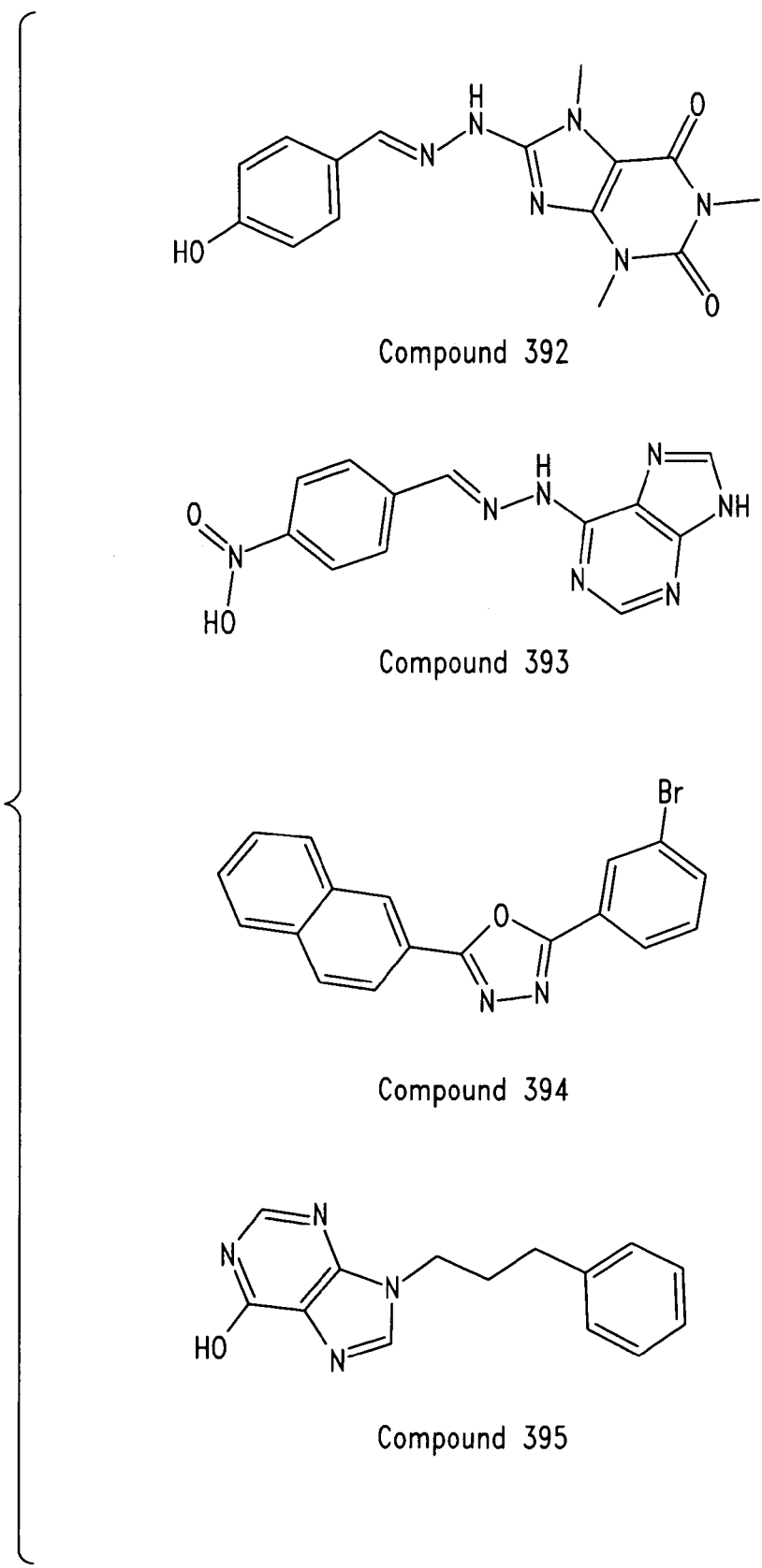
Figure 23A:
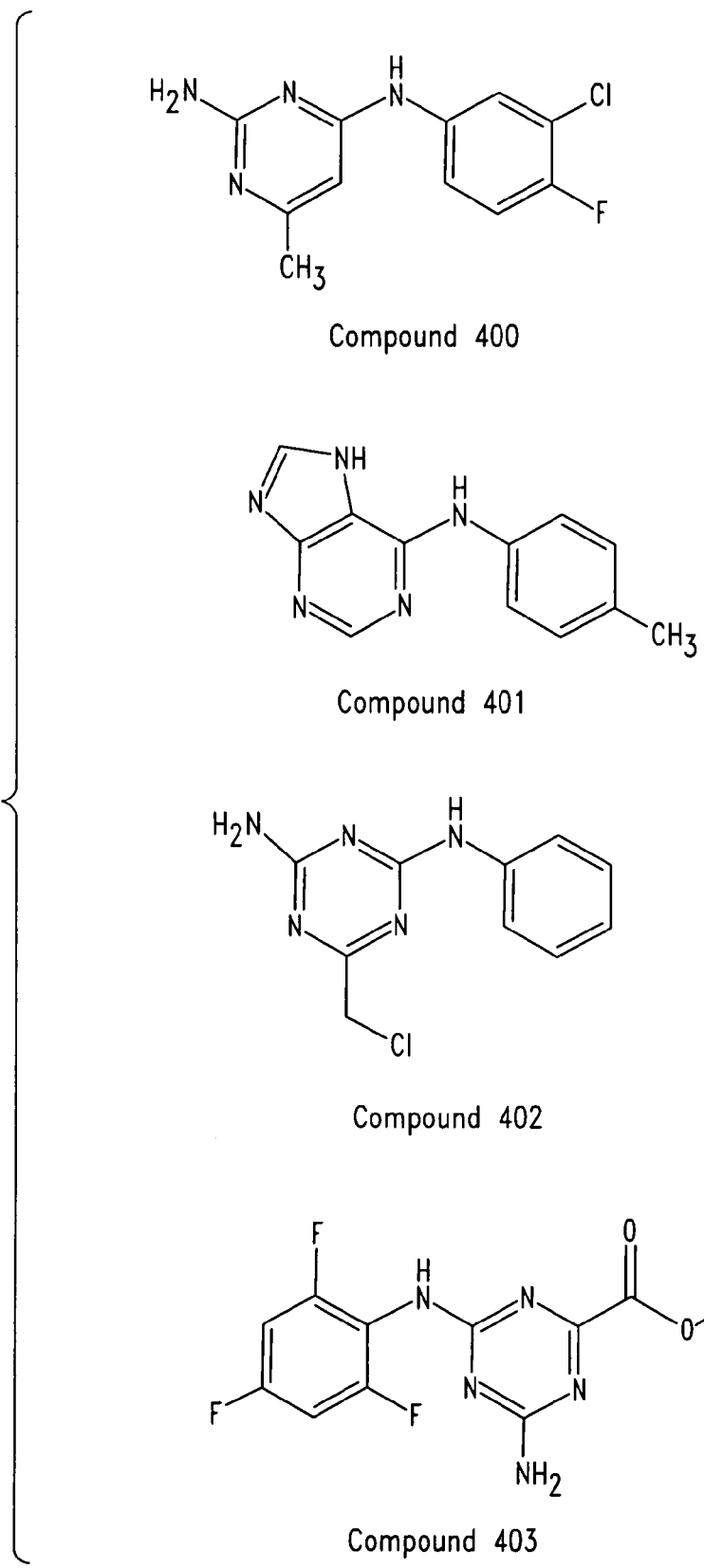
Figure 28:
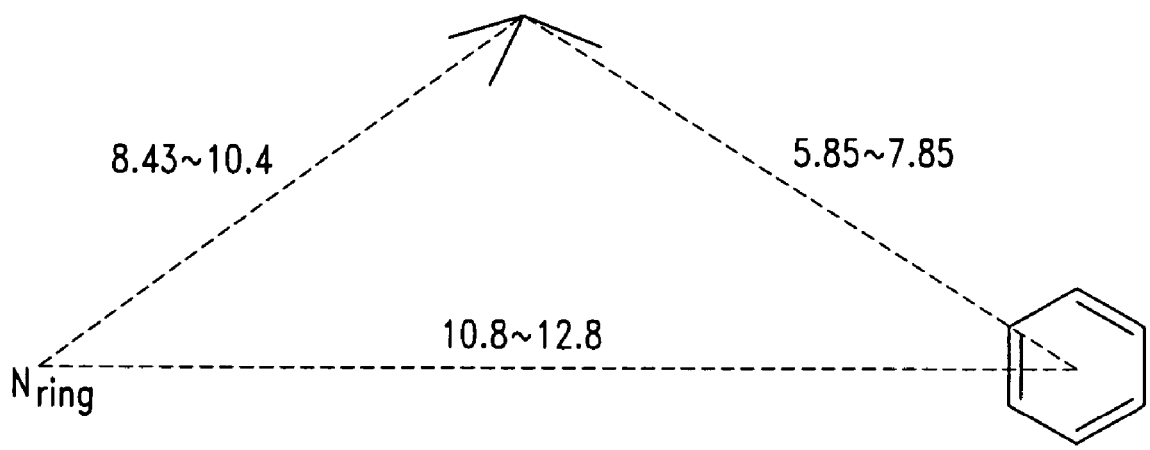
FIG. 28 depicts a second pharmacophore query derived from the pharmacophore in N—Ac—CHAVC—Y—NH$_2$ (SEQ ID NO:81) and used in chemical database searches.
Figure 29A:
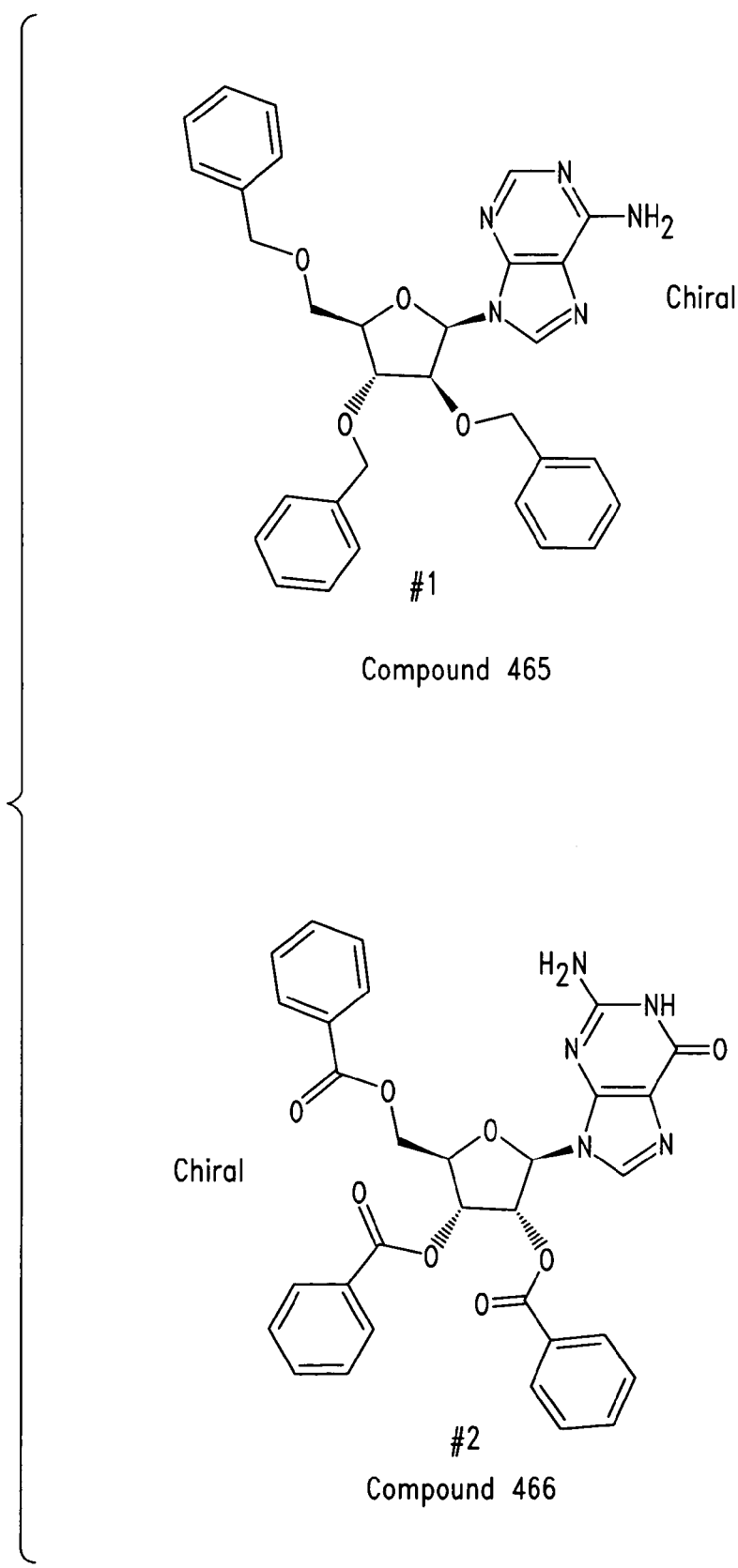
Figure 29C:
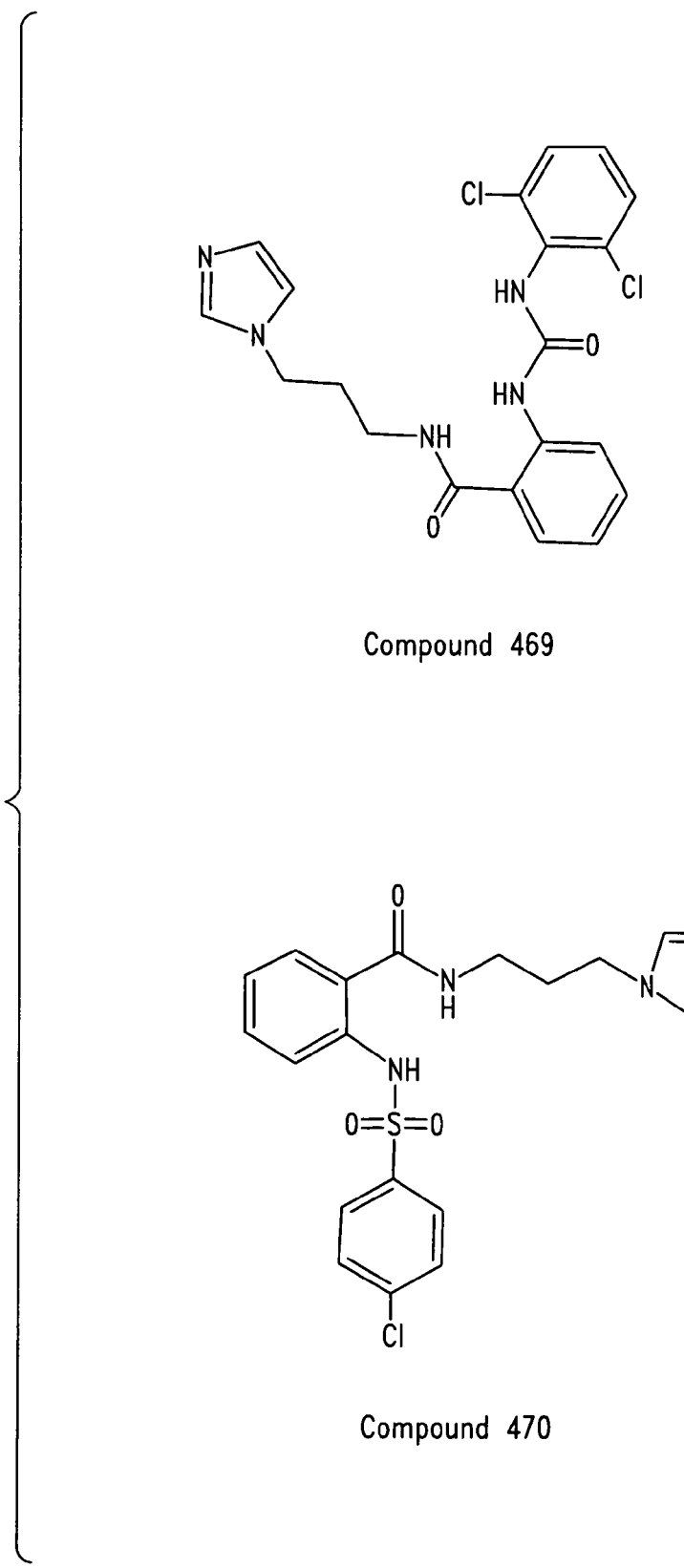
Figure 30:
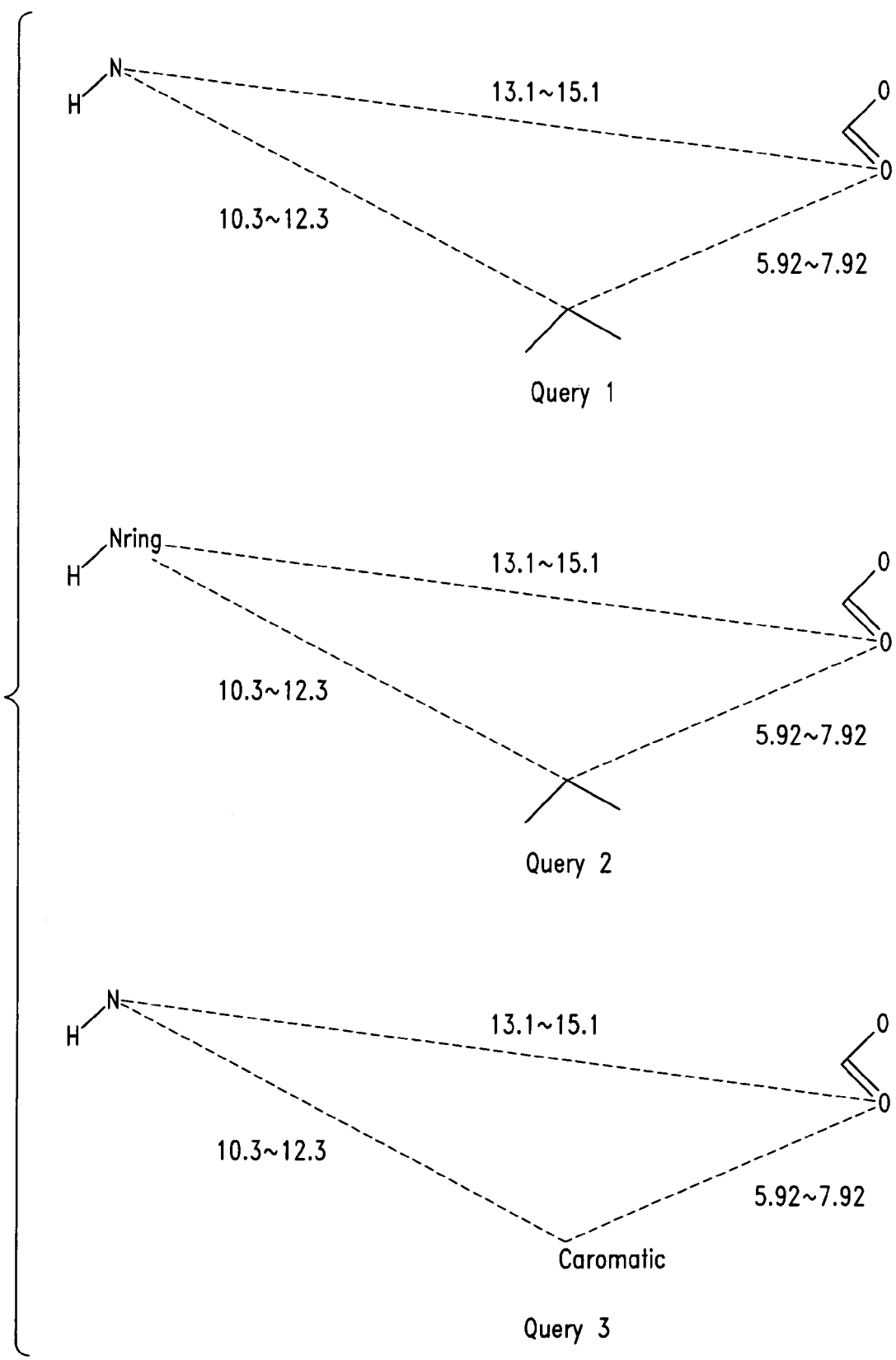
FIG. 30 illustrates the pharmacophore queries derived from the pharmacophore in N—Ac—CHAVDC—NH$_2$ (SEQ ID NO:20) and used in chemical database searches.

A pharmacophore search typically involves three steps. The first step is the generation of a pharmacophore query. Such queries may be developed from an evaluation of critical distances in the three dimensional structure of a cyclic peptide. Certain such critical distances are indicated in FIG. 14A, which shows two examples of distances obtained from low energy conformations of N—Ac—CHAVC—NH$_2$ (SEQ ID NO:10). Critical features of these conformations are the nitrogen atoms on the imidazole ring and the hydrophobic portion of the valine residue. In one low energy conformation, the distance d1 is 9.4 angstroms, d2 is 9.2 angstroms and d3 is 2.2 angstroms. In another low energy conformation, d4 is 7.5 angstroms, d5 is 7.0 angstroms and d6 is 2.2 angstroms. Specific pharmacophore queries that were developed for N—Ac—CHAVC—NH$_2$ (SEQ ID NO:10) are provided in FIGS. 14B and 14C. FIGS. 16 and 28 depict pharmacophore queries that were developed for N—Ac—CHAVC—Y—NH$_2$ (SEQ ID NO:81). FIG. 30 illustrates the pharmacophore queries derived from the pharmacophore in N—Ac—CHAVDC—NH$_2$ (SEQ ID NO:20). Using the pharmacophore query of interest, a distance bit screening is performed on the database to identify compounds that fulfill the required geometrical constraints. In other words, compounds that satisfy the specified critical pair-wise distances are identified. After a compound passed the distance bit screening step, the program next checks whether the compound meets the substructural requirements as specified in the pharmacophore query. After a compound passes this sub-structural check, it is finally subjected to a conformational analysis. In this step, conformations are generated and evaluated with regard to geometric requirements specified in the pharmacophore query. Compounds that have at least one conformation satisfying the geometric requirements, are considered as 'hits' and are recorded in a result database.

Figure 15A:
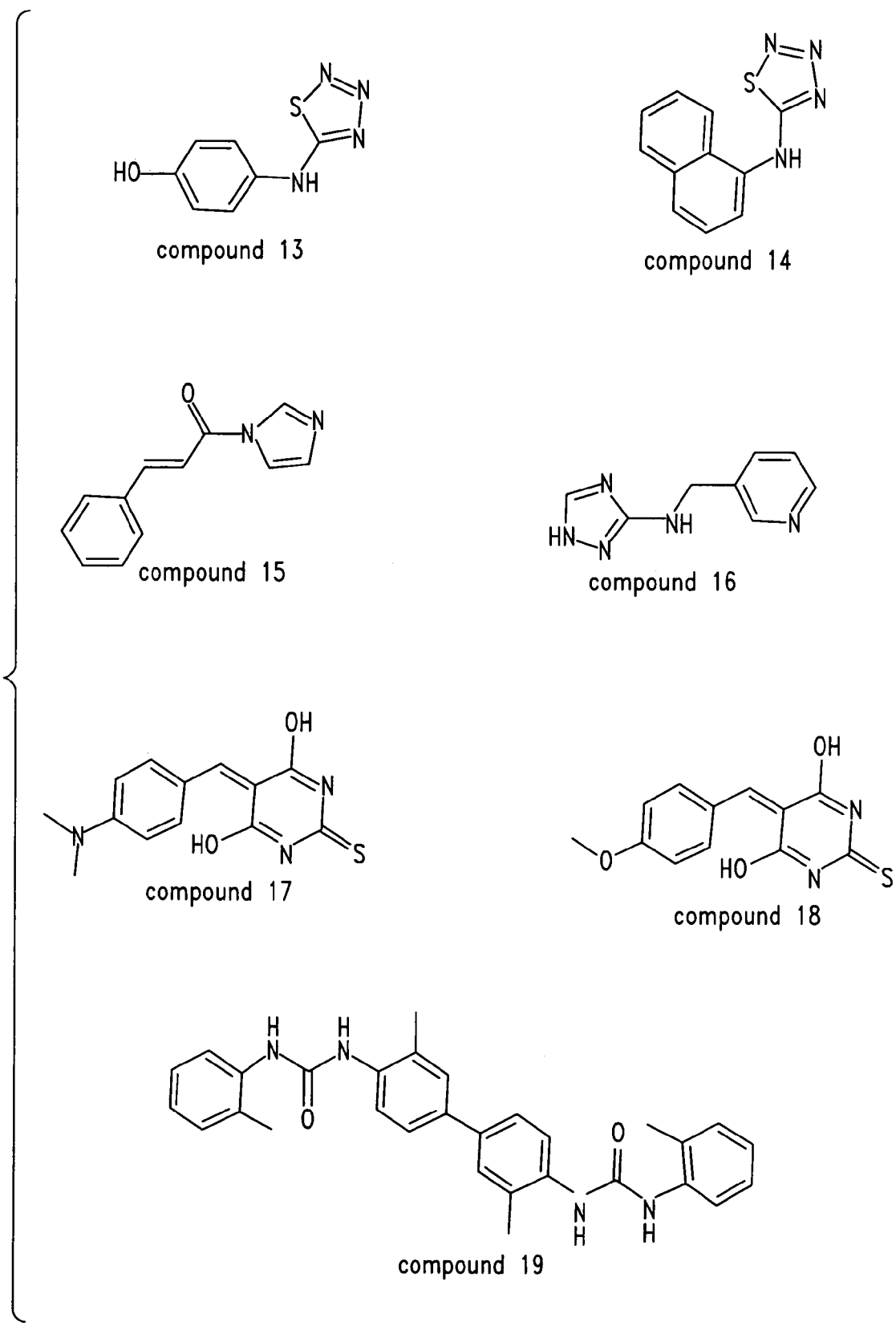
FIGS. 15A–15BG depict structures of representative non-peptidyl analogues of N—Ac—CHAVC—NH$_2$ (SEQ ID NO:10) derived from 3D-pharmacophore database searching using the pharmacophore queries depicted in FIGS. 14A–14C (compounds 13–282).
Figure 15C:
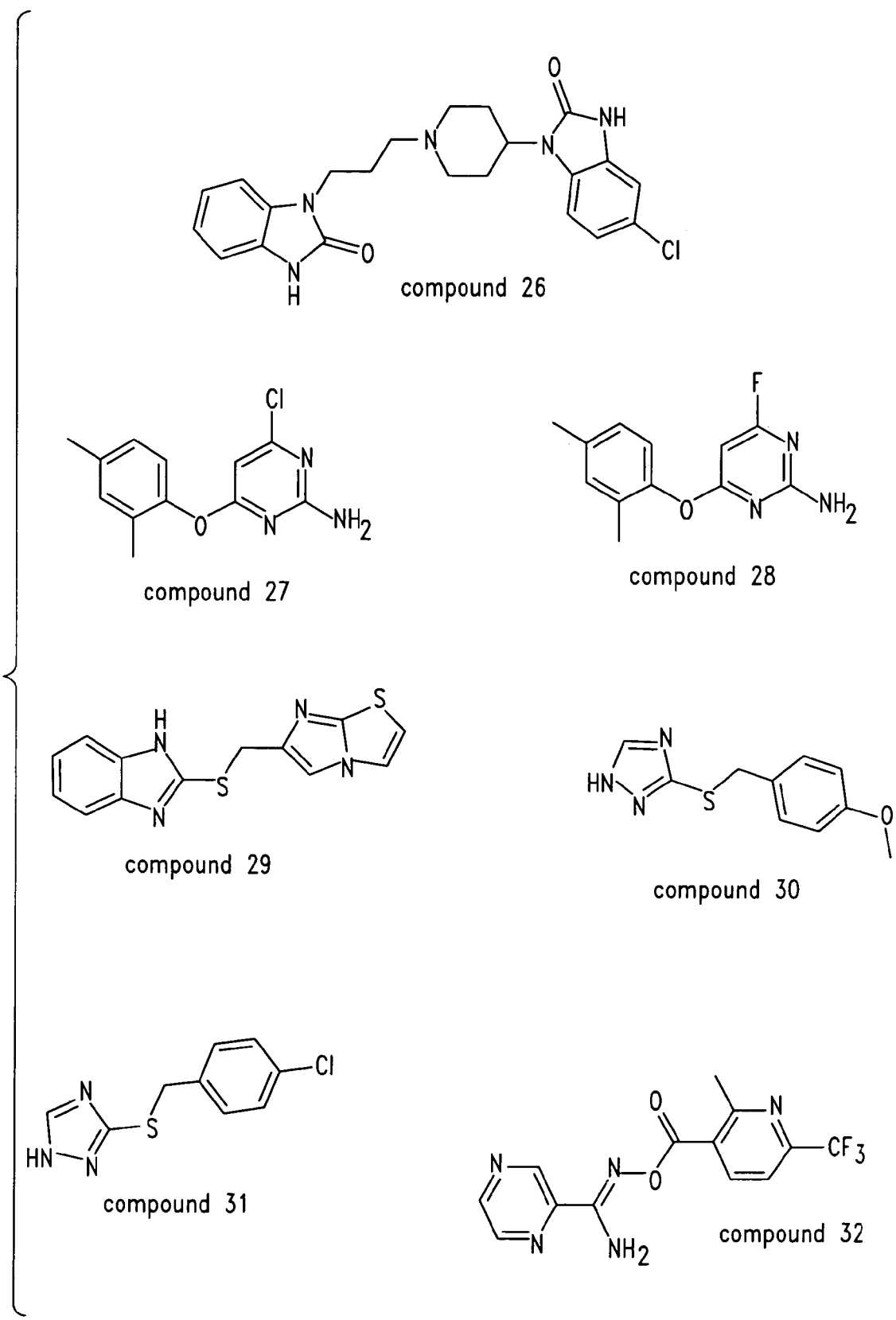
Figure 15D:
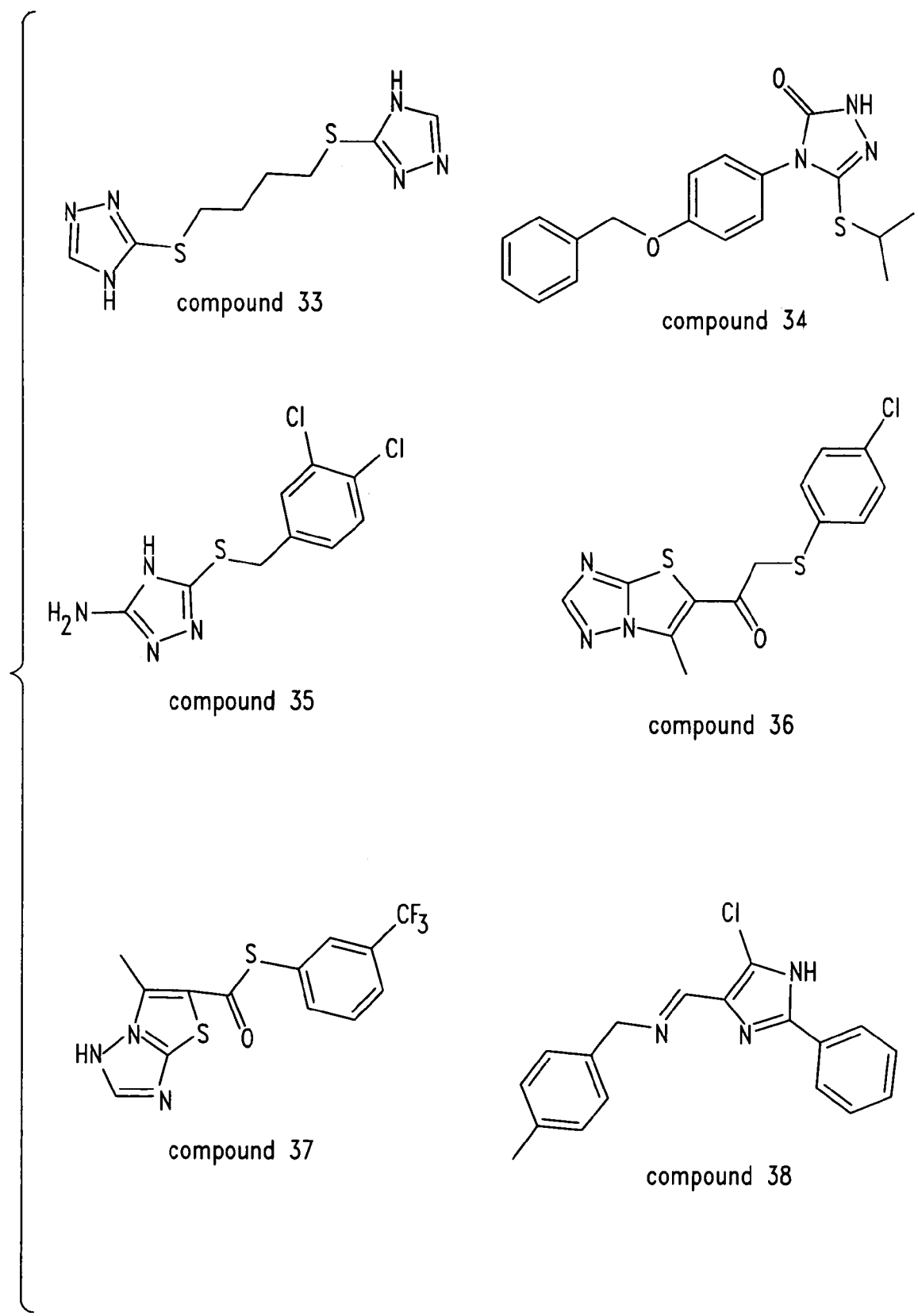
Figure 15E:
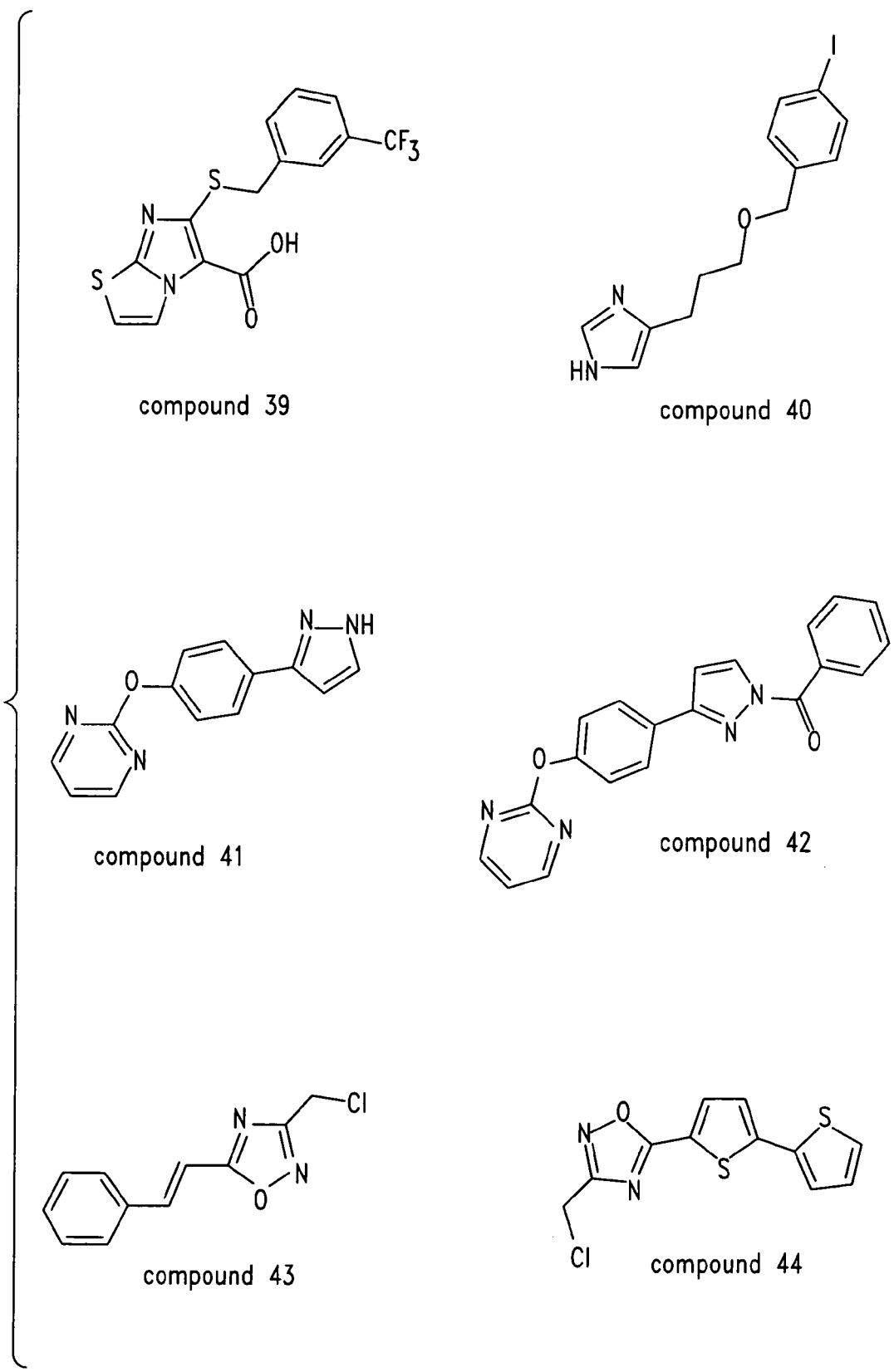
Figure 15F:
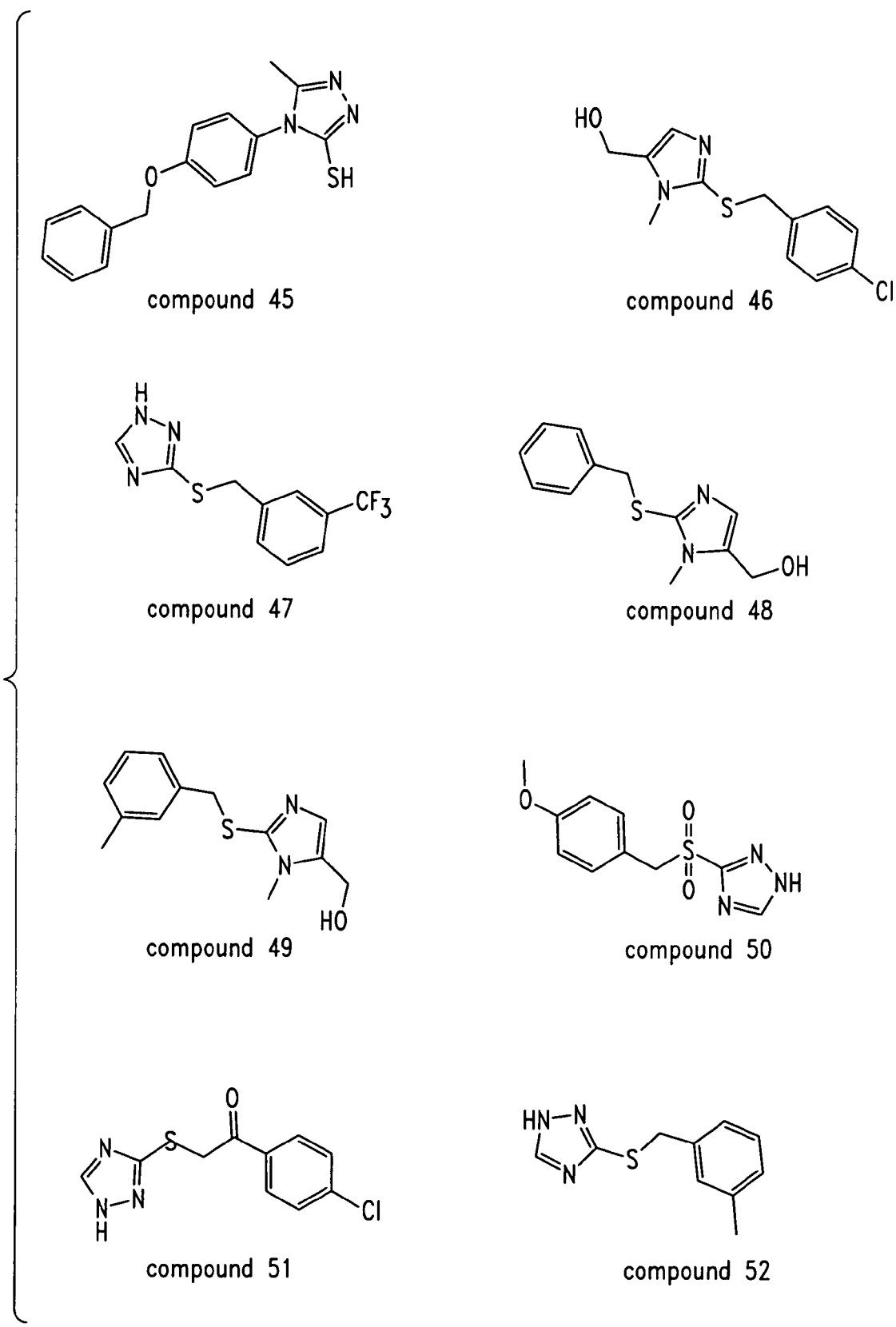
Figure 15G:
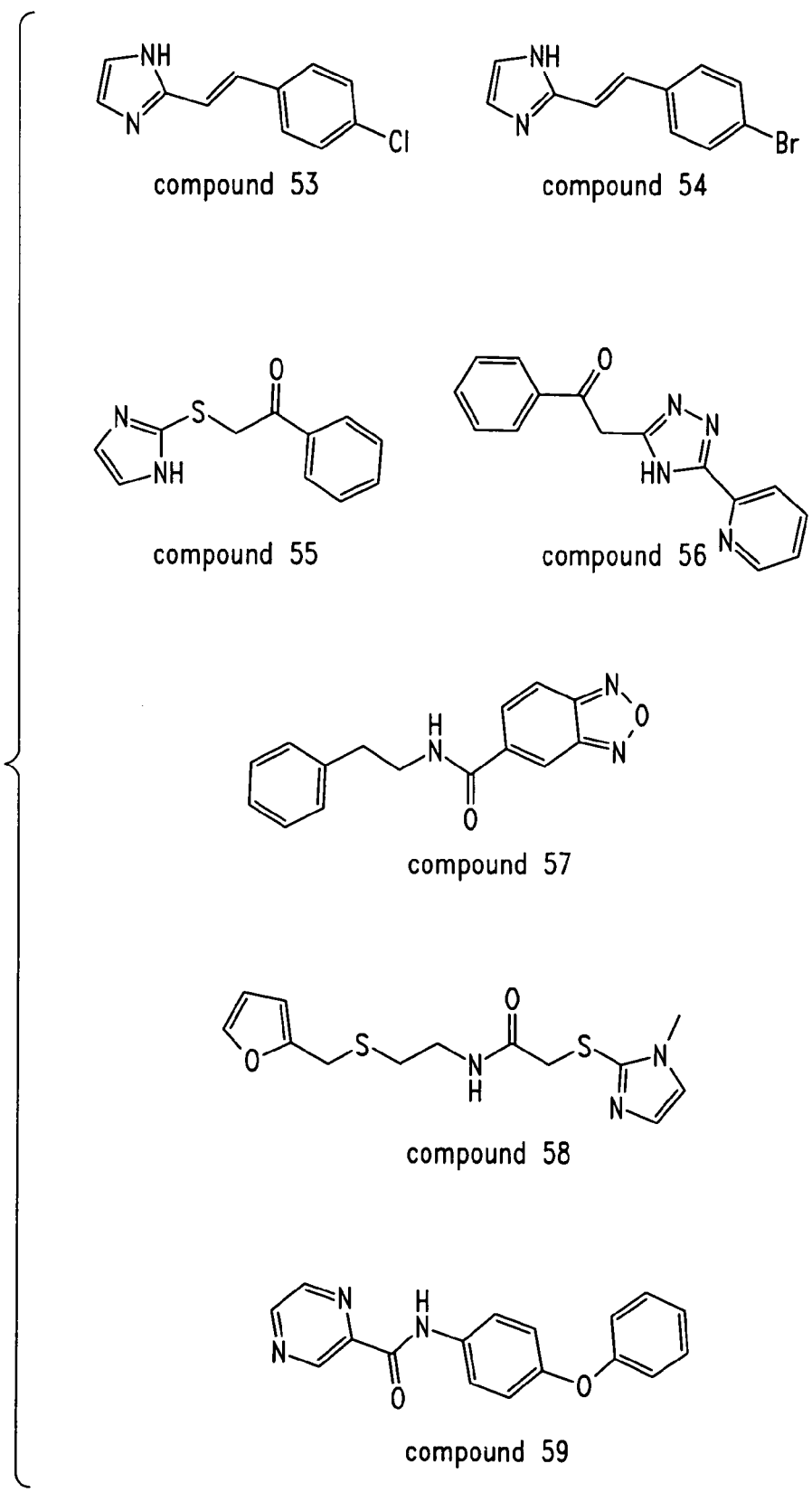
Figure 15H:
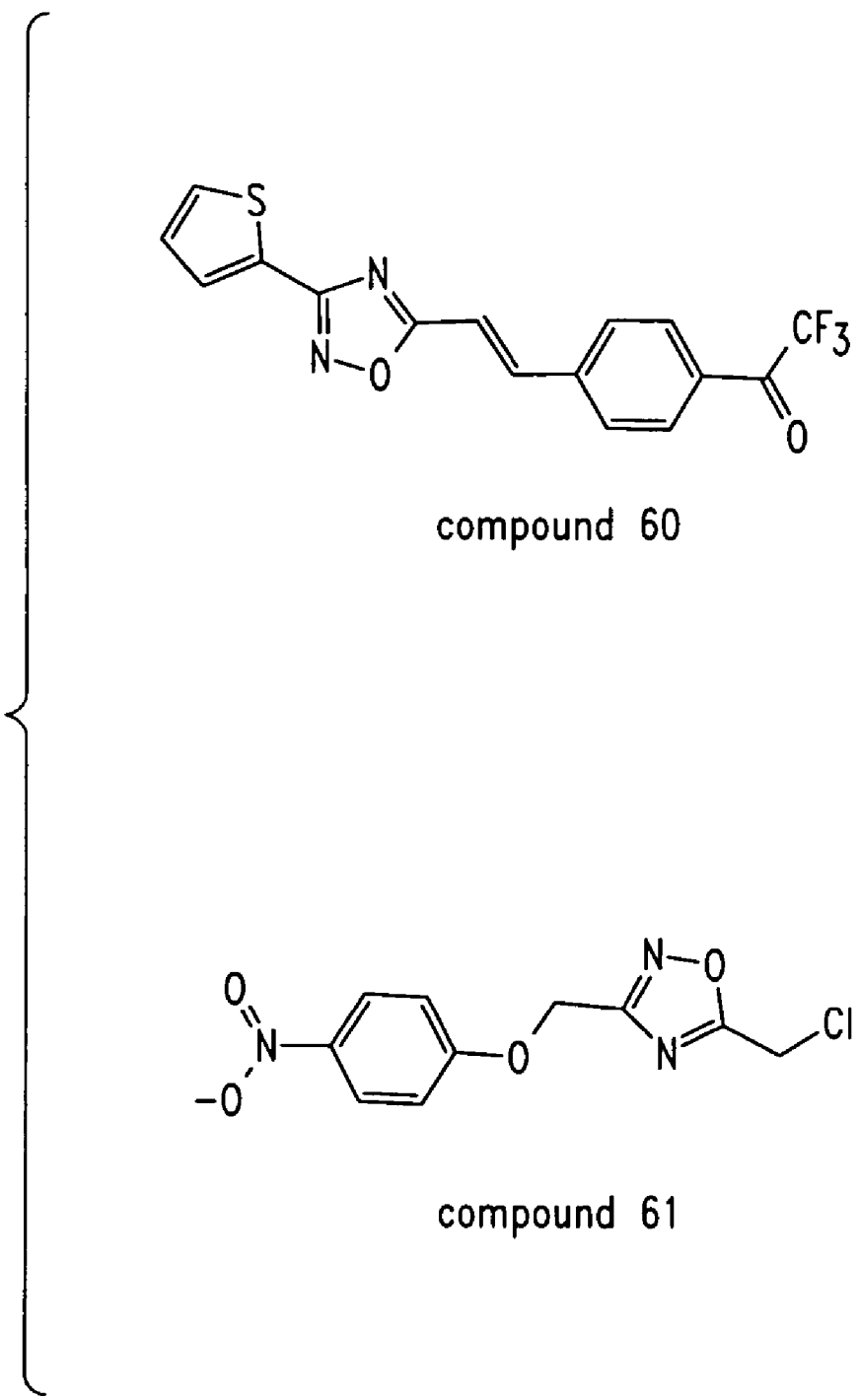
Figure 15I:
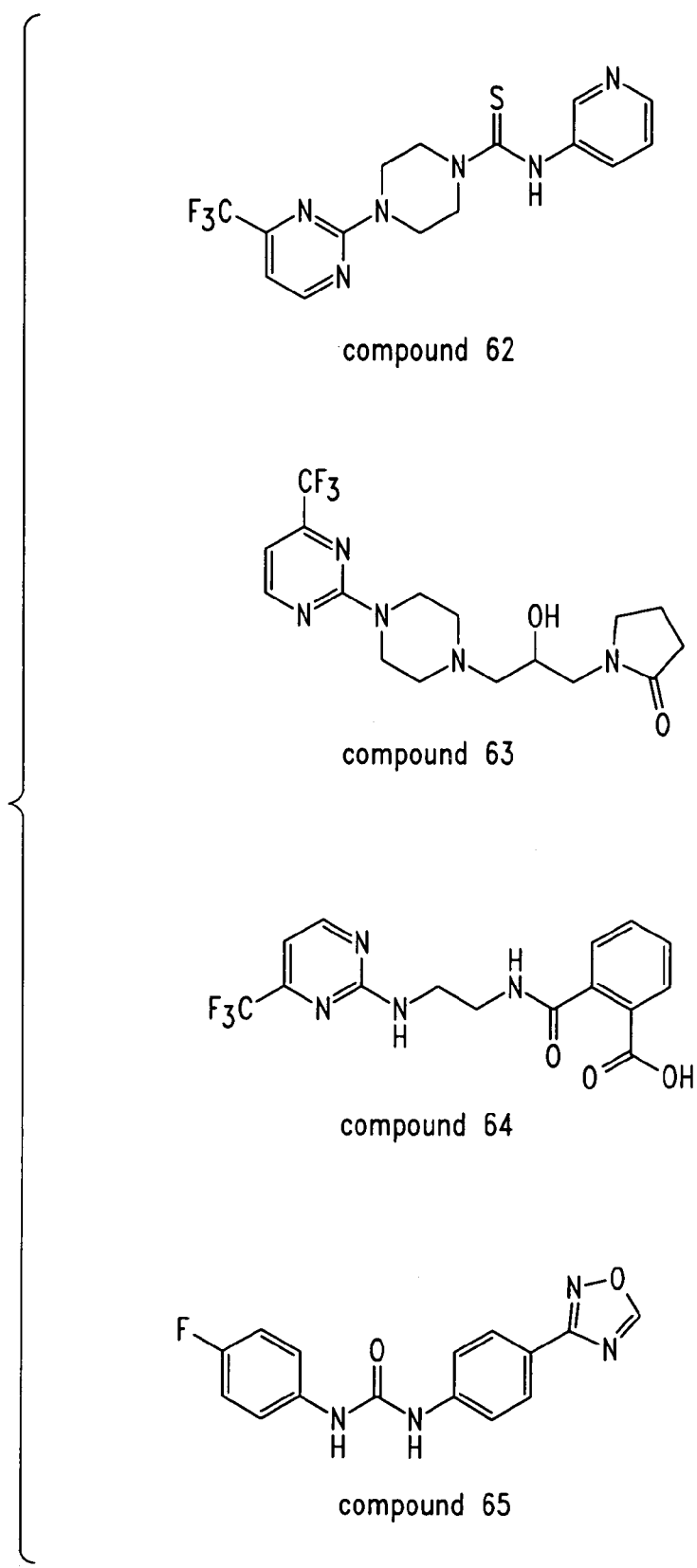
Figure 15K:
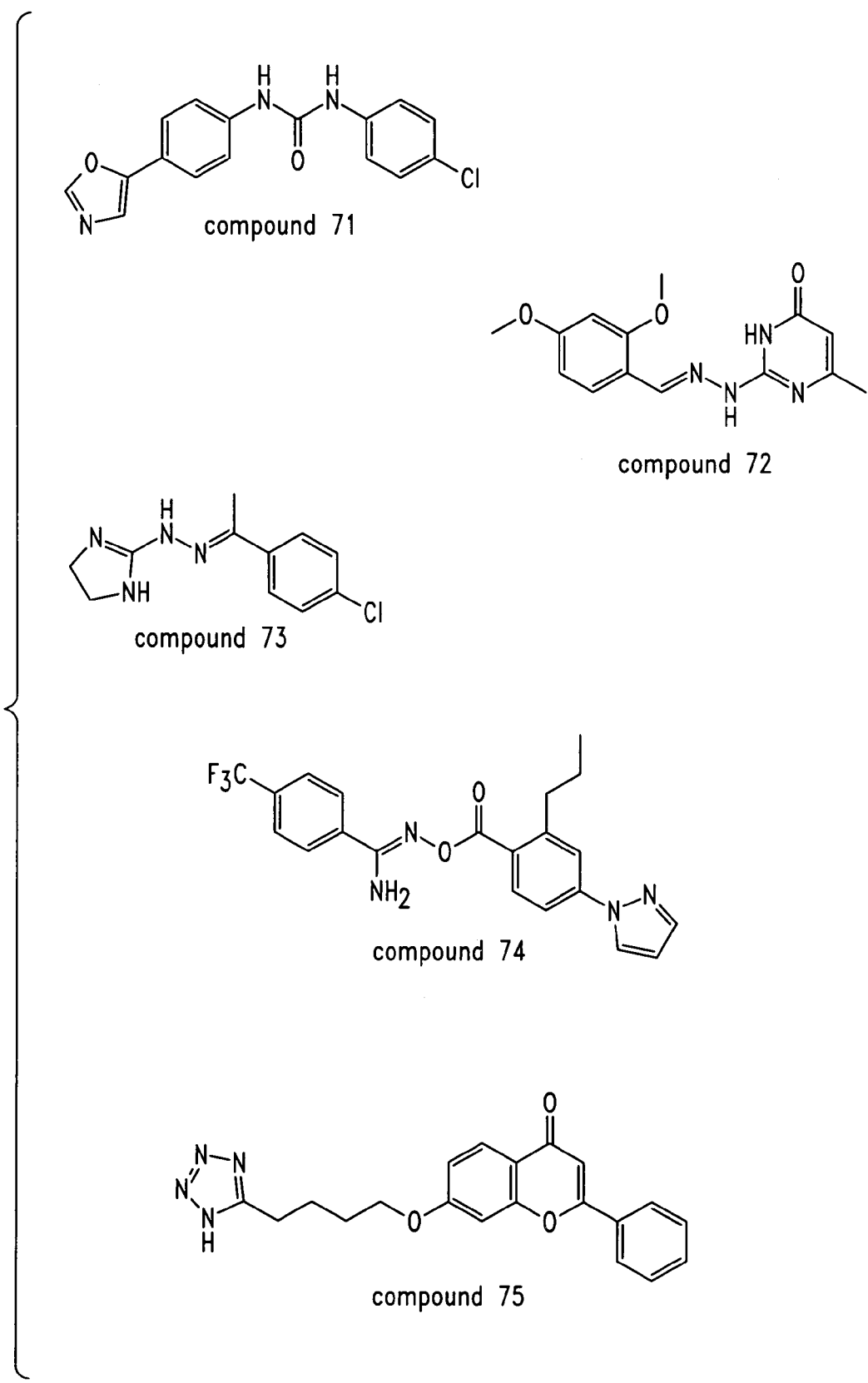
Figure 15M:
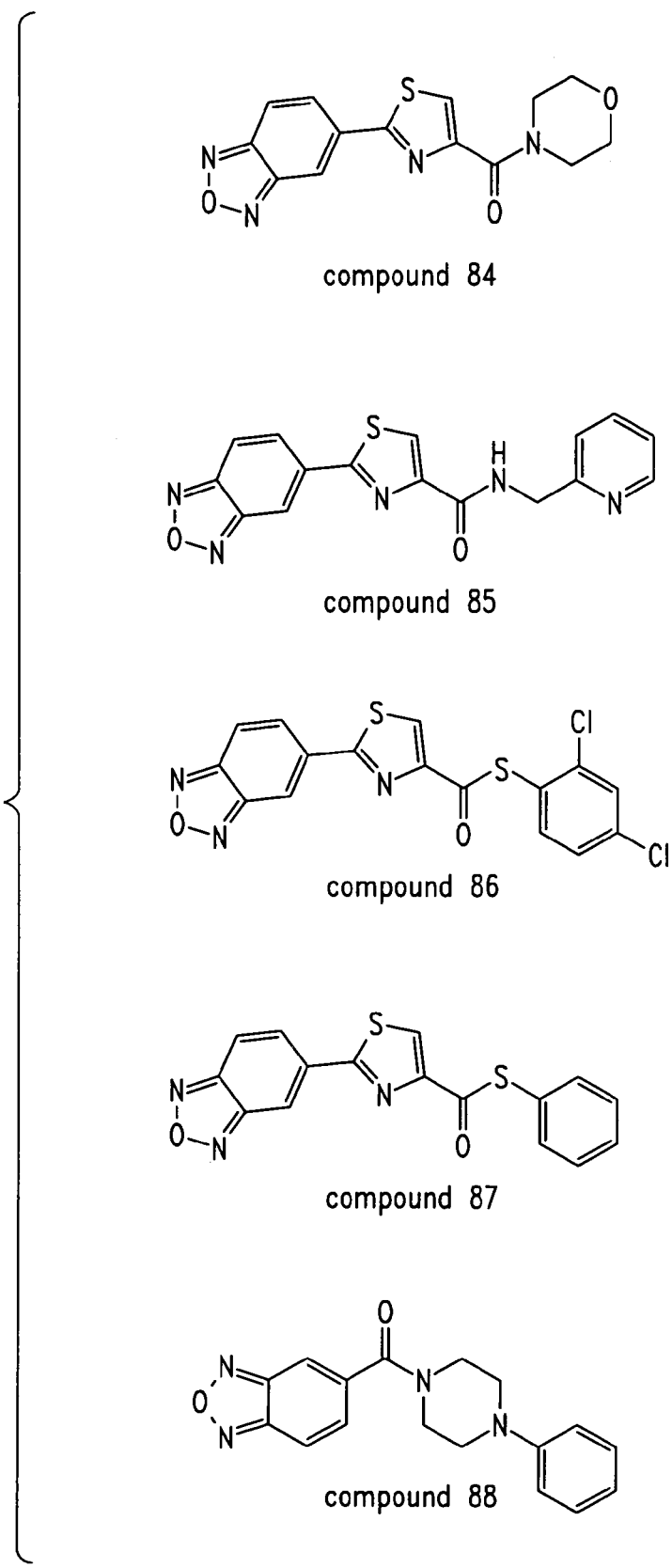
Figure 15N:
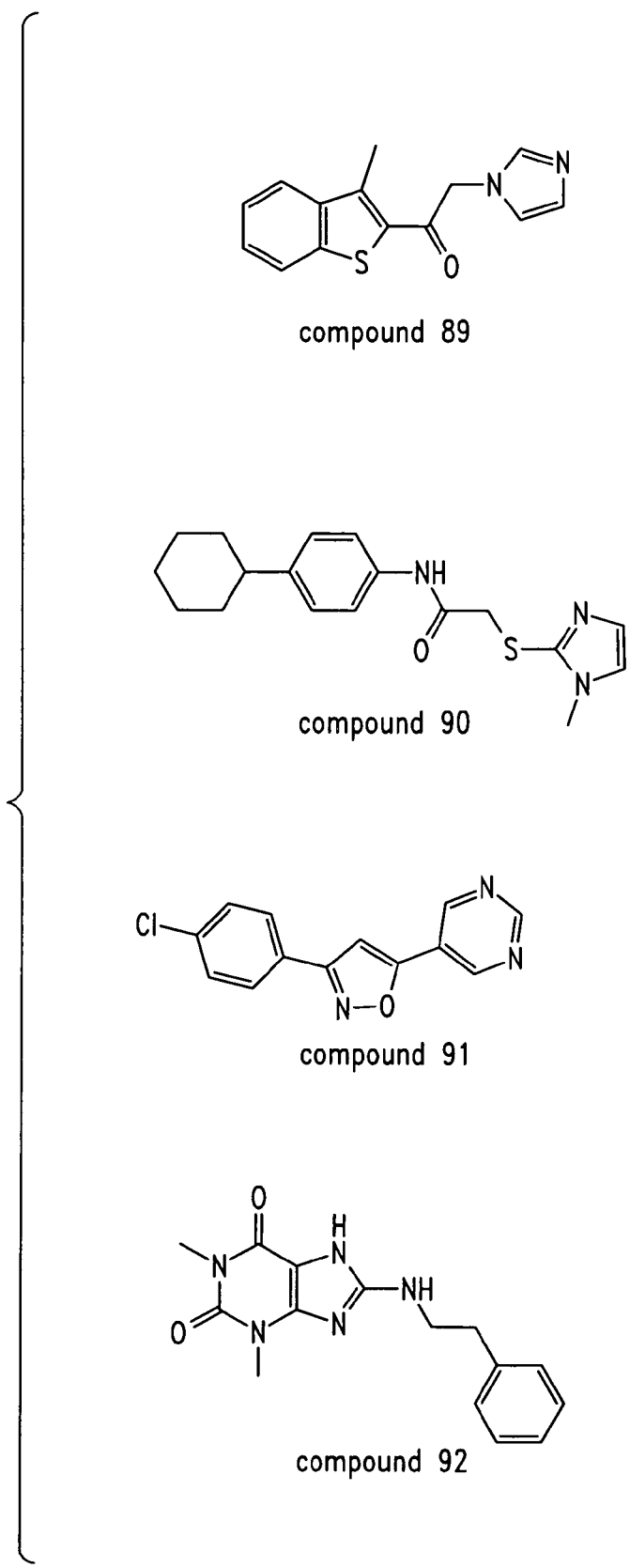
Figure 15T:
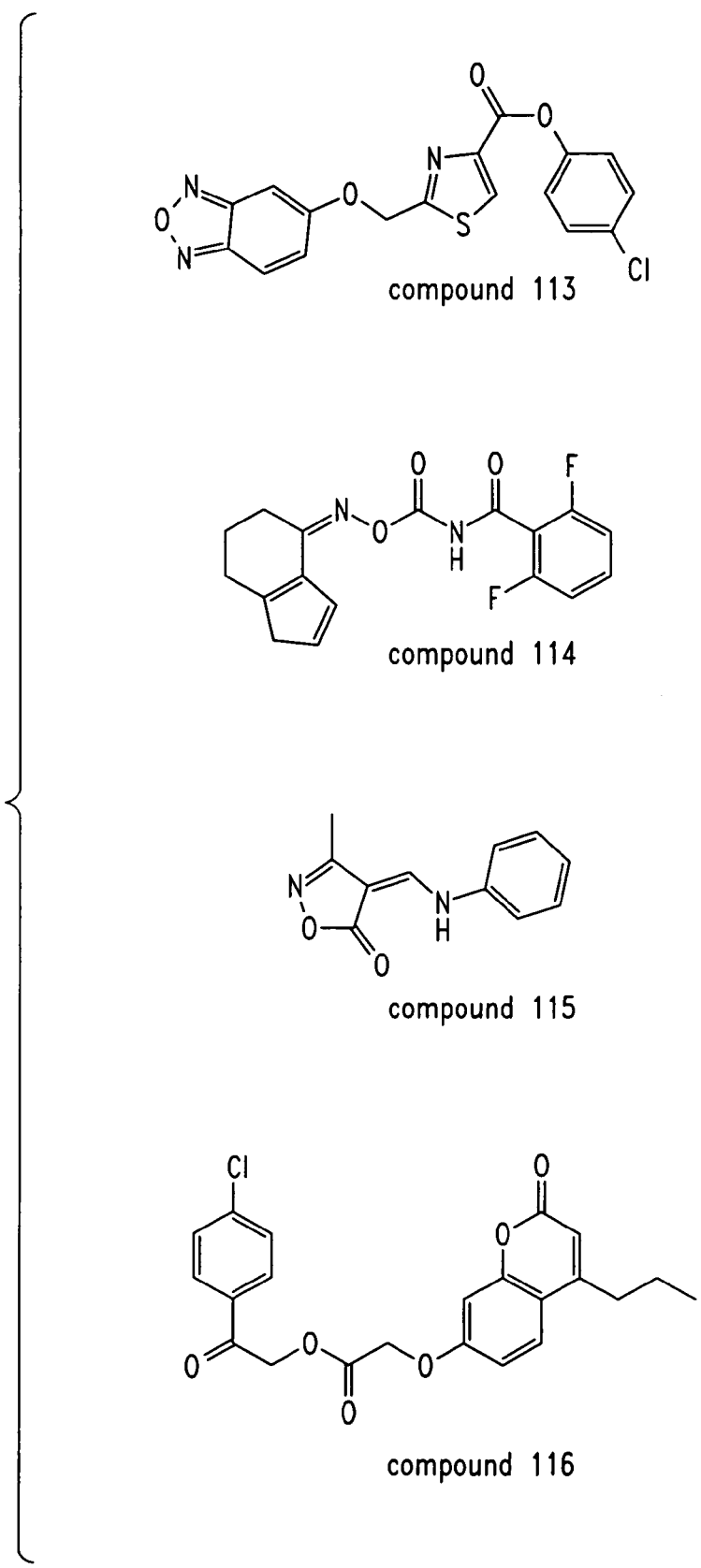
Figure 15U:
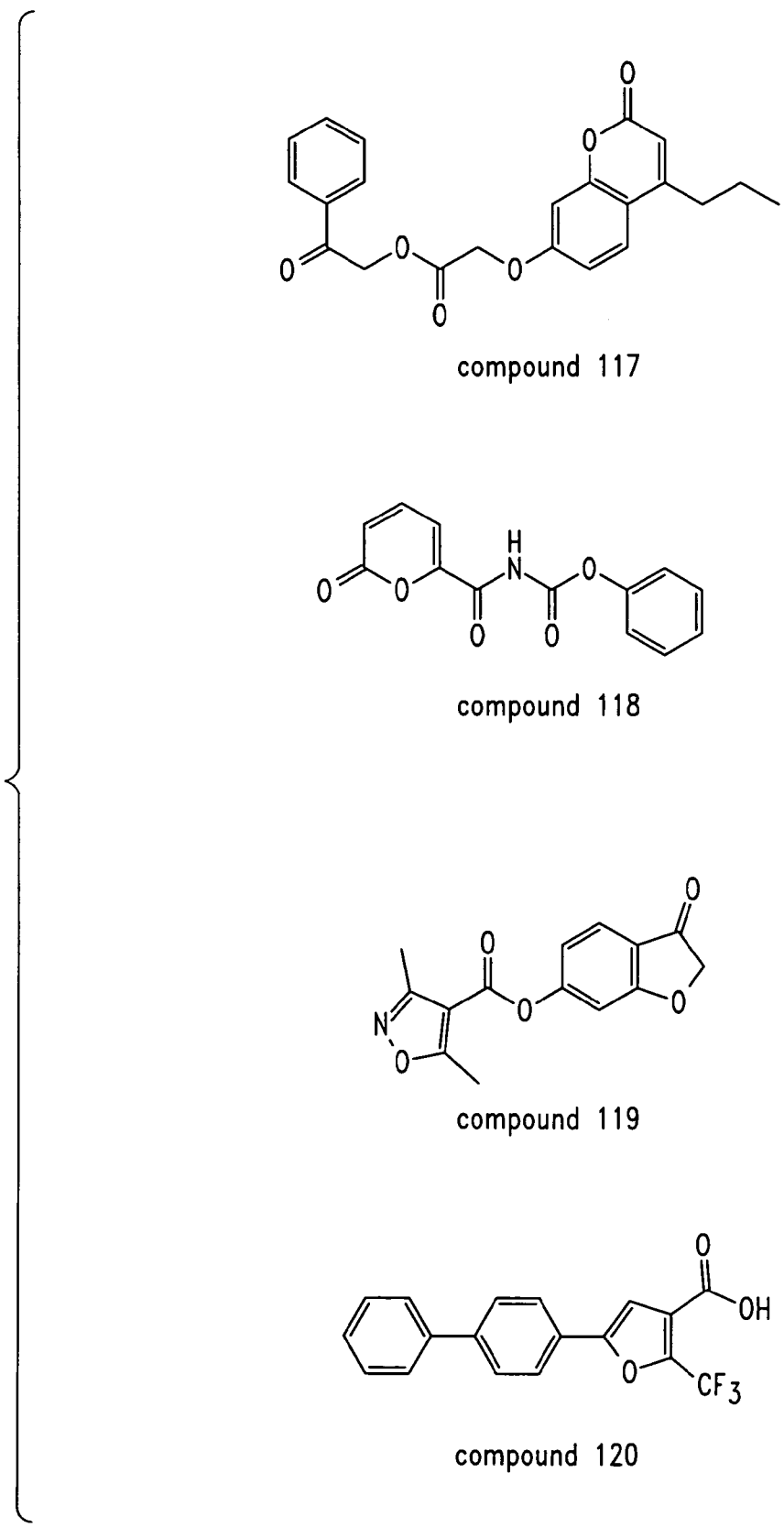
Figure 15V:
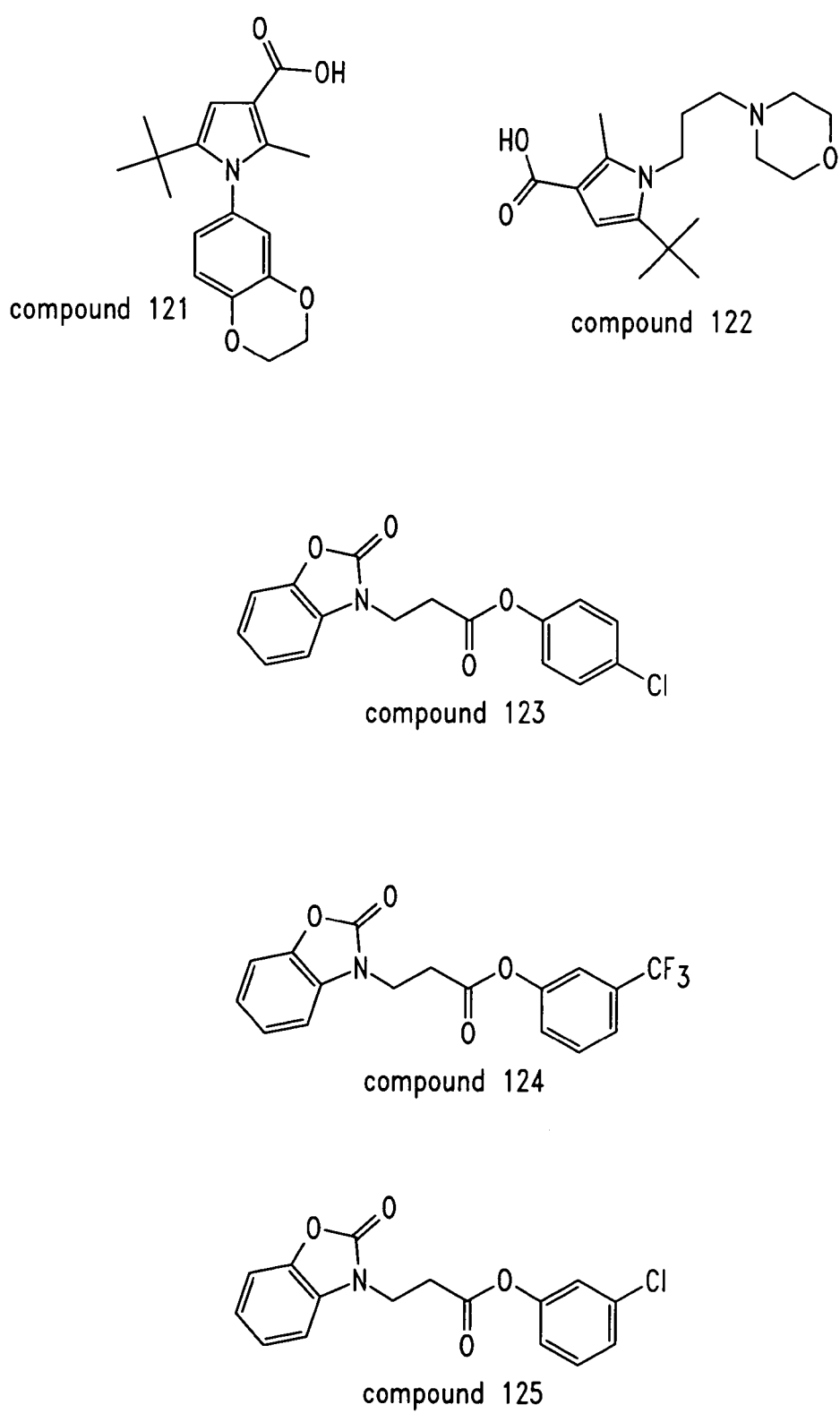
Figure 15W:
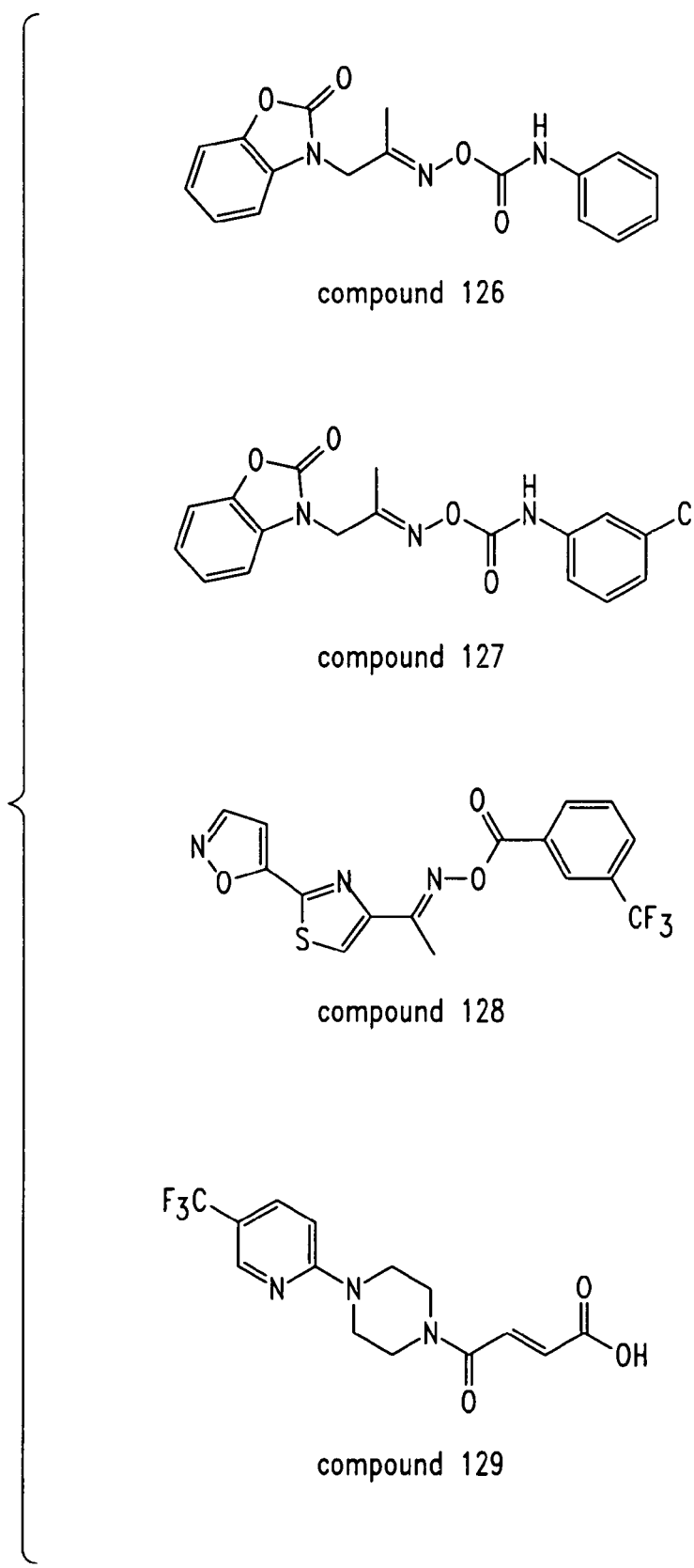
Figure 15X:
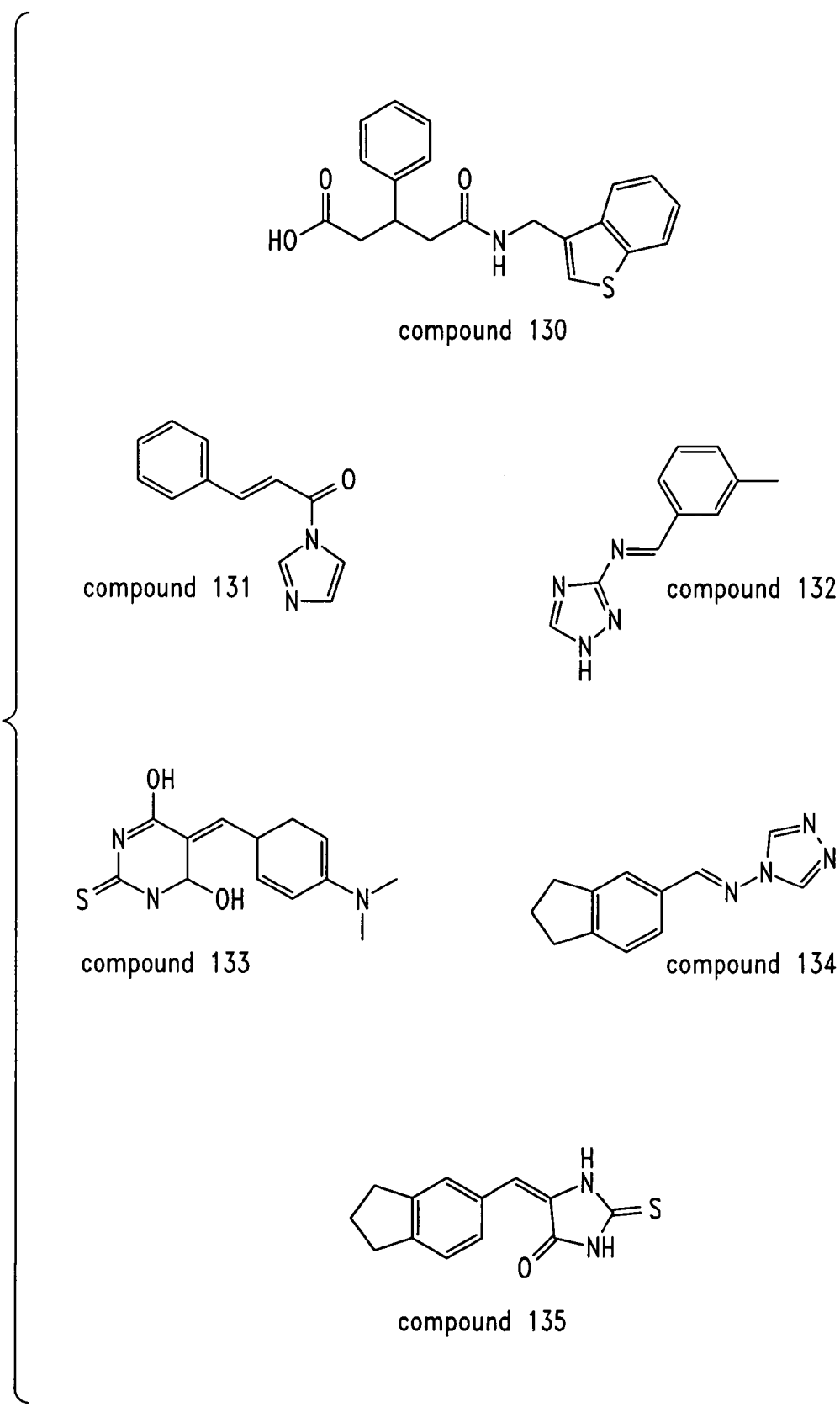
Figure 15Z:
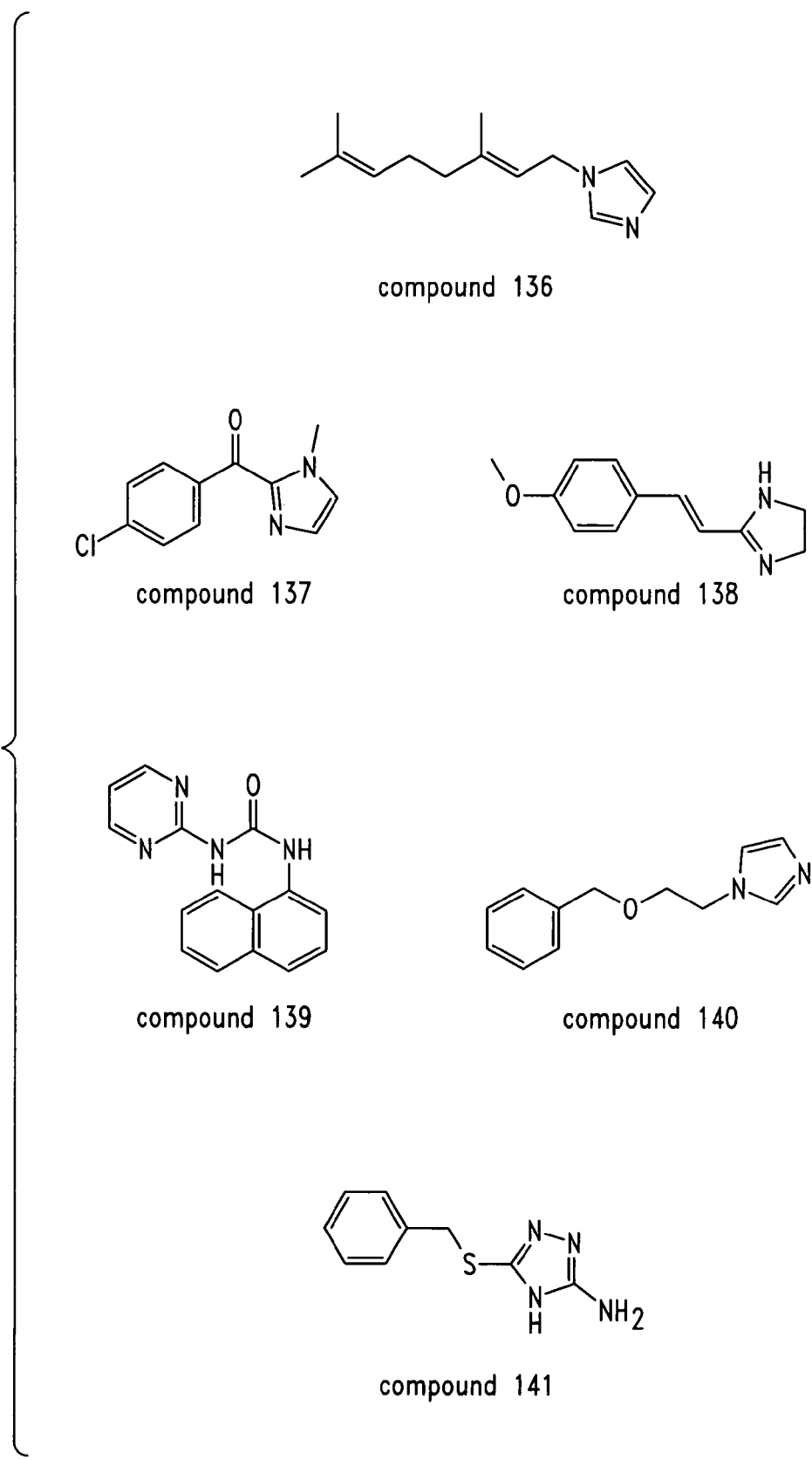
Figure 15A:
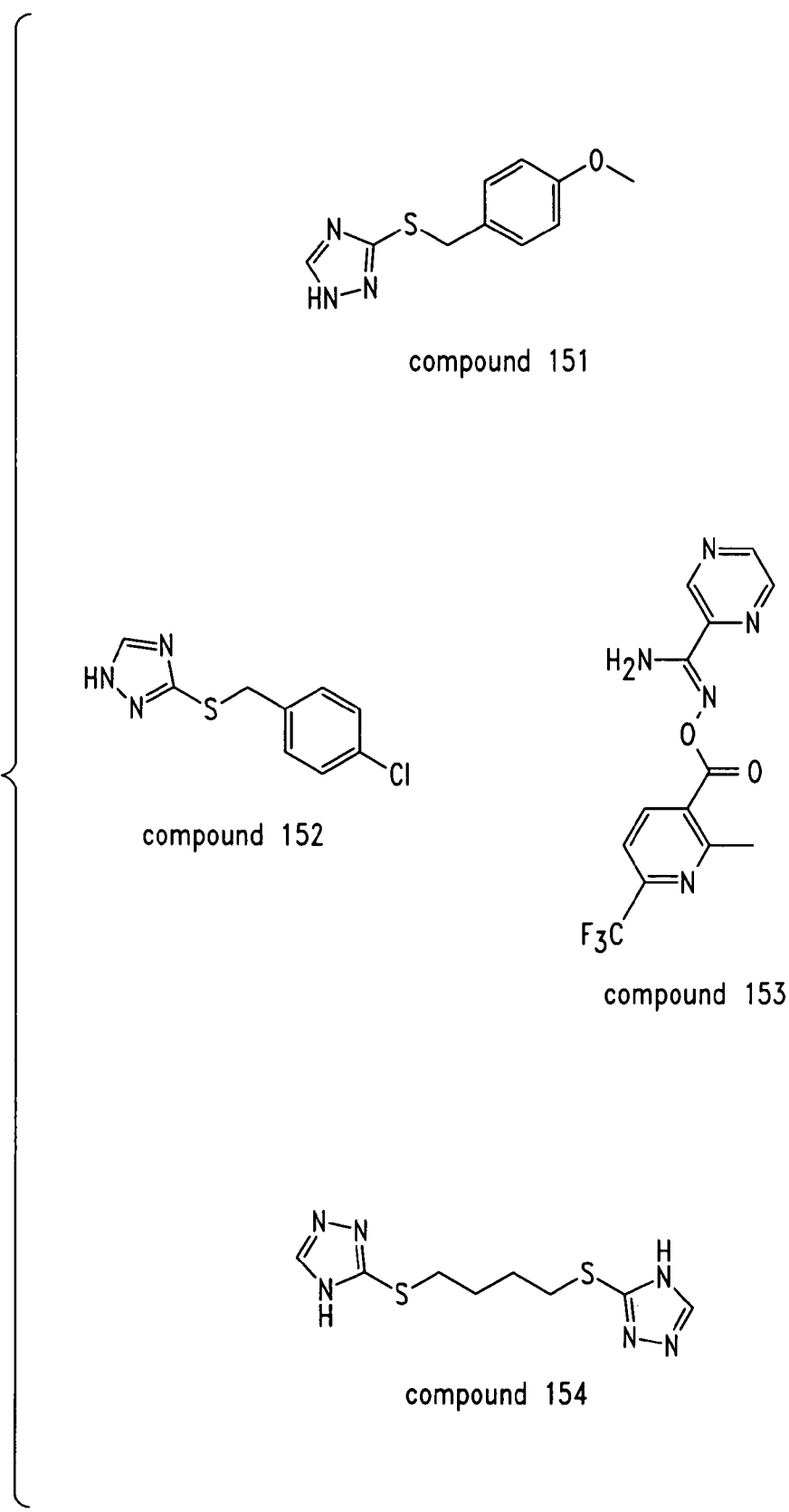
Figure 15A:
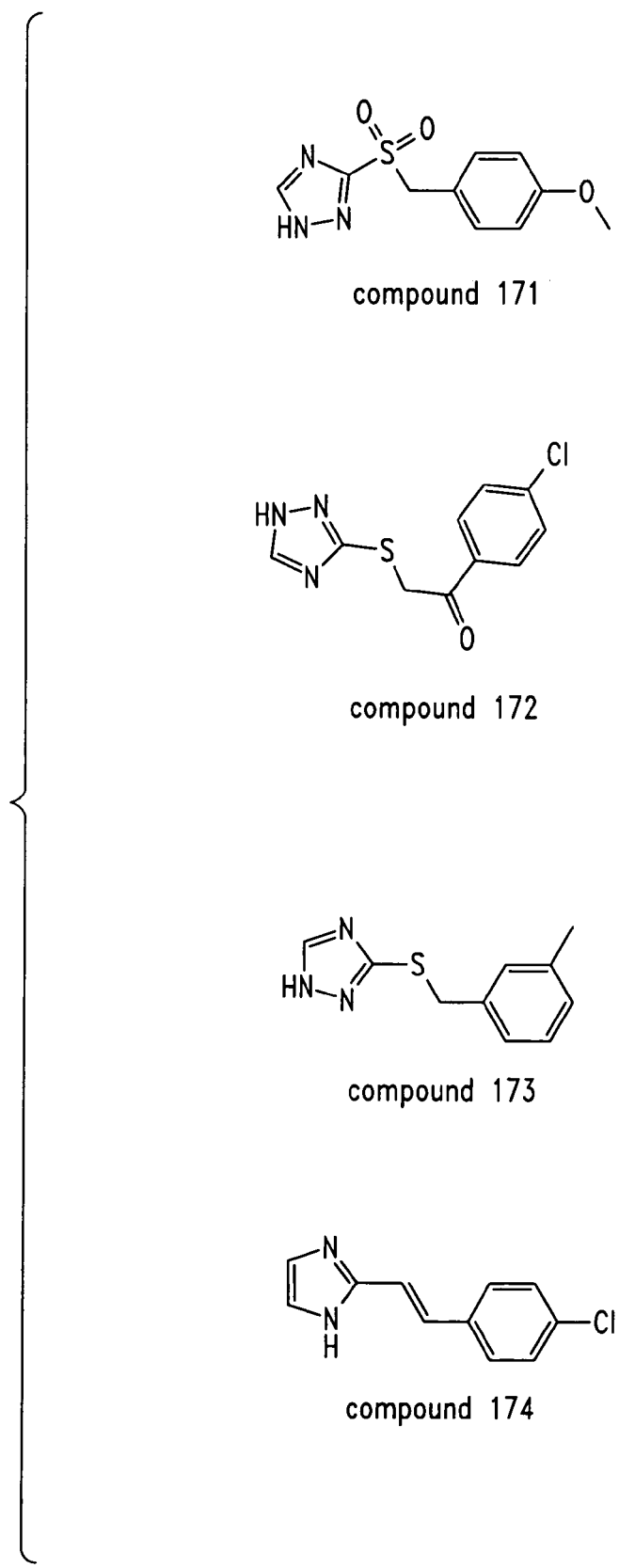
Figure 15A:
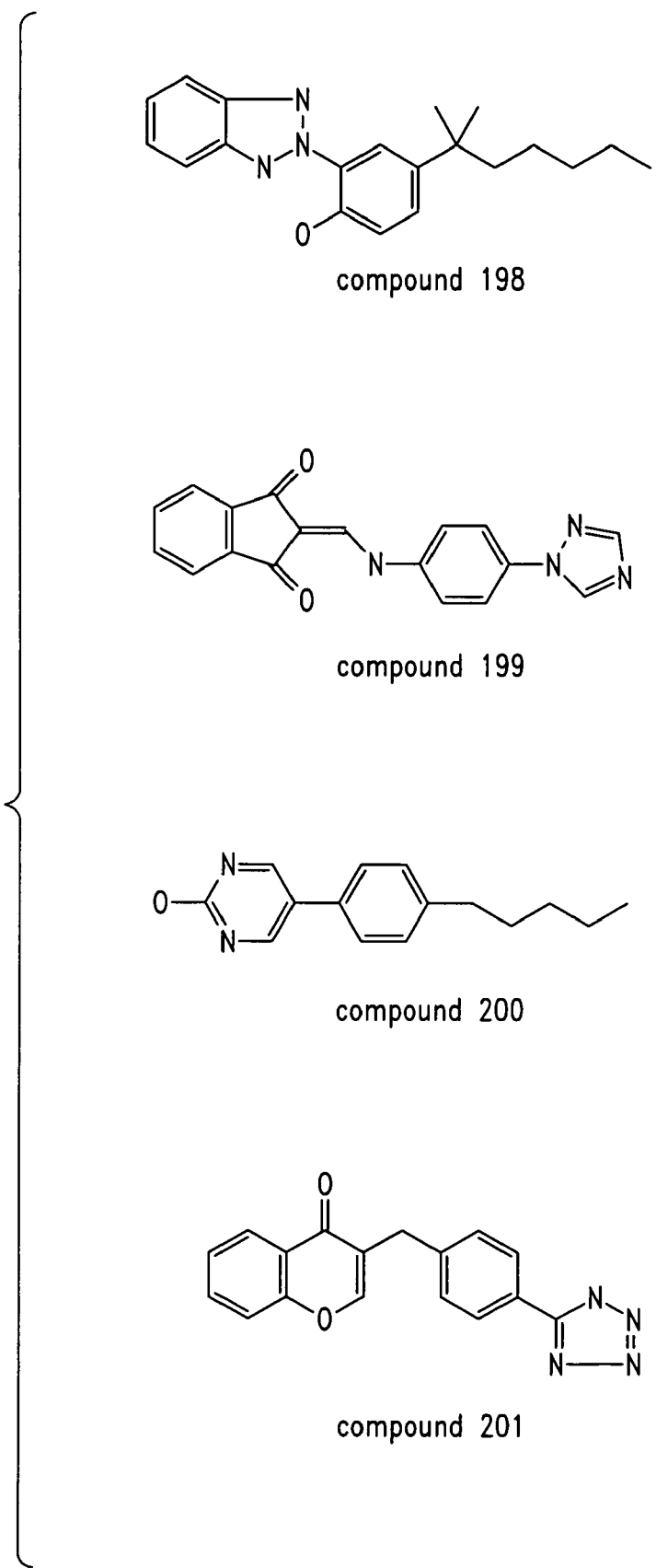
Figure 15A:
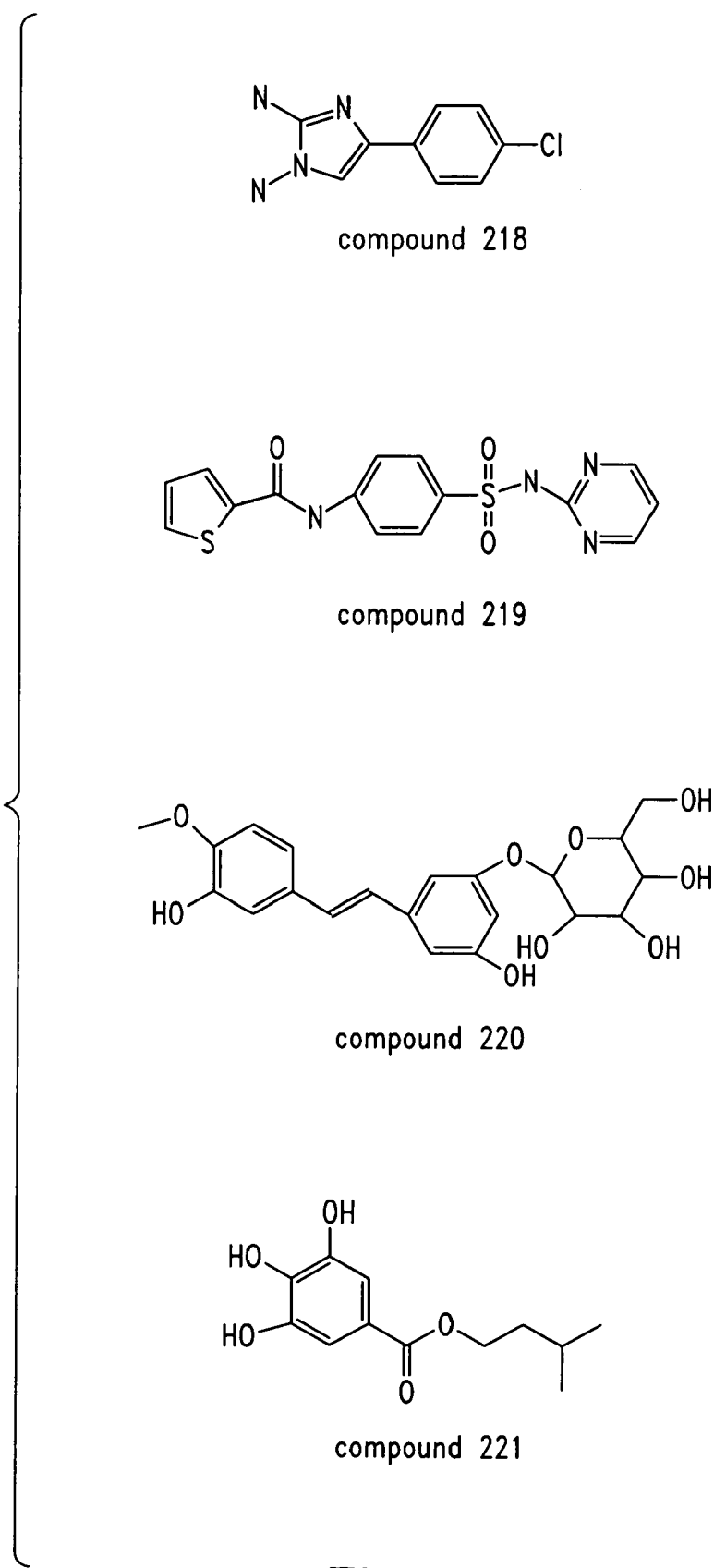
Figure 15A:
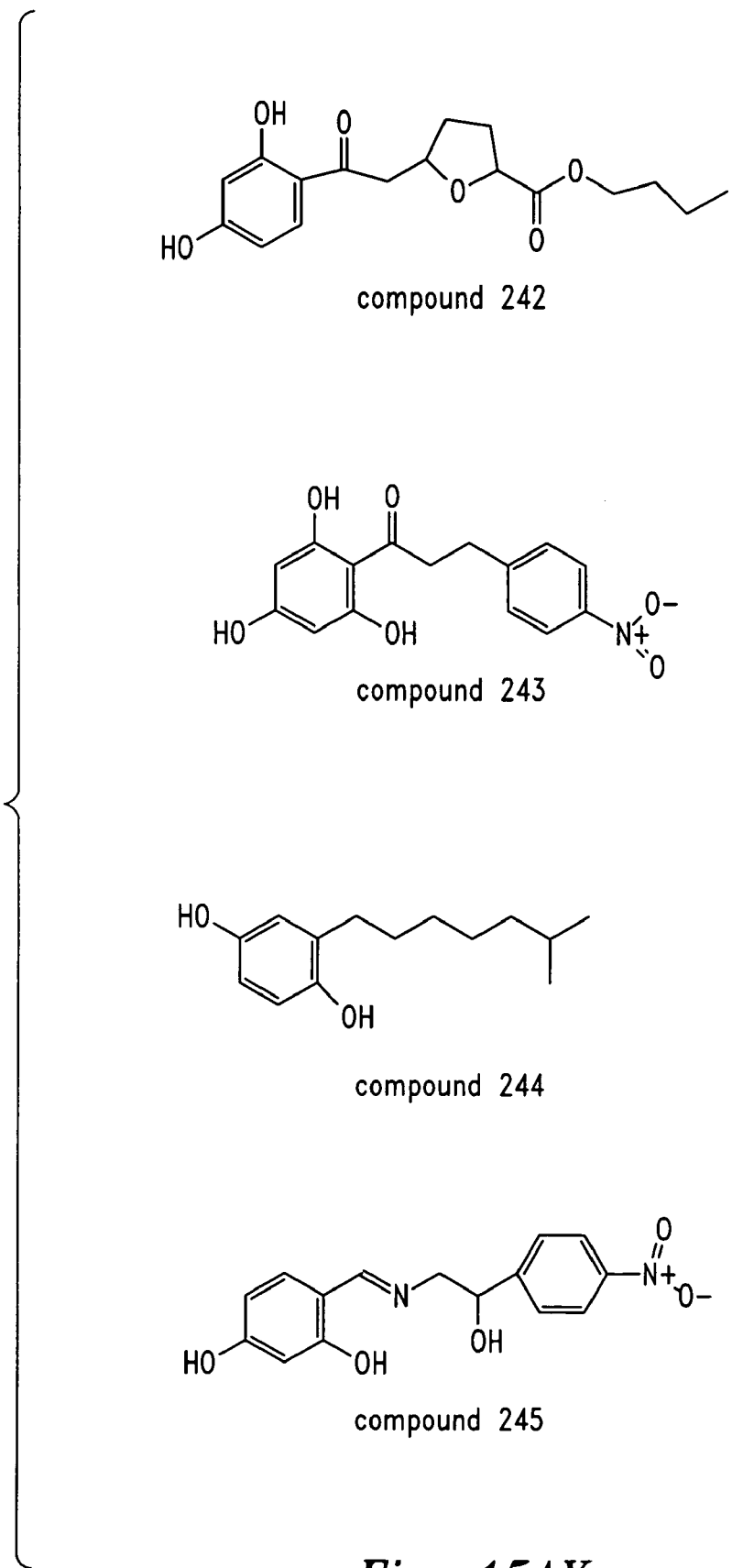
Figure 15A:
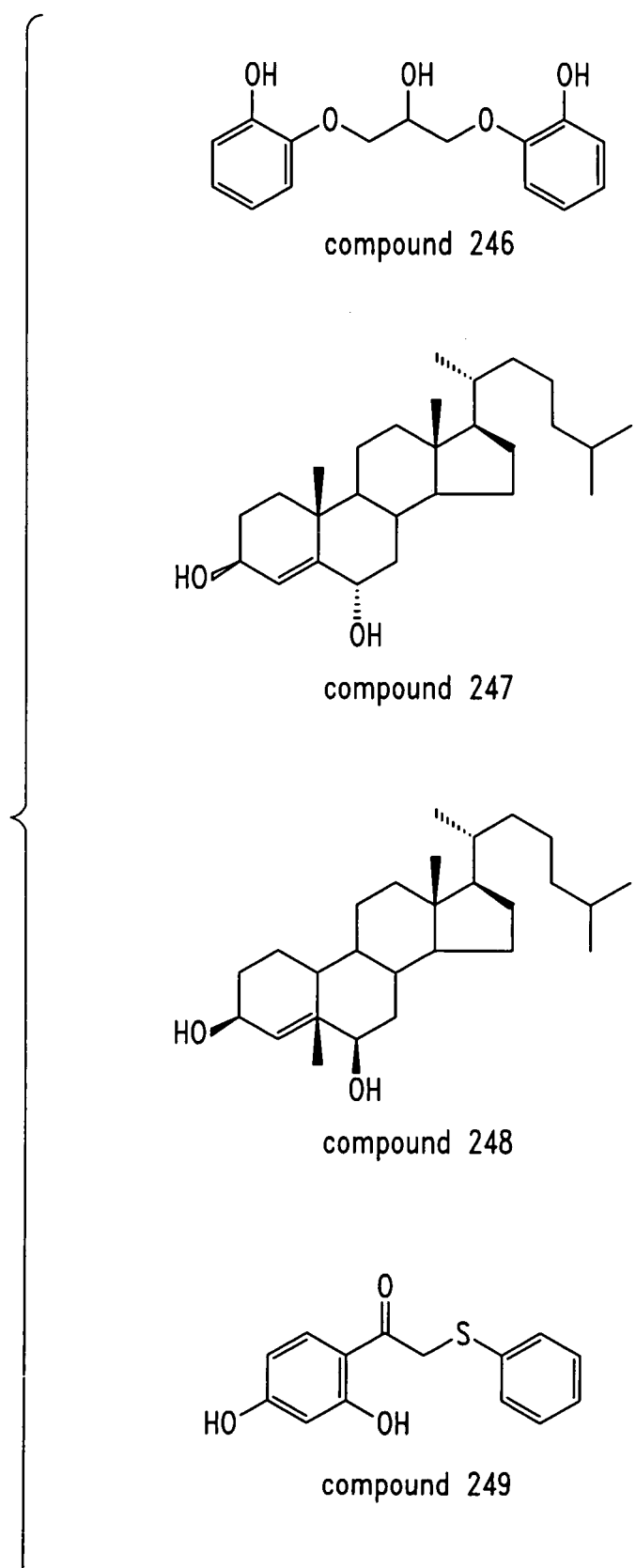
Figure 15B:
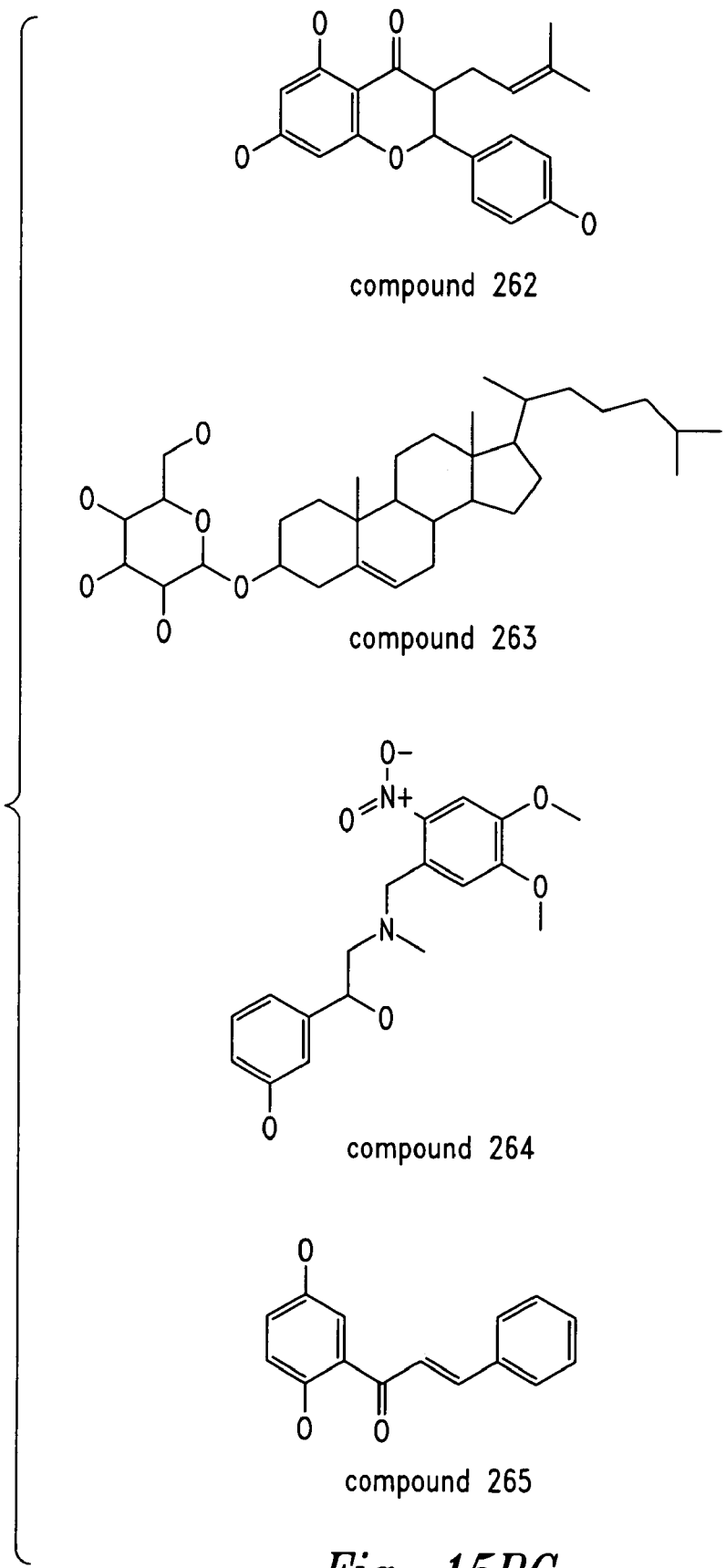
Figure 15B:
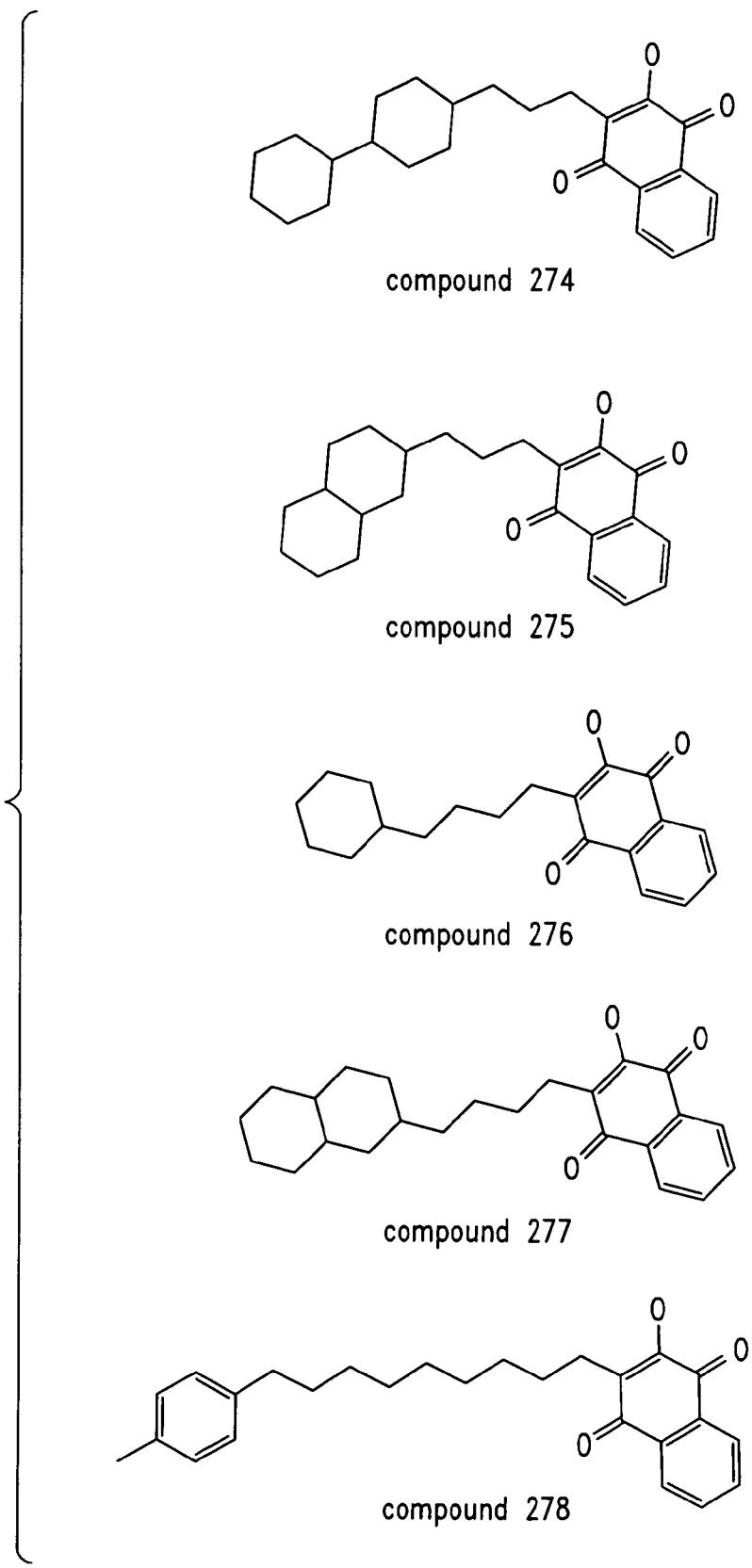
Figure 15B:
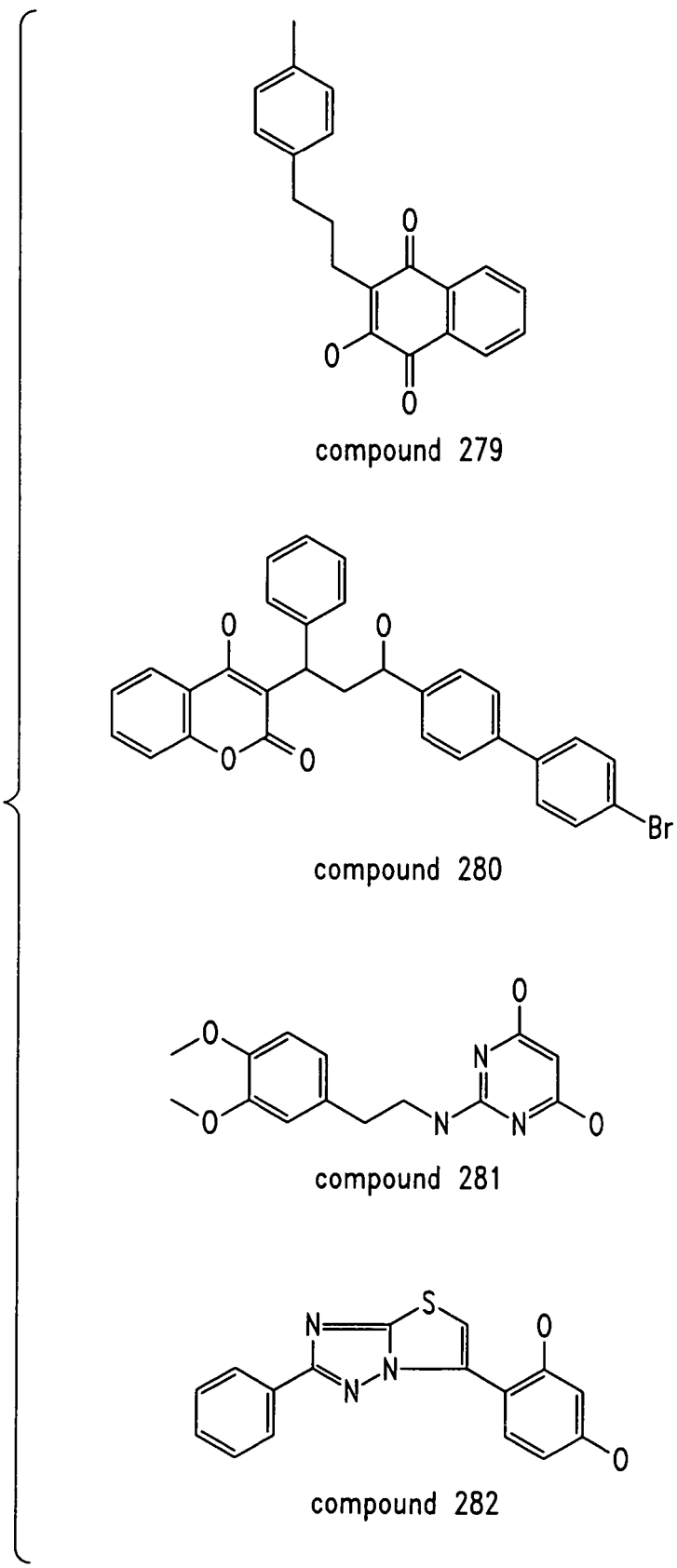

Representative compounds identified using such searches are presented herein in FIGS. 15A–15BG (compounds 13–282) and FIGS. 17A–17J (compounds 283–311), FIGS. 18A–18E (compounds 312–331) and FIGS. 19A–19E (compounds 332–334), FIGS. 21A–21N, 29A–29G, and 31A–31AI (compounds 345–399, 465–481, 482–593). While these compounds satisfy the requirements for three-dimensional similarity, it will be apparent to those of ordinary skill in the art that further biological testing may be used to select compounds with optimal activity. It will further be apparent that other criteria may be considered when selecting specific compounds for particular applications, such as the simplicity of the chemical structure, low molecular weight, chemical structure diversity and water solubility. The application of such criteria is well understood by medicinal, computational and structural chemists.

It will be apparent that a compound structure may be optimized using screens as provided herein. Within such screens, the effect of specific alterations of a candidate compound on three-dimensional structure may be evaluated, in order to optimize three-dimensional similarity to a cyclic peptide. Such alterations include, for example, changes in hydrophobicity, steric bulk, electrostatic properties, size and bond angle.

Biological testing of candidate compounds may be used to confirm peptidomimetic activity. In general, peptidomimetics should function in a substantially similar manner as a structurally similar cyclic peptide. In other words, a peptidomimetic of the cyclic peptide N—Ac—CHAVC—NH$_2$ (SEQ ID NO:10) should bind to a classical cadherin with an affinity that is at least half the affinity of the cyclic peptide N—Ac—CHAVC—NH$_2$ (SEQ ID NO:10), as measured using standard binding assays. Further, a peptidomimetic of the cyclic peptide N—Ac—CHAVC—NH$_2$ (SEQ ID NO:10) should modulate a classical cadherin-mediated function using a representative assay provided herein at a level that is at least half the level of modulation achieved using N—Ac—CHAVC—NH$_2$ (SEQ ID NO:10).

Once an active peptidomimetic has been identified, related analogues may be identified using two-dimensional similarity searching. Such searching may be performed, for example, using the program ISIS Base (Molecular Design Limited). Two-dimensional similarity searching permits the identification of other available, closely related compounds, which may be readily screened to optimize biological activity. Such searching was used to identify compounds that are structurally similar to compounds 35 and 47. The identified compounds are presented in FIGS. 18A–18E and 19A–19E, respectively. Such searching was also used to identify compounds that are structurally similar to compounds 65 and and 184. The identified compounds are presented in FIGS. 22A–22H and 23A–23F, respectively (compounds 434–464 and 400–433).

Cell Adhesion Modulating Agents

The term "cell adhesion modulating agent," as used herein, refers to a molecule comprising at least one peptidomimetic of a cyclic peptide that contains the classical cadherin cell adhesion recognition (CAR) sequence HAV (His-Ala-Val). As noted above, multiple peptidomimetics may be present within a modulating agent. Further, additional CAR sequences (specifically bound by an adhesion molecule) may be included within a modulating agent. As used herein, an "adhesion molecule" is any molecule that mediates cell adhesion via a receptor on the cell's surface. Adhesion molecules include members of the cadherin gene superfamily that are not classical cadherins (e.g., proteins that do not contain an HAV sequence and/or one or more of the other characteristics recited above for classical cadherins), such as desmogleins (Dsg) and desmocollins (Dsc); integrins; members of the immunoglobulin supergene family, such as N—CAM; and other uncategorized transmembrane proteins, such as occludin, as well as extracellular matrix proteins such as laminin, fibronectin, collagens, vitronectin, entactin and tenascin. Preferred CAR sequences for inclusion within a modulating agent include (a) Arg-Gly-Asp (RGD), which is bound by integrins (see Cardarelli et al., *J. Biol. Chem.* 267:23159–64, 1992); (b) Tyr-Ile-Gly-Ser-Arg (YIGSR; SEQ ID NO:52), which is bound by α6β1 integrin; (c) KYSFNYDGSE (SEQ ID NO:53), which is bound by N—CAM; (d) the N—CAM heparin sulfate-binding site IWKHKGRDVILKKDVRF (SEQ ID NO:54); (e) the occludin CAR sequence LYHY (SEQ ID NO:55); (f) claudin CAR sequences comprising at least four consecutive amino acids present within a claudin region that has the formula: Trp-Lys/Arg-Aaa-Baa-Ser/Ala-Tyr/Phe-Caa-Gly (SEQ ID NO:56), wherein Aaa, Baa and Caa indicate independently selected amino acid residues; Lys/Arg is an amino acid that is lysine or arginine; Ser/Ala is an amino acid that is serine or alanine; and Tyr/Phe is an amino acid that is tyrosine or phenylalanine; and (g) nonclassical cadherin CAR sequences comprising at least three consecutive amino acids present within a nonclassical cadherin region that has the formula: Aaa-Phe-Baa-Ile/Leu/Val-Asp/Asn/ Glu-Caa-Daa-Ser/Thr/Asn-Gly (SEQ ID NO:57), wherein Aaa, Baa, Caa and Daa are independently selected amino acid residues; Ile/Leu/Val is an amino acid that is selected from the group consisting of isoleucine, leucine and valine, Asp/Asn/Glu is an amino acid that is selected from the group consisting of aspartate, asparagine and glutamate; and Ser/ Thr/Asn is an amino acid that is selected from the group consisting of serine, threonine or asparagine. Representative claudin CAR sequences include IYSY (SEQ ID NO:58), TSSY (SEQ ID NO:59), VTAF (SEQ ID NO:60) and VSAF (SEQ ID NO:61). Representative nonclassical cadherin CAR sequences include the VE-cadherin (cadherin-5) CAR sequence DAE; the cadherin-6 CAR sequences EEY, NEN, ESE and DSG; the cadherin-7 CAR sequences DEN, EPK and DAN; the cadherin-8 CAR sequences EEF and NDV; the OB-cadherin (cadherin-11) CAR sequences DDK, EEY and EAQ; the cadherin-12 CAR sequences DET and DPK; the cadherin-14 CAR sequences DDT, DPK and DAN; the cadherin-15 CAR sequences DKF and DEL; the PB-cadherin CAR sequences EEY, DEL, DPK and DAD; the protocadherin CAR sequences DLV, NRD, DPK and DPS; the dsg CAR sequences NQK, NRN and NKD; the dsc CAR sequences EKD and ERD and the cadherin-related neuronal receptor CAR sequences DPV, DAD, DSV, DSN, DSS, DEK and NEK.

Linkers may, but need not, be used to separate CAR sequences, peptidomimetics and/or antibody sequences within a modulating agent. Linkers may also, or alternatively, be used to attach one or more modulating agents to a support molecule or material, as described below. A linker may be any molecule (including peptide and/or non-peptide sequences as well as single amino acids or other molecules), that does not contain a CAR sequence and that can be covalently linked to at least two peptide sequences and/or peptidomimetics. Using a linker, peptidomimetics and other peptide or protein sequences may be joined in a variety of orientations.

Linkers preferably produce a distance between CAR sequences and/or peptidomimetics between 0.1 to 10,000 nm, more preferably about 0.1–400 nm. A separation distance between recognition sites may generally be determined according to the desired function of the modulating agent. For inhibitors of cell adhesion, the linker distance should be small (0.1–400 nm). For enhancers of cell adhesion, the linker distance should be 400–10,000 nm. One linker that can be used for such purposes is (H$_2$N(CH$_2$)$_n$ CO$_2$H) or derivatives thereof, where n ranges from 1 to 10 and m ranges from 1 to 4000. For example, if glycine (H$_2$NCH$_2$CO$_2$H) or a multimer thereof is used as a linker, each glycine unit corresponds to a linking distance of 2.45 angstroms, or 0.245 nm, as determined by calculation of its lowest energy conformation when linked to other amino acids using molecular modeling techniques. Similarly, aminopropanoic acid corresponds to a linking distance of 3.73 angstroms, aminobutanoic acid to 4.96 angstroms, aminopentanoic acid to 6.30 angstroms and amino hexanoic acid to 6.12 angstroms. Other linkers that may be used will be apparent to those of ordinary skill in the art and include, for example, linkers based on repeat units of 2,3-diaminopropanoic acid, lysine and/or ornithine. 2,3-Diaminopropanoic acid can provide a linking distance of either 2.51 or 3.11 angstroms depending on whether the side-chain amino or terminal amino is used in the linkage. Similarly, lysine can provide linking distances of either 2.44 or 6.95 angstroms and ornithine 2.44 or 5.61 angstroms. Peptide and non-peptide linkers may generally be incorporated into a modulating agent using any appropriate method known in the art.

Modulating agents that inhibit cell adhesion may contain one or more peptidomimetics, provided that such peptidomimetics are adjacent to one another (i.e., without intervening sequences) or in close proximity (i.e., separated by peptide and/or non-peptide linkers to give a distance between the peptidomimetics that ranges from about 0.1 to 400 nm). It will be apparent that other CAR sequences, as discussed above, may also be included. Such modulating agents may generally be used within methods in which it is desirable to simultaneously disrupt cell adhesion mediated by multiple adhesion molecules. Within certain preferred embodiments, an additional CAR sequence is derived from fibronectin and is recognized by an integrin (i.e., RGD; see Cardarelli et al., *J. Biol. Chem.* 267:23159–23164, 1992), or is an occludin CAR sequence (e.g., LYHY; SEQ ID NO:55). One or more antibodies, or fragments thereof, may similarly be used within such embodiments.

Modulating agents that enhance cell adhesion may contain multiple peptidomimetics joined by linkers as described above. Enhancement of cell adhesion may also be achieved by attachment of multiple modulating agents to a support molecule or material, as discussed further below. Such modulating agents may additionally comprise one or more CAR sequence for one or more different adhesion molecules (including, but not limited to, other CAMs) and/or one or more antibodies or fragments thereof that bind to such sequences, to enhance cell adhesion mediated by multiple adhesion molecules.

As noted above, a modulating agent may consist entirely of one or more peptidomimetics, or may contain additional peptide and/or non-peptide components. Peptide portions may be synthesized as described above or may be prepared using recombinant methods. Within such methods, all or part of a modulating agent can be synthesized in living cells, using any of a variety of expression vectors known to those of ordinary skill in the art to be appropriate for the particular host cell. Suitable host cells may include bacteria, yeast cells, mammalian cells, insect cells, plant cells, algae and other animal cells (e.g., hybridoma, CHO, myeloma). The DNA sequences expressed in this manner may encode portions of an endogenous cadherin or other adhesion molecule. Such sequences may be prepared based on known cDNA or genomic sequences (see Blaschuk et al., *J. Mol. Biol.* 211:679–682, 1990), or from sequences isolated by screening an appropriate library with probes designed based on the sequences of known cadherins. Such screens may generally be performed as described in Sambrook et al., *Molecular Cloning: A Laboratory Manual*, Cold Spring Harbor Laboratories, Cold Spring Harbor, N.Y., 1989 (and references cited therein). Polymerase chain reaction (PCR) may also be employed, using oligonucleotide primers in methods well known in the art, to isolate nucleic acid molecules encoding all or a portion of an endogenous adhesion molecule. To generate a nucleic acid molecule encoding a peptide portion of a modulating agent, an endogenous sequence may be modified using well known techniques. Alternatively, portions of the desired nucleic acid sequences may be synthesized using well known techniques, and then ligated together to form a sequence encoding a portion of the modulating agent.

As noted above, a modulating agent may comprise an antibody, or antigen-binding fragment thereof, that specifically binds to a CAR sequence. As used herein, an antibody, or antigen-binding fragment thereof, is said to "specifically bind" to a CAR sequence (with or without flanking amino acids) if it reacts at a detectable level (within, for example, an ELISA, as described by Newton et al., *Develop. Dynamics* 197:1–13, 1993) with a peptide containing that sequence, and does not react detectably with peptides containing a different CAR sequence or a sequence in which the order of amino acid residues in the cadherin CAR sequence and/or flanking sequence is altered.

Antibodies and fragments thereof may be prepared using standard techniques. See, e.g., Harlow and Lane, *Antibodies: A Laboratory Manual*, Cold Spring Harbor Laboratory, 1988. In one such technique, an immunogen comprising a CAR sequence is initially injected into any of a wide variety of mammals (e.g., mice, rats, rabbits, sheep or goats). Small immunogens (i.e., less than about 20 amino acids) should be joined to a carrier protein, such as bovine serum albumin or keyhole limpet hemocyanin. Following one or more injections, the animals are bled periodically. Polyclonal antibodies specific for the CAR sequence may then be purified from such antisera by, for example, affinity chromatography using the modulating agent or antigenic portion thereof coupled to a suitable solid support.

Monoclonal antibodies specific for a CAR sequence may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity from spleen cells obtained from an animal immunized as described above. The spleen cells are immortalized by, for example, fusion with a myeloma cell fusion partner, preferably one that is syngeneic with the immunized animal. Single colonies are selected and their culture supernatants tested for binding activity against the modulating agent or antigenic portion thereof. Hybridomas having high reactivity and specificity are preferred.

Monoclonal antibodies may be isolated from the supernatants of growing hybridoma colonies, with or without the use of various techniques known in the art to enhance the yield. Contaminants may be removed from the antibodies by conventional techniques, such as chromatography, gel filtration, precipitation, and extraction. Antibodies having the desired activity may generally be identified using immunofluorescence analyses of tissue sections, cell or other samples where the target cadherin is localized.

Within certain embodiments, monoclonal antibodies may be specific for particular cadherins (e.g., the antibodies bind to E-cadherin, but do not bind significantly to N-cadherin, or vise versa). Such antibodies may be prepared as described above, using an immunogen that comprises (in addition to the HAV sequence) sufficient flanking sequence to generate the desired specificity (e.g., 5 amino acids on each side is generally sufficient). One representative immunogen is the 15-mer FHLRAHAVDINGNQV—NH$_2$ (SEQ ID NO:75), linked to KLH (see Newton et al., *Dev. Dynamics* 197:1–13, 1993). To evaluate the specificity of a particular antibody, representative assays as described herein and/or conventional antigen-binding assays may be employed. Such antibodies may generally be used for therapeutic, diagnostic and assay purposes, as described herein. For example, such antibodies may be linked to a drug and administered to a mammal to target the drug to a particular cadherin-expressing cell, such as a leukemic cell in the blood.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988; see especially page 309) and digested by papain to yield Fab and Fe fragments. The Fab and Fe fragments may be separated by affinity chromatography on protein A bead columns (Harlow and Lane, 1988, pages 628–29).

Evaluation of Modulating Agent Activity

As noted above, peptidomimetics and modulating agents are capable of modulating (i.e., enhancing or inhibiting) classical cadherin-mediated cell adhesion. The ability of a modulating agent to modulate cell adhesion may generally be evaluated in vitro by assaying the effect on one or more of the following: (1) neurite outgrowth, (2) adhesion between endothelial cells, (3) adhesion between epithelial cells (e.g., normal rat kidney cells and/or human skin) and/or (4) adhesion between cancer cells. In general, a modulating agent is an inhibitor of cell adhesion if, within one or more of these representative assays, contact of the test cells with the modulating agent results in a discernible disruption of cell adhesion. Modulating agents that enhance cell adhesion are considered to be modulators of cell adhesion if they are capable of enhancing neurite outgrowth as described below and/or are capable of promoting cell adhesion, as judged by plating assays to assess epithelial cell adhesion to a modulating agent attached to a support material, such as tissue culture plastic. For modulating agents that affect N-cadherin mediated functions, assays involving endothelial or cancer cell adhesion or neurite outgrowth are preferred.

Within a representative neurite outgrowth assay, neurons may be cultured on a monolayer of cells (e.g., 3T3) that express N-cadherin. Neurons grown on such cells (under suitable conditions and for a sufficient period of time) extend longer neurites than neurons cultured on cells that do not express N-cadherin. For example, neurons may be cultured on monolayers of 3T3 cells transfected with cDNA encoding N-cadherin essentially as described by Doherty and Walsh, *Curr. Op. Neurobiol.* 4:49–55, 1994; Williams et al., *Neuron* 13:583–594, 1994; Hall et al., *Cell Adhesion and Commun.* 3:441–450, 1996; Doherty and Walsh, *Mol. Cell. Neurosci.* 8:99–111, 1994; and Safell et al., *Neuron* 18:231–242, 1997. Briefly, monolayers of control 3T3 fibroblasts and 3T3 fibroblasts that express N-cadherin may be established by overnight culture of 80,000 cells in individual wells of an 8-chamber well tissue culture slide. 3000 cerebellar neurons isolated from post-natal day 3 mouse brains may be cultured for 18 hours on the various monolayers in control media (SATO/2% FCS), or media supplemented with various concentrations of the modulating agent or control peptide. The cultures may then be fixed and stained for GAP43, which specifically binds to the neurons and their neurites. The length of the longest neurite on each GAP43 positive neuron may be measured by computer assisted morphometry.

A modulating agent that modulates N-cadherin-mediated cell adhesion may inhibit or enhance such neurite outgrowth. Under the conditions described above, the presence of 500 μg/mL of a modulating agent that disrupts neural cell adhesion should result in a decrease in the mean neurite length by at least 50%, relative to the length in the absence of modulating agent or in the presence of a negative control peptide. Alternatively, the presence of 500 μg/mL of a modulating agent that enhances neural cell adhesion should result in an increase in the mean neurite length by at least 50%.

Within one representative cell adhesion assay, the addition of a modulating agent to cells that express a cadherin results in disruption of cell adhesion. A "cadherin-expressing cell," as used herein, may be any type of cell that expresses at least one cadherin on the cell surface at a detectable level, using standard techniques such as immunocytochemical protocols (Blaschuk and Farookhi, *Dev. Biol.* 136:564–567, 1989). Cadherin-expressing cells include endothelial (e.g., bovine pulmonary artery endothelial cells), epithelial and/or cancer cells (e.g., the human ovarian cancer cell line SKOV3 (ATCC #HB-77)). For example, such cells may be plated under standard conditions that permit cell adhesion in the presence and absence of modulating agent (e.g., 500 μg/mL). Disruption of cell adhesion may be determined visually within 24 hours, by observing retraction of the cells from one another.

For use within one such assay, bovine pulmonary artery endothelial cells may be harvested by sterile ablation and digestion in 0.1% collagenase (type II; Worthington Enzymes, Freehold, N.J.). Cells may be maintained in Dulbecco's minimum essential medium supplemented with 10% fetal calf serum and 1% antibiotic-antimycotic at 37° C. in 7% $CO_2$ in air. Cultures may be passaged weekly in trypsin-EDTA and seeded onto tissue culture plastic at 20,000 cells/$cm^2$. Endothelial cultures may be used at 1 week in culture, which is approximately 3 days after culture confluency is established. The cells may be seeded onto coverslips and treated (e.g., for 30 minutes) with modulating agent or a control compound at, for example, 500 μg/ml and then fixed with 1% paraformaldehyde. As noted above, disruption of cell adhesion may be determined visually within 24 hours, by observing retraction of the cells from one another. This assay evaluates the effect of a modulating agent on N-cadherin mediated cell adhesion.

Within another such assay, the effect of a modulating agent on normal rat kidney (NRK) cells may be evaluated. According to a representative procedure, NRK cells (ATCC #1571-CRL) may be plated at 10–20,000 cells per 35 mm tissue culture flasks containing DMEM with 10% FCS and sub-cultured periodically (Laird et al., *J. Cell Biol.* 131: 1193–1203, 1995). Cells may be harvested and replated in 35 mm tissue culture flasks containing 1 mm coverslips and incubated until 50–65% confluent (24–36 hours). At this time, coverslips may be transferred to a 24-well plate, washed once with fresh DMEM and exposed to modulating agent at a concentration of, for example, 1 mg/mL for 24 hours. Fresh modulating agent may then be added, and the cells left for an additional 24 hours. Cells may be fixed with 100% methanol for 10 minutes and then washed three times with PBS. Coverslips may be blocked for 1 hour in 2% BSA/PBS and incubated for a further 1 hour in the presence of mouse anti-E-cadherin antibody (Transduction Labs, 1:250 dilution). Primary and secondary antibodies may be diluted in 2% BSA/PBS. Following incubation in the primary antibody, coverslips may be washed three times for 5 minutes each in PBS and incubated for 1 hour with donkey anti-mouse antibody conjugated to fluorescein (diluted 1:200). Following further washes in PBS (3×5 min) coverslips can be mounted and viewed by confocal microscopy.

In the absence of modulating agent, NRK cells form characteristic tightly adherent monolayers with a cobblestone morphology in which cells display a polygonal shape. NRK cells that are treated with a modulating agent that disrupts E-cadherin mediated cell adhesion may assume a non-polygonal and elongated morphology (i.e., a fibroblast-like shape) within 48 hours of treatment with 1 mg/mL of modulating agent. Gaps appear in confluent cultures of such cells. In addition, 1 mg/mL of such a modulating agent reproducibly induces a readily apparent reduction in cell surface staining of E-cadherin, as judged by immunofluorescence microscopy (Laird et al., *J. Cell Biol.* 131:1193–1203, 1995), of at least 75% within 48 hours.

A third cell adhesion assay involves evaluating the effect of a modulating agent on permeability of adherent epithelial and/or endothelial cell layers. For example, the effect on permeability of human skin may be evaluated. Such skin may be derived from a natural source or may be synthetic. Human abdominal skin for use in such assays may generally be obtained from humans at autopsy within 24 hours of death. Briefly, a cyclic peptide and a test marker (e.g., the fluorescent markers Oregon Green™ and Rhodamine Green™ Dextran) may be dissolved in a sterile buffer, and the ability of the marker to penetrate through the skin and into a receptor fluid may be measured using a Franz Cell apparatus (Franz, *Curr. Prob. Dermatol.* 7:58–68, 1978; Franz, *J. Invest. Dermatol.* 64:190–195, 1975). In general, a modulating agent that enhances the permeability of human skin results in a statistically significant increase in the amount of marker in the receptor compartment after 6–48 hours in the presence of 500 µg/mL modulating agent. This assay evaluates the effect of a modulating agent on E-cadherin mediated cell adhesion.

Alternatively, cells that do not naturally express a cadherin may be used within such assays. Such cells may be stably transfected with a polynucleotide (e.g., a cDNA) encoding a classical cadherin of interest, such that the cadherin is expressed on the surface of the cell. Transfection of cells for use in cell adhesion assays may be performed using standard techniques and published cadherin sequences. Expression of the cadherin may be confirmed by assessing adhesion of the transfected cells, in conjunction with immunocytochemical techniques using antibodies directed against the cadherin of interest. The stably transfected cells that aggregate, as judged by light microscopy, following transfection express sufficient levels of the cadherin. Preferred cells for use in such assays include L cells, which do not detectably adhere in the absence of transfection (Nagafuchi et al., *Nature* 329:341–343, 1987). Following transfection of L cells with a cDNA encoding a cadherin, aggregation may be observed. Modulating agents that detectably inhibit such aggregation may be used to modulate functions mediated by the cadherin. Such assays have been used for numerous nonclassical cadherins, including OB-cadherin (Okazaki et al., *J. Biol. Chem.* 269:12092–98, 1994), cadherin-5 (Breier et al., *Blood* 87:630–641, 1996), cadherin-6 (Mbalaviele et al., *J. Cell. Biol.* 141:1467–1476, 1998), cadherin-8 (Kido et al., *Genomics* 48:186–194, 1998), cadherin-15 (Shimoyama et al., *J. Biol. Chem.* 273: 10011–10018, 1998), PB-cadherin (Sugimoto et al., *J. Biol. Chem.* 271:11548–11556, 1996), LI-cadherin (Kreft et al., *J. Cell Biol.* 136:1109–1121, 1997), protocadherin 42 and 43 (Sano et al., *EMBO J.* 12:2249–2256, 1993) and desmosomal cadherins (Marcozzi et al., *J. Cell Sci.* 111:495–509, 1998). It will be apparent to those of ordinary skill in the art that assays may be performed in a similar manner for classical cadherins. In general, a modulating agent that is derived from a particular cadherin CAR sequence (i.e., comprises such a peptidomimetic thereof) and that modulates adhesion of a cell that expresses the same cadherin is considered to modulate a function mediated by the cadherin.

Modulating Agent Modification and Formulations

A modulating agent as described herein may, but need not, be linked to one or more additional molecules. In particular, as discussed below, it may be beneficial for certain applications to link multiple modulating agents (which may, but need not, be identical) to a support molecule (e.g., keyhole limpet hemocyanin) or a solid support, such as a polymeric matrix (which may be formulated as a membrane or microstructure, such as an ultra thin film), a container surface (e.g., the surface of a tissue culture plate or the interior surface of a bioreactor), or a bead or other particle, which may be prepared from a variety of materials including glass, plastic or ceramics. For certain applications, biodegradable support materials are preferred, such as cellulose and derivatives thereof, collagen, spider silk or any of a variety of polyesters (e.g. those derived from hydroxy acids and/or lactones) or sutures (see U.S. Pat. No. 5,245,012). Within certain embodiments, modulating agents and molecules comprising other CAR sequence(s) (e.g., an RGD and/or LYHY (SEQ ID NO:55) sequence) may be attached to a support such as a polymeric matrix, preferably in an alternating pattern.

Suitable methods for linking a modulating agent to a support material will depend upon the composition of the support and the intended use, and will be readily apparent to those of ordinary skill in the art. Attachment may generally be achieved through noncovalent association, such as adsorption or affinity or, preferably, via covalent attachment (which may be a direct linkage between a modulating agent and functional groups on the support, or may be a linkage by way of a cross-linking agent or linker). Attachment of a modulating agent by adsorption may be achieved by contact, in a suitable buffer, with a solid support for a suitable amount of time. The contact time varies with temperature, but is generally between about 5 seconds and 1 day, and typically between about 10 seconds and 1 hour.

Covalent attachment of a modulating agent to a molecule or solid support may generally be achieved by first reacting the support material with a bifunctional reagent that will also react with a functional group, such as a hydroxyl, thiol, carboxyl, ketone or amino group, on the modulating agent. For example, a modulating agent may be bound to an appropriate polymeric support or coating using benzoquinone, by condensation of an aldehyde group on the support with an amine and an active hydrogen on the modulating agent or by condensation of an amino group on the support with a carboxylic acid on the modulating agent. A preferred method of generating a linkage is via amino groups using glutaraldehyde. A modulating agent may be linked to cellulose via ester linkages. Similarly, amide linkages may be suitable for linkage to other molecules such as keyhole limpet hemocyanin or other support materials. Multiple modulating agents and/or molecules comprising other CAR sequences may be attached, for example, by random coupling, in which equimolar amounts of such molecules are mixed with a matrix support and allowed to couple at random.

Although modulating agents as described herein may preferentially bind to specific tissues or cells, and thus may be sufficient to target a desired site in vivo, it may be beneficial for certain applications to include an additional targeting agent. Accordingly, a targeting agent may also, or alternatively, be linked to a modulating agent to facilitate targeting to one or more specific tissues. As used herein, a "targeting agent," may be any substance (such as a compound or cell) that, when linked to a modulating agent enhances the transport of the modulating agent to a target tissue, thereby increasing the local concentration of the modulating agent. Targeting agents include antibodies or fragments thereof, receptors, ligands and other molecules that bind to cells of, or in the vicinity of, the target tissue. Known targeting agents include serum hormones, antibodies against cell surface antigens, lectins, adhesion molecules, tumor cell surface binding ligands, steroids, cholesterol, lymphokines, fibrinolytic enzymes and those drugs and proteins that bind to a desired target site. Among the many monoclonal antibodies that may serve as targeting agents are anti-TAC, or other interleukin-2 receptor antibodies; 9.2.27 and NR-ML-05, reactive with the 250 kilodalton human melanoma-associated proteoglycan; and NR-LU-10, reactive with a pancarcinoma glycoprotein. An antibody targeting agent may be an intact (whole) molecule, a fragment thereof, or a functional equivalent thereof. Examples of antibody fragments are F(ab')2, –Fab', Fab and F[v] fragments, which may be produced by conventional methods or by genetic or protein engineering. Linkage is generally covalent and may be achieved by, for example, direct condensation or other reactions, or by way of bi- or multi-functional linkers. Within other embodiments, it may also be possible to target a polynucleotide encoding a modulating agent to a target tissue, thereby increasing the local concentration of modulating agent. Such targeting may be achieved using well known techniques, including retroviral and adenoviral infection.

For certain embodiments, it may be beneficial to also, or alternatively, link a drug to a modulating agent. As used herein, the term "drug" refers to any bioactive agent intended for administration to a mammal to prevent or treat a disease or other undesirable condition. Drugs include hormones, growth factors, proteins, peptides and other compounds. The use of certain specific drugs within the context of the present invention is discussed below.

Within certain aspects of the present invention, one or more modulating agents as described herein may be present within a pharmaceutical composition. A pharmaceutical composition comprises one or more modulating agents in combination with one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. A modulating agent (alone or in combination with a targeting agent and/or drug) may, but need not, be encapsulated within liposomes using well known technology. Compositions of the present invention may be formulated for any appropriate manner of administration, including for example, topical, oral, nasal, intravenous, intracranial, intraperitoneal, subcutaneous, or intramuscular administration. For certain topical applications, formulation as a cream or lotion, using well known components, is preferred.

For certain embodiments, as discussed below, a pharmaceutical composition may further comprise a modulator of cell adhesion that is mediated by one or more molecules other than cadherins. Such modulators may generally be prepared as described above, incorporating one or more non-cadherin CAR sequences and/or antibodies thereto in place of the cadherin CAR sequences and antibodies. Such compositions are particularly useful for situations in which it is desirable to inhibit cell adhesion mediated by multiple cell-adhesion molecules, such as other members of the cadherin gene superfamily that are not classical cadherins (e.g., Dsg and Dsc); claudins; integrins; members of the immunoglobulin supergene family, such as N—CAM; and other uncategorized transmembrane proteins, such as occludin, as well as extracellular matrix proteins such as laminin, fibronectin, collagens, vitronectin, entactin and tenascin. Preferred CAR sequences for use are as described above.

A pharmaceutical composition may also contain one or more drugs, which may be linked to a modulating agent or may be free within the composition. Virtually any drug may be administered in combination with a modulating agent as described herein, for a variety of purposes as described below. Examples of types of drugs that may be administered with a modulating agent include analgesics, anesthetics, antianginals, antifungals, antibiotics, anticancer drugs (e.g., taxol or mitomycin C), antiinflammatories (e.g., ibuprofen and indomethacin), anthelmintics, antidepressants, antidotes, antiemetics, antihistamines, antihypertensives, antimalarials, antimicrotubule agents (e.g., colchicine or vinca alkaloids), antimigraine agents, antimicrobials, antipsychotics, antipyretics, antiseptics, anti-signaling agents (e.g., protein kinase C inhibitors or inhibitors of intracellular calcium mobilization), antiarthritics, antithrombin agents, antituberculotics, antitussives, antivirals, appetite suppressants, cardioactive drugs, chemical dependency drugs, cathartics, chemotherapeutic agents, coronary, cerebral or peripheral vasodilators, contraceptive agents, depressants, diuretics, expectorants, growth factors, hormonal agents, hypnotics, immunosuppression agents, narcotic antagonists, parasympathomimetics, sedatives, stimulants, sympathomimetics, toxins (e.g., cholera toxin), tranquilizers and urinary antiinfectives.

For imaging purposes, any of a variety of diagnostic agents may be incorporated into a pharmaceutical composition, either linked to a modulating agent or free within the composition. Diagnostic agents include any substance administered to illuminate a physiological function within a patient, while leaving other physiological functions generally unaffected. Diagnostic agents include metals, radioactive isotopes and radioopaque agents (e.g., gallium, technetium, indium, strontium, iodine, barium, bromine and phosphorus-containing compounds), radiolucent agents, contrast agents, dyes (e.g., fluorescent dyes and chromophores) and enzymes that catalyze a colorimetric or fluorometric reaction. In general, such agents may be attached using a variety of techniques as described above, and may be present in any orientation.

The compositions described herein may be administered as part of a sustained release formulation (i.e., a formulation such as a capsule or sponge that effects a slow release of modulating agent following administration). Such formulations may generally be prepared using well known technology and administered by, for example, oral, rectal or subcutaneous implantation, or by implantation at the desired target site. Sustained-release formulations may contain a modulating agent dispersed in a carrier matrix and/or contained within a reservoir surrounded by a rate controlling membrane (see, e.g., European Patent Application 710,491A). Carriers for use within such formulations are biocompatible, and may also be biodegradable; preferably the formulation provides a relatively constant level of modulating agent release. The amount of modulating agent contained within a sustained release formulation depends upon the site of implantation, the rate and expected duration of release and the nature of the condition to be treated or prevented.

Pharmaceutical compositions of the present invention may be administered in a manner appropriate to the disease to be treated (or prevented). Appropriate dosages and the duration and frequency of administration will be determined by such factors as the condition of the patient, the type and severity of the patient's disease and the method of administration. In general, an appropriate dosage and treatment regimen provides the modulating agent(s) in an amount sufficient to provide therapeutic and/or prophylactic benefit. Within particularly preferred embodiments of the invention, a modulating agent or pharmaceutical composition as described herein may be administered at a dosage ranging from 0.001 to 50 mg/kg body weight, preferably from 0.1 to 20 mg/kg, on a regimen of single or multiple daily doses. For topical administration, a cream typically comprises an amount of modulating agent ranging from 0.00001% to 1%, preferably 0.0001% to 0.2%, and more preferably from 0.0001% to 0.002%. Fluid compositions typically contain about 10 ng/ml to 5 mg/ml, preferably from about 10 µg to 2 mg/mL peptidomimetic. Appropriate dosages may generally be determined using experimental models and/or clinical trials. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

Modulating Agent Methods of Use

In general, the modulating agents and compositions described herein may be used for modulating the adhesion of classical cadherin-expressing cells (i.e., cells that express one or more of E-cadherin, N-cadherin, P-cadherin, R-cadherin and/or other cadherin(s) containing the HAV sequence, including as yet undiscovered classical cadherins) in vitro and/or in vivo. To modulate classical cadherin-mediated cell adhesion, a cadherin-expressing cell is contacted with a modulating agent either in vivo or in vitro. As noted above, modulating agents for purposes that involve the disruption of cadherin-mediated cell adhesion may comprise a single peptidomimetic or multiple peptidomimetics in close proximity. When it is desirable to also disrupt cell adhesion mediated by other adhesion molecules, a modulating agent may additionally comprise one or more CAR sequences bound by such adhesion molecules (and/or antibodies or fragments thereof that bind such sequences), preferably separated by linkers. As noted above, such linkers may or may not comprise one or more amino acids. For enhancing cell adhesion, a modulating agent may contain multiple peptidomimetics, preferably separated by linkers, and/or may be linked to a single molecule or to a support material as described above.

Certain methods involving the disruption of cell adhesion as described herein have an advantage over prior techniques in that they permit the passage of molecules that are large and/or charged across barriers of cadherin-expressing cells. As discussed in greater detail below, modulating agents as described herein may also be used to disrupt or enhance cell adhesion in a variety of other contexts. Within the methods described herein, one or more modulating agents may generally be administered alone, or within a pharmaceutical composition. In each specific method described herein, as noted above, a targeting agent may be employed to increase the local concentration of modulating agent at the target site.

In one such aspect, the present invention provides methods for reducing unwanted cellular adhesion by administering a modulating agent as described herein. Unwanted cellular adhesion can occur between tumor cells, between tumor cells and normal cells or between normal cells as a result of surgery, injury, chemotherapy, disease, inflammation or other condition jeopardizing cell viability or function. Preferred modulating agents for use within such methods comprise a single peptidomimetic of a cyclic peptide as described above, such as N—Ac—CHAVC—Y—NH$_2$ (SEQ ID NO:81), N—Ac—CHAVDC—NH$_2$ (SEQ ID NO:20), N—Ac—CSHAVC—NH$_2$ (SEQ ID NO:36) or N—Ac—CHAVC—NH$_2$ (SEQ ID NO:10). In addition, a modulating agent may comprise the sequence RGD, which is bound by integrins, and/or the sequence LYHY (SEQ ID NO:55), which is bound by occludin, separated from the peptidomimetic via a linker. Other CAR sequences that may be present include OB-cadherin, dsg and dsc CAR sequences as described above. Alternatively, a separate modulator of integrin, occludin-, OB-cadherin-, dsc- and/or dsg-mediated cell adhesion may be administered in conjunction with the modulating agent(s), either within the same pharmaceutical composition or separately. Topical administration of the modulating agent(s) is generally preferred, but other means may also be employed. Preferably, a fluid composition for topical administration (comprising, for example, physiological saline) comprises an amount of peptidomimetic as described above, and more preferably an amount ranging from 10 µg/mL to 1 mg/mL. Creams may generally be formulated as described above. Topical administration in the surgical field may be given once at the end of surgery by irrigation of the wound, as an intermittent or continuous irrigation with use of surgical drains in the post operative period, or by the use of drains specifically inserted in an area of inflammation, injury or disease in cases where surgery does not need to be performed. Alternatively, parenteral or transcutaneous administration may be used to achieve similar results.

In another aspect, methods are provided for enhancing the delivery of a drug through the skin of a mammal. Transdermal delivery of drugs is a convenient and non-invasive method that can be used to maintain relatively constant blood levels of a drug. In general, to facilitate drug delivery via the skin, it is necessary to perturb adhesion between the epithelial cells (keratinocytes) and the endothelial cells of the microvasculature. Using currently available techniques, only small, uncharged molecules may be delivered across skin in vivo. The methods described herein are not subject to the same degree of limitation. Accordingly, a wide variety of drugs may be transported across the epithelial and endothelial cell layers of skin, for systemic or topical administration. Such drugs may be delivered to melanomas or may enter the blood stream of the mammal for delivery to other sites within the body.

To enhance the delivery of a drug through the skin, a modulating agent as described herein and a drug are contacted with the skin surface. Preferred modulating agents for use within such methods comprise a single peptidomimetic of a cyclic peptide as described above, such as N—Ac—CHAVC—Y—NH$_2$ (SEQ ID NO:81), N—Ac—CHAVDC—NH$_2$ (SEQ ID NO:20), N—Ac—CSHAVC—NH$_2$ (SEQ ID NO:36) or N—Ac—CHAVC—NH$_2$ (SEQ ID NO:10). Multifunctional modulating agents comprising such a peptidomimetic linked to one or more of the Dsc and/or the Dsg CAR sequences may also be used to disrupt epithelial cell adhesion. Such modulating agents may also, or alternatively, comprise the fibronectin CAR sequence RGD, which is recognized by integrins, the occludin CAR sequence LYHY (SEQ ID NO:55) and/or a claudin CAR sequences as described above. Alternatively, a separate modulator of non-classical cadherin-mediated cell adhesion may be administered in conjunction with the modulating agent(s), either within the same pharmaceutical composition or separately.

Contact may be achieved by direct application of the modulating agent, generally within a composition formulated as a cream or gel, or using any of a variety of skin contact devices for transdermal application (such as those described in European Patent Application No. 566,816 A; U.S. Pat. No. 5,613,958; U.S. Pat. No. 5,505,956). A skin patch provides a convenient method of administration (particularly for slow-release formulations). Such patches may contain a reservoir of modulating agent and drug separated from the skin by a membrane through which the drug diffuses. Within other patch designs, the modulating agent and drug may be dissolved or suspended in a polymer or adhesive matrix that is then placed in direct contact with the patient's skin. The modulating agent and drug may then diffuse from the matrix into the skin. Modulating agent(s) and drug(s) may be contained within the same composition or skin patch, or may be separately administered, although administration at the same time and site is preferred. In general, the amount of modulating agent administered via the skin varies with the nature of the condition to be treated or prevented, but may vary as described above. Such levels may be achieved by appropriate adjustments to the device used, or by applying a cream formulated as described above. Transfer of the drug across the skin and to the target tissue may be predicted based on in vitro studies using, for example, a Franz cell apparatus, and evaluated in vivo by appropriate means that will be apparent to those of ordinary skill in the art. As an example, monitoring of the serum level of the administered drug over time provides a convenient measure of the drug transfer across the skin.

Transdermal drug delivery as described herein is particularly useful in situations in which a constant rate of drug delivery is desired, to avoid fluctuating blood levels of a drug. For example, morphine is an analgesic commonly used immediately following surgery. When given intermittently in a parenteral form (intramuscular, intravenous), the patient usually feels sleepy during the first hour, is well during the next 2 hours and is in pain during the last hour because the blood level goes up quickly after the injection and goes down below the desirable level before the 4 hour interval prescribed for re-injection is reached. Transdermal administration as described herein permits the maintenance of constant levels for long periods of time (e.g., days), which allows adequate pain control and mental alertness at the same time. Insulin provides another such example. Many diabetic patients need to maintain a constant baseline level of insulin which is different from their needs at the time of meals. The baseline level may be maintained using transdermal administration of insulin, as described herein. Antibiotics may also be administered at a constant rate, maintaining adequate bactericidal blood levels, while avoiding the high levels that are often responsible for the toxicity (e.g., levels of gentamycin that are too high typically result in renal toxicity).

Drug delivery by the methods of the present invention also provide a more convenient method of drug administration. For example, it is often particularly difficult to administer parenteral drugs to newborns and infants because of the difficulty associated with finding veins of acceptable caliber to catheterize. However, newborns and infants often have a relatively large skin surface as compared to adults. Transdermal drug delivery permits easier management of such patients and allows certain types of care that can presently be given only in hospitals to be given at home. Other patients who typically have similar difficulties with venous catheterization are patients undergoing chemotherapy or patients on dialysis. In addition, for patients undergoing prolonged therapy, transdermal administration as described herein is more convenient than parenteral administration.

Transdermal administration as described herein also allows the gastrointestinal tract to be bypassed in situations where parenteral uses would not be practical. For example, there is a growing need for methods suitable for administration of therapeutic small peptides and proteins, which are typically digested within the gastrointestinal tract. The methods described herein permit administration of such compounds and allow easy administration over long periods of time. Patients who have problems with absorption through their gastrointestinal tract because of prolonged ileus or specific gastrointestinal diseases limiting drug absorption may also benefit from drugs formulated for transdermal application as described herein.

Further, there are many clinical situations where it is difficult to maintain compliance. For example, patients with mental problems (e.g., patients with Alzheimer's disease or psychosis) are easier to manage if a constant delivery rate of drug is provided without having to rely on their ability to take their medication at specific times of the day. Also patients who simply forget to take their drugs as prescribed are less likely to do so if they merely have to put on a skin patch periodically (e.g. every 3 days). Patients with diseases that are without symptoms, like patients with hypertension, are especially at risk of forgetting to take their medication as prescribed.

For patients taking multiple drugs, devices for transdermal application such as skin patches may be formulated with combinations of drugs that are frequently used together. For example, many heart failure patients are given digoxin in combination with furosemide. The combination of both drugs into a single skin patch facilitates administration, reduces the risk of errors (taking the correct pills at the appropriate time is often confusing to older people), reduces the psychological strain of taking "so many pills," reduces skipped dosage because of irregular activities and improves compliance.

The methods described herein are particularly applicable to humans, but also have a variety of veterinary uses, such as the administration of growth factors or hormones (e.g., for fertility control) to an animal.

As noted above, a wide variety of drugs may be administered according to the methods provided herein. Some examples of drug categories that may be administered transdermally include anti-inflammatory drugs (e.g., in arthritis and in other condition) such as all NSAID, indomethacin, prednisone, etc.; analgesics (especially when oral absorption is not possible, such as after surgery, and when parenteral administration is not convenient or desirable), including morphine, codeine, Demerol, acetaminophen and combinations of these (e.g., codeine plus acetaminophen); antibiotics such as Vancomycin (which is not absorbed by the GI tract and is frequently given intravenously) or a combination of INH and Rifampicin (e.g., for tuberculosis); anticoagulants such as heparin (which is not well absorbed by the 61 tract and is generally given parenterally, resulting in fluctuation in the blood levels with an increased risk of bleeding at high levels and risks of inefficacy at lower levels) and Warfarin (which is absorbed by the GI tract but cannot be administered immediately after abdominal surgery because of the normal ileus following the procedure); antidepressants (e.g., in situations where compliance is an issue as in Alzheimer's disease or when maintaining stable blood levels results in a significant reduction of anti-cholinergic side effects and better tolerance by patients), such as amitriptylin, imipramin, prozac, etc.; antihypertensive drugs (e.g., to improve compliance and reduce side effects associated with fluctuating blood levels), such as diuretics and beta-blockers (which can be administered by the same patch; e.g., furosemide and propanolol); antipsychotics (e.g., to facilitate compliance and make it easier for care giver and family members to make sure that the drug is received), such as haloperidol and chlorpromazine; and anxiolytics or sedatives (e.g., to avoid the reduction of alertness related to high blood levels after oral administration and allow a continual benefit throughout the day by maintaining therapeutic levels constant).

Numerous other drugs may be administered as described herein, including naturally occurring and synthetic hormones, growth factors, proteins and peptides. For example, insulin and human growth hormone, growth factors like erythropoietin, interleukins and interferons may be delivered via the skin.

Kits for administering a drug via the skin of a mammal are also provided within the present invention. Such kits generally comprise a device for transdermal application (i.e., skin patch) in combination with, or impregnated with, one or more modulating agents. A drug may additionally be included within such kits.

Within a related embodiment, the use of modulating agents as described herein to increase skin permeability may also facilitate sampling of the blood compartment by passive diffusion, permitting detection and/or measurement of the levels of specific molecules circulating in the blood. For example, application of one or more modulating agents to the skin, via a skin patch as described herein, permits the patch to function like a sponge to accumulate a small quantity of fluid containing a representative sample of the serum. The patch is then removed after a specified amount of time and analyzed by suitable techniques for the compound of interest (e.g., a medication, hormone, growth factor, metabolite or marker). Alternatively, a patch may be impregnated with reagents to permit a color change if a specific substance (e.g., an enzyme) is detected. Substances that can be detected in this manner include, but are not limited to, illegal drugs such as cocaine, HIV enzymes, glucose and PSA. This technology is of particular benefit for home testing kits.

Within a further aspect, methods are provided for enhancing delivery of a drug to a tumor in a mammal, comprising administering a modulating agent in combination with a drug to a tumor-bearing mammal. Modulating agents for use within such methods include those designed to disrupt E-cadherin and/or N-cadherin mediated cell adhesion, such as agents that comprise a single peptidomimetic of a cyclic peptide as described above, such as N—Ac—CHAVC—Y—NH$_2$ (SEQ ID NO:81), N—Ac—CHAVDC—NH$_2$ (SEQ ID NO:20), N—Ac—CSHAVC—NH$_2$ (SEQ ID NO:36) or N—Ac—CHAVC—NH$_2$ (SEQ ID NO:10).

In one particularly preferred embodiment, a modulating agent is capable of disrupting cell adhesion mediated by multiple adhesion molecules. For example, a single branched modulating agent (or multiple agents linked to a single molecule or support material) may disrupt E-cadherin, N-cadherin, occludin, Dsc and Dsg mediated cell adhesion, thereby disrupting adherens junctions, tight junctions and desmosomes. Such an agent may comprise one or more peptidomimetics, as well as one or more of the fibronectin CAR sequence RGD, which is recognized by integrins; a dsg CAR sequence; a dsc CAR sequence; a claudin CAR sequence; an occludin CAR sequence and/or an OB-cadherin CAR sequence. Such agents serve as multifunctional disrupters of cell adhesion. Alternatively, a separate modulator of non-classical cadherin-mediated cell adhesion may be administered in conjunction with the modulating agent(s), either within the same pharmaceutical composition or separately. Antibodies or Fab fragments directed against a cadherin CAR sequence and/or an occludin CAR sequence may also be employed, either incorporated into a modulating agent or within a separate modulator that is administered concurrently.

Preferably, the modulating agent and the drug are formulated within the same composition or drug delivery device prior to administration. In general, a modulating agent may enhance drug delivery to any tumor, and the method of administration may be chosen based on the type of target tumor. For example, injection or topical administration as described above may be preferred for melanomas and other accessible tumors (e.g., metastases from primary ovarian tumors may be treated by flushing the peritoneal cavity with the composition). Other tumors (e.g., bladder tumors) may be treated by injection of the modulating agent and the drug (such as mitomycin C) into the site of the tumor. In other instances, the composition may be administered systemically, and targeted to the tumor using any of a variety of specific targeting agents. Suitable drugs may be identified by those of ordinary skill in the art based upon the type of cancer to be treated (e.g., mitomycin C for bladder cancer). In general, the amount of modulating agent administered varies with the method of administration and the nature of the tumor, within the typical ranges provided above, preferably ranging from about 11 g/mL to about 2 mg/mL, and more preferably from about 10 µg/mL to 100 µg/mL. Transfer of the drug to the target tumor may be evaluated by appropriate means that will be apparent to those of ordinary skill in the art, such as a reduction in tumor size. Drugs may also be labeled (e.g., using radionuclides) to permit direct observation of transfer to the target tumor using standard imaging techniques.

Within a related aspect, the present invention provides methods for inhibiting the development of a cancer (i.e., for treating or preventing cancer and/or inhibiting metastasis) in a mammal. Cancer tumors are solid masses of cells, growing out of control, which require nourishment via blood vessels. The formation of new capillaries is a prerequisite for tumor growth and the emergence of metastases. Administration of a modulating agent as described herein may disrupt the growth of such blood vessels, thereby providing effective therapy for the cancer and/or inhibiting metastasis. Modulating agents comprising peptidomimetics may also be used to treat leukemias. Preferred modulating agents for use within such methods include those that disrupt N-cadherin mediated cell adhesion, such as agents that comprise a peptidomimetic of a cyclic peptide as described above (e.g., N—Ac—CHAVC—Y—NH$_2$ (SEQ ID NO:81), N—Ac—CHAVDC—NH$_2$ (SEQ ID NO:20), N—Ac—CSHAVC—NH$_2$ (SEQ ID NO:36) or N—Ac—CHAVC—NH$_2$ (SEQ ID NO:10)). In addition, a modulating agent may comprise the sequence RGD, which is recognized by integrins, and/or the occludin CAR sequence LYHY (SEQ ID NO:55) separated via a linker. Other CAR sequences that may be present include an OB-cadherin CAR sequence; dsc CAR sequence. dsg CAR sequence and/or claudin CAR sequence. Alternatively, a separate modulator of integrin-OB-cadherin-, dsc-, dsg-, claudin- and/or occludin-mediated cell adhesion may be administered in conjunction with the modulating agent(s), either within the same pharmaceutical composition or separately.

A modulating agent may be administered alone (e.g., via the skin) or within a pharmaceutical composition. For melanomas and certain other accessible tumors, injection or topical administration as described above may be preferred. For ovarian cancers, flushing the peritoneal cavity with a composition comprising one or more modulating agents may prevent metastasis of ovarian tumor cells. Other tumors (e.g., bladder tumors, bronchial tumors or tracheal tumors) may be treated by injection of the modulating agent into the cavity. In other instances, the composition may be administered systemically, and targeted to the tumor using any of a variety of specific targeting agents, as described above. In general, the amount of modulating agent administered varies depending upon the method of administration and the nature of the cancer, but may vary within the ranges identified above. The effectiveness of the cancer treatment or inhibition of metastasis may be evaluated using well known clinical observations such as the level of serum markers (e.g., CEA or PSA).

Within a further related aspect, a modulating agent may be used to inhibit angiogenesis (i.e., the growth of blood vessels from pre-existing blood vessels) in a mammal. In general, inhibition of angiogenesis may be beneficial in patients afflicted with diseases such as cancer or arthritis. Preferred modulating agents for use within such methods comprise a single peptidomimetic of a cyclic peptide as described above, such as N—Ac—CHAVC—Y—NH$_2$ (SEQ ID NO:81), N—Ac—CHAVDC—NH$_2$ (SEQ ID NO:20), N—Ac—CSHAVC—NH$_2$ (SEQ ID NO:36) or N—Ac—CHAVC—NH$_2$ (SEQ ID NO:10). In addition, a modulating agent for use in inhibiting angiogenesis may comprise the sequence RGD, which is recognized by integrins, the occludin CAR sequence LYHY (SEQ ID NO:55) and/or a claudin CAR sequence, separated from the peptidomimetic via a linker. Alternatively, a separate modulator of integrin- and/or occludin-mediated cell adhesion may be administered in conjunction with the modulating agent(s), either within the same pharmaceutical composition or separately.

The effect of a particular modulating agent on angiogenesis may generally be determined by evaluating the effect of the agent on blood vessel formation. Such a determination may generally be performed, for example, using a chick chorioallantoic membrane assay (Iruela-Arispe et al., *Molecular Biology of the Cell* 6:327–343, 1995). Briefly, a modulating agent may be embedded in a mesh composed of vitrogen at one or more concentrations (e.g., ranging from about 1 to 100 μg/mlsh). The mesh(es) may then be applied to chick chorioallantoic membranes. After 24 hours, the effect of the agent may be determined using computer assisted morphometric analysis. A modulating agent should inhibit angiogenesis by at least 25% at a concentration of 33 μg/mlsh.

The addition of a targeting agent may be beneficial, particularly when the administration is systemic. Suitable modes of administration and dosages depend upon the condition to be prevented or treated but, in general, administration by injection is appropriate. Dosages may vary as described above. The effectiveness of the inhibition may be evaluated grossly by assessing the inability of the tumor to maintain growth and microscopically by an absence of nerves at the periphery of the tumor.

In yet another related aspect, the present invention provides methods for inducing apoptosis in a cadherin-expressing cell. In general, patients afflicted with cancer may benefit from such treatment. Preferred modulating agents for use within such methods comprise a single peptidomimetic of a cyclic peptide as described above, such as N—Ac—CHAVC—Y—NH$_2$ (SEQ ID NO:81), N—Ac—CHAVDC—NH$_2$ (SEQ ID NO:20), N—Ac—CSHAVC—NH$_2$ (SEQ ID NO:36) or N—Ac—CHAVC—NH$_2$ (SEQ ID NO:10). Modulating agents comprising a CAR sequence for a second adhesion molecule (e.g., RGD, LYHY (SEQ ID NO:55) or a CAR sequence for OB-cadherin, a desmoglein, a desmocollin or claudin) are also preferred. Alternatively, a separate modulator of cell adhesion mediated by an adhesion molecule that is not a cadherin may be administered in conjunction with the modulating agent(s), either within the same pharmaceutical composition or separately. Administration may be topical, via injection or by other means, and the addition of a targeting agent may be beneficial, particularly when the administration is systemic. Suitable modes of administration and dosages depend upon the location and nature of the cells for which induction of apoptosis is desired but, in general, dosages may vary as described above. A biopsy may be performed to evaluate the level of induction of apoptosis.

The present invention also provides methods for enhancing drug delivery to the central nervous system of a mammal. The blood/brain barrier is largely impermeable to most neuroactive agents, and delivery of drugs to the brain of a mammal often requires invasive procedures. Using a modulating agent as described herein, however, delivery may be by, for example, systemic administration of a peptidomimetic-drug-targeting agent combination, injection of a peptidomimetic (alone or in combination with a drug and/or targeting agent) into the carotid artery or application of a skin patch comprising a modulating agent to the head of the patient. Certain preferred peptidomimetics for use within such methods are relatively small (e.g., peptidomimetics of cyclic peptides having a ring size of 4–10 residues; preferably 5–7 residues) and include peptidomimetics of peptides comprising a 5-residue ring such as N—Ac—CHAVC—NH$_2$ (SEQ ID NO:10) and N—Ac—KHAVD—NH$_2$ (SEQ ID NO:12). Other preferred modulating agents for use within such methods comprise a peptidomimetic of N—Ac—CHAVC—Y—NH$_2$ (SEQ ID NO:81), N—Ac—CSHAVC—NH$_2$ (SEQ ID NO:36) or N—Ac—CHAVDC—NH$_2$ (SEQ ID NO:20). Also preferred are bifunctional modulating agents comprising an occludin CAR sequence LYHY (SEQ ID NO:55) and/or claudin CAR sequence, preferably joined by a linker. Alternatively, a separate modulator of occludin-mediated cell adhesion may be administered in conjunction with the modulating agent(s), either within the same pharmaceutical composition or separately. Modulating agents may further comprise antibodies or Fab fragments directed against the N-cadherin CAR sequence FHLRAHAVDINGNQV—NH$_2$ (SEQ ID NO:75). Fab fragments directed against the occludin CAR sequence region GVNPTAQSSGSLYGSQIYALCNQFYTPAATGLYVDQYLYHYCVVDPQE (SEQ ID NO:78) may also be employed, either incorporated into the modulating agent or administered concurrently as a separate modulator.

In general, the amount of modulating agent administered varies with the method of administration and the nature of the condition to be treated or prevented, but typically varies as described above. Transfer of the drug to the central nervous system may be evaluated by appropriate means that will be apparent to those of ordinary skill in the art, such as magnetic resonance imaging (MRI) or PET scan (positron emitted tomography).

In still further aspects, the present invention provides methods for enhancing adhesion of cadherin-expressing cells. Within certain embodiments, a modulating agent may be linked to a support molecule or to a solid support as described above, resulting in a matrix that comprises multiple modulating agents. Within one such embodiment, the support is a polymeric matrix to which modulating agents and molecules comprising other CAR sequence(s) are attached (e.g., modulating agents and molecules comprising RGD, LYHY (SEQ ID NO:55) or a CAR sequence for OB-cadherin, a desmoglein, a desmocollin or claudin, may be attached to the same matrix, preferably in an alternating pattern). Such matrices may be used in contexts in which it is desirable to enhance adhesion mediated by multiple cell adhesion molecules. Alternatively, the modulating agent itself may comprise multiple peptidomimetics, separated by linkers as described above. Either way, the modulating agent(s) function as a "biological glue" to bind multiple cadherin-expressing cells within a variety of contexts.

Within one embodiment, such modulating agents may be used to enhance wound healing and/or reduce scar tissue in a mammal. Preferred modulating agents for use within such methods comprise a single peptidomimetic of a cyclic peptide as described above, such as N—Ac—CHAVC—Y—NH$_2$ (SEQ ID NO:81), N—Ac—CHAVDC—NH$_2$ (SEQ ID NO:20), N—Ac—CSHAVC—NH$_2$ (SEQ ID NO:36) or N—Ac—CHAVC—NH$_2$ (SEQ ID NO:10). Modulating agents that are linked to a biocompatible and biodegradable matrix such as cellulose or collagen are particularly preferred. For use within such methods, a modulating agent should have a free amino or hydroxyl group. Multi-functional modulating agents further comprising the fibronectin CAR sequence RGD, which is recognized by integrins, as well CAR sequences for OB-cadherin, claudin, dsc and/or dsg, may also be used as potent stimulators of wound healing and/or to reduce scar tissue. Such agents may also, or alternatively, comprise the occludin CAR sequence LYHY (SEQ ID NO:55). Alternatively, one or more separate modulators of integrin-, Dsc-, Dsg-, claudin-, OB-cadherin- and/or occludin-mediated cell adhesion may be administered in conjunction with the modulating agent(s), either within the same pharmaceutical composition or separately.

The modulating agents are generally administered topically to the wound, where they may facilitate closure of the wound and may augment, or even replace, stitches. Similarly, administration of matrix-linked modulating agents may facilitate cell adhesion in foreign tissue implants (e.g., skin grafting and prosthetic implants) and may prolong the duration and usefulness of collagen injection. In general, the amount of matrix-linked peptidomimetic administered to a wound, graft or implant site varies with the severity of the wound and/or the nature of the wound, graft, or implant, but may vary as discussed above.

Within another embodiment, one or more modulating agents may be linked to the interior surface of a tissue culture plate or other cell culture support, such as for use in a bioreactor. Such linkage may be performed by any suitable technique, as described above. Modulating agents linked in this fashion may generally be used to immobilize cadherin-expressing cells. For example, dishes or plates coated with one or more modulating agents may be used to immobilize cadherin-expressing cells within a variety of assays and screens. Within bioreactors (i.e., systems for larger scale production of cells or organoids), modulating agents may generally be used to improve cell attachment and stabilize cell growth. Modulating agents may also be used within bioreactors to support the formation and function of highly differentiated organoids derived, for example, from dispersed populations of fetal mammalian cells. Bioreactors containing biomatrices of peptidomimetic(s) may also be used to facilitate the production of specific proteins.

Modulating agents as described herein may be used within a variety of bioreactor configurations. In general, a bioreactor is designed with an interior surface area sufficient to support larger numbers of adherent cells. This surface area can be provided using membranes, tubes, microtiter wells, columns, hollow fibers, roller bottles, plates, dishes, beads or a combination thereof. A bioreactor may be compartmentalized. The support material within a bioreactor may be any suitable material known in the art; preferably, the support material does not dissolve or swell in water. Preferred support materials include, but are not limited to, synthetic polymers such as acrylics, vinyls, polyethylene, polypropylene, polytetrafluoroethylene, nylons, polyurethanes, polyamides, polysulfones and poly(ethylene terephthalate); ceramics; glass and silica.

Modulating agents may also be used, within other aspects of the present invention, to enhance and/or direct neurological growth. In one aspect, neurite outgrowth may be enhanced and/or directed by contacting a neuron with one or more modulating agents. Preferred modulating agents for use within such methods are linked to a polymeric matrix or other support, and comprise a peptidomimetic of a cyclic peptide as described above, such as N—Ac—CHAVC—Y—NH$_2$ (SEQ ID NO:81), N—Ac—CHAVDC—NH$_2$ (SEQ ID NO:20), N—Ac—CSHAVC—NH$_2$ (SEQ ID NO:36) or N—Ac—CHAVC—NH$_2$ (SEQ ID NO:10). In addition, a modulating agent further comprising RGD and/or YIGSR (SEQ ID NO:52), which are bound by integrins, and/or the N—CAM CAR sequence KYSFNYDGSE (SEQ ID NO:53) may further facilitate neurite outgrowth. Other CAR sequences that may also, or alternatively, be included are CAR sequences for cadherin-7, cadherin-8, cadherin-12, cadherin-14, cadherin-15, PB-cadherin, protocadherins and cadherin-related neuronal receptors. Modulating agents comprising antibodies, or fragments thereof, may be used within this aspect of the present invention without the use of linkers or support materials. Preferred antibody modulating agents include Fab fragments directed against the N-cadherin CAR sequence FHLRAHAVDINGNQV—NH$_2$ (SEQ ID NO:75). Fab fragments directed against the N—CAM CAR sequence KYSFNYDGSE (SEQ ID NO:53) may also be employed, either incorporated into the modulating agent or administered concurrently as a separate modulator.

The method of achieving contact and the amount of modulating agent used will depend upon the location of the neuron and the extent and nature of the outgrowth desired. For example, a neuron may be contacted (e.g., via implantation) with modulating agent(s) linked to a support material such as a suture, fiber nerve guide or other prosthetic device such that the neurite outgrowth is directed along the support material. Alternatively, a tubular nerve guide may be employed, in which the lumen of the nerve guide contains a composition comprising the modulating agent(s). In vivo, such nerve guides or other supported modulating agents may be implanted using well known techniques to, for example, facilitate the growth of severed neuronal connections and/or to treat spinal cord injuries. It will be apparent to those of ordinary skill in the art that the structure and composition of the support should be appropriate for the particular injury being treated. In vitro, a polymeric matrix may similarly be used to direct the growth of neurons onto patterned surfaces as described, for example, in U.S. Pat. No. 5,510,628.

Within another such aspect, one or more modulating agents may be used for therapy of a demyelinating neurological disease in a mammal. There are a number of demyelinating diseases, such as multiple sclerosis, characterized by oligodendrocyte death. It has been found, within the context of the present invention, that Schwann cell migration on astrocytes is inhibited by N-cadherin. Modulating agents that disrupt N-cadherin mediated cell adhesion as described herein may be implanted into the central nervous system with cells capable of replenishing an oligodendrocyte population, such as Schwann cells, oligodendrocytes or oligodendrocyte precursor cells. Such therapy may facilitate of the cell capable of replenishing an oligodendrocyte population and permit the practice of Schwann cell or oligodendrocyte replacement therapy.

Multiple sclerosis patients suitable for treatment may be identified by criteria that establish a diagnosis of clinically definite or clinically probable MS (see Poser et al., *Ann. Neurol.* 13:227, 1983). Candidate patients for preventive therapy may be identified by the presence of genetic factors, such as HLA-type DR2a and DR2b, or by the presence of early disease of the relapsing remitting type.

Schwann cell grafts may be implanted directly into the brain along with the modulating agent(s) using standard techniques. Preferred modulating agents for use within such methods comprise a peptidomimetic of a cyclic peptide as described above, such as N—Ac—CHAVC—Y—NH$_2$ (SEQ ID NO:81), N—Ac—CHAVDC—NH$_2$ (SEQ ID NO:20), N—Ac—CSHAVC—NH$_2$ (SEQ ID NO:36) or N—Ac—CHAVC—NH$_2$ (SEQ ID NO:10). Modulating agents comprising antibodies, or fragments thereof, may also be used within this aspect of the present invention. Preferred antibody modulating agents include Fab fragments directed against the N-cadherin CAR sequence FHLRAHAVDINGNQV—NH$_2$ (SEQ ID NO:75). Suitable amounts of peptidomimetic generally range as described above, preferably from about 10 µg/mL to about 1 mg/ML.

Alternatively, a modulating agent may be implanted with oligodendrocyte progenitor cells (OPs) derived from donors not afflicted with the demyelinating disease. The myelinating cell of the CNS is the oligodendrocyte. Although mature oligodendrocytes and immature cells of the oligodendrocyte lineage, such as the oligodendrocyte type 2 astrocyte progenitor, have been used for transplantation, OPs are more widely used. OPs are highly motile and are able to migrate from transplant sites to lesioned areas where they differentiate into mature myelin-forming oligodendrocytes and contribute to repair of demyelinated axons (see e.g., Groves et al., *Nature* 362:453–55, 1993; Baron-Van Evercooren et al., *Glia* 16:14764, 1996). OPs can be isolated using routine techniques known in the art (see e.g., Milner and French-Constant, *Development* 120:3497–3506, 1994), from many regions of the CNS including brain, cerebellum, spinal cord, optic nerve and olfactory bulb. Substantially greater yields of OP's are obtained from embryonic or neonatal rather than adult tissue. OPs may be isolated from human embryonic spinal cord and cultures of neurospheres established. Human fetal tissue is a potential valuable and renewable source of donor OP's for future, long range transplantation therapies of demyclinating diseases such as MS.

OPs can be expanded in vitro if cultured as "homotypic aggregates" or "spheres" (Avellana-Adalid et al, *J. Neurosci. Res.* 45:558–70, 1996). Spheres (sometimes called "oligospheres" or "neurospheres") are formed when OPs are grown in suspension in the presence of growth factors such as PDGF and FGF. OPs can be harvested from spheres by mechanical dissociation and used for subsequent transplantation or establishment of new spheres in culture. Alternatively, the spheres themselves may be transplanted, providing a "focal reservoir" of OPs (Avellana-Adalid et al, *J. Neurosci. Res.* 45:558–70, 1996).

An alternative source of OP may be spheres derived from CNS stem cells. Recently, Reynolds and Weiss, *Dev. Biol.* 165:1–13, 1996 have described spheres formed from EGF-responsive cells derived from embryonic neuroepithelium, which appear to retain the pluripotentiality exhibited by neuroepithelium in vivo. Cells dissociated from these spheres are able to differentiate into neurons, oligodendrocytes and astrocytes when plated on adhesive substrates in the absence of EGF, suggesting that EGF-responsive cells derived from undifferentiated embryonic neuroepithelium may represent CNS stem cells (Reynolds and Weiss, *Dev. Biol.* 165:1–13, 1996). Spheres derived from CNS stem cells provide an alternative source of OP which may be manipulated in vitro for transplantation in vivo. Spheres composed of CNS stem cells may further provide a microenvironment conducive to increased survival, migration, and differentiation of the OPs in vivo.

The use of neurospheres for the treatment of MS may be facilitated by modulating agents that enhance cell migration from the spheres. In the absence of modulating agent, the cells within the spheres adhere tightly to one another and migration out of the spheres is hindered. Modulating agents that disrupt N-cadherin mediated cell adhesion as described herein, when injected with neurospheres into the central nervous system, may improve cell migration and increase the efficacy of OP replacement therapy. Neurosphere grafts may be implanted directly into the central nervous system along with the modulating agent(s) using standard techniques.

Alternatively, a modulating agent may be administered alone or within a pharmaceutical composition. The duration and frequency of administration win be determined by such factors as the condition of the patient, and the type and severity of the patient's disease. Within particularly preferred embodiments of the invention, the peptidomimetic or pharmaceutical composition may be administered at a dosage ranging from 0.1 mg/kg to 20 mg/kg, although appropriate dosages may be determined by clinical trials. Methods of administration include injection, intravenous or intrathecal (i.e., directly in cerebrospinal fluid).

Effective treatment of multiple sclerosis may be evidenced by any of the following criteria: EDSS (extended disability status scale), appearance of exacerbations or MRI (magnetic resonance imaging). The EDSS is a means to grade clinical impairment due to MS (Kurtzke, *Neurology* 33:1444, 1983), and a decrease of one full step defines an effective treatment in the context of the present invention (Kurtzke, *Ann. Neurol.* 36:573–79, 1994). Exacerbations are defined as the appearance of a new symptom that is attributable to MS and accompanied by an appropriate new neurologic abnormality (Sipe et al., *Neurology* 34:1368, 1984). Therapy is deemed to be effective if there is a statistically significant difference in the rate or proportion of exacerbation-free patients between the treated group and the placebo group or a statistically significant difference in the time to first exacerbation or duration and severity in the treated group compared to control group. MRI can be used to measure active lesions using gadolinium-DTPA-enhanced imaging (McDonald et al. *Ann. Neurol.* 36:14, 1994) or the location and extent of lesions using $T_2$-weighted techniques. The presence, location and extent of MS lesions may be determined by radiologists using standard techniques. Improvement due to therapy is established when there is a statistically significant improvement in an individual patient compared to baseline or in a treated group versus a placebo group.

Efficacy of the modulating agent in the context of prevention may be judged based on clinical measurements such as the relapse rate and EDSS. Other criteria include a change in area and volume of T2 images on MRI, and the number and volume of lesions determined by gadolinium enhanced images.

Within a related aspect, the present invention provides methods for facilitating migration of an N-cadherin expressing cell on astrocytes, comprising contacting an N-cadherin expressing cell with (a) a cell adhesion modulating agent that inhibits cadherin-mediated cell adhesion, wherein the modulating agent comprises a peptidomimetic as provided herein; and (b) one or more astrocytes; and thereby facilitating migration of the N-cadherin expressing cell on the astrocytes. Preferred N-cadherin expressing cells include Schwann cells, oligodendrocytes and oligodendrocyte progenitor cells.

Within another aspect, modulating agents as described herein may be used for modulating the immune system of a mammal in any of several ways. Cadherins are expressed on immature B and T cells (thymocytes and bone marrow pre-B cells), as well as on specific subsets of activated B and T lymphocytes and some hematological malignancies (see Lee et al., *J. Immunol.* 152:5653–5659, 1994; Munro et al., *Cellular Immunol.* 169:309–312, 1996; Tsutsui et al., *J. Biochem.* 120:1034–1039, 1996; Cepek et al., *Proc. Natl. Acad. Sci. USA* 93:6567–6571, 1996). Modulating agents may generally be used to modulate specific steps within cellular interactions during an immune response or during the dissemination of malignant lymphocytes.

For example, a modulating agent as described herein may be used to treat diseases associated with excessive generation of otherwise normal T cells. Without wishing to be bound by any particular theory, it is believed that the interaction of cadherins on maturing T cells and B cell subsets contributes to protection of these cells from programmed cell death. A modulating agent may decrease such interactions, leading to the induction of programmed cell death. Accordingly, modulating agents may be used to treat certain types of diabetes and rheumatoid arthritis, particularly in young children where the cadherin expression on thymic pre-T cells is greatest.

Modulating agents may also be administered to patients afflicted with certain skin disorders (such as cutaneous lymphomas), acute B cell leukemia and excessive immune reactions involving the humoral immune system and generation of immunoglobulins, such as allergic responses and antibody-mediated graft rejection. In addition, patients with circulating cadherin-positive malignant cells (e.g., during regimes where chemotherapy or radiation therapy is eliminating a major portion of the malignant cells in bone marrow and other lymphoid tissue) may benefit from treatment with a peptidomimetic. Such treatment may also benefit patients undergoing transplantation with peripheral blood stem cells.

Preferred modulating agents for use within such methods include those that disrupt E-cadherin and/or N-cadherin mediated cell adhesion, such as agents that comprise a peptidomimetic of a cyclic peptide as described above (e.g., N—Ac—CHAVC—Y—NH$_2$ (SEQ ID NO:81), N—Ac—CHAVDC—NH$_2$ (SEQ ID NO:20), N—Ac—CSHAVC—NH$_2$ (SEQ ID NO:36) or N—Ac—CHAVC—NH$_2$ (SEQ ID NO:10)). In addition, a preferred modulating agent may comprise one or more additional CAR sequences, such as the sequence RGD, which is bound by integrins, as well as CAR sequences for occludin, N—CAM, OB-cadherin, cadherin-5, cadherin-6 and cadherin-8. As noted above, such additional sequence(s) may be separated from the peptidomimetic via a linker. Alternatively, a separate modulator of integrin-mediated cell adhesion may be administered in conjunction with the modulating agent(s), either within the same pharmaceutical composition or separately.

Within the above methods, the modulating agent(s) are preferably administered systemically (usually by injection) or topically. A peptidomimetic may be linked to a targeting agent. As noted above, a modulating agent may further be linked to a targeting agent. For example, targeting to the bone marrow may be beneficial. A suitable dosage is sufficient to effect a statistically significant reduction in the population of B and/or T cells that express cadherin and/or an improvement in the clinical manifestation of the disease being treated. Typical dosages range as described above.

Within further aspects, the present invention provides methods and kits for preventing pregnancy in a mammal. In general, disruption of E-cadherin function prevents the adhesion of trophoblasts and their subsequent fusion to form syncitiotrophoblasts. In one embodiment, one or more modulating agents as described herein may be incorporated into any of a variety of well known contraceptive devices, such as sponges suitable for intravaginal insertion (see, e.g., U.S. Pat. No. 5,417,224) or capsules for subdermal implantation. Other modes of administration are possible, however, including transdermal administration, for modulating agents linked to an appropriate targeting agent. Preferred modulating agents for use within such methods comprise a single peptidomimetic of a cyclic peptide as described above, such as N—Ac—CHAVC—Y—NH$_2$ (SEQ ID NO:81), N—Ac—CHAVDC—NH$_2$ (SEQ ID NO:20), N—Ac—CSHAVC—NH$_2$ (SEQ ID NO:36) or N—Ac—CHAVC—NH$_2$ (SEQ ID NO:10). In addition, a preferred modulating agent may comprise additional CAR sequences, such as the sequence RGD, which is bound by integrins. As noted above, such additional sequences may be separated from the peptidomimetic via a linker. Alternatively, a separate modulator of integrin-mediated cell adhesion may be administered in conjunction with the modulating agent(s), either within the same pharmaceutical composition or separately.

Suitable methods for incorporation into a contraceptive device depend upon the type of device and are well known in the art. Such devices facilitate administration of the peptidomimetic(s) to the uterine region and may provide a sustained release of the peptidomimetic(s). In general, peptidomimetic(s) may be administered via a contraceptive device at a dosage ranging from 0.1 to 20 mg/kg, although appropriate dosages may be determined by monitoring hCG levels in the urine. hCG is produced by the placenta, and levels of this hormone rise in the urine of pregnant women. The urine hCG levels can be assessed by radio-immunoassay using well known techniques. Kits for preventing pregnancy generally comprise a contraceptive device impregnated with one or more peptidomimetics.

Alternatively, a sustained release formulation of one or more peptidomimetics may be implanted, typically subdermally, in a mammal for the prevention of pregnancy. Such implantation may be performed using well known techniques. Preferably, the implanted formulation provides a dosage as described above, although the minimum effective dosage may be determined by those of ordinary skill in the art using, for example, an evaluation of hCG levels in the urine of women.

The present invention also provides methods for increasing vasopermeability in a mammal by administering one or more modulating agents or pharmaceutical compositions. Within blood vessels, endothelial cell adhesion (mediated by N-cadherin) results in decreased vascular permeability.

Accordingly, modulating agents as described herein may be used to increase vascular permeability. Within certain embodiments, preferred modulating agents for use within such methods include peptides capable of decreasing both endothelial and tumor cell adhesion. Such modulating agents may be used to facilitate the penetration of anti-tumor therapeutic or diagnostic agents (e.g., monoclonal antibodies) through endothelial cell permeability barriers and tumor barriers. Preferred modulating agents for use within such methods comprise a single peptidomimetic of a cyclic peptide as described above, such as N—Ac—CHAVC—Y—NH$_2$ (SEQ ID NO:81), N—Ac—CHAVDC—NH$_2$ (SEQ ID NO:20), N—Ac—CSHAVC—NH$_2$ (SEQ ID NO:36) or N—Ac—CHAVC—NH$_2$ (SEQ ID NO:10). In addition, a preferred modulating agent may comprise an occludin CAR sequence LYHY (SEQ ID NO:55) and/or a CAR sequence for OB-cadherin or claudin. As noted above, such an additional sequence may be separated from the peptidomimetic via a linker. Alternatively, a separate modulator of occludin mediated cell adhesion may be administered in conjunction with one or modulating agents, either within the same pharmaceutical composition or separately.

Within certain embodiments, preferred modulating agents for use within such methods include peptidomimetics capable of decreasing both endothelial and tumor cell adhesion. Such modulating agents may be used to facilitate the penetration of anti-tumor therapeutic or diagnostic agents (e.g., monoclonal antibodies) through endothelial cell permeability barriers and tumor barriers. For example, a modulating agent may comprise a peptidomimetic of a cyclic peptide having flanking E-cadherin-specific sequences and a peptidomimetic of a cyclic peptide having an HAV sequence with flanking N-cadherin-specific sequences. Alternatively, separate modulating agents capable of disrupting N— and E-cadherin mediated adhesion may be administered concurrently.

In one particularly preferred embodiment, a modulating agent is further capable of disrupting cell adhesion mediated by multiple adhesion molecules. Such an agent may additionally comprise an RGD sequence, a Dsc CAR sequence, a Dsg CAR sequence and/or the occludin CAR sequence LYHY (SEQ ID NO:55). Alternatively, a separate modulator of non-classical cadherin-mediated cell adhesion may be administered in conjunction with the modulating agent(s), either within the same pharmaceutical composition or separately. Fab fragments directed against any of the above CAR sequences may also be employed, either incorporated into a modulating agent or within a separate modulator that is administered concurrently.

Treatment with a modulating agent may be appropriate, for example, prior to administration of an anti-tumor therapeutic or diagnostic agent (e.g., a monoclonal antibody or other macromolecule), an antimicrobial agent or an antiinflammatory agent, in order to increase the concentration of such agents in the vicinity of the target tumor, organism or inflammation without increasing the overall dose to the patient. Modulating agents for use within such methods may be linked to a targeting agent to further increase the local concentration of modulating agent, although systemic administration of a vasoactive agent even in the absence of a targeting agent increases the perfusion of certain tumors relative to other tissues. Suitable targeting agents include antibodies and other molecules that specifically bind to tumor cells or to components of structurally abnormal blood vessels. For example, a targeting agent may be an antibody that binds to a fibrin degradation product or a cell enzyme such as a peroxidase that is released by granulocytes or other cells in necrotic or inflamed tissues.

Administration via intravenous injection or transdermal administration is generally preferred. Effective dosages are generally sufficient to increase localization of a subsequently administered diagnostic or therapeutic agent to an extent that improves the clinical efficacy of therapy of accuracy of diagnosis to a statistically significant degree. Comparison may be made between treated and untreated tumor host animals to whom equivalent doses of the diagnostic or therapeutic agent are administered. In general, dosages range as described above.

Within a further aspect, modulating agents as described herein may be used for controlled inhibition of synaptic stability, resulting in increased synaptic plasticity. Within this aspect, administration of one or more modulating agents may be advantageous for repair processes within the brain, as well as learning and memory, in which neural plasticity is a key early event in the remodeling of synapses. Cell adhesion molecules, particularly N-cadherin and E-cadherin, can function to stabilize synapses, and loss of this function is thought to be the initial step in the remodeling of the synapse that is associated with learning and memory (Doherty et al., *J. Neurobiology*, 26:437–446, 1995; Martin and Kandel, *Neuron*, 17:567–570, 1996; Fannon and Colman, *Neuron*, 17:423–434, 1996). Inhibition of cadherin function by administration of one or more modulating agents that inhibit cadherin function may stimulate learning and memory.

Preferred modulating agents for use within such methods include those that disrupt E-cadherin and/or N-cadherin mediated cell adhesion, such as agents that comprise a single peptidomimetic of a cyclic peptide as described above (e.g., N—Ac—CHAVC—Y—NH$_2$ (SEQ ID NO:81), N—Ac—CHAVDC—NH$_2$ (SEQ ID NO:20), N—Ac—CSHAVC—NH$_2$ (SEQ ID NO:36) or N—Ac—CHAVC—NH$_2$ (SEQ ID NO:10)). In addition, a preferred modulating agent may comprise one or more non-classical cadherin CAR sequences, such as the sequence RGD, which is bound by integrins, the N—CAM CAR sequence KYSFNYDGSE (SEQ ID NO:53) and/or a cadherin-related neuronal receptor CAR sequence. As noted above, such additional sequence(s) may be separated from the peptidomimetic via a linker. Alternatively, a separate modulator of integrin and/or N—CAM mediated cell adhesion may be administered in conjunction with the modulating agent(s), either within the same pharmaceutical composition or separately. For such aspects, administration may be via encapsulation into a delivery vehicle such as a liposome, using standard techniques, and injection into, for example, the carotid artery. Alternatively, a modulating agent may be linked to a disrupter of the blood-brain barrier. In general dosages range as described above.

Within further aspects, peptidomimetics may be used to facilitate cell identification and sorting in vitro or imaging in vivo, permitting the selection of cells expressing different cadherins (or different cadherin levels). Preferably, the peptidomimetic(s) for use in such methods are linked to a detectable marker. Suitable markers are well known in the art and include radionuclides, luminescent groups, fluorescent groups, enzymes, dyes, constant immunoglobulin domains and biotin. Within one preferred embodiment, a peptidomimetic linked to a fluorescent marker, such as fluorescein, is contacted with the cells, which are then analyzed by fluorescence activated cell sorting (FACS).

The following Examples are offered by way of illustration and not by way of limitation.

EXAMPLE 1

Preparation of Representative Cyclic Peptides

This Example illustrates the solid phase synthesis of representative cyclic peptides.

Peptides were generally assembled on methylbenzhydrylamine resin (MBHA resin) for the C-terminal amide peptides. The traditional Merrifield resins were used for any C-terminal acid peptides. Bags of a polypropylene mesh material were filled with the resin and soaked in dichloromethane. The resin packets were washed three times with 5% diisopropylethylamine in dichloromethane and then washed with dichloromethane. The packets are then sorted and placed into a Nalgene bottle containing a solution of the amino acid of interest in dichloromethane. An equal amount of diisopropylcarbodiimide (DIC) in dichloromethane was added to activate the coupling reaction. The bottle was shaken for one hour to ensure completion of the reaction. The reaction mixture was discarded and the packets washed with DMF. The N-α-Boc was removed by acidolysis using a 55% TFA in dichloromethane for 30 minutes leaving the TFA salt of the α-amino group. The bags were washed and the synthesis completed by repeating the same procedure while substituting for the corresponding amino acid at the coupling step. Acetylation of the N-terminal was performed by reacting the peptide resins with a solution of acetic anhydride in dichloromethane in the presence of diisopropylethylamine. The peptide was then side-chain deprotected and cleaved from the resin at 0° C. with liquid HF in the presence of anisole as a carbocation scavenger.

The crude peptides were purified by reversed-phase high-performance liquid chromatography. Purified linear precursors of the cyclic peptides were solubilized in 75% acetic acid at a concentration of 2–10 mg/mL. A 10% solution of iodine in methanol was added dropwise until a persistent coloration was obtained. A 5% ascorbic acid solution in water was then added to the mixture until discoloration. The disulfide bridge containing compounds were then purified by HPLC and characterized by analytical HPLC and by mass spectral analysis.

N—Ac—CHAVC—NH$_2$ (SEQ ID NO:10) was synthesized on a 396–5000 Advanced ChemTech synthesizer using a Rink resin (4-(2',4'-Dimethoxyphenyl-Fmoc-aminomethyl)-phenoxy resin), which provided C-terminal amides using Fmoc chemistries. The Fmoc protecting group on the resin was removed with piperidine and coupling of the amino acids to the resin initiated. Two coupling reactions in NMP (N-methylpyrrolidinone) per amino acid were performed. The first coupling was carried out using DIC (diisopropylcarbodiimide) and the second coupling used HBTU (O-benzotriazole-N,N,N',N',-tetramethyluronium hexafluorophosphate) in the presence of DIPEA (diisopropylethylamine). Both couplings were done in the presence of HOBt (hydroxybenzotriazole) with the exception of histidine and the final cysteine. The trityl protecting group of the imidazole side chain of histidine is not stable in the presence of HOBt. Acetylation of the free amine on the N-terminus was carried out with acetic anhydride in NMP in the presence of DIPEA. The linear peptide was then cleaved from the resin with TFA in dichloromethane. This procedure also removed the trityl protecting group on the imidazole side chain of histidine. The crude linear peptide amide was then cyclized using chlorosilane-sulfoxide oxidation method to give the disulfide peptide. The crude cyclic peptide was purified using reverse-phase liquid chromatography. N—Ac—CHAVC—Y—NH$_2$ (SEQ ID NO:81) and N—Ac—CHAVDC—NH$_2$ (SEQ ID NO:20) were synthesized using the same procedure, except that the cleavage cocktail (TFA, Dichloromethane) will also remove the OtBu protecting group of tyrosine.

EXAMPLE 2

Generation of Three-Dimensional Structures of Representative Cyclic Peptides

This Example illustrates the use of Nuclear Magnetic Resonance techniques to determine the three-dimensional structure of the representative cyclic peptides N—Ac—CHAVC—NH$_2$ (SEQ ID NO:10), N—Ac—CHAVDC—NH$_2$ (SEQ ID NO:20), N—Ac—CHAVC—Y—NH$_2$ (SEQ ID NO:81) and N—Ac—CSHAVC—NH$_2$ (SEQ ID NO:36).

The 3-dimensional structure of N—Ac—CHAVC—NH$_2$ (SEQ ID NO:10) was determined using Nuclear Magnetic Resonance (NMR) techniques combined with molecular modelling. Experiments were performed using either a Bruker Avance-800 or Bruker Avance-500 NMR spectrometer equipped with pulse field gradient units. NMR data acquisition was carried out in aqueous systems that closely mimic physiological conditions. More specifically, all samples were analyzed in buffer containing 20 mM NaPO$_4$, 0.2 mM EDTA, 150 mM NaCl and 10% D$_2$O, with the pH adjusted to 6.8 both before and after the addition of DMSO-d$_6$. The final volume inside the NMR tube was 500 μL. The ratio of DMSO:buffer was 2:1 (333 μL DMSO: 166.67 μL Buffer/10% D$_2$O; pH 6.8). Data acquisition for N—Ac—CHAVC—NH$_2$ (Seq ID NO:10) was carried out at 288K using the Bruker AMX-800 NMR spectrometer. Data acquisition for N—Ac—CHAVC—Y—NH$_2$ (SEQ ID NO:81) was carried out at both 278K and 288K using the Bruker Avance-500 NMR spectrometer, and data acquisition for N—Ac—CHAVDC—NH$_2$ (SEQ ID NO:20) was carried out at 278K. Data was collected at two different temperatures for this compound in an attempt to remove the degeneracy observed at 288K with the NH proton of valine and the Hε1 ring proton of histidine and thus remove any ambiguity to the subsequent assignment. As the degeneracy was not affected by the temperature change, the data acquired at 288K was used for the proton assignment. Data acquisition for N—Ac—CSHAVC—NH$_2$ (SEQ ID NO:36) was carried out at 288K and at 278K using the Bruker Avance-800 NMR spectrometer. Data was collected at the lower temperature in an attempt to increase the number of crosspeaks in the NOESY spectra. A greater number of crosspeaks were observed in the NOESY spectral data acquired at 278K and this data set was used for the proton assignment and structure determination. The concentration of compound present in the NMR tube was dependent on whether or not aggregation was present as observed by visual inspection of the solution or via changes to the $^1$H NMR spectrum. Therefore $^1$H NMR were run at various decreasing concentrations until no further changes to the spectrum were observed. The concentration used for N—Ac—CHAVC—NH$_2$ (SEQ ID NO:10) was 8 mM, the concentration used for N—Ac—CHAVC—Y—NH$_2$ (SEQ ID NO:81) was 2 mM, the concentration used for N—Ac—CHAVDC—NH$_2$ (SEQ ID NO:20) was 1 mM and the concentration used for N—Ac—CSHAVC—NH$_2$ (SEQ ID NO:36) was 1 mM. As some changes to the $^1$H NMR spectra of N—Ac—CHAVC—NH$_2$ (SEQ ID NO:10) were observed with decreasing concentration, 2D-NMR (i e., NOESY, DQF-COSY and TOCSY) experiments with N—Ac—CHAVC—NH$_2$ (SEQ ID NO:10) were also carried out at 2 mM. The concentration effects observed in the $^1$H NMR spectra of N—Ac—CHAVC—NH$_2$ (SEQ ID NO:10) did not influence the 3-D structure determined at 2 mM, as the latter was virtually identical to that obtained when the NMR experiments were carried out at 8 mM.

The water solvent resonance was suppressed by using the WATERGATE procedure (Piotto et al., *J. Biomol. NMR* 2:661–665, 1992). A purging field gradient pulse and a water flipback pulse were applied at the end of the mixing period for NOESY, ROESY and TOCSY experiments to maintain water at equilibrium conditions. These special pulse sequences help minimize the loss of resonance intensities of fast exchanging NH protons at neutral pH conditions (Fulton et al., *J. Biomol. NMR* 8:213–218, 1996). Sine modulation along the t1-dimension was applied with an initial t1 delay adjusted so that the zero and first-order phase corrections along F1 were 90 and 0 degrees respectively (Ni, *J. Magn. Reson.* 96:651–656, 1992). The mixing times were 100 and 200 ms at 800 MHz for NOESY experiments and 71.28 ms for TOCSY experiments with the TOWNY-16 mixing sequence (Kadkhodaei et al., *J. Magn. Reson.* A105:104–107, 1993). The mixing times were 150 and 250 ms at 500 MHz for NOESY experiments and 70 ms for TOCSY experiments with the TOWNY-16 mixing sequence (Kadkhodaei et al., *J. Magn. Reson.* A105:104–107, 1993). Typically, the FID data were acquired with 2048 data points for each FID with 256 and 512 t1-increments with the 800 MHz instrument and 512 and 1024 t1-increments with the 500 MHz instrument. All NMR data were processed using spectrometer software. Baseline corrections were applied to the NOESY, ROESY and TOCSY spectra using the standard Bruker polynomial method.

The sequence-specific assignments of the proton resonances were accomplished by use of standard methods (see Wuthrich, *NMR of Proteins and Nucleic Acids*, Wiley & Sons, New York, 1986). That is, each spin system was identified by COSY and TOCSY NMR data and then these identified spin systems were sequentially assigned based on the NOE connectivities. All of the spin systems were observed in the NH region of the TOCSY spectrum with a mixing time of 70 ms (500 MHz TOCSY experiment) or 71.28 ms (800 MHz TOCSY experiment). Spectral assignment was carried out by a combination of TOCSY and NOESY spectra starting from the resonance signals of valine and alanine. The spin systems of the valine and alanine residues were assigned based on the presence of strong NOEs between the NH protons of these amino acids to their corresponding side chain (i.e., Cβ-methyl of alanine and Cβ and Cγ of valine) and from the TOCSY spectra. The proton chemical shifts were obtained from the TOCSY spectra.

The $^3$JCαNH coupling constants were calculated using the method of Kim and Prestegard (*J. Magn. Reson.* 89:9–13, 1989) in which the anti-phase COSY patterns were produced by an F1-inphase COSY experiment. The COSY and TOCSY spectra were extended by linear prediction from 256 to 512 points in the t1 dimension and zero-filling on two dimensions to obtain a final spectrum with a size of 32 k (F2) by 1K (F1). For each cross peak, several (typically 5–10) traces along F1 were co-added to reduce noise prior to fitting, which was possible as a result of the in-phase absorption pattern of the cross peaks along the F1 dimension in the F1 in-phase COSY spectra. In the fitting procedure, spectrum A was generated by convoluting the COSY-type anti-phase absorption peaks with an in-phase stick doublet of separation Jtrial. Spectrum B was produced by convoluting the corresponding TOCSY multiplet with an anti-phase stick doublet of the same interval. The RMS value of the difference between spectrum A and B is minimum when Jtrial=$^3$JCαNH.

For the conformational calculations of N—Ac—CHAVC—NH$_2$ (SEQ ID NO:10), N—Ac—CHAVC—Y—NH$_2$ (SEQ ID NO:81) and N—Ac—CHAVDC—NH$_2$ (SEQ ID NO:20), the NOE cross peaks were characterized as strong, medium or weak as determined from the number of contours and converted to distance upper bounds of 2.7, 3.7 and 5.0 angstroms respectively. However, a uniform distance upper and lower bounds of 1.8–5.0 angstroms regardless of the NOE intensities was used in the initial structural calculations. For N—Ac—CSHAVC—NH$_2$ (SEQ ID NO:36), the intensity of the crosspeak was estimated by integrating the crosspeak volume. In this case, the uniform distance upper and lower bounds of 1.8–5.0 angstroms was maintained in all calculations and a ±5% range was assigned to each crosspeak volumes and used in the initial structural calculations. The NOE distances were refined iteratively through a comparison of computed and experimental NOEs at the various mixing times. This was performed in a manner similar to the PEPFLEX-II procedure (Wang et al., Techniques in Protein Chemistry IV, 1993, Evaluation of NMR Based Structure Determination for Flexible Peptides: Application to Desmopressin p. 569), except that initial NOE-based distances with very loose upper bounds (5 angstroms) were used to guarantee the generation of a more complete set of conformations in agreement with experimental data. In the structure calculations for N—Ac—CSHAVC—NH$_2$ (SEQ ID NO:36), the refinement was achieved using both distance constraints and via automated NOE intensity comparison. Dihedral-angle constraints were derived from the values of the $^3$JCαH coupling constants. A tolerance value of 40 degrees was added to each of the dihedral angle constraints to account for the conformational flexibility of the peptide. Distance geometry calculations were carried out using fixed bond lengths and bond angles provided in the ECEPP/2 database (Ni et al., *Biochemistry* 31:11551–11557, 1989). The ω-angles were fixed at 180 degrees, but all other dihedral angles were varied during structure optimization. Structures with the lowest constraint violations were subjected to energy minimization using a distance-restrained Monte Carlo method (Ripoll and Ni, *Biopolymers* 32:359–365, 1992; Ni, *J. Magn. Reson.* B106:147–155, 1995), and modified to include the ECEPP/3 force field (Ni et al., *J. Mol. Biol.* 252:656–671, 1995). All ionizable groups were treated as charged during constrained Monte Carlo minimization of the ECEPP/3 energy. Electrostatic interactions among all charges were screened by use of a distance-dependent dielectric to account for the absence of solvent effects in conformational energy calculations. In addition, hydrogen-bonding interactions were reduced to 25% of the full scale while van der Waals and electrostatic terms were kept to full strengths. These special treatments help to ensure that the conformational search was guided primarily by the experimental NMR constraints and that the computed conformations were less biased by the empirical conformational energy parameters (Warder et al., *FEBS Lett.* 411:19–26, 1997).

Low-energy conformations of the peptide from Monte Carlo calculations were used in NOE simulations to identify proximate protons with no observable NOEs and sets of distance upper bounds that warrant recalibration. The refined set of NOE distances including distance lower bounds derived from absent NOEs were used in the next cycles of Monte Carlo calculations until the resulting conformations produced simulated NOE spectra close to those observed experimentally (Ning et al., *Biopolymers* 34:1125–1137, 1994; Ni et al., *J. Mol. Biol.* 252:656–671, 1995). Theoretical NOE spectra were calculated using a methyl group correlation time of 25.0 ps and an overall correlation time of 1000.0 ps based on the molecular weight of the peptide and the experimental temperature (Cantor and Schimmel, *Biophysical Chemistry*, W. H. Freeman & Co., San Francisco, 1980). All candidate peptide conformations were included with equal weights in an ensemble-averaged relaxation matrix analysis of interconverting conformations (Ni and Zhu, *J. Magn. Reson.* B102:180–184, 1994). NOE simulations also incorporated parameters to account for the effects of incomplete relaxation decay of the proton demagnitizations (Ning et al., Biopolymers 34:1125–1137, 1994). The computed NOE intensities were converted to the two-dimensional FID's (Ni, *J. Magn. Reson.* B106:147–155, 1995) by use of an in-house program, GFIDSJ, using the chemical shift assignments, estimated linewidths and coupling constants for all resolved proton resonances. The program GFIDSJ converts the computed NOE intensities to the two-dimensional theoretical FIDs by inclusion of resonance splitting and peak intensities in lineshape calculation. The NMR parameters such as lineshape function, spectral width and proton assignments were supplied to the program. Two-dimensional processing of the data converted the theoretical FIDs to NOESY spectra. The following window functions were used: shifted 90 degrees sine square along F2 and Kaiser window along F1. Water suppression and baseline correction were not necessary. Calculated FIDs were converted to simulated NOESY spectra using identical processing procedures as used for the experimental NOE data sets.

These experiments allowed the determination of the 3-D conformation of N—Ac—CHAVC—NH$_2$ (SEQ ID NO:10). The high resolution molecular map of the pharmacophore of N—Ac—CHAVC—NH$_2$ (SEQ ID NO:10) is shown in FIGS. 7A–7C. There are three low energy conformations, which are all depicted in FIGS. 7A–7C (Structure 1, Structure 2 and Structure 3). The co-ordinates for these three low energy conformations are given in Appendix 1.

NMR data collected in a similar manner for N—Ac—CHGVC—NH$_2$ (SEQ ID NO:11) indicated that there was too much conformational freedom to be able to determine a preferred 3-D structure.

The above process with the exceptions noted above was repeated for N—Ac—CHAVC—Y—NH$_2$ (SEQ ID NO:81), N—Ac—CHAVDC—NH$_2$ (SEQ ID NO:20) and N—Ac—CSHAVC—NH$_2$ (SEQ ID NO:36). The high resolution molecular map of the pharmacophore of N—Ac—CHAVC—Y—NH$_2$ (SEQ ID NO:81) is shown in FIGS. 9A–9D, each of which depicts one of the four low energy conformations. The co-ordinates for these four low energy conformations are given in Appendix 2. The high resolution molecular map of the pharmacophore of N—Ac—CHAVDC—NH$_2$ (SEQ ID NO:20) is shown in FIGS. 20A–20D, each of which depicts one of the four low energy conformations. The co-ordinates for these low energy conformations are given in Appendix 3. The high resolution molecular map of the pharmacophore of N—Ac—CSHAVC—NH$_2$ (SEQ ID NO:) is shown in FIGS. 32A–32B, each of which depicts one of the low energy conformations. The co-ordinates for these low energy conformations are given in Appendix 4.

EXAMPLE 3

Identification of Peptidomimetics

This Example illustrates the use of cyclic peptide pharmacophores to identify peptidomimetics.

Certain peptidomimetics were identified based on a visual inspection of the N—Ac—CHAVC—NH$_2$ (SEQ ID NO:10) pharmacophore. From FIGS. 8A and 8B (which compare the that the N—Ac—CHAVC—NH$_2$ (SEQ ID NO:10) pharmacophore with the x-ray crystal structure of the HAV sequence in N-cadherin), it is apparent that the hydrophobic valine could be replaced with unnatural amino acids carrying bulky groups, such as that found in compound 1 (FIG. 11). This is expected to restrict rotation of the amide bonds, and possibly eliminate the need for cyclization. Alternatively the hydrophobic valine residue can be incorporated into a cyclic rigid structure such as that found in compounds 2 and 3 (FIG. 11).

EXAMPLE 4

Identification of Further Peptidomimetics

This Example illustrates the identification of peptidomimetics by comparing the three-dimensional structure of a candidate compound with a cyclic peptide pharmacophore.

The analysis of the solution conformation of N—AC—CHAVC—NH$_2$ indicated that a suitable peptidomimetic could be designed based on the cyclization shown in FIG. 12A. Compound 4 was designed and its low energy conformation determined using the CHARMM molecular mechanics and molecular dynamics program. The TIP3P water model was used to represent water molecules. Superimposition of the low energy conformation of compound 4 and N—Ac—CHAVC—NH$_2$ (FIG. 12C; SEQ ID NO:10) indicates that there is a good overlap between the crucial binding elements in the peptidomimetic and N—Ac—CHAVC—N—H$_2$ (SEQ ID NO:10).

EXAMPLE 5

Identification of Non-Peptidyl Peptidomimetics

This Example illustrates the identification of non-peptidyl peptidomimetics by comparing the three-dimensional structures of databases of candidate compounds with a cyclic peptide pharmacophore.

Within the database searches, the first three pharmacophore models used were the three three-dimensional structures of N—Ac—CHAVC—NH$_2$ (SEQ ID NO:10), shown in FIGS. 7A–7C, as determined from its solution structure.

Figure 14B:
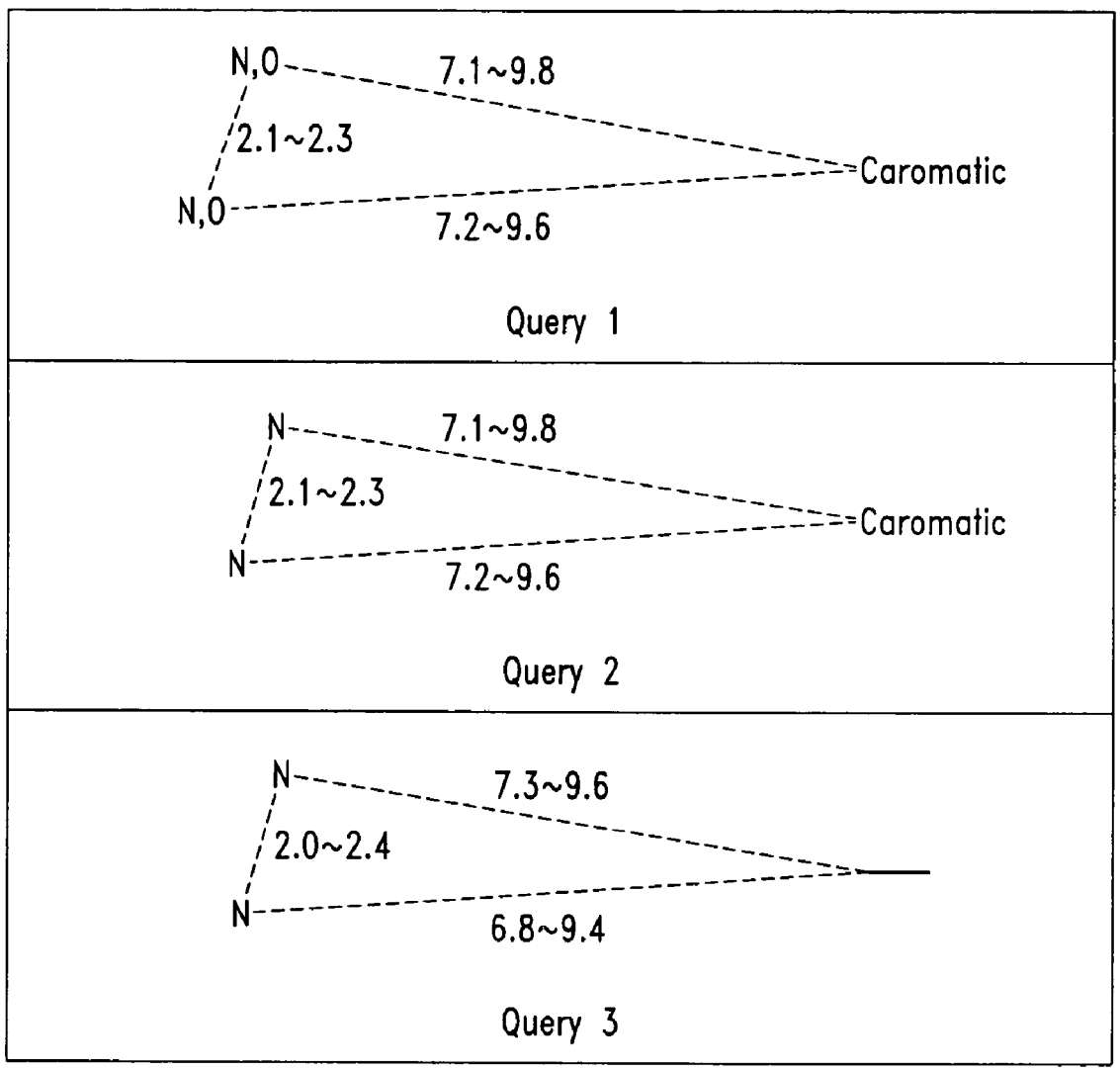
Figure 14C:
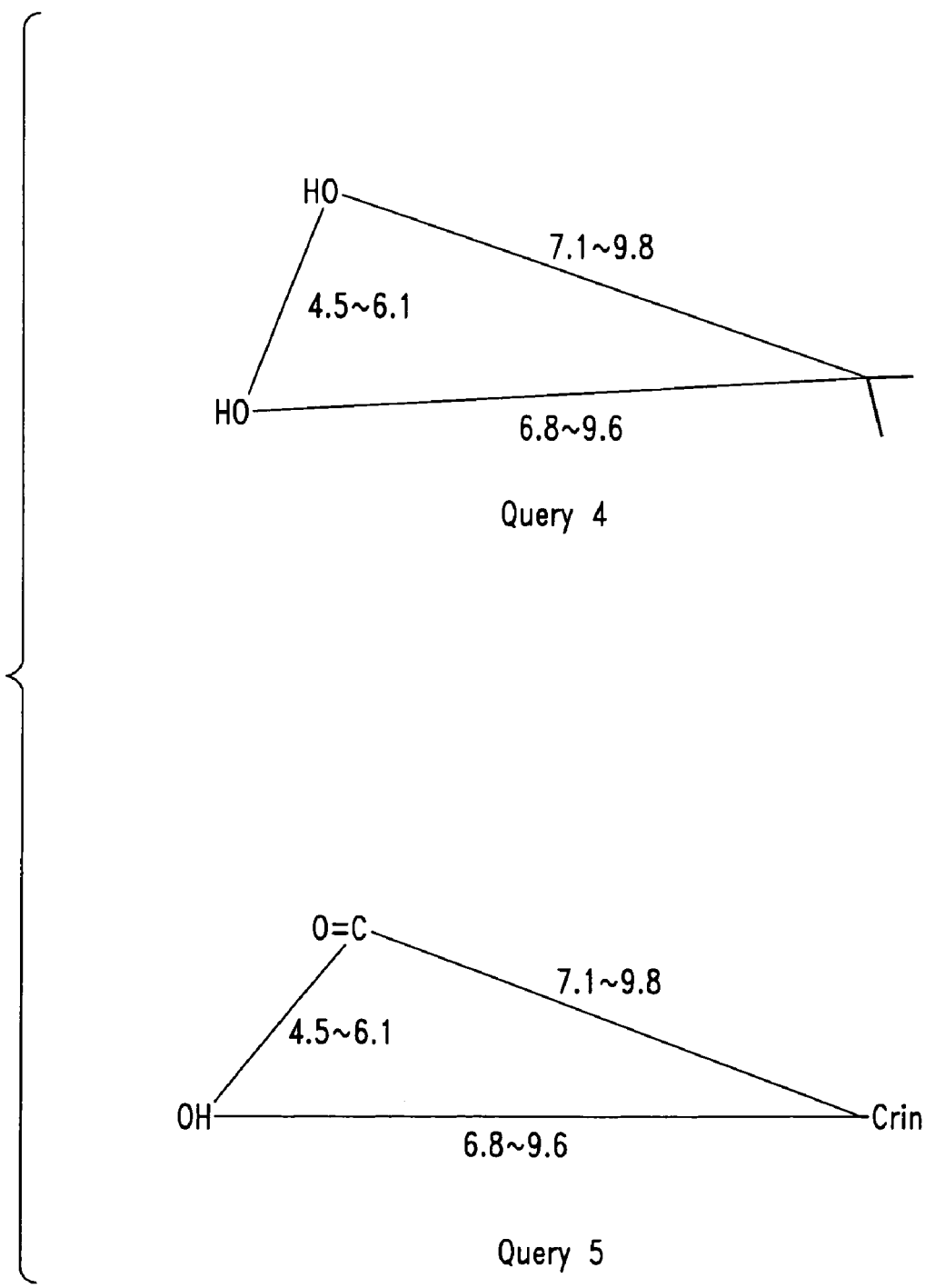

A total of five pharmacophore queries were derived from these three-dimensional structures (see FIGS. 14B and 14C). Two databases were searched. The National Cancer Institute (NCI) 3D-database contains nearly half a million compounds that have been tested for activity against various forms of cancer. Three-dimensional structures were generated for each compound in this database using molecular modelling. The NCI database was converted to a 3D-database using the program CONCORD (R S Pearlman, *Chem. Des. Auto. News* 2:1–6, 1987) and Chem-X. Initially, 2D coordinates of each compound in the database were converted using CONCORD into 3D coordinates. It is of note that only a single conformation was generated for each compound using the CONCORD program. The resulting 3D structures were used to generate a 3D-database using the database-building module within the Chem-X program, and multiple conformations were generated and stored in the database (Milne et al., *J. Chem. Inf. Comput. Sci.* 34:1219–1224, 1994).

The second database used was the Available Chemical Database (ACD), which contained 255,153 unique chemicals from 543 supplier catalogues, including about 50,000 compounds which are known drugs. The entire ACD database was also converted into 3-D conformations for searching using the Chem-X program.

The Chem-X program, running on a Silicon Graphics Indigo2 R10000, was used to carry out 3D-database pharmacophore searching. A maximum of 3 million conformations for a single compound were searched. Searching was carried out on both NCI and ACD databases. There were no significant structural overlaps between the two databases. The actual pharmacophore search involved 3 steps. The first step was distance bit screening, which determined whether pair-wise distance constraints specified in the pharmacophore were met, using the distance information stored in the three-dimensional database. After a compound passed the distance bit screening step, the program next checked whether the compound meets the substructural requirements as specified in the pharmacophore query. In this step, all substructures specified in the model were required to be met. After a compound passed this sub-structural check, it was finally subjected to conformational analysis. In this step, conformations were generated and evaluated with regard to geometric requirements specified in the pharmacophore query. Compounds that had at least one conformation satisfying the geometric requirements were considered 'hits' and were recorded in a result database. Approximately five thousand compounds met the requirements of the pharmacophore models. A number of additional criteria were used in the selection of the compounds for biological evaluation such as simple chemical structure, small molecular weight, nonpeptidyl, chemical structural diversity and sample availability. Applying these criteria, 269 compounds were selected as potential cadherin inhibitors (FIGS. 15A–15BG; compounds 13–282).

A similar database search was performed using the pharmacophore queries derived from the three-dimensional structures for N—Ac—CHAVC—Y—NH$_2$ (SEQ ID NO:81) (see FIG. 16). This search identified compounds 283–311 (FIGS. 17A–17S).

A similar database search was performed using the pharmacophore queries derived from the three-dimensional structures for N—Ac—CHAVC—NH$_2$ (SEQ ID NO:10) as illustrated in FIGS. 14B and 14C. This search identified compounds 345–464 (FIGS. 21–23).

A similar database search was performed using the pharmacophore queries (FIG. 28) derived from the three-dimensional structures for N—Ac—CHAVC—Y—NH$_2$ (SEQ ID NO:81). This search identified compounds 465–481 (FIG. 29).

Figure 31A:
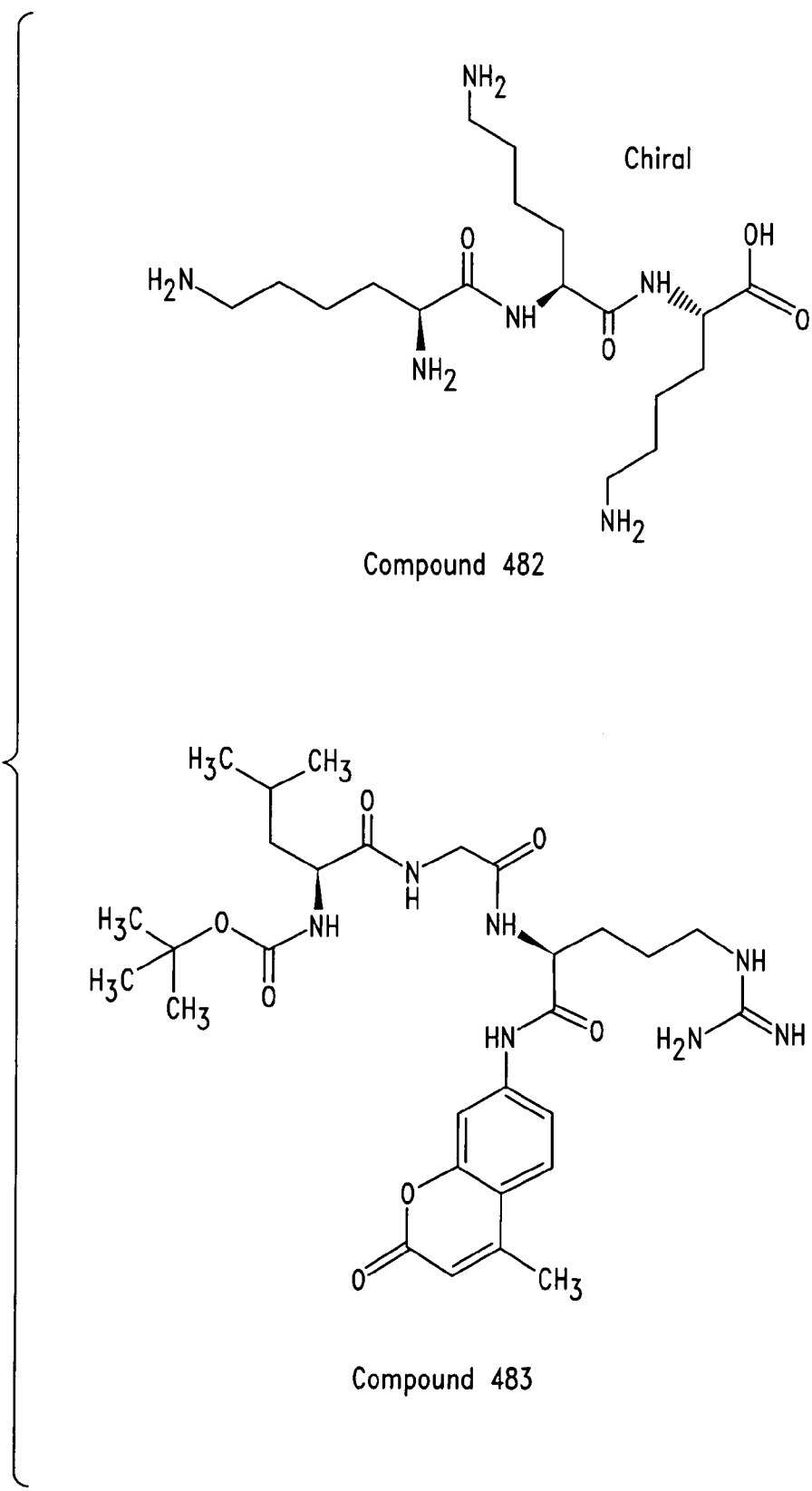
FIGS. 31A–31AI depict structures of representative non-peptidyl analogues of N—Ac—CHAVDC—NH$_2$ (SEQ ID NO:20) derived from 3D-pharmacophore database searching using the pharmacophore queries depicted in FIG. 30 (compounds 482–593).
Figure 31C:
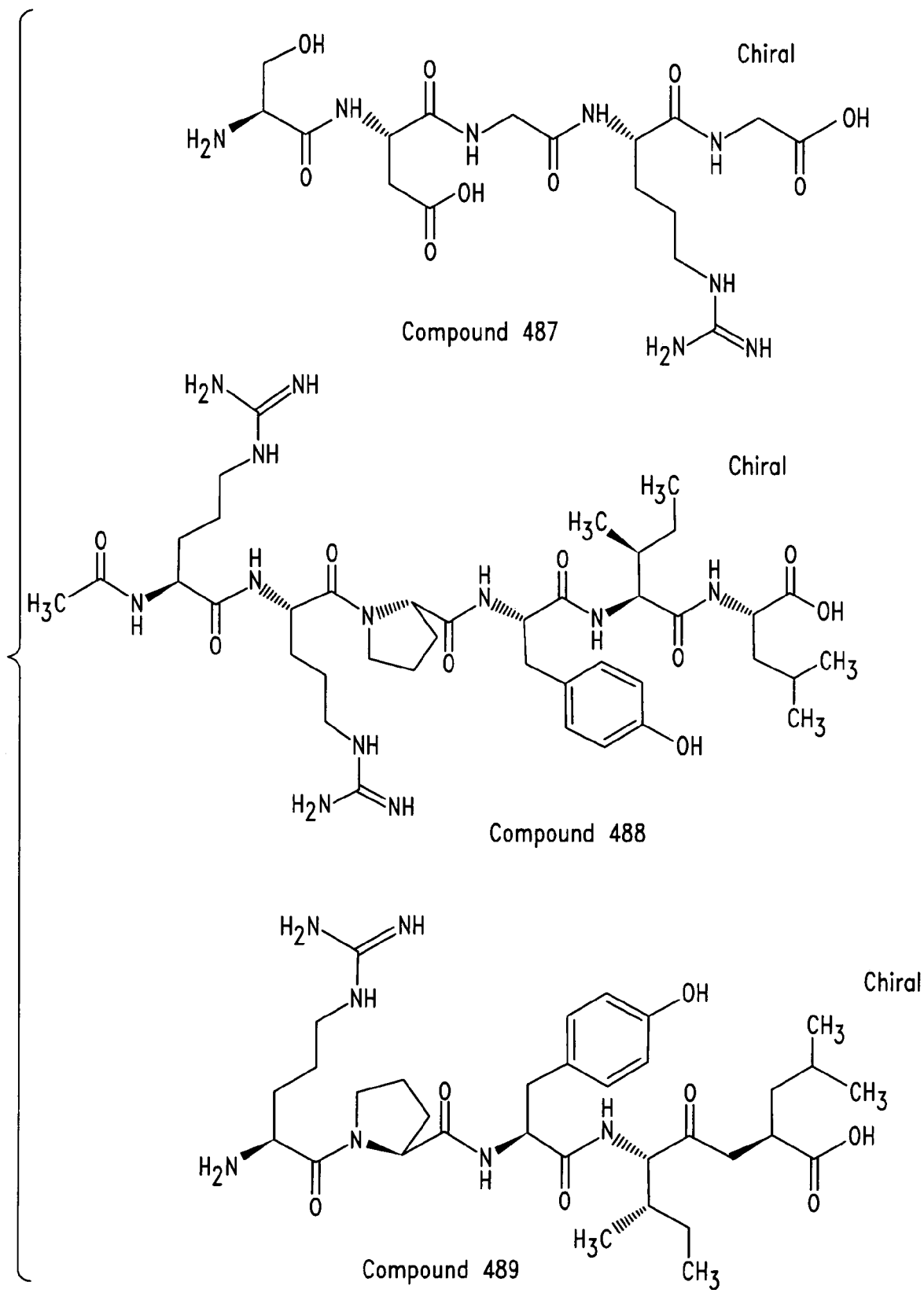
Figure 31D:
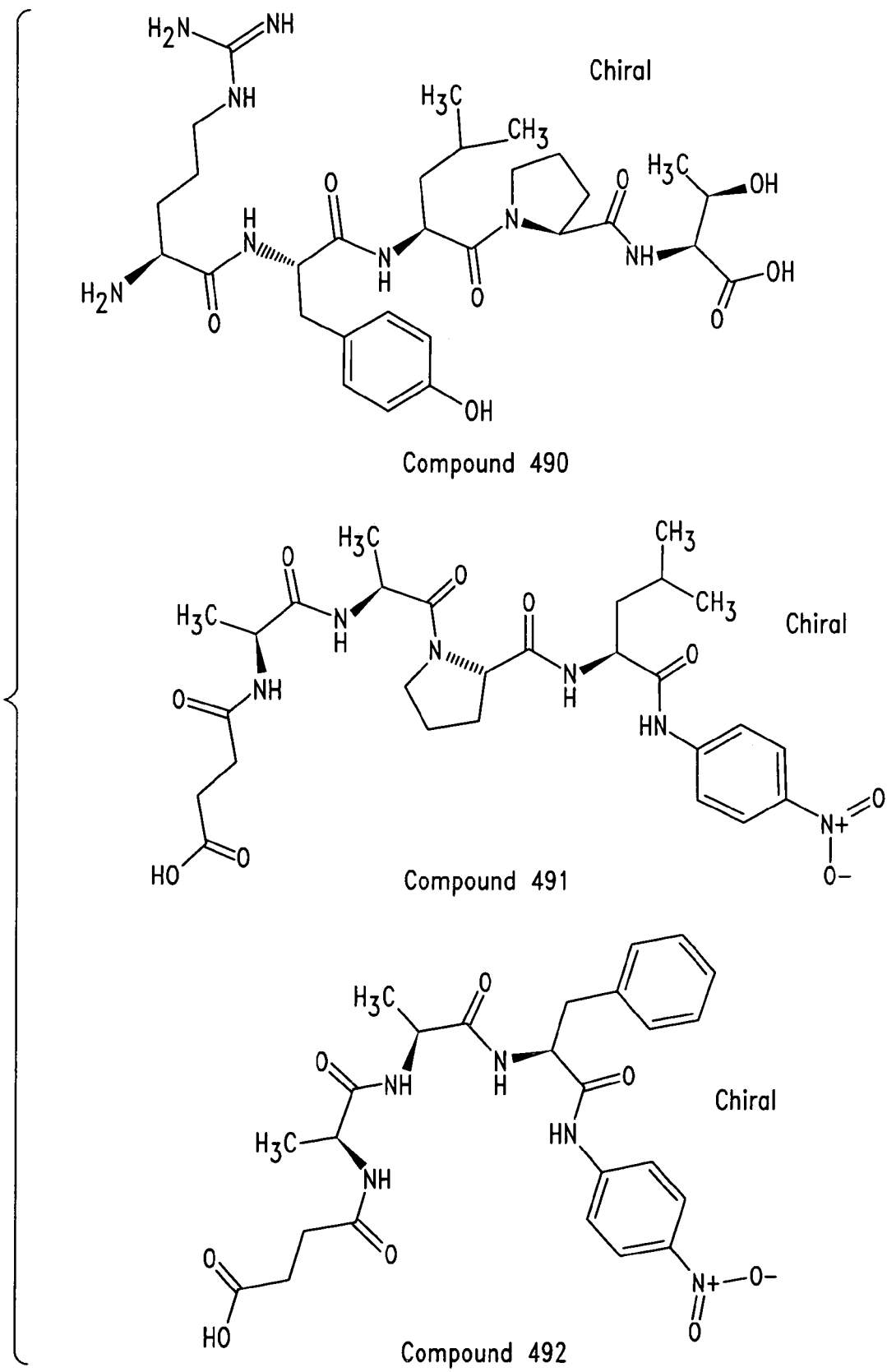
Figure 31F:
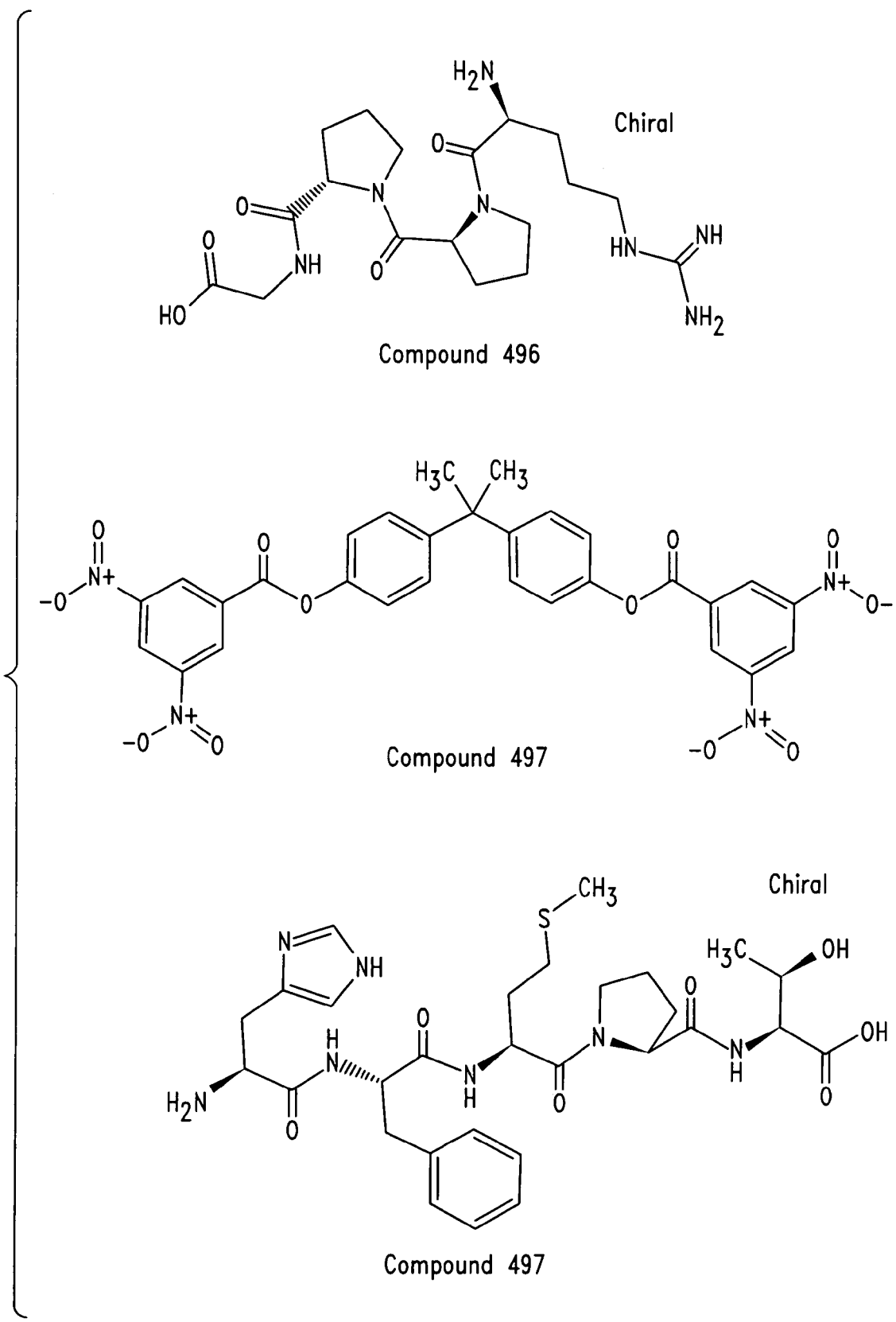
Figure 31G:
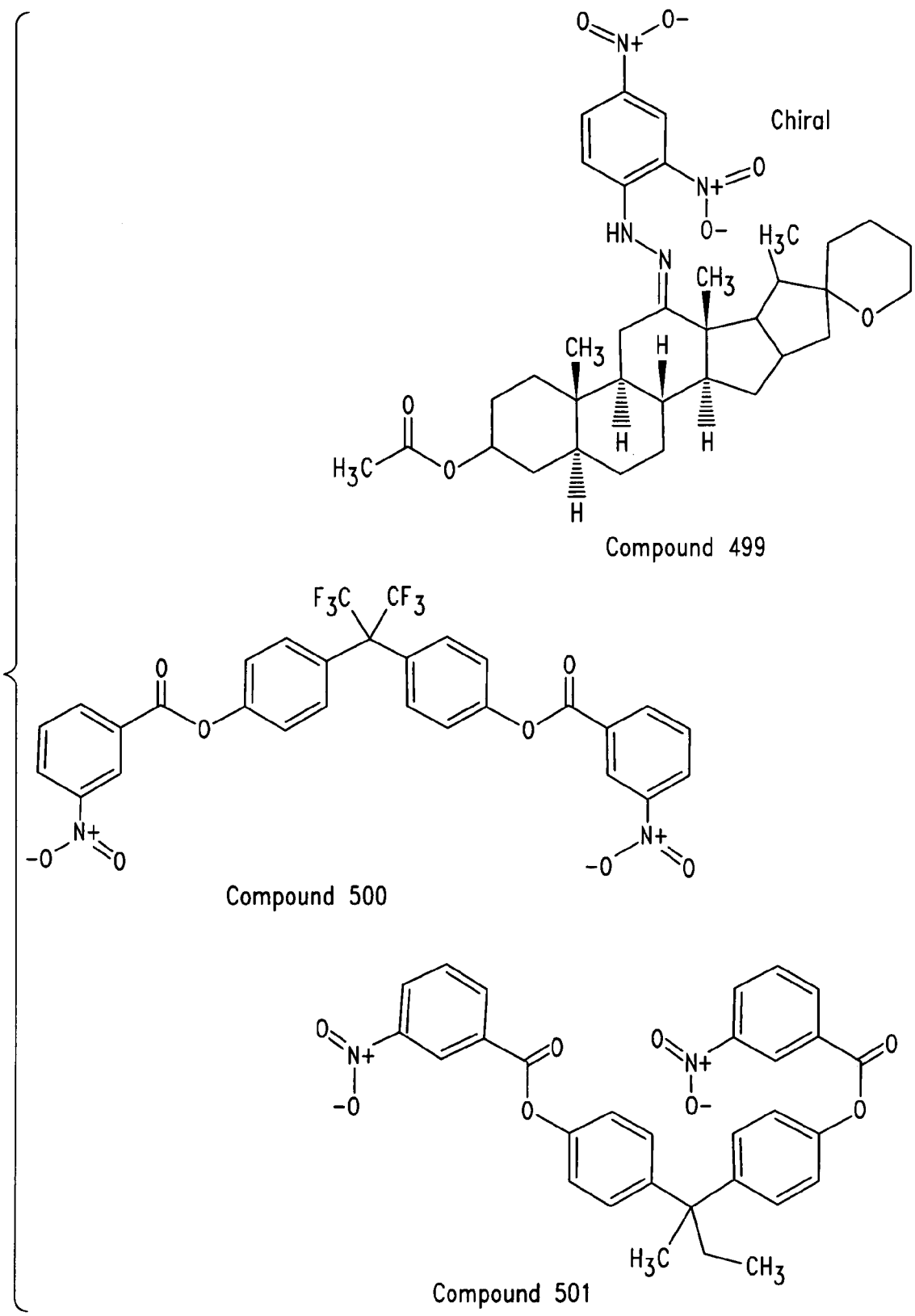
Figure 31H:
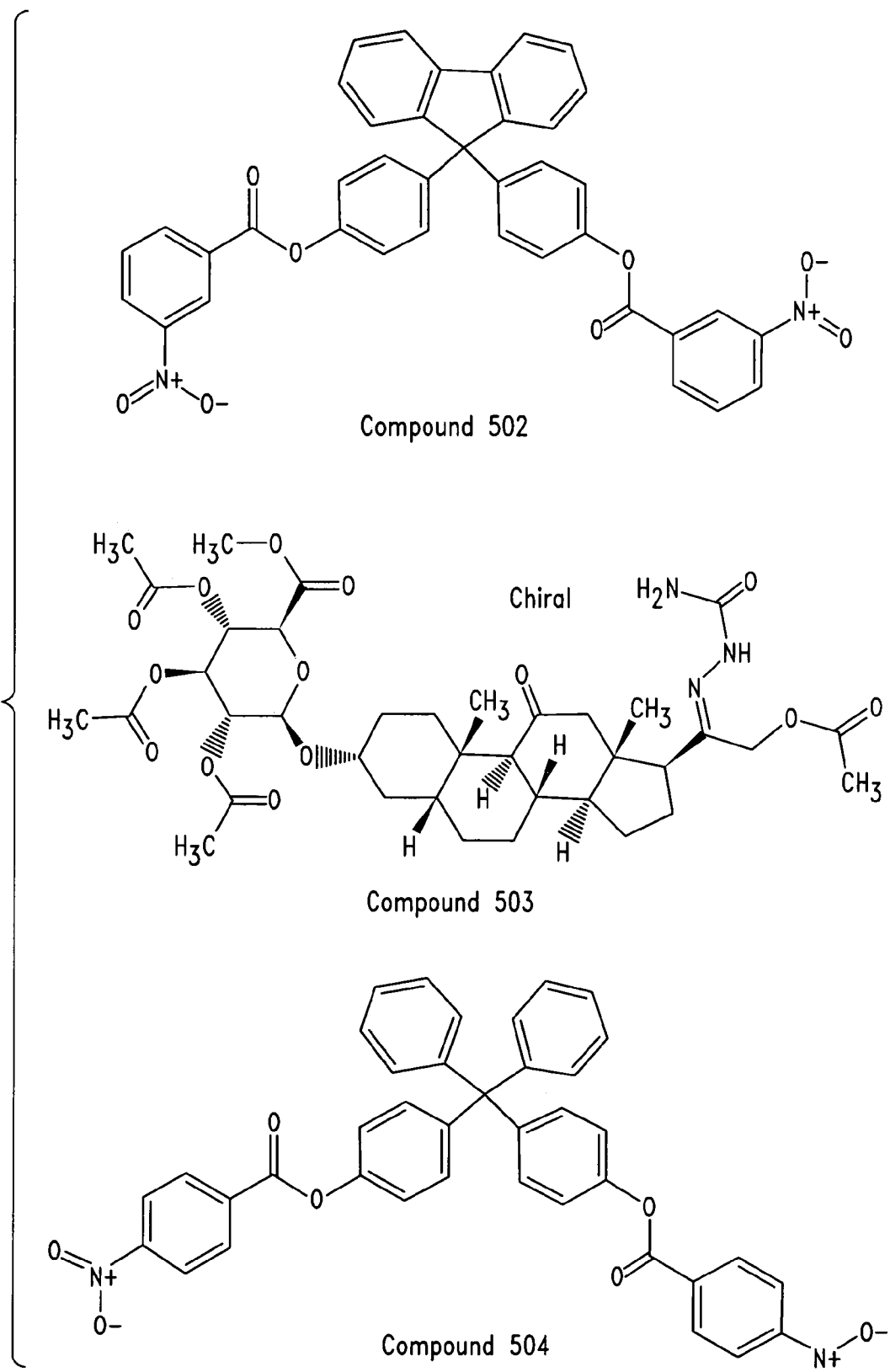
Figure 31I:
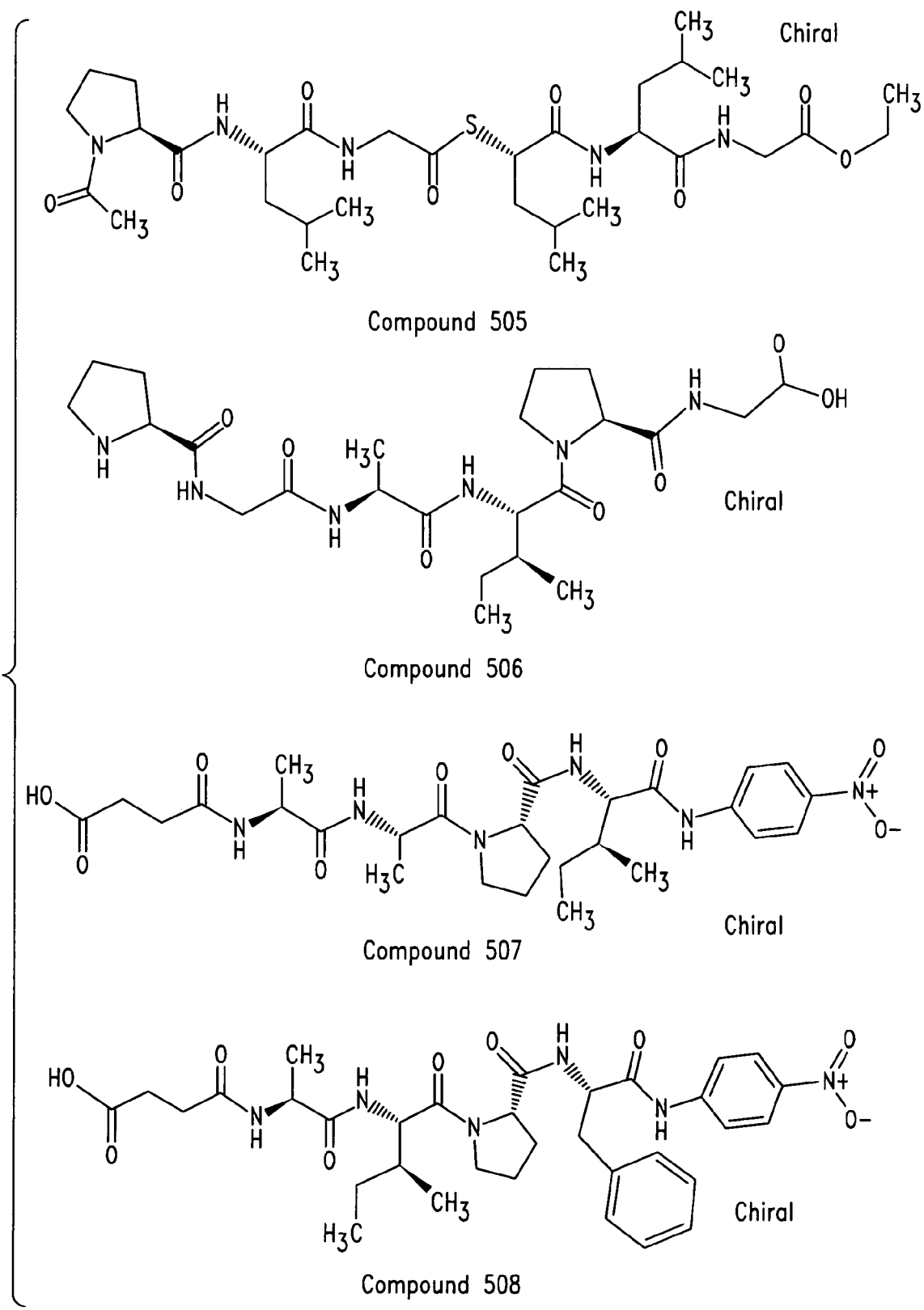
Figure 31K:
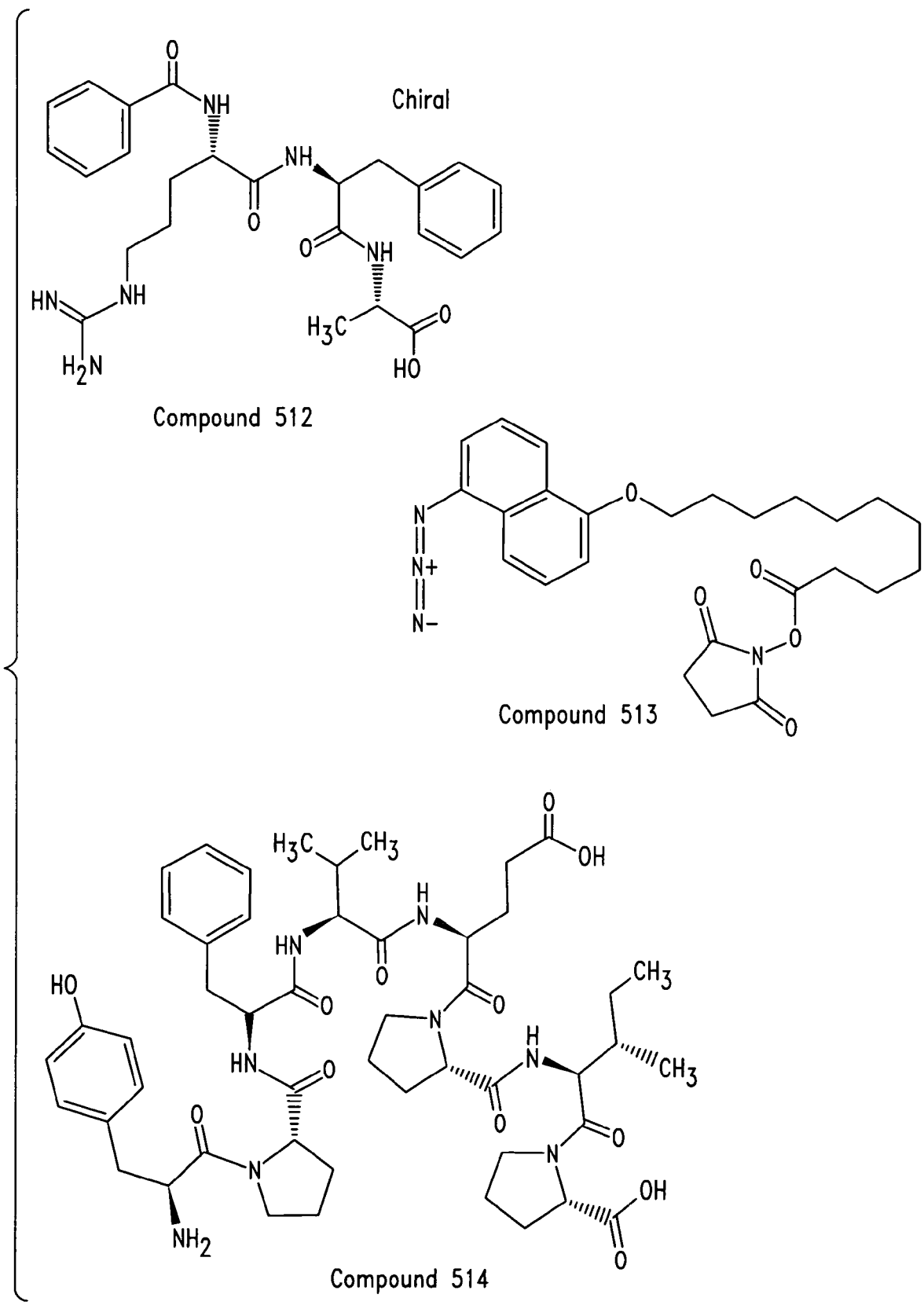
Figure 31L:
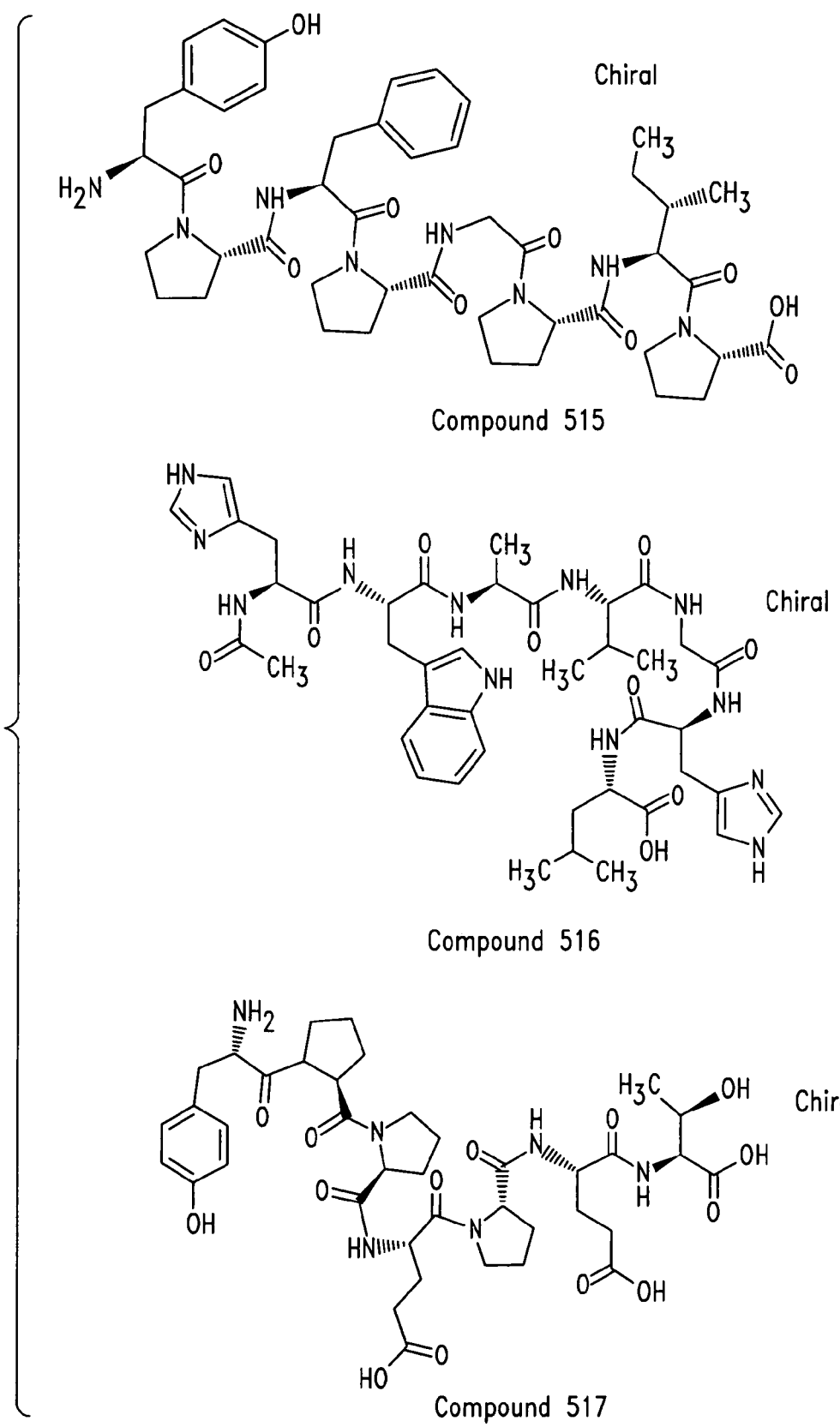
Figure 31N:
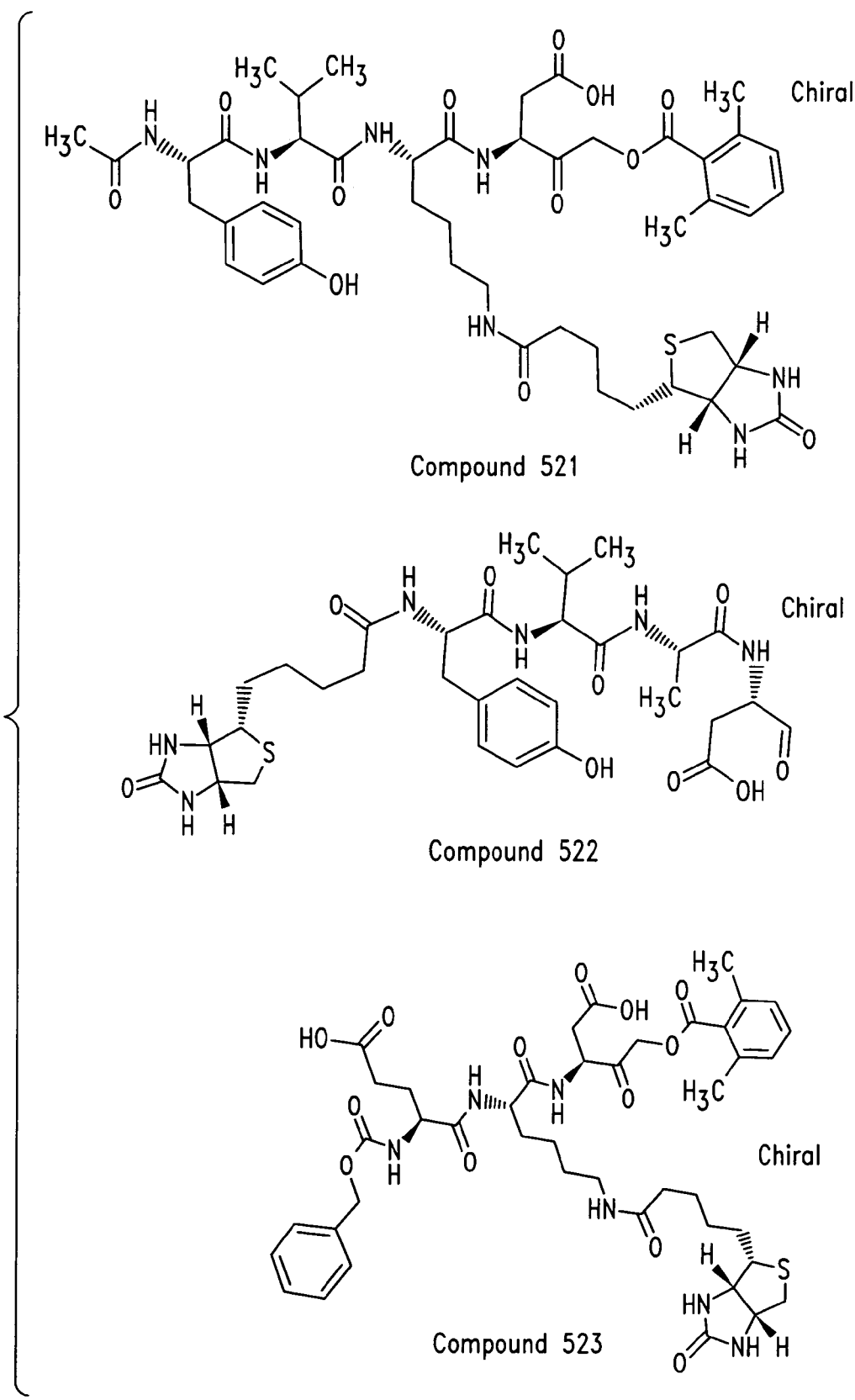
Figure 310:
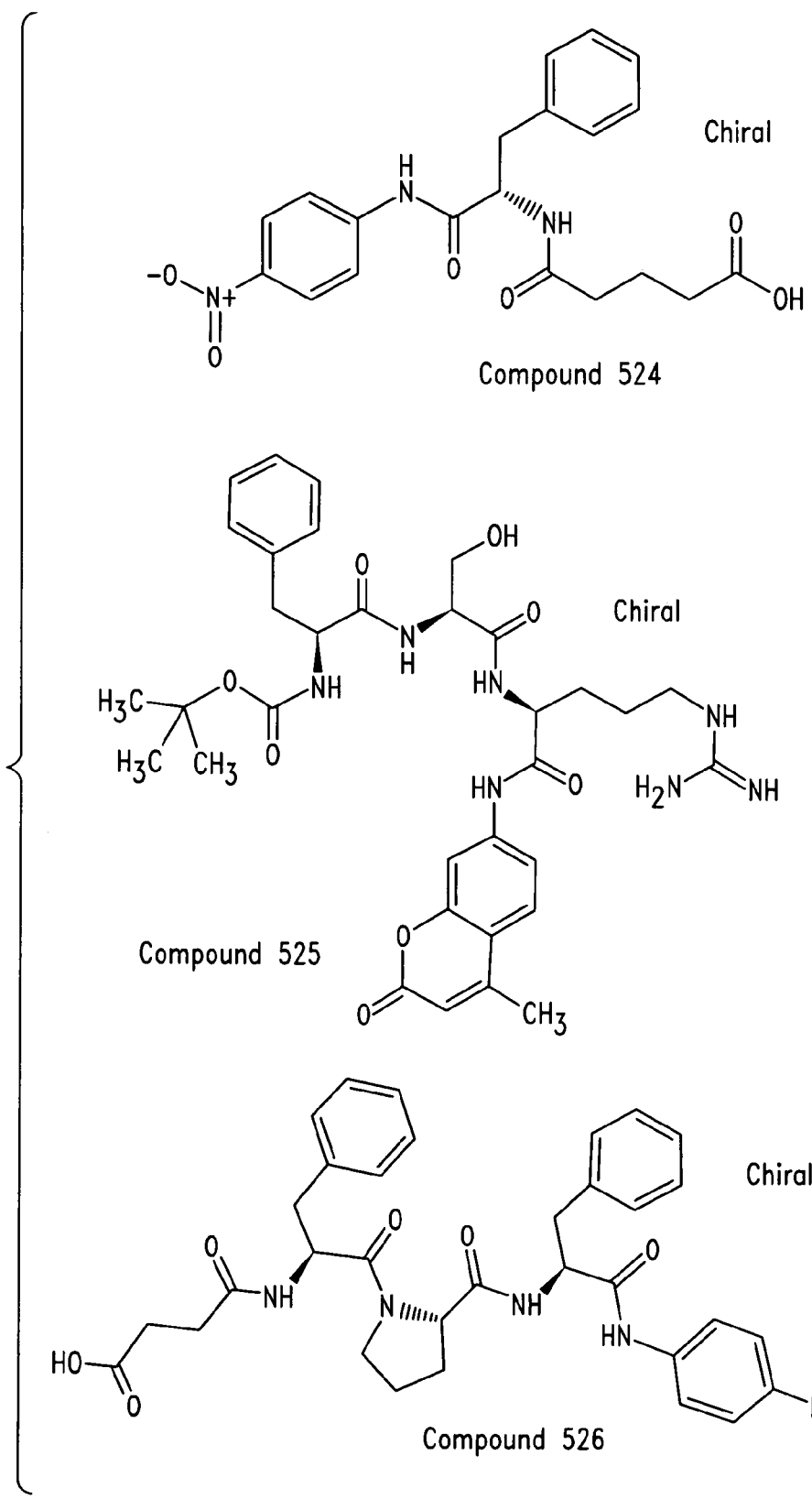
Figure 31P:
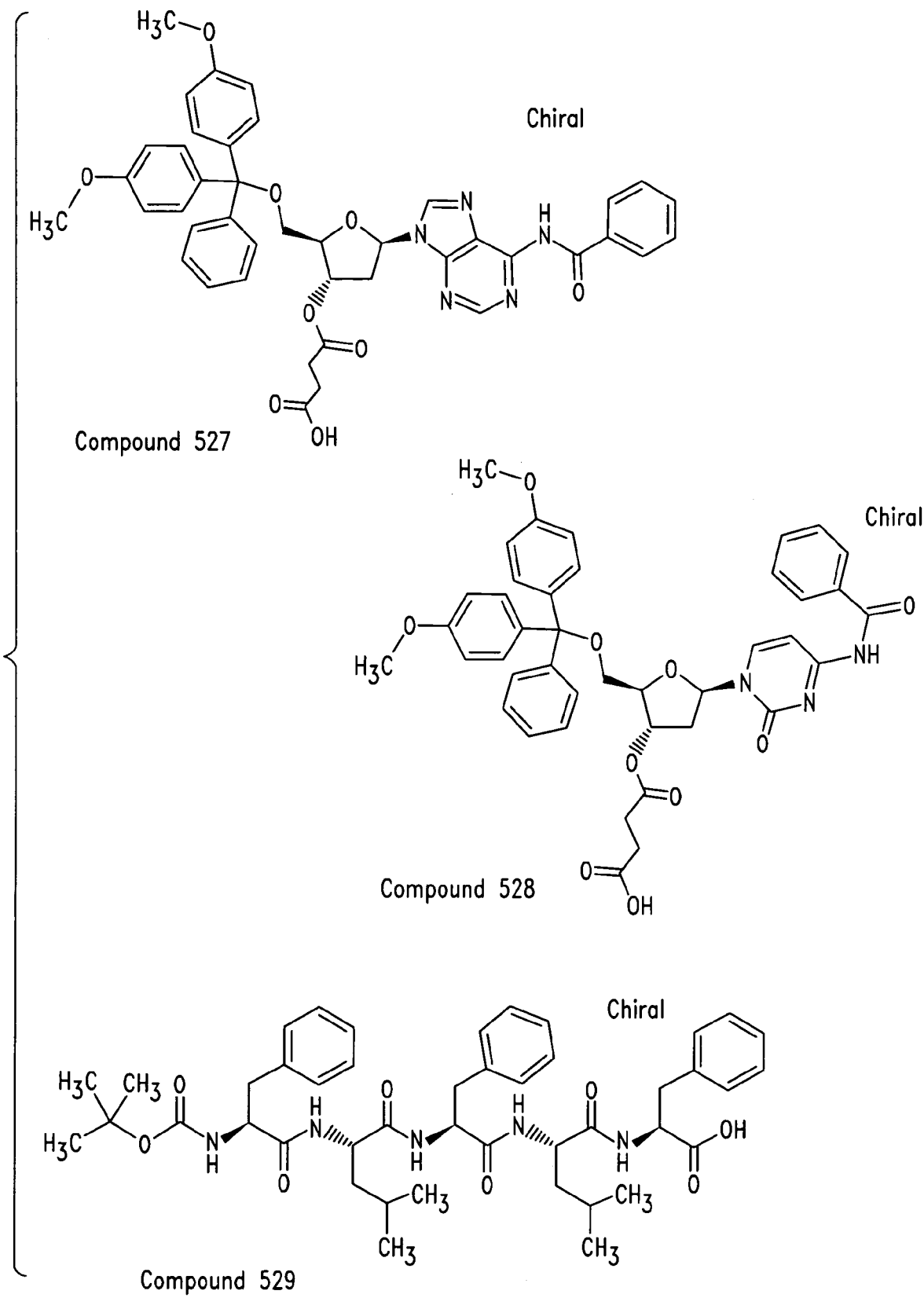
Figure 31Q:
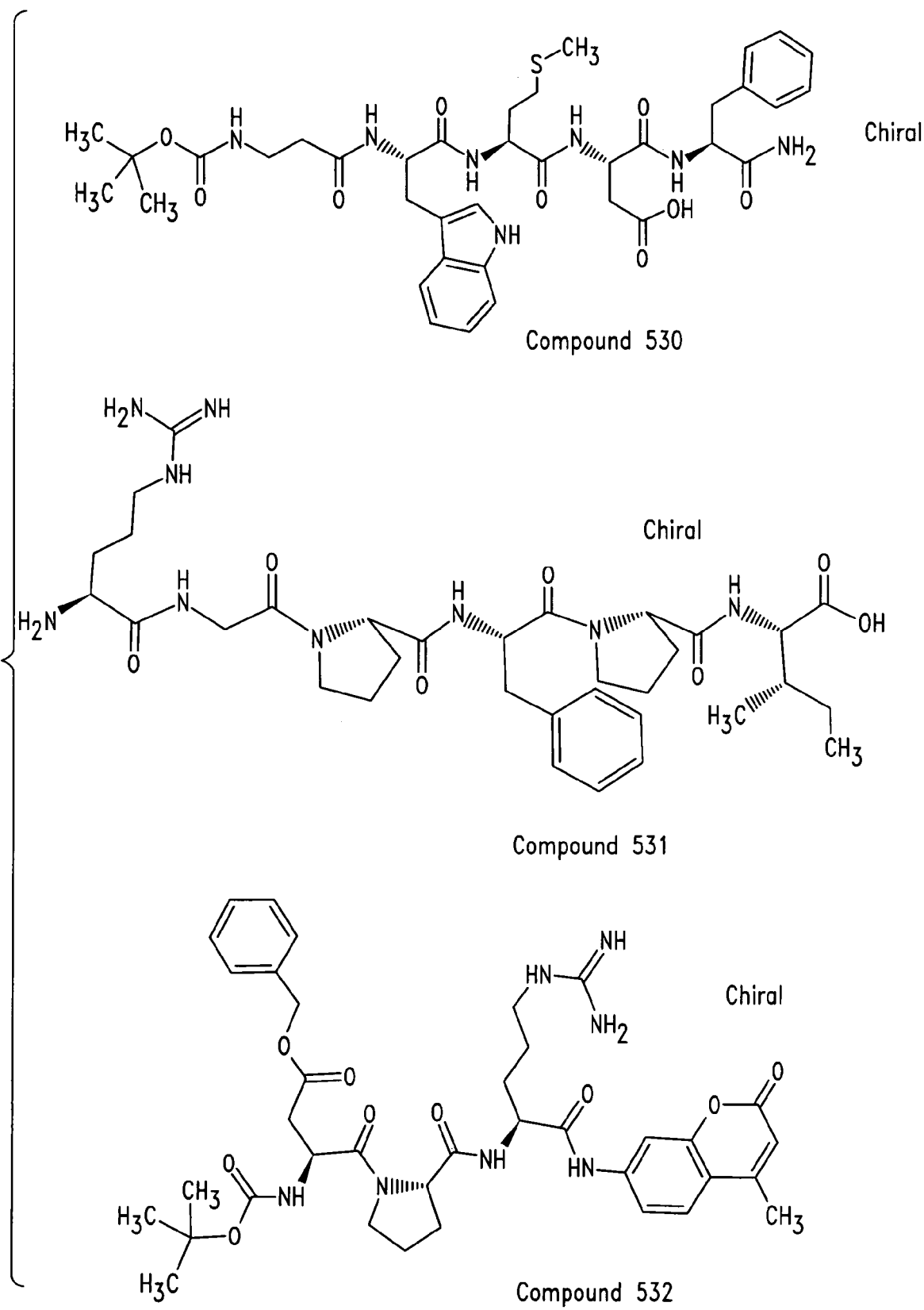
Figure 31R:
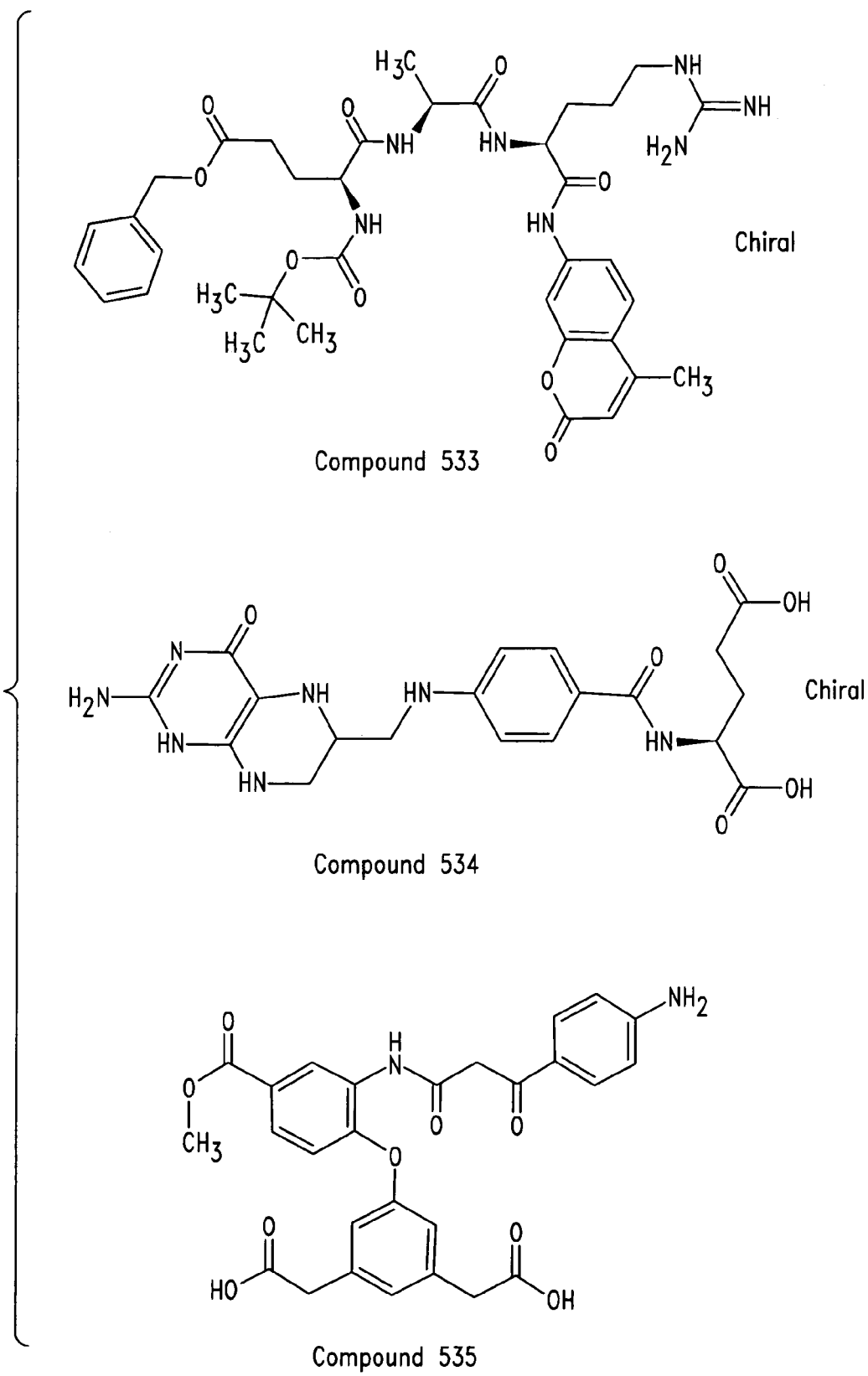
Figure 31T:
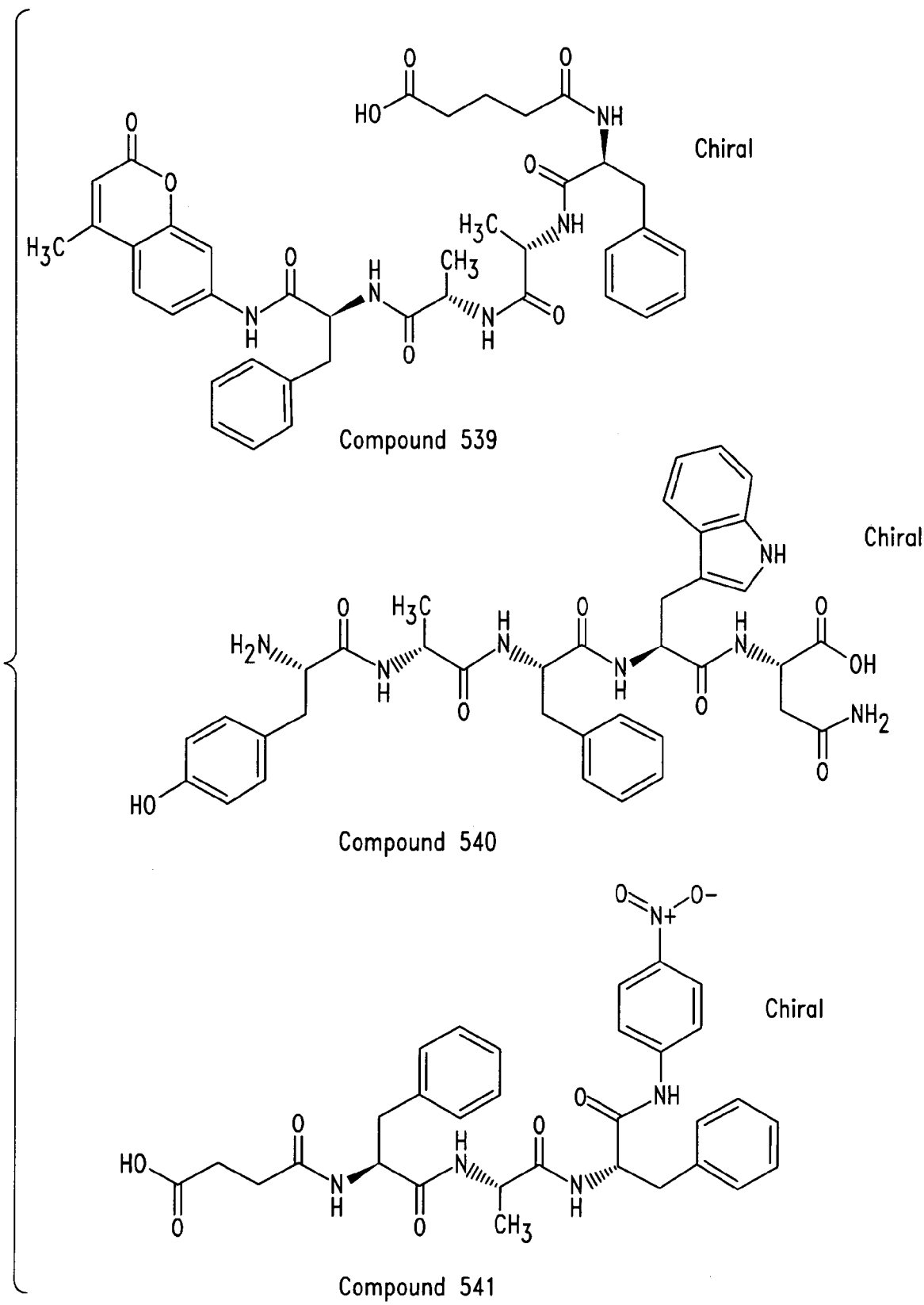
Figure 31V:
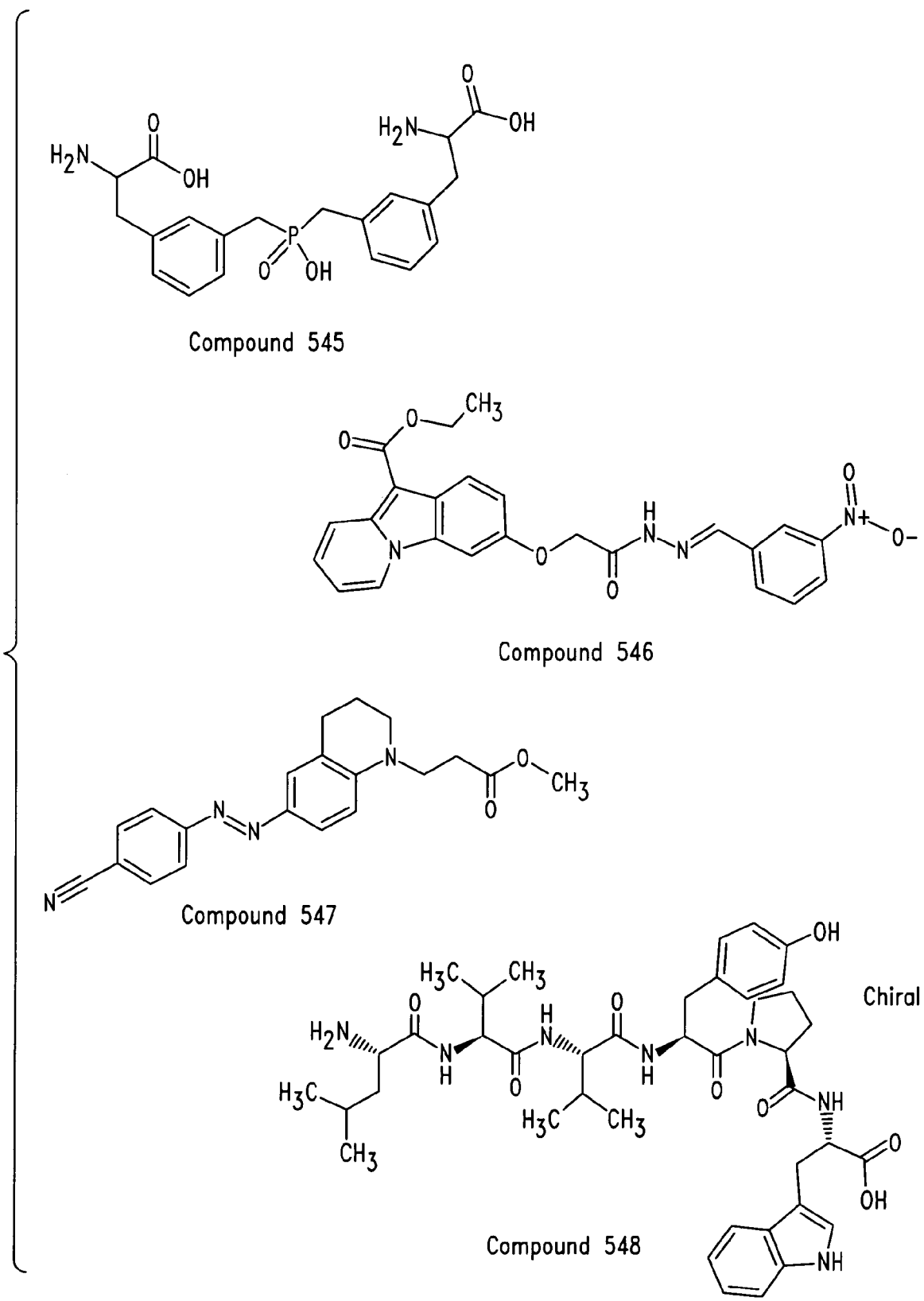
Figure 31Y:
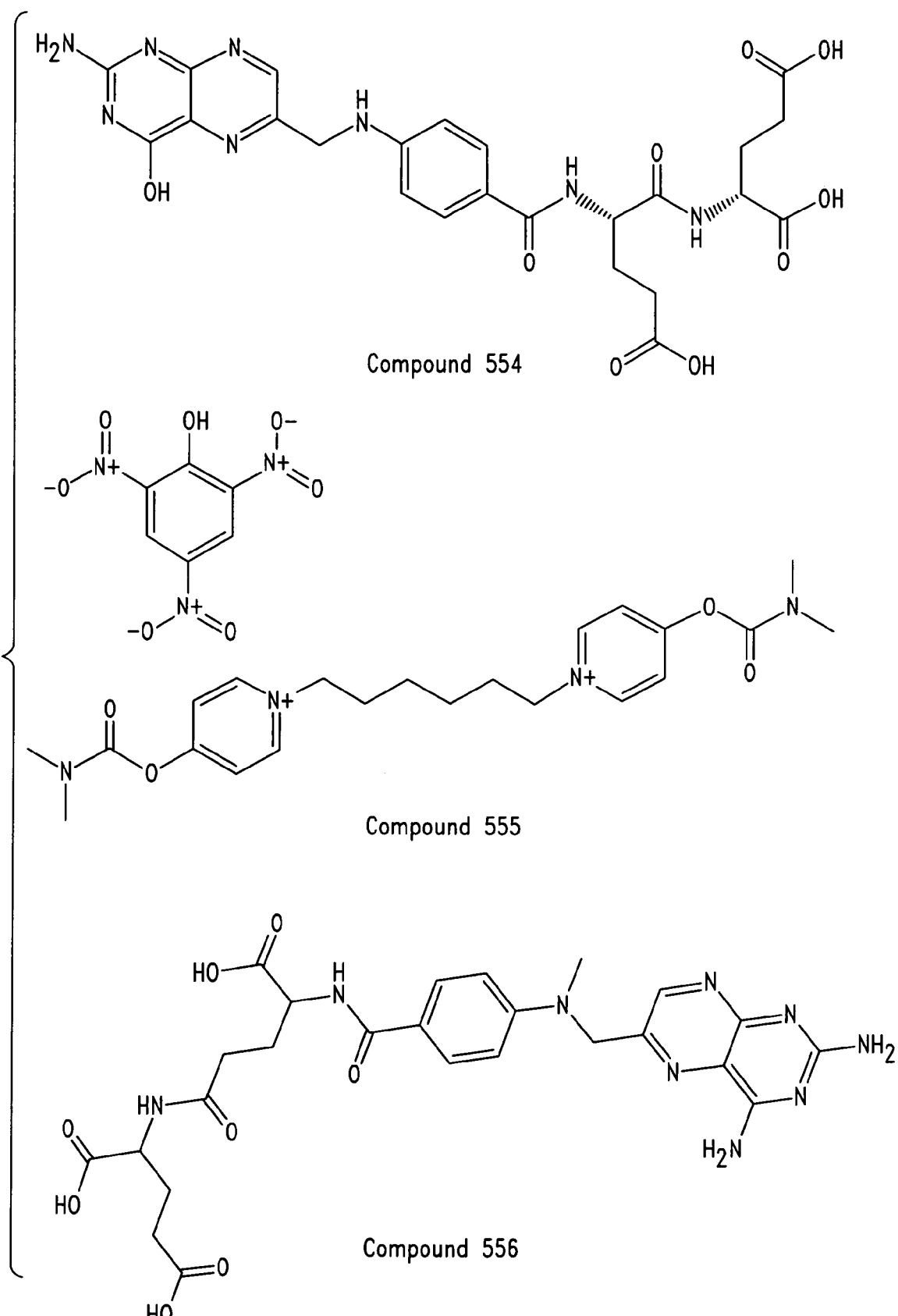
Figure 31Z:
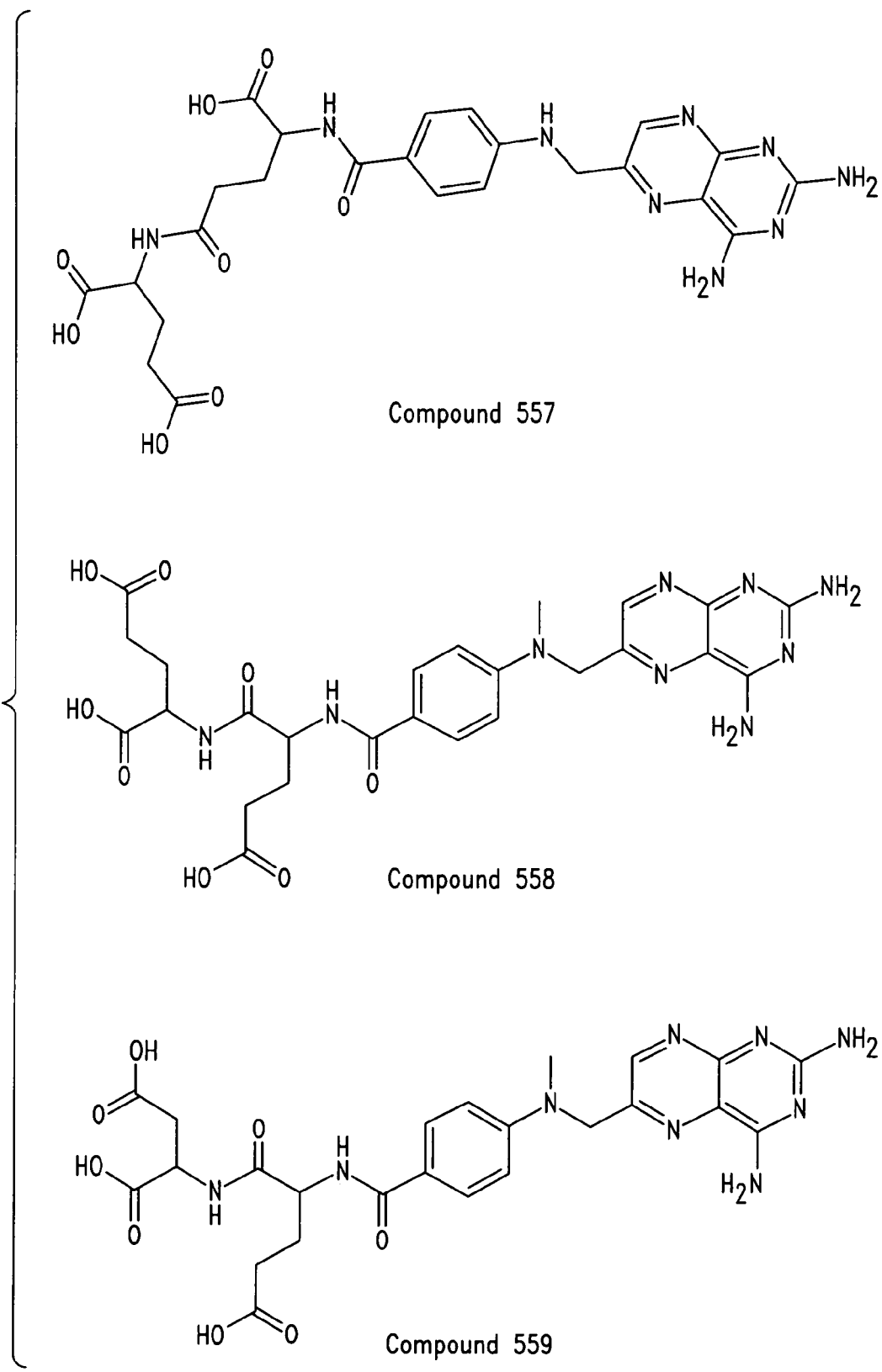
Figure 31A:
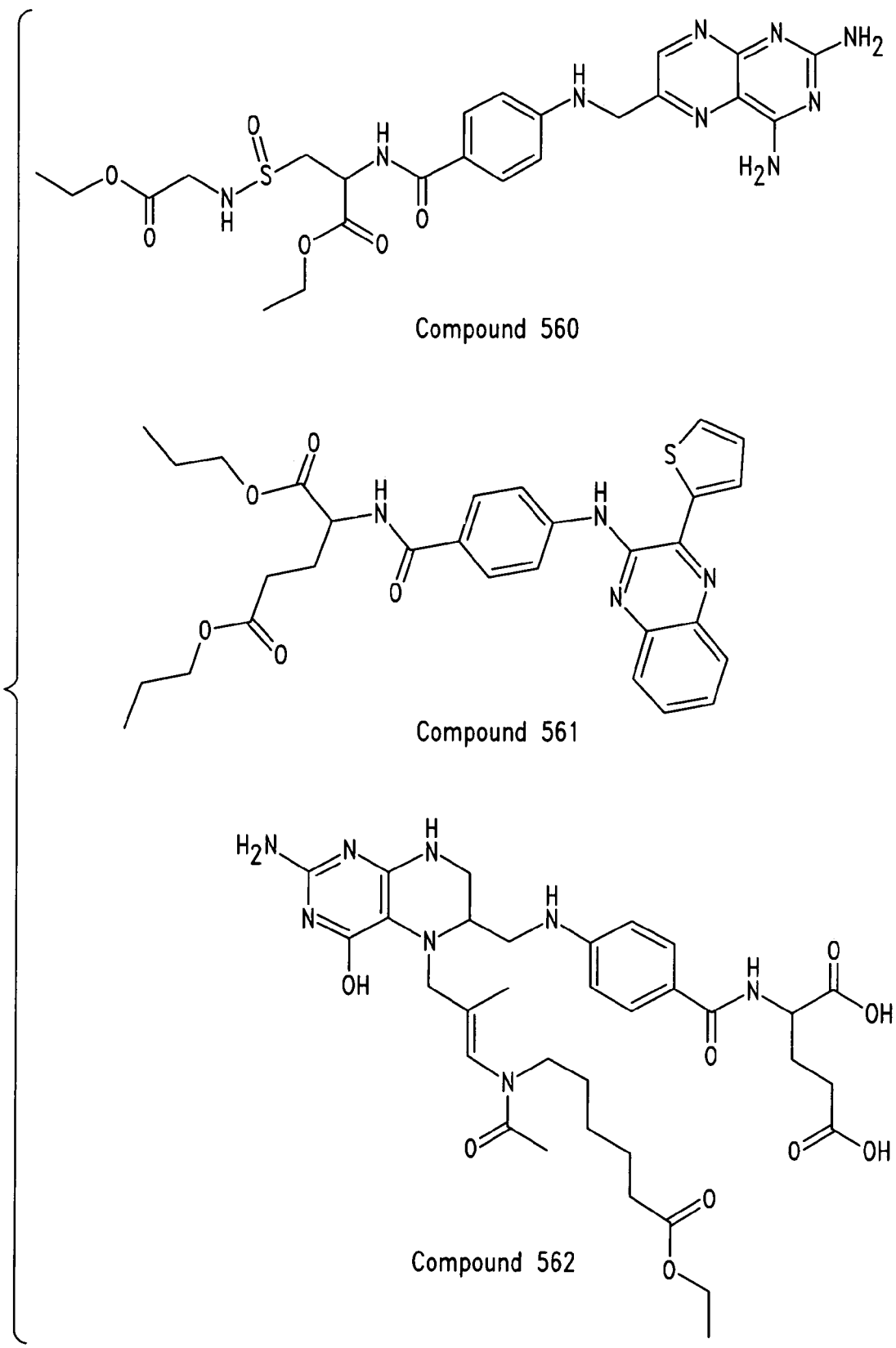
Figure 31A:
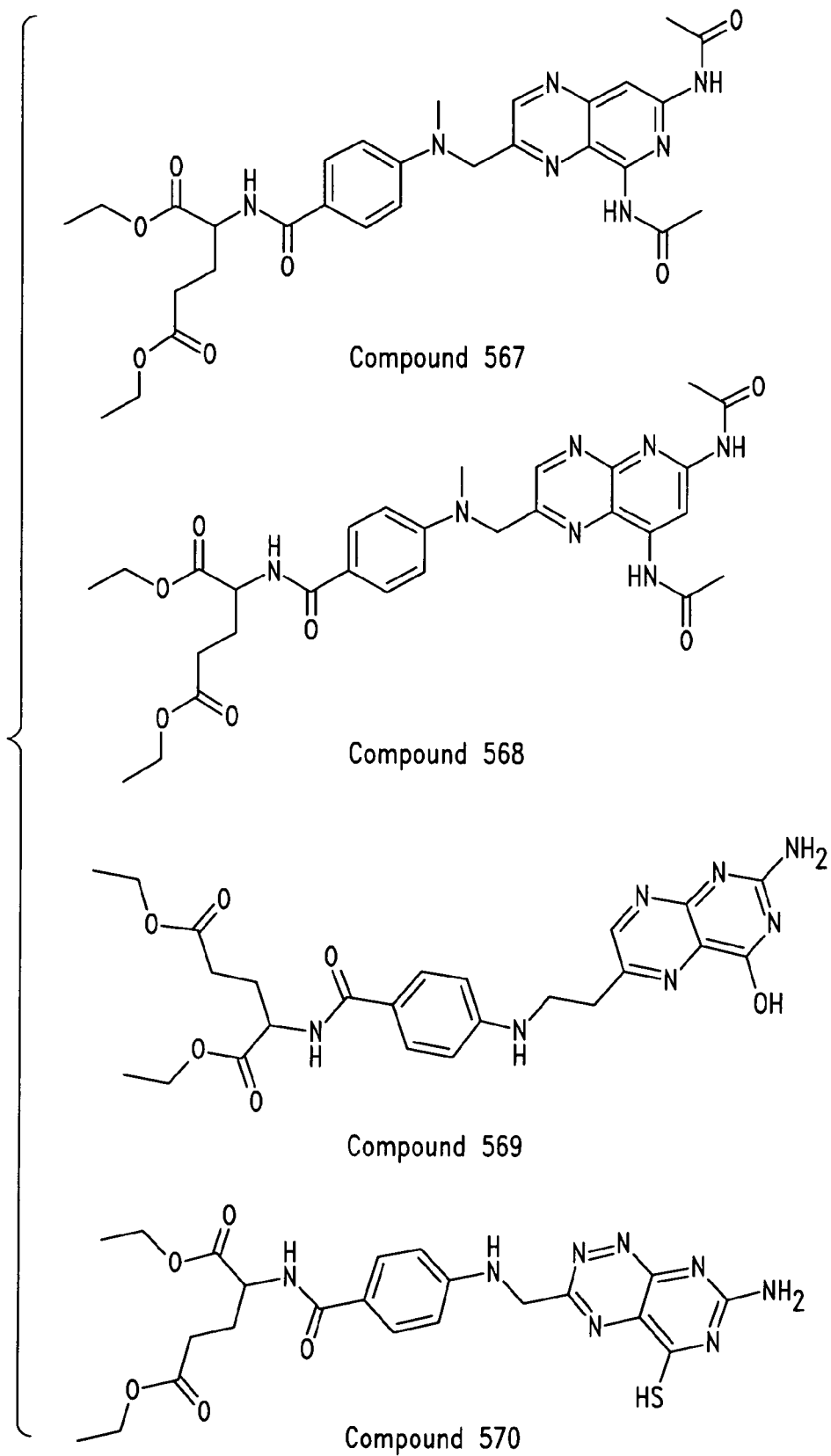
Figure 31A:
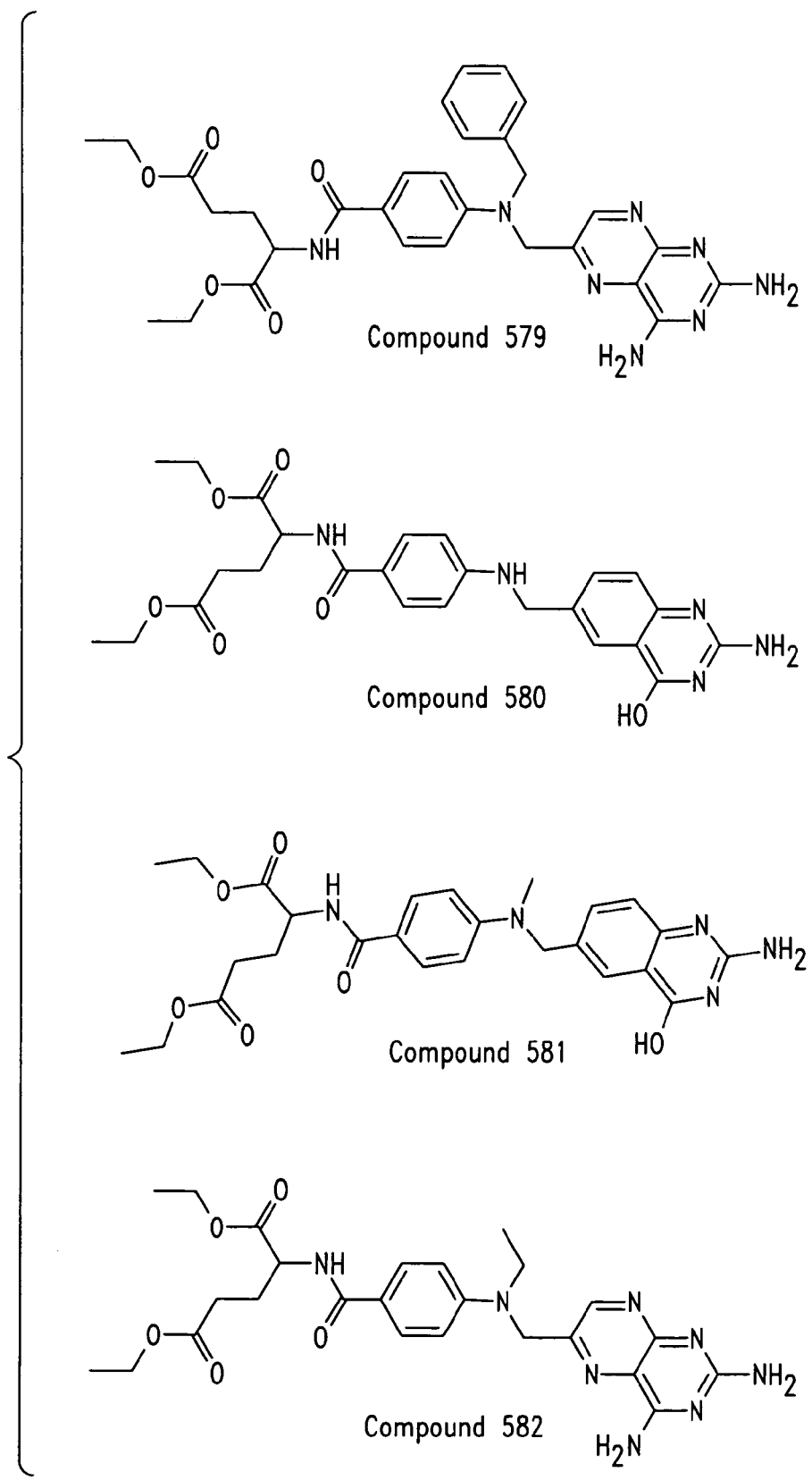
Figure 31A:
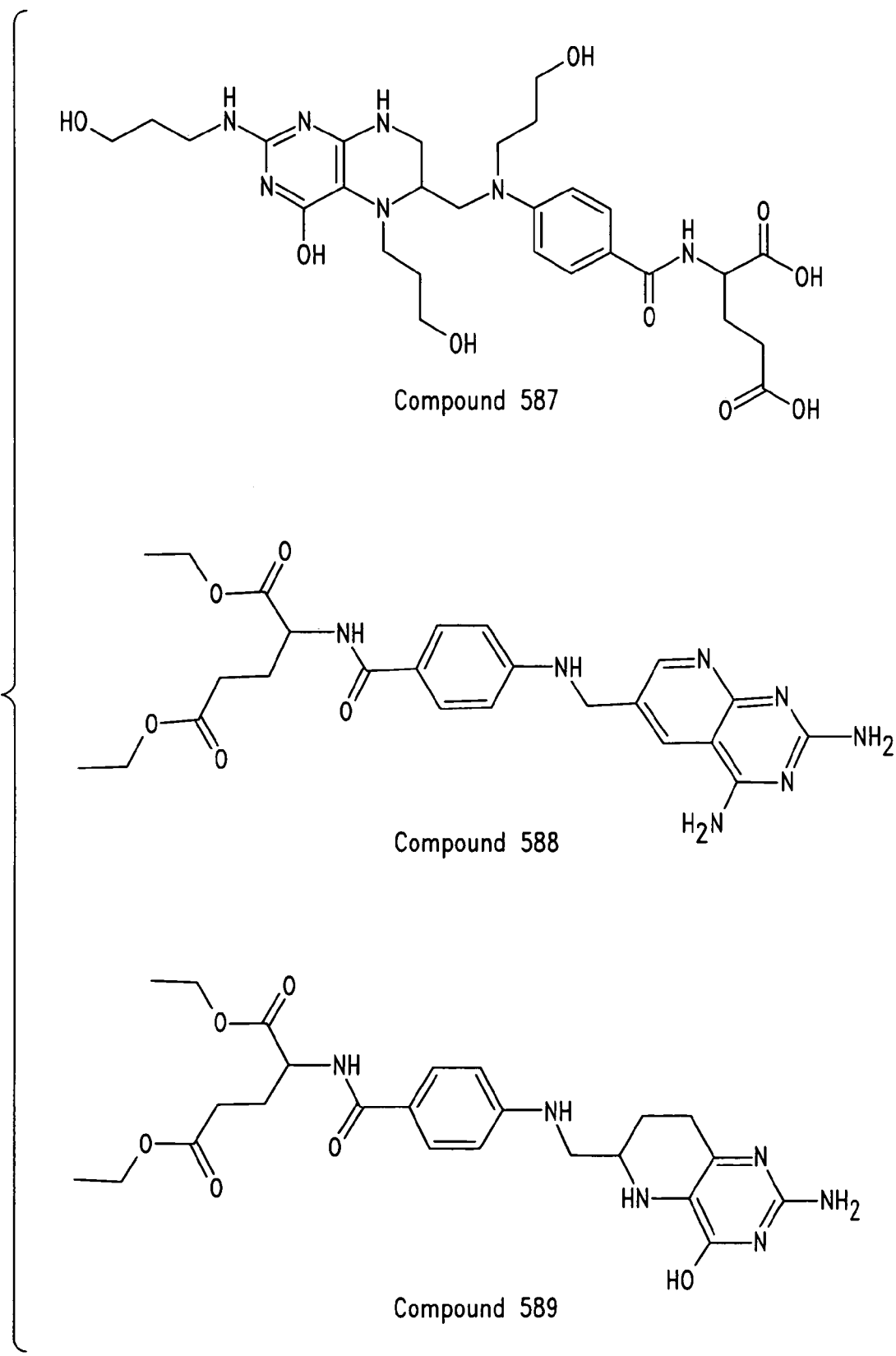
Figure 31A:
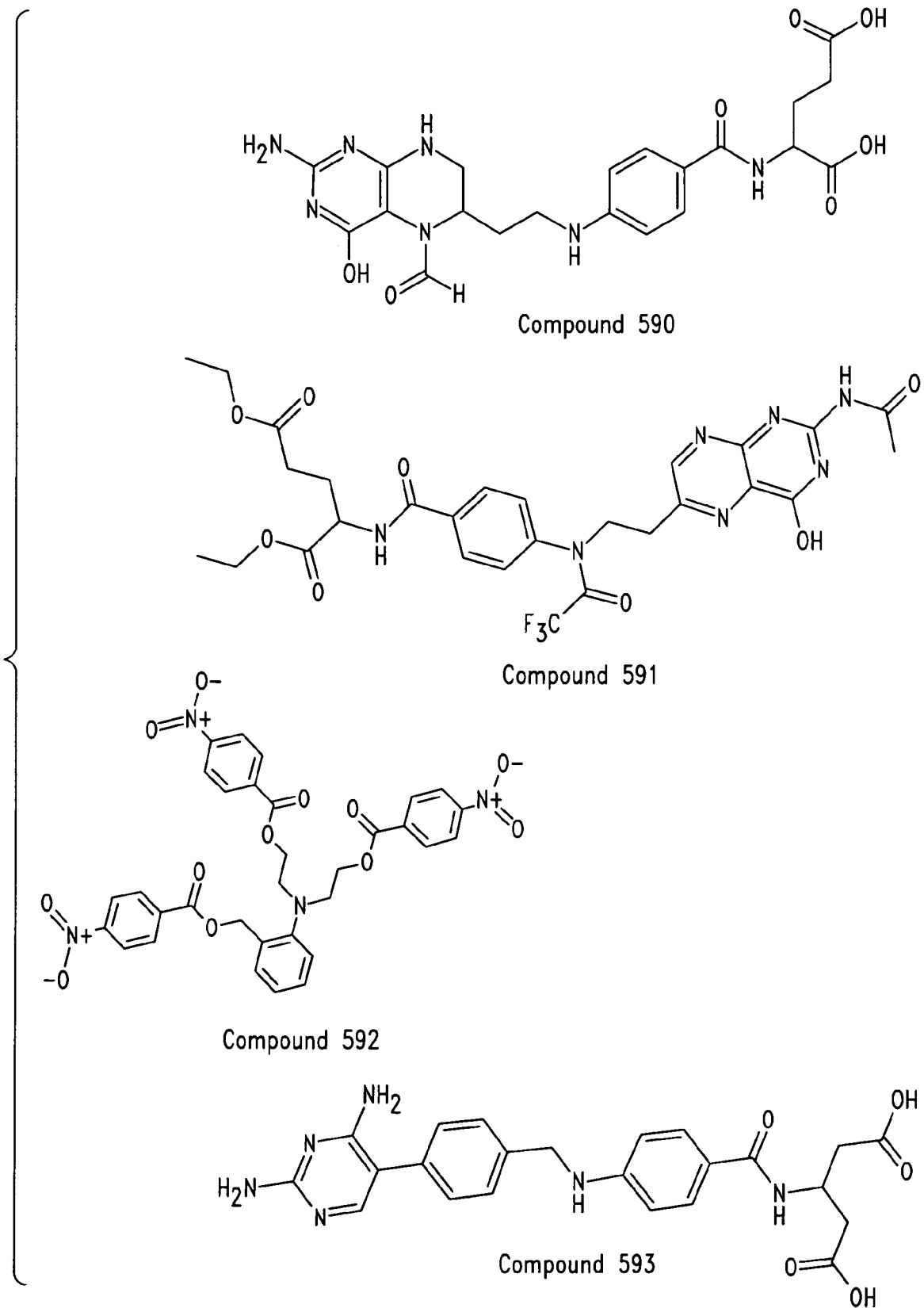

A similar database search was performed using the pharmacophore queries (FIG. 30) derived from the three-dimensional structures for N—Ac—CHAVDC—NH$_2$ (SEQ ID NO:20). This search identified compounds 482–593 (FIGS. 31A–31AI).

EXAMPLE 6

Effects of Peptidomimetics on Neurite Outgrowth

This Example illustrates the effect selected non-peptidyl cadherin antagonists on neurite outgrowth.

Cell culture and neurite outgrowth assays. Co-cultures of cerebellar neurons on monolayers of control 3T3 cells and monolayers of transfected 3T3 cells that express physiological levels of chick N-cadherin or human L1 were established as previously described (Williams et al., *Neuron* 13:583–594, 1994). In brief, 80,000 3T3 cells (control and transfected) were plated into individual chambers of an eight-chamber tissue culture slide coated with polylysine and fibronectin and cultured in DMEM/10% FCS. After 24 hours, when confluent monolayers had formed, the medium was removed and 3000 cerebellar neurons isolated from post-natal day 2–3 rats were plated into each well in SATO media (Doherty et al., *Nature* 343:464–466, 1990) supplemented with 2% FCS. All of the test peptides were added immediately before the neurons as a 2× stock prepared in SATO/2% FCS. The co-cultures were maintained for 16–18 hours, at which time they were fixed and immunostained for GAP-43, which is present only in the neurons and delineates the neuritic processes. The mean length of the longest neurite per cell was measured for 150–200 neurons sampled in replicate cultures as previously described (Williams et al., *Neuron* 13:583–594, 1994). The percentage inhibition of neurite outgrowth at various peptide concentrations was calculated as the average of at least three independent experiments. Dose-response curves were evaluated and the $EC_{50}$ vales determined.

All compounds tested are available commercially from Bionet Research Ltd. (Cornwall, UK), Aldrich Chemical Co. Inc. (Milwaukee, Wis.) or Ryan Scientific Inc. (Isle of Palms, S.C.). They were dissolved in DMSO at a concentration of 25 mg/mL and diluted with media to carry out the assay.

Effects of Peptidomimetics on N-cadherin function. The ability of certain of the non-peptidyl cadherin antagonists shown in FIGS. 11, 13, 15A–15BG, 17A–17J, 18A–18E and 19A–19E to inhibit neurite outgrowth was tested as described above. As can be seen in Table 2, these compounds are effective modulators of N-cadherin function.

TABLE 2

Percent Inhibition of Neurite Outgrowth by Representative Peptidomimetics

| Compound No. | Percent Inhibition of Neurite Outgrowth | | |
|---|---|---|---|
| | At 0.4 µg/mL | At 2 µg/mL | At 10 µg/mL |
| 59 | 95.6 | | |
| 65 | 85.5 | | |
| 181 | 61.8 | | |
| 13 | 52.4 | 70.0 | |
| 25 | 35.0 | 95.3 | |
| 70 | 25.4 | 55.0 | |
| 109 | | 60.9 | |
| 66 | 15.9 | 84.4 | |
| 30 | | 58.3 | |
| 184 | | 51.8 | |
| 47 | | 15.2 | 101.0 |
| 35 | | 13.1 | 90.2 |
| 31 | | 34.3 | 61.6 |
| 176 | | 33.7 | 64.2 |

EXAMPLE 7

Use of Representative Peptidomimetics to Decrease Electrical Resistance Across MDCK Cells This example illustrates the use of representative peptidomimetics to disrupt adhesion of MDCK cells as measured by a decrease in the electrical resistance across the monolayer.

Madin Darby canine kidney (MDCK) cells were plated in Millicells (Millipore, Bedford, Mass.), at a density of 300, 000 cells per Millicell, and cultured in Dulbecco's Modified Eagle Medium (DMEM; Sigma, St. Louis, Mo.) containing 5% fetal calf serum (Sigma, St. Louis, Mo.) until monolayers formed. Monolayers were exposed to the modulating agent dissolved in medium. The electrical resistance was measured using the EVOM device (World Precision Instruments, Sarasota, Fla.). At the time of measurement, fresh medium, with or without the modulating agent, may be added to the Millicells.

Table 3 provides the approximate $ED_{50}$ values for which various peptidomimetics were able to abolish electrical resistance across MDCK cell monolayers cultured for 18 hours in medium containing the various peptidomimetics. These results demonstrate the ability of peptidomimetics to inhibit the formation of tight junctions in epithelial cells.

TABLE 3

Effects of Peptidomimetics on Electrical Resistance across MDCK Cell Monolayer

| Compound Number | $ED_{50}(\mu g/ml)$ |
|---|---|
| 76 | 4–8 |
| 84 | 10 |
| 102 | 10 |
| 101 | 10–40 |
| 103 | 10–40 |
| 65 | 40 |
| 82 | 50–100 |
| 86 | 50–100 |
| 87 | 50–100 |
| 184 | 80–100 |

From the foregoing, it will be evident that although specific embodiments of the invention have been described herein for the purpose of illustrating the invention, various modifications may be made without deviating from the spirit and scope of the invention. Accordindly, the present invention is not limited except as by the appended claims.

EXAMPLE 8

Identification of Thioether Analogues of N—Ac—CHAVC—NH$_2$

This Example illustrates the identification of three thioether analogues (FIGS. 24A–24C) of N—Ac—CHAVC—NH$_2$(SEQ ID NO:10), designed by comparing the three-dimensional NMR structures of N—Ac—CHAVC—NH$_2$ (SEQ ID NO:10) with the modeled 3D conformations of the thioethers.

Modeling studies were used to predict the conformations of potential thioether analogues of N—Ac—CHAVC—NH$_2$ (SEQ ID NO:10). All the molecular modeling studies were carried out using the QUANTA molecular modeling package and its associated molecular mechanics program CHARMM (Brooks, B. R.; Bruccoleri, R. E.; Olafson, B. D.; States, D. J.; Swaminathan, S.; Karplus, M. CHARMM: A program for macromolecular energy minimization and dynamics calculations. J. Comput. Chem. 1983, 4, 187–217), running on an SGI workstation with IRIX6.5.

The initial structures of the thioethers were built using the Sequence Builder module within the QUANTA package. Each structure was then energy minimized. An adopted-basis Newton-Raphson alogorithm, implemented in the CHARMM program, was used in the energy minimization. Energy was minimized for 5000 steps, or until convergence, defined as an energy gradient tolerance of 0.001 kcal mol$^{-1}$ Å$^{-1}$ or less. A constant dielectric was used throughout the calculation and set to either 1 to mimic the vacuum environment or 80 to mimic the water environment, respectively.

The non-bonded cutoff distance was set to 14.0 Å. A shifted smoothing function was used for the van der Waals interaction and a switch function for the electrostatic energy.

To properly sample the conformational space of these compounds, high-temperature (HT) molecular dynamics (MD) simulation was used. In the MD simulation, the system was heated to 1000K in a period of 10 ps and equilibrated for 10 ps at 1000K. Finally, a constant temperature dynamics simulation was performed for 10,000 ps at 1000K with a time step of 0.001 ps. The simulation trajectory was recorded every 1000 steps during the final 1000 ps simulations and a total of 1000 conformers were recorded. A SHAKE algorithm was used to constrain bonds to hydrogen.

For each MD simulation, each of these 1000 conformers was energy-minimized. These energy-minimized conformers were clustered by calculating the pair-wise RMS differences between structures using a least square-fitting algorithm as implemented in the conformational analysis module in the QUANTA program. The conformer with the lowest energy within each cluster was selected to represent the conformational cluster and used to compare its molecular similarities with the experimental NMR structures as seen in FIGS. 7A–7C.

In order to validate our modeling technique, molecular modeling was used to predict the low energy 3D conformations of N—Ac—CHAVC—NH$_2$ (SEQ ID NO:10) The calculated conformations were then compared to the solution 3D conformations of N—Ac—CHAVC—NH$_2$ (SEQ ID NO:10) obtained using the NMR techniques described above. Two different criteria were used to cluster the conformers. Either a RMS deviation of 2.0 Å for all heavy atom pairs was set as the criterion for clustering the conformers or a RMS deviation of 1.5 Å for all heavy atoms in the HAV sequence was set as the criterion for clustering the conformers. In each cluster, the lowest-energy conformer was selected to represent the cluster. The potential energy values as well as the energy difference between the corresponding conformer and the lowest-energy conformer (global minimum) of all the conformers was calculated using the CHARMM program.

A total of 4 different groups of conformers were obtained for N—Ac—CHAVC—NH$_2$ (SEQ ID NO:10) due to both the use of two dielectric constants and the two different clustering criteria. These are given in Tables 4a–4d respectively.

TABLE 4a

Conformer group A of modeled N-Ac-CHAVC-NH$_2$

| No | Conformers | E (kcal mol$^{-1}$) | ÄE (kcal mol$^{-1}$) |
|---|---|---|---|
| 1 | 124 | −186.68 | 10.32 |
| 2 | 163 | −185.06 | 11.94 |
| 3 | 171 | −197.00 | .00 |
| 4 | 198 | −187.46 | 9.54 |
| 5 | 27 | −178.68 | 18.32 |
| 6 | 309 | −184.39 | 12.61 |
| 7 | 510 | −185.12 | 11.88 |
| 8 | 616 | −193.92 | 3.08 |
| 9 | 765 | −191.89 | 5.11 |
| 10 | 786 | −189.66 | 7.34 |
| 11 | 792 | −188.74 | 8.26 |
| 12 | 917 | −186.63 | 10.37 |

Conformers in this table were energy-minimized using a dielectric constant of 1, and clustered by calculating all pair-wise RMS differences among structures using least square fitting of all heavy atoms in the molecules. The criterion to cluster the conformers was set to be 2.0 Å for the RMS value. In each cluster, the lowest-energy conformer was selected to represent the cluster. The numbers in the second column were the serial number of the conformer in the cluster. Their potential energy values as calculated using the CHARMM program were listed in the 3rd column. ÄE was calculated as the energy difference between the corresponding conformer and the lowest-energy conformer (global minimum) of all the conformers.

TABLE 4b

Conformer group B of modeled N-Ac-CHAVC-NH$_2$

| No | Conformers | E (kcal mol$^{-1}$) | ÄE (kcal mol$^{-1}$) |
|---|---|---|---|
| 1 | 171 | −197.00 | .00 |
| 2 | 196 | −192.63 | 4.37 |
| 3 | 261 | −181.65 | 15.35 |
| 4 | 296 | −191.68 | 5.32 |
| 5 | 299 | −184.24 | 12.76 |
| 6 | 333 | −187.94 | 9.06 |
| 7 | 351 | −184.56 | 12.44 |
| 8 | 480 | −190.07 | 6.93 |
| 9 | 596 | −180.44 | 16.56 |
| 10 | 62 | −188.86 | 8.14 |
| 11 | 68 | −178.94 | 18.06 |
| 12 | 73 | −181.35 | 15.65 |
| 13 | 754 | −185.70 | 11.30 |
| 14 | 786 | −189.66 | 7.34 |
| 15 | 82 | −180.40 | 16.60 |
| 16 | 916 | −176.08 | 20.92 |

Conformers in this table were energy-minimized using a dielectric constant of 1, and clustered by calculating all pair-wise RMS differences among structures using least square fitting of all heavy atoms in the HAV sequence of the molecules. The criterion to cluster the conformers was set to be 1.5 Å for the RMS value. In each cluster, the lowest-energy conformer was selected to represent the cluster. The numbers in the second column were the serial number of the conformer in the cluster. Their potential energy values as calculated using the CHARMM program were listed in the 3rd column. ÄE was calculated as the energy difference between the corresponding conformer and the lowest-energy conformer (global minimum) of all the conformers.

TABLE 4c

Conformer group C of modeled N-Ac-CHAVC-NH$_2$

| No | Conformers | E (kcal mol$^{-1}$) | ÄE (kcal mol$^{-1}$) |
|---|---|---|---|
| 1 | 168 | −15.52 | .00 |
| 2 | 196 | −14.34 | 1.18 |
| 3 | 301 | −10.00 | 5.52 |
| 4 | 311 | −10.24 | 5.28 |
| 5 | 331 | −12.43 | 3.09 |
| 6 | 389 | −9.25 | 6.27 |
| 7 | 404 | −8.93 | 6.59 |
| 8 | 423 | −12.32 | 3.20 |
| 9 | 617 | −14.48 | 1.04 |
| 10 | 739 | −13.46 | 2.06 |

Conformers in this table were energy-minimized using a dielectric constant of 80, and clustered by calculating all pair-wise RMS differences among structures using least square fitting of all heavy atoms in the molecules. The criterion to cluster the conformers was set to be 2.0 Å for the RMS value. In each cluster, the lowest-energy conformer was selected to represent the cluster. The numbers in the second column were the serial number of the conformer in the cluster. Their potential energy values as calculated using the CHARMM program were listed in the 3rd column. ÄE was caluculated as the energy difference between the corresponding conformer and the lowest-energy conformer (global minimum) of all the conformers.

TABLE 4d

Conformer group D of modeled N-Ac-CHAVC-NH$_2$

| No | Conformers | E (kcal mol$^{-1}$) | ÄE (kcal mol$^{-1}$) |
|---|---|---|---|
| 1 | 13 | −12.14 | 3.38 |
| 2 | 166 | −10.63 | 4.89 |
| 3 | 168 | −15.52 | .00 |
| 4 | 196 | −14.34 | 1.18 |
| 5 | 331 | −12.43 | 3.09 |
| 6 | 344 | −12.34 | 3.18 |
| 7 | 42 | −12.86 | 2.66 |
| 8 | 475 | −14.36 | 1.16 |
| 9 | 617 | −14.48 | 1.04 |
| 10 | 868 | −13.33 | 2.19 |
| 11 | 887 | −10.54 | 4.98 |
| 12 | 979 | −13.86 | 1.66 |
| 13 | 99 | −6.04 | 9.48 |

Conformers in this table were energy-minimized using a dielectric constant of 80, and clustered by calculating all pair-wise RMS differences among structures using least square fitting of all heavy atoms in the HAV sequence of the molecules. The criterion to cluster the conformers was set to be 1.5 Å for the RMS value. In each cluster, the lowest-energy conformer was selected to represent the cluster. The numbers in the second column were the serial number of the conformer in the cluster. Their potential energy values as calculated using the CHARMM program were listed in the 3rd column. ÄE was calculated as the energy difference between the corresponding conformer and the lowest-energy conformer (global minimum) of all the conformers.

In Table 4e, the CHARMM energies of the 3 NMR solution conformations of N—Ac—CHAVC—NH$_2$ (SEQ ID NO:10) are provided. Energies of the three NMR structures of N—Ac—CHAVC—NH$_2$ (SEQ ID NO:10) were first calculated directly without minimization and them with energy minimization. Again both dielectric constant of 1 (to represent a vacuum) and 80 (to represent a water environment) were used. As can be seen, the 3 NMR solution structures have large energy differences. This is likely due to a difference in the force field used in the NMR structure calculations and field. After minimization the 3 structures have similar energies.

TABLE 4e

Energies of the NMR conformers of N-Ac-CHAVC-NH$_2$ (kcal mol$^{-1}$).

| NMR solution structure | As Is | | Minimized | |
|---|---|---|---|---|
| | å = 80 | å = 1 | å = 80 | å = 1 |
| 1 | 15.36 | −138.63 | −11.26 | −184.27 |
| 2 | 9.99 | −143.31 | −11.51 | −179.83 |
| 3 | 44.74 | −117.62 | −13.08 | −185.80 |

Energies of three NMR structures of N-Ac-CHAVC-NH$_2$ (SEQ ID NO: 10) were first calculated, as is, then minimized using CHARMM program. A dielectric constant (å) was used throughout the calculation and set to either 1 to mimic the vacuum environment or 80 to mimic the water environment.

The conformers listed in Table 4a–d were compared to the NMR solution structures of N—Ac—CHAVC—NH$_2$ (SEQ ID NO:10) and the Results Summarized in Tables 5a–d.

TABLE 5a

Comparison between modeled (group A) and NMR structures for N-Ac-CHAVC-NH$_2$ (SEQ ID NO: 10).

| No | NMR Structure 1 | | | NMR Structure 2 | | | NMR Structure 3 | | |
|---|---|---|---|---|---|---|---|---|---|
| | RMS | E | ÄE | RMS | E | ÄE | RMS | E | ÄE |
| 1 | 2.10 | −197.00 | .00 | 2.46 | −187.46 | 9.54 | 2.07 | −193.92 | 3.08 |
| 2 | 2.33 | −178.68 | 18.32 | 2.46 | −178.68 | 18.32 | 2.18 | −184.39 | 12.61 |
| 3 | 2.35 | −193.92 | 3.08 | 2.52 | −197.00 | .00 | 2.33 | −178.68 | 18.32 |
| 4 | 2.37 | −184.39 | 12.61 | 2.55 | −188.74 | 8.26 | 2.41 | −187.46 | 9.54 |
| 5 | 2.43 | −187.46 | 9.54 | 2.59 | −193.92 | 3.08 | 2.48 | −197.00 | .00 |
| 6 | 2.53 | −185.12 | 11.88 | 2.62 | −189.66 | 7.34 | 2.59 | −191.89 | 5.11 |
| 7 | 2.57 | −189.66 | 7.34 | 2.72 | −184.39 | 12.61 | 2.96 | −189.66 | 7.34 |
| 8 | 2.59 | −191.89 | 5.11 | 2.73 | −191.89 | 5.11 | 3.05 | −188.74 | 8.26 |
| 9 | 2.62 | −186.68 | 10.32 | 2.74 | −185.12 | 11.88 | 3.07 | −186.68 | 10.32 |
| 10 | 2.68 | −188.74 | 8.26 | 2.85 | −186.68 | 10.32 | 3.10 | −185.12 | 11.88 |
| 11 | 3.17 | −186.63 | 10.37 | 2.86 | −186.63 | 10.37 | 3.29 | −186.63 | 10.37 |
| 12 | 3.38 | −185.06 | 11.94 | 3.10 | −185.06 | 11.94 | 3.36 | −185.06 | 11.94 |

Conformers in this table were compared to the different NMR solution structures of N—Ac—CHAVC—NH$_2$ (SEQ ID NO:10) RMS values were obtained by comparing all heavy atoms in the molecules using least square fitting. The potential energy values of each conformer (E) and the energy difference (ÄE) between the corresponding conformer and the lowest-energy conformer (global minimum) of all the conformers were also listed in the table.

TABLE 5b

Comparison between modeled (group B) and NMR structures for N-Ac-CHAVC-NH$_2$ (SEQ ID NO: 10).

| No | NMR Structure 1 | | | NMR Structure 2 | | | NMR Structure 3 | | |
|---|---|---|---|---|---|---|---|---|---|
| | RMS | E | ÄE | RMS | E | ÄE | RMS | E | ÄE |
| 1 | 1.34 | −181.65 | 15.35 | 1.45 | −184.24 | 12.76 | 1.35 | −188.86 | 8.14 |
| 2 | 1.56 | −187.94 | 9.06 | 1.74 | −184.56 | 12.44 | 1.44 | −181.65 | 15.35 |
| 3 | 1.61 | −188.86 | 8.14 | 1.84 | −181.65 | 15.35 | 1.44 | −187.94 | 9.06 |
| 4 | 1.64 | −184.24 | 12.76 | 1.86 | −187.94 | 9.06 | 1.48 | −197.00 | .00 |
| 5 | 1.65 | −197.00 | .00 | 1.90 | −197.00 | .00 | 1.68 | −184.56 | 12.44 |
| 6 | 1.71 | −184.56 | 12.44 | 1.91 | −192.63 | 4.37 | 2.00 | −190.07 | 6.93 |
| 7 | 1.85 | −190.07 | 6.93 | 1.98 | −180.40 | 16.60 | 2.30 | −184.24 | 12.76 |
| 8 | 2.20 | −185.70 | 11.30 | 2.07 | −190.07 | 6.93 | 2.45 | −185.70 | 11.30 |
| 9 | 2.27 | −192.63 | 4.37 | 2.08 | −176.08 | 20.92 | 2.53 | −192.63 | 4.37 |
| 10 | 2.28 | −180.44 | 16.56 | 2.13 | −188.86 | 8.14 | 2.61 | −181.35 | 15.65 |
| 11 | 2.28 | −180.40 | 16.60 | 2.23 | −185.70 | 11.30 | 2.64 | −178.94 | 18.06 |
| 12 | 2.35 | −189.66 | 7.34 | 2.29 | −191.68 | 5.32 | 2.65 | −180.44 | 16.56 |
| 13 | 2.46 | −176.08 | 20.92 | 2.33 | −189.66 | 7.34 | 2.74 | −189.66 | 7.34 |
| 14 | 2.53 | −191.68 | 5.32 | 2.37 | −180.44 | 16.56 | 2.81 | −191.68 | 5.32 |
| 15 | 2.57 | −178.94 | 18.06 | 2.40 | −178.94 | 18.06 | 2.85 | −176.08 | 20.92 |
| 16 | 2.69 | −181.35 | 15.65 | 2.62 | −181.35 | 15.65 | 2.88 | −180.40 | 16.60 |

Conformers in this table were compared to the different NMR solution structures of N—Ac—CHAVC—NH$_2$ (SEQ ID NO:10) RMS values were obtained by comparing all heavy atoms the HAV sequence in the molecules using least square fitting. The potential energy values of each conformer (E) and the energy difference (ÄE) between the corresponding conformer and the lowest-energy conformer (global minimum) of all the conformers were also listed in the table.

TABLE 5c

Comparison between modeled (group C) and NMR structures for N-Ac-CHAVC-NH$_2$ (SEQ ID NO: 10).

| No | NMR Structure 1 | | | NMR Structure 2 | | | NMR Structure 3 | | |
|---|---|---|---|---|---|---|---|---|---|
| | RMS | E | ÄE | RMS | E | ÄE | RMS | E | ÄE |
| 1 | 1.85 | −15.52 | .00 | 1.93 | −13.46 | 2.06 | 2.15 | −15.52 | .00 |
| 2 | 2.08 | −13.46 | 2.06 | 2.35 | −15.52 | .00 | 2.26 | −14.48 | 1.04 |

TABLE 5c-continued

Comparison between modeled (group C) and NMR structures for N-Ac-CHAVC-NH$_2$ (SEQ ID NO: 10).

| No | NMR Structure 1 | | | NMR Structure 2 | | | NMR Structure 3 | | |
|---|---|---|---|---|---|---|---|---|---|
| | RMS | E | ÄE | RMS | E | ÄE | RMS | E | ÄE |
| 3 | 2.32 | −12.43 | 3.09 | 2.58 | −14.34 | 1.18 | 2.35 | −12.43 | 3.09 |
| 4 | 2.54 | −14.34 | 1.18 | 2.59 | −12.32 | 3.20 | 2.56 | −14.34 | 1.18 |
| 5 | 2.54 | −14.48 | 1.04 | 2.66 | −14.48 | 1.04 | 2.80 | −13.46 | 2.06 |
| 6 | 2.60 | −9.25 | 6.27 | 2.81 | −12.43 | 3.09 | 2.82 | −8.93 | 6.59 |
| 7 | 2.77 | −12.32 | 3.20 | 2.89 | −10.00 | 5.52 | 3.03 | −9.25 | 6.27 |
| 8 | 2.79 | −10.00 | 5.52 | 2.96 | −9.25 | 6.27 | 3.09 | −10.24 | 5.28 |
| 9 | 2.96 | −8.93 | 6.59 | 2.98 | −10.24 | 5.28 | 3.11 | −10.00 | 5.52 |
| 10 | 3.12 | −10.24 | 5.28 | 3.03 | −8.93 | 6.59 | 3.36 | −12.32 | 3.20 |

Conformers in this table were compared to the different NMR solution structures of N—Ac—CHAVC—NH$_2$ (SEQ ID NO:10) RMS values were obtained by comparing all heavy atoms in the molecules using least square fitting. The potential energy values of each conformer (E) and the energy difference (ÄE) between the corresponding conformer and the lowest-energy conformer (global minimum) of all the conformers were also listed in the table.

TABLE 5d

Comparison between modeled (group D) and NMR structures for N-Ac-CHAVC-NH$_2$ (SEQ ID NO: 10).

| No | NMR Structure 1 | | | NMR Structure 2 | | | NMR Structure 3 | | |
|---|---|---|---|---|---|---|---|---|---|
| | RMS | E | ÄE | RMS | E | ÄE | RMS | E | ÄE |
| 1 | 1.30 | −15.52 | .00 | 1.07 | −13.86 | 1.66 | 1.12 | −15.52 | .00 |
| 2 | 1.38 | −12.43 | 3.09 | 1.49 | −12.86 | 2.66 | 1.42 | −12.43 | 3.09 |
| 3 | 1.47 | −14.36 | 1.16 | 1.50 | −14.36 | 1.16 | 1.84 | −14.34 | 1.18 |
| 4 | 1.68 | −14.48 | 1.04 | 1.71 | −14.48 | 1.04 | 1.88 | −14.36 | 1.16 |
| 5 | 1.78 | −13.86 | 1.66 | 1.75 | −12.43 | 3.09 | 1.92 | −14.48 | 1.04 |
| 6 | 1.87 | −12.86 | 2.66 | 1.81 | −10.54 | 4.98 | 1.99 | −12.86 | 2.66 |
| 7 | 1.92 | −12.34 | 3.18 | 1.90 | −15.52 | .00 | 2.36 | −12.34 | 3.18 |
| 8 | 1.99 | −14.34 | 1.18 | 1.94 | −14.34 | 1.18 | 2.44 | −13.86 | 1.66 |
| 8 | 2.21 | −10.54 | 4.98 | 1.96 | −12.34 | 3.18 | 2.51 | −10.54 | 4.98 |
| 10 | 2.31 | −13.33 | 2.19 | 2.00 | −13.33 | 2.19 | 2.70 | −10.63 | 4.89 |
| 11 | 2.37 | −10.63 | 4.89 | 2.02 | −10.63 | 4.89 | 2.78 | −12.14 | 3.38 |
| 12 | 2.67 | −12.14 | 3.38 | 2.28 | −12.14 | 3.38 | 2.87 | −13.33 | 2.19 |
| 13 | 2.71 | −6.04 | 9.48 | 2.31 | −6.04 | 9.48 | 3.12 | −6.04 | 9.48 |

Conformers in this table were compared to the different NMR solution structures of N—Ac—CHAVC—NH$_2$ (SEQ ID NO:10) RMS values were obtained by comparing all heavy atoms in the HAV sequence in the molecules using least square fitting. The potential energy values of each conformer (E) and the energy difference (ÄE) between the corresponding conformer and the lowest-energy conformer (global minimum) of all the conformers were also listed in the table.

As can be seen from Table 5a, the RMS values of the modeled structure with the lowest energy compared to the 3 NMR solution structures using all the heavy atoms in the structures are 2.10, 2.52, and 2.48 Å, respectively. The lowest RMS values of the modeled structures compared to the 3 NMR solution structures are 2.10, 2.46, and 2.07 Å, respectively. These results indicate that the modeled structures when using a dielectric constant of 1 during the minimization process have a reasonable agreement with the NMR solution structures for N—Ac—CHAVC—NH$_2$ (SEQ ID NO:10).

From our structure-activity relationship studies, it is known that the HAV residues in N—Ac—CHAVC—NH$_2$ (SEQ ID NO:10) likely represent the most crucial binding elements. Therefore, it is probably more meaningful to compare the modeled structures with the NMR solution structures using the HAV residues only. As can be seen from Table 5b, the RMS values of the modeled structure with the lowest energy compared to the 3 NMR solution structures using the heavy atoms in the HAV residues are 1.65, 1.90, and 1.48 Å, respectively. The lowest RMS values of the modeled structures compared to the 3 NMR solution structures are 1.34, 1.45, and 1.35 Å, respectively. These results indicate that the HAV residues of the modeled structures superimpose on the HAV residues of the NMR solution structures very well.

A dielectric constant of 1 mimics the vacuum environment but the NMR structures of the peptide was determined in aqueous solution. To mimic the aqueous solution environment, a dielectric constant of 80 was used in energy-minimization. As can be seen from Table 5c, the RMS values of the modeled structure with the lowest energy compared to the 3 NMR solution structures using all the heavy atoms in the structures are 1.85, 2.35, and 2.15 Å, respectively. The lowest RMS values of the modeled structures compared to the 3 NMR solution structures are 1.85, 1.93, and 2.15 Å, respectively. As compared to Table 5a, the modeled structures using a dielectric constant of 80 during minimization are overall more similar to the NMR solution structures than the modeled structures using a dielectric constant of 1 during minimization. As can be seen from Table 5d, the RMS values of the modeled structure with the lowest energy compared to the 3 NMR solution structures using the heavy atoms in the HAV residues are 1.30, 1.90, and 1.12 Å, respectively. The lowest RMS values of the modeled structures compared to the 3 NMR solution structures are 1.30, 1.07, and 1.12 Å, respectively. These results showed that conformations of the HAV residues between modeled structures using a dielectric constant of 80 during minimization and the NMR solution structures are very similar.

In summary, the modeled structures of N—Ac—CHAVC—NH$_2$ (SEQ ID NO:10) are similar to the NMR solution structures and more similar structures were obtained when a dielectric constant of 80 was used in minimization. Therefore, for modeling of the thioether analogues a dielectric constant of 80 was employed for all the energy-minimizations.

Figure 24A:
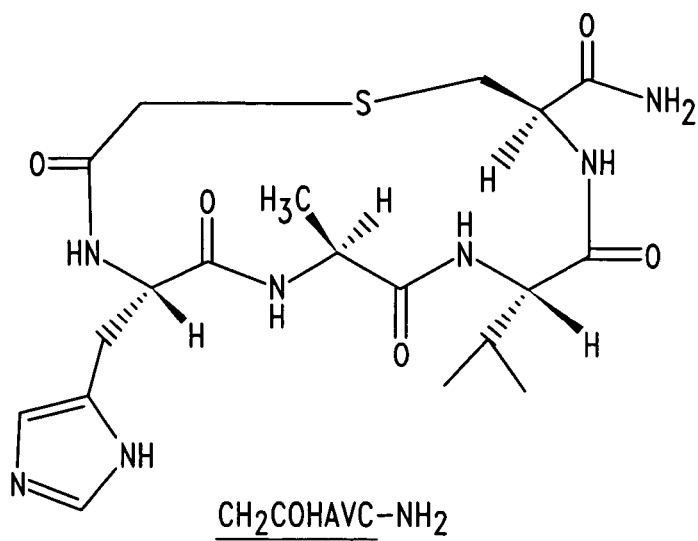
FIGS. 24A–24C shows the structures of thioether analogues of N—Ac—CHAVC—NH$_2$. (SEQ ID NO:10).
Figure 24B:
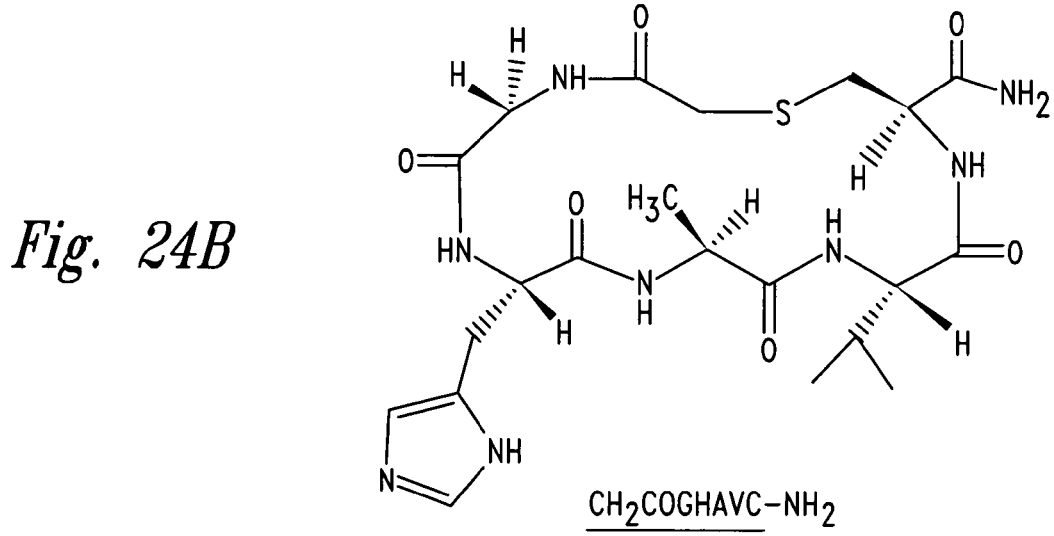
Figure 24C:
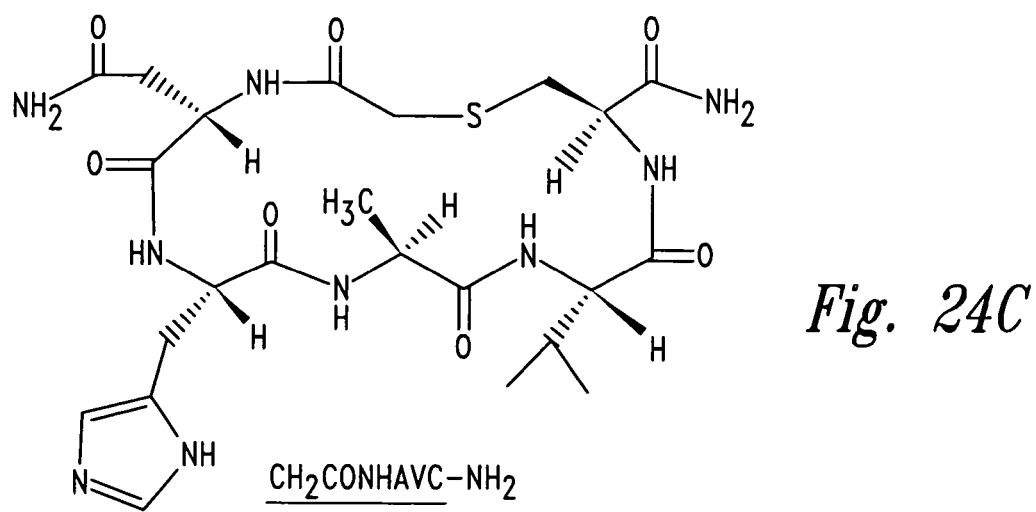

Based on the modeling results obtained for N—Ac—CHAVC—NH$_2$ (SEQ ID NO:10), it was believed that reasonably accurate solution structures of the thioethers depicted in FIGS. 24A–C (CH$_2$COHAVC—NH$_2$ (SEQ ID NO:94) could be obtained using a molecular modeling approach. The results should be more accurate when a dielectric constant of 80 is used in minimization. Therefore, using the same protocol (HTMD, minimization using a dielectric constant of 80, followed by cluster analysis), the conformations of 3 thioether analogs (FIGS. 24A–C) of N—Ac—CHAVC—NH$_2$ (SEQ ID NO:10) have been studied in an effort to improve compound stability while still retaining the activity.

Figure 25A:
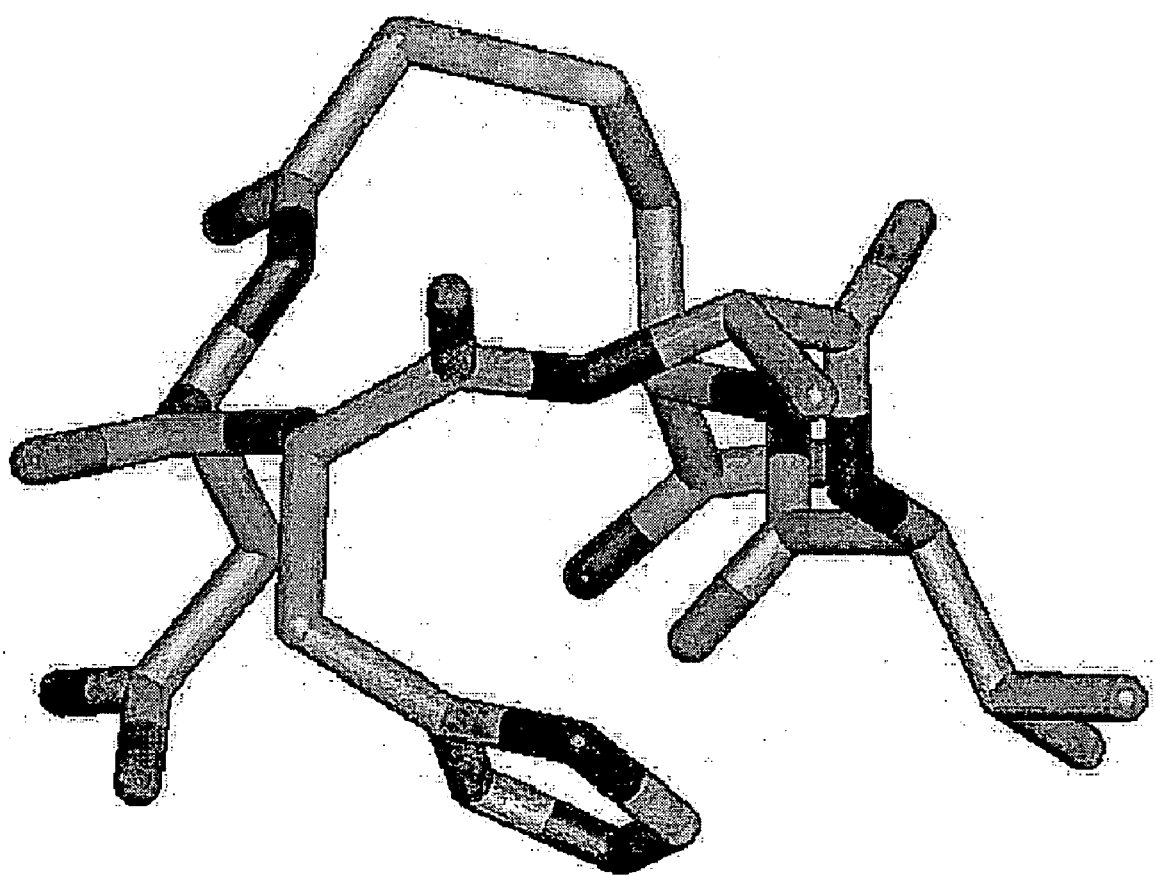
FIG. 25A depicts the lowest energy conformation of CH$_2$COHAVC—NH$_2$.(SEQ ID NO:94).
Figure 25B:
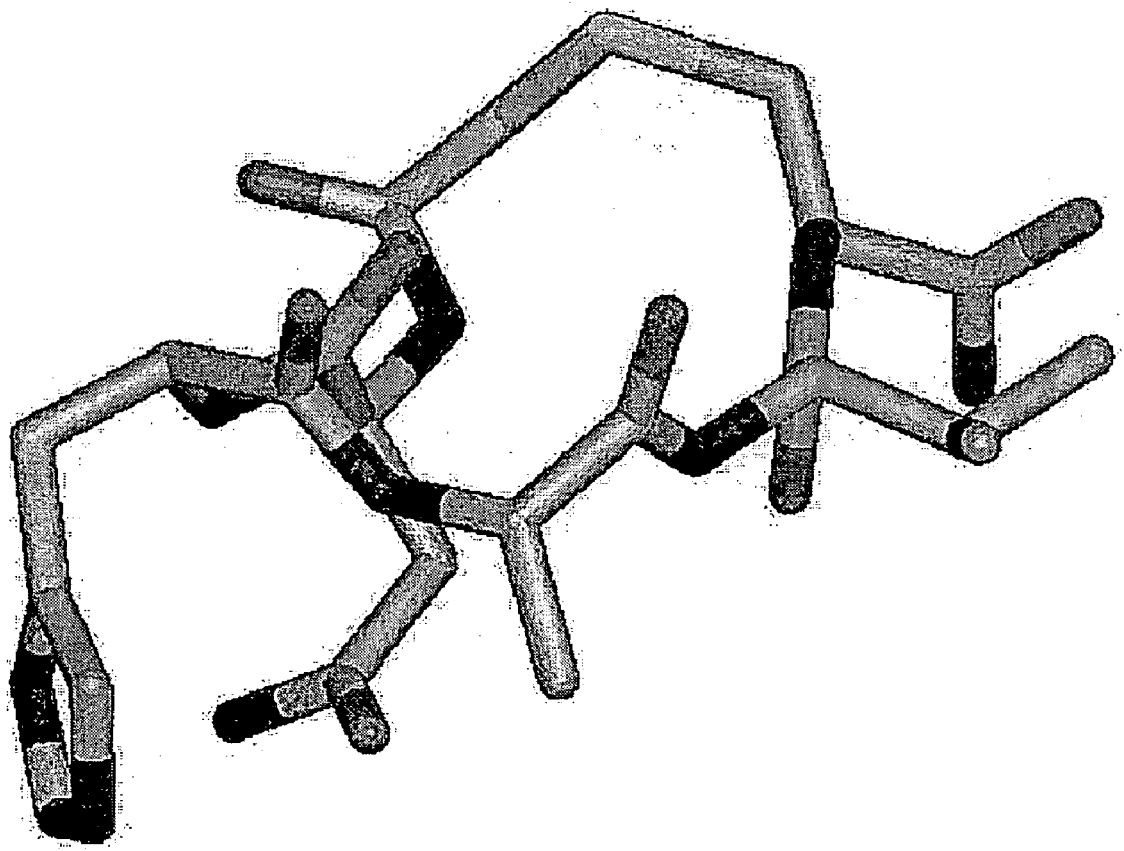
FIG. 25B depicts the conformation of CH$_2$COHAVC—NH$_2$ (SEQ ID NO:94) with the lowest RMS deviation from solution 3D conformations of N—Ac—CHAVC—NH$_2$ (SEQ ID NO:10) depicted in FIGS. 7A and 7B.
Figure 25C:
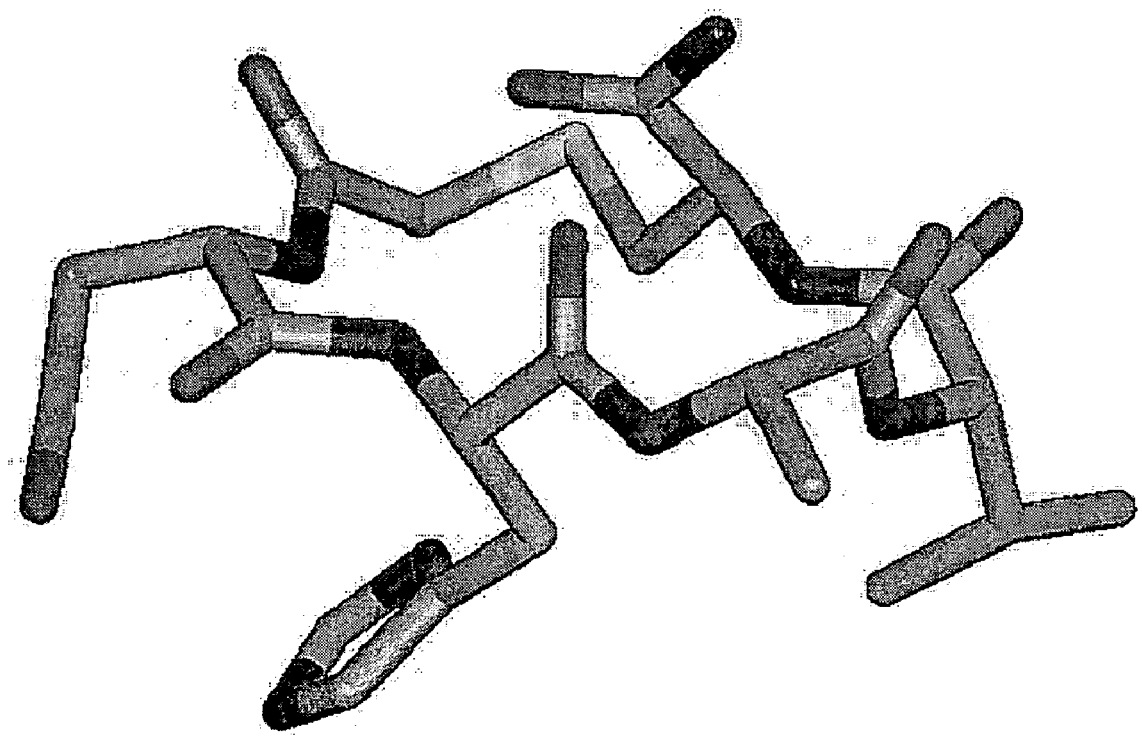
FIG. 25C depicts the conformation of CH$_2$COHAVC—NH$_2$ (SEQ ID NO:94) with the lowest RMS deviation from the solution 3D conformation of N—Ac—CHAVC—NH$_2$ (SEQ ID NO:10) depicted in FIG. 7C.

All the heavy atoms in the HAV residues were used for the calculation of the pair-wise RMS value between two structures and the threshold value for the RMS used was set as 1.5 Å. A total of 11 conformational clusters were obtained for CH$_2$COHAVC—NH$_2$ (SEQ ID NO:94) The conformer number of each representative conformation for each cluster, the potential energy for each representative conformation, and the energy difference between each conformer and the conformer with the lowest energy are provided in Table 6. The results of structural comparison between these 11 conformers for CH$_2$COHAVC—NH$_2$ (SEQ ID NO:94) and N—Ac—CHAVC—NH$_2$ (SEQ ID NO:10) are provided in Table 7. As can be seen, the RMS values between the conformer with the lowest energy and the 3 NMR solution structures of N—Ac—CHAVC—NH$_2$ (SEQ ID NO:10) using all the heavy atoms in the HAV residues are 1.42, 1.89 and 1.26 Å, respectively. The structure of the global minimum of CH$_2$COHAVC—NH$_2$ (SEQ ID NO:94) is shown in FIG. 25a. The best RMS values between all the 11 conformers and the 3 NMR solution structures of N—Ac—CHAVC—NH$_2$ (SEQ ID NO:10) using all the heavy atoms in the HAV residues are 1.12, 0.85, 0.98 Å, respectively. The structures with best RMS values are shown in FIGS. 25B and 25C, respectively. It is of note that the conformers with best RMS values don't have much higher potential energies, all within 2.0 kcal/mol from the global minimum. These results suggest that the structures of thioether CH$_2$COHAVC—NH$_2$ (SEQ ID NO:94) have reasonably good overlaps with the 3 solution structures of N—Ac—CHAVC—NH$_2$ (SEQ ID NO:10) in terms of the conformation of the HAV residues and indicate that CH$_2$COHAVC—NH$_2$ (SEQ ID NO:94) may be a good mimetic of N—Ac—CHAVC—NH$_2$ (SEQ. ID NO:10).

TABLE 6

Energies of the conformers of the thioether CH$_2$COHAVC-NH$_2$ (kcal mol$^{-1}$)

| No | Conformers | E | ÄE |
|---|---|---|---|
| 1 | 50 | −5.38 | 3.15 |
| 2 | 502 | −1.38 | 7.15 |
| 3 | 579 | −6.85 | 1.68 |
| 4 | 594 | −7.86 | .67 |
| 5 | 768 | −7.80 | .73 |
| 6 | 78 | −8.53 | .00 |
| 7 | 793 | −5.00 | 3.53 |
| 8 | 805 | 0.75 | 9.28 |
| 9 | 9 | −5.38 | 3.15 |
| 10 | 908 | −3.78 | 4.75 |
| 11 | 931 | −7.46 | 1.07 |

Conformers in this table were energy-minimized using a dielectric constant of 80, and clustered by calculating all pair-wise RMS differences among structures using least square fitting of all heavy atoms in the HAV sequence in the molecules. The criterion to cluster the conformers was set to be 1.5 Å for the RMS value. In each cluster, the lowest-energy conformer was selected to represent the cluster. The numbers in the second column were the serial number of the conformer in the cluster. Their potential energy values as calculated using the CHARMM program were listed in the 3rd column. ÄE was calculated as the energy difference between the corresponding conformer and the lowest-energy conformer (global minimum) of all the conformers.

TABLE 7

Comparison between modeled thioether CH$_2$COHAVC-NH$_2$ (SEQ ID NO: 94) and NMR structures of N-Ac-CHAVC-NH$_2$ (SEQ ID NO: 10).

| | NMR Structure 1 | | | NMR Structure 2 | | | NMR Structure 3 | | |
|---|---|---|---|---|---|---|---|---|---|
| No | RMS | E | ÄE | RMS | E | ÄE | RMS | E | ÄE |
| 1 | 1.86 | −5.38 | 3.15 | 1.36 | −5.38 | 3.15 | 2.21 | −5.38 | 3.15 |
| 2 | 2.43 | −1.38 | 7.15 | 2.11 | −1.38 | 7.15 | 2.42 | −1.38 | 7.15 |
| 3 | 1.12 | −6.85 | 1.68 | 0.85 | −6.85 | 1.68 | 1.40 | −6.85 | 1.68 |
| 4 | 1.25 | −7.86 | .67 | 1.77 | −7.86 | .67 | 0.98 | −7.86 | .67 |
| 5 | 1.50 | −7.80 | .73 | 1.28 | −7.80 | .73 | 1.67 | −7.80 | .73 |
| 6 | 1.42 | −8.53 | .00 | 1.89 | −8.53 | .00 | 1.26 | −8.53 | .00 |
| 7 | 2.50 | −5.00 | 3.53 | 2.17 | −5.00 | 3.53 | 2.80 | −5.00 | 3.53 |
| 8 | 1.93 | 0.75 | 9.28 | 1.53 | 0.75 | 9.28 | 2.20 | 0.75 | 9.28 |
| 9 | 1.99 | −5.38 | 3.15 | 1.34 | −5.38 | 3.15 | 2.37 | −5.38 | 3.15 |
| 10 | 1.52 | −3.78 | 4.75 | 1.39 | −3.78 | 4.75 | 1.75 | −3.78 | 4.75 |
| 11 | 1.31 | −7.46 | 1.07 | 1.64 | −7.46 | 1.07 | 1.43 | −7.46 | 1.07 |

Conformers in this table were compared to the different NMR solution structures of N—Ac—CHAVC—NH$_2$ (SEQ ID NO:10) RMS values were obtained by comparing all heavy atoms in the HAV sequence in the molecules using least square fitting. The potential energy values of each conformer (E) and the energy difference (ÄE) between the corresponding conformer and the lowest-energy conformer (global minimum) of all the conformers were also listed in the table.

For the second thioether analogue CH$_2$COGHAVC—NH$_2$ (SEQ ID NO:95), a total of 13 conformational clusters were obtained. The conformer number of each representative conformation for each cluster, the potential energy for each representative conformation, and the energy difference between each conformer and the conformer with the lowest energy are provided in Table 8. The results of structural comparison between these 13 conformers for CH$_2$COGHAVC—NH$_2$ (SEQ ID NO:95) and N—Ac—

Figure 26A:
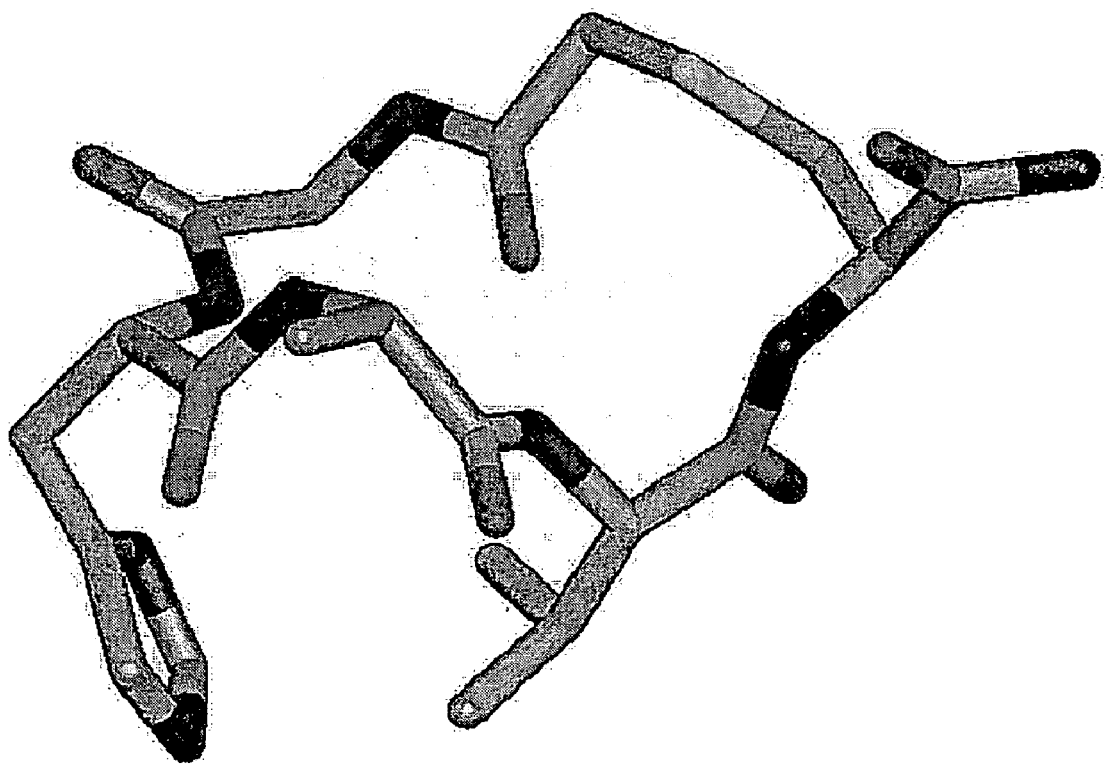
FIG. 26A depicts the lowest energy conformation of CH$_2$COGHAVC—NH$_2$ (SEQ ID NO:95).
Figure 26B:
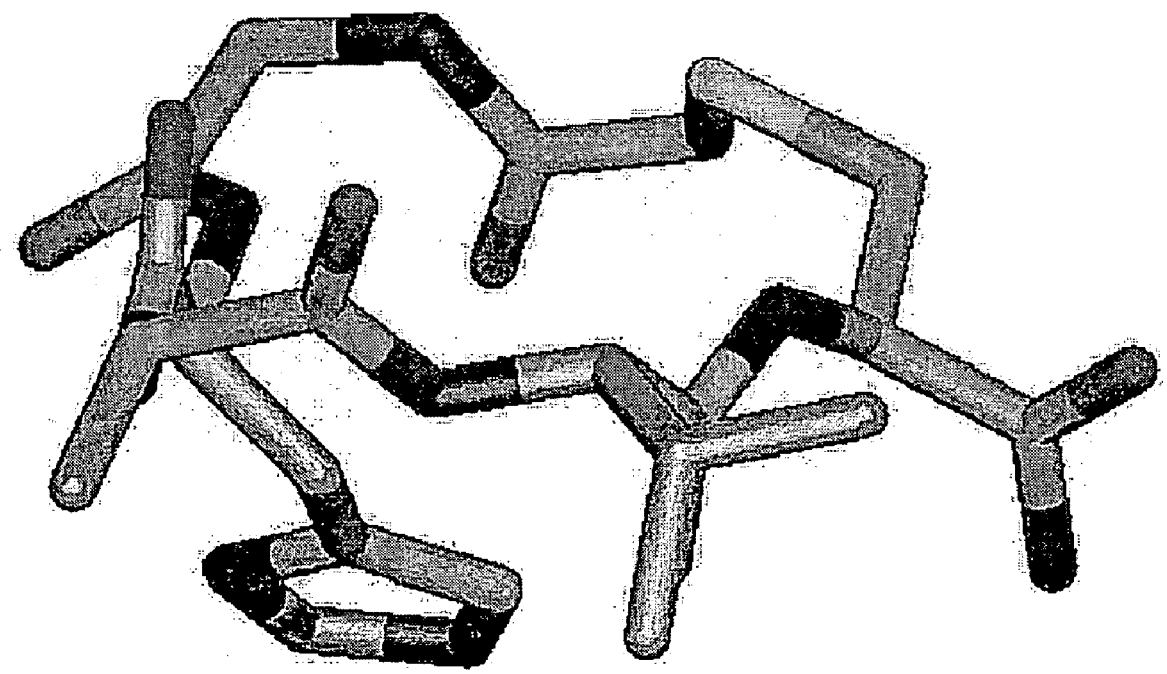
FIG. 26B depicts the conformation of CH$_2$COGHAVC—NH$_2$ (SEQ ID NO:95) with the lowest RMS deviation from solution 3D conformations of N—Ac—CHAVC—NH$_2$ (SEQ ID NO:10) depicted in FIGS. 7A and 7B.
Figure 26C:
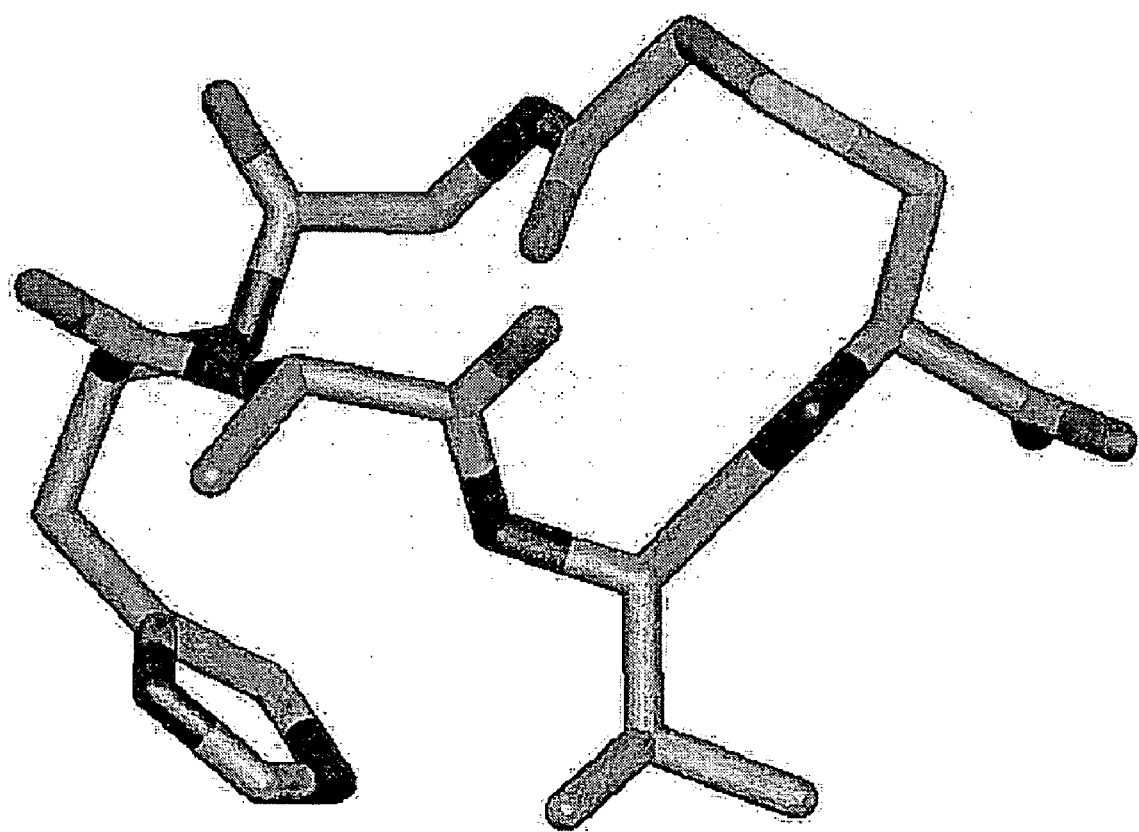
FIG. 26C depicts the conformation of CH$_2$COGHAVC—NH$_2$ (SEQ ID NO:95) with the lowest RMS deviation from the solution 3D conformation of N—Ac—CHAVC—NH$_2$ (SEQ ID NO:10) as depicted in FIG. 7C.

CHAVC—NH₂ (SEQ ID NO:10) are provided in Table 9. As can be seen, the RMS values between the conformer with the lowest energy and the 3 NMR solution structures of N—Ac—CHAVC—NH₂ (SEQ ID NO:10) using all the heavy atoms in the HAV residues are 1.40, 1.85 and 1.18 Å, respectively. The structure of the global minimum of CH₂COGHAVC—NH₂ (SEQ ID NO:95) is shown in FIG. 26A. The best RMS values between all the 13 conformers and the 3 NMR solution structures of N—Ac—CHAVC—NH₂ (SEQ ID NO:10) using all the heavy atoms in the HAV residues are 1.21, 0.95 and 0.95 Å, respectively. The structures with best RMS values are shown in FIGS. 26B and 26C, respectively. These conformers with best RMS values don't have much higher potential energies, all within 4.0 kcal/mol from the global minimum. These results suggest that the structures of thioether CH₂COGHAVC—NH₂ (SEQ ID NO:95) also have reasonably good overlaps with the 3 solution structures of N—Ac—CHAVC—NH₂ (SEQ ID NO:10) in terms of the conformation of the HAV residues and indicate that CH₂COGHAVC—NH₂ (SEQ ID NO:95) may be a good mimetic of N—Ac—CHAVC—NH₂ (SEQ ID NO:10).

TABLE 8

Energies of the conformers of the thioether CH₂COGHAVC-NH₂ (kcal mol⁻¹)

| No | Conformers | E | ÄE |
| --- | --- | --- | --- |
| 1 | 1 | −11.51 | 1.16 |
| 2 | 132 | −12.67 | .00 |
| 3 | 229 | −10.91 | 1.76 |
| 4 | 293 | −10.09 | 2.58 |
| 5 | 31 | −10.21 | 2.46 |
| 6 | 429 | −10.74 | 1.93 |
| 7 | 506 | −10.41 | 2.26 |
| 8 | 566 | −11.85 | .82 |
| 9 | 69 | −9.07 | 3.60 |
| 10 | 699 | −9.44 | 3.23 |
| 11 | 712 | −12.00 | .67 |
| 12 | 774 | −10.76 | 1.91 |
| 13 | 976 | −10.66 | 2.01 |

Conformers in this table were energy-minimized using a dielectric constant of 80, and clustered by calculating all pair-wise RMS differences among structures using least square fitting of all heavy atoms in the HAV sequence in the molecules. The criterion to cluster the conformers was set to be 1.5 Å for the RMS value. In each cluster, the lowest-energy conformer was selected to represent the cluster. The numbers in the second column were the serial number of the conformer in the cluster. Their potential energy values as calculated using the CHARMM program were listed in the 3rd column. ÄE was calculated as the energy difference between the corresponding conformer and the lowest-energy conformer (global minimum) of all the conformers.

TABLE 9

Comparison between modeled thioether CH₂COGHAVC-NH₂ (SEQ ID NO: 95) and NMR structures of N-Ac-CHAVC-NH₂ (SEQ ID NO: 10).

| | NMR Structure 1 | | | NMR Structure 2 | | | NMR Structure 3 | | |
| --- | --- | --- | --- | --- | --- | --- | --- | --- | --- |
| No | RMS | E | ÄE | RMS | E | ÄE | RMS | E | ÄE |
| 1 | 1.34 | −11.51 | 1.16 | 1.63 | −11.51 | 1.16 | 0.95 | −11.51 | 1.16 |
| 2 | 1.40 | −12.67 | .00 | 1.85 | −12.67 | .00 | 1.18 | −12.67 | .00 |
| 3 | 2.38 | −10.91 | 1.76 | 2.14 | −10.91 | 1.76 | 2.57 | −10.91 | 1.76 |
| 4 | 1.47 | −10.09 | 2.58 | 1.75 | −10.09 | 2.58 | 1.21 | −10.09 | 2.58 |
| 5 | 1.46 | −10.21 | 2.46 | 1.92 | −10.21 | 2.46 | 1.40 | −10.21 | 2.46 |
| 6 | 1.91 | −10.74 | 1.93 | 1.85 | −10.74 | 1.93 | 2.19 | −10.74 | 1.93 |
| 7 | 1.92 | −10.41 | 2.26 | 1.52 | −10.41 | 2.26 | 2.29 | −10.41 | 2.26 |
| 8 | 1.52 | −11.85 | .82 | 1.05 | −11.85 | .82 | 1.74 | −11.85 | .82 |
| 9 | 1.21 | −9.07 | 3.60 | 0.95 | −9.07 | 3.60 | 1.47 | −9.07 | 3.60 |
| 10 | 2.64 | −9.44 | 3.23 | 2.31 | −9.44 | 3.23 | 2.68 | −9.44 | 3.23 |
| 11 | 1.88 | −12.00 | .67 | 1.35 | −12.00 | .67 | 2.17 | −12.00 | .67 |
| 12 | 1.79 | −10.76 | 1.91 | 1.78 | −10.76 | 1.91 | 2.07 | −10.76 | 1.91 |
| 13 | 2.02 | −10.66 | 2.01 | 2.10 | −10.66 | 2.01 | 2.39 | −10.66 | 2.01 |

Conformers in this table were compared to the different NMR solution structures of N—Ac—CHAVC—NH₂ (SEQ ID NO:10) RMS values were obtained by comparing all heavy atoms in the HAV sequence in the molecules using least square fitting. The potential energy values of each conformer (E) and the energy difference (ÄE) between the corresponding conformer and the lowest-energy conformer (global minimum) of all the conformers were also listed in the table.

Figure 27A:
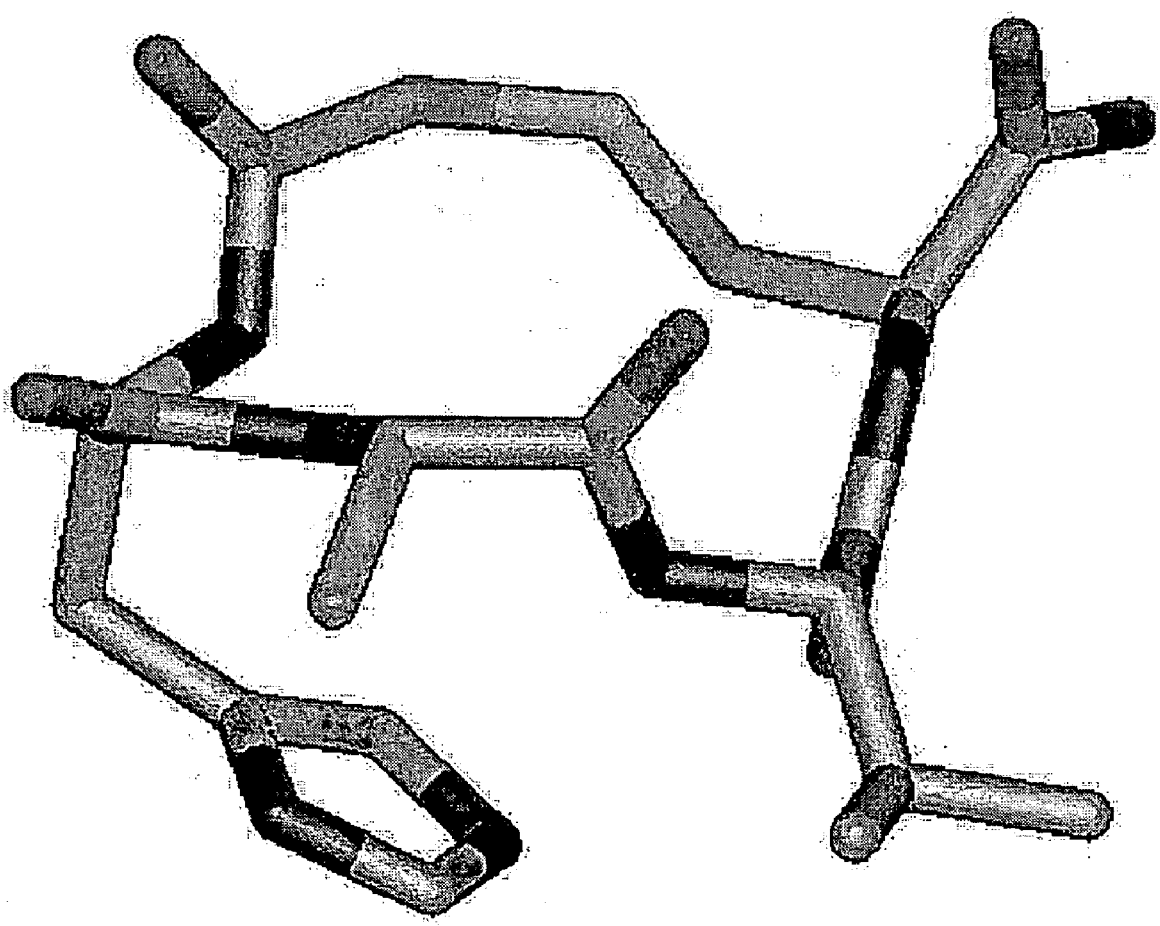
FIG. 27A depicts the lowest energy conformation of CH$_2$CONHAVC—NH$_2$ (SEQ ID NO:96) which also has the lowest RMS deviation from the solution 3D conformation of N—Ac—CHAVC—NH$_2$ (SEQ ID NO:10) as depicted in FIG. 7B.
Figure 27B:
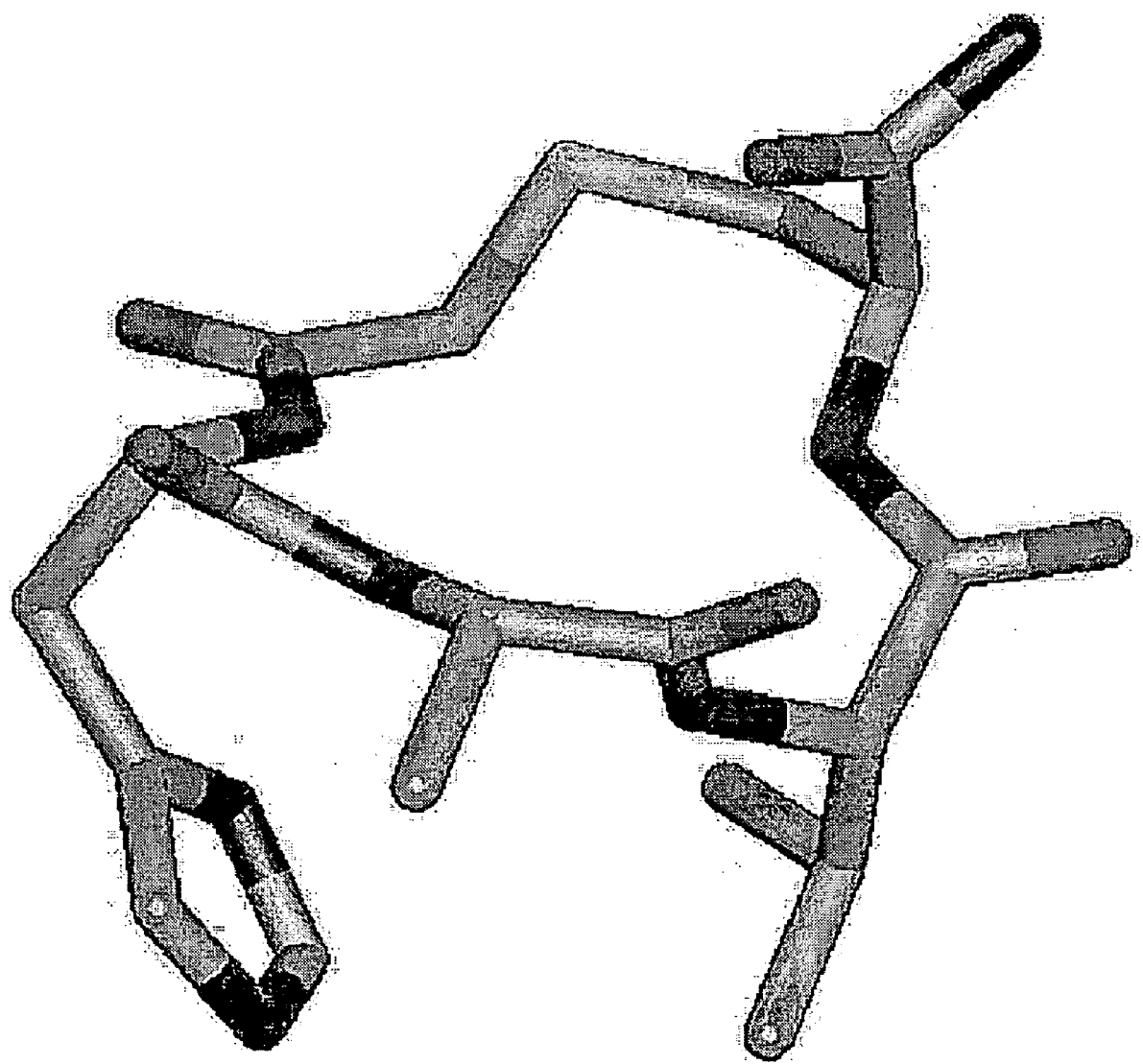
FIG. 27B depicts the conformation of CH$_2$CONHAVC—NH$_2$ (SEQ ID NO:96) with the lowest RMS deviation from solution 3D conformations of N—Ac—CHAVC—NH$_2$ (SEQ ID NO:10) depicted in FIG. 7A.
Figure 27C:
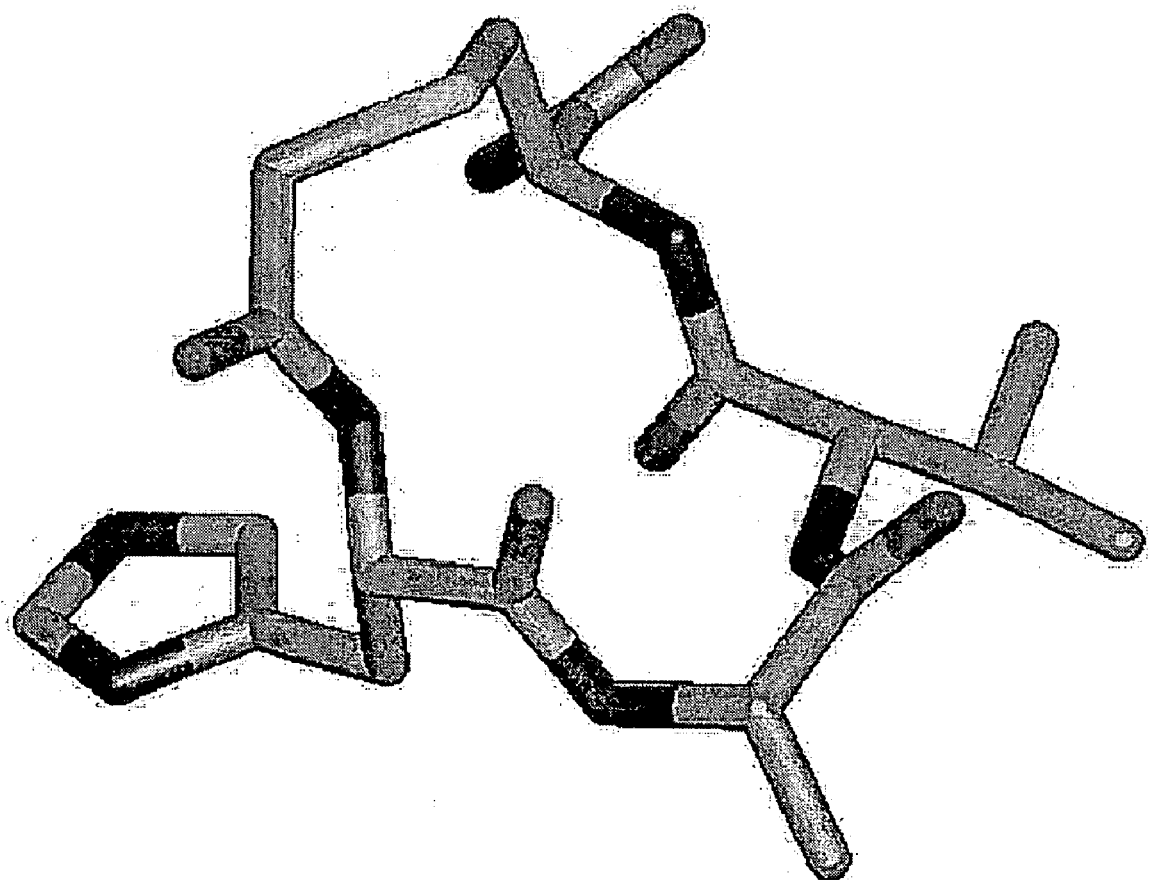
FIG. 27C depicts the conformation of CH$_2$COHAVC—NH$_2$ (SEQ ID NO:96) with the lowest RMS deviation from the solution 3D conformation of N—Ac—CHAVC—NH$_2$ (SEQ ID NO:10) as depicted in FIG. 7C.

For CH₂COHAVC—NH₂ (SEQ ID NO:96), a total of 12 conformational clusters were obtained. The conformer number of each representative conformation for each cluster, the potential energy for each representative conformation, and the energy difference between each conformer and the conformer with the lowest energy are provided in Table 10. The results of structural comparison between these 12 conformers for CH₂COHAVC—NH₂ (SEQ ID NO:96) and N—Ac—CHAVC—NH₂ (SEQ ID NO:10) are provided in Table 11. As can be seen, the RMS values between the conformer with the lowest energy and the 3 NMR solution structures of N—Ac—CHAVC—NH₂ (SEQ ID NO:10) using all the heavy atoms in the HAV residues are 1.25, 1.20 and 1.28 Å, respectively. The structure of the global minimum of CH₂COHAVC—NH₂ (SEQ ID NO:96) is shown in FIG. 27A. The best RMS values between all the 12 conformers and the 3 NMR solution structures of N—Ac—CHAVC—NH₂ (SEQ ID NO:10) using all the heavy atoms in the HAV residues are 1.18, 1.20 and 1.24 Å, respectively. The structures with best RMS values are shown in FIGS. 27B and 27C, respectively. These conformers with best RMS values don't have much higher potential energies, all within 2.0 kcal/mol from the global minimum. It is of note that for CH$_2$COHAVC—NH$_2$ (SEQ ID NO:96), the global minimum has an RMS value, either the best or very close to the best, in comparison to the 3 NMR solution structures. These results suggest that the structures of thioether CH$_2$COHAVC—NH$_2$ (SEQ ID NO:96) also have reasonably good overlaps with the 3 solution structures of peptide #1 in terms of the conformation of the HAV residues and indicate that CH$_2$COHAVC—NH$_2$ (SEQ ID NO:96) may be a good mimetic of N—Ac—CHAVC—NH$_2$.(SEQ ID NO:10).

In summary, these 3 analogs all have reasonably good structural overlaps with the 3 NMR solution structures of N—Ac—CHAVC—NH$_2$ (SEQ ID NO:10) in terms of the HAV conformation, suggesting that they may also be able to achieve similar activity to N—Ac—CHAVC—NH$_2$ (SEQ ID NO:10).

TABLE 10

Energies of the conformers of the thioether CH$_2$CONHAVC-NH$_2$ (SEQ ID NO:96) (kcal mol$^{-1}$).

| No | Conformers | E | ÄE |
|---|---|---|---|
| 1 | 102 | −6.11 | 7.23 |
| 2 | 130 | −12.11 | 1.23 |
| 3 | 143 | −13.34 | .00 |
| 4 | 297 | −11.58 | 1.76 |
| 5 | 312 | −12.42 | .92 |
| 6 | 455 | −10.84 | 2.50 |
| 7 | 769 | −9.48 | 3.86 |
| 8 | 796 | −11.50 | 1.84 |
| 9 | 886 | −8.56 | 4.78 |
| 10 | 941 | −8.66 | 4.68 |
| 11 | 959 | −12.95 | .39 |
| 12 | 97 | −7.48 | 5.86 |

Conformers in this table were energy-minimized using a dielectric constant of 80, and clustered by calculating all pair-wise RMS differences among structures using least square fitting of all heavy atoms in the HAV sequence in the molecules. The criterion to cluster the conformers was set to be 1.5 Å for the RMS value. In each cluster, the lowest-energy conformer was selected to represent the cluster. The numbers in the second column were the serial number of the conformer in the cluster. Their potential energy values as calculated using the CHARMM program were listed in the 3rd column. ÄE was calculated as the energy difference between the corresponding conformer and the lowest-energy conformer (global minimum) of all the conformers.

TABLE 11

Comparison between modeled thioether $\underline{CH_2CONHAVC}$-$NH_2$ (SEQ ID NO: 96) and NMR structures of N-Ac-CHAVC-$NH_2$ (SEQ ID NO: 10).

| | NMR Structure 1 | | | NMR Structure 2 | | | NMR Structue 3 | | |
|---|---|---|---|---|---|---|---|---|---|
| No | RMS | E | ÄE | RMS | E | ÄE | RMS | E | ÄE |
| 1 | 2.12 | −6.11 | 7.23 | 1.97 | −6.11 | 7.23 | 2.50 | −6.11 | 7.23 |
| 2 | 1.18 | −12.11 | 1.23 | 1.35 | −12.11 | 1.23 | 1.65 | −12.11 | 1.23 |
| 3 | 1.25 | −13.34 | .00 | 1.20 | −13.34 | .00 | 1.28 | −13.34 | .00 |
| 4 | 1.94 | −11.58 | 1.76 | 1.35 | −11.58 | 1.76 | 2.26 | −11.58 | 1.76 |
| 5 | 2.30 | −12.42 | .92 | 1.89 | −12.42 | .92 | 2.59 | −12.42 | .92 |
| 6 | 1.74 | −10.84 | 2.50 | 1.93 | −10.84 | 2.50 | 1.37 | −10.84 | 2.50 |
| 7 | 1.87 | −9.48 | 3.86 | 1.87 | −9.48 | 3.86 | 1.89 | −9.48 | 3.86 |
| 8 | 1.97 | −11.50 | 1.84 | 1.53 | −11.50 | 1.84 | 2.27 | −11.50 | 1.84 |
| 9 | 2.64 | −8.56 | 4.78 | 2.30 | −8.56 | 4.78 | 2.71 | −8.56 | 4.78 |
| 10 | 2.18 | −8.66 | 4.68 | 2.03 | −8.66 | 4.68 | 2.45 | −8.66 | 4.68 |
| 11 | 1.41 | −12.95 | .39 | 1.90 | −12.95 | .39 | 1.24 | −12.95 | .39 |
| 12 | 2.66 | −7.48 | 5.86 | 2.62 | −7.48 | 5.86 | 2.87 | −7.48 | 5.86 |

Conformers in this table were compared to the different NMR solution structures of N—Ac—CHAVC—$NH_2$ (SEQ ID NO:10) RMS values were obtained by comparing all heavy atoms in the HAV sequence in the molecules using least square fitting. The potential energy values of each conformer (E) and the energy difference (ÄE) between the corresponding conformer and the lowest-energy conformer (global minimum) of all the conformers were also listed in the table.

EXAMPLE 9

Synthesis of Thioether Analogues of N—Ac—CHAVC—$NH_2$

The solid phase synthesis of the three thioether analogues of N—Ac—CHAVC—$NH_2$ was using Fmoc chemistry on a Rink amide AM resin (4-(2',4'-Dimethoxyphenyl-Fmoc-aminomethyl)-phenoxyacetamidoaminomethyl, 0.65 meq/g, 1% DVB Grain size 200–400 mesh). In the synthesis of all analogues the cysteine and the imidazole group of the histidine residue are protected with the triphenylmethyl group (trityl). For the analogue containing-asparagine, the side chain is also protected with the trityl group. Two coupling procedures were used for the addition of each amino acid to ensure complete coupling (DIC (N,N'-diisopropylcarbodiimide) and HBTU (O-(benzotriazol-1-yl)-N,N,N',N'-tetramethyluronium hexaflurophosphate)). The coupling reactions were initiated by adding a solution (1.170 mL) containing 6 equivalents each of the amino acid to a suspension of the resin in NMP (1.00 mL). This was followed by the addition of 6 equivalents of HOBt (0.390 mL) and DIC (1.170 mL) solutions. The suspension was mixed for one hour and the resin wash with DMF. The HBTU coupling reaction was initiated by adding a solution (1.170 mL) containing 6 equivalents each of the amino acid to a suspension of the resin in NMP (1.00 mL) followed by the addtion of 6 equivalents of the HBTU contain (6 equivalents of HOBt solution) (1.170 mL) and 12 equivalents of DIPEA (0.584 mL). The suspension was stirred for 30 minutes and them washed. After removal of the final Fmoc protecting group, the resin was coupled to bromoaceticacid. The coupling reaction to bromoacetic acid was initiated by the addition of 4 equivalents of bromoacetic acid (1.170 mL, in 25% DCM/DMF) and 8 equivalents of DIC (1.170 mL, in NMP) to a suspension of the resin in NMP (1.00 mL). The suspension was mixed for two hours and then washed with DMF and methanol. Cleavage from the resin was carried out by suspending the resin in a cleavage cocktail (10 mL, consisting of 5% TES (triethyl silane) in TFA) with occasional shaking for 4 hours. The resin was then filtered and washed with dichloromethane. The solvent volume was reduced under vacuum (water aspirator) to approximately 2 mL and the crude product precipitated with the addition of cold ether. This cleavage procedure removes all protecting groups and provide crude linear products. A solution of the crude linear peptide was added dropwise to a stirring solution (250 mL) of water pH 8.0 (20% aqueous solution of triethylamine was used to adjust the pH using a pH meter). While adding the peptide, the pH of the solution was adjusted to be around 8 using the same 20% aqueous solution of triethylamine. After the addition of all the peptide the solution was kept stirring at pH 8 and the cyclization was monitored by HPLC. Upon completion of the cyclization, the solution was acidified with acetic acid and lyophilized. The crude cyclic product was purified by gel filtration followed by HPLC.

What is claimed is:

1. A method for modulating cellular adhesion, comprising contacting a cell with a cell adhesion modulating agent that is compound 13 of FIG. 15A.

2. The method according to claim 1, wherein the cell adhesion modulating agent inhibits cell adhesion.

3. The method according to claim 1, wherein the cell adhesion modulating agent is present within a composition comprising a physiologically acceptable carrier.

* * * * *

UNITED STATES PATENT AND TRADEMARK OFFICE
CERTIFICATE OF CORRECTION

PATENT NO. : 7,268,115 B2  
APPLICATION NO. : 10/412701  
DATED : September 11, 2007  
INVENTOR(S) : Barbara J. Gour et al.

Page 1 of 1

It is certified that error appears in the above-identified patent and that said Letters Patent is hereby corrected as shown below:

On Title Page  
Item 22  
<u>Page One</u>  
Filing Date: "Apr. 10, 2003" should read as -- Apr. 9, 2003--

Signed and Sealed this

Eighteenth Day of December, 2007

JON W. DUDAS  
*Director of the United States Patent and Trademark Office*